US011078268B2

(12) United States Patent
Cook et al.

(10) Patent No.: US 11,078,268 B2
(45) Date of Patent: Aug. 3, 2021

(54) IL-11 ANTIBODIES

(71) Applicants: Singapore Health Services PTE LTD., Singapore (SG); National University of Singapore, Singapore (SG)

(72) Inventors: Stuart Alexander Cook, Singapore (SG); Sebastian Schaefer, Singapore (SG)

(73) Assignees: Singapore Health Services PTE LTD, Singapore (SG); National University of Singapore, Singapore (SG)

( * ) Notice: Subject to any disclaimer, the term of this patent is extended or adjusted under 35 U.S.C. 154(b) by 0 days.

(21) Appl. No.: 16/726,173

(22) Filed: Dec. 23, 2019

(65) Prior Publication Data

US 2020/0199218 A1    Jun. 25, 2020

Related U.S. Application Data

(63) Continuation of application No. 15/843,173, filed on Dec. 15, 2017, now abandoned.

(30) Foreign Application Priority Data

Dec. 16, 2016 (GB) .................................. 1621446.2
Jun. 15, 2017 (GB) .................................. 1709535.7

(51) Int. Cl.
| | |
|---|---|
| C07K 16/24 | (2006.01) |
| A61P 17/02 | (2006.01) |
| A61P 43/00 | (2006.01) |
| C07K 14/715 | (2006.01) |
| C07K 14/54 | (2006.01) |
| A61K 47/68 | (2017.01) |
| A61K 39/00 | (2006.01) |
| A61P 35/00 | (2006.01) |
| A61P 27/02 | (2006.01) |
| A61P 1/16 | (2006.01) |
| A61P 9/00 | (2006.01) |
| A61P 17/00 | (2006.01) |
| A61P 13/12 | (2006.01) |
| A61P 11/00 | (2006.01) |

(52) U.S. Cl.
CPC ........ *C07K 16/244* (2013.01); *A61K 47/6845* (2017.08); *A61P 1/16* (2018.01); *A61P 9/00* (2018.01); *A61P 11/00* (2018.01); *A61P 13/12* (2018.01); *A61P 17/00* (2018.01); *A61P 17/02* (2018.01); *A61P 27/02* (2018.01); *A61P 35/00* (2018.01); *A61P 43/00* (2018.01); *C07K 14/5431* (2013.01); *C07K 14/7155* (2013.01); *A61K 2039/505* (2013.01); *C07K 2317/20* (2013.01); *C07K 2317/21* (2013.01); *C07K 2317/24* (2013.01); *C07K 2317/33* (2013.01); *C07K 2317/515* (2013.01); *C07K 2317/52* (2013.01); *C07K 2317/56* (2013.01); *C07K 2317/565* (2013.01); *C07K 2317/622* (2013.01); *C07K 2317/76* (2013.01); *C07K 2317/92* (2013.01); *C07K 2319/75* (2013.01)

(58) Field of Classification Search
None
See application file for complete search history.

(56) References Cited

U.S. PATENT DOCUMENTS

| | | |
|---|---|---|
| 5,679,339 A | 10/1997 | Keith et al. |
| 6,126,933 A | 10/2000 | Warne et al. |
| 6,540,993 B1 | 4/2003 | Warne et al. |
| 6,846,907 B1 | 1/2005 | Shaughnessy et al. |
| 6,953,777 B2 | 10/2005 | Keith et al. |
| 6,998,123 B1 | 2/2006 | Shaughnessy et al. |
| 7,993,637 B2 | 8/2011 | Baca |
| 8,182,814 B2 | 5/2012 | Baca et al. |
| 8,361,966 B2 | 1/2013 | Azuma et al. |
| 8,518,888 B2 | 8/2013 | Jenkins et al. |
| 8,540,977 B2 | 9/2013 | Baca |
| 9,340,618 B2 | 5/2016 | Edwards et al. |
| 10,035,852 B2 | 7/2018 | Cook et al. |
| 10,106,603 B2 | 10/2018 | Cook et al. |
| 2003/0147849 A1 | 8/2003 | Warne et al. |
| 2004/0126358 A1 | 7/2004 | Warne et al. |
| 2004/0142871 A1 | 7/2004 | Shaughnessy et al. |
| 2006/0062760 A1 | 3/2006 | Keith et al. |
| 2007/0160577 A1 | 7/2007 | Damle et al. |
| 2009/0191147 A1 | 7/2009 | Keith et al. |
| 2009/0202533 A1 | 8/2009 | Baca et al. |
| 2010/0062058 A1 | 3/2010 | Warne et al. |
| 2010/0093976 A1 | 4/2010 | Azuma et al. |
| 2010/0183544 A1 | 7/2010 | Jenkins et al. |
| 2013/0302277 A1 | 11/2013 | Jenkins et al. |
| 2014/0219919 A1 | 8/2014 | Edwards et al. |
| 2016/0031999 A1 | 2/2016 | Edwards et al. |

(Continued)

FOREIGN PATENT DOCUMENTS

| | | |
|---|---|---|
| CN | 105497893 A | 4/2016 |
| EP | 1630232 A2 | 3/2006 |

(Continued)

OTHER PUBLICATIONS

International Search Report and Written Opinion for PCT/EP2016/081430 dated Apr. 18, 2017.

(Continued)

*Primary Examiner* — Gary B Nickol
*Assistant Examiner* — Jegatheesan Seharaseyon
(74) *Attorney, Agent, or Firm* — Wolf, Greenfield & Sacks, P.C.

(57) ABSTRACT

IL-11 antibodies are disclosed. Also disclosed are compositions comprising the IL-11 antibodies, and methods using the IL-11 antibodies.

11 Claims, 192 Drawing Sheets

Specification includes a Sequence Listing.

(56) References Cited

U.S. PATENT DOCUMENTS

| | | |
|---|---|---|
| 2017/0174759 A1 | 6/2017 | Cook et al. |
| 2018/0186871 A1 | 7/2018 | Cook et al. |
| 2018/0186872 A1 | 7/2018 | Cook et al. |
| 2018/0265579 A1 | 9/2018 | Cook et al. |
| 2018/0362633 A1 | 12/2018 | Cook et al. |
| 2018/0362634 A1 | 12/2018 | Cook et al. |
| 2018/0362635 A1 | 12/2018 | Cook et al. |
| 2018/0362636 A1 | 12/2018 | Cook et al. |
| 2018/0362637 A1 | 12/2018 | Cook et al. |
| 2018/0362638 A1 | 12/2018 | Cook et al. |
| 2018/0362639 A1 | 12/2018 | Cook et al. |
| 2018/0362640 A1 | 12/2018 | Cook et al. |
| 2018/0362641 A1 | 12/2018 | Cook et al. |
| 2018/0371077 A1 | 12/2018 | Cook et al. |
| 2018/0371078 A1 | 12/2018 | Cook et al. |
| 2019/0002553 A1 | 1/2019 | Cook et al. |
| 2019/0389957 A1 | 12/2019 | Cook et al. |
| 2020/0031918 A1 | 1/2020 | Cook et al. |

FOREIGN PATENT DOCUMENTS

| | | |
|---|---|---|
| KR | 20110047179 A | 5/2011 |
| RU | 2016 125 115 A | 12/2017 |
| RU | 2016 151 730 A | 6/2018 |
| WO | WO 1996/019574 A1 | 6/1996 |
| WO | WO 1998/36061 A2 | 8/1998 |
| WO | WO 1999/020755 A2 | 4/1999 |
| WO | WO 2000/078336 A1 | 12/2000 |
| WO | WO 2002/020609 A2 | 3/2002 |
| WO | WO 2005/058956 A1 | 6/2005 |
| WO | WO 2005/070446 A1 | 8/2005 |
| WO | WO 2005/098041 A2 | 10/2005 |
| WO | WO 2009/052588 A1 | 4/2009 |
| WO | WO 2014/121325 A1 | 8/2014 |
| WO | WO 2017/103108 A1 | 6/2017 |
| WO | WO 2018/109170 A2 | 6/2018 |
| WO | WO 2018/109174 A2 | 6/2018 |

OTHER PUBLICATIONS

Chapter II Demand filed Aug. 14, 2017 for International Patent Application No. PCT/EP2016/081430.

International Preliminary Report on Patentability (Chapter II) for International Patent Application No. PCT/EP2016/081430, dated Nov. 6, 2017.

International Search Report and Written Opinion for Application No. PCT/EP2017/083043 dated Jul. 23, 2018.

International Search Report and Written Opinion for Application No. PCT/EP2017/083051 dated Aug. 13, 2018.

[No Author Listed] Human IL-11 Antibody. Monoclonal Mouse IgG2A. Clone No. 22626. Cat. No. MAB218. R& D Systems: A Biotechne Brand. Rev. Feb. 7, 2018. 1 page.

[No Author Listed] Human Il-11 Rα Antibody. Monoclonal Mouse IgG1. Clone No. 473143. Cat. No. MAB1977. R& D Systems: A Biotechne Brand. Rev. Feb. 7, 2018. 1 page.

[No Author Listed] Recombinant Human anti-human IL11 antibody. 2 pages. May 8, 2018.

[No Author Listed] Section 2, Definition, Pathophsiology and Pathogenesis of Asthma, and Natural History of Asthma. Aug. 28, 2007. 24 pages.

Ancey et al., A fusion protein of the gp130 and interleukin-6Ralpha ligand-binding domains acts as a potent interleukin-6 inhibitor. J Biol Chem. May 9, 2003;278(19):16968-72.

Blanc et al., Monoclonal antibodies against the human interleukin-11 receptor alpha-chain (IL-11Ralpha) and their use in studies of human mononuclear cells. J Immunol Methods. Jul. 31, 2000;241(1-2):43-59.

Bravo et al., Crystal structure of a cytokine-binding region of gp130. EMBO J. Mar. 16, 1998;17(6):1665-74.

Carr et al., Asthma heterogeneity and severity. World Allergy Organ J. 2016; 9(1): 41. EPub Nov. 29, 2016. doi: 10.1186/s40413-016-0131-2. 8 pages.

Chen et al., Enhancement and destruction of antibody function by somatic mutation: unequal occurrence is controlled by V gene combinatorial associations. The EMBO Journal. 1995;14(12):2784-94.

Chen et al., IL-11 receptor alpha in the pathogenesis of IL-13-induced inflammation and remodeling. J Immunol. Feb. 15, 2005;174(4):2305-13.

Cheng et al., Cross-reactivity of antibody against SARS-coronavirus nucleocapsid protein with IL-11. Biochem Biophys Res Commun. Dec. 23, 2005;338(3):1654-60. Epub Oct. 25, 2005.

Chow et al., Structure of an extracellular gp130 cytokine receptor signaling complex. Science. Mar. 16, 2001;291(5511):2150-5.

Colman, Effects of Amino Acid Sequence Changes on Antibody-Antigen Interactions. Research in Immunology. 1994;145:33-6.

Deguchi et al., Generation of and characterization of anti-IL-11 antibodies using newly established Il11-deficient mice. Biochem Biophys Res Commun. Oct. 28, 2018;505(2):453-459. doi: 10.1016/j.bbrc.2018.09.128. Epub Sep. 26, 2018.

Du et al., A bone marrow stromal-derived growth factor, interleukin-11, stimulates recovery of small intestinal mucosal cells after cytoablative therapy. Blood. Jan. 1, 1994;83(1):33-7.

Du et al., Interleukin-11: review of molecular, cell biology, and clinical use. Blood. Jun. 1, 1997;89(11):3897-908.

Forth, et al., Allgemeine und spezielle Pharmakologie und Toxikologie. 11th Edition. Aktories et al., Editors. Urban & Fischer. Sep. 17, 2013;Chapter 16:362-4.

Friedlander, Fibrosis and diseases of the eye. J Clin Invest. Mar. 2007;117(3):576-86.

Garbers et al., Interleukin-6 and interleukin-11: same same but different. Biol Chem. Sep. 2013;394(9):1145-61. doi: 10.1515/hsz-2013-0166.

Gu et al., Anti-gp130 transducer monoclonal antibodies specifically inhibiting ciliary neurotrophic factor, interleukin-6, interleukin-11, leukemia inhibitory factor or oncostatin M. J Immunol Methods. Mar. 28, 1996;190(1):21-7.

Halwani et al., Airway remodeling in asthma. Curr Opin Pharmacol. Jun. 2010;10(3):236-45. doi: 10.1016/j.coph.2010.06.004.

Ham et al., Critical role of interleukin-11 in isoflurane-mediated protection against ischemic acute kidney injury in mice. Anesthesiology. Dec. 2013;119(6):1389-401. doi: 10.1097/ALN.0b013e3182a950da.

Hennersdorf, et al., Das Herz bei arterieller Hypertonie. Internist. 2007;48(3): 236-45. https://doi.org/10.1007/s00108-006-1762-0.

Hermann et al., Important immunoregulatory role of interleukin-11 in the inflammatory process in rheumatoid arthritis. Arthritis Rheum. Aug. 1998;41(8):1388-97.

Johnstone et al., Emerging roles for IL-11 signaling in cancer development and progression: Focus on breast cancer. Cytokine Growth Factor Rev. Oct. 2015;26(5):489-98. doi: 10.1016/j.cytogfr.2015.07.015. Epub Jul. 14, 2015.

Kapina et al., Interleukin-11 drives early lung inflammation during *Mycobacterium tuberculosis* infection in genetically susceptible mice. PLoS One. 2011;6(7):e21878. doi: 10.1371/journal.pone.0021878.

Keith et al., IL-11, a pleiotropic cytokine: exciting new effects of IL-11 on gastrointestinal mucosal biology. Stem Cells. 1994;12 Suppl 1:79-89; discussion 89-90.

Khan et al., Fibrosis in heart disease: understanding the role of transforming growth factor-beta in cardiomyopathy, valvular disease and arrhythmia. Immunology. May 2006;118(1):10-24.

Kimura et al., Identification of cardiac myocytes as the target of interleukin 11, a cardioprotective cytokine. Cytokine. May 2007;38(2):107-15.

King, A scar-y movie, starring IL-11. Science Translational Medicine. Nov. 29, 2017;9(418):eaar2443. doi: 10.1126/scitranslmed.aar2443.

Kussie et al., A single engineered amino acid substitution changes antibody fine specificity. J Immunol. Jan. 1, 1994;152(1):146-52.

Lee et al., Cysteinyl leukotriene upregulates IL-11 expression in allergic airway disease of mice. J Allergy Clin Immunol. Jan. 2007;119(1):141-9. Epub Oct. 27, 2006.

(56) References Cited

OTHER PUBLICATIONS

Lee et al., Endogenous IL-11 signaling is essential in Th2- and IL-13-induced inflammation and mucus production. Am J Respir Cell Mol Biol. Dec. 2008;39(6):739-46. doi: 10.1165/rcmb.2008-00530C. Epub Jul. 10, 2008.

Lemoli et al., Interleukin-11 (IL-11) acts as a synergistic factor for the proliferation of human myeloid leukaemic cells. Br J Haematol. Oct. 1995;91(2):319-26.

Lindahl et al., Microarray profiling reveals suppressed interferon stimulated gene program in fibroblasts from scleroderma-associated interstitial lung disease. Respir Res. Aug. 2, 2013;14:80. doi: 10.1186/1465-9921-14-80.

Lokau et al., Generation of soluble interleukin-11 and interleukin-6 receptors: a crucial function for proteases during inflammation. Mediators of Inflammation. 2016. Article ID:1785021.10 pages.

Lokau et al., Proteolytic Cleavage Governs Interleukin-11 Trans-signaling. Cell Rep. 2016; 14(7): 1761-1773.

Lokau et al., Signal transduction of Interleukin-11 and Interleukin-6 α-Receptors. Recep Clin Investigation. 2016;3.

Mccoy et al., IL-11 produced by breast cancer cells augments osteoclastogenesis by sustaining the pool of osteoclast progenitor cells. BMC Cancer. Jan. 11, 2013;13:16. doi: 10.1186/1471-2407-13-16. 11 pages.

Metz et al., Characterization of the Interleukin (IL)-6 Inhibitor IL-6-RFP: fused receptor domains act as high affinity cytokine-binding proteins. J Biol Chem. Jan. 12, 2007;282(2):1238-48. Epub Nov. 3, 2006.

Minshall et al., IL-11 expression is increased in severe asthma: association with epithelial cells and eosinophils. J Allergy Clin Immunol. Feb. 2000;105(2 Pt 1):232-8.

Molet et al., IL-11 and IL-17 expression in nasal polyps: relationship to collagen deposition and suppression by intranasal fluticasone propionate. Laryngoscope. Oct. 2003;113(10):1803-12.

Murray et al., Targeting Interleukin-13 with Tralokinumab Attenuates Lung Fibrosis and Epithelial Damage in a Humanized SCID Idiopathic Pulmonary Fibrosis Model Am. J. Resp. Cell Mol. Biol. 2014; 50(5): 985-994, & Data Suppl.

Obana et al., Therapeutic activation of signal transducer and activator of transcription 3 by interleukin-11 ameliorates cardiac fibrosis after myocardial infarction. Circulation. Feb. 9, 2010;121(5):684-91. doi: 10.1161/CIRCULATIONAHA.109.893677. Epub Jan. 25, 2010.

Obana et al., Therapeutic administration of IL-11 exhibits the postconditioning effects against ischemia-reperfusion injury via STAT3 in the heart. Am J Physiol Heart Circ Physiol. Sep. 1, 2012;303(5):H569-77. doi: 10.1152/ajpheart.00060.2012.

Panka et al., Variable region framework differences result in decreased or increased affinity of variant anti-digoxin antibodies. Proc. Natl. Acad. Sci. USA. 1988; 85(9): 3080-3084.

Park et al., Monoclonal antibody therapy. Advances in Protein Chemistry. 2001;56:369-421. https://doi.org/10.1016/S0065-3233(01)56010-6.

Putoczki et al., IL-11 signaling as a therapeutic target for cancer. Immunotherapy. 2015;7(4):441-53. doi: 10.2217/imt.15.17.

Putoczki et al., Interleukin-11 is the dominant IL-6 family cytokine during gastrointestinal tumorigenesis and can be targeted therapeutically. Cancer Cell. Aug. 12, 2013;24(2):257-71. doi: 10.1016/j.ccr.2013.06.017.

Ray et al., Regulated overexpression of interleukin 11 in the lung. Use to dissociate development-dependent and -independent phenotypes. J Clin Invest. Nov. 15, 1997;100(10):2501-11.

Redlich et al., IL-11 enhances survival and decreases TNF production after radiation-induced thoracic injury. J Immunol. Aug. 15, 1996;157(4):1705-10.

Relevance of third-party observation dated Aug. 5, 2018. 3 pages.

Rudikoff et al., Single amino acid substitution altering antigen-binding specificity. Proc Natl Acad Sci U S A. Mar. 1982; 79(6): 1979-1983. doi: 10.1073/pnas.79.6.1979.

Schafer et al., IL-11 is a crucial determinant of cardiovascular fibrosis. Nature. 2017; 552(7683): 110-115.

Shepelkova et al., Therapeutic Effect of Recombinant Mutated Interleukin 11 in the Mouse Model of Tuberculosis. J Infect Dis. Aug. 1, 2016;214(3):496-501. doi: 10.1093/infdis/jiw176.

Sommer et al., Constitutively active mutant gp130 receptor protein from inflammatory hepatocellular adenoma is inhibited by an anti-gp130 antibody that specifically neutralizes interleukin 11 signaling. J Biol Chem. Apr. 20, 2012;287(17):13743-51. doi: 10.1074/jbc.M111.349167.

Stangou et al., Effect of IL-11 on glomerular expression of TGF-beta and extracellular matrix in nephrotoxic nephritis in Wistar Kyoto rats. J Nephrol. Jan.-Feb. 2011;24(1):106-11. Author Manuscript.

Tang et al., Targeted expression of IL-11 in the murine airway causes lymphocytic inflammation, bronchial remodeling, and airways obstruction. J Clin Invest. Dec. 15, 1996;98(12):2845-53.

Tang et al., Transforming Growth Factor-b Stimulates Interleukin-11 Transcription via Complex Activating Protein-1-dependent Pathways. J. Biol. Chem. 1998; 273(10): 5506-5513.

Third Party Observations for application No. EP20160822941, dated Aug. 5, 2018. 3 pages.

Third Party Submission Under 37 C.F.R. § 1.290 for U.S. Appl. No. 15/381,622, filed Apr. 30, 2018.

Toda et al., Polarized in vivo expression of IL-11 and IL-17 between acute and chronic skin lesions. J Allergy Clin Immunol. Apr. 2003;111(4):875-81.

Trepicchio et al., The therapeutic utility of Interleukin-11 in the treatment of inflammatory disease. Expert Opin Investig Drugs. Sep. 1998;7(9):1501-4.

Winship et al., Targeting Interleukin-11 Receptor-α Impairs Human Endometrial Cancer Cell Proliferation and Invasion In Vitro and Reduces Tumor Growth and Metastasis in Vivo. Mol Cancer Ther. Apr. 2016;15(4):720-30. doi: 10.1158/1535-7163.MCT-15-0677. Epub Feb. 4, 2016.

Wong et al., Endogenous IL-11 is pro-inflammatory in acute methylated bovine serum albumin/interleukin-1-induced (mBSA/IL-1)arthritis. Cytokine. Jan. 21, 2005;29(2):72-6.

Wynn, Cellular and molecular mechanisms of fibrosis. J Pathol. Jan. 2008;214(2):199-210. Author Manuscript.

Wynn, Fibrotic Disease and the TH1/TH2 Paradigm. Nat Rev Immunol. Aug. 2004; 4(8): 583-594. doi: 10.1038/nri1412.

Yashiro et al., Transforming growth factor-beta stimulates interleukin-11 production by human periodontal ligament and gingival fibroblasts. J Clin Periodontol. Mar. 2006;33(3):165-71.

Zheng et al., IL-11: insights in asthma from overexpression transgenic modeling. J Allergy Clin Immunol. Oct. 2001;108(4):489-96.

Zhu et al., IL-11 Attenuates Liver Ischemia/Reperfusion Injury (IRI) through STAT3 Signaling Pathway in Mice. PLoS One. May 6, 2015;10(5):e0126296. doi: 10.1371/journal.pone.0126296.

Zong-Jiang et al., Anti-gp 130 transducer monoclonal antibodies specifically inhibiting ciliary neurotrophic factor, interleukin-6, interleukin-11, leukemia inhibitory factor or oncostatin M. J. Immunol. Methods. 1996; 190(1): 21-27.

Affo et al., The Role of Cancer-Associated Fibroblasts and Fibrosis in Liver Cancer. Annu Rev Pathol. Jan. 24, 2017;12:153-186. Author manuscript, 39 pgs.

Barbas III et al., In vitro evolution of a neutralizing human antibody to human immunodeficiency virus type 1 to enhance affinity and broaden strain cross-reactivity. Proceedings of the National Academy of Science USA. Apr. 1994;91(9):3809-3813.

Better et al., *Escherichia coli* secretion of an active chimeric antibody fragment. Science. May 20, 1988;240(4855):1041-1043.

Bird et al., Single-Chain Antigen-Binding Proteins. Science. Oct. 21, 1988;242(4877):423-426.

Buck et al., Detection of S-phase cell cycle progression using 5-ethynyl-2?-deoxyuridine incorporation with click chemistry, an alternative to using 5-bromo-2?-deoxyuridine antibodies. BioTechniques. Jun. 2008;44(7):927-929.

Caballero et al., Anti-sphingosine-1-phosphate monoclonal antibodies inhibit angiogenesis and sub-retinal fibrosis in a murine model of laser-induced choroidal neovascularization. Exp Eye Res. Mar. 2009;88(3):367-77. doi: 10.1016/j.exer.2008.07.012. Epub Aug. 6, 2008.

(56) References Cited

OTHER PUBLICATIONS

Ciliberto et al. Cytokine Inhibitors: Chapter 8. Marcel Dekker, Inc. 2001.
Concepcion et al., Label-free detection of biomolecular interactions using BioLayer interferometry for kinetic characterization. Comb Chem High Throughput Screen. Sep. 2009;12(8):791-800. doi: 10.2174/138620709789104915.
Curtis et al., Recombinant Soluble Interleukin-11 (IL-11) Receptor ?-Chain Can Act as an IL-11 Antagonist. Blood. Dec. 1, 1997; 90(11): 4403-4412.
Daba et al., Drug-induced pulmonary fibrosis. Saudi Medical Journal. 2004;25(6):700-706.
Dotti et al., Design and Development of Therapies using Chimeric Antigen Receptor-Expressing T cells. Immunol Rev. Jan. 2014;257(1)107-26, Author Manuscript. 35 pages.
Elias et al., IL-1 and transforming growth factor-beta regulation of fibroblast-derived IL-11. J Immunol. Mar. 1, 1994;152(5):2421-9.
Ernst et al., STAT3 and STAT1 mediate IL-11-dependent and inflammation-associated gastric tumorigenesis in gp130 receptor mutant mice. The Journal of Clinical Investigation. May 2008;118(5):1727-1738.
French R., How to Make Bispecific Antibodies, Diagnostic and Therapeutic Antibodies, Methods in Molecular Medicine. 2008;40:333-339.
Gourdie et al., Novel therapeutic strategies targeting fibroblasts and fibrosis in heart disease. Nat Rev Drug Discov. Sep. 2016;15(9):620-638. Author Manuscript, 38 pages.
Grivennikov et al., Autocrine IL-6 Signaling: A Key Event in Tumorigenesis? Cancer Cell. Jan. 2008;13:7-9.
GTEX Consortium, The Genotype-Tissue Expression (GTEx) pilot analysis: Multitissue gene regulation in humans. Science. May 8, 2015;348(6235):648-660.
Guo et al., Signaling cross-talk between TGF-?BMP and other pathways. Cell Res. Jan. 2009;19(1):71-88, Author Manuscript. 27 pages.
Haverick et al., Separation of mAbs molecular variants by analytical hydrophobic interaction chromatography HPLC. mAbs. 2014;6(4):852-858. Epub Apr. 1, 2014.
Hawkins et al., Selection of Phage Antibodies by Binding Affinity Mimicking Affinity Maturation. Journal of Molecular Biology. 1992;226:889-896.
Hearty et al., Measuring antibody-antigen binding kinetics using surface plasmon resonance. Methods Mol Biol. 2012;907:411-42. doi: 10.1007/978-1-61779-974-7_24.
Hilton et al., Cloning of a murine IL-11 receptor ?-chain; requirement for gp130 for high affinity binding and signal transduction. The EMBO Journal. 1994;13(20):4765-4775.
Hinz et al., Biological Perspectives. The Myofibroblast. On Function, Multiple Origins. Am J Pathol. Jun. 2007;170(60):1807-1816. doi: 10.2353/ajpath.2007.070112.
Hornbeck, Enzyme-Linked Immunosorbent Assays. Curr Protoc Immunol. 2015;110:2.1.1-2.1.23.
Hornig et al., Chapter 40: Production of bispecific antibodies: diabodies and tandem scFv. Methods Mol Biol. 2012;907:713-727. doi:10.1007/978-1-61779-974-7_40.
Hsu et al., Whole Genome Expression Differences in Human Left and Right Atria Ascertained by RNA Sequencing. Circulation Cardiovascular Genetics. Jun. 2012;5(3):327-335.
Hunter et al., IL-6 as a keystone cytokine in helath and disease. Nature Immunology. May 2015;16(5)448-457. Epub Apr. 21, 2015.
Hurrell, Monoclonal Hybridoma Antibodies: Techniques and Applications. CRC Press. 1982.
Huston et al., Protein engineering of antibody binding sites: Recovery of specific activity in an anti-digoxin single-chain Fv analogue produced in *Escherichia coli*. Proceedings of the National Academy of Sciences of the United States of America. Aug. 1988;85:5879-5883.
Jackson et al., In vitro antibody maturation. Improvement of a high affinity, neutralizing antibody against IL-1 beta. J Immunol. 1995;154(7):3310-3319.

Jerabek-Willemsen et al., Molecular interaction studies using microscale thermophoresis. Assay and Drug Development Technologies. Aug. 2011;9(4):342-353.
Karpovich et al., Expression and function of interleukin-11 and its receptor ? in the human endometrium. Mol Hum Reprod. Feb. 2003;9(2):75-80. Author Manuscript, 15 pages.
Khaw et al., Modulation of wound healing after glaucoma surgery. Curr Opin Ophthalmol. Apr. 2001;12(2):143-8.
Kontermann, Dual targeting strategies with bispecific antibodies. mAbs. 2012;4(2):182-197.
Kurahar er al., Significant contribution of TRPC6 channel-mediated Ca2+ influx to the pathogenesis of Crohn's disease fibrotic stenosis. Journal of Smooth Muscle Research. 2016;52:78-92. Epub Nov. 3, 2016.
Lacob et al., Investigating monoclonal antibody aggregation using a combination of H/DX-MS and other biophysical measurements. J Pharm Sci., Dec. 2013;102(12):4315-4329, Author Manuscript, 25 pages.
Lad et al., High-Throughput Kinetic Screening of Hybridomas to Identify High-Affinity Antibodies Using Bio-Layer Interferometry. Journal of Biomolecular Screening. 2015;20(4):498-507.
Leask et al., TGF?? signaling and the fibrotic response. The FASEB Journal. 2004;18:816-827.
Liang et al., In vitro scratch assay: a convenient and inexpensive method for analysis of cell migration in vitro. Nature Protocols. 2007;2(2):329-333. Epub Mar. 1, 2007.
Marks et al., By-passing immunization: building high affinity human antibodies by chain shuffling. Biotechnology. Jul. 1992;10(7):779-783.
Marks J.D., Antibody Affinity Maturation by Chain Shuffling. Antibody Engineering: Methods and Protocols. Methods in Molecular Biology 2004;248:327-343.
Martineau P., Affinity Measurements by Competition ELISA. Antibody Engineering. 2010;1:657-665.
Mead et al., Evaluation of Anti-TGF-2 Antibody as a New Postoperative Anti-scarring Agent in Glaucoma Surgery. IOVS. Aug. 2003;44(8):3394-3401.
Menzen et al., High-Throughput Melting-Temperature Analysis of a Monoclonal Antibody by Differential Scanning Fluorimetry in the Presence of Surfactants. Journal of Pharmaceutical Sciences. Feb. 2013;102(2):415-428.
Morrison et al., Chimeric human antibody molecules: Mouse antigen-binding domains with human constant region domains. Proc Natl Acad Sci USA. Nov. 1984;81:6851-6855.
Nandurkar et al., The human IL-11 receptor requires gp130 for signalling: demonstration by molecular cloning of the receptor. Oncogene. 1996;12:585-593.
Nanthakumar et al., Dissecting fibrosis: therapeutic insights from the small-molecule toolbox. Nature Reviews. Oct. 2015;14:693-720. Epub Sep. 4, 2015.
Neuberger et al. Antibody Engineering. 8th International Biotechnology Symposium Part 2. 1988:792-799.
Pflanz et al., A fusion protein of interleukin-11 and soluble interleukin-11 receptor acts as a superagonist on cells expressing gp130. FEBS Lett. Apr. 30, 1999;450(1-2):117-122.
Putoczki et al., More than a sidekick: the IL-6 family cytokine IL-11 links inflammation to cancer. Journal of Leukocyte Biology. Dec. 2010;88:1109-1117.
Retter et al., VBASE2, an integrative V gene database. Nucleic Acids Research. 2005;33:D671-D674.
Rich et al., Extracting kinetic rate constants from surface plasmon resonance array systems. Analytical Biochemistry. 2008;373(1):112-120. Epub Aug. 19, 2007.
Rockey et al., Fibrosis—a common pathway to organ injury and failure. N Engl J Med. Mar. 19, 2015;372(12):1138-49. doi: 10.1056/NEJMra1300575.
Sadelain et al., The basic principles of chimeric antigen receptor (CAR) design. Cancer Discov. Apr. 2013;3(4):388-398. Author Manuscript, 21 pages.
Salic et al., A chemical method for fast and sensitive detection of DNA synthesis in vivo. PNAS. Feb. 19, 2008;105(7):2415-2420.
Schier et al., Identification of functional and structural amino-acid residues by parsimonious mutagenesis. Gene. 1996;169:147-155.

(56) References Cited

OTHER PUBLICATIONS

Seet et al., Validation of the Glaucoma Filtration Surgical Mouse Model for Antifibrotic Drug Evaluation. Mol Med. 2011;17(5-6):557-567. Epub Jan. 11, 2011.
Segal et al., Production of Bispecific Antibodies. Current Protocols in Immunology. 1995:2.13(1-16).
Sittampalam et al., Assay Guidance Manual, Eli Lilly & Company and the National Center for Advancing Translational Sciences. 2004 (last updated Jul. 1, 2016), 10 pages.
Skerra et al., Assembly of a Functional Immunoglobulin Fv Fragment in *Escherichia coli*. Science. May 20, 1988;240:1038-1041.
Szendröi et al., Polarization Colours of Collagen Fibres: A Sign of Collagen Production Activity in Fibrotic Processes. Acta Morphol Hung. 1984;32(1):47-55.
Tao et al., Cancer-associated fibroblasts treated with cisplatin facilitates chemoresistance of lung adenocarcinoma through IL-11/IL-11R/STAT3 signaling pathway. Scientific Reports. Dec. 6, 2016;6:38408 (1-12). doi: 10.1038/srep38408, Supplemental Information, 11 pages.
Tarnavski et al., Mouse cardiac surgery: comprehensive techniques for the generation of mouse models of human diseases and their application for genomic studies. Physiol Genomics. 2004;16:349-360. Epub Dec. 16, 2003.
Unverdorben et al., Pharmacokinetic properties of IgG and various Fc fusion proteins in mice. mAbs. Jan. 2016;8(1):120-128.
Walia et al., TGF-B down-regulates IL-6 signaling in intestinal epithelial cells: Critical role of SMAD-2. The FASEB Journal. Nov. 2003;17(14):20 Pages. Epub Sep. 18, 2003.
Ward et al., Binding activities of a repertoire of single immunoglobulin variable domains secreted from *Escherichia coli*. Nature. 1989;341(6242):544-546.
Widjaja et al., Inhibiting Interleukin 11 Signaling Reduces Hepatocyte Death and Liver Fibrosis, Inflammation, and Steatosis in Mouse Models of Nonalcoholic Steatohepatitis. Gastroenterology. Sep. 2019;157(3):777-792.e14. doi: 10.1053/j.gastro.2019.05.002.
Winter et al., Man-made antibodies. Nature. Jan. 24, 1991;349:293-299.
Wong et al., Matrix Metalloproteinase Inhibition Modulates Postoperative Scarring after Experimental Glaucoma Filtration Surgery. Investigative Ophthalmology & Visual Science. Mar. 2003;44(3):1097-1103.
Wong et al., Prolonged Antiscarring Effects of Ilomastat and MMC after Experimental Glaucoma Filtration Surgery. Investigative Ophthalmology & Visual Science. Jun. 2005;46(6):2018-2022.
Wynn et al., Mechanisms of fibrosis: therapeutic translation for fibrotic disease. Nat Med. Jul. 6, 2012;18(7):1028-1041. Author Manuscript, 28 pages.
Xu et al., The role of IL-11 in immunity and cancer. Cancer Letters. 2016;373:156-163.
Yelton et al., Affinity Maturation of the BR96 Anti-Carcinoma Antibody by Codon-Based Mutagenesis. The Journal of Immunology. 1995;155:1994-2004.
Zhang et al., IL-11 in multiple sclerosis. Oncotarget. Oct. 7, 2015;6(32):32297-32298.
Zola, Monoclonal Antibodies: A Manual of Techniques. CRC Press. 1988.

YU33-A2

DVVMTQSPSSLSASVGDRVTITCRAS<u>QDVGRY</u>VAWYQQKVGKVPRLLIY<u>AAS</u>ALQSGVPS
RFSGTASETSFTLTISSLQPEDVASYYC<u>QQYRSAPLA</u>FGGGTGVEIK (SEQ ID NO:1)

LC-CDR1:    QDVGRY (SEQ ID NO:101)
    LC-CDR2:    AAS (SEQ ID NO:102)
    LC-CDR3:    QQYRSAPLA (SEQ ID NO:103)

YU33-B3/H3

LPVLTQPHSVSESPGRTVTISCTRN<u>TGNIASNR</u>VQWYQQRPASAPTVVIY<u>DNH</u>QRPSGVPD
RFSGSIDTSPNSAYLTISGLKTEDEADYYC<u>QSYDYSSVI</u>FGGGTQLTVL (SEQ ID NO:2)

LC-CDR1:    TGNIASNR (SEQ ID NO:104)
    LC-CDR2:    DNH (SEQ ID NO:105)
    LC-CDR3:    QSYDYSSVI (SEQ ID NO:106)

YU33-B4/YU45-G2/A3

QSALTQPASVSGSPGQSITISCTGT<u>SSDVGGYNY</u>VSWYQQHPGKAPKLMIY<u>DVS</u>NRPSGV
SNRFSGSKSGNTASLTIFGLQAEDEADYYC<u>SSYTSSSSWV</u>FGGGTKLTVL (SEQ ID NO:3)

LC-CDR1:    SSDVGGYNY (SEQ ID NO:107)
    LC-CDR2:    DVS (SEQ ID NO:108)
    LC-CDR3:    SSYTSSSSWV (SEQ ID NO:109)

YU33-E6

QSALTQPASVSGSPGQSITISCTGT<u>SSDVGAYNY</u>VSWYQQHPGKAPKLMIY<u>EVS</u>HRPSGV
SNRFSGSKSGNTASLTISGLQAEDEADYYC<u>SSYTSSNTLV</u>FGGGTKLTVL (SEQ ID NO:4)

LC-CDR1:    SSDVGAYNY (SEQ ID NO:110)
    LC-CDR2:    EVS (SEQ ID NO:111)
    LC-CDR3:    SSYTSSNTLV (SEQ ID NO:112)

QSALTQPASVSGSPGQSITISCTGT<u>SSDVGGYNY</u>VSWYQQHPGKAPKLMIY<u>DVS</u>NRPSGV
SNRFSGSKSGNTASLTISGLQAEDEADYYC<u>SSYTSSSTVV</u>FGGGTKLTVL (SEQ ID NO:5)

LC-CDR1:    SSDVGGYNY (SEQ ID NO:107)
    LC-CDR2:    DVS (SEQ ID NO:108)
    LC-CDR3:    SSYTSSSTVV (SEQ ID NO:113)

YU45-D11/F11

QSALTQPASVSGSPGQSITISCTGT<u>SSDIGAYNY</u>VSWYQQHPGKAPKLMIY<u>DVS</u>HRPSGVS
NRFSGSKSGNAASLTISGVQAEDGADYYC<u>SSYTTSSTVV</u>FGGGTQLTVL (SEQ ID NO:6)

LC-CDR1:    SSDIGAYNY (SEQ ID NO:114)
    LC-CDR2:    DVS (SEQ ID NO:108)
    LC-CDR3:    SSYTTSSTVV (SEQ ID NO:115)

YU45-E11/E12

QSVLTQPPSASGTPGQRVTISCSGS<u>SSNIGSNY</u>VYWYQQLPGTAPKLLIY<u>RNN</u>QRPSGVPD
RFSGSKSGTSASLAISGLRSEDEADYYC<u>AAWDGSLSGWV</u>FGGGTKLTVL (SEQ ID NO:7)

LC-CDR1:    SSNIGSNY (SEQ ID NO:116)
    LC-CDR2:    RNN (SEQ ID NO:117)
    LC-CDR3:    AAWDGSLSGWV (SEQ ID NO:118)

YU45-H11/D12

QSALTQPASVSGSPGQSITISCTGT<u>SSDVGGYNY</u>VSWYQQHPGKAPKLMIY<u>DVS</u>NRPSGV
SNRFSGSKSGNTASLTISGLQAEDEADYYC<u>SSYTSSSTWV</u>FGGGTKLTVL (SEQ ID NO:8)

LC-CDR1:    SSDVGGYNY (SEQ ID NO:107)
    LC-CDR2:    DVS (SEQ ID NO:108)
    LC-CDR3:    SSYTSSSTWV (SEQ ID NO:119)

QSVLTQPPSASGTPGQRVTISCSGS<u>SSNIGSNY</u>VYWYQQLPGTAPKLLIY<u>RNN</u>QRPSGVPD
RFSGSKSGTSASLAISGLRSEDEADYYC<u>AAWDGSLSGWV</u>FGGGTKLTVL (SEQ ID NO:9)

LC-CDR1: SSNIGSNY (SEQ ID NO:116)
    LC-CDR2: RNN (SEQ ID NO:117)
    LC-CDR3: AAWDGSLSGWV (SEQ ID NO:118)

YU45-G1

QSALTQPRSVSGSPGQSVTISCTGT<u>SSDVGGYNY</u>VSWYQQHPGKAPKLMIY<u>DVS</u>KRPSGV
PDRFSGSKSGNTASLTVSGLQAEDEADYYC<u>CSYAGSYTFV</u>FGGGTKLTVL (SEQ ID NO:10)

LC-CDR1: SSDVGGYNY (SEQ ID NO:107)
    LC-CDR2: DVS (SEQ ID NO:108)
    LC-CDR3: CSYAGSYTFV (SEQ ID NO:120)

YU45-C2/A7/B10

QSALTQPPSASGSPGQSVTISCTGT<u>SSDVGGYNY</u>VSWYQQHPGKAPKLMIY<u>DVS</u>KRPSGV
PDRFSGSRSGNTASLTISGLQAEDEADYYC<u>NSYTSSTPYV</u>FGTGTKVTVL (SEQ ID NO:11)

LC-CDR1: SSDVGGYNY (SEQ ID NO:107)
    LC-CDR2: DVS (SEQ ID NO:108)
    LC-CDR3: NSYTSSTPYV (SEQ ID NO:121)

YU45-D2/H2/C7/F3/C9/E1/E9/C10/G3/H9/C5/A2/A5

QSALTQPRSVSGSPGQSVTISCTGT<u>ISDVGGYNY</u>VSWYQQHPGKAPKLMIY<u>DVT</u>KRPSGV
PDRFSGSKSGNTASLTISGLQAEDEAGYYC<u>SSYAGSYTWV</u>FGGGTELTVL (SEQ ID NO:12)

LC-CDR1: ISDVGGYNY (SEQ ID NO:122)
    LC-CDR2: DVT (SEQ ID NO:123)
    LC-CDR3: SSYAGSYTWV (SEQ ID NO:124)

QSALTQPRSVSGSPGQSVTISCTGTISDVGGYNYVSWYQQHPGKAPKLMIYDVTKRPSGV
PDRFSGSKSGNTASLTISGLQAEDEAGYYCSSYAGSYTWVFGGGTELTVL (SEQ ID
NO:13)

LC-CDR1:    ISDVGGYNY (SEQ ID NO:122)
    LC-CDR2:    DVT (SEQ ID NO:123)
    LC-CDR3:    SSYAGSYTWV (SEQ ID NO:124)

YU45-C8/E8

QSALTQPASVSGSPGQSITISCTGTSSDVGGYNYVSWYQQHPGKAPKLMVYDVSNRPSGV
SDRFSGSKSGNTASLTISGLQAEDEADYYCGSYTSSNTQVFGGGTKLTVL (SEQ ID NO:14)

LC-CDR1:    SSDVGGYNY (SEQ ID NO:107)
    LC-CDR2:    DVS (SEQ ID NO:108)
    LC-CDR3:    GSYTSSNTQV (SEQ ID NO:125)

YU45-F8

QPVLTQPPSVSAAPGQKVTISCSGSSSNIGNNLVYWYQQLPGTAPKLLIYRNNQRPSGVPD
RFSGSKSGTSASLAISGLRSEDEADYYCAAWDDSLSAGVFGGGTKLTAL (SEQ ID NO:15)

LC-CDR1:    SSNIGNNL (SEQ ID NO:126)
    LC-CDR2:    RNN (SEQ ID NO:117)
    LC-CDR3:    AAWDDSLSAGV (SEQ ID NO:127)

YU45-G8/H6

QSALTQPASVSGSPGQSITISCTGTSSDVGGYDYVSWYQQHPGTAPKLMISDVHNRPLGV
SNRFSGSKSGNTASLTISGLQAEDEADYYCSSYTSSITWVFGGGTKLTVL (SEQ ID NO:16)

LC-CDR1:    SSDVGGYDY (SEQ ID NO:128)
    LC-CDR2:    DVH (SEQ ID NO:129)
    LC-CDR3:    SSYTSSITWV (SEQ ID NO:130)

QSALTQPRSVSRSPGQSVTISCTGT<u>SSDVGGYNY</u>VSWYQQHPGKAPKLMIY<u>DVS</u>KRPSGV
PDRFSGSKSGNTASLTISGLQAEDEADYYC<u>CSYAGSYTWV</u>FGGGTKLTVL (SEQ ID
NO:17)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

YU45-H10

QSALTQPASVSGSPGQSITISCTGT<u>SSDVGGYNY</u>VSWYQQHPGKAPKLMIY<u>DVS</u>NRPSGV
SNRFSGSKSGNTASLTISGLQAEDEADYYC<u>SSYTSSSTWV</u>FGGGTKLTVL (SEQ ID NO:18)

LC-CDR1:    SSDVGGYNY (SEQ ID NO:107)
    LC-CDR2:    DVS (SEQ ID NO:108)
    LC-CDR3:    SSYTSSSTWV (SEQ ID NO:119)

YU46-A10

QPVLTQPPSVSAAPGQKVTISCSGS<u>SSNIGNNL</u>VYWYQQLPGTAPKLLIY<u>RNN</u>QRPSGVPD
RFSGSKSGTSASLAISGLRSEDEADYYC<u>AAWDDSLSAGV</u>FGGGTKLTAL (SEQ ID NO:19)

LC-CDR1:    SSNIGNNL (SEQ ID NO:126)
    LC-CDR2:    RNN (SEQ ID NO:117)
    LC-CDR3:    AAWDDSLSAGV (SEQ ID NO:127)

YU45-F2

QPVLTQPRSVSGSPGQSVTISCTGT<u>SSDVGGYNY</u>VSWYQQHPGKAPKVMIY<u>DVS</u>KRPSG
VPDRFSGSKSGNTASLTISGLQAEDEADYYC<u>CSYAGSYTWV</u>FGGGTKLTVL (SEQ ID
NO:20)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

QSALTQPASVSGSPGQSITISCTGT<u>SSDVGGYNY</u>VSWYQQHPGKAPKLMIY<u>DVS</u>NRPSGV
SNRFSGSKSGNTASLTISGLQAEDEADYYC<u>SSYTSSSTVV</u>FGGGTKLTVL (SEQ ID NO:21)

LC-CDR1:    SSDVGGYNY (SEQ ID NO:107)
    LC-CDR2:    DVS (SEQ ID NO:108)
    LC-CDR3:    SSYTSSSTVV (SEQ ID NO:113)

YU45-A1

QSALTQPASVSGSPGQSITISCTGT<u>SSDVGGYNY</u>VSWYQQHPGKAPKLMIY<u>DVS</u>NRPSGV
SNRFSGSKSGNTASLTISGLQAEDEADYYC<u>GSYTSSSTWV</u>FGGGTKLTVL (SEQ ID NO:22)

LC-CDR1:    SSDVGGYNY (SEQ ID NO:107)
    LC-CDR2:    DVS (SEQ ID NO:108)
    LC-CDR3:    GSYTSSSTWV (SEQ ID NO:132)

YU45-A8/C6

QSALTQPASVSGSPGQSITISCTGT<u>SSDVGGYNY</u>VSWYQQHPGKAPKLMIY<u>DVG</u>NRPSGV
SNRFSGSKSGNTASLTISGLQAEDEADYYC<u>SSYTSGSTWV</u>FGGGTKLTVL (SEQ ID NO:23)

LC-CDR1:    SSDVGGYNY (SEQ ID NO:107)
    LC-CDR2:    DVG (SEQ ID NO:133)
    LC-CDR3:    SSYTSGSTWV (SEQ ID NO:134)

YU45-B5/A4

QSALTQPPSASGSPGQSVTISCTGT<u>SSDVGGYNY</u>VSWYQQHPGKAPKLMIY<u>EVN</u>KRPSGV
PDRFSGSKSGNTASLTVSGLQAEDEADYYC<u>SSYAGTNNFVV</u>FGGGTKLTVL (SEQ ID NO:24)

LC-CDR1:    SSDVGGYNY (SEQ ID NO:107)
    LC-CDR2:    EVN (SEQ ID NO:135)
    LC-CDR3:    SSYAGTNNFVV (SEQ ID NO:136)

QSALTQPRSVSGSPGQSVTISCTGT<u>SSDVGGYNY</u>VSWYQQHPGKAPKLMIY<u>DVT</u>KRPSGV
PDRFSGSKSGNTASLTISGLQAEDEADYYC<u>CSYAGSYTWV</u>FGGGTKLTVL (SEQ ID
NO:25)

LC-CDR1:    SSDVGGYNY (SEQ ID NO:107)
    LC-CDR2:    DVT (SEQ ID NO:123)
    LC-CDR3:    CSYAGSYTWV (SEQ ID NO:131)

YU45-D1

ETTLTQSPATLSVSPGERATLSCRAS<u>QSVSSN</u>LAWYQQKPGQAPRLLIY<u>GAS</u>SRATGIPAR
FSGSGSGTEFTLTISSLQSEDFAVYYC<u>QQYNNWPLTFGGGTKVEFK</u> (SEQ ID NO:26)

LC-CDR1:    QSVSSN (SEQ ID NO:137)
    LC-CDR2:    GAS (SEQ ID NO:138)
    LC-CDR3:    QQYNNWPLTFGGGTKVEFK (SEQ ID NO:139)

YU45-D9/D3

QSVLTQPPSVSAAPGQEVTISCSGS<u>SSNIGNNY</u>VSWYQHLPGTAPKLLIY<u>DNT</u>ERPSGIPDR
FSGSRSGTSVTLGITGLQTGDEADYYC<u>GTWDSSLSGGV</u>FGGGTKLTVL (SEQ ID NO:27)

LC-CDR1:    SSNIGNNY (SEQ ID NO:140)
    LC-CDR2:    DNT (SEQ ID NO:141)
    LC-CDR3:    GTWDSSLSGGV (SEQ ID NO:142)

YU45-E5

QSALTQPRSVSGSPGQSVTISCTGT<u>ISDVGGYNY</u>VSWYQQHPGKAPKLMIY<u>DVT</u>KRPSGV
PDRFSGSKSGNTASLTISGLQAEDEAGYYC<u>SSYAGSYTWGVRRRDRADRP</u> (SEQ ID
NO:28)

LC-CDR1:    ISDVGGYNY (SEQ ID NO:122)
    LC-CDR2:    DVT (SEQ ID NO:123)
    LC-CDR3:    SSYAGSYTWGVRRRDRADRP (SEQ ID NO:143)

QSVLTQPPSVSAAPGRTVTISCSGS<u>YSNVGSNL</u>VSWYQQLPGTAPKLVIY<u>EDD</u>KRLSGIPD
RFSGSKSGTSASLAISGLQSEDEADYY<u>CAAWDDSLKGHV</u>FGGGTQLTVL (SEQ ID NO:29)

LC-CDR1:    YSNVGSNL (SEQ ID NO:144)
    LC-CDR2:    EDD (SEQ ID NO:145)
    LC-CDR3:    AAWDDSLKGHV (SEQ ID NO:146)

YU45-B4

QSVLTQPPSASGTPGQRVTISCSGS<u>SSNIGSNT</u>VNWYQQLPGTAPKLLIY<u>INN</u>QRPSGVPD
RFSGSKSGTSASLAISGLQSEDETDYY<u>CAAWDDSLNGWV</u>FGGGTKLTVL (SEQ ID NO:30)

LC-CDR1:    SSNIGSNT (SEQ ID NO:147)
    LC-CDR2:    INN (SEQ ID NO:148)
    LC-CDR3:    AAWDDSLNGWV (SEQ ID NO:149)

YU45-H4

QSALTQPASVSGSPGQSITISCTGT<u>SSDVGGYNY</u>VSWYQQHPGKAPKLMIY<u>DVS</u>KRPSGV
PDRFSGSKSGNTASLTISGLQAEDEADYY<u>CCSYAGSYTWV</u>FGGGTKLTAL (SEQ ID NO:31)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

YU45-B6

QSALTQPRSVSGSPGQSVTISCTGT<u>SRDVGGYNY</u>VSWYQQHPGEAPKLMIF<u>DVS</u>KRPSGV
PDRFSGSKSGNTASLTISGLQAEDEADYY<u>CCSYADYYTWV</u>FGGGTKVTVL (SEQ ID NO:32)

LC-CDR1:    SRDVGGYNY (SEQ ID NO:150)
    LC-CDR2:    DVS (SEQ ID NO:108)
    LC-CDR3:    CSYADYYTWV (SEQ ID NO:151)

QPVLTQPPSVSAAPGQKVTISCSGS<u>SSNIGNNL</u>VYWYQQLPGTAPKLLIY<u>RNN</u>QRPSGVPD
RFSGSKSGTSASLAISGLRSEDEADYYC<u>AAWDDSLSAGV</u>FGGGTKLTAL (SEQ ID NO:33)

LC-CDR1:    SSNIGNNL (SEQ ID NO:126)
    LC-CDR2:    RNN (SEQ ID NO:117)
    LC-CDR3:    AAWDDSLSAGV (SEQ ID NO:127)

YU45-E7

LPVLTQPHSVSESPGKTVTISCTGS<u>SGSIASNY</u>VQWYQQRPGSAPTTVIY<u>DDN</u>QRPSGVPD
RFSGSIDSSSNSASLTISGLKTEDEADYYC<u>QSYDSSNLWV</u>FGGGTKLTVL (SEQ ID NO:34)

LC-CDR1:    SGSIASNY (SEQ ID NO:152)
    LC-CDR2:    DDN (SEQ ID NO:153)
    LC-CDR3:    QSYDSSNLWV (SEQ ID NO:154)

YU45-F5

DIQMTQSPSFLSASVGDRVTITCRAS<u>QIISSY</u>LNWYQQKPGKAPKLLIY<u>AAS</u>SLQSGVPSRF
SGSGSGTDFTLTISSLQPEDFATYYC<u>QQSYSTPTWT</u>FGQGTKVEIK (SEQ ID NO:35)

LC-CDR1:    QIISSY (SEQ ID NO:155)
    LC-CDR2:    AAS (SEQ ID NO:102)
    LC-CDR3:    QQSYSTPTWT (SEQ ID NO:156)

YU45-H7/46-B5

QSALTQPPSASGSPGQSITISCTGT<u>SSDVGGYNY</u>VSWYQQHPGKAPKLMIY<u>DVS</u>NRPSGV
SNRFSGSKSGNTASLTISGLQAEDEADYYC<u>SSYTSSSTWV</u>FGGGTKLTVL (SEQ ID NO:36)

LC-CDR1:    SSDVGGYNY (SEQ ID NO:107)
    LC-CDR2:    DVS (SEQ ID NO:108)
    LC-CDR3:    SSYTSSSTWV (SEQ ID NO:119)

LPVLTQPHSVSESPGKTVTISCTRS<u>SGSIASNY</u>VQWYQQRPGSSPTTVIY<u>EDN</u>QRPSGVPD
RFSGSIDSSSNSASLTISGLRTEDEADYYC<u>QSYNSSKVV</u>FGGGTKLTVL (SEQ ID NO:37)

LC-CDR1:     SGSIASNY (SEQ ID NO:152)
       LC-CDR2:     EDN (SEQ ID NO:157)
       LC-CDR3:     QSYNSSKVV (SEQ ID NO:158)

YU46-A2

QSALTQPRSVSGSPGQSITISCTGT<u>SSDVGGYEY</u>VSWYQQHPGKAPRLLIY<u>DVS</u>NRPSGVS
NRFSGSKSGNTASLTVSGLQAEDEADYYC<u>NSYTSSGTLVV</u>FGGGTKLTVL (SEQ ID NO:38)

LC-CDR1:     SSDVGGYEY (SEQ ID NO:159)
       LC-CDR2:     DVS (SEQ ID NO:108)
       LC-CDR3:     NSYTSSGTLVV (SEQ ID NO:160)

YU46-A8

QSALTQPRSVSGSPGQSITISCTGT<u>SSDVGGYEY</u>VSWYQQHPGKAPRLLIY<u>DVS</u>NRPSGVS
NRFSGSKSGNTASLTVSGLQAEDEADYYC<u>NSYTSSGTLVV</u>FGGGTKLTVL (SEQ ID NO:39)

LC-CDR1:     SSDVGGYEY (SEQ ID NO:159)
       LC-CDR2:     DVS (SEQ ID NO:108)
       LC-CDR3:     NSYTSSGTLVV (SEQ ID NO:160)

YU46-B2

QPVLTQPRSVSGSPGQSVTISCTGT<u>SSDVGGYNY</u>VSWYQQHPGKAPKLMIY<u>DVS</u>KRPSGV
PDRFSGSKSGNTASLTISGLQAEDEADYYC<u>CSYAGSYTWV</u>FGGGTKLTVL (SEQ ID NO:40)

LC-CDR1:     SSDVGGYNY (SEQ ID NO:107)
       LC-CDR2:     DVS (SEQ ID NO:108)
       LC-CDR3:     CSYAGSYTWV (SEQ ID NO:131)

SSELTQDPAVSVALGQTVRITCQGDSLRGYYATWYQQKPGQAPVVVMYGNNNRPSGIPD
RFSGSSSGNTASLTITGAQAEDEADYYCDSRGRSGDHWLFGGGTKLTVL (SEQ ID NO:41)

LC-CDR1:    SLRGYY (SEQ ID NO:161)
    LC-CDR2:    GNN (SEQ ID NO:162)
    LC-CDR3:    DSRGRSGDHWL (SEQ ID NO:163)

YU46-C1

QAVLTQPPSASGTPGQRVSISCSGSSSNIGSYYVYWYQQVPGTAPKLIYRNDERPSGVPD
RFSGSKSGTSASLAISGLRSEDEAHYYCATWDDGLSGWVFGGGTKLTVL (SEQ ID NO:42)

LC-CDR1:    SSNIGSYY (SEQ ID NO:164)
    LC-CDR2:    RND (SEQ ID NO:165)
    LC-CDR3:    ATWDDGLSGWV (SEQ ID NO:166)

YU46-D7

QSVLTQPPSASGSPGQSVTISCAGTSSDVGAYNYVAWYQQHPGKAPKLIISEVFRRPSGVP
DRFSGSKSGTTAFLTVSGLQADDEAVYFCNSYVTGNNWAFGGGTKLTVL (SEQ ID NO:43)

LC-CDR1:    SSDVGAYNY (SEQ ID NO:110)
    LC-CDR2:    EVF (SEQ ID NO:168)
    LC-CDR3:    NSYVTGNNWA (SEQ ID NO:169)

YU46-E3

QSALTQPASVSGSPGQSITISCTGTSSDVGGYNYVSWYQQHPGKAPKLMIYDVSNRPSGV
SNRFSGSKSGNTASLTISGLQAEDEADYYCSSYTSSSTWVFGGGTKLTVL (SEQ ID NO:44)

LC-CDR1:    SSDVGGYNY (SEQ ID NO:107)
    LC-CDR2:    DVS (SEQ ID NO:108)
    LC-CDR3:    SSYTSSSTWV (SEQ ID NO:119)

QSVLTQPPSASGTPGQRVTISCSGS<u>SSNIGYDA</u>VNWYQQLPGTAPKLVIS<u>NDN</u>RRPSGVPA
RFSGSKSGTSASLAISGLQSEDEAYYYC<u>AAWDDSLSGWV</u>FGGGTKLTVL (SEQ ID NO:45)

LC-CDR1:    SSNIGYDA (SEQ ID NO:170)
    LC-CDR2:    NDN (SEQ ID NO:171)
    LC-CDR3:    AAWDDSLSGWV (SEQ ID NO:172)

YU46-H8

DIQMTQSPSSLSASVGDRVTITCRAS<u>QGSSSY</u>LAWYQQKPGKAPKLLIY<u>AAS</u>SLQSGVPSR
FSGSGSGTDFTLTISSLQPEDFATYYC<u>QQSYSTPLYT</u>FGQGTKLEIK (SEQ ID NO:46)

LC-CDR1:    QGSSSY (SEQ ID NO:173)
    LC-CDR2:    AAS (SEQ ID NO:102)
    LC-CDR3:    QQSYSTPLYT (SEQ ID NO:174)

YU46-G9

QPVLTQPRSVSGSPGQSVTISCTGT<u>SSDVGGYKY</u>VSWYQQHPGKAPELIIY<u>DVS</u>KRPSGVP
DRFSGSKSGNTASLTISGLQAEDEADYYC<u>CSYAGNYTWL</u>FGGGTKVTVL (SEQ ID NO:47)

LC-CDR1:    SSDVGGYKY (SEQ ID NO:175)
    LC-CDR2:    DVS (SEQ ID NO:108)
    LC-CDR3:    CSYAGNYTWL (SEQ ID NO:176)

YU46-G8

DIQMTQSPSSLSASVGDRVTITCRAS<u>QGSSSY</u>LAWYQQKPGKAPKLLIY<u>AAS</u>SLQSGVPSR
FSGSGSGTDFTLTISSLQPEDFATYYC<u>QQSYSTPLYT</u>FGQGTKLEIK (SEQ ID NO:48)

LC-CDR1:    QGSSSY (SEQ ID NO:173)
    LC-CDR2:    AAS (SEQ ID NO:102)
    LC-CDR3:    QQSYSTPLYT (SEQ ID NO:174)

QSALTQPASVSGSPGQSITISCTGT<u>SSDVGGYNY</u>VSWYQQHPGKAPKLMIY<u>DVS</u>NRPSGVSNRFSGSKSGNTASLTISGLQAEDEADYYC<u>TSYSSSSTLVA</u>FGGGTKLTVL (SEQ ID NO:49)

LC-CDR1:  SSDVGGYNY (SEQ ID NO:107)
    LC-CDR2:  DVS (SEQ ID NO:108)
    LC-CDR3:  TSYSSSSTLVA (SEQ ID NO:177)

YU46-D3

QSALTQPASVSGSPGQSITISCTGT<u>SSDVGNYKY</u>VSWYQQHPGKAPKLMIY<u>DVS</u>NRPSGVSNRFSGSKSGNTASLTISGLQAEDEADYYC<u>SSYTSSSTLVV</u>FGGGTKLTVL (SEQ ID NO:50)

LC-CDR1:  SSDVGNYKY (SEQ ID NO:178)
    LC-CDR2:  DVS (SEQ ID NO:108)
    LC-CDR3:  SSYTSSSTLVV (SEQ ID NO:179)

QLQQSGPGLVKPSQTLSLTCAISGDSVSSNSAAWNWIRQSPSRGLEWLGRTYYRSKWYN
DYAVSVKSRITINPDTSKNQFTLQLNSVTPDDTAVYYCARGTRGYFDYWGQGTLVTVSS
(SEQ ID NO:51)

HC-CDR1:    VSSNSAAWN (SEQ ID NO:180)
    HC-CDR2:    YRSKWYN (SEQ ID NO:181)
    HC-CDR3:    ARGTRGYFDY (SEQ ID NO:182)

YU33-B3/H3

EVQLVESGGGFVKPGGSLSISCAASGFTFSGAYMNWVRQAPGKGLEWVAVISYDGSNKYY
ADSVKGRFTISRDNSKNTLYLQMNSLRAEDTAVYYCARDLYAFDIWGQGTMVTVSS (SEQ
ID NO:52)

HC-CDR1:    GFTFSGAY (SEQ ID NO:183)
    HC-CDR2:    ISYDGSNK (SEQ ID NO:184)
    HC-CDR3:    ARDLYAFDI (SEQ ID NO:185)

YU33-B4/YU45-G2/A3

EVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:53)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU33-E6

QVQLQQSGGGVVQPGRSLRLSCAASGFTFSSYGMHWVRQAPGKGLEWVAVISYDGSDK
YYADSVKGRFTISRDNSKNTVYLQMNSLRAEDTAVYYCAKDLSGLPIIDYWGQGTLVTVSS
(SEQ ID NO:54)

HC-CDR1:    GFTFSSYG (SEQ ID NO:186)
    HC-CDR2:    ISYDGSDK (SEQ ID NO:188)
    HC-CDR3:    AKDLSGLPIIDY (SEQ ID NO:189)

EVQLLESGGGVVQPGRSLRLSCAAS<u>GFTFSSYA</u>MHWVRQAPGEGLEWVAV<u>ISYDGSNKY</u>YADSVKGRFTISRDNAKDSLYLQMNSLRDEDTAVYYC<u>ARRGYFDY</u>WGQGTLVTVSS (SEQ ID NO:55)

HC-CDR1:   GFTFSSYA (SEQ ID NO:190)
    HC-CDR2:   ISYDGSNK (SEQ ID NO:184)
    HC-CDR3:   ARRGYFDY (SEQ ID NO:191)

YU45-D11/F11

EVQLVESGGGLVQPGGSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>ARIAAADGMDV</u>WGQGTTVTVSS (SEQ ID NO:56)

HC-CDR1:   GFTFSSYG (SEQ ID NO:186)
    HC-CDR2:   ISYDGSNK (SEQ ID NO:184)
    HC-CDR3:   ARIAAADGMDV (SEQ ID NO:192)

YU45-E11/E12

QVQLVQSGGGVVLPGRSLRLSCAAS<u>GFSFRSYG</u>MHWVRQAPGKGLEWVAV<u>ISYDGSNKY</u>YADSVKGRFTISRDNSKNTLYLQMNSLRTGDTAVYYC<u>ARITHDYGDFSDAFDI</u>WGQGTMVAVSS (SEQ ID NO:57)

HC-CDR1:   GFSFRSYG (SEQ ID NO:193)
    HC-CDR2:   ISYDGSNK (SEQ ID NO:184)
    HC-CDR3:   ARITHDYGDFSDAFDI (SEQ ID NO:194)

YU45-H11/D12

EVQLLESGGGVVQPGRSRRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKLYSGSSNFDY</u>WGQGTLVTVSS (SEQ ID NO:58)

HC-CDR1:   GFTFSSYG (SEQ ID NO:186)
    HC-CDR2:   ISYDGSNK (SEQ ID NO:184)
    HC-CDR3:   AKLYSGSSNFDY (SEQ ID NO:195)

QVQLVQSGGGVVLPGRSLRLSCAAS<u>GFTFRSYG</u>MHWVRQAPGKGLEWVAV<u>ISYDGSNKY</u>YADSVKGRFTISRDNSKNTLYLQMNSLRTGDTAVYYC<u>ARITHDYGDFSDAFDI</u>WGQGTMVAVSS (SEQ ID NO:59)

HC-CDR1:     GFTFRSYG (SEQ ID NO:196)
      HC-CDR2:     ISYDGSNK (SEQ ID NO:184)
      HC-CDR3:     ARITHDYGDFSDAFDI (SEQ ID NO:194)

YU45-G1

EVQLLESGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKLSGPNGVDY</u>WGQGTLVTVSS (SEQ ID NO:60)

HC-CDR1:     GFTFSSYG (SEQ ID NO:186)
      HC-CDR2:     ISYDGSNK (SEQ ID NO:184)
      HC-CDR3:     AKLSGPNGVDY (SEQ ID NO:197)

YU45-C2/A7/B10

EVQLLESGGGVVQPGRSLRLSCAAS<u>GFTFSSYA</u>MHWVRQAPGKGLEWVAV<u>ISYDGSNKY</u>YADSVKGRFTISRDNSKNTLYLQMNSLRAEDTAVYYC<u>ARGQNVDL</u>WGQGTLVTVSS (SEQ ID NO:61)

HC-CDR1:     GFTFSSYA (SEQ ID NO:190)
      HC-CDR2:     ISYDGSNK (SEQ ID NO:184)
      HC-CDR3:     ARGQNVDL (SEQ ID NO:198)

YU45-D2/H2/C7/F3/C9/E1/E9/C10/G3/H9/C5/A2/A5

EVQLVESGGGVVQPGRSLRLSCAAS<u>GFTFSSYA</u>MHWVRQAPGKGLEWVAV<u>ISYDGSNKY</u>YADSVKGRFTISRDNSKNTLYLQMNSLRAEDTAVYYC<u>ARIMGYDYGDYDVVDY</u>WGQGTLVTVSS (SEQ ID NO:62)

HC-CDR1:     GFTFSSYA (SEQ ID NO:190)
      HC-CDR2:     ISYDGSNK (SEQ ID NO:184)
      HC-CDR3:     ARIMGYDYGDYDVVDY (SEQ ID NO:199)

EVQLVESGGGVVQPGRSLRLSCAAS<u>GFSFSSYA</u>MHWVRQAPGKGLEWVAV<u>ISYDGSNKY</u>YADSVKGRFTISRDNSKNTLYLQMNSLRAEDTAVYYC<u>ARIMGYDYGDYDVVDY</u>WGQGTLVTVSS (SEQ ID NO:63)

HC-CDR1:    GFSFSSYA (SEQ ID NO:212)
    HC-CDR2:    ISYDGSNK (SEQ ID NO:184)
    HC-CDR3:    ARIMGYDYGDYDVVDY (SEQ ID NO:199)

YU45-C8/E8

QVQLVQSGGGVVQPGRSLRLSCAAS<u>GFTFSSYG</u>MHWVRQAPGKGLEWVAV<u>ISYDGSNKY</u>YADSVKGRFTISRDNAKNSLYLQMNSLRDEDTAVYYC<u>ARRGYGDY</u>WGQGTLVTVSS (SEQ ID NO:64)

HC-CDR1:    GFTFSSYG (SEQ ID NO:186)
    HC-CDR2:    ISYDGSNK (SEQ ID NO:184)
    HC-CDR3:    ARRGYGDY (SEQ ID NO:213)

YU45-F8

RSAAGGVWGRRGPAWEVPETLLCSL<u>WIFLKSYA</u>MHWVRQAPGKGLEWVAV<u>ISYDGSNKY</u>YADSVKGRFTISRDNSKNTLYLQMTSLRAEDTAVYYC<u>ARVGFSSWYPDLYYFDY</u>WGQGTLVTVSS (SEQ ID NO:65)

HC-CDR1:    WIFLKSYA (SEQ ID NO:204)
    HC-CDR2:    ISYDGSNK (SEQ ID NO:184)
    HC-CDR3:    ARVGFSSWYPDLYYFDY (SEQ ID NO:205)

YU45-G8/H6

EVQLVESGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKFARGVYLFDY</u>WGQGTLVTVSS (SEQ ID NO:66)

HC-CDR1:    GFTFSSYG (SEQ ID NO:186)
    HC-CDR2:    ISYDGSNK (SEQ ID NO:184)
    HC-CDR3:    AKFARGVYLFDY (SEQ ID NO:215)

EVQLVQSGGGVVQPGRSLRLSCAAS<u>GFTFSSYA</u>MHWVRQAPGKGLEWVAV<u>ISYDGSNKY</u>
YADSVKGRFTISRDNSKNTLYLQMNSLRAEDTAVYYC<u>ARVQSGEPESDY</u>WGQGTLVTVSS
(SEQ ID NO:67)

HC-CDR1:    GFTFSSYA (SEQ ID NO:190)
      HC-CDR2:    ISYDGSNK (SEQ ID NO:184)
      HC-CDR3:    ARVQSGEPESDY (SEQ ID NO:216)

YU45-H10

EVQLLESGGGVVQPGRSRRLSCAAS<u>GFSLNSYG</u>MHWVRQAPGKGLEWVAV<u>ISYDGSNKY</u>
YADSVKGRFTISRDNSKNTLYLQMNSLRAEDTAVYYC<u>AKLYSGSSNFDY</u>WGQGTLVTVSS
(SEQ ID NO:68)

HC-CDR1:    GFSLNSYG (SEQ ID NO:217)
      HC-CDR2:    ISYDGSNK (SEQ ID NO:184)
      HC-CDR3:    AKLYSGSSNFDY (SEQ ID NO:195)

YU46-A10

EVQLVESGGGVVQPGRSLRLSCAAS<u>GFTFSSYA</u>MHWVRQAPGKGLEWVAV<u>ISYDGSNKY</u>
YADSVKGRFTISRDNSKNTLYLQMTSLRAEDTAVYYC<u>ARVGFSSWYPDLYYFDY</u>WGQGTL
VTVSS (SEQ ID NO:69)

HC-CDR1:    GFTFSSYA (SEQ ID NO:190)
      HC-CDR2:    ISYDGSNK (SEQ ID NO:184)
      HC-CDR3:    ARVGFSSWYPDLYYFDY (SEQ ID NO:205)

YU45-F2

EVQLVESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKLSGPNGVDY</u>WGQGTLVTVSS
(SEQ ID NO:70)

HC-CDR1:    GFTFSSYG (SEQ ID NO:186)
      HC-CDR2:    ISYDGSNK (SEQ ID NO:184)
      HC-CDR3:    AKLSGPNGVDY (SEQ ID NO:197)

EVQLVESGGGVVQPGRSLRLSCAAS<u>GFTFSSYA</u>MHWVRQAPGKGLEWVAV<u>ISYDGSNKY</u>YADSVKGRLTISRDNSKNTLYLQMNSLRAEDTAVYYC<u>ARMVNLYYGDAFDI</u>WGQGTMVTVSS (SEQ ID NO:71)

HC-CDR1: GFTFSSYA (SEQ ID NO:190)
  HC-CDR2: ISYDGSNK (SEQ ID NO:184)
  HC-CDR3: ARMVNLYYGDAFDI (SEQ ID NO:218)

YU45-A1

QLQLQESGGGVVQPGRSLRLSCAAS<u>GFTFSSYA</u>MHWVRQAPGKGLEWVAV<u>ISYDGSNKY</u>YADSVKGRFTISRDNSKNTLYLQMNSLRAEDTAVYYC<u>ARLVGATADDY</u>WGQGTLVTVSS (SEQ ID NO:72)

HC-CDR1: GFTFSSYA (SEQ ID NO:190)
  HC-CDR2: ISYDGSNK (SEQ ID NO:184)
  HC-CDR3: ARLVGATADDY (SEQ ID NO:219)

YU45-A8/C6

QVQLVESGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKLSGPNGVDY</u>WGQGTLVTVSS (SEQ ID NO:73)

HC-CDR1: GFTFSSYG (SEQ ID NO:186)
  HC-CDR2: ISYDGSNK (SEQ ID NO:184)
  HC-CDR3: AKLSGPNGVDY (SEQ ID NO:197)

YU45-B5/A4

QVQLVQSGAEVKKPGSSVKVSCKAS<u>GGTFSSYA</u>ISWVRQAPGQGLEWMGG<u>IIPIFGTANY</u>AQKFQGRVTITADESTSTAYMELSSLRSEDTAVYYC<u>ARGLITGTTP</u>WGQGTLVTVSS (SEQ ID NO:74)

HC-CDR1: GGTFSSYA (SEQ ID NO:209)
  HC-CDR2: IIPIFGTA (SEQ ID NO:210)
  HC-CDR3: ARGLITGTTP (SEQ ID NO:211)

EVQLVESGGGVVQPGRSLRLSCAAS<u>GFTFSSYG</u>MHWVRQAPGKGLEWVAV<u>ISYDGSNK</u>Y YADSVKGRFTISRDNSKNTLYLQMNSLRAEDTAVYYC<u>AKLSGPNGVDY</u>WGQGTLVTVSS (SEQ ID NO:75)

HC-CDR1:    GFTFSSYG (SEQ ID NO:186)
    HC-CDR2:    ISYDGSNK (SEQ ID NO:184)
    HC-CDR3:    AKLSGPNGVDY (SEQ ID NO:197)

YU45-D1

AQVQLQESGPGLVKPSGTLSLTCAVS<u>GGSISSSNW</u>WSWVRQPPGKGLEWIGE<u>IYHSGST</u>N YNPSLKSRVTISVDKSKNQFSLKLSSVTAADTAVYYC<u>ARVQNLGGGSYYVGAFDY</u>WGQGT LVTVSS (SEQ ID NO:76)

HC-CDR1:    GGSISSSNW (SEQ ID NO:220)
    HC-CDR2:    IYHSGST (SEQ ID NO:221)
    HC-CDR3:    ARVQNLGGGSYYVGAFDY (SEQ ID NO:222)

YU45-D9/D3

EVQLVESGGGVVQPGRSLRLSCAAS<u>GFTFSSYG</u>MHWVRQAPGKGLEWVAV<u>ISYDGSNK</u>Y YADSVKGRFTISRDNSKNTLYLQMNSLRAEDTAVYYC<u>ARLHFSQYFSTIDAFDI</u>WGQGTMV TISS (SEQ ID NO:77)

HC-CDR1:    GFTFSSYG (SEQ ID NO:186)
    HC-CDR2:    ISYDGSNK (SEQ ID NO:184)
    HC-CDR3:    ARLHFSQYFSTIDAFDI (SEQ ID NO:223)

YU45-E5

EVQLVESGGGVVQPGRSLRLSCAAS<u>GFTFSSYA</u>MHWVRQAPGKGLEWVAV<u>ISYDGSNK</u>Y YADSVKGRFTISRDNSKNTLYLQMNSLRAEDTAVYYC<u>ARIMGYDYGDYDVVDY</u>WGQGTLV TVSS (SEQ ID NO:78)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

QVQLVESGGGVVQPGRSLRLSCAAS<u>GFTFSSYA</u>MHWVRQAPGKGLEWVAV<u>ISYDGSNKY</u>YADSVKGRFTISRDNSKNTLYLQMNSLRAEDTAVYYC<u>ARDVGYSSGWYFDY</u>WGQGTLVTVSS (SEQ ID NO:79)

HC-CDR1:    GFTFSSYA (SEQ ID NO:190)
    HC-CDR2:    ISYDGSNK (SEQ ID NO:184)
    HC-CDR3:    ARDVGYSSGWYFDY (SEQ ID NO:200)

YU45-B4

EVQLVESGGGVVQPGRSLRLSCAAS<u>GFSLSSYG</u>MHWVRQAPGKGLEWVAV<u>ISYDGSNKY</u>YADSVKGRFTISRDNSKNTLYLQMNSLRAEDTAVYYC<u>ARLAQSYSSSWYEWEPGREHAFDI</u>WGQGTMVTVSS (SEQ ID NO:80)

HC-CDR1:    GFSLSSYG (SEQ ID NO:201)
    HC-CDR2:    ISYDGSNK (SEQ ID NO:184)
    HC-CDR3:    ARLAQSYSSSWYEWEPGREHAFDI (SEQ ID NO:202)

YU45-H4

EVQLVESGGGVVQPGRSLRLSCAAS<u>GFTFSSYA</u>MHWVRQAPGKGLEWVAV<u>ISYDGSNKY</u>YADSVKGRFTISRDNSKNTLYLQMNSLRAEDTAVYYC<u>ARPDDDY</u>WGQGTLVTVSS (SEQ ID NO:81)

HC-CDR1:    GFTFSSYA (SEQ ID NO:190)
    HC-CDR2:    ISYDGSNK (SEQ ID NO:184)
    HC-CDR3:    ARPDDDY (SEQ ID NO:203)

YU45-B6

EVQLVESGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKLSGPNGVDY</u>WGQGTLVTVSS (SEQ ID NO:82)

HC-CDR1:    GFTFSSYG (SEQ ID NO:186)
    HC-CDR2:    ISYDGSNK (SEQ ID NO:184)
    HC-CDR3:    AKLSGPNGVDY (SEQ ID NO:197)

RSAAGGVWGRRGPAWEVPETLLCSL<u>WIFLKSYA</u>MHWVRQAPGKGLEWVAV<u>ISYDGSNKY</u>YADSVKGRFTISRDNSKNTLYLQMTSLRAEDTAVYYC<u>ARVGFSSWYPDLYYFDY</u>WGQGTLVTVSS (SEQ ID NO:83)

HC-CDR1:    WIFLKSYA (SEQ ID NO:204)
    HC-CDR2:    ISYDGSNK (SEQ ID NO:184)
    HC-CDR3:    ARVGFSSWYPDLYYFDY (SEQ ID NO:205)

YU45-E7

EVQLVESGGGVVQPGRSLRLSCAAS<u>GFTFSSYA</u>MHWVRQAPGKGLEWVAV<u>ISYDGSNKY</u>YADSVKGRFTISRDNAKNSLYLQMNSLRAEDTAVYYC<u>ARLYSGYPSRYYYGMDV</u>WGQGTTVTVSS (SEQ ID NO:84)

HC-CDR1:    GFTFSSYA (SEQ ID NO:190)
    HC-CDR2:    ISYDGSNK (SEQ ID NO:184)
    HC-CDR3:    ARLYSGYPSRYYYGMDV (SEQ ID NO:206)

YU45-F5

*VTLKESGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKGGKSYYGFDY</u>WGQGTLVTVSS (SEQ ID NO:85)

HC-CDR1:    GFTFSSYG (SEQ ID NO:186)
    HC-CDR2:    ISYDGSNK (SEQ ID NO:184)
    HC-CDR3:    AKGGKSYYGFDY (SEQ ID NO:207)

YU45-H7/46-B5

EVQLVESGGGVVQPGRSLRLSCAAS<u>GFTFSSYA</u>MHWVRQAPGKGLEWVAV<u>ISYDGSNKY</u>YADSVKGRFTISRDNSKNTLYLQMNSLRAEDTAVYYC<u>ARLHSGRNWGDAFDI</u>WGQGTMVTVSS (SEQ ID NO:86)

HC-CDR1:    GFTFSSYA (SEQ ID NO:190)
    HC-CDR2:    ISYDGSNK (SEQ ID NO:184)
    HC-CDR3:    ARLHSGRNWGDAFDI (SEQ ID NO:208)

QV*LVQSGAEVKKPGSSVKVSCKAS<u>GGTFSSYA</u>ISWVRQAPGQGLEWMGG<u>IIPIFGTA</u>NYA
QKFQGRVTITADKSTSTAYMELSSLRSEDTAVYYC<u>ARGGGPYYDFWSGYYTEFDY</u>WGQG
TLVTVSS (SEQ ID NO:87)

HC-CDR1:    GGTFSSYA (SEQ ID NO:209)
    HC-CDR2:    IIPIFGTA (SEQ ID NO:210)
    HC-CDR3:    ARGGGPYYDFWSGYYTEFDY (SEQ ID NO:224)

YU46-A2

EVQLLESGGGVVQPGRSLKLSCAAS<u>GFTFSSYA</u>MHWVRQAPGKGLEWVAV<u>ISYDGSNK</u>Y
YADSVKGRFTISRDNSKNTLYLQMNSLRAEDTAVYYC<u>ARDSGYSSGWYFDY</u>WGQGTLVTV
SS (SEQ ID NO:88)

HC-CDR1:    GFTFSSYA (SEQ ID NO:190)
    HC-CDR2:    ISYDGSNK (SEQ ID NO:184)
    HC-CDR3:    ARDSGYSSGWYFDY (SEQ ID NO:225)

YU46-A8

EVQLLESGGGVVQPGRSLKLSCAAS<u>GFTFSSYA</u>MHWVRQAPGKGLEWVAV<u>ISYDGSNK</u>Y
YADSVKGRFTISRDNSKNTLYLQMNSLRAEDTAVYYC<u>ARDSGYSSGWYFDY</u>WGQGTLVTV
SS (SEQ ID NO:89)

HC-CDR1:    GFTFSSYA (SEQ ID NO:190)
    HC-CDR2:    ISYDGSNK (SEQ ID NO:184)
    HC-CDR3:    ARDSGYSSGWYFDY (SEQ ID NO:225)

YU46-B2

GAAGGVWGRRGPAWEVPETLLCSLW<u>ILPSDSYA</u>MHWVRQAPGKGLEWVAV<u>ISYDGSNK</u>Y
YADSVKGRFTISRDNSKNTLYLQMNSLRAEDTAVYYC<u>ARIAAAGRDAFDI</u>WGQGTMVTVSS
(SEQ ID NO:90)

HC-CDR1:    ILPSDSYA (SEQ ID NO:226)
    HC-CDR2:    ISYDGSNK (SEQ ID NO:184)
    HC-CDR3:    ARIAAAGRDAFDI (SEQ ID NO:227)

QVQLVQSGAEVKKPGASVKVSCKAS<u>GYTFTSYG</u>ISWVRQAPGQGLEWMGW<u>ISAYNGNTN</u>YAQKLQGRVTMTTDTSTSTAYMELRSLRSDDTAVYYC<u>ARVVAAARSYYYYMDV</u>WGKGTTVTVSS (SEQ ID NO:91)

HC-CDR1:    GYTFTSYG (SEQ ID NO:228)
      HC-CDR2:    ISAYNGNT (SEQ ID NO:229)
      HC-CDR3:    ARVVAAARSYYYYMDV (SEQ ID NO:230)

YU46-C1

QVQLVQSGAEVKKPGSSVKVSCKAS<u>GGTFSSYA</u>ISWVRQAPGQGLEWMGG<u>IIPIFGTA</u>NYAQKFQGRVTITADKSTSTAYMELSSLRSEDTAVYYC<u>ARADSSAGGGPYYYGMDV</u>WGQGTTVTVSS (SEQ ID NO:92)

HC-CDR1:    GGTFSSYA (SEQ ID NO:209)
      HC-CDR2:    IIPIFGTA (SEQ ID NO:210)
      HC-CDR3:    ARADSSAGGGPYYYGMDV (SEQ ID NO:231)

YU46-D7

EVQLLESGGGVVQPGRSLRLSCAAS<u>GFTFSSYG</u>MHWVRQAPGKGLEWVAV<u>ISYDGSNK</u>YADSVKGRFTISRDNSKNTLYLQMNSLGAEDTAVYYC<u>AKFARGVYLFDY</u>WGQGTLVTVSS (SEQ ID NO:93)

HC-CDR1:    GFTFSSYG (SEQ ID NO:186)
      HC-CDR2:    ISYDGSNK (SEQ ID NO:184)
      HC-CDR3:    AKFARGVYLFDY (SEQ ID NO:215)

YU46-E3

QVQLVESGGGVVQPGRSLRLSCAAS<u>GFTFSSYG</u>MHWVRQAPGKGLEWVAV<u>ISYDGSNK</u>YADSVKGRFTISRDNSKNTLYLQMNSLRAEDTAVYYC<u>ARIGGYDDFDY</u>WGQGTLVTVSS (SEQ ID NO:94)

HC-CDR1:    GFTFSSYG (SEQ ID NO:186)
      HC-CDR2:    ISYDGSNK (SEQ ID NO:184)
      HC-CDR3:    ARIGGYDDFDY (SEQ ID NO:232)

QVQLVESGGGVVQPGRSLRLSCAAS<u>GFTFSSYA</u>MHWVRQAPGKGLEWVAV<u>ISYDGSNKY</u>
YADSVKGRFTISRDNSKNTLYLQMNSLRAEDTAVYYC<u>ARVYYDSSGTQGDSFDY</u>WGQGTL
VTVSS (SEQ ID NO:95)

HC-CDR1:    GFTFSSYA (SEQ ID NO:190)
        HC-CDR2:    ISYDGSNK (SEQ ID NO:184)
        HC-CDR3:    ARVYYDSSGTQGDSFDY (SEQ ID NO:233)

YU46-H8

EVQLVESGGGVVQPGRSLRLSCAAS<u>GFTFGSYG</u>MHWVRQAPGKGLEWVAV<u>ISYDGSNKY</u>
YADSVKGRFTISRDNSKNTLYLQMNSLRAEDTAVYYC<u>AKGSYYFDY</u>WGQGTLVTVSS
(SEQ ID NO:96)

HC-CDR1:    GFTFGSYG (SEQ ID NO:234)
        HC-CDR2:    ISYDGSNK (SEQ ID NO:184)
        HC-CDR3:    AKGSYYFDY (SEQ ID NO:235)

YU46-G9

EVQLVESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKLSGPNGVDY</u>WGQGTLVTVSS
(SEQ ID NO:97)

HC-CDR1:    GFTFSSYG (SEQ ID NO:186)
        HC-CDR2:    ISYDGSNK (SEQ ID NO:184)
        HC-CDR3:    AKLSGPNGVDY (SEQ ID NO:197)

YU46-G8

EVQLVESGGGVVQPGRSLRLSCAAS<u>GFSLGSYG</u>MHWVRQAPGKGLEWVAV<u>ISYDGSNKY</u>
YADSVKGRFTISRDNSKNTLYLQMNSLRAEDTAVYYC<u>AKGSYYFDY</u>WGQGTLVTVSS
(SEQ ID NO:98)

HC-CDR1:    GFSLGSYG (SEQ ID NO:238)
        HC-CDR2:    ISYDGSNK (SEQ ID NO:184)
        HC-CDR3:    AKGSYYFDY (SEQ ID NO:235)

QVQLVESGGGVVQPGRSLRLSCAAS<u>GFTFSSY</u>AMHWVRQAPGKGLEWVAV<u>ISYDGSNK</u>YYADSVKGRFTISRDNSKNTLYLQMNSLRAEDTAVYYC<u>ARGVLFDY</u>WGQGTLVTVSS (SEQ ID NO:99)

HC-CDR1:    GFTFSSYA (SEQ ID NO:190)
    HC-CDR2:    ISYDGSNK (SEQ ID NO:184)
    HC-CDR3:    ARGVLFDY (SEQ ID NO:236)

YU46-D3

EVQLLESGGGVVQPGRSLRLSCAAS<u>GFTFSSY</u>AMHWVRQAPGKGLEWVAV<u>ISYDGSNK</u>YYADSVKGRFTSSRDNSKNTLYLQMNSLRAEDTAVYYC<u>ARSGVLDY</u>WGQGTLVTVSS (SEQ ID NO:100)

HC-CDR1:    GFTFSSYA (SEQ ID NO:190)
    HC-CDR2:    ISYDGSNK (SEQ ID NO:184)
    HC-CDR3:    ARSGVLDY (SEQ ID NO:237)

FIG. 16 (Cont.)

| Clone | CDR 1 | CDR 2 | CDR 3 |
|---|---|---|---|
| Light Chain | | | |
| YU33-A2 | QDVGRY (SEQ ID NO:101) | AAS (SEQ ID NO:102) | QQYRSAPLA (SEQ ID NO:103) |
| YU33-B3/H3 | TGNIASNR (SEQ ID NO:104) | DNH (SEQ ID NO:105) | QSYDYSSVI (SEQ ID NO:106) |
| YU33-B4/YU45-G2/A3 | SSDVGGYNY (SEQ ID NO:107) | DVS (SEQ ID NO:108) | SSYTSSSSWV (SEQ ID NO:109) |
| YU33-E6 | SSDVGAYNY (SEQ ID NO:110) | EVS (SEQ ID NO:111) | SSYTSSNTLV (SEQ ID NO:112) |
| YU45-C11/A10 | SSDVGGYNY (SEQ ID NO:107) | DVS (SEQ ID NO:108) | SSYTSSSTVV (SEQ ID NO:113) |
| YU45-D11/F11 | SSDIGAYNY (SEQ ID NO:114) | DVS (SEQ ID NO:108) | SSYTTSSTVV (SEQ ID NO:115) |
| YU45-E11/E12 | SSNIGSNY (SEQ ID NO:116) | RNN (SEQ ID NO:117) | AAWDGSLSGWV (SEQ ID NO:118) |
| YU45-H11/D12 | SSDVGGYNY (SEQ ID NO:107) | DVS (SEQ ID NO:108) | SSYTSSSTWV (SEQ ID NO:119) |
| YU45-A12/G10 | SSNIGSNY (SEQ ID NO:116) | RNN (SEQ ID NO:117) | AAWDGSLSGWV (SEQ ID NO:118) |
| YU45-G1 | SSDVGGYNY (SEQ ID NO:107) | DVS (SEQ ID NO:108) | CSYAGSYTFV (SEQ ID NO:120) |
| YU45-C2/A7/B10 | SSDVGGYNY (SEQ ID NO:107) | DVS (SEQ ID NO:108) | NSYTSSTPYV (SEQ ID NO:121) |
| YU45-D2/H2/C7/F3/C9/E1/E9/C10/G3/H9/C5/A2/A5 | ISDVGGYNY (SEQ ID NO:122) | DVT (SEQ ID NO:123) | SSYAGSYTWV (SEQ ID NO:124) |
| YU45-E3 | ISDVGGYNY (SEQ ID NO:122) | DVT (SEQ ID NO:123) | SSYAGSYTWV (SEQ ID NO:124) |
| YU45-C8/E8 | SSDVGGYNY (SEQ ID NO:107) | DVS (SEQ ID NO:108) | GSYTSSNTQV (SEQ ID NO:125) |
| YU45-F8 | SSNIGNNL (SEQ ID NO:126) | RNN (SEQ ID NO:117) | AAWDDSLSAGV (SEQ ID NO:127) |
| YU45-G8/H6 | SSDVGGYDY (SEQ ID NO:128) | DVH (SEQ ID NO:129) | SSYTSSITWV (SEQ ID NO:130) |
| YU45-F9 | SSDVGGYNY (SEQ ID NO:107) | DVS (SEQ ID NO:108) | CSYAGSYTWV (SEQ ID NO:131) |
| YU45-H10 | SSDVGGYNY (SEQ ID NO:107) | DVS (SEQ ID NO:108) | SSYTSSSTWV (SEQ ID NO:119) |
| YU46-A10 | SSNIGNNL (SEQ ID NO:126) | RNN (SEQ ID NO:117) | AAWDDSLSAGV (SEQ ID NO:127) |
| YU45-F2 | SSDVGGYNY (SEQ ID NO:107) | DVS (SEQ ID NO:108) | CSYAGSYTWV (SEQ ID NO:131) |
| YU45-H3 | SSDVGGYNY (SEQ ID NO:107) | DVS (SEQ ID NO:108) | SSYTSSSTVV (SEQ ID NO:113) |
| YU45-A1 | SSDVGGYNY (SEQ ID NO:107) | DVS (SEQ ID NO:108) | GSYTSSSTWV (SEQ ID NO:132) |
| YU45-A8/C6 | SSDVGGYNY (SEQ ID NO:107) | DVG (SEQ ID NO:133) | SSYTSGSTWV (SEQ ID NO:134) |
| YU45-B5/A4 | SSDVGGYNY (SEQ ID NO:107) | EVN (SEQ ID NO:135) | SSYAGTNNFVV (SEQ ID NO:136) |

FIG. 17

| Clone | CDR 1 | CDR 2 | CDR 3 |
|---|---|---|---|
| YU45-C3/A6 | SSDVGGYNY (SEQ ID NO:107) | DVT (SEQ ID NO:123) | CSYAGSYTWV (SEQ ID NO:131) |
| YU45-D1 | QSVSSN (SEQ ID NO:137) | GAS (SEQ ID NO:138) | QQYNNWPLTFGGGTKVEFK (SEQ ID NO:139) |
| YU45-D9/D3 | SSNIGNNY (SEQ ID NO:140) | DNT (SEQ ID NO:141) | GTWDSSLSGGV (SEQ ID NO:142) |
| YU45-E5 | ISDVGGYNY (SEQ ID NO:122) | DVT (SEQ ID NO:123) | SSYAGSYTWGVRRRDRADRP (SEQ ID NO:143) |
| YU45-G7 | YSNVGSNL (SEQ ID NO:144) | EDD (SEQ ID NO:145) | AAWDDSLKGHV (SEQ ID NO:146) |
| YU45-B4 | SSNIGSNT (SEQ ID NO:147) | INN (SEQ ID NO:148) | AAWDDSLNGWV (SEQ ID NO:149) |
| YU45-H4 | SSDVGGYNY (SEQ ID NO:107) | DVS (SEQ ID NO:108) | CSYAGSYTWV (SEQ ID NO:131) |
| YU45-B6 | SRDVGGYNY (SEQ ID NO:150) | DVS (SEQ ID NO:108) | CSYADYYTWV (SEQ ID NO:151) |
| YU45-D6 | SSNIGNNL (SEQ ID NO:126) | RNN (SEQ ID NO:117) | AAWDDSLSAGV (SEQ ID NO:127) |
| YU45-E7 | SGSIASNY (SEQ ID NO:152) | DDN (SEQ ID NO:153) | QSYDSSNLWV (SEQ ID NO:154) |
| YU45-F5 | QIISSY (SEQ ID NO:155) | AAS (SEQ ID NO:102) | QQSYSTPTWT (SEQ ID NO:156) |
| YU45-H7/B5 | SSDVGGYNY (SEQ ID NO:107) | DVS (SEQ ID NO:108) | SSYTSSSTWV (SEQ ID NO:119) |
| YU46-G1 | SGSIASNY (SEQ ID NO:152) | EDN (SEQ ID NO:157) | QSYNSSKVV (SEQ ID NO:158) |
| YU46-A2 | SSDVGGYEY (SEQ ID NO:159) | DVS (SEQ ID NO:108) | NSYTSSGTLVV (SEQ ID NO:160) |
| YU46-A8 | SSDVGGYEY (SEQ ID NO:159) | DVS (SEQ ID NO:108) | NSYTSSGTLVV (SEQ ID NO:160) |
| YU46-B2 | SSDVGGYNY (SEQ ID NO:107) | DVS (SEQ ID NO:108) | CSYAGSYTWV (SEQ ID NO:131) |
| YU46-B6 | SLRGYY (SEQ ID NO:161) | GNN (SEQ ID NO:162) | DSRGRSGDHWL (SEQ ID NO:163) |
| YU46-C1 | SSNIGSYY (SEQ ID NO:164) | RND (SEQ ID NO:165) | ATWDDGLSGWV (SEQ ID NO:166) |
| YU46-D7 | SSDVGAYNY (SEQ ID NO:167) | EVF (SEQ ID NO:168) | NSYVTGNNWA (SEQ ID NO:169) |
| YU46-E3 | SSDVGGYNY (SEQ ID NO:107) | DVS (SEQ ID NO:108) | SSYTSSSTWV (SEQ ID NO:119) |
| YU46-E7 | SSNIGYDA (SEQ ID NO:170) | NDN (SEQ ID NO:171) | AAWDDSLSGWV (SEQ ID NO:172) |
| YU46-H8 | QGSSSY (SEQ ID NO:173) | AAS (SEQ ID NO:102) | QQSYSTPLYT (SEQ ID NO:174) |
| YU46-G9 | SSDVGGYKY (SEQ ID NO:175) | DVS (SEQ ID NO:108) | CSYAGNYTWL (SEQ ID NO:176) |
| YU46-G8 | QGSSSY (SEQ ID NO:173) | AAS (SEQ ID NO:102) | QQSYSTPLYT (SEQ ID NO:174) |
| YU46-B7 | SSDVGGYNY (SEQ ID NO:107) | DVS (SEQ ID NO:108) | TSYSSSSTLVA (SEQ ID NO:177) |
| YU46-D3 | SSDVGNYKY (SEQ ID NO:178) | DVS (SEQ ID NO:108) | SSYTSSSTLVV (SEQ ID NO:179) |

FIG. 17 (Cont.)

| Clone | CDR 1 | CDR 2 | CDR 3 |
|---|---|---|---|
| Heavy Chain | | | |
| YU33-A2 | VSSNSAAWN (SEQ ID NO:180) | YRSKWYN (SEQ ID NO:181) | ARGTRGYFDY (SEQ ID NO:182) |
| YU33-B3/H3 | GFTFSGAY (SEQ ID NO:183) | ISYDGSNK (SEQ ID NO:184) | ARDLYAFDI (SEQ ID NO:185) |
| YU33-B4/YU45-G2/A3 | GFTFSSYG (SEQ ID NO:186) | ISYDGSNK (SEQ ID NO:184) | AKIGATDPLDY (SEQ ID NO:187) |
| YU33-E6 | GFTFSSYG (SEQ ID NO:186) | ISYDGSDK (SEQ ID NO:188) | AKDLSGLPIIDY (SEQ ID NO:189) |
| YU45-C11/A10 | GFTFSSYA (SEQ ID NO:190) | ISYDGSNK (SEQ ID NO:184) | ARRGYFDY (SEQ ID NO:191) |
| YU45-D11/F11 | GFTFSSYG (SEQ ID NO:186) | ISYDGSNK (SEQ ID NO:184) | ARIAAADGMDV (SEQ ID NO:192) |
| YU45-E11/E12 | GFSFRSYG (SEQ ID NO:193) | ISYDGSNK (SEQ ID NO:184) | ARITHDYGDFSDAFDI (SEQ ID NO:194) |
| YU45-H11/D12 | GFTFSSYG (SEQ ID NO:186) | ISYDGSNK (SEQ ID NO:184) | AKLYSGSSNFDY (SEQ ID NO:195) |
| YU45-A12/G10 | GFTFRSYG (SEQ ID NO:196) | ISYDGSNK (SEQ ID NO:184) | ARITHDYGDFSDAFDI (SEQ ID NO:194) |
| YU45-G1 | GFTFSSYG (SEQ ID NO:186) | ISYDGSNK (SEQ ID NO:184) | AKLSGPNGVDY (SEQ ID NO:197) |
| YU45-C2/A7/B10 | GFTFSSYA (SEQ ID NO:190) | ISYDGSNK (SEQ ID NO:184) | ARGQNVDL (SEQ ID NO:198) |
| YU45-D2/H2/C7/F3/C9/E1/E9/C10/G3/H9/C5/A2/A5 | GFTFSSYA (SEQ ID NO:190) | ISYDGSNK (SEQ ID NO:184) | ARIMGYDYGDYDVVDY (SEQ ID NO:199) |
| YU45-E3 | GFSFSSYA (SEQ ID NO:212) | ISYDGSNK (SEQ ID NO:184) | ARIMGYDYGDYDVVDY (SEQ ID NO:199) |
| YU45-C8/E8 | GFTFSSYG (SEQ ID NO:186) | ISYDGSNK (SEQ ID NO:184) | ARRGYGDY (SEQ ID NO:213) |
| YU45-F8 | WIFLKSYA (SEQ ID NO:204) | ISYDGSNK (SEQ ID NO:184) | ARVGFSSWYPDLYYFDY (SEQ ID NO:205) |
| YU45-G8/H6 | GFTFSSYG (SEQ ID NO:186) | ISYDGSNK (SEQ ID NO:184) | AKFARGVYLFDY (SEQ ID NO:215) |
| YU45-F9 | GFTFSSYA (SEQ ID NO:190) | ISYDGSNK (SEQ ID NO:184) | ARVQSGEPESDY (SEQ ID NO:216) |
| YU45-H10 | GFSLNSYG (SEQ ID NO:217) | ISYDGSNK (SEQ ID NO:184) | AKLYSGSSNFDY (SEQ ID NO:195) |
| YU46-A10 | GFTFSSYA (SEQ ID NO:190) | ISYDGSNK (SEQ ID NO:184) | ARVGFSSWYPDLYYFDY (SEQ ID NO:205) |
| YU45-F2 | GFTFSSYG (SEQ ID NO:186) | ISYDGSNK (SEQ ID NO:184) | AKLSGPNGVDY (SEQ ID NO:197) |
| YU45-H3 | GFTFSSYA (SEQ ID NO:190) | ISYDGSNK (SEQ ID NO:184) | ARMVNLYYGDAFDI (SEQ ID NO:218) |
| YU45-A1 | GFTFSSYA (SEQ ID NO:190) | ISYDGSNK (SEQ ID NO:184) | ARLVGATADDY (SEQ ID NO:219) |
| YU45-A8/C6 | GFTFSSYG (SEQ ID NO:186) | ISYDGSNK (SEQ ID NO:184) | AKLSGPNGVDY (SEQ ID NO:197) |

FIG. 18

| Clone | CDR 1 | CDR 2 | CDR 3 |
|---|---|---|---|
| YU45-B5/A4 | GGTFSSYA (SEQ ID NO:209) | IIPIFGTA (SEQ ID NO:210) | ARGLITGTTP (SEQ ID NO:211) |
| YU45-C3/A6 | GFTFSSYG (SEQ ID NO:186) | ISYDGSNK (SEQ ID NO:184) | AKLSGPNGVDY (SEQ ID NO:197) |
| YU45-D1 | GGSISSSNW (SEQ ID NO:220) | IYHSGST (SEQ ID NO:221) | ARVQNLGGGSYYVGAFDY (SEQ ID NO:222) |
| YU45-D9/D3 | GFTFSSYG (SEQ ID NO:186) | ISYDGSNK (SEQ ID NO:184) | ARLHFSQYFSTIDAFDI (SEQ ID NO:223) |
| YU45-E5 | GFTFSSYA (SEQ ID NO:190) | ISYDGSNK (SEQ ID NO:184) | ARIMGYDYGDYDVVDY (SEQ ID NO:199) |
| YU45-G7 | GFTFSSYA (SEQ ID NO:190) | ISYDGSNK (SEQ ID NO:184) | ARDVGYSSGWYFDY (SEQ ID NO:200) |
| YU45-B4 | GFSLSSYG (SEQ ID NO:201) | ISYDGSNK (SEQ ID NO:184) | ARLAQSYSSSWYEWEPGREHAFDI (SEQ ID NO:202) |
| YU45-H4 | GFTFSSYA (SEQ ID NO:190) | ISYDGSNK (SEQ ID NO:184) | ARPDDDY (SEQ ID NO:203) |
| YU45-B6 | GFTFSSYG (SEQ ID NO:186) | ISYDGSNK (SEQ ID NO:184) | AKLSGPNGVDY (SEQ ID NO:197) |
| YU45-D6 | WIFLKSYA (SEQ ID NO:204) | ISYDGSNK (SEQ ID NO:184) | ARVGFSSWYPDLYYFDY (SEQ ID NO:205) |
| YU45-E7 | GFTFSSYA (SEQ ID NO:190) | ISYDGSNK (SEQ ID NO:184) | ARLYSGYPSRYYYGMDV (SEQ ID NO:206) |
| YU45-F5 | GFTFSSYG (SEQ ID NO:186) | ISYDGSNK (SEQ ID NO:184) | AKGGKSYYGFDY (SEQ ID NO:207) |
| YU45-H7/B5 | GFTFSSYA (SEQ ID NO:190) | ISYDGSNK (SEQ ID NO:184) | ARLHSGRNWGDAFDI (SEQ ID NO:208) |
| YU46-G1 | GGTFSSYA (SEQ ID NO:209) | IIPIFGTA (SEQ ID NO:210) | ARGGPYYDFWSGYYTEFDY (SEQ ID NO:224) |
| YU46-A2 | GFTFSSYA (SEQ ID NO:190) | ISYDGSNK (SEQ ID NO:184) | ARDSGYSSGWYFDY (SEQ ID NO:225) |
| YU46-A8 | GFTFSSYA (SEQ ID NO:190) | ISYDGSNK (SEQ ID NO:184) | ARDSGYSSGWYFDY (SEQ ID NO:225) |
| YU46-B2 | ILPSDSYA (SEQ ID NO:226) | ISYDGSNK (SEQ ID NO:184) | ARIAAAGRDAFDI (SEQ ID NO:227) |
| YU46-B6 | GYTFTSYG (SEQ ID NO:228) | ISAYNGNT (SEQ ID NO:229) | ARVVAAARSYYYYMDV (SEQ ID NO:230) |
| YU46-C1 | GGTFSSYA (SEQ ID NO:209) | IIPIFGTA (SEQ ID NO:210) | ARADSSAGGGPYYYGMDV (SEQ ID NO:231) |
| YU46-D7 | GFTFSSYG (SEQ ID NO:186) | ISYDGSNK (SEQ ID NO:184) | AKFARGVYLFDY (SEQ ID NO:215) |
| YU46-E3 | GFTFSSYG (SEQ ID NO:186) | ISYDGSNK (SEQ ID NO:184) | ARIGGYDDFDY (SEQ ID NO:232) |
| YU46-E7 | GFTFSSYA (SEQ ID NO:190) | ISYDGSNK (SEQ ID NO:184) | ARVYYDSSGTQGDSFDY (SEQ ID NO:233) |
| YU46-H8 | GFTFGSYG (SEQ ID NO:234) | ISYDGSNK (SEQ ID NO:184) | AKGSYYFDY (SEQ ID NO:235) |
| YU46-G9 | GFTFSSYG (SEQ ID NO:186) | ISYDGSNK (SEQ ID NO:184) | AKLSGPNGVDY (SEQ ID NO:197) |
| YU46-G8 | GFSLGSYG (SEQ ID NO:238) | ISYDGSNK (SEQ ID NO:184) | AKGSYYFDY (SEQ ID NO:235) |
| YU46-B7 | GFTFSSYA (SEQ ID NO:190) | ISYDGSNK (SEQ ID NO:184) | ARGVLFDY (SEQ ID NO:236) |
| YU46-D3 | GFTFSSYA (SEQ ID NO:190) | ISYDGSNK (SEQ ID NO:184) | ARSGVLDY (SEQ ID NO:237) |

FIG. 18 (Cont.)

| Clone(s) | LC-CDR1 | Sequence family | Family Consensus |
|---|---|---|---|
| YU46-D3 | SSDVGNYKY | LC-CDR1-1 | $X_1X_2DX_3GX_4YX_5Y$ (SEQ ID NO:239)<br><br>$X_1$ = S or I<br>$X_2$ = S or R<br>$X_3$ = V or I<br>$X_4$ = G, A or N<br>$X_5$ = N, E, K or D |
| YU46-G9 | SSDVGGYKY | | |
| YU46-A2, YU46-A8 | SSDVGGYEY | | |
| YU45-B6 | SRDVGGYNY | | |
| YU45-G8/H6 | SSDVGGYDY | | |
| YU45-E5, YU45-E3, YU45-D2/H2/C7/F3/C9/E1/E9/C10/G3/H9/C5/A2/A5 | ISDVGGYNY | | |
| YU45-D11/F11 | SSDIGAYNY | | |
| YU33-B4/YU45-G2/A3, YU45-C11/A10, YU45-H11/D12, YU45-G1, YU45-C2/A7/B10, YU45-C8/E8, YU45-F9, YU45-H10, YU45-F2, YU45-H3, YU45-A1, YU45-A8/C6, YU45-B5/A4, YU45-C3/A6, YU45-H4, YU45-H7/46-B5, YU46-B2, YU46-E3, YU46-B7 | SSDVGGYNY | | |
| YU33-E6, YU46-D7 | SSDVGAYNY | | |

FIG. 19A

| Clone(s) | LC-CDR1 | Sequence family | Family Consensus |
|---|---|---|---|
| YU46-E7 | SSNIGYDA | LC-CDR1-2 | $X_6SNX_7GX_8X_9X_{10}$ (SEQ ID NO:240) $X_6$ = S or Y $X_7$ = I or V $X_8$ = S, N or Y $X_9$ = N, Y or D $X_{10}$ = L, Y, T or A |
| YU45-G7 | YSNVGSNL | | |
| YU46-C1 | SSNIGSYY | | |
| YU45-B4 | SSNIGSNT | | |
| YU45-D6, YU45-F8, YU45-A10 | SSNIGNNL | | |
| YU45-E11/E12, YU45-A12/G10 | SSNIGSNY | | |
| YU45-D9/D3 | SSNIGNNY | | |
| YU45-F5 | QIISSY | LC-CDR1-3 | $QX_{11}X_{12}SSX_{13}$ (SEQ ID NO:241) $X_{11}$ = G, S or I $X_{12}$ = S, I or V $X_{13}$ = Y or N |
| YU46-H8, YU46-G8 | QGSSSY | | |
| YU45-D1 | QSVSSN | | |
| YU33-B3/H3 | TGNIASNR | LC-CDR1-4 | $X_{14}GX_{15}IASNX_{16}$ (SEQ ID NO:242) $X_{14}$ = S or T $X_{15}$ = S or N $X_{16}$ = Y or R |
| YU45-E7, YU46-G1 | SGSIASNY | | |
| YU33-A2 | QDVGRY | LC-CDR1-5 | QDVGRY (SEQ ID NO:101) |
| YU46-B6 | SLRGYY | LC-CDR1-6 | SLRGYY (SEQ ID NO:161) |

FIG. 19A (Cont.)

| Clone(s) | LC-CDR2 | Sequence family | Family Consensus |
|---|---|---|---|
| YU45-A8/C6 | DVG | LC-CDR2-1 | DVX$_{17}$ (SEQ ID NO:243) $X_{17}$ = S, T or G |
| YU45-D2/H2/C7/F3/C9/E1/E9/C10/G3/H9/C5/A2/A5, YU45-E3, YU45-C3/A6, YU45-E5 | DVT | | |
| YU33-B4/YU45-G2/A3, YU45-C11/A10, YU45-D11/F11, YU45-H11/D12, YU45-G1, YU45-C2/A7/B10, YU45-C8/E8, YU45-F9, YU45-H10, YU45-F2, YU45-H3, YU45-A1, YU45-H4, YU45-B6, YU45-H7/46-B5, YU46-A2, YU46-A8, YU46-B2, YU46-E3, YU46-G9, YU46-B7, YU46-D3, | DVS | | |

FIG. 19B

| Clone(s) | LC-CDR2 | Sequence family | Family Consensus |
|---|---|---|---|
| YU46-C1 | RND | LC-CDR2-2 | $X_{18}NX_{19}$ (SEQ ID NO:244) $X_{18}$ = R, I or G $X_{19}$ = N or D |
| YU45-E11/E12, YU45-A12/G10, YU45-F8, YU46-A10, YU45-D6 | RNN | | |
| YU45-B4 | INN | | |
| YU46-B6 | GNN | | |
| YU33-A2, YU45-F5, YU46-H8, YU46-G8 | AAS | LC-CDR2-3 | $X_{20}AS$ (SEQ ID NO:245) $X_{20}$ = A or G |
| YU45-D1 | GAS | | |
| YU45-G7 | EDD | LC-CDR2-4 | $X_{21}DX_{22}$ (SEQ ID NO:246) $X_{21}$ = E, D or N $X_{22}$ = N or D |
| YU45-E7 | DDN | | |
| YU46-G1 | EDN | | |
| YU46-E7 | NDN | | |
| YU33-E6 | EVS | LC-CDR2-5 | $EVX_{23}$ (SEQ ID NO:247) $X_{23}$ = S, F or N |
| YU46-D7 | EVF | | |
| YU45-B5/A4 | EVN | | |
| YU45-D9/D3 | DNT | LC-CDR2-6 | $DX_{24}X_{25}$ (SEQ ID NO:248) $X_{24}$ = N or V $X_{25}$ = H or T |
| YU33-B3/H3 | DNH | | |
| YU45-G8/H6 | DVH | | |

FIG. 19B (Cont.)

| Clone(s) | LC-CDR3 | Sequence family | Family Consensus |
|---|---|---|---|
| YU45-A8/C6 | SSYTSGSTWV | LC-CDR3-1 | $X_{26}SYTX_{27}X_{28}X_{29}X_{30}X_{31}VX_{32}$ (SEQ ID NO:249) |
| YU45-A1 | GSYTSSSTWV | | |
| YU45-G8/H6 | SSYTSSITWV | | $X_{26}$ = S, N or G |
| YU33-B4/YU45-G2/A3 | SSYTSSSSWV | | $X_{27}$ = S or T |
| YU45-H11/D12, YU45-H10, YU45-H7/46-B5, YU46-E3, | SSYTSSSTWV | | $X_{28}$ = S or G<br>$X_{29}$ = S, N, G or I<br>$X_{30}$ = T or S<br>$X_{31}$ = W, L, V or Q<br>$X_{32}$ = absent or V |
| YU45-C8/E8 | GSYTSSNTQV | | |
| YU46-A2, YU46-A8 | NSYTSSGTLVV | | |
| YU33-E6 | SSYTSSNTLV | | |
| YU46-D3 | SSYTSSSTLVV | | |
| YU45-C11/A10, YU45-H3 | SSYTSSSTVV | | |
| YU45-D11/F11 | SSYTTSSTVV | | |
| YU45-B5/A4 | SSYAGTNNFVV | LC-CDR3-2 | $X_{33}SYAX_{34}X_{35}X_{36}X_{37}X_{38}X_{39}X_{40}X_{41}X_{42}X_{43}X_{44}X_{45}X_{46}X_{47}X_{48}X_{49}$ (SEQ ID NO:250) |
| YU46-G9 | CSYAGNYTWL | | |
| YU45-B6 | CSYADYYTWV | | $X_{33}$ = C or S |
| YU45-E5 | SSYAGSYTWGVRRRDRADRP | | $X_{34}$ = G or D |
| YU45-D2/H2/C7/F3/C9/E1/E9/C10/G3/H9/C5/A2/A5, YU45-E3 | SSYAGSYTWV | | $X_{35}$ = S, Y, N or T<br>$X_{36}$ = Y or N<br>$X_{37}$ = T or N<br>$X_{38}$ = W or F |
| YU45-G1 | CSYAGSYTFV | | $X_{39}$ = V, G or L |
| YU45-F9, YU45-F2, YU45-C3/A6, YU45-H4, YU46-B2 | CSYAGSYTWV | | $X_{40}$ = absent or V<br>$X_{41}$ = absent or R<br>$X_{42}$ = absent or R<br>$X_{43}$ = absent or R<br>$X_{44}$ = absent or D<br>$X_{45}$ = absent or R<br>$X_{46}$ = absent or A<br>$X_{47}$ = absent or D<br>$X_{48}$ = absent or R<br>$X_{49}$ = absent or P |

FIG. 19C

| Clone(s) | LC-CDR3 | Sequence family | Family Consensus |
|---|---|---|---|
| YU45-D9/D3 | GTWDSSLSGGV | LC-CDR3-3 | $X_{50}X_{51}WDX_{52}X_{53}LX_{54}X_{55}X_{56}V$ (SEQ ID NO:251) $X_{50}$ = A or G $X_{51}$ = A or T $X_{52}$ = D, G or S $X_{53}$ = S or G $X_{54}$ = S, K or N $X_{55}$ = G or A $X_{56}$ = W, G or H |
| YU46-C1 | ATWDDGLSGWV | | |
| YU45-G7 | AAWDDSLKGHV | | |
| YU45-F8, YU46-A10, YU45-D6, | AAWDDSLSAGV | | |
| YU45-B4 | AAWDDSLNGWV | | |
| YU45-E11/E12, YU45-A12/G10 | AAWDGSLSGWV | | |
| YU46-E7 | AAWDDSLSGWV | | |
| YU45-F5 | QQSYSTPTWT | LC-CDR3-4 | $QQX_{57}X_{58}X_{59}PX_{60}X_{61}X_{62}X_{63}X_{64}X_{65}X_{66}X_{67}X_{68}X_{69}X_{70}X_{71}X_{72}$ (SEQ ID NO:252) $X_{57}$ = S or Y $X_{58}$ = Y, R or N $X_{59}$ = S or N $X_{60}$ = T, A or W $X_{61}$ = L or T $X_{62}$ = Y, A, W or T $X_{63}$ = T, absent or F $X_{64}$ = absent or G $X_{65}$ = absent or G $X_{66}$ = absent or G $X_{67}$ = absent or T $X_{68}$ = absent or K $X_{69}$ = absent or V $X_{70}$ = absent or E $X_{71}$ = absent or F $X_{72}$ = absent or K |
| YU46-H8, YU46-G8 | QQSYSTPLYT | | |
| YU33-A2 | QQYRSAPLA | | |
| YU45-D1 | QQYNNWPLTFGGGTKVEFK | | |

FIG. 19C (Cont.)

| Clone(s) | LC-CDR3 | Sequence family | Family Consensus |
|---|---|---|---|
| YU46-G1 | QSYNSSKVV | LC-CDR3-5 | QSYX$_{73}$X$_{74}$SX$_{75}$X$_{76}$X$_{77}$X$_{78}$ (SEQ ID NO:253)<br><br>X$_{73}$ = D or N<br>X$_{74}$ = S or Y<br>X$_{75}$ = K, S or N<br>X$_{76}$ = V or L<br>X$_{77}$ = I, V or W<br>X$_{78}$ = absent or V |
| YU33-B3/H3 | QSYDYSSVI | | |
| YU45-E7 | QSYDSSNLWV | | |
| YU45-C2/A7/B10 | NSYTSSTPYV | LC-CDR3-6 | X$_{79}$SYX$_{80}$SSX$_{81}$X$_{82}$X$_{83}$VX$_{84}$ (SEQ ID NO:254)<br><br>X$_{79}$ = T or N<br>X$_{80}$ = T or S<br>X$_{81}$ = T or S<br>X$_{82}$ = P or T<br>X$_{83}$ = Y or L<br>X$_{84}$ = absent or A |
| YU46-B7 | TSYSSSSTLVA | | |
| YU46-D7 | NSYVTGNNWA | LC-CDR3-7 | NSYVTGNNWA (SEQ ID NO:169) |
| YU46-B6 | DSRGRSGDHWL | LC-CDR3-8 | DSRGRSGDHWL (SEQ ID NO:163) |

FIG. 19C (Cont.)

| Clone(s) | HC-CDR1 | Sequence family | Family Consensus |
|---|---|---|---|
| YU33-B4/YU45-G2/A3, YU33-E6, YU45-D11/F11, YU45-H11/D12, YU45-G1, YU45-C8/E8, YU45-G8/H6, YU45-F2, YU45-A8/C6, YU45-C3/A6, YU45-D9/D3, YU45-B6, YU45-F5, YU46-D7, YU46-E3, YU46-G9 | GFTFSSYG | HC-CDR1-1 | GFTFSSY$X_{85}$ (SEQ ID NO:255)<br><br>$X_{85}$ = A or G |
| YU45-C11/A10, YU45-C2/A7/B10, YU45-D2/H2/C7/F3/C9/E1/E9/C10/G3/H9/C5/A2/A5, YU45-F9, YU46-A10, YU45-H3, YU45-A1, YU45-E5, YU45-G7, YU45-H4, YU45-E7, YU45-H7/46-B5, YU46-A2, YU46-A8, YU46-E7, YU46-B7, YU46-D3 | GFTFSSYA | | |
| YU45-H10 | GFSLNSYG | HC-CDR1-2 | G$X_{86}X_{87}X_{88}X_{89}$SYG (SEQ ID NO:256)<br><br>$X_{86}$ = F or Y<br>$X_{87}$ = S or T<br>$X_{88}$ = L or F<br>$X_{89}$ = G, R, T, S or N |
| YU45-B4 | GFSLSSYG | | |
| YU46-G8 | GFSLGSYG | | |
| YU46-B6 | GYTFTSYG | | |
| YU45-E11/E12 | GFSFRSYG | | |
| YU45-A12/G10 | GFTFRSYG | | |
| YU46-H8 | GFTFGSYG | | |

FIG. 20A

| Clone(s) | HC-CDR1 | Sequence family | Family Consensus |
|---|---|---|---|
| YU45-B5/A4, YU46-G1, YU46-C1 | GGTFSSYA | HC-CDR1-3 | $X_{90}X_{91}X_{92}X_{93}X_{94}SYA$ (SEQ ID NO:257) |
| YU45-E3 | GFSFSSYA | | $X_{90}$ = G or I |
| YU46-B2 | ILPSDSYA | | $X_{91}$ = G, F or L $X_{92}$ = T, S or P $X_{93}$ = F or S $X_{94}$ = S or D |
| YU45-F8, YU45-D6 | WIFLKSYA | HC-CDR1-4 | WIFLKSYA (SEQ ID NO:204) |
| YU33-A2 | VSSNSAAWN | HC-CDR1-5 | VSSNSAAWN (SEQ ID NO:180) |
| YU45-D1 | GGSISSSNW | HC-CDR1-6 | GGSISSSNW (SEQ ID NO:220) |
| YU33-B3/H3 | GFTFSGAY | HC-CDR1-7 | GFTFSGAY (SEQ ID NO:183 |

FIG. 20A (Cont.)

| Clone(s) | HC-CDR2 | Sequence family | Family Consensus |
|---|---|---|---|
| YU33-B3/H3, YU33-B4/YU45-G2/A3, YU45-C11/A10, YU45-D11/F11, YU45-E11/E12, YU45-H11/D12, YU45-A12/G10, YU45-G1, YU45-C2/A7/B10, YU45-D2/H2/C7/F3/C9/E1/E9/C10/G3/H9/C5/A2/A5, YU45-E3, YU45-C8/E8, YU45-F8, YU45-G8/H6, YU45-F9, YU45-H10, YU46-A10, YU45-F2, YU45-H3, YU45-A1, YU45-A8/C6, YU45-C3/A6, YU45-D9/D3, YU45-E5, YU45-G7, YU45-B4, YU45-H4, YU45-B6, YU45-D6, YU45-E7, YU45-F5, YU45-H7/B5, YU46-A2, YU46-A8, YU46-B2, YU46-D7, YU46-E3, YU46-E7, YU46-H8, YU46-G9, YU46-G8, YU46-B7, YU46-D3 | ISYDGSNK | HC-CDR2-1 | ISYDGSX$_{95}$K (SEQ ID NO:258)  $X_{95}$ = N or D |
| YU33-E6 | ISYDGSDK | | |

FIG. 20B

| Clone(s) | HC-CDR2 | Sequence family | Family Consensus |
|---|---|---|---|
| YU45-B5/A4, YU46-G1, YU46-C1 | IIPIFGTA | HC-CDR2-2 | IIPIFGTA (SEQ ID NO:210) |
| YU33-A2 | YRSKWYN | HC-CDR2-3 | YRSKWYN (SEQ ID NO:181) |
| YU46-B6 | ISAYNGNT | HC-CDR2-4 | ISAYNGNT (SEQ ID NO:229) |
| YU45-D1 | IYHSGST | HC-CDR2-4 | IYHSGST (SEQ ID NO:221) |

FIG. 20B (Cont.)

| Clone(s) | HC-CDR3 | Sequence family | Family Consensus |
|---|---|---|---|
| YU45-G1, YU45-F2, YU45-A8/C6, YU45-C3/A6, YU45-B6, YU46-G9 | AKLSGPNGVDY | HC-CDR3-1 | AKLSGPNGVDY (SEQ ID NO:197) |
| YU33-E6 | AKDLSGLPIIDY | HC-CDR3-2 | AKX$_{96}$X$_{97}$X$_{98}$GX$_{99}$X$_{100}$X$_{101}$X$_{102}$DY (SEQ ID NO:259)<br><br>X$_{96}$ = L, F or D<br>X$_{97}$ = Y, A or L<br>X$_{98}$ = S or R<br>X$_{99}$ = S, V or L<br>X$_{100}$ = S, Y or P<br>X$_{101}$ = N, L or I<br>X$_{102}$ = F or I |
| YU45-H11/D12, YU45-H10 | AKLYSGSSNFDY | | |
| YU45-G8/H6, YU46-D7 | AKFARGVYLFDY | | |
| YU45-G7 | ARDVGYSSGWYFDY | HC-CDR3-3 | ARDX$_{103}$GYSSGWYFDY (SEQ ID NO:260)<br><br>X$_{103}$ = S or V |
| YU46-A2, YU46-A8 | ARDSGYSSGWYFDY | | |
| YU45-H7/46-B5 | ARLHSGRNWGDAFDI | HC-CDR3-4 | ARLX$_{104}$X$_{105}$X$_{106}$X$_{107}$X$_{108}$X$_{109}$X$_{110}$X$_{111}$X$_{112}$X$_{113}$X$_{114}$X$_{115}$X$_{116}$X$_{117}$X$_{118}$X$_{119}$X$_{120}$AFDI (SEQ ID NO:261)<br><br>X$_{104}$ = H or A<br>X$_{105}$ = S, Q or F<br>X$_{106}$ = S or G<br>X$_{107}$ = absent or Y<br>X$_{108}$ = absent or S<br>X$_{109}$ = absent, R or S<br>X$_{110}$ = Q, N or S<br>X$_{111}$ = W or Y<br>X$_{112}$ = absent, Y or F<br>X$_{113}$ = absent or E<br>X$_{114}$ = absent or W<br>X$_{115}$ = absent or E<br>X$_{116}$ = absent or P<br>X$_{117}$ = absent, G or S<br>X$_{118}$ = absent, R or T<br>X$_{119}$ = G, E or I<br>X$_{120}$ = D or H |
| YU45-B4 | ARLAQSYSSSWYEWEPGREHAFDI | | |
| YU45-D9/D3 | ARLHFSQYFSTIDAFDI | | |

FIG. 20C

| Clone(s) | HC-CDR3 | Sequence family | Family Consensus |
|---|---|---|---|
| YU45-D2/H2/C7/F3/C9/E1/E9/C10/G3/H9/C5/A2/A5, YU45-E3, YU45-E5 | ARIMGYDYGDYDVVDY | HC-CDR3-5 | ARIMGYDYGDYDVVDY (SEQ ID NO:199) |
| YU46-E3 | ARIGGYDDFDY | HC-CDR3-6 | ARIX$_{121}$X$_{122}$X$_{123}$X$_{124}$X$_{125}$X$_{126}$D X$_{127}$X$_{128}$X$_{129}$X$_{130}$ (SEQ ID NO:262) X$_{121}$ = A or G X$_{122}$ = A or G X$_{123}$ = A or Y X$_{124}$ = D or absent X$_{125}$ = G or D X$_{126}$ = F, M or R X$_{127}$ = V, Y or A X$_{128}$ = absent or F X$_{129}$ = absent or D X$_{130}$ = absent or I |
| YU45-D11/F11 | ARIAAADGMDV | | |
| YU46-B2 | ARIAAAGRDAFDI | | |
| YU45-F8, YU46-A10, YU45-D6 | ARVGFSSWYPDLYYFDY | HC-CDR3-7 | ARVGFSSWYPDLYYFDY (SEQ ID NO:205) |
| YU45-C11/A10 | ARRGYFDY | HC-CDR3-8 | X$_{131}$X$_{132}$X$_{133}$X$_{134}$RGYX$_{135}$DY (SEQ ID NO:263) X$_{131}$ = absent or A X$_{132}$ = absent or R X$_{133}$ = A or G X$_{134}$ = R or T X$_{135}$ = F or G |
| YU45-C8/E8 | ARRGYGDY | | |
| YU33-A2 | ARGTRGYFDY | | |
| YU45-E11/E12, YU45-A12/G10 | ARITHDYGDFSDAFDI | HC-CDR3-9 | ARITHDYGDFSDAFDI (SEQ ID NO:194) |
| YU46-D3 | ARSGVLDY | HC-CDR3-10 | ARX$_{136}$GVLX$_{137}$DY (SEQ ID NO:264) X$_{136}$ = absent or S X$_{137}$ = absent or F |
| YU46-B7 | ARGVLFDY | | |
| YU46-H8, YU46-G8 | AKGSYYFDY | HC-CDR3-11 | AKGSYYFDY (SEQ ID NO:235) |

FIG. 20C (Cont.)

| Clone(s) | HC-CDR3 | Sequence family | Family Consensus |
|---|---|---|---|
| YU45-E7 | ARLYSGYPSRYYYGMDV | HC-CDR3-12 | ARLYSGYPSRYYYGMDV (SEQ ID NO:206) |
| YU45-F9 | ARVQSGEPESDY | HC-CDR3-13 | ARVQSGEPESDY (SEQ ID NO:216) |
| YU33-B4/YU45-G2/A3 | AKIGATDPLDY | HC-CDR3-14 | AKIGATDPLDY (SEQ ID NO:187) |
| YU33-B3/H3 | ARDLYAFDI | HC-CDR3-15 | ARDLYAFDI (SEQ ID NO:185) |
| YU45-H4 | ARPDDDY | HC-CDR3-16 | ARPDDDY (SEQ ID NO:203) |
| YU45-F5 | AKGGKSYYGFDY | HC-CDR3-17 | AKGGKSYYGFDY (SEQ ID NO:207) |
| YU46-C1 | ARADSSAGGGPYYYGMDV | HC-CDR3-18 | ARADSSAGGGPYYYGMDV (SEQ ID NO:231) |
| YU46-E7 | ARVYYDSSGTQGDSFDY | HC-CDR3-19 | ARVYYDSSGTQGDSFDY (SEQ ID NO:233) |
| YU46-B6 | ARVVAAARSYYYYMDV | HC-CDR3-20 | ARVVAAARSYYYYMDV (SEQ ID NO:230) |
| YU46-G1 | ARGGGPYYDFWSGYYTEFDY | HC-CDR3-21 | ARGGGPYYDFWSGYYTEFDY (SEQ ID NO:224) |
| YU45-H3 | ARMVNLYYGDAFDI | HC-CDR3-22 | ARMVNLYYGDAFDI (SEQ ID NO:2218) |
| YU45-B5/A4 | ARGLITGTTP | HC-CDR3-23 | ARGLITGTTP (SEQ ID NO:211) |
| YU45-C2/A7/B10 | ARGQNVDL | HC-CDR3-24 | ARGQNVDL (SEQ ID NO:198) |
| YU45-D1 | ARVQNLGGGSYYVGAFDY | HC-CDR3-25 | ARVQNLGGGSYYVGAFDY (SEQ ID NO:222) |
| YU45-A1 | ARLVGATADDY | HC-CDR3-26 | ARLVGATADDY (SEQ ID NO:219) |

FIG. 20C (Cont.)

| Strategy No | Round 1 | Round 2 | Round 3 | biotinylated | No first hits |
|---|---|---|---|---|---|
| 1 | h-IL11 | m-IL11 | h-IL11 | Yes | 1 |
| 2 | h-IL11 | h-IL11 | h-IL11 | Yes | - |
| 3 | h-IL11 | h-IL11 | m-IL11 | Yes | - |
| 4 | m-IL11 | m-IL11 | m-IL11 | Yes | 5 |
| 5 | m-IL11 | h-IL11 | m-IL11 | Yes | - |
| 6 | m-IL11 | h-IL11 | h-IL11 | Yes | - |
| 7 | h-IL11 | h-IL11 | h-IL11 | No | 11 |
| 8 | h-IL11 | m-IL11 | h-IL11 | No | 14 |
| 9 | h-IL11 | m-IL11 | h-IL11 | Round 2 | 17 |
| 10 | h-IL11 | h-IL11 | m-IL11 | No | 19 |
| 11 | h-IL11 | h-IL11 | m-IL11 | Round 3 | 5 |
| 12 | m-IL11 | h-IL11 | m-IL11 | Round 3 | 10 |
| 13 | m-IL11 | m-IL11 | h-IL11 | Round 1, 2 | 6 |
| 14 | m-IL11 | m-IL11 | m-IL11 | No | 36 |
| 15 | m-IL11 | h-IL11 | m-IL11 | No | 15 |
| 16 | m-IL11 | m-IL11 | h-IL11 | No | 36 |

FIG. 21

| Identical Sequence | Clone ID | Fc-part | Identical Sequence | Clone ID | Fc-part |
|---|---|---|---|---|---|
| 1 | YU33-A2 | hIgG1-Fc (IgG) | 20 | YU45-H8 | hIgG1-Fc |
| 2 | YU33-B3 | hIgG1-Fc (IgG) | 21 | YU45-F9 | hIgG1-Fc |
|  | YU33-H3 | hIgG1-Fc (IgG) | 22 | YU45-H10 | hIgG1-Fc |
|  | YU33-B4 | hIgG1-Fc (IgG) | 23 | YU46-A10 | hIgG1-Fc |
| 3 | YU45-G2 | hIgG1-Fc | 24 | YU45-F2 | hIgG1-Fc |
|  | YU45-A3 | hIgG1-Fc | 25 | YU45-H3 | hIgG1-Fc |
| 4 | YU33-E3 | hIgG1-Fc (IgG) | 26 | YU45-A1 | hIgG1-Fc |
| 5 | YU33-E6 | hIgG1-Fc (IgG) | 27 | YU45-A8 | hIgG1-Fc |
| 6 | YU45-C11 | hIgG1-Fc |  | YU45-C6 | hIgG1-Fc |
|  | YU45-A10 | hIgG1-Fc | 28 | YU45-B5 | hIgG1-Fc |
| 7 | YU45-D11 | hIgG1-Fc |  | YU45-A4 | hIgG1-Fc |
|  | YU45-F11 | hIgG1-Fc | 29 | YU45-C3 | hIgG1-Fc |
| 8 | YU45-E11 | hIgG1-Fc |  | YU45-A6 | hIgG1-Fc |
|  | YU45-E12 | hIgG1-Fc | 30 | YU45-D1 | hIgG1-Fc |
| 9 | YU45-H11 | hIgG1-Fc | 31 | YU45-D9 | hIgG1-Fc |
|  | YU45-D12 | hIgG1-Fc |  | YU45-D3 | hIgG1-Fc |
| 10 | YU45-A12 | hIgG1-Fc | 32 | YU45-E5 | hIgG1-Fc |
|  | YU45-G10 | hIgG1-Fc | 33 | YU45-G7 | hIgG1-Fc |
| 11 | YU45-G1 | hIgG1-Fc | 34 | YU45-B4 | hIgG1-Fc |
| 12 | YU45-B2 | hIgG1-Fc | 35 | YU45-H4 | hIgG1-Fc |
|  | YU45-C2 | hIgG1-Fc | 36 | YU45-B6 | hIgG1-Fc |
| 13 | YU45-A7 | hIgG1-Fc | 37 | YU45-D6 | hIgG1-Fc |
|  | YU45-B10 | hIgG1-Fc | 38 | YU45-E7 | hIgG1-Fc |
| 14 | YU45-D2 | hIgG1-Fc | 39 | YU45-F5 | hIgG1-Fc |
|  | YU45-H2 | hIgG1-Fc | 40 | YU45-H7 | hIgG1-Fc |
|  | YU45-C7 | hIgG1-Fc |  | YU46-B5 | hIgG1-Fc |
|  | YU45-F3 | hIgG1-Fc | 41 | YU45-B8 | hIgG1-Fc |
|  | YU45-C9 | hIgG1-Fc | 42 | YU45-C1 | hIgG1-Fc |
|  | YU45-E1 | hIgG1-Fc | 43 | YU46-G1 | hIgG1-Fc |
|  | YU45-E9 | hIgG1-Fc | 44 | YU46-A2 | hIgG1-Fc |
|  | YU45-C10 | hIgG1-Fc | 45 | YU46-A8 | hIgG1-Fc |
|  | YU45-G3 | hIgG1-Fc | 46 | YU46-B2 | hIgG1-Fc |
|  | YU45-H9 | hIgG1-Fc | 47 | YU46-B6 | hIgG1-Fc |
|  | YU45-C5 | hIgG1-Fc | 48 | YU46-C1 | hIgG1-Fc |
|  | YU45-A2 | hIgG1-Fc | 49 | YU46-D7 | hIgG1-Fc |
|  | YU45-A5 | hIgG1-Fc | 50 | YU46-E3 | hIgG1-Fc |
| 15 | YU45-B3 | hIgG1-Fc | 51 | YU46-E7 | hIgG1-Fc |
| 16 | YU45-E3 | hIgG1-Fc | 52 | YU46-H8 | hIgG1-Fc |
| 17 | YU45-C8 | hIgG1-Fc | 53 | YU46-G9 | hIgG1-Fc |
|  | YU45-E8 | hIgG1-Fc | 54 | YU46-G8 | hIgG1-Fc |
| 18 | YU45-F8 | hIgG1-Fc | 55 | YU46-B7 | hIgG1-Fc |
| 19 | YU45-G8 | hIgG1-Fc | 56 | YU46-D3 | hIgG1-Fc |
|  | YU45-H6 | hIgG1-Fc |  |  |  |

FIG. 23

| Antibody Candidate | Human IL11 Activated fibroblasts (norm.) | Mouse IL11 Activated atrial fibroblasts (norm.) | Trans IL11 Activated fibroblasts (norm.) | Mouse IL11 Activated dermal fibroblasts (norm.) |
|---|---|---|---|---|
| - | 1 | | | |
| - | 1.81 | 2.16 | 2.13 | 1.95 |
| Industry Standard | | | | |
| 1 | 1.91 | 1.75 | 2.16 | 1.98 |
| 2 | 1.95 | 1.83 | 2.09 | 1.91 |
| 3 | | | | 1.59 |
| 4 | 1.85 | 1.85 | 2.13 | 1.83 |
| 5 | 1.78 | 1.72 | 2.13 | 1.82 |
| 6 | | | 2.26 | |
| 7 | | 1.79 | 2.18 | 1.93 |
| 8 | | 1.83 | 2.05 | 1.85 |
| 9 | | | | |
| 10 | 1.67 | 1.75 | | 1.86 |
| 11 | | | 2.61 | |
| 12 | | 1.83 | | 1.94 |
| 13 | 1.76 | 1.91 | | 2.09 |
| 14 | | | 2.04 | |
| 15 | 1.57 | | | |
| 16 | | | | 1.76 |
| 17 | 1.55 | 1.70 | | 1.76 |
| 18 | | | 1.85 | |
| 19 | | | 1.77 | |
| 20 | 1.65 | 1.78 | | 1.76 |
| 21 | | 1.83 | 2.06 | 1.83 |
| 22 | | | 2.02 | |
| 23 | 1.69 | | 2.27 | 1.72 |
| 24 | | 1.87 | | 1.89 |
| 25 | | | 2.04 | |
| 26 | 1.68 | 1.92 | 2.50 | 1.94 |
| 27 | | | 2.15 | |
| 28 | | 2.19 | 2.12 | 1.79 |
| 29 | 1.65 | | 2.10 | 1.81 |
| 30 | 1.63 | 1.89 | 1.89 | 1.88 |
| 31 | | | 1.76 | |
| 32 | 1.68 | 2.03 | 2.00 | 1.85 |
| 33 | | | 1.94 | 1.79 |
| 34 | 1.59 | 1.88 | 1.94 | 1.83 |
| 35 | 1.76 | 1.86 | 2.06 | 1.73 |
| 36 | | | 1.99 | |
| 37 | 1.81 | 1.92 | 1.82 | 1.75 |
| 38 | 1.54 | 1.91 | 1.98 | 1.81 |
| 39 | | 1.47 | | 1.82 |
| 40 | | 1.78 | 1.97 | 1.85 |
| 41 | 1.57 | 1.78 | 1.87 | 1.69 |
| 42 | | | 2.04 | |
| 43 | 1.54 | 1.78 | 2.06 | 1.72 |
| 44 | 1.57 | 1.71 | 2.13 | 1.81 |
| 45 | | | | 1.79 |
| 46 | 1.67 | 1.72 | 2.11 | 1.77 |
| 47 | | 1.81 | 1.90 | 1.79 |
| 48 | 1.50 | | 1.94 | |
| 49 | 1.60 | 1.70 | 1.89 | 1.70 |
| 50 | | 1.81 | 1.83 | 1.82 |
| 51 | 1.55 | 1.46 | 2.09 | 1.66 |
| 52 | 1.62 | | 2.09 | |
| 53 | 1.47 | 1.57 | 1.90 | 1.69 |
| 54 | | | | 1.82 |
| 55 | 1.56 | 1.61 | 2.16 | 1.80 |
| 56 | | | 1.87 | |

FIG. 27

| Sequence Group | Clone | Format | EC50 |
|---|---|---|---|
| 3 | YU45-A3 | hIgG-Fc | 14.22 |
| 6 | YU45-A10 | hIgG-Fc | 67.67 |
| 7 | YU45-D11 | hIgG-Fc | 186.5 |
| 8 | YU45-E11 | hIgG-Fc | 15.66 |
| 9 | YU45-D12 | hIgG-Fc | 14.55 |
| 11 | YU45-G1 | hIgG-Fc | 42.75 |
| 12 | YU45-B2 | hIgG-Fc | 6.409 |
| 14 | YU45-A5 | hIgG-Fc | 6.543 |
| 16 | YU45-E3 | hIgG-Fc | 33.19 |
| 18 | YU45-F8 | hIgG-Fc | 7.786 |
| 19 | YU45-G8 | hIgG-Fc | 6.288 |
| 21 | YU45-F9 | hIgG-Fc | 4.016 |
| 22 | YU45-H10 | hIgG-Fc | 24.8 |
| 24 | YU45-F2 | hIgG-Fc | 4.239 |
| 25 | YU45-H3 | hIgG-Fc | 126.1 |
| 27 | YU45-A8 | hIgG-Fc | 710 |
| 31 | YU45-D9 | hIgG-Fc | 709.8 |
| 33 | YU45-G7 | hIgG-Fc | 10.15 |
| 36 | YU45-B6 | hIgG-Fc | 4984 |
| 39 | YU45-F5 | hIgG-Fc | 10.07 |
| 40 | YU46-B5 | hIgG-Fc | 234.1 |
| 42 | YU45-C1 | hIgG-Fc | 217 |
| 45 | YU46-A8 | hIgG-Fc | 351.2 |
| 47 | YU46-B6 | hIgG-Fc | 222.3 |
| 50 | YU46-E3 | hIgG-Fc | 706.7 |
| 54 | YU46-G8 | hIgG-Fc | 32.27 |
| 56 | YU46-D3 | hIgG-Fc | 654.8 |
| 3 | Yu33-B4 | hIgG-Fc | 197.6 |

FIG. 29

| ID | Clone |
|---|---|
| A1 | BSN-1H2 |
| A2 | BSN-1H7 |
| A3 | BSN-2E1 |
| A4 | BSN-2F5 |
| A5 | BSN-2G6 |
| A6 | BSN-3C6 |
| A7 | BSN-3C11 |
| A8 | BSN-5A6 |
| A9 | BSN-5B8 |
| A10 | BSN-5F6 |
| A11 | BSN-6F3 |
| A12 | BSN-7D4 |
| A13 | BSN-7E4 |
| A14 | BSN-7F9 |
| A15 | BSN-8C4 |
| A16 | BSN-8H11 |

| Antibody Candidate | Human IL11 activated fibroblasts (norm.) | Mouse IL11 activated fibroblasts (norm.) | Trans IL11 MMP2 (norm.) |
|---|---|---|---|
| Unstimulated | 1 | 1 | 1 |
| Stimulated | 1.58 | 2.24 | 2.34 |
| Industry Standard | 0.69 | 1.44 | 1.32 |
| A1 | 1.11 | 1.63 | 1.45 |
| A2 | 1.28 | 2.17 | 1.55 |
| A3 | 1.16 | 1.30 | 1.57 |
| A4 | 1.41 | 2.14 | 1.78 |
| A5 | 0.96 | 1.28 | 1.11 |
| A6 | 0.92 | 1.31 | 1.09 |
| A7 | 0.86 | 2.24 | 1.51 |
| A8 | 1.05 | 1.49 | 1.86 |
| A9 | 1.00 | 1.91 | 1.05 |
| A10 | 1.52 | 1.80 | 1.52 |
| A11 | 1.09 | 1.99 | 1.91 |
| A12 | 1.12 | 1.82 | 1.07 |
| A13 | 1.63 | 1.99 | 1.53 |
| A14 | 1.04 | 1.89 | 1.93 |
| A15 | 1.53 | 1.64 | 1.79 |
| A16 | 1.08 | 1.82 | 1.66 |

| No | Clone | GMFI | % positive | Isotype |
|---|---|---|---|---|
| | | Hybridoma supernatants incubated on cells transfected with pB1-IL11-hum.FL | | |
| | | flow cytometry (Attunes) | | |
| | | Results of subcloning | | |
| 1 | BSN-1H2 | 197496 | 157% | IgG1/kappa |
| 2 | BSN-1H7 | 247434 | 197% | IgG2a&IgG2c/kappa |
| 3 | BSN-2E1 | 206192 | 164% | IgG1/kappa |
| 4 | BSN-2F5 | 238332 | 190% | IgG1/kappa |
| 5 | BSN-2G6 | 28568 | 23% | IgG2b/kappa |
| 6 | BSN-3C6 | 221636 | 176% | IgG1/kappa |
| 7 | BSN-3C11 | 1667 | 1% | n.d./kappa |
| 8 | BSN-5A6 | 182487 | 145% | IgG1/kappa |
| 9 | BSN-5B6 | 236341 | 188% | IgG1/kappa |
| 10 | BSN-5F6 | 199029 | 158% | IgG1/kappa |
| 11 | BSN-6F3 | 156008 | 124% | IgG2a&IgG2c/kappa |
| 12 | BSN-7D4 | 220736 | 176% | IgG2a&IgG2c/kappa |
| 13 | BSN-7E4 | 263377 | 209% | IgG1/kappa |
| 14 | BSN-7F9 | 12798 | 10% | IgG1/kappa |
| 15 | BSN-8C4 | 275552 | 219% | IgG1/kappa |
| 16 | BSN-8H11 | 238663 | 190% | IgG2b/kappa |
| | positive control | 125733 | 100% | |
| | negative control | 1028 | 1% | |

FIG. 36A

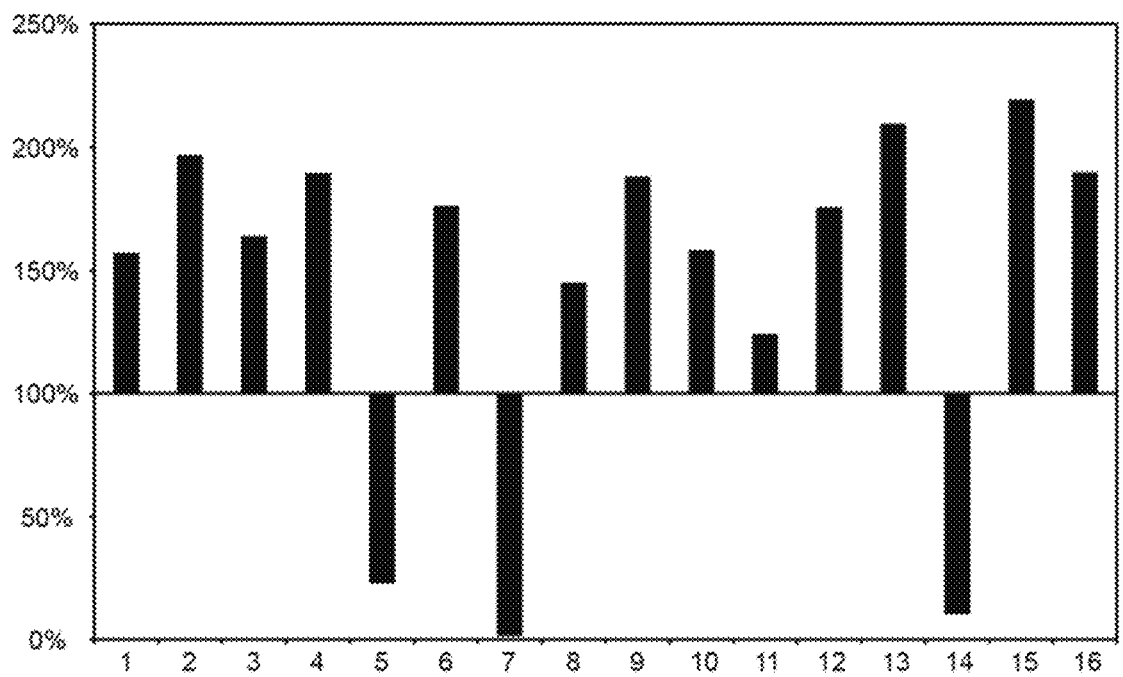

LPVLTQPASVSGSPGQSITISCTGT<u>SSDVGAYNY</u>VSWYQQHPGKAPELMIY<u>DVS</u>NRPSGVS
NRFSGSKSGNTASLTISGLQPEDEADYYC<u>SSFTTSIAWV</u>FGGGTKLTVL (SEQ ID NO:267)

LC-CDR1:    SSDVGAYNY (SEQ ID NO:110)
    LC-CDR2:    DVS (SEQ ID NO:108)
    LC-CDR3:    SSFTTSIAWV (SEQ ID NO:268)

YU100-A11

QSALTQPRSVSGSPGQSVTISCTGT<u>SSDVGGYNY</u>VSWYQQHPGKAPKLMIY<u>DVS</u>KRPSGV
PDRFSGSKSGNTASLTISGLQAEDEADYYC<u>CSYAGSYTWV</u>FGGGTKLTVL (SEQ ID NO:269)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

YU100-A12

LPVLTQPRSVSGSPGQSVTISCTGT<u>SSDVGGYNY</u>VSWYQQHPGKAPKLMIY<u>DVS</u>KRPSGV
PDRFSGSKSGDTASLTISGLQAEDEADYYC<u>SSYAGSYTWV</u>FGGGTKLTVL (SEQ ID NO:270)

LC-CDR1:    SSDVGGYNY (SEQ ID NO:107)
    LC-CDR2:    DVS (SEQ ID NO:108)
    LC-CDR3:    SSYAGSYTWV (SEQ ID NO:124)

YU100-B01

QSALTQPRSVSGSPGQSVTISCTGT<u>NTDVGAYNY</u>VSWYQQYPGKAPKLIIY<u>DVS</u>KRPSGVP
DRFSGSKSGNTASLTISGLQAEDEADYYC<u>CSYAGSYSWV</u>FGGGTKLTVL (SEQ ID NO:271)

LC-CDR1:    NTDVGAYNY (SEQ ID NO:272)
    LC-CDR2:    DVS (SEQ ID NO:108)
    LC-CDR3:    CSYAGSYSWV (SEQ ID NO:273)

YU100-B03

QSVLTQPRSVSGSPGRSVTISCTGT<u>SSDVGGYNY</u>VSWYQQHPGKAPKLTLY<u>DVV</u>KRPSGV
PDRYSGSKSGNTASLTISGLQAEDEADYYC<u>CSYAGGYTWV</u>FGGGTKVTVVCSYAGSYSW
V (SEQ ID NO:274)

LC-CDR1:    SSDVGGYNY (SEQ ID NO:107)
    LC-CDR2:    DVV (SEQ ID NO:275)
    LC-CDR3:    CSYAGGYTWV (SEQ ID NO:276)

QSALTQPASVSGSPGQSITISCTGT<u>SSDVGGYNY</u>VSWYQQHPGKAPKLMIY<u>DVS</u>KRPSGV
PDRFSGSKSGNTASLTISGLQAEDEADYYC<u>NSYAGSYTWV</u>FGGGTKLTVL (SEQ ID
NO:277)

LC-CDR1:    SSDVGGYNY (SEQ ID NO:107)
    LC-CDR2:    DVS (SEQ ID NO:108)
    LC-CDR3:    NSYAGSYTWV (SEQ ID NO:278)

YU100-B07

QSALTQPRSVSGSPGQSVTMSCTGT<u>SRDVGGYNY</u>VSWYQHHPGKAPKLMIY<u>DVS</u>KRPSG
VPDRFSGSKSGNTASLTISELQAEDEADYYC<u>CSYAGSYTWV</u>FGGGTKLTVL (SEQ ID
NO:279)

LC-CDR1:    SRDVGGYNY (SEQ ID NO:150)
    LC-CDR2:    DVS (SEQ ID NO:108)
    LC-CDR3:    CSYAGSYTWV (SEQ ID NO:131)

YU100-B08

QSALTQPASVSGSPGQSITISCTGT<u>SSDVGGYNY</u>VSWYQQHPGKVPRLLIYDVSNRPSGVS
TRFSGSKSGNTASLTISGLQGEDEAEYYC<u>SSFTSSTTWV</u>FGGGTKLTVL (SEQ ID NO:280)

LC-CDR1:    SSDVGGYNY (SEQ ID NO:107)
    LC-CDR2:    DVS (SEQ ID NO:108)
    LC-CDR3:    SSFTSSTTWV (SEQ ID NO:281)

YU100-B09

QSALTQPASVSGSPGQSITISCTGT<u>SSDVGGYNY</u>VSWYQQHPGKAPKLMIY<u>DVS</u>DRPSGV
SNRFSGSKSGNTASLTISGLQPEDEADYYC<u>SSYRSGSTLGVRRRDQADRPR</u> (SEQ ID
NO:540)

LC-CDR1:    SSDVGGYNY (SEQ ID NO:107)
    LC-CDR2:    DVS (SEQ ID NO:108)
    LC-CDR3:    SSYRSGSTLGVRRRDQADRPR (SEQ ID NO:282)

YU100-B12

QSALTQPRSVSGSPGQSVTISCTGT<u>SSDVGGYNY</u>VSWYQQHPGKAPKLMIY<u>DVS</u>KRPSGV
PDRFSGSKSGNTASLTISGLQAEDEADYYC<u>CSYAGSYTWV</u>FGGGTKLTVL (SEQ ID
NO:269)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

QSALTQPRSVSGSPGQSVTISCTGTSSNVGGYNYVSWYQQHPGKAPKLMIYDVSKRPSGV
PDRFSGSKSGNTASLTISGLQAEDEADYYCCSYAGSYVWVFGGGTKLTVL (SEQ ID
NO:283)

LC-CDR1:    SSNVGGYNY (SEQ ID NO:284)
    LC-CDR2:    DVS (SEQ ID NO:108)
    LC-CDR3:    CSYAGSYVWV (SEQ ID NO:285)

YU100-C04

QSALTQPRSVSGSPGQSVTISCTGTSSDVGGYNYVSWYQHHPGKAPKLIIYDVTKRPSGVP
DRFSGSKSGNTASLAISGLQAEEEADYYCCSYAGGYTWVFGGGTKLTVL (SEQ ID
NO:286)

LC-CDR1:    SSDVGGYNY (SEQ ID NO:107)
    LC-CDR2:    DVT (SEQ ID NO:123)
    LC-CDR3:    CSYAGGYTWV (SEQ ID NO:276)

YU100-C05

QSALTQPASVSGSPGQSITISCTGTSSDVGGYNYVSWYQQHPGKAPKLMIYDVSNRPSGIS
NRFSGSKSGNTASLTISGLQAEDEADYYCSSYTSSISWVFGGGTKLTVL (SEQ ID NO:287)

LC-CDR1:    SSDVGGYNY (SEQ ID NO:107)
    LC-CDR2:    DVS (SEQ ID NO:108)
    LC-CDR3:    SSYTSSISWV (SEQ ID NO:288)

YU100-C10

QSALTQPASVSGSPGQSITISCTGTRSDIGGYDYVSWYQQHPGKAPKLMIYDVNNRPSGVS
NRFSGSKSGNTASLTISGLQAEDEAEYYCSSYTSSITWVFGGGTKVTVL (SEQ ID NO:289)

LC-CDR1:    RSDIGGYDY (SEQ ID NO:290)
    LC-CDR2:    DVN (SEQ ID NO:291)
    LC-CDR3:    SSYTSSITWV (SEQ ID NO:130)

YU100-C11

QSALTQPASVSGSPGQSITISCTGTSSDVGGYNYVSWYQQRPGKAPKLMIYDVSNRPSGV
SNRFSGSKSGNTASLTISGLQPDDEADYYCSSYTNSRTWVFGGGTKLTVL (SEQ ID
NO:353)

LC-CDR1:    SSDVGGYNY (SEQ ID NO:107)
    LC-CDR2:    DVS (SEQ ID NO:108)
    LC-CDR3:    SSYTNSRTWV (SEQ ID NO:292)

QSALTQPRSVSGSPGQSVTISCTGTSSDVGGYNYVSWYQQHPGKAPKLMIYDVSKRPSGV
PDRFSGSKSGNTASLTISGLQAEDEADYYCCSYAGSYTWVFGGGTKLTVL (SEQ ID
NO:269)

LC-CDR1: SSDVGGYNY (SEQ ID NO:107)
  LC-CDR2: DVS (SEQ ID NO:108)
  LC-CDR3: CSYAGSYTWV (SEQ ID NO:131)

YU100-D01

QSALTQPPSASGSPGQSVTISCTGTSSDVGGYNFVSWYQQHPGKAPKLLIYDVDKRPSGV
PDRFSGSKSGRTASLTISGLQTEDEAKYYCCSYAGRYTWIFGGGTKLTVL (SEQ ID
NO:293)

LC-CDR1: SSDVGGYNF (SEQ ID NO:294)
  LC-CDR2: DVD (SEQ ID NO:295)
  LC-CDR3: CSYAGRYTWI (SEQ ID NO:296)

YU100-D02

QSALTQPRSVSGSPGQSVTISCTGTSGDVGTYNYVSWYQQHPGKAPKLMIFDVSKRPSGV
PDRFSGSKSGNTASLTISGLQAEDEADYYCNSYAGSYTWVFGGGTKLTVL (SEQ ID
NO:297)

LC-CDR1: SGDVGTYNY (SEQ ID NO:298)
  LC-CDR2: DVS (SEQ ID NO:108)
  LC-CDR3: NSYAGSYTWV (SEQ ID NO:278)

YU100-D05

QSALTQPASVSGSPGQLITISCTGTNSDVGGYNYVSWYQQHPGKAPKLMIYDVSNRPSGV
SNRFSGSKSGNTASLTISGLQAEDEADYYCCSYAGSYTWVFGGGTKLTVL (SEQ ID
NO:299)

LC-CDR1: NSDVGGYNY (SEQ ID NO:300)
  LC-CDR2: DVS (SEQ ID NO:108)
  LC-CDR3: CSYAGSYTWV (SEQ ID NO:131)

YU100-D07

QSALTQPRSVSGSPGQSVTISCTGTSGDVGTYDYVSWYQQHPGKAPKLMIYDVSKRPSGV
PDRFSGSKSGNTASLTISGLQAEDEADYYCNSYAGSYTWVFGGGTKLTVL (SEQ ID
NO:301)

LC-CDR1: SGDVGTYDY (SEQ ID NO:302)
  LC-CDR2: DVS (SEQ ID NO:108)
  LC-CDR3: NSYAGSYTWV (SEQ ID NO:278)

QSALTQPRSVSGSPGQSVTISCTGTSSNVGGYNYVSWYQQHPGKAPKLMIYDVSKRPSGV
PDRFSGSKSGNTASLTISGLQAEDEANYYCASYAGNYNWVFGGGTKLTVL (SEQ ID
NO:303)

LC-CDR1:    SSNVGGYNY (SEQ ID NO:284)
    LC-CDR2:    DVS (SEQ ID NO:108)
    LC-CDR3:    ASYAGNYNWV (SEQ ID NO:304)

YU100-E01

QSALTQPASVSGSPGQSITISCTGTSNDIGAYNYVSWYQQHPGKAPKLLIYDVNRPSGVS
DRFSGSKSGNTASLTISGLQAEDEADYYCCSYAGSYSWVFGGGTKLTVL (SEQ ID
NO:305)

LC-CDR1:    SNDIGAYNY (SEQ ID NO:306)
    LC-CDR2:    DVN (SEQ ID NO:291)
    LC-CDR3:    CSYAGSYSWV (SEQ ID NO:273)

YU100-E04

QSALTQPRSVSGSPGQSVTISCTGTSSDVGGYNYVSWYQQHPGKTPKLMIYDVTKRPSGV
PDHFSGSKSGNTASLTISGLQAEDEADYYCCSYAGSHIWVFGGGTKLTVL (SEQ ID
NO:307)

LC-CDR1:    SSDVGGYNY (SEQ ID NO:107)
    LC-CDR2:    DVT (SEQ ID NO:123)
    LC-CDR3:    CSYAGSHIWV (SEQ ID NO:308)

YU100-E05

QAVLTQPRSVSGSPGQSVTISCTGTSSDVGGYNYVSWYQQHPGKAPKLMIYDVSKRPSGV
PDRFSGSKSGNTASLTISGLQAEDEADYYCCSYAGSYSWVFGGGTKLTVL (SEQ ID
NO:309)

LC-CDR1:    SSDVGGYNY (SEQ ID NO:107)
    LC-CDR2:    DVS (SEQ ID NO:108)
    LC-CDR3:    CSYAGSYSWV (SEQ ID NO:273)

YU100-E06

QSALTQPASVSGFPEQSITISCTGTSSDVGGYDYVSWYQQHPGKAPKLMIYDVTNRPSGVS
NRFSGSKSGNTASLTISGLQPEDEADYYCSSYTSNTTWVFGGGTKLTVLRQPKAAPSVTLF
PPSS (SEQ ID NO:310)

LC-CDR1:    SSDVGGYDY (SEQ ID NO:128)
    LC-CDR2:    DVT (SEQ ID NO:123)
    LC-CDR3:    SSYTSNTTWV (SEQ ID NO:311)

QSALTQPRSVSGSPGQSVTISCTGTSSDVGGYDYVSWYQQHPGKAPELMIYDVTKRPSGV
ADRFSGSKSGNTASLTISGLQAEDEADYYCCSYAGRYTWVFGGGTKLTVL (SEQ ID
NO:312)

LC-CDR1:     SSDVGGYDY (SEQ ID NO:128)
    LC-CDR2:     DVT (SEQ ID NO:123)
    LC-CDR3:     CSYAGRYTWV (SEQ ID NO:313)

YU100-E08

QSALTQPRSVSGSPGQSVTISCTGTSSDVGGYNYVSWYQQHPGKAPKLMIYDVSRRPSGV
PDRFSGSKSGNTASLTISGLQAEDEADYYCCSYAGNYTWMFGGGTKLTVL (SEQ ID
NO:314)

LC-CDR1:     SSDVGGYNY (SEQ ID NO:107)
    LC-CDR2:     DVS (SEQ ID NO:108)
    LC-CDR3:     CSYAGNYTWM (SEQ ID NO:315)

YU100-E09

QSALTQPRSVSGSPGQSVTISCTGTSSDVGDYDYVSWYQQHPGKAPKLIIYDVTKRPSGIP
DRFSGSKSGNTASLTISGLQAEDEADYYCCSYAGSYTWVFGRGTKLTVL (SEQ ID NO:316)

LC-CDR1:     SSDVGDYDY (SEQ ID NO:317)
    LC-CDR2:     DVT (SEQ ID NO:123)
    LC-CDR3:     CSYAGSYTWV (SEQ ID NO:131)

YU100-E10

QSALTQPRSVSGSPGQSVTISCTGTSSDVGGYNYVSWYQQHPGKAPKLMIFDVSQRPSGV
PDRFSASKSGNTASLTISGLQAEDEADYYCCSYAGSYTWVFGGGTKLTVL (SEQ ID
NO:318)

LC-CDR1:     SSDVGGYNY (SEQ ID NO:107)
    LC-CDR2:     DVS (SEQ ID NO:108)
    LC-CDR3:     CSYAGSYTWV (SEQ ID NO:131)

YU100-E11

QSALTQPRSVSGSPGQSVTISCTGTSSDVGGYNYVSWYQQHPGKAPKLMIYDVSKRPSGV
PDRFSGSKSGNTASLTISGLQAEDEADYYCCSYAGSYTWVFGGGTKLTVL (SEQ ID
NO:269)

LC-CDR1:     SSDVGGYNY (SEQ ID NO:107)
    LC-CDR2:     DVS (SEQ ID NO:108)
    LC-CDR3:     CSYAGSYTWV (SEQ ID NO:131)

QSALTQPASVSGSPGQSITISCTGT<u>SSDVGGYNY</u>VSWYQQHPGTAPKLMIY<u>DVS</u>NRPSGV
SNRFSGSKSGNTASLTISGLQAEDEADYYC<u>SSYTSSTTWV</u>FGGGTKLTVL (SEQ ID
NO:319)

LC-CDR1:     SSDVGGYNY (SEQ ID NO:107)
       LC-CDR2:     DVS (SEQ ID NO:108)
       LC-CDR3:     SSYTSSTTWV (SEQ ID NO:320)

YU100-F01

QSALTQPASVSGSPGQSITISCTGT~~GSDVGAYDY~~VSWYQQHPGKAPKLMIY~~DVN~~NRPSGV
SNRFSGSKSGNTASLTISGLQAEDEAEYYC~~SSFATSISWV~~FGGGTRLTVL (SEQ ID
NO:321)

LC-CDR1:     GSDVGAYDY (SEQ ID NO:322)
       LC-CDR2:     DVN (SEQ ID NO:291)
       LC-CDR3:     SSFATSISWV (SEQ ID NO:-408)

YU100-F02

QSALTQPRSVSGSPGQSVTISCTGT<u>SSDVGGYNY</u>VSWYQQHPGKAPKLMIY<u>DVT</u>KRPSGV
PDRFSGSKSGNTASLTISGLQADDEADYYC<u>CSYAGSYTWI</u>FGGGTKLTVL (SEQ ID
NO:323)

LC-CDR1:     SSDVGGYNY (SEQ ID NO:107)
       LC-CDR2:     DVT (SEQ ID NO:123)
       LC-CDR3:     CSYAGSYTWI (SEQ ID NO:324)

YU100-F05

QAVLTQPASVSGSPGQSITISCTGT<u>SSDIGGYNY</u>VSWYQQHPGTAPKLMIY<u>DVS</u>SRPSGVS
NRFSGSKSGNTASLTISGLQAEDEADYYC<u>CSYAGSYTWV</u>FGGGTKMTVL (SEQ ID
NO:325)

LC-CDR1:     SSDIGGYNY (SEQ ID NO:326)
       LC-CDR2:     DVS (SEQ ID NO:108)
       LC-CDR3:     CSYAGSYTWV (SEQ ID NO:131)

YU100-F06

QSALTQPRSVSGSPGQSVTISCTGS<u>SSDVGGYNF</u>VSWYRQHPGEAPKLVIF<u>DVN</u>KRPSGV
PDRFSGSKSGNTASLTISGLQTEDEADYFC<u>CSYAGGYTWV</u>FGGGTKVTVV (SEQ ID
NO:327)

LC-CDR1:     SSDVGGYNF (SEQ ID NO:294)
       LC-CDR2:     DVN (SEQ ID NO:291)
       LC-CDR3:     CSYAGGYTWV (SEQ ID NO:276)

QSALTQPRSVSVSPGQSVTISCTGTSSDVGGYEYVSWYQQHPGKAPKLMIYDVTKRPSGV
PDRFSGSKSGNTASLTISGLQGEDAADYYCCSYAGSYTWVFGGGTTVTVL (SEQ ID
NO:328)

LC-CDR1:    SSDVGGYEY (SEQ ID NO:159)
    LC-CDR2:    DVT (SEQ ID NO:123)
    LC-CDR3:    CSYAGSYTWV (SEQ ID NO:131)

YU100-F11

QSALTQPASVSGSPGQSITISCTGSSSDVAGYNYVSWYQQHPGKAPKLMIYDVTKRPSGV
PDRFSGSKSGNTASLTISGLQAEDEADYYCCSYAGSYTWVFGGGTQLTVL (SEQ ID
NO:329)

LC-CDR1:    SSDVAGYNY (SEQ ID NO:330)
    LC-CDR2:    DVT (SEQ ID NO:123)
    LC-CDR3:    CSYAGSYTWV (SEQ ID NO:131)

YU100-G01

QSALTQPRSVSASPGQSVTISCTGTSSDVGAYNYVSWYQQHPGKAPKLMLYDVNKRPSG
VPDRFSGSKSGNTASLTISRLQAEDEADYYCCSYAGSYTWVFGGGTKLTVL (SEQ ID
NO:331)

LC-CDR1:    SSDVGAYNY (SEQ ID NO:110)
    LC-CDR2:    DVN (SEQ ID NO:291)
    LC-CDR3:    CSYAGSYTWV (SEQ ID NO:131)

YU100-G07

QSALTQPASVSGSPGQSITISCTGTSSDVGAYDYVSWYQQHPGKAPKLMIYDVTNRPSGV
SNRFSGSKSGNTASLTISGLQAEDEADYYCASYTRSSVWVFGGGTKLTVL (SEQ ID
NO:332)

LC-CDR1:    SSDVGAYDY (SEQ ID NO:333)
    LC-CDR2:    DVT (SEQ ID NO:123)
    LC-CDR3:    ASYTRSSVWV (SEQ ID NO:334)

YU100-G08

QSALTQPRSVSGSPGQSVTLSCTGTSSDVGGYNYVSWYQHYPGKAPKLMIFDVNERSSG
VPDRFSGSKSGNTASLTISGLQAEDEADYYCCSYAGRYTWMFGGGTKVTVL (SEQ ID
NO:335)

LC-CDR1:    SSDVGGYNY (SEQ ID NO:107)
    LC-CDR2:    DVN (SEQ ID NO:291)
    LC-CDR3:    CSYAGRYTWM (SEQ ID NO:336)

QSALTQPRSVSGSPGQSVTISCTGT<u>ISDVGGYNY</u>VSWYQQHPGKAPKLMIY<u>DVT</u>KRPSGV
PDRFSGSKSGNTASLTISGLQAEDEAGYYC<u>SSYAGSYTWV</u>FGGGTKLTVL (SEQ ID
NO:337)

LC-CDR1:    ISDVGGYNY (SEQ ID NO:122)
    LC-CDR2:    DVT (SEQ ID NO:123)
    LC-CDR3:    SSYAGSYTWV (SEQ ID NO:124)

YU100-G10

QSALTQPASVSGSLGQSITMSCTGT<u>RRDVGGYDF</u>VSWYQQYPGKAPKLIIY<u>DVS</u>NRPSGV
SNRFTGSKSGNTASLTISGLQAEDEADYYC<u>CSYAGTYTWV</u>FGGGTKVTVL (SEQ ID
NO:338)

LC-CDR1:    RRDVGGYDF (SEQ ID NO:339)
    LC-CDR2:    DVS (SEQ ID NO:108)
    LC-CDR3:    CSYAGTYTWV (SEQ ID NO:340)

YU100-G11

QSALTQPRSVSGSPGQSVTISCTGT<u>SSDVGGYNY</u>VSWYQQHPGKAPKLTLY<u>DVG</u>KRPSG
VPDRFSGSKSGNTASLTISGLQAEDEADYYC<u>CSYAGGYTWV</u>FGGGTKVTVV (SEQ ID
NO:341)

LC-CDR1:    SSDVGGYNY (SEQ ID NO:107)
    LC-CDR2:    DVG (SEQ ID NO:133)
    LC-CDR3:    CSYAGGYTWV (SEQ ID NO:276)

YU100-H01

QSALTQPRSVSGSPGQSVTISCTGT<u>SSDVGAYNY</u>VSWYQQHPGKAPKLMIY<u>DVS</u>ERPSGV
PDRFSGSKSGNTASLTISGLQAEDEADYYC<u>CSYAGSYTWV</u>FGGGTKLTVL (SEQ ID
NO:342)

LC-CDR1:    SSDVGAYNY (SEQ ID NO:110)
    LC-CDR2:    DVS (SEQ ID NO:108)
    LC-CDR3:    CSYAGSYTWV (SEQ ID NO:131)

YU100-H02

QSALTQPRSVSRSPGQSVTISCTGT<u>SSDVGTYNY</u>VSWYQQHPGKAPKLMIY<u>DVS</u>KRPSGV
PDRFSGSKSGNTASLTISGLQAEDEADYYC<u>CSYAGFYTWV</u>FGGGTKLTVL (SEQ ID
NO:343)

LC-CDR1:    SSDVGTYNY (SEQ ID NO:344)
    LC-CDR2:    DVS (SEQ ID NO:108)
    LC-CDR3:    CSYAGFYTWV (SEQ ID NO:345)

QSALTQPASVSGSPGQSITISCTGTSSDIGVYNYVSWYQQHPGKAPKLMIYDVSKRPSGVP
DRFSGSKSGNTASLTISGLQAEDEADYYCCSYAGSYTWVFGGGTKLTVL (SEQ ID
NO:346)

LC-CDR1:    SSDIGVYNY (SEQ ID NO:347)
    LC-CDR2:    DVS (SEQ ID NO:108)
    LC-CDR3:    CSYAGSYTWV (SEQ ID NO:131)

YU100-H05

QAVLTQPRSVSGSPGQSITISCTGTGSNVGGYNYVSWYQQHPGQAPKLMIYDVSKRPSGV
PDRFSGSKSGNTASLTISGLQAEDEADYYCCSYAGTYTWVFGGGTKLTVL (SEQ ID
NO:348)

LC-CDR1:    GSNVGGYNY (SEQ ID NO:349)
    LC-CDR2:    DVS (SEQ ID NO:108)
    LC-CDR3:    CSYAGTYTWV (SEQ ID NO:340)

YU100-H06

QSALTQPRSVSGSPGQSVTISCTGTSSDVGGYNYVSWYQQHPGKAPKLMIYDVTKRPSGV
PDRFSGSKSGNTASLTISGLQAEDEADYYCSSYAGSYTWVFGGGTKLTVL (SEQ ID NO:
214)

LC-CDR1:    SSDVGGYNY (SEQ ID NO:107)
    LC-CDR2:    DVT (SEQ ID NO:123)
    LC-CDR3:    SSYAGSYTWV (SEQ ID NO:124)

YU100-H09

QSALTQPASVSGSPGQSITISCTGTSSDVGGYNYVSWYQQHPGKAPKLMIYDVSNRPSGV
SNRFSGSKSGNTASLTISGLQAEDEADYYCCSYAGSYTWVFGGGTKLTVL (SEQ ID
NO:350)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

YU100-H11

QSALTQPASVSGSPGQSITISCTGTSSDVGGYNYVSWYQQHPGKAPKLMIYDVSNRPSGV
SNRFSGSKSGNTASLTISGLQAEDEADYYCCSYAGSYTWVFGGGTKLTVL (SEQ ID
NO:350)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

QSALTQPRSVSGSPGQSVTISCTGT<u>ISDVGGYNY</u>VSWYQQHPGKAPKLMIY<u>DVT</u>KRPSGV
PDRFSGSKSGNTASLTISGLQAEDEAGYYC<u>SSYAGSYTWV</u>FGGGTELTVL (SEQ ID
NO:13)

LC-CDR1:    ISDVGGYNY (SEQ ID NO:122)
    LC-CDR2:    DVT (SEQ ID NO:123)
    LC-CDR3:    SSYAGSYTWV (SEQ ID NO:124)

YU112-B06

QSALTQPASVSGSPGQSITISCTGT<u>SSDVGGYNY</u>VSWYQQHPGKAPKLMIY<u>DVS</u>NRPSGV
SNRFSGSKSGNTASLTIFGLQAEDEADYYC<u>SSYTSSSSWV</u>FGGGTKLTVL (SEQ ID NO:3)

LC-CDR1:    SSDVGGYNY (SEQ ID NO:107)
    LC-CDR2:    DVS (SEQ ID NO:108)
    LC-CDR3:    SSYTSSSSWV (SEQ ID NO:109)

YU112-C03

DSVMTQSPSSLSASVGDRVTITCRAS<u>QAINSY</u>LNWYQQKPGKAPKLLIY<u>AAS</u>SLQSGVPSR
FSGSGSGTDFTLTISGLQPEDFATYYC<u>QQSYSTPSWT</u>FGQGTKVEIK (SEQ ID NO:351)

LC-CDR1:    QAINSY (SEQ ID NO:352)
    LC-CDR2:    AAS (SEQ ID NO:102)
    LC-CDR3:    QQSYSTPSWT (SEQ ID NO:354)

YU112-C05

QSALTQPRSVSGSPGQSVTISCTGT<u>ISDVGGYNY</u>VSWYQQHPGKAPKLMIY<u>DVT</u>KRPSGV
PDRFSGSKSGNTASLTISGLQAEDEAGYYC<u>SSYAGSYTWV</u>FGGGTELTVL (SEQ ID NO:13)

LC-CDR1:    ISDVGGYNY (SEQ ID NO:122)
    LC-CDR2:    DVT (SEQ ID NO:123)
    LC-CDR3:    SSYAGSYTWV (SEQ ID NO:124)

YU112-C09

ETTLTQSPATLSVSPGERATLSCRAS<u>QSFSSSY</u>LAWYQQKPGQAPRLLIY<u>GAS</u>RRAPGIPD
RFSGSGSGTDFSLTISRLEPEDFAVYYC<u>QQSSTSPTWA</u>FGRGTKVEVK (SEQ ID NO:355)

LC-CDR1:    QSFSSSY (SEQ ID NO:356)
    LC-CDR2:    GAS (SEQ ID NO:138)
    LC-CDR3:    QQSSTSPTWA (SEQ ID NO:357)

QSALTQPRSVSGSPGQSVTISCTGT<u>ISDVGGYNY</u>VSWYQQHPGKAPKLMIY<u>DVT</u>KRPSGV
PDRFSGSKSGNTASLTISGLQAEDEAGYYC<u>SSYAGSYTWV</u>FGGGTELTVL (SEQ ID
NO:13)

LC-CDR1:    ISDVGGYNY (SEQ ID NO:122)
    LC-CDR2:    DVT (SEQ ID NO:123)
    LC-CDR3:    SSYAGSYTWV (SEQ ID NO:124)

YU112-E07

EIVMTQSPDSLAVSLGERATINCKSS<u>QSVNSAY</u>LAWYQHKPGQPPRLLIY<u>GAS</u>RRVTGVPD
RFSGSGSGTDFTLTISSLQPEDFATYYC<u>QQSYSDPRWT</u>FGQGTKVEIK (SEQ ID NO:358)

LC-CDR1:    QSVNSAY (SEQ ID NO:359)
    LC-CDR2:    GAS (SEQ ID NO:138)
    LC-CDR3:    QQSYSDPRWT (SEQ ID NO:360)

YU112-E08

DIQMTQSPSFLSASVGDRVTITCRAS<u>QIISSY</u>LNWYQQKPGKAPKLLIY<u>AAS</u>SLQSGVPSRF
SGSGSGTDFTLTISSLQPEDFATYYC<u>QQSYSTPTWT</u>FGQGTKVEIK (SEQ ID NO:35)

LC-CDR1:    QIISSY (SEQ ID NO:155)
    LC-CDR2:    AAS (SEQ ID NO:102)
    LC-CDR3:    QQSYSTPTWT (SEQ ID NO:156)

YU112-F05

QSALTQPRSVSGSPGQSVTISCTGT<u>SSDVGGYNY</u>VSWYQQHPGKAPKLIIY<u>DVN</u>RPSGV
SNRFSASKSGNTASLTISGLQAEDEADYYC<u>NSYTSGSTWV</u>FGGGTKLTVL (SEQ ID
NO:361)

LC-CDR1:    SSDVGGYNY (SEQ ID NO:107)
    LC-CDR2:    DVN (SEQ ID NO:291)
    LC-CDR3:    NSYTSGSTWV (SEQ ID NO:362)

YU112-G01

QSALTQPRSVSGSPGQSVTISCTGT<u>ISDVGGYNY</u>VSWYQQHPGKAPKLMIY<u>DVT</u>KRPSGV
PDRFSGSKSGNTASLTISGLQAEDEAGYYC<u>SSYAGSYTWV</u>FGGGTELTVL (SEQ ID
NO:13)

LC-CDR1:    ISDVGGYNY (SEQ ID NO:122)
    LC-CDR2:    DVT (SEQ ID NO:123)
    LC-CDR3:    SSYAGSYTWV (SEQ ID NO:124)

QSALTQPRSVSGSPGQSVTISCTGTISDVGGYNYVSWYQQHPGKAPKLMIYDVTKRRSGV
PDRFSGSKSGNTASLTISGLQAEDEAGYYCSSYAGGYTWVFGGGTELTVL (SEQ ID
NO:363)

LC-CDR1:    ISDVGGYNY (SEQ ID NO:122)
    LC-CDR2:    DVT (SEQ ID NO:123)
    LC-CDR3:    SSYAGGYTWV (SEQ ID NO:364)

YU112-G09

DIQMTQSPSFLSASVGDRVTITCRASQIISSYLNWYQQKPGKAPKLLIYAASSLQSGVPSRF
SGSGSGTDFTLTISSLQPGRFCNLLLSTELQYPHV (SEQ ID NO:365)

LC-CDR1:    QIISSY (SEQ ID NO:155)
    LC-CDR2:    AAS (SEQ ID NO:102)

YU112-H01

ETTLTQSPGTLSLSPGERATLSCRASQSVSSSYLAWYQQKPGQAPRLLIYGASSRATGIPD
RFSGSGSGTDFTLTISSLQPDDFATYYCQQSYSTPTWTFGQGTKVEIK (SEQ ID NO:366)

LC-CDR1:    QSVSSSY (SEQ ID NO:367)
    LC-CDR2:    GAS (SEQ ID NO:138)
    LC-CDR3:    QQSYSTPTWT (SEQ ID NO:156)

YU112-H02

QPVLTQPRSVSGSPGQSVTISCTGTSSDVGGYNYVSWYQQHPGKAPKVMIYDVSKRPSG
VPDRFSGSKSGNTASLTISGLQAEDEADYYCCSYAGSYTWVFGGGTKLTVL (SEQ ID
NO:20)

LC-CDR1:    SSDVGGYNY (SEQ ID NO:107)
    LC-CDR2:    DVS (SEQ ID NO:108)
    LC-CDR3:    CSYAGSYTWV (SEQ ID NO:131)

EVQLVESGGGVVQPGRSLRLSCAAS<u>GFTFSSYG</u>MHWVRQAPGKGLEWVAV<u>ISYDGSNK</u>Y
YADSVKGRFTISRDNSKNTLYLQMNSLRAEDTAVYYC<u>AKIGATDPLDY</u>WGQGTLVTVSS
(SEQ ID NO:53)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-A11

EVQLQQSGGGVVQPGRSLRLSCAAS<u>GFTFSSYG</u>MHWVRQAPGKGLEWVAV<u>ISYDGSNK</u>Y
YADSVKGRFTISRDNSKNTLYLQMNSLRAEDTAVYYC<u>AKIGATDPLDY</u>WGQGTLVTVSS
(SEQ ID NO:368)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-A12

QVQLVESGGGVVQPGRSLRLSCAAS<u>GFTFSSYG</u>MHWVRQAPGKGLEWVAV<u>ISYDGSNK</u>Y
YADSVKGRFTISRDNSKNTLYLQMNSLRAEDTAVYYC<u>AKIGATDPLDY</u>WGQGTLVTVSS
(SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-B01

QVQLVQSGGGVVQPGRSLRLSCAAS<u>GFTFSSYG</u>MHWVRQAPGKGLEWVAV<u>ISYDGSNK</u>Y
YADSVKGRFTISRDNSKNTLYLQMNSLRAEDTAVYYC<u>AKIGATDPLDY</u>WGQGTLVTVSS
(SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-B03

QVQLVQSGGGVVQPGRSLRLSCAAS<u>GFTFSSYG</u>MHWVRQAPGKGLEWVAV<u>ISYDGSNK</u>Y
YADSVKGRFTISRDNSKNTLYLQMNSLRAEDTAVYYC<u>AKIGATDPLDY</u>WGQGTLVTVSS
(SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

QVQLVESGGGVVQPGRSLRLSCAAS<u>GFTFSSYG</u>MHWVRQAPGKGLEWVAV<u>ISYDGSNKY</u>
YADSVKSRFTISRDNSKNTLYLQMNSLRAEDTAVYYC<u>AKIGATDPLDY</u>WGQGTLVTVSS
(SEQ ID NO:371)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-B07

QVQLVESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-B08

EVQLVQSGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:372)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-B09

QVQLVQSGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-B12

QVQLVESGGGVVQPGRSLRLSCAAS<u>GFTFSSYA</u>MHWVRQAPGKGLEWVAV<u>ISYDGSNKY</u>
YADSVKDRFTISRDNSKNTLYLQMNSLRAEDTAVYYC<u>ARIMGYDYGDYDVVDY</u>WGQGTLV
TVSS (SEQ ID NO:373)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-C04

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-C05

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-C10

QVQLVESGGGVVQPGRSLRLSCAASGFTFGSYGMHWVRQAPGKGLEWVAVISYDGSNKY
YADSVKGRFTISRDNSKNTLYLQMNSLRAEDTAVYYCAKIGATDPLDYWGQGTLITVSS
(SEQ ID NO:374)

HC-CDR1:    GFTFGSYG (SEQ ID NO:234)
    HC-CDR2:    ISYDGSNK (SEQ ID NO:184)
    HC-CDR3:    AKIGATDPLDY (SEQ ID NO:187)

YU100-C11

QVQLVQSGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

EVQLVQSGGGVVQPGRSLRLSCAAS<u>GFTFSSYA</u>MHWVRQAPGKGLEWVAV<u>ISYDGSNK</u>Y
YADSVKGRFTISRDNSKNTLYLQMNSLRAEDTAVYYC<u>ARIMGYDYGDYDVVDY</u>WGQGTLV
TVSS (SEQ ID NO:375)

HC-CDR1:     GFTFSSYA (SEQ ID NO:190)
    HC-CDR2:     ISYDGSNK (SEQ ID NO:184)
    HC-CDR3:     ARIMGYDYGDYDVVDY (SEQ ID NO:199)

YU100-D01

QVQLQQSGGGVVQPGRSLRLSCAAS<u>GFTFSSYA</u>MHWVRQAPGKGLEWVAV<u>ISYDGSNK</u>Y
YADSVKGRFTISRDNSKNTLYLQMNSLRAEDTAVYYC<u>ARIMGYDYGDYDVVDY</u>WGQGTLV
TVSS (SEQ ID NO:376)

HC-CDR1:     GFTFSSYA (SEQ ID NO:190)
    HC-CDR2:     ISYDGSNK (SEQ ID NO:184)
    HC-CDR3:     ARIMGYDYGDYDVVDY (SEQ ID NO:199)

YU100-D02

QVRLVQSGGGVVQPGRSLRLSCAAS<u>GFTFSSYG</u>MHWVRQAPGKGLEWVAV<u>ISYDGSNK</u>Y
YADSVKGRFTISRDNSKNTLYLQMNSLRAEDTAVYYC<u>AKIGATDPLDY</u>WGQGTLVTVSS
(SEQ ID NO:377)

HC-CDR1:     GFTFSSYG (SEQ ID NO:186)
    HC-CDR2:     ISYDGSNK (SEQ ID NO:184)
    HC-CDR3:     AKIGATDPLDY (SEQ ID NO:187)

YU100-D05

QVQLQQSGGGVVQPGRSLRLSCAAS<u>GFTFSSYG</u>MHWVRQAPGKGLEWVAV<u>ISYDGSNK</u>
YYADSVKGRFTISRDNSKNTLYLQMNSLRAEDTAVYYC<u>AKIGATDPLDY</u>WGQGTLVTVSS
(SEQ ID NO:378)

HC-CDR1:     GFTFSSYG (SEQ ID NO:186)
    HC-CDR2:     ISYDGSNK (SEQ ID NO:184)
    HC-CDR3:     AKIGATDPLDY (SEQ ID NO:187)

YU100-D07

QVQLVESGGGVVQPGRSLRLSCAAS<u>GFTFSSYA</u>MHWVRQAPGKGLEWVAV<u>ISYDGSNK</u>Y
YADSVKGRLTISRDNSKNTLYLQMNSLRAEDTAVYYC<u>ARIMGYDYGDYDVVDY</u>WGQGTLV
TVSS (SEQ ID NO:379)

HC-CDR1:     GFTFSSYA (SEQ ID NO:190)
    HC-CDR2:     ISYDGSNK (SEQ ID NO:184)
    HC-CDR3:     ARIMGYDYGDYDVVDY (SEQ ID NO:199)

QVQLVQSGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:370)

HC-CDR1: GFTFSSYG (SEQ ID NO:186)
  HC-CDR2: ISYDGSNK (SEQ ID NO:184)
  HC-CDR3: AKIGATDPLDY (SEQ ID NO:187)

YU100-E01

QVQLQQSGGGVVQPGRSLRLSCAAS<u>GFTFSSYG</u>MHWVRQAPGKGLEWVAV<u>ISYDGSNK</u>
YYADSVKGRFTISRDNSKNTLYLQMNSLRAEDTAVYYC<u>AKIGATDPLDY</u>WGQGTLVTVSS
(SEQ ID NO:378)

HC-CDR1: GFTFSSYG (SEQ ID NO:186)
  HC-CDR2: ISYDGSNK (SEQ ID NO:184)
  HC-CDR3: AKIGATDPLDY (SEQ ID NO:187)

YU100-E04

QVQLQQSGGGVVQPGRSLRLSCAAS<u>GFTFSSYG</u>MHWVRQAPGKGLEWVAV<u>ISYDGSNK</u>
YYADSVKGRFTISRDNSKNTLYLQMNSLRAEDTAVYYC<u>AKIGATDPLDY</u>WGQGTLVTVSS
(SEQ ID NO:378)

HC-CDR1: GFTFSSYG (SEQ ID NO:186)
  HC-CDR2: ISYDGSNK (SEQ ID NO:184)
  HC-CDR3: AKIGATDPLDY (SEQ ID NO:187)

YU100-E05

EVQLVQSGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:372)

HC-CDR1: GFTFSSYG (SEQ ID NO:186)
  HC-CDR2: ISYDGSNK (SEQ ID NO:184)
  HC-CDR3: AKIGATDPLDY (SEQ ID NO:187)

YU100-E06

QVQLVESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:369)

HC-CDR1: GFTFSSYG (SEQ ID NO:186)
  HC-CDR2: ISYDGSNK (SEQ ID NO:184)
  HC-CDR3: AKIGATDPLDY (SEQ ID NO:187)

QVQLQESGGGVVQPGRSLRLSCAAS<u>GFTFSSYG</u>MHWVRQAPGKGLEWVAV<u>ISYDGSNR</u>YYADSVKGRFAISRDNSKNTLYLQMNSLRAEDTAVYYC<u>AKIGATDPLDY</u>WGQGTLVTVSS (SEQ ID NO:380)

HC-CDR1:    GFTFSSYG (SEQ ID NO:186)
    HC-CDR2:    ISYDGSNR (SEQ ID NO:381)
    HC-CDR3:    AKIGATDPLDY (SEQ ID NO:187)

YU100-E08

QVQLVQSGGGVVQPGRSLRLSCAAS<u>GFTFSSYA</u>MHWVRQAPGKGLEWVAV<u>ISYDGSNK</u>YYADSVKGRFTISRDNSKNTLYLQMNSLRAEDTAVYYC<u>ARIMGYDYGDYDVVDY</u>WGQGTLVTVSS (SEQ ID NO:382)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

YU100-E09

QVQLVESGGGVVQPGRSLRLSCAAS<u>GFTFSSYA</u>MHWVRQAPGKGLEWVAV<u>ISYDGSNK</u>YYADSVKGRFTISRDNSKNTLYLQMNSLRAEDTAVYYC<u>ARIMGYDYGDYDVVDY</u>WGQGTLVTVSS (SEQ ID NO:383)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

YU100-E10

QVQLVQSGGGVVQPGRSLRLSCAAS<u>GFTFSSYG</u>MHWVRQAPGKGLEWVAV<u>ISYDGSNK</u>YYADSVKGRFTISRDNSKNTLYLQMNSLRAEDTAVYYC<u>AKIGATDPLDY</u>WGQGTLVTVSS (SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-E11

QVQLVESGGGVVQPGRSLRLSCAAS<u>GFTFSSYG</u>MHWVRQAPGKGLEWVAV<u>ISYDGSNK</u>YYADSVKGRFTISRDNSKNTLYLQMNSLRAEDTAVYYC<u>ARIMGYDYGDYDVVDY</u>WGQGTLVTVSS (SEQ ID NO:384)

HC-CDR1:    GFTFSSYG (SEQ ID NO:186)
    HC-CDR2:    ISYDGSNK (SEQ ID NO:184)
    HC-CDR3:    ARIMGYDYGDYDVVDY (SEQ ID NO:199)

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-F01

QVQLVQSGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-F02

EVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:53)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-F05

QVQLQQSGGGVVQPGRSLRLSCAASGFTFSSYGMHWVRQAPGKGLEWVAVISYDGSNK
YYADSVKGRFTISRDNSKNTLYLQMNSLRAEDTAVYYCAKIGATDPLDYWGQGTLVTVSS
(SEQ ID NO:378)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-F06

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCARIMGYDYGDYDVVDYWGQGTLV
TVSS (SEQ ID NO:384)

HC-CDR1:    GFTFSSYG (SEQ ID NO:186)
    HC-CDR2:    ISYDGSNK (SEQ ID NO:184)
    HC-CDR3:    ARIMGYDYGDYDVVDY (SEQ ID NO:199)

QVQLVESGGGVVQPGRSLRLSCAAS<u>GFTFSSYA</u>MHWVRQAPGKGLEWVAV<u>ISYDGSNKY</u>YADSVKGRFTISRDNSKNTLYLQMNSLRAEDTAVYYC<u>ARIMGYDYGDYDVVDY</u>WGQGTLVTVSS (SEQ ID NO:383)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

YU100-F11

QVQLVESGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKIGATDPLDY</u>WGQGTLVTVSS (SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-G01

QVQLVQSGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKIGATDPLDY</u>WGQGTLVTVSS (SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-G07

QVQLVESGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKIGATDPLDY</u>WGQGTLVTVSS (SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-G08

QVQLVQSGGGVVQPGRSLRLSCAAS<u>GFTFSSYG</u>MHWVRQAPGKGLEWVAV<u>ISYDGSNKY</u>YADSVKGRFTISRDNSKNTLYLQMNSLRAEDTAVYYC<u>AKIGATDPLDY</u>WGQGTLVTVSS (SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

EVQLVESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:53)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-G10

QVQLVQSGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-G11

QVQLVESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>ARIMGYDYGDYDVVDY</u>WGQGTLV
TVSS (SEQ ID NO:384)

HC-CDR1:    GFTFSSYG (SEQ ID NO:186)
    HC-CDR2:    ISYDGSNK (SEQ ID NO:184)
    HC-CDR3:    ARIMGYDYGDYDVVDY (SEQ ID NO:199)

YU100-H01

QVQLVQSGGGVVQPGRSLRLSCAAS<u>GFTFSSYA</u>MHWVRQAPGKGLEWVAV<u>ISYDGSNKY</u>
YADSVKGRFTISRDNSKNTLYLQMNSLRAEDTAVYYC<u>ARIMGYDYGDYDVVDY</u>WGQGTLV
TVSS (SEQ ID NO:382)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

YU100-H02

QVQLQQSGGGVVQPGRSLRLSCAAS<u>GFTFSSYG</u>MHWVRQAPGKGLEWVAV<u>ISYDGSNK</u>
YYADSVKGRFTISRDNSKNTLYLQMNSLRAEDTAVYYC<u>ARIMGYDYGDYDVVDY</u>WGQGTL
VTVSS (SEQ ID NO:385)

HC-CDR1:    GFTFSSYG (SEQ ID NO:186)
    HC-CDR2:    ISYDGSNK (SEQ ID NO:184)
    HC-CDR3:    ARIMGYDYGDYDVVDY (SEQ ID NO:199)

QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARIMGYDYGDYDVVDYWGQGTLVTVSS (SEQ ID NO:383)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

YU100-H05

QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAKIGATDPLDYWGQGTLVTVSS (SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-H06

QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAKIGATDPLDYWGQGTLVTVSS (SEQ ID NO:369)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU100-H09

QVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARIMGYDYGDYDVVDYWGQGTLVTVSS (SEQ ID NO:382)

HC-CDR1:    GFTFSSYA (SEQ ID NO:190)
    HC-CDR2:    ISYDGSNK (SEQ ID NO:184)
    HC-CDR3:    ARIMGYDYGDYDVVDY (SEQ ID NO:199)

YU100-H11

QVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKIGATDPLDYWGQGTLVTVSS (SEQ ID NO:370)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

QVQLVESGGGVVQPGRSLRLSCAASGFTFSSYGMHWVRQAPGKGLEWVAVISYDGSNKY
YTDSVKGRFTISRDNSKNTLYLQMNSLRAEDTAVYYCAKIGATDPLDYWGQGTLVTVSS
(SEQ ID NO:386)

HC-CDR1:     GFTFSSYG (SEQ ID NO:186)
    HC-CDR2:     ISYDGSNK (SEQ ID NO:184)
    HC-CDR3:     AKIGATDPLDY (SEQ ID NO:187)

YU112-B06

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:369)

HC-CDR1:     GFTFSSYG (SEQ ID NO:186)
    HC-CDR2:     ISYDGSNK (SEQ ID NO:184)
    HC-CDR3:     AKIGATDPLDY (SEQ ID NO:187)

YU112-C03

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKGGKSYYGFDYWGQGTLVTVSS
(SEQ ID NO:387)

HC-CDR1:     GFTFSSYG (SEQ ID NO:186)
    HC-CDR2:     ISYDGSNK (SEQ ID NO:184)
    HC-CDR3:     AKGGKSYYGFDY (SEQ ID NO:207)

YU112-C05

EVQLVESGGGVVQPGRSLRLSCAASGFTFSSYAMHWVRQAPGKGLEWVAVISYDGSNKY
YADSVKGRFTISRDNSKNTLYLQMNSLRAEDTAVYYCARIMGYDYGDYDVVDYWGQGTLV
TVSS (SEQ ID NO:62)

HC-CDR1:     GFTFSSYA (SEQ ID NO:190)
    HC-CDR2:     ISYDGSNK (SEQ ID NO:184)
    HC-CDR3:     ARIMGYDYGDYDVVDY (SEQ ID NO:199)

YU112-C09

QVQLVQSGGGVVQPGRSLRLSCAASGFTFGSYGMHWVRQAPGKGLEWVAVISYDGSNK
YYADSVKGRFTISRDNSKNTLYLQMNSLRAEDTAVYYCAKGSYYFDYWGQGTLVTVSS
(SEQ ID NO:388)

HC-CDR1:     GFTFGSYG (SEQ ID NO:234)
    HC-CDR2:     ISYDGSNK (SEQ ID NO:184)
    HC-CDR3:     AKGSYYFDY (SEQ ID NO:235)

QVQLVESGGGVVQPGRSLRLSCAASGFTFSSYGMHWVRQAPGKGLEWVAVISYDGSNKY
YADSVEGRFTISRDNSKNTLYLQMNSLRAEDTAVYYCAKIGATDPLDYWGQGTLVTVSS
(SEQ ID NO:389)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU112-E07

QVQLVQSGGGVVQPGRSLRLSCAASGFTFGSYGMHWVRQAPGKGLEWVAVISYDGSNK
YYADSVKGRFTISRDNSKNTLYLQMNSLRAEDTAVYYCAKGSYYFDYWGQGTLVTVSS
(SEQ ID NO:388)

HC-CDR1:    GFTFGSYG (SEQ ID NO:234)
    HC-CDR2:    ISYDGSNK (SEQ ID NO:184)
    HC-CDR3:    AKGSYYFDY (SEQ ID NO:235)

YU112-E08

*VTLKESGGGVVQPGRSLRLSCAASGFTFSSYGMHWVRQAPGKGLEWVAVISYDGSNKYY
ADSVKGRFTISRDNSKNTLYLQMNSLRAEDTAVYYCAKGGKSYYGFDYWGQGTLVTVSS
(SEQ ID NO:85)

HC-CDR1:    GFTFSSYG (SEQ ID NO:186)
    HC-CDR2:    ISYDGSNK (SEQ ID NO:184)
    HC-CDR3:    AKGGKSYYGFDY (SEQ ID NO:207)

YU112-F05

EVQLVQSGGGVVQPGRSLRLSCAASGFTFGSYGMHWVRQAPGKGLEWVAVISYDGSNKY
YADSVKGRFTISRDNSKNTLYLQMNSLRAEDTAVYYCAKIGATDPLDYWGQGTLVTVSS
(SEQ ID NO:390)

HC-CDR1:    GFTFGSYG (SEQ ID NO:234)
    HC-CDR2:    ISYDGSNK (SEQ ID NO:184)
    HC-CDR3:    AKIGATDPLDY (SEQ ID NO:187)

YU112-G01

QVQLVESGGGVVQPGRSLRLSCAASGFTFSSYGMHWVRQAPGKGLEWVAVISYDGSNKY
YADSVKGRFTISRDNSKNTLYLQMNSLRAEDTAVYYCAKLSGPNGVDYWGQGTLVTVSS
(SEQ ID NO:73)

HC-CDR1:    GFTFSSYG (SEQ ID NO:186)
    HC-CDR2:    ISYDGSNK (SEQ ID NO:184)
    HC-CDR3:    AKLSGPNGVDY (SEQ ID NO:197)

QVQLQESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKIGATDPLDY</u>WGQGTLVTVSS
(SEQ ID NO:391)

HC-CDR1:    GFTFSSYG (SEQ ID NO:186)
    HC-CDR2:    ISYDGSNK (SEQ ID NO:184)
    HC-CDR3:    AKIGATDPLDY (SEQ ID NO:187)

YU112-G09

*VTLKESGGGVVQPGRSLRLSCAAS<u>GFTFSSYG</u>MHWVRQAPGKGLEWVAV<u>ISYDGSNKY</u>Y
ADSVKGRFTISRDNSKNTLYLQMNSLRAEDTAVYYC<u>AKGGKSYYGFDY</u>WGQGTLVTVSS
(SEQ ID NO:85)

HC-CDR1:    GFTFSSYG (SEQ ID NO:186)
    HC-CDR2:    ISYDGSNK (SEQ ID NO:184)
    HC-CDR3:    AKGGKSYYGFDY (SEQ ID NO:207)

YU112-H01

QVQLVESGGGVVQPGRSLRLSCAAS<u>GFTFGSYG</u>MHWVRQAPGKGLEWVAV<u>ISYDGSNKY</u>
YADSVKGRFTISRDNSKNTLYLQMNSLRAEDTAVYYC<u>AKGSYYFDY</u>WGQGTLVTVSS
(SEQ ID NO:392)

HC-CDR1:    GFTFGSYG (SEQ ID NO:234)
    HC-CDR2:    ISYDGSNK (SEQ ID NO:184)
    HC-CDR3:    AKGSYYFDY (SEQ ID NO:235)

YU112-H02

QVQLVESGGGVVQPGRSLRLSCAAS<u>GFTFSSYG</u>MHWVRQAPGKGLEWVAV<u>ISYDGSNKY</u>
YADSVKGRFTISRDNSKNTLYLQMNSLRAEDTAVYYC<u>AKLSGPNGVDY</u>WGQGTLVTVSS
(SEQ ID NO:73)

HC-CDR1:    GFTFSSYG (SEQ ID NO:186)
    HC-CDR2:    ISYDGSNK (SEQ ID NO:184)
    HC-CDR3:    AKLSGPNGVDY (SEQ ID NO:197)

FIG. 45 (Cont.)

| Clone | CDR 1 | CDR 2 | CDR 3 |
|---|---|---|---|
| \multicolumn{4}{Light Chain} | | | |
| YU100-A10 | SSDVGAYNY (SEQ ID NO:110) | DVS (SEQ ID NO:108) | SSFTTSIAWV (SEQ ID NO:268) |
| YU100-A11, YU100-B12, YU100-C12, YU100-E10, YU100-E11, YU100-H09, YU100-H11, YU112-H02 | SSDVGGYNY (SEQ ID NO:107) | DVS (SEQ ID NO:108) | CSYAGSYTWV (SEQ ID NO:131) |
| YU100-A12 | SSDVGGYNY (SEQ ID NO:107) | DVS (SEQ ID NO:108) | SSYAGSYTWV (SEQ ID NO:124) |
| YU100-B01 | NTDVGAYNY (SEQ ID NO:272) | DVS (SEQ ID NO:108) | CSYAGSYSWV (SEQ ID NO:273) |
| YU100-B03 | SSDVGGYNY (SEQ ID NO:107) | DVV (SEQ ID NO:275) | CSYAGGYTWV (SEQ ID NO:276) |
| YU100-B06 | SSDVGGYNY (SEQ ID NO:107) | DVS (SEQ ID NO:108) | NSYAGSYTWV (SEQ ID NO:278) |
| YU100-B07 | SRDVGGYNY (SEQ ID NO:150) | DVS (SEQ ID NO:108) | CSYAGSYTWV (SEQ ID NO:131) |
| YU100-B08 | SSDVGGYNY (SEQ ID NO:107) | DVS (SEQ ID NO:108) | SSFTSSTTWV (SEQ ID NO:281) |
| YU100-B09 | SSDVGGYNY (SEQ ID NO:107) | DVS (SEQ ID NO:108) | SSYRSGSTLGVRRRDQADRPR (SEQ ID NO:282) |
| YU100-C02 | SSNVGGYNY (SEQ ID NO:284) | DVS (SEQ ID NO:108) | CSYAGSYVWV (SEQ ID NO:285) |
| YU100-C04 | SSDVGGYNY (SEQ ID NO:107) | DVT (SEQ ID NO:123) | CSYAGGYTWV (SEQ ID NO:276) |
| YU100-C05 | SSDVGGYNY (SEQ ID NO:107) | DVS (SEQ ID NO:108) | SSYTSSISWV (SEQ ID NO:288) |
| YU100-C10 | RSDIGGYDY (SEQ ID NO:290) | DVN (SEQ ID NO:291) | SSYTSSITWV (SEQ ID NO:130) |
| YU100-C11 | SSDVGGYNY (SEQ ID NO:107) | DVS (SEQ ID NO:108) | SSYTNSRTWV (SEQ ID NO:292) |
| YU100-D01 | SSDVGGYNF (SEQ ID NO:294) | DVD (SEQ ID NO:295) | CSYAGRYTWI (SEQ ID NO:296) |
| YU100-D02 | SGDVGTYNY (SEQ ID NO:298) | DVS (SEQ ID NO:108) | NSYAGSYTWV (SEQ ID NO:278) |
| YU100-D05 | NSDVGGYNY (SEQ ID NO:300) | DVS (SEQ ID NO:108) | CSYAGSYTWV (SEQ ID NO:131) |
| YU100-D07 | SGDVGTYDY (SEQ ID NO:302) | DVS (SEQ ID NO:108) | NSYAGSYTWV (SEQ ID NO:278) |
| YU100-D11 | SSNVGGYNY (SEQ ID NO:284) | DVS (SEQ ID NO:108) | ASYAGNYNWV (SEQ ID NO:304) |
| YU100-E01 | SNDIGAYNY (SEQ ID NO:306) | DVN (SEQ ID NO:291) | CSYAGSYSWV (SEQ ID NO:273) |
| YU100-E04 | SSDVGGYNY (SEQ ID NO:107) | DVT (SEQ ID NO:123) | CSYAGSHIWV (SEQ ID NO:308) |
| YU100-E05 | SSDVGGYNY (SEQ ID NO:107) | DVS (SEQ ID NO:108) | CSYAGSYSWV (SEQ ID NO:273) |
| YU100-E06 | SSDVGGYDY (SEQ ID NO:128) | DVT (SEQ ID NO:123) | SSYTSNTTWV (SEQ ID NO:311) |
| YU100-E07 | SSDVGGYDY (SEQ ID NO:128) | DVT (SEQ ID NO:123) | CSYAGRYTWV (SEQ ID NO:313) |

FIG. 46

| Clone | CDR 1 | CDR 2 | CDR 3 |
|---|---|---|---|
| \multicolumn{4}{c}{Light Chain} | | | |
| YU100-E08 | SSDVGGYNY (SEQ ID NO:107) | DVS (SEQ ID NO:108) | CSYAGNYTWM (SEQ ID NO:315) |
| YU100-E09 | SSDVGDYDY (SEQ ID NO:317) | DVT (SEQ ID NO:123) | CSYAGSYTWV (SEQ ID NO:131) |
| YU100-E12 | SSDVGGYNY (SEQ ID NO:107) | DVS (SEQ ID NO:108) | SSYTSSTTWV (SEQ ID NO:320) |
| YU100-F01 | GSDVGAYDY (SEQ ID NO:322) | DVN (SEQ ID NO:291) | SSFATSISWV (SEQ ID NO:408) |
| YU100-F02 | SSDVGGYNY (SEQ ID NO:107) | DVT (SEQ ID NO:123) | CSYAGSYTWI (SEQ ID NO:324) |
| YU100-F05 | SSDIGGYNY (SEQ ID NO:326) | DVS (SEQ ID NO:108) | CSYAGSYTWV (SEQ ID NO:131) |
| YU100-F06 | SSDVGGYNF (SEQ ID NO:294) | DVN (SEQ ID NO:291) | CSYAGGYTWV (SEQ ID NO:276) |
| YU100-F07 | SSDVGGYEY (SEQ ID NO:159) | DVT (SEQ ID NO:123) | CSYAGSYTWV (SEQ ID NO:131) |
| YU100-F11 | SSDVAGYNY (SEQ ID NO:330) | DVT (SEQ ID NO:123) | CSYAGSYTWV (SEQ ID NO:131) |
| YU100-G01 | SSDVGAYNY (SEQ ID NO:110) | DVN (SEQ ID NO:291) | CSYAGSYTWV (SEQ ID NO:131) |
| YU100-G07 | SSDVGAYDY (SEQ ID NO:333) | DVT (SEQ ID NO:123) | ASYTRSSVWV (SEQ ID NO:334) |
| YU100-G08 | SSDVGGYNY (SEQ ID NO:107) | DVN (SEQ ID NO:291) | CSYAGRYTWM (SEQ ID NO:336) |
| YU100-G09, YU112-A07, YU112-C05, YU112-D08, YU112-G01 | ISDVGGYNY (SEQ ID NO:122) | DVT (SEQ ID NO:123) | SSYAGSYTWV (SEQ ID NO:124) |
| YU100-G10 | RRDVGGYDF (SEQ ID NO:339) | DVS (SEQ ID NO:108) | CSYAGTYTWV (SEQ ID NO:340) |
| YU100-G11 | SSDVGGYNY (SEQ ID NO:107) | DVG (SEQ ID NO:133) | CSYAGGYTWV (SEQ ID NO:276) |
| YU100-H01 | SSDVGAYNY (SEQ ID NO:110) | DVS (SEQ ID NO:108) | CSYAGSYTWV (SEQ ID NO:131) |
| YU100-H02 | SSDVGTYNY (SEQ ID NO:344) | DVS (SEQ ID NO:108) | CSYAGFYTWV (SEQ ID NO:345) |
| YU100-H04 | SSDIGVYNY (SEQ ID NO:347) | DVS (SEQ ID NO:108) | CSYAGSYTWV (SEQ ID NO:131) |
| YU100-H05 | GSNVGGYNY (SEQ ID NO:349) | DVS (SEQ ID NO:108) | CSYAGTYTWV (SEQ ID NO:340) |
| YU100-H06 | SSDVGGYNY (SEQ ID NO:107) | DVT (SEQ ID NO:123) | SSYAGSYTWV (SEQ ID NO:124) |
| YU112-B06 | SSDVGGYNY (SEQ ID NO:107) | DVS (SEQ ID NO:108) | SSYTSSSWV (SEQ ID NO:109) |
| YU112-C03 | QAINSY (SEQ ID NO:352) | AAS (SEQ ID NO:102) | QQSYSTPSWT (SEQ ID NO:354) |
| YU112-C09 | QSFSSSY (SEQ ID NO:356) | GAS (SEQ ID NO:138) | QQSSTSPTWA (SEQ ID NO:357) |

FIG. 46 (Cont.)

| Clone | CDR 1 | CDR 2 | CDR 3 |
|---|---|---|---|
| Light Chain | | | |
| YU112-E07 | QSVNSAY (SEQ ID NO:359) | GAS (SEQ ID NO:138) | QQSYSDPRWT (SEQ ID NO:360) |
| YU112-E08 | QIISSY (SEQ ID NO:155) | AAS (SEQ ID NO:102) | QQSYSTPTWT (SEQ ID NO:156) |
| YU112-F05 | SSDVGGYNY (SEQ ID NO:107) | DVN (SEQ ID NO:291) | NSYTSGSTWV (SEQ ID NO:362) |
| YU112-G06 | ISDVGGYNY (SEQ ID NO:122) | DVT (SEQ ID NO:123) | SSYAGGYTWV (SEQ ID NO:364) |
| YU112-G09 | QIISSY (SEQ ID NO:155) | AAS (SEQ ID NO:102) | |
| YU112-H01 | QSVSSSY (SEQ ID NO:367) | GAS (SEQ ID NO:138) | QQSYSTPTWT (SEQ ID NO:156) |

FIG. 46 (Cont.)

| Clone | CDR 1 | CDR 2 | CDR 3 |
|---|---|---|---|
| Heavy Chain | | | |
| YU100-A10, YU100-A11, YU100-A12, YU100-B01, YU100-B03, YU100-B06, YU100-B07, YU100-B08, YU100-B09, YU100-C02, YU100-C04, YU100-C05, YU100-C11, YU100-D02, YU100-D05, YU100-D11, YU100-E01, YU100-E04, YU100-E05, YU100-E06, YU100-E10, YU100-E12, YU100-F01, YU100-F02, YU100-F05, YU100-F11, YU100-G01, YU100-G07, YU100-G08, YU100-G09, YU100-G10, YU100-H05, YU100-H06, YU100-H11, YU112-A07, YU112-B06, YU112-D08, YU112-G06 | GFTFSSYG (SEQ ID NO:186) | ISYDGSNK (SEQ ID NO:184) | AKIGATDPLDY (SEQ ID NO:187) |
| YU100-B12, YU100-C12, YU100-D01, YU100-D07, YU100-E08, YU100-E09, YU100-F07, YU100-H01, YU100-H04, YU100-H09, YU112-C05 | GFTFSSYA (SEQ ID NO:190) | ISYDGSNK (SEQ ID NO:184) | ARIMGYDYGDYDVVDY (SEQ ID NO:199) |
| YU100-C10, YU112-F05 | GFTFGSYG (SEQ ID NO:234) | ISYDGSNK (SEQ ID NO:184) | AKIGATDPLDY (SEQ ID NO:187) |

FIG. 47

| Clone | CDR 1 | CDR 2 | CDR 3 |
|---|---|---|---|
| Heavy Chain | | | |
| YU100-E07 | GFTFSSYG (SEQ ID NO:186) | ISYDGSNR (SEQ ID NO:381) | AKIGATDPLDY (SEQ ID NO:187) |
| YU100-E11, YU100-F06, YU100-G11, YU100-H02 | GFTFSSYG (SEQ ID NO:186) | ISYDGSNK (SEQ ID NO:184) | ARIMGYDYGDYDVVDY (SEQ ID NO:199) |
| YU112-C03, YU112-E08, YU112-G09 | GFTFSSYG (SEQ ID NO:186) | ISYDGSNK (SEQ ID NO:184) | AKGGKSYYGFDY (SEQ ID NO:207) |
| YU112-C09, YU112-E07, YU112-H01 | GFTFGSYG (SEQ ID NO:234) | ISYDGSNK (SEQ ID NO:184) | AKGSYYFDY (SEQ ID NO:235) |
| YU112-G01, YU112-H02 | GFTFSSYG (SEQ ID NO:186) | ISYDGSNK (SEQ ID NO:184) | AKLSGPNGVDY (SEQ ID NO:197) |

FIG. 47 (Cont.)

| Clone(s) | LC-CDR1 | Sequence family | Family Consensus |
|---|---|---|---|
| YU100-D01, YU100-F06 | SSDVGGYNF | matLC-CDR1-1 | $X_{138}X_{139}DVGGYX_{140}X_{141}$ (SEQ ID NO:393) |
| YU100-F07 | SSDVGGYEY | | |
| YU100-B07 | SRDVGGYNY | | $X_{138}$ = S, N or I |
| YU100-D05 | NSDVGGYNY | | $X_{139}$ = S or R |
| YU100-E06, YU100-E07 | SSDVGGYDY | | $X_{140}$ = N, E or D |
| | | | $X_{141}$ = Y or F |
| YU100-A11, YU100-B12, YU100-C12, YU100-E10, YU100-E11, YU100-H09, YU100-H11, YU112-H02, YU100-A12, YU100-B03, YU100-B06, YU100-B08, YU100-B09, YU100-C04, YU100-C05, YU100-C11, YU100-E04, YU100-E05, YU100-E08, YU100-E12, YU100-F02, YU100-G08, YU100-G11, YU100-H06, YU112-B06, YU112-F05 | SSDVGGYNY | | |
| YU100-G09, YU112-A07, YU112-C05, YU112-D08, YU112-G01, YU112-G06 | ISDVGGYNY | | |
| YU100-E09 | SSDVGDYDY | matLC-CDR1-2 | $SSDVX_{142}X_{143}YX_{144}Y$ (SEQ ID NO:394) |
| YU100-F11 | SSDVAGYNY | | |
| YU100-H02 | SSDVGTYNY | | $X_{142}$ = G or A |
| | | | $X_{143}$ = D, G or T |
| | | | $X_{144}$ = N or D |
| YU100-B01 | NTDVGAYNY | matLC-CDR1-3 | $X_{145}X_{146}DX_{147}GAYNY$ (SEQ ID NO:395) |
| YU100-E01 | SNDIGAYNY | | |
| YU100-A10, YU100-G01, YU100-H01 | SSDVGAYNY | | $X_{145}$ = S or N |
| | | | $X_{146}$ = N, T or S |
| | | | $X_{147}$ = V or I |

FIG. 48A

| Clone(s) | LC-CDR1 | Sequence family | Family Consensus |
|---|---|---|---|
| YU100-H04 | SSDIGVYNY | matLC-CDR1-4 | SSDIGX$_{148}$YNY (SEQ ID NO:396) |
| YU100-F05 | SSDIGGYNY | | |
| | | | X$_{148}$ = V or G |
| YU100-G07 | SSDVGAYDY | matLC-CDR1-5 | X$_{149}$SDVGAYDY (SEQ ID NO:397) |
| YU100-F01 | GSDVGAYDY | | |
| | | | X$_{149}$ = S or G |
| YU100-D02 | SGDVGTYNY | matLC-CDR1-6 | SGDVGTYX$_{150}$Y (SEQ ID NO:398) |
| YU100-D07 | SGDVGTYDY | | |
| | | | X$_{150}$ = N or D |
| YU112-C03 | QAINSY | matLC-CDR1-7 | QX$_{151}$IX$_{152}$SY (SEQ ID NO:399) |
| YU112-E08, YU112-G09 | QIISSY | | |
| | | | X$_{151}$ = A or I |
| | | | X$_{152}$ = N or S |
| YU112-C09 | QSFSSSY | matLC-CDR1-8 | QSX$_{153}$SSSY (SEQ ID NO:400) |
| YU112-H01 | QSVSSSY | | |
| | | | X$_{153}$ = F or V |
| YU100-C10 | RSDIGGYDY | matLC-CDR1-9 | RX$_{154}$DX$_{155}$GGYDX$_{156}$ (SEQ ID NO:401) |
| YU100-G10 | RRDVGGYDF | | |
| | | | X$_{154}$ = S or R |
| | | | X$_{155}$ = I or V |
| | | | X$_{156}$ = Y or F |
| YU100-C02, YU100-D11 | SSNVGGYNY | matLC-CDR1-10 | SSNVGGYNY (SEQ ID NO:284) |
| YU100-H05 | GSNVGGYNY | matLC-CDR1-11 | GSNVGGYNY (SEQ ID NO:349) |
| YU112-E07 | QSVNSAY | matLC-CDR1-12 | QSVNSAY (SEQ ID NO:359) |

FIG. 48A (Cont.)

| Clone(s) | LC-CDR2 | Sequence family | Family Consensus |
|---|---|---|---|
| YU100-A10, YU100-A11, YU100-B12, YU100-C12, YU100-E10, YU100-E11, YU100-H09, YU100-H11, YU112-H02, YU100-A12, YU100-B01, YU100-B06, YU100-B07, YU100-B08, YU100-B09, YU100-C02, YU100-C05, YU100-C11, YU100-D02, YU100-D05, YU100-D07, YU100-D11, YU100-E05, YU100-E08, YU100-E12, YU100-F05, YU100-G10, YU100-H01, YU100-H02, YU100-H04, YU100-H05, YU112-B06 | DVS | matLC-CDR2-1 | $DVX_{157}$ (SEQ ID NO:402)<br><br>$X_{157}$ = S, T, N, G, V or D |
| YU100-B03 | DVV | | |
| YU100-C04, YU100-E04, YU100-E06, YU100-E07, YU100-E09, YU100-F02, YU100-F07, YU100-F11, YU100-G07, YU100-G09, YU112-A07, YU112-C05, YU112-D08, YU112-G01, YU100-H06, YU112-G06, | DVT | | |

FIG. 48B

| Clone(s) | LC-CDR2 | Sequence family | Family Consensus |
|---|---|---|---|
| YU100-D01 | DVD | matLC-CDR2-1 | DVX$_{157}$ (SEQ ID NO:402) |
| YU100-C10 | DVN | | |
| YU100-E01 | | | $X_{157}$ = S, T, N, G, V or D |
| YU100-F01 | | | |
| YU100-F06 | | | |
| YU100-G01 | | | |
| YU100-G08 | | | |
| YU112-F05 | | | |
| YU100-G11 | DVG | | |
| YU112-C03, | AAS | matLC-CDR2-2 | $X_{158}$AS (SEQ ID NO:403) |
| YU112-E08, | | | |
| YU112-G09 | | | $X_{158}$ = A or G |
| YU112-C09 | GAS | | |
| YU112-E07 | | | |
| YU112-H01 | | | |

FIG. 48B (Cont.)

| Clone(s) | LC-CDR3 | Sequence family | Family Consensus |
|---|---|---|---|
| YU100-A11, YU100-B12, YU100-C12, YU100-E10, YU100-E11, YU100-H09, YU100-H11, YU112-H02, YU100-B07, YU100-D05, YU100-E09, YU100-F05, YU100-F07, YU100-F11, YU100-G01, YU100-H01, YU100-H04 | CSYAGSYTWV | matLC-CDR3-1 | $X_{159}SYAGX_{160}X_{161}X_{162}WX_{163}$ (SEQ ID NO:404)<br><br>$X_{159}$ = C, S, A or N<br>$X_{160}$ = S, R, N, G, T or F<br>$X_{161}$ = Y or H<br>$X_{162}$ = T, N, I, S or V<br>$X_{163}$ = V, M or I |
| YU100-A12, YU100-G09, YU112-A07, YU112-C05, YU112-D08, YU112-G01, YU100-H06 | SSYAGSYTWV | | |
| YU100-B01, YU100-E01, YU100-E05 | CSYAGSYSWV | | |
| YU100-B03, YU100-C04, YU100-F06, YU100-G11 | CSYAGGYTWV | | |
| YU100-B06, YU100-D02, YU100-D07 | NSYAGSYTWV | | |
| YU100-C02 | CSYAGSYVWV | | |
| YU100-D01 | CSYAGRYTWI | | |
| YU100-G08 | CSYAGRYTWM | | |
| YU100-G10, YU100-H05 | CSYAGTYTWV | | |
| YU100-H02 | CSYAGFYTWV | | |
| YU100-E04 | CSYAGSHIWV | | |
| YU100-E07 | CSYAGRYTWV | | |
| YU100-E08 | CSYAGNYTWM | | |
| YU100-F02 | CSYAGSYTWI | | |
| YU100-D11 | ASYAGNYNWV | | |
| YU112-G06 | SSYAGGYTWV | | |
| YU100-C11 | SSYTNSRTWV | matLC-CDR3-2 | $SSYTX_{164}X_{165}X_{166}X_{167}WV$ (SEQ ID NO:405)<br><br>$X_{164}$ = S or N<br>$X_{165}$ = S or N<br>$X_{166}$ = T, I, S or R<br>$X_{167}$ = T or S |
| YU100-E06 | SSYTSNTTWV | | |
| YU100-E12 | SSYTSSTTWV | | |
| YU112-B06 | SSYTSSSSWV | | |
| YU100-C05 | SSYTSSISWV | | |
| YU100-C10 | SSYTSSITWV | | |

FIG. 48C

| Clone(s) | LC-CDR3 | Sequence family | Family Consensus |
|---|---|---|---|
| YU112-C03 | QQSYSTPSWT | matLC-CDR3-3 | QQSYSX$_{168}$PX$_{169}$WT (SEQ ID NO:406) |
| YU112-E07 | QQSYSDPRWT | | |
| YU112-E08, YU112-H01 | QQSYSTPTWT | | X$_{168}$ = T or D<br>X$_{169}$ = S, R or T |
| YU100-A10 | SSFTTSIAWV | matLC-CDR3-4 | SSFX$_{170}$X$_{171}$SX$_{172}$X$_{173}$WV (SEQ ID NO:407) |
| YU100-B08 | SSFTSSTTWV | | X$_{170}$ = T or A<br>X$_{171}$ = T or S<br>X$_{172}$ = I or T |
| YU100-F01 | SSFATSISWV | | X$_{173}$ = A or T |
| YU112-F05 | NSYTSGSTWV | matLC-CDR3-5 | NSYTSGSTWV (SEQ ID NO:362) |
| YU100-G07 | ASYTRSSVWV | matLC-CDR3-6 | ASYTRSSVWV (SEQ ID NO:334) |
| YU112-C09 | QQSSTSPTWA | matLC-CDR3-7 | QQSSTSPTWA (SEQ ID NO:357) |
| YU100-B09 | SSYRSGSTLGVRRRDQADRPR | matLC-CDR3-8 | SSYRSGSTLGVRRRDQADRPR (SEQ ID NO:282) |

FIG. 48C (Cont.)

| Clone(s) | HC-CDR1 | Sequence family | Family Consensus |
|---|---|---|---|
| YU100-A10, YU100-A11, YU100-A12, YU100-B01, YU100-B03, YU100-B06, YU100-B07, YU100-B08, YU100-B09, YU100-C02, YU100-C04, YU100-C05, YU100-C11, YU100-D02, YU100-D05, YU100-D11, YU100-E01, YU100-E04, YU100-E05, YU100-E06, YU100-E10, YU100-E12, YU100-F01, YU100-F02, YU100-F05, YU100-F11, YU100-G01, YU100-G07, YU100-G08, YU100-G09, YU100-G10, YU100-H05, YU100-H06, YU100-H11, YU112-A07, YU112-B06, YU112-D08, YU112-G06 YU100-E07, YU100-E11, YU100-F06, YU100-G11, YU100-H02, YU112-C03, YU112-E08, YU112-G09, YU112-G01, YU112-H02 | GFTFSSYG | matHC-CDR1-1 | GFTFX$_{174}$SYX$_{175}$ (SEQ ID NO:409)<br><br>X$_{174}$ = S or G<br>X$_{175}$ = G or A |

FIG. 49A

| Clone(s) | HC-CDR1 | Sequence family | Family Consensus |
|---|---|---|---|
| YU100-B12, YU100-C12, YU100-D01, YU100-D07, YU100-E08, YU100-E09, YU100-F07, YU100-H01, YU100-H04, YU100-H09, YU112-C05 | GFTFSSYA | matHC-CDR1-1 | GFTFX$_{174}$SYX$_{175}$ (SEQ ID NO:409)<br><br>X$_{174}$ = S or G<br>X$_{175}$ = G or A |
| YU100-C10, YU112-F05, YU112-C09, YU112-E07, YU112-H01 | GFTFGSYG | | |

FIG. 49A (Cont.)

| Clone(s) | HC-CDR2 | Sequence family | Family Consensus |
|---|---|---|---|
| YU100-A10, YU100-A11, YU100-A12, YU100-B01, YU100-B03, YU100-B06, YU100-B07, YU100-B08, YU100-B09, YU100-C02, YU100-C04, YU100-C05, YU100-C11, YU100-D02, YU100-D05, YU100-D11, YU100-E01, YU100-E04, YU100-E05, YU100-E06, YU100-E10, YU100-E12, YU100-F01, YU100-F02, YU100-F05, YU100-F11, YU100-G01, YU100-G07, YU100-G08, YU100-G09, YU100-G10, YU100-H05, YU100-H06, YU100-H11, YU112-A07, YU112-B06, YU112-D08, YU112-G06 YU100-B12, YU100-C12, YU100-D01, YU100-D07, YU100-E08, YU100-E09, YU100-F07, YU100-H01, YU100-H04, YU100-H09, YU112-C05, | ISYDGSNK | matHC-CDR2-1 | ISYDGSN$X_{176}$ (SEQ ID NO:410)<br><br>$X_{176}$ = K or R |

FIG. 49B

| Clone(s) | HC-CDR2 | Sequence family | Family Consensus |
|---|---|---|---|
| YU100-C10, YU112-F05, YU100-E11, YU100-F06, YU100-G11, YU100-H02, YU112-C03, YU112-E08, YU112-G09, YU112-C09, YU112-E07, YU112-H01, YU112-G01, YU112-H02 | ISYDGSNK | matHC-CDR2-1 | ISYDGSNX$_{176}$ (SEQ ID NO:410)<br><br>X$_{176}$ = K or R |
| YU100-E07 | ISYDGSNR | | |

FIG. 49B (Cont.)

| Clone(s) | HC-CDR3 | Sequence family | Family Consensus |
|---|---|---|---|
| YU100-A10, YU100-A11, YU100-A12, YU100-B01, YU100-B03, YU100-B06, YU100-B07, YU100-B08, YU100-B09, YU100-C02, YU100-C04, YU100-C05, YU100-C11, YU100-D02, YU100-D05, YU100-D11, YU100-E01, YU100-E04, YU100-E05, YU100-E06, YU100-E10, YU100-E12, YU100-F01, YU100-F02, YU100-F05, YU100-F11, YU100-G01, YU100-G07, YU100-G08, YU100-G09, YU100-G10, YU100-H05, YU100-H06, YU100-H11, YU112-A07, YU112-B06, YU112-D08, YU112-G06, YU100-C10, YU112-F05, YU100-E07 | AKIGATDPLDY | matHC-CDR3-1 | AKIGATDPLDY (SEQ ID NO:187) |

FIG. 49C

| Clone(s) | HC-CDR3 | Sequence family | Family Consensus |
|---|---|---|---|
| YU100-B12, YU100-C12, YU100-D01, YU100-D07, YU100-E08, YU100-E09, YU100-F07, YU100-H01, YU100-H04, YU100-H09, YU112-C05, YU100-E11, YU100-F06, YU100-G11, YU100-H02 | ARIMGYDYGDYDVVDY | matHC-CDR3-2 | ARIMGYDYGDYDVVDY (SEQ ID NO:199) |
| YU112-G01, YU112-H02 | AKLSGPNGVDY | matHC-CDR3-3 | AKLSGPNGVDY (SEQ ID NO:197) |
| YU112-C03, YU112-E08, YU112-G09 | AKGGKSYYGFDY | matHC-CDR3-4 | AKGX$_{177}$X$_{178}$SYYX$_{179}$FDY (SEQ ID NO:411) |
| YU112-C09, YU112-E07, YU112-H01 | AKGSYYFDY | | X$_{177}$ = absent or G<br>X$_{178}$ = absent or K<br>X$_{179}$ = absent or G |

FIG. 49C (Cont.)

YU100-A10
EVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVLPVLTQPASVSGSPGQSITISCTGTSSDVGAYNYVSWYQQHPGKAPELMIYDVSNRPSGVSNR
FSGSKSGNTASLTISGLQPEDEADYYCSSFTTSIAWVFGGGTKLTVLGQPKAAPSVTLFPPSS (SEQ
ID NO:412)

YU100-A11
EVQLQQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSSDVGGYNYVSWYQQHPGKAPKLMIYDVSKRPSGVPD
RFSGSKSGNTASLTISGLQAEDEADYYCCSYAGSYTWVFGGGTKLTVLGQPKAAPSVTLFPPSS
(SEQ ID NO:413)

YU100-A12
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVLPVLTQPRSVSGSPGQSVTISCTGTSSDVGGYNYVSWYQQHPGKAPKLMIYDVSKRPSGVPD
RFSGSKSGDTASLTISGLQAEDEADYYCSSYAGSYTWVFGGGTKLTVLGQPKAAPSVTLFPPSS
(SEQ ID NO:414)

YU100-B01
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTNTDVGAYNYVSWYQQYPGKAPKLIIYDVSKRPSGVPDR
FSGSKSGNTASLTISGLQAEDEADYYCCSYAGSYSWVFGGGTKLTVLGQPKAAPSVTLFPPSS (SEQ
ID NO:415)

YU100-B03
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSVLTQPRSVSGSPGRSVTISCTGTSSDVGGYNYVSWYQQHPGKAPKLTLYDVVKRPSGVPD
RYSGSKSGNTASLTISGLQAEDEADYYCCSYAGGYTWVFGGGTKVTVVGQPKAAPSVTLFPPSS
(SEQ ID NO:416)

YU100-B06
QVQLVESGGGVVQPGRSLRLSCAASGFTFSSYGMHWVRQAPGKGLEWVAVISYDGSNKYYADSVK
SRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQHPGKAPKLMIYDVSKRPSGVPD
RFSGSKSGNTASLTISGLQAEDEADYYCNSYAGSYTWVFGGGTKLTVLGQPKAAPSVTLFPPSS
(SEQ ID NO:417)

YU100-B07
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTMSCTGTSRDVGGYNYVSWYQHHPGKAPKLMIYDVSKRPSGVP
DRFSGSKSGNTASLTISELQAEDEADYYCCSYAGSYTWVFGGGTKLTVLGQPKAAPSVTLFPPSS
(SEQ ID NO:418)

FIG. 50

YU100-B08
EVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQHPGKVPRLLIYDVSNRPSGVSTR
FSGSKSGNTASLTISGLQGEDEAEYYCSSFTSSTTWVFGGGTKLTVLGQPKAAPSVTLFPPSS (SEQ
ID NO:419)

YU100-B09
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQHPGKAPKLMIYDVSDRPSGVSN
RFSGSKSGNTASLTISGLQPEDEADYYCSSYRSGSTLGVRRRDQADRPRSAQGCPLGHSVPALL
(SEQ ID NO:420)

YU100-B12
QVQLVESGGGVVQPGRSLRLSCAASGFTFSSYAMHWVRQAPGKGLEWVAVISYDGSNKYYADSVK
DRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSSDVGGYNYVSWYQQHPGKAPKLMIYDVSKR
PSGVPDRFSGSKSGNTASLTISGLQAEDEADYYCCSYAGSYTWVFGGGTKLTVLGQPKAAPSVTLFP
PSS (SEQ ID NO:421)

YU100-C02
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSSNVGGYNYVSWYQQHPGKAPKLMIYDVSKRPSGVPD
RFSGSKSGNTASLTISGLQAEDEADYYCCSYAGSYVWVFGGGTKLTVLGQPKAAPSVTLFPPSS
(SEQ ID NO:422)

YU100-C04
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSSDVGGYNYVSWYQHHPGKAPKLIIYDVTKRPSGVPDR
FSGSKSGNTASLAISGLQAEEEADYYCCSYAGGYTWVFGGGTKLTVLGQPKAAPSVTLFPPSS
(SEQ ID NO:423)

YU100-C05
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQHPGKAPKLMIYDVSNRPSGISNR
FSGSKSGNTASLTISGLQAEDEADYYCSSYTSSISWVFGGGTKLTVLGQPKAAPSVTLFPPSS (SEQ
ID NO:424)

YU100-C10
QVQLVESGGGVVQPGRSLRLSCAASGFTFGSYGMHWVRQAPGKGLEWVAVISYDGSNKYYADSVK
GRFTISRDNSKNTLYLQMNSLRAEDTAVYYCAKIGATDPLDYWGQGTLITVSSGSASAPKLEEGEFSE
ARVQSALTQPASVSGSPGQSITISCTGTRSDIGGYDYVSWYQQHPGKAPKLMIYDVNNRPSGVSNRF
SGSKSGNTASLTISGLQAEDEAEYYCSSYTSSITWVFGGGTKVTVLGQPKAAPSVTLFPPSS (SEQ
ID NO:425)

FIG. 50 (Cont.)

YU100-C11
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQRPGKAPKLMIYDVSNRPSGVSN
RFSGSKSGNTASLTISGLQPDDEADYYCSSYTNSRTWVFGGGTKLTVLSQPKAAPSVTLFPPSS
(SEQ ID NO:426)

YU100-C12
EVQLVQSGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSSDVGGYNYVSWYQQHPGKAPKLMIYDVSKR
PSGVPDRFSGSKSGNTASLTISGLQAEDEADYYCSYAGSYTWVFGGGTKLTVLGQPKAAPSVTLFP
PSS (SEQ ID NO:427)

YU100-D01
QVQLQQSGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPPSASGSPGQSVTISCTGTSSDVGGYNFVSWYQQHPGKAPKLLIYDVDKR
PSGVPDRFSGSKSGRTASLTISGLQTEDEAKYYCSYAGRYTWIFGGGTKLTVLGQPKAAPSVILFPP
SS (SEQ ID NO:428)

YU100-D02
QVRLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSGDVGTYNYVSWYQQHPGKAPKLMIFDVSKRPSGVPD
RFSGSKSGNTASLTISGLQAEDEADYYCNSYAGSYTWVFGGGTKLTVLGQPKAAPSVTLFPPSS
(SEQ ID NO:429)

YU100-D05
QVQLQQSGGGVVQPGRSLRLSCAASGFTFSSYGMHWVRQAPGKGLEWVAVISYDGSNKYYADSV
KGRFTISRDNSKNTLYLQMNSLRAEDTAVYYCAKIGATDPLDYWGQGTLVTVSSGSASAPKLEEGEF
SEARVQSALTQPASVSGSPGQLITISCTGTNSDVGGYNYVSWYQQHPGKAPKLMIYDVSNRPSGVS
NRFSGSKSGNTASLTISGLQAEDEADYYCSYAGSYTWVFGGGTKLTVLGQPKAAPSVTLFPPSS
(SEQ ID NO:430)

YU100-D07
QVQLVESGGGVVQPGRSLRLSCAASGFTFSSYAMHWVRQAPGKGLEWVAVISYDGSNKYYADSVK
GRLTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSGDVGTYDYVSWYQQHPGKAPKLMIYDVSKR
PSGVPDRFSGSKSGNTASLTISGLQAEDEADYYCNSYAGSYTWVFGGGTKLTVLGQPKTAPSVTLFP
PSS (SEQ ID NO:431)

YU100-D11
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSSNVGGYNYVSWYQQHPGKAPKLMIYDVSKRPSGVPD
RFSGSKSGNTASLTISGLQAEDEANYYCASYAGNYNWVFGGGTKLTVLGQPKAAPSVTLFPPSS
(SEQ ID NO:432)

FIG. 50 (Cont.)

YU100-E01
QVQLQQSGGGVVQPGRSLRLSCAASGFTFSSYGMHWVRQAPGKGLEWVAVISYDGSNKYYADSV
KGRFTISRDNSKNTLYLQMNSLRAEDTAVYYCAKIGATDPLDYWGQGTLVTVSSGSASAPKLEEGEF
SEARVQSALTQPASVSGSPGQSITISCTGTSNDIGAYNYVSWYQQHPGKAPKLLIYDVNNRPSGVSD
RFSGSKSGNTASLTISGLQAEDEADYYCCSYAGSYSWVFGGGTKLTVLGQPKANPTVTLFPPSS
(SEQ ID NO:433)

YU100-E04
QVQLQQSGGGVVQPGRSLRLSCAASGFTFSSYGMHWVRQAPGKGLEWVAVISYDGSNKYYADSV
KGRFTISRDNSKNTLYLQMNSLRAEDTAVYYCAKIGATDPLDYWGQGTLVTVSSGSASAPKLEEGEF
SEARVQSALTQPRSVSGSPGQSVTISCTGTSSDVGGYNYVSWYQQHPGKTPKLMIYDVTKRPSGVP
DHFSGSKSGNTASLTISGLQAEDEADYYCCSYAGSHIWVFGGGTKLTVLGQPKAAPSVTLFPPSS
(SEQ ID NO:434)

YU100-E05
EVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQAVLTQPRSVSGSPGQSVTISCTGTSSDVGGYNYVSWYQQHPGKAPKLMIYDVSKRPSGVPD
RFSGSKSGNTASLTISGLQAEDEADYYCCSYAGSYSWVFGGGTKLTVLGQPKAAPSVTLFPPSS
(SEQ ID NO:435)

YU100-E06
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGFPEQSITISCTGTSSDVGGYDYVSWYQQHPGKAPKLMIYDVTNRPSGVSN
RFSGSKSGNTASLTISGLQPEDEADYYCSSYTSNTTWVFGGGTKLTVLRQPKAAPSVTLFPPSS
(SEQ ID NO:436)

YU100-E07
QVQLQESGGGVVQPGRSLRLSCAASGFTFSSYGMHWVRQAPGKGLEWVAVISYDGSNRYYADSVK
GRFAISRDNSKNTLYLQMNSLRAEDTAVYYCAKIGATDPLDYWGQGTLVTVSSGSASAPKLEEGEFS
EARVQSALTQPRSVSGSPGQSVTISCTGTSSDVGGYDYVSWYQQHPGKAPELMIYDVTKRPSGVAD
RFSGSKSGNTASLTISGLQAEDEADYYCCSYAGRYTWVFGGGTKLTVLGQPKAAPSVTLFPPSS
(SEQ ID NO:437)

YU100-E08
QVQLVQSGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSSDVGGYNYVSWYQQHPGKAPKLMIYDVSRR
PSGVPDRFSGSKSGNTASLTISGLQAEDEADYYCCSYAGNYTWMFGGGTKLTVLGQPKAAPSVTLF
PPSS (SEQ ID NO:438)

YU100-E09
QVQLVESGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSSDVGDYDYVSWYQQHPGKAPKLIYDVTKRP
SGIPDRFSGSKSGNTASLTISGLQAEDEADYYCCSYAGSYTWVFGRGTKLTVLGQPKAAPSVTLFPP
ST (SEQ ID NO:439)

FIG. 50 (Cont.)

YU100-E10
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSSDVGGYNYVSWYQQHPGKAPKLMIFDVSQRPSGVPD
RFSASKSGNTASLTISGLQAEDEADYYCCSYAGSYTWVFGGGTKLTVLGQPKAAPSVTLFPPSS
(SEQ ID NO:440)

YU100-E11
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSSDVGGYNYVSWYQQHPGKAPKLMIYDVSKR
PSGVPDRFSGSKSGNTASLTISGLQAEDEADYYCCSYAGSYTWVFGGGTKLTVLGQPKAAPSVTLFP
PSS (SEQ ID NO:441)

YU100-E12
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQHPGTAPKLMIYDVSNRPSGVSN
RFSGSKSGNTASLTISGLQAEDEADYYCSSYTSSTTWVFGGGTKLTVLGQPKAAPSVTLFPPSS
(SEQ ID NO:442)

YU100-F01
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTGSDVGAYDYVSWYQQHPGKAPKLMIYDVNNRPSGVSN
RFSGSKSGNTASLTISGLQAEDEAEYYCSSFATSISWVFGGGTRLTVLGQPKAAPSVTLFPPSS (SEQ
ID NO:443)

YU100-F02
EVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSSDVGGYNYVSWYQQHPGKAPKLMIYDVTKRPSGVPD
RFSGSKSGNTASLTISGLQADDEADYYCCSYAGSYTWIFGGGTKLTVLGQPKAAPSVTLFPPSS
(SEQ ID NO:444)

YU100-F05
QVQLQQSGGGVVQPGRSLRLSCAASGFTFSSYGMHWVRQAPGKGLEWVAVISYDGSNKYYADSV
KGRFTISRDNSKNTLYLQMNSLRAEDTAVYYCAKIGATDPLDYWGQGTLVTVSSGSASAPKLEEGEF
SEARVQAVLTQPASVSGSPGQSITISCTGTSSDIGGYNYVSWYQQHPGTAPKLMIYDVSSRPSGVSN
RFSGSKSGNTASLTISGLQAEDEADYYCCSYAGSYTWVFGGGTKMTVLGQPKAAPSVTLFPPSS
(SEQ ID NO:445)

YU100-F06
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGSSSDVGGYNFVSWYRQHPGEAPKLVIFDVNKR
PSGVPDRFSGSKSGNTASLTISGLQTEDEADYFCCSYAGGYTWVFGGGTKVTVVGQPKAAPSVTLF
PPSS (SEQ ID NO:446)

FIG. 50 (Cont.)

YU100-F07
QVQLVESGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSVSPGQSVTISCTGTSSDVGGYEYVSWYQQHPGKAPKLMIYDVTKR
PSGVPDRFSGSKSGNTASLTISGLQGEDAADYYCCSYAGSYTWVFGGGTTVTVLGQPKAAPSVTLF
PPSS (SEQ ID NO:447)

YU100-F11
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGSSSDVAGYNYVSWYQQHPGKAPKLMIYDVTKRPSGVPD
RFSGSKSGNTASLTISGLQAEDEADYYCCSYAGSYTWVFGGGTQLTVLGQPKAAPSVTLFPPSS
(SEQ ID NO:448)

YU100-G01
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSASPGQSVTISCTGTSSDVGAYNYVSWYQQHPGKAPKLMLYDVNKRPSGVP
DRFSGSKSGNTASLTISRLQAEDEADYYCCSYAGSYTWVFGGGTKLTVLGQPKAAPSVTLFPPSS
(SEQ ID NO:449)

YU100-G07
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGAYDYVSWYQQHPGKAPKLMIYDVTNRPSGVSN
RFSGSKSGNTASLTISGLQAEDEADYYCASYTRSSVWVFGGGTKLTVLGQPKAASSVTLFPPSS
(SEQ ID NO:450)

YU100-G08
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTLSCTGTSSDVGGYNYVSWYQHPGKAPKLMIFDVNERSSGVP
DRFSGSKSGNTASLTISGLQAEDEADYYCCSYAGRYTWMFGGGTKVTVLGQPKAAPSVTLFPPSS
(SEQ ID NO:451)

YU100-G09
EVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTISDVGGYNYVSWYQQHPGKAPKLMIYDVTKRPSGVPD
RFSGSKSGNTASLTISGLQAEDEAGYYCSSYAGSYTWVFGGGTKLTVLGQPKAAPSVTLFPPSS
(SEQ ID NO:452)

YU100-G10
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSLGQSITMSCTGTRRDVGGYDFVSWYQQYPGKAPKLIIYDVSNRPSGVSN
RFTGSKSGNTASLTISGLQAEDEADYYCCSYAGTYTWVFGGGTKVTVLGQPKAAPSVTLFPPSS
(SEQ ID NO:453)

FIG. 50 (Cont.)

YU100-G11
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSSDVGGYNYVSWYQQHPGKAPKLTLYDVGKR
PSGVPDRFSGSKSGNTASLTISGLQAEDEADYYCCSYAGGYTWVFGGGTKVTVVGQPKAAPSVTLF
PPSS (SEQ ID NO:454)

YU100-H01
QVQLVQSGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTSSDVGAYNYVSWYQQHPGKAPKLMIYDVSER
PSGVPDRFSGSKSGNTASLTISGLQAEDEADYYCCSYAGSYTWVFGGGTKLTVLGQPKAAPSVTLFP
PSS (SEQ ID NO:455)

YU100-H02
QVQLQQSGGGVVQPGRSLRLSCAASGFTFSSYGMHWVRQAPGKGLEWVAVISYDGSNKYYADSV
KGRFTISRDNSKNTLYLQMNSLRAEDTAVYYCARIMGYDYGDYDVVDYWGQGTLVTVSSGSASAPK
LEEGEFSEARVQSALTQPRSVSRSPGQSVTISCTGTSSDVGTYNYVSWYQQHPGKAPKLMIYDVSK
RPSGVPDRFSGSKSGNTASLTISGLQAEDEADYYCCSYAGFYTWVFGGGTKLTVLGQPKAAPSVTLF
PPSS (SEQ ID NO:456)

YU100-H04
QVQLVESGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPASVSGSPGQSITISCTGTSSDIGVYNYVSWYQQHPGKAPKLMIYDVSKRP
SGVPDRFSGSKSGNTASLTISGLQAEDEADYYCCSYAGSYTWVFGGGTKLTVLGQPKAAPSVTLFPP
SS (SEQ ID NO:457)

YU100-H05
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQAVLTQPRSVSGSPGQSITISCTGTGSNVGGYNYVSWYQQHPGQAPKLMIYDVSKRPSGVPD
RFSGSKSGNTASLTISGLQAEDEADYYCCSYAGTYTWVFGGGTKLTVLGQPKAAPSVTLFPPSS
(SEQ ID NO:458)

YU100-H06
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARIQSALTQPRSVSGSPGQSVTISCTGTSSDVGGYNYVSWYQQHPGKAPKLMIYDVTKRPSGVPD
RFSGSKSGNTASLTISGLQAEDEADYYCSSYAGSYTWVFGGGTKLTVLGQPKAAPSVTLFPPSS
(SEQ ID NO:459)

YU100-H09
QVQLVQSGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPASVSGSPGQSITISCTGTSSDVGGYNYVSWYQQHPGKAPKLMIYDVSNR
PSGVSNRFSGSKSGNTASLTISGLQAEDEADYYCCSYAGSYTWVFGGGTKLTVLGQPKAAPSVTLFP
PSS (SEQ ID NO:460)

FIG. 50 (Cont.)

YU100-H11
QVQLVQSGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQHPGKAPKLMIYDVSNRPSGVSN
RFSGSKSGNTASLTISGLQAEDEADYYCCSYAGSYTWVFGGGTKLTVLGQPKAAPSVTLFPPSS
(SEQ ID NO:461)

YU112-A07
QVQLVESGGGVVQPGRSLRLSCAASGFTFSSYGMHWVRQAPGKGLEWVAVISYDGSNKYYTDSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTISDVGGYNYVSWYQQHPGKAPKLMIYDVTKRPSGVPD
RFSGSKSGNTASLTISGLQAEDEAGYYCSSYAGSYTWVFGGGTELTVLSQPKAAPSVTLFPPSS
(SEQ ID NO:462)

YU112-B06
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPASVSGSPGQSITISCTGTSSDVGGYNYVSWYQQHPGKAPKLMIYDVSNRPSGVSN
RFSGSKSGNTASLTIFGLQAEDEADYYCSSYTSSSSWVFGGGTKLTVLGQPKAAPSVTLFPPSS
(SEQ ID NO:463)

YU112-C03
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKGGKSYYGFDYWGQGTLVTVSSGSASAPKLEEGE
FSEARVDSVMTQSPSSLSASVGDRVTITCRASQAINSYLNWYQQKPGKAPKLLIYAASSLQSGVPSR
FSGSGSGTDFTLTISGLQPEDFATYYCQQSYSTPSWTFGQGTKVEIKRTVAAPSV (SEQ ID NO:464)

YU112-C05
EVQLVESGGGVVQPGRSLRLSCAASGFTFSSYAMHWVRQAPGKGLEWVAVISYDGSNKYYADSVK
GRFTISRDNSKNTLYLQMNSLRAEDTAVYYCARIMGYDYGDYDVVDYWGQGTLVTVSSGSASAPKL
EEGEFSEARVQSALTQPRSVSGSPGQSVTISCTGTISDVGGYNYVSWYQQHPGKAPKLMIYDVTKR
PSGVPDRFSGSKSGNTASLTISGLQAEDEAGYYCSSYAGSYTWVFGGGTELTVLSQPKAAPSVTLFP
PSS (SEQ ID NO:465)

YU112-C09
QVQLVQSGGGVVQPGRSLRLSCAASGFTFGSYGMHWVRQAPGKGLEWVAVISYDGSNKYYADSV
KGRFTISRDNSKNTLYLQMNSLRAEDTAVYYCAKGSYYFDYWGQGTLVTVSSGSASAPKLEEGEFS
EARVETTLTQSPATLSVSPGERATLSCRASQSFSSSYLAWYQQKPGQAPRLLIYGASRRAPGIPDRF
SGSGSGTDFSLTISRLEPEDFAVYYCQQSSTSPTWAFGRGTKVEVKRTVAAPSV (SEQ ID NO:466)

YU112-D08
QVQLVESGGGVVQPGRSLRLSCAASGFTFSSYGMHWVRQAPGKGLEWVAVISYDGSNKYYADSVE
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTISDVGGYNYVSWYQQHPGKAPKLMIYDVTKRPSGVPD
RFSGSKSGNTASLTISGLQAEDEAGYYCSSYAGSYTWVFGGGTELTVLSQPKAAPSVTLFPPSS
(SEQ ID NO:467)

FIG. 50 (Cont.)

YU112-E07
QVQLVQSGGGVVQPGRSLRLSCAASGFTFGSYGMHWVRQAPGKGLEWVAVISYDGSNKYYADSV
KGRFTISRDNSKNTLYLQMNSLRAEDTAVYYCAKGSYYFDYWGQGTLVTVSSGSASAPKLEEGEFS
EARVEIVMTQSPDSLAVSLGERATINCKSSQSVNSAYLAWYQHKPGQPPRLLIYGASRRVTGVPDRF
SGSGSGTDFTLTISSLQPEDFATYYCQQSYSDPRWTFGQGTKVEIKRTVAAPSV (SEQ ID NO:468)

YU112-E08
*VTLKESGGGVVQPGRSLRLSCAASGFTFSSYGMHWVRQAPGKGLEWVAVISYDGSNKYYADSVK
GRFTISRDNSKNTLYLQMNSLRAEDTAVYYCAKGGKSYYGFDYWGQGTLVTVSSGSASAPKLEEGE
FSEARVDIQMTQSPSFLSASVGDRVTITCRASQIISSYLNWYQQKPGKAPKLLIYAASSLQSGVPSRFS
GSGSGTDFTLTISSLQPEDFATYYCQQSYSTPTWTFGQGTKVEIKRTVAAPSV (SEQ ID NO:469)

YU112-F05
EVQLVQSGGGVVQPGRSLRLSCAASGFTFGSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTSSDVGGYNYVSWYQQHPGKAPKLIIYDVNNRPSGVSN
RFSASKSGNTASLTISGLQAEDEADYYCNSYTSGSTWVFGGGTKLTVLGQPKAAPSVTLFPPSS
(SEQ ID NO:470)

YU112-G01
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKLSGPNGVDYWGQGTLVTVSSGSASAPKLEEGEF
SEARVQSALTQPRSVSGSPGQSVTISCTGTISDVGGYNYVSWYQQHPGKAPKLMIYDVTKRPSGVP
DRFSGSKSGNTASLTISGLQAEDEAGYYCSSYAGSYTWVFGGGTELTVLSQPKAAPSVTLFPPSS
(SEQ ID NO:471)

YU112-G06
QVQLQESGGGVVQPGRSLRLSCAASGFTFSSYGMHWVRQAPGKGLEWVAVISYDGSNKYYADSVK
GRFTISRDNSKNTLYLQMNSLRAEDTAVYYCAKIGATDPLDYWGQGTLVTVSSGSASAPKLEEGEFS
EARVQSALTQPRSVSGSPGQSVTISCTGTISDVGGYNYVSWYQQHPGKAPKLMIYDVTKRRSGVPD
RFSGSKSGNTASLTISGLQAEDEAGYYCSSYAGGYTWVFGGGTELTVLSQPKAAPSVTLFPPSS
(SEQ ID NO:472)

YU112-G09
*VTLKESGGGVVQPGRSLRLSCAASGFTFSSYGMHWVRQAPGKGLEWVAVISYDGSNKYYADSVK
GRFTISRDNSKNTLYLQMNSLRAEDTAVYYCAKGGKSYYGFDYWGQGTLVTVSSGSASAPKLEEGE
FSEARVDIQMTQSPSFLSASVGDRVTITCRASQIISSYLNWYQQKPGKAPKLLIYAASSLQSGVPSRFS
GSGSGTDFTLTISSLQPGRFCNLLLSTELQYPHV (SEQ ID NO:473)

YU112-H01
QVQLVESGGGVVQPGRSLRLSCAASGFTFGSYGMHWVRQAPGKGLEWVAVISYDGSNKYYADSVK
GRFTISRDNSKNTLYLQMNSLRAEDTAVYYCAKGSYYFDYWGQGTLVTVSSGSASAPKLEEGEFSE
ARVETTLTQSPGTLSLSPGERATLSCRASQSVSSSYLAWYQQKPGQAPRLLIYGASSRATGIPDRFS
GSGSGTDFTLTISSLQPDDFATYYCQQSYSTPTWTFGQGTKVEIKRTVAAPSV (SEQ ID NO:474)

FIG. 50 (Cont.)

YU112-H02
QVQLVESGGGVVQPGRSLRLSCAASGFTFSSYGMHWVRQAPGKGLEWVAVISYDGSNKYYADSVK
GRFTISRDNSKNTLYLQMNSLRAEDTAVYYCAKLSGPNGVDYWGQGTLVTVSSGSASAPKLEEGEF
SEARVQPVLTQPRSVSGSPGQSVTISCTGTSSDVGGYNYVSWYQQHPGKAPKVMIYDVSKRPSGVP
DRFSGSKSGNTASLTISGLQAEDEADYYCCSYAGSYTWVFGGGTKLTVLGQPKAAPSVTLFPPSS
(SEQ ID NO:475)

FIG. 50 (Cont.)

YU100-A10
GAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACTGCCTGTGCTGACTCAGCCCGCCTCCGTGTCTGGGTC
TCCTGGACAGTCGATCACCATCTCCTGCACTGGAACCAGCAGTGACGTTGGTGCTTATAACTATG
TCTCCTGGTACCAACAACACCCAGGCAAAGCCCCCGAACTCATGATTTATGATGTCAGTAATCGG
CCCTCCGGGGTTTCTAATCGCTTCTCTGGCTCCAAGTCTGGCAACACGGCCTCCCTGACCATCT
CTGGGCTCCAGCCTGAGGACGAGGCTGATTATTACTGCAGCTCATTTACGACCAGCATCGCTTG
GGTGTTCGGCGGAGGGACCAAGCTGACCGTCCTAGGTCAGCCCAAGGCTGCCCCCTCGGTCAC
TCTGTTCCCGCCCTCCTCT (SEQ ID NO:476)

YU100-A11
GAGGTGCAGCTGCAGCAGTCGGGGGGGGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACAGCACCCAGGCAAAGCCCCCAAACTCATGATTTATGATGTCAGTAAGCG
GCCCTCAGGGGTCCCTGATCGCTTCTCTGGCTCCAAGTCTGGCAACACGGCCTCCCTGACCATC
TCTGGGCTCCAGGCTGAGGATGAGGCTGATTATTACTGCTGCTCATATGCAGGCAGCTACACTT
GGGTATTCGGCGGAGGGACCAAGCTGACCGTCCTAGGTCAGCCCAAGGCTGCCCCCTCGGTCA
CTCTGTTCCCACCCTCCTCT (SEQ ID NO:477)

YU100-A12
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACTGCCTGTGCTGACTCAGCCCGCTCAGTGTCCGGGTC
TCCTGGACAGTCAGTCACCATCTCCTGCACTGGAACCAGCAGTGATGTTGGTGGTTATAACTATG
TCTCCTGGTACCAACAGCACCCAGGCAAAGCCCCCAAACTCATGATTTATGATGTCAGTAAGCG
GCCCTCAGGGGTCCCTGATCGCTTCTCTGGCTCCAAGTCTGGCGACACGGCCTCCCTGACCATC
TCTGGGCTCCAGGCTGAGGATGAGGCTGATTATTACTGTTCCTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCGCCCTCCTCT (SEQ ID NO:478)

FIG. 51

YU100-B01
CAGGTGCAGCTGGTGCAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAACACTGATGTTGGTGCTTATAACTATG
TCTCCTGGTACCAACAGTACCCAGGCAAAGCCCCCAAACTCATCATTTATGATGTCAGTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGATTATTACTGCTGCTCATATGCAGGCAGCTACTCTTG
GGTGTTCGGCGGAGGGACCAAGCTGACCGTCCTAGGTCAGCCCAAGGCTGCCCCCTCGGTCAC
TCTGTTCCCGCCGTCCTCT (SEQ ID NO:479)

YU100-B03
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGTGCTGACTCAGCCCCGCTCAGTGTCCGGGTC
TCCTGGGCGGTCAGTCACCATCTCATGCACTGGAACCAGCAGTGATGTTGGTGGTTATAACTAT
GTCTCCTGGTACCAACAGCACCCAGGCAAGGCCCCCAAACTCACACTTTATGATGTCGTTAAGC
GGCCCTCAGGGGTCCCTGATCGCTACTCTGGCTCCAAGTCTGGCAACACGGCCTCCCTGACCAT
CTCTGGGCTCCAGGCTGAGGATGAGGCCGATTATTACTGCTGCTCATATGCAGGCGGCTACACT
TGGGTGTTCGGCGGAGGGACCAAGGTGACCGTCGTTGGTCAGCCCAAGGCTGCCCCCTCGGTC
ACTCTGTTCCCACCCTCCTCT (SEQ ID NO:480)

YU100-B06
CAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGAGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGTAGTGACGTTGGTGGTTATAACTATG
TCTCCTGGTACCAACAGCACCCAGGCAAAGCCCCCAAACTCATGATTTATGATGTCAGTAAGCG
GCCCTCAGGGGTCCCTGATCGCTTCTCTGGCTCCAAGTCTGGCAACACGGCCTCCCTGACCATC
TCTGGGCTCCAGGCTGAGGATGAGGCTGATTATTACTGCAACTCATATGCAGGCAGCTACACTT
GGGTGTTCGGCGGAGGGACCAAGCTGACCGTCCTAGGTCAGCCCAAGGCTGCCCCCTCGGTCA
CTCTGTTCCCACCCTCCTCT (SEQ ID NO:481)

FIG. 51 (Cont.)

YU100-B07
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATACGATGGAAGTAATAAATACTATGCAGACTCCG
TGAAGGGCCGATTCACCATCTCCAGAGACAATTCCAAGAACACGCTGTACCTGCAAATGAACAG
CCTGAGAGCTGAGGACACGGCTGTGTATTACTGTGCGAAAATAGGAGCTACTGACCCCCTTGAC
TACTGGGGCCAGGGAACCCTGGTCACCGTCTCCTCAGGGAGTGCATCCGCCCCAAAGCTTGAA
GAAGGTGAATTTTCAGAAGCACGCGTACAGTCTGCCCTGACTCAGCCTCGCTCAGTGTCCGGGT
CTCCTGGACAGTCAGTCACCATGTCCTGCACTGGAACCAGCAGAGATGTTGGTGGTTATAATTAT
GTCTCCTGGTACCAACATCACCCAGGCAAAGCCCCCAAACTCATGATTTATGATGTCAGTAAGCG
GCCCTCAGGGGTCCCTGATCGCTTCTCTGGCTCCAAGTCTGGCAACACGGCCTCCCTGACCATC
TCTGAGCTCCAGGCTGAGGATGAGGCTGATTATTACTGTTGCTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCACCCTCCTCT (SEQ ID NO:482)

YU100-B08
GAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGGCAGTCGATCACCATCTCCTGCACTGGAACCAGCAGTGACGTTGGTGGTTATAACTAT
GTCTCCTGGTACCAACAACACCCAGGCAAAGTCCCCAGACTCTTGATTTATGATGTCAGTAACCG
GCCCTCAGGGGTTTCTACTCGCTTCTCTGGCTCCAAGTCTGGCAACACGGCCTCCCTGACCATC
TCTGGGCTCCAGGGTGAGGACGAGGCTGAGTATTACTGCAGTTCATTTACGAGTAGTACCACTT
GGGTGTTCGGCGGAGGGACCAAGCTGACCGTCCTGGGTCAGCCCAAGGCTGCCCCCTCGGTC
ACTCTGTTCCCACCGTCCTCT (SEQ ID NO:483)

YU100-B09
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAGTGACGTTGGTGGTTATAACTATG
TCTCCTGGTACCAACAACACCCAGGCAAAGCCCCCAAACTTATGATTTATGATGTCAGTGATCGG
CCCTCAGGGGTTTCTAATCGCTTCTCTGGCTCCAAGTCTGGCAACACGGCCTCCCTGACCATCT
CTGGGCTCCAGCCTGAGGACGAGGCTGATTATTACTGCAGTTCATATAGAAGCGGCAGCACTTT
GGGTGTTCGGCGGAGGGACCAAGCTGACCGTCCTAGGTCAGCCCAAGGCTGCCCCCTCGGTCA
CTCTGTTCCCGCCCTCCTCT (SEQ ID NO:484)

FIG. 51 (Cont.)

YU100-B12
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGACCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGAACCAGCAGTGATGTT
GGTGGTTATAACTATGTCTCCTGGTACCAACAGCACCCAGGCAAAGCCCCCAAACTCATGATTTA
TGATGTCAGTAAGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CAGGCAGCTACACTTGGGTGTTCGGCGGAGGGACCAAGCTGACCGTCCTAGGTCAGCCCAAGG
CTGCCCCCTCGGTCACTCTGTTCCCACCCTCCTCT (SEQ ID NO:485)

YU100-C02
CAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCCGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTAATGTTGGTGGTTATAACTATG
TCTCCTGGTACCAACAGCACCCAGGCAAAGCCCCCAAACTCATGATTTATGATGTCAGTAAGCG
GCCCTCAGGGGTCCCTGATCGCTTCAGTGGCTCCAAGTCTGGCAACACGGCCTCCCTGACCATC
TCTGGGCTCCAGGCTGAGGATGAGGCTGATTATTACTGCTGCTCATATGCAGGCAGCTACGTTT
GGGTGTTCGGCGGAGGGACCAAGCTGACCGTCCTCGGTCAGCCCAAGGCTGCCCCCTCGGTCA
CTCTGTTCCCGCCGTCCTCT (SEQ ID NO:486)

YU100-C04
CAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
TTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACACCACCCAGGCAAAGCCCCCAAACTCATAATTTATGATGTCACTAAGCGG
CCCTCAGGGGTCCCTGATCGCTTCTCTGGCTCCAAGTCTGGCAACACGGCCTCCCTGGCCATCT
CTGGGCTCCAGGCTGAGGAAGAGGCTGATTATTACTGCTGCTCATATGCAGGCGGGTACACTTG
GGTGTTCGGCGGAGGGACCAAGCTGACCGTCCTAGGTCAGCCCAAGGCTGCCCCCTCGGTCAC
TCTGTTCCCGCCGTCCTCT (SEQ ID NO:487)

FIG. 51 (Cont.)

YU100-C05
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAGTGACGTTGGGGGTTATAATTAT
GTCTCCTGGTATCAACAACACCCAGGCAAAGCCCCCAAACTCATGATTTATGATGTCAGTAATCG
GCCCTCAGGGATTTCTAATCGCTTCTCTGGCTCCAAGTCTGGCAACACGGCCTCCCTGACCATC
TCTGGGCTCCAGGCTGAGGACGAGGCTGATTATTACTGCAGCTCATACACAAGCAGCATTTCTT
GGGTGTTCGGCGGAGGGACCAAACTGACCGTCCTAGGTCAGCCCAAGGCTGCCCCCTCGGTCA
CTCTGTTCCCGCCCTCCTCT (SEQ ID NO:488)

YU100-C10
CAGGTGCAGCTGGTGGAGTCGGGGGGAGGCGTGGTCCAGCCTGGGAGGTCCCTGAGACTCTC
CTGTGCAGCCTCTGGATTCACCTTCGGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGATCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCCGCAGTGACATTGGTGGTTATGACTAT
GTCTCCTGGTATCAACAGCACCCAGGCAAAGCCCCCAAACTCATGATTTATGACGTCAATAATCG
GCCCTCAGGGGTTTCTAATCGCTTCTCTGGCTCCAAGTCTGGCAACACGGCCTCCCTGACCATC
TCTGGGCTCCAGGCTGAGGACGAGGCTGAGTATTACTGCTCCTCATATACAAGCAGCATCACTT
GGGTGTTCGGCGGAGGGACCAAGGTGACCGTCCTAGGTCAGCCCAAGGCTGCCCCCTCGGTCA
CTCTGTTCCCACCCTCCTCT (SEQ ID NO:489)

YU100-C11
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAGTGACGTTGGTGGTTATAACTATG
TCTCCTGGTACCAACAGCGCCCAGGCAAGGCCCCCAAACTCATGATTTATGATGTCAGTAATCG
GCCCTCAGGGGTTTCTAATCGCTTCTCTGGCTCCAAGTCTGGCAACACGGCCTCCCTGACCATC
TCTGGGCTCCAGCCTGACGACGAGGCTGATTATTACTGCAGCTCATATACAAACAGCAGGACTT
GGGTGTTCGGCGGAGGGACCAAGTTGACCGTCCTAAGTCAGCCCAAGGCTGCCCCCTCGGTCA
CTCTGTTCCCACCGTCCTCT (SEQ ID NO:490)

FIG. 51 (Cont.)

YU100-C12
GAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGAACCAGCAGTGATGTT
GGTGGTTATAACTATGTCTCCTGGTACCAACAGCACCCAGGCAAAGCCCCCAAACTCATGATTTA
TGATGTCAGTAAGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CAGGCAGCTACACTTGGGTGTTCGGCGGAGGGACCAAGCTGACCGTCCTAGGTCAGCCCAAGG
CTGCCCCCTCGGTCACTCTGTTCCCACCGTCCTCT (SEQ ID NO:491)

YU100-D01
CAGGTGCAGCTGCAGCAGTCGGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCC
CTCCGCGTCCGGGTCTCCTGGACAGTCAGTCACCATCTCCTGCACTGGAACCAGCAGTGATGTC
GGTGGTTACAACTTTGTCTCCTGGTATCAACAACACCCCGGCAAAGCCCCCAAACTCTTGATTTA
TGATGTCGATAAGCGGCCCTCAGGGGTCCCTGATCGCTTCTCTGGCTCCAAGTCTGGCAGAACG
GCCTCCCTGACCATCTCTGGGCTCCAGACTGAGGATGAGGCTAAATATTATTGCTGCTCATATGC
AGGCAGGTACACTTGGATATTCGGCGGAGGGACCAAGCTGACCGTCCTCGGTCAGCCCAAGGC
TGCCCCCTCGGTCATTCTGTTCCCACCGTCCTCT (SEQ ID NO:492)

YU100-D02
CAGGTGCGGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCGGTGATGTTGGTACTTATAACTATG
TCTCCTGGTACCAACAACACCCAGGCAAAGCCCCCAAACTCATGATTTTTGATGTCAGTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGATTATTGCAACTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCACCCTCCTCT (SEQ ID NO:493)

FIG. 51 (Cont.)

YU100-D05
CAGGTGCAGCTGCAGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTTGATCACCATCTCCTGCACTGGAACCAACAGTGACGTTGGTGGTTATAACTATG
TCTCCTGGTACCAACAACACCCAGGCAAAGCCCCCAAACTCATGATTTATGATGTCAGTAATCGG
CCCTCAGGGGTTTCTAATCGCTTCTCTGGCTCCAAGTCTGGCAACACGGCCTCCCTGACCATCT
CTGGGCTCCAGGCTGAGGATGAGGCTGATTATTACTGCTGCTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCACCGTCCTCT (SEQ ID NO:494)

YU100-D07
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGACTCACCATCTCCAGAGACAATTCCAAGAACACGCTGTATCTGCAAATGAACAG
CCTGAGAGCTGAGGACACGGCTGTGTATTACTGTGCGAGAATCATGGGCTATGACTACGGTGAC
TACGACGTAGTTGACTACTGGGGCCAGGGAACCCTGGTCACCGTCTCCTCAGGGAGTGCATCC
GCCCCAAAGCTTGAAGAAGGTGAATTTTCAGAAGCACGCGTACAGTCTGCCCTGACTCAGCCTC
GCTCAGTGTCCGGGTCTCCTGGACAGTCAGTCACCATCTCCTGCACTGGAACCAGCGGTGATGT
TGGTACTTATGACTATGTCTCCTGGTACCAACAGCACCCAGGCAAAGCCCCCAAACTCATGATTT
ATGATGTCAGTAAGCGGCCCTCAGGGGTCCCTGATCGCTTCTCTGGCTCCAAGTCTGGCAACAC
GGCCTCCCTGACCATCTCTGGGCTCCAGGCTGAGGATGAGGCTGATTATTACTGCAACTCATAT
GCAGGCAGCTACACTTGGGTGTTCGGCGGAGGGACCAAGCTGACCGTCCTAGGTCAGCCCAAG
ACTGCCCCCTCGGTCACTCTGTTCCCGCCCTCCTCT (SEQ ID NO:495)

YU100-D11
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTAATGTTGGTGGTTATAACTATG
TCTCCTGGTACCAACAGCACCCAGGCAAAGCCCCCAAACTCATGATTTATGATGTCAGTAAGCG
GCCCTCAGGGGTCCCTGATCGCTTCTCTGGCTCCAAGTCTGGCAACACGGCCTCCCTGACCATC
TCTGGGCTCCAGGCTGAAGATGAGGCTAATTATTACTGCGCCTCATATGCAGGCAACTACAATTG
GGTGTTCGGCGGAGGGACCAAGCTGACCGTCCTTGGTCAGCCCAAGGCTGCCCCCTCGGTCAC
TCTGTTCCCACCCTCCTCT (SEQ ID NO:496)

FIG. 51 (Cont.)

YU100-E01
CAGGTGCAGCTGCAGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAATGACATAGGTGCTTATAACTATG
TCTCCTGGTACCAACAACACCCAGGCAAAGCCCCCAAACTCCTGATTTATGATGTCAATAATCGG
CCCTCAGGGGTTTCTGATCGCTTCTCTGGCTCCAAGTCTGGCAACACGGCCTCCCTGACCATCT
CTGGGCTCCAGGCTGAGGATGAGGCTGATTATTACTGCTGCTCATATGCAGGCAGCTACTCTTG
GGTGTTCGGCGGAGGGACCAAACTGACCGTCCTAGGTCAGCCCAAGGCCAACCCCACTGTCAC
TCTGTTCCCACCCTCCTCT (SEQ ID NO:497)

YU100-E04
CAGGTGCAGCTGCAGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACAACACCCAGGCAAAACCCCCAAACTCATGATTTATGATGTCACTAAGCGG
CCCTCAGGGGTCCCTGATCACTTCTCTGGCTCCAAGTCTGGCAACACGGCCTCCCTGACCATCT
CTGGGCTCCAGGCTGAGGATGAGGCTGATTATTACTGCTGCTCATATGCAGGCAGTCACATTTG
GGTGTTCGGCGGAGGGACCAAGTTGACCGTCCTAGGTCAGCCCAAGGCTGCCCCTCGGTCAC
TCTGTTCCCGCCCTCCTCT (SEQ ID NO:498)

YU100-E05
GAGGTGCAGCTGGTGCAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGGCTGTGCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACAGCACCCAGGCAAAGCCCCCAAACTCATGATTTATGATGTCAGTAAGCG
GCCCTCAGGGGTCCCTGATCGCTTCTCTGGCTCCAAGTCTGGCAACACGGCCTCCCTGACCATC
TCTGGGCTCCAGGCTGAGGATGAGGCTGATTATTACTGCTGCTCATATGCAGGCAGCTACTCCT
GGGTGTTCGGCGGAGGGACCAAGCTGACCGTCCTAGGTCAGCCCAAGGCTGCCCCTCGGTCA
CTCTGTTCCCGCCCTCCTCT (SEQ ID NO:499)

FIG. 51 (Cont.)

YU100-E06
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTT
TCCTGAACAGTCGATCACCATCTCCTGCACTGGAACCAGCAGTGACGTTGGTGGTTATGACTATG
TCTCCTGGTACCAACAACACCCAGGCAAAGCCCCCAAACTCATGATTTATGATGTCACTAATCGG
CCCTCAGGGGTTTCTAATCGCTTCTCTGGCTCCAAGTCTGGCAACACGGCCTCCCTGACCATCT
CTGGCCTCCAACCTGAGGACGAGGCTGATTATTATTGCAGCTCATATACAAGCAACACCACTTGG
GTGTTCGGCGGAGGGACCAAGCTGACCGTCCTACGTCAGCCCAAGGCTGCCCCCTCGGTCACT
CTGTTCCCACCGTCCTCT (SEQ ID NO:500)

YU100-E07
CAGGTGCAGCTGCAGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAGATACTATGCAGACTCCG
TGAAGGGCCGATTCGCCATCTCCAGAGACAATTCCAAGAACACGCTGTACCTGCAAATGAACAG
CCTGAGAGCTGAGGACACGGCTGTGTATTACTGTGCGAAAATAGGAGCTACTGACCCCCTTGAC
TACTGGGGCCAGGGAACCCTGGTCACCGTCTCCTCAGGGAGTGCATCCGCCCCAAAGCTTGAA
GAAGGTGAATTTTCAGAAGCACGCGTACAGTCTGCCCTGACTCAGCCTCGCTCAGTGTCCGGGT
CTCCTGGACAGTCAGTCACCATCTCCTGCACTGGAACCAGCAGTGATGTTGGTGGTTATGACTAT
GTCTCCTGGTACCAACAGCACCCAGGCAAAGCCCCGAACTCATGATTTATGATGTCACTAAGC
GGCCCTCAGGGGTCGCTGATCGCTTCTCTGGCTCCAAGTCTGGCAACACGGCCTCCCTGACCAT
CTCTGGGCTCCAGGCTGAGGATGAGGCTGATTATTACTGCTGCTCATATGCAGGCAGGTACACT
TGGGTGTTCGGCGGAGGGACCAAGCTGACCGTCCTAGGTCAGCCCAAGGCTGCCCCCTCGGTC
ACTCTGTTCCCACCCTCCTCT (SEQ ID NO:501)

YU100-E08
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGAACCAGCAGTGATGTT
GGTGGTTATAACTATGTCTCCTGGTACCAACAGCACCCAGGCAAAGCCCCCAAACTCATGATTTA
TGATGTCAGTAGGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CAGGCAATTACACTTGGATGTTCGGCGGAGGGACCAAGCTGACCGTCCTAGGTCAGCCCAAGG
CTGCCCCCTCGGTCACTCTGTTCCCACCGTCCTCT (SEQ ID NO:502)

FIG. 51 (Cont.)

YU100-E09
CAGGTGCAGCTGGTGGAGTCGGGGGGAGGCGTGGTCCAGCCTGGGAGGTCCCTGAGACTCTC
CTGTGCAGCCTCTGGGTTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGAACCAGCAGTGATGTT
GGTGATTATGACTATGTCTCCTGGTACCAACAACACCCAGGCAAAGCCCCCAAACTCATTATTTA
TGATGTCACTAAACGGCCCTCAGGGATCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CAGGCAGTTACACTTGGGTGTTCGGCAGAGGGACCAAGCTGACCGTCCTAGGTCAGCCCAAGG
CTGCCCCCTCGGTCACTCTGTTCCCACCCTCCACT (SEQ ID NO:503)

YU100-E10
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACAACACCCAGGCAAAGCCCCCAAACTCATGATTTTTGATGTCAGTCAGCGG
CCCTCAGGGGTCCCTGATCGCTTCTGCCTCCAAGTCCGGCAACACGGCCTCCCTGACCATCT
CTGGGCTCCAGGCTGAGGATGAGGCTGATTATTACTGCTGCTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCACCCTCCTCT (SEQ ID NO:504)

YU100-E11
CAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGAACCAGCAGTGATGTT
GGTGGTTATAACTATGTCTCCTGGTACCAACAGCACCCAGGCAAAGCCCCCAAACTCATGATTTA
TGATGTCAGTAAGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CAGGCAGCTACACTTGGGTGTTCGGCGGAGGGACCAAGCTGACCGTCCTAGGTCAGCCCAAGG
CTGCCCCCTCGGTCACTCTGTTCCCACCCTCCTCT (SEQ ID NO:505)

FIG. 51 (Cont.)

YU100-E12
CAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAGTGACGTTGGTGGTTATAACTATG
TCTCCTGGTACCAACAGCACCCAGGCACAGCCCCCAAACTCATGATTTATGATGTCAGTAATCGG
CCCTCAGGGGTTTCTAATCGCTTCTCTGGCTCCAAGTCTGGCAACACGGCCTCCCTGACCATCT
CTGGGCTCCAGGCTGAGGACGAGGCTGATTATTACTGCAGCTCATATACAAGCAGCACCACTTG
GGTGTTCGGCGGAGGGACCAAGCTGACCGTCCTAGGTCAGCCCAAGGCTGCCCCCTCGGTCAC
TCTGTTCCCGCCCTCCTCT (SEQ ID NO:506)

YU100-F01
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCGGCAGTGACGTTGGTGCTTATGACTAT
GTCTCCTGGTACCAACAACACCCAGGCAAAGCCCCCAAACTCATGATTTATGATGTCAATAATCG
GCCCTCAGGAGTTTCTAATCGCTTCTCTGGCTCCAAGTCTGGCAACACGGCCTCCCTGACCATC
TCTGGGCTCCAAGCTGAGGACGAGGCTGAATATTACTGCAGTTCATTTGCAACTAGCATTTCTTG
GGTGTTCGGCGGAGGGACCAGACTGACCGTCCTAGGTCAGCCCAAGGCTGCCCCCTCGGTCAC
TCTGTTCCCGCCCTCCTCT (SEQ ID NO:507)

YU100-F02
GAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACAGCACCCAGGCAAAGCCCCCAAACTCATGATTTATGATGTCACTAAGCGG
CCCTCAGGGGTCCCTGATCGCTTCTCTGGCTCCAAGTCTGGCAACACGGCCTCCCTGACCATCT
CTGGGCTCCAGGCTGACGATGAGGCTGATTATTACTGCTGCTCATATGCAGGCAGCTACACTTG
GATATTCGGCGGAGGGACCAAGCTGACCGTCCTAGGTCAGCCCAAGGCTGCCCCCTCGGTCAC
TCTGTTCCCACCCTCCTCT (SEQ ID NO:508)

FIG. 51 (Cont.)

YU100-F05
CAGGTGCAGCTGCAGCAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGGCCGTGCTGACTCAGCCCGCCTCCGTGTCTGGGTC
TCCTGGACAGTCGATCACCATTTCCTGCACTGGAACCAGCAGTGACATTGGTGGTTATAACTATG
TCTCCTGGTACCAGCAACACCCAGGCACAGCCCCCAAACTCATGATTTATGATGTCAGTAGTCG
GCCCTCAGGGGTTTCTAATCGCTTCTCTGGCTCCAAGTCTGGCAACACGGCCTCCCTGACCATC
TCTGGGCTCCAGGCTGAGGACGAGGCTGATTATTACTGCTGCTCATATGCAGGCAGTTACACTT
GGGTGTTCGGCGGAGGGACCAAGATGACCGTCCTGGGTCAGCCCAAGGCTGCCCCCTCGGTCA
CTCTGTTCCCACCCTCCTCT (SEQ ID NO:509)

YU100-F06
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGATCCAGCAGTGATGTT
GGTGGTTATAACTTTGTCTCCTGGTACCGACAACACCCAGGCGAAGCCCCCAAACTCGTGATTTT
TGATGTCAATAAGCGGCCCTCAGGGGTCCCTGATCGCTTCTCTGGCTCCAAGTCTGGCAACACG
GCCTCCCTGACCATCTCAGGGCTGCAAACTGAGGATGAGGCTGATTATTTCTGCTGCTCATATGC
AGGCGGCTACACTTGGGTGTTCGGCGGAGGGACCAAGGTGACCGTCGTTGGTCAGCCCAAGGC
TGCCCCCTCGGTCACTCTGTTCCCACCCTCCTCT (SEQ ID NO:510)

YU100-F07
CAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGTGTCTCCTGGACAGTCAGTCACCATCTCCTGCACTGGAACCAGCAGTGACGTT
GGCGGTTATGAATATGTCTCCTGGTACCAACAACACCCAGGCAAAGCCCCCAAACTCATGATTTA
TGATGTCACTAAGAGGCCCTCAGGGGTCCCTGATCGCTTCTCTGGCTCCAAGTCTGGCAACACG
GCCTCCCTGACCATCTCTGGGCTCCAGGGTGAAGATGCGGCTGATTATTACTGCTGTTCATATG
CAGGCTCTTACACTTGGGTATTCGGCGGAGGCACCACGGTGACCGTCCTAGGTCAGCCCAAGG
CTGCCCCCTCGGTCACTCTGTTCCCACCGTCCTCT (SEQ ID NO:511)

FIG. 51 (Cont.)

YU100-F11
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGGAGCAGTAGTGACGTTGCTGGTTATAACTATG
TCTCCTGGTACCAACAGCACCCAGGCAAAGCCCCCAAACTCATGATTTATGATGTCACTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGATTATTACTGCTGCTCATATGCAGGCAGTTACACTTG
GGTTTTCGGCGGAGGGACCCAGCTGACCGTCCTAGGTCAGCCCAAGGCTGCCCCTCGGTCAC
TCTGTTCCCGCCGTCCTCT (SEQ ID NO:512)

YU100-G01
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGCGTC
TCCTGGACAGTCAGTCACCATCTCCTGCACTGGAACCAGCAGTGATGTTGGTGCTTATAACTATG
TCTCCTGGTACCAACAACACCCGGCAAAGCCCCCAAACTCATGCTTTATGATGTCAATAAGCGG
CCCTCAGGGGTCCCTGATCGCTTCTCTGGCTCCAAGTCTGGCAACACGGCCTCCCTGACCATCT
CTAGGCTCCAGGCTGAGGATGAGGCTGATTATTACTGCTGCTCATATGCAGGCAGCTACACTTG
GGTGTTCGGCGGAGGGACCAAGCTGACCGTCCTAGGTCAGCCCAAGGCTGCCCCTCGGTCAC
TCTGTTCCCGCCCTCCTCT (SEQ ID NO:513)

YU100-G07
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAGTGACGTTGGTGCTTATGACTAT
GTCTCCTGGTATCAACAACACCCAGGCAAAGCCCCCAAACTCATGATTTATGATGTCACTAATCG
GCCCTCAGGGGTTTCTAATCGCTTCTCTGGCTCCAAGTCTGGCAACACGGCCTCCCTGACCATC
TCTGGGCTCCAGGCTGAGGACGAGGCTGATTATTACTGCGCCTCATACACACGCAGCAGCGTTT
GGGTGTTCGGCGGAGGGACCAAACTGACCGTCTTAGGTCAGCCCAAGGCTGCCTCCTCGGTCA
CTCTGTTCCCACCCTCCTCT (SEQ ID NO:514)

FIG. 51 (Cont.)

YU100-G08
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCCTCCTGTACTGGAACCAGCAGTGATGTTGGTGGTTATAACTATG
TCTCCTGGTACCAACACTACCCAGGCAAAGCCCCCAAACTCATGATTTTTGATGTCAATGAGCGG
TCCTCAGGAGTCCTGATCGCTTCTCTGGCTCCAAGTCTGGCAACACGGCCTCCCTGACCATCT
CTGGGCTCCAGGCTGAGGATGAGGCTGATTATTACTGCTGCTCATATGCAGGCAGGTACACTTG
GATGTTCGGCGGAGGGACCAAAGTGACCGTCCTAGGTCAGCCCAAGGCTGCCCCTCGGTCAC
TCTGTTCCCGCCCTCCTCT (SEQ ID NO:515)

YU100-G09
GAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCATCAGTGATGTTGGTGGTTATAACTATG
TCTCCTGGTACCAACAGCACCCAGGCAAAGCCCCCAAACTCATGATTTATGATGTCACTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGGTTATTACTGCTCCTCATATGCAGGCAGCTACACTTG
GGTGTTCGGCGGAGGGACCAAGCTGACCGTCCTAGGTCAGCCCAAGGCTGCCCCTCGGTCAC
TCTGTTCCCACCCTCCTCT (SEQ ID NO:516)

YU100-G10
CAGGTGCAGCTGGTGCAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGT
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCTTGGACAGTCGATCACCATGTCCTGCACTGGAACCAGAAGAGACGTTGGTGGTTATGACTTTG
TCTCCTGGTACCAACAGTACCCCGGCAAAGCCCCCAAGCTCATCATTTACGATGTCAGCAATCG
GCCCTCGGGGGTTTCTAATCGCTTCACTGGCTCCAAGTCTGGCAACACGGCCTCCCTGACCATC
TCTGGGCTCCAGGCTGAGGATGAGGCTGATTATTACTGCTGCTCATATGCAGGCACCTACACTT
GGGTGTTCGGCGGAGGGACCAAGGTGACCGTCCTAGGTCAGCCCAAGGCTGCCCCTCGGTCA
CTCTGTTCCCGCCCTCCTCT (SEQ ID NO:517)

FIG. 51 (Cont.)

YU100-G11
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGGCAGTCAGTCACCATCTCATGCACTGGAACCAGCAGTGATGTT
GGTGGTTATAACTATGTCTCCTGGTACCAACAGCACCCAGGCAAGGCCCCCAAACTCACGCTTT
ATGATGTCGGTAAGCGGCCCTCAGGGGTCCCTGATCGCTTCTCTGGCTCCAAGTCTGGCAACAC
GGCCTCCCTGACCATCTCTGGGCTCCAGGCTGAGGATGAGGCTGATTATTACTGCTGCTCATAT
GCAGGCGGCTACACTTGGGTGTTCGGCGGAGGGACCAAGGTGACCGTCGTAGGTCAGCCCAAG
GCTGCCCCCTCGGTCACTCTGTTCCCACCCTCCTCT (SEQ ID NO:518)

YU100-H01
CAGGTGCAGCTGGTGCAGTCGGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGAACCAGCAGTGATGTT
GGTGCTTATAACTATGTCTCCTGGTACCAGCAGCACCCAGGCAAAGCCCCCAAACTCATGATTTA
TGATGTCAGTGAGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CAGGCAGCTACACTTGGGTGTTCGGCGGAGGGACCAAGCTGACCGTCCTAGGTCAGCCCAAGG
CTGCCCCCTCGGTCACTCTGTTCCCACCGTCCTCT (SEQ ID NO:519)

YU100-H02
CAGGTGCAGCTGCAGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCAGGTCTCCTGGACAGTCAGTCACCATCTCCTGCACTGGAACCAGCAGTGATGTT
GGTACTTATAACTATGTCTCCTGGTACCAACAGCACCCAGGCAAAGCCCCCAAACTCATGATTTA
TGATGTCAGTAAGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CAGGCTTCTACACTTGGGTGTTCGGCGGAGGGACCAAGCTGACCGTCCTAGGTCAGCCCAAGG
CTGCCCCCTCGGTCACTCTGTTCCCACCGTCCTCT (SEQ ID NO:520)

FIG. 51 (Cont.)

YU100-H04
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTGC
CTCCGTGTCTGGGTCTCCTGGACAGTCGATCACCATCTCCTGCACGGGAACCAGCAGTGACATT
GGTGTTTATAACTATGTCTCCTGGTACCAACAGCACCCAGGCAAAGCCCCCAAACTCATGATTTA
TGATGTCAGTAAGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGATTATTACTGCTGCTCATATG
CGGGCAGCTACACCTGGGTGTTCGGCGGAGGGACCAAGCTGACCGTCCTAGGTCAGCCCAAGG
CTGCCCCCTCGGTCACTCTGTTCCCGCCCTCCTCT (SEQ ID NO:521)

YU100-H05
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGGCTGTGCTGACTCAGCCTCGCTCAGTGTCCGGGTC
TCCTGGACAGTCAATCACCATCTCCTGCACTGGAACCGGCAGTAATGTTGGTGGTTATAACTATG
TCTCCTGGTATCAACAACACCCAGGCCAAGCCCCCAAACTCATGATTTATGATGTCAGTAAGAGG
CCCTCAGGGGTCCCTGATCGCTTCTCTGGCTCCAAGTCTGGCAACACGGCCTCCCTGACCATCT
CTGGGCTCCAGGCTGAGGATGAGGCTGATTATTATTGCTGCTCATATGCAGGCACCTACACTTG
GGTGTTCGGCGGAGGGACCAAGCTGACCGTCCTAGGTCAGCCCAAGGCTGCCCCCTCGGTCAC
TCTGTTCCCACCCTCCTCT (SEQ ID NO:522)

YU100-H06
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGNATACAGTCTGCCCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACAGCACCCAGGCAAAGCCCCCAAATTGATGATTTATGATGTCACTAAGCGG
CCCTCAGGGGTCCCTGATCGCTTCTCTGGCTCCAAGTCTGGCAACACGGCCTCCCTGACCATCT
CTGGGCTCCAGGCTGAAGATGAGGCTGATTATTATTGCTCCTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCACCCTCCTCT (SEQ ID NO:523)

FIG. 51 (Cont.)

YU100-H09
CAGGTGCAGCTGGTGCAGTCGGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGATTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTGC
CTCCGTGTCTGGGTCTCCTGGACAGTCGATCACCATCTCCTGCACTGGAACCAGCAGTGACGTT
GGTGGTTATAACTATGTCTCCTGGTACCAACAGCACCCAGGCAAAGCCCCCAAACTCATGATTTA
TGATGTCAGTAATCGGCCCTCAGGGGTTTCTAATCGCTTCTCTGGCTCCAAGTCTGGCAACACG
GCCTCCCTGACCATCTCTGGGCTCCAGGCTGAGGACGAGGCTGATTATTACTGCTGTTCATATG
CAGGCAGCTACACTTGGGTGTTCGGCGGAGGGACCAAGCTGACCGTCCTAGGTCAGCCCAAGG
CTGCCCCCTCGGTCACTCTGTTCCCGCCGTCCTCT (SEQ ID NO:524)

YU100-H11
CAGGTGCAGCTGGTGCAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAGTGACGTTGGTGGTTATAACTATG
TCTCCTGGTACCAACAACACCCAGGCAAAGCCCCCAAACTCATGATTTATGATGTCAGTAATCGG
CCCTCAGGGGTTTCTAATCGCTTCTCTGGCTCCAAGTCTGGCAACACGGCCTCCCTGACCATCT
CTGGGCTCCAGGCTGAGGATGAGGCTGATTATTACTGCTGCTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCACCCTCCTCT (SEQ ID NO:525)

YU112-A07
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATACAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCATCAGTGATGTTGGTGGTTATAACTATG
TCTCCTGGTACCAACAGCACCCAGGCAAAGCCCCCAAACTCATGATTTATGATGTCACTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGGTTATTACTGCTCCTCATATGCAGGCAGCTACACTTG
GGTGTTCGGCGGAGGGACCGAGCTGACCGTCCTGAGTCAGCCCAAGGCTGCCCCCTCGGTCAC
TCTGTTCCCGCCCTCCTCT (SEQ ID NO:526)

FIG. 51 (Cont.)

YU112-B06
CAGGTGCAGCTGGTGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTGCCTCCGTGTCTGGGTC
TCCTGGACAGTCGATCACCATCTCCTGCACTGGAACCAGCAGTGACGTTGGTGGTTATAACTATG
TCTCCTGGTACCAACAGCACCCAGGCAAAGCCCCCAAACTCATGATTTATGATGTCAGTAATCGG
CCCTCAGGGGTTTCTAATCGCTTCTCTGGCTCCAAGTCTGGCAACACGGCCTCCCTGACCATCTT
TGGGCTCCAGGCTGAGGACGAGGCTGATTATTACTGCAGCTCATATACAAGCAGTAGCAGTTGG
GTGTTCGGCGGAGGGACCAAGCTGACCGTCCTAGGTCAGCCCAAGGCTGCCCCCTCGGTCACT
CTGTTCCCGCCCTCCTCT (SEQ ID NO:527)

YU112-C03
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAAGGGGGGAAGAGCTACTACGGATTTG
ACTACTGGGGCCAGGGAACCCTGGTCACCGTCTCCTCAGGGAGTGCATCCGCCCCAAAGCTTG
AAGAAGGTGAATTTTCAGAAGCACGCGTAGACAGCGTGATGACCCAGTCTCCATCCTCCCTGTC
TGCATCTGTAGGGGACAGAGTCACCATCACTTGCCGGGCAAGTCAGGCCATTAACAGCTATTTA
AATTGGTATCAGCAGAAACCAGGGAAAGCCCCTAAGCTCCTGATCTATGCTGCATCCAGTTTGCA
GAGTGGGGTCCCATCAAGGTTCAGTGGCAGTGGATCTGGGACAGATTTCACTCTCACCATCAGC
GGTCTGCAACCTGAAGATTTTGCAACTTACTACTGTCAACAGAGTTACAGTACCCCTTCGTGGAC
GTTCGGCCAAGGGACCAAGGTGGAAATCAAACGAACTGTGGCTGCACCATCTGTC (SEQ ID
NO:528)

YU112-C05
GAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGCTATGCACTGGGTCCGCCAGGCTCCAGGC
AAGGGGCTGGAGTGGGTGGCAGTTATATCATATGATGGAAGCAATAAATACTACGCAGACTCCG
TGAAGGGCCGATTCACCATCTCCAGAGACAATTCCAAGAACACGCTGTATCTGCAAATGAACAGC
CTGAGAGCTGAGGACACGGCTGTGTATTACTGTGCGAGAATCATGGGCTATGACTACGGTGACT
ACGACGTAGTTGACTACTGGGGCCAGGGAACCCTGGTCACCGTCTCCTCAGGGAGTGCATCCG
CCCCAAAGCTTGAAGAAGGTGAATTTTCAGAAGCACGCGTACAGTCTGCCCTGACTCAGCCTCG
CTCAGTGTCCGGGTCTCCTGGACAGTCAGTCACCATCTCCTGCACTGGAACCATCAGTGATGTT
GGTGGTTATAACTATGTCTCCTGGTACCAACAGCACCCAGGCAAAGCCCCCAAACTCATGATTTA
TGATGTCACTAAGCGGCCCTCAGGGGTCCCTGATCGCTTCTCTGGCTCCAAGTCTGGCAACACG
GCCTCCCTGACCATCTCTGGGCTCCAGGCTGAGGATGAGGCTGGTTATTACTGCCTCATATG
CAGGCAGCTACACTTGGGTGTTCGGCGGAGGGACCGAGCTGACCGTCCTGAGTCAGCCCAAGG
CTGCCCCCTCGGTCACTCTGTTCCCGCCCTCCTCT (SEQ ID NO:529)

FIG. 51 (Cont.)

YU112-C09
CAGGTGCAGCTGGTGCAGTCTGGGGGAGGCGTGGTCCAGCCTGGGAGGTCCCTGAGACTCTC
CTGTGCAGCCTCTGGATTCACCTTCGGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAAGGTTCGTACTACTTTGACTACTGGG
GCCAGGGAACCCTGGTCACCGTCTCCTCAGGGAGTGCATCCGCCCCAAAGCTTGAAGAAGGTG
AATTTTCAGAAGCACGCGTAGAAACGACACTCACGCAGTCTCCAGCCACCCTGTCTGTGTCTCCA
GGGGAAAGAGCCACCCTCTCCTGCAGGGCCAGTCAGAGTTTTAGCAGCAGCTACTTAGCCTGGT
ACCAGCAGAAACCTGGCCAGGCTCCCAGGCTCCTCATCTATGGTGCATCCAGAAGAGCCCTG
GCATCCCAGACAGGTTCAGTGGCAGTGGGTCTGGGACAGACTTCAGTCTCACCATCAGCAGACT
GGAGCCTGAAGATTTTGCAGTGTATTACTGTCAGCAGTCTAGCACCTCACCCACGTGGGCGTTC
GGCCGAGGGACCAAGGTGGAAGTCAAACGAACTGTGGCTGCACCATCTGTC (SEQ ID NO:530)

YU112-D08
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GGAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCATCAGTGATGTTGGTGGTTATAACTATG
TCTCCTGGTACCAACAGCACCCAGGCAAAGCCCCCAAACTCATGATTTATGATGTCACTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGGTTATTACTGCTCCTCATATGCAGGCAGCTACACTTG
GGTGTTCGGCGGAGGGACCGAGCTGACCGTCCTGAGTCAGCCCAAGGCTGCCCCCTCGGTCAC
TCTGTTCCCGCCCTCCTCT (SEQ ID NO:531)

YU112-E07
CAGGTGCAGCTGGTGCAGTCGGGGGGAGGCGTGGTCCAGCCTGGGAGGTCCCTGAGACTCTC
CTGTGCAGCCTCTGGATTCACCTTCGGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAAGGTTCGTACTACTTTGACTACTGGG
GCCAGGGAACCCTGGTCACCGTCTCCTCAGGGAGTGCATCCGCCCCAAAGCTTGAAGAAGGTG
AATTTTCAGAAGCACGCGTAGAAATTGTGATGACTCAGTCTCCAGACTCCCTGGCTGTGTCTCTG
GGCGAGAGGGCCACCATCAACTGCAAGTCCAGCCAGAGTGTTAACAGCGCCTACTTAGCCTGGT
ACCAGCACAAACCTGGCCAGCCTCCCAGACTCCTCATTTATGGTGCATCTCGCAGGGTCACTGG
CGTCCCAGACAGGTTCAGTGGCAGTGGGTCTGGGACAGACTTCACTCTCACCATCAGCAGTCTG
CAACCAGAAGATTTTGCAACTTACTACTGTCAACAGAGTTACAGTGACCCTCGGTGGACGTTCGG
CCAAGGGACCAAGGTGGAAATCAAACGAACTGTGGCTGCACCATCTGTC (SEQ ID NO:532)

FIG. 51 (Cont.)

YU112-E08
TAGGTCACCTTGAAGGAGTCTGGGGGAGGCGTGGTCCAGCCTGGGAGGTCCCTGAGACTCTCC
TGTGCAGCCTCTGGATTCACCTTCAGTAGCTATGGCATGCACTGGGTCCGCCAGGCTCCAGGCA
AGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAAGGGGGGAAGAGCTACTACGGATTTG
ACTACTGGGGCCAGGGAACCCTGGTCACCGTCTCCTCAGGGAGTGCATCCGCCCCAAAGCTTG
AAGAAGGTGAATTTTCAGAAGCACGCGTAGACATCCAGATGACCCAGTCTCCATCCTTCCTGTCT
GCATCTGTAGGAGACAGAGTCACCATCACTTGCCGGGCAAGTCAGATCATTAGCAGCTATTTAAA
TTGGTATCAGCAGAAACCAGGGAAAGCCCCTAAACTCCTGATCTATGCTGCATCCAGTTTGCAAA
GTGGGGTCCCATCAAGGTTCAGTGGCAGTGGATCTGGGACAGATTTCACTCTCACCATCAGCAG
TCTGCAACCTGAAGATTTTGCAACTTACTACTGTCAACAGAGTTACAGTACCCCACGTGGACGT
TCGGCCAAGGGACCAAGGTGGAAATCAAACGAACTGTGGCTGCACCATCTGTC (SEQ ID
NO:533)

YU112-F05
GAGGTGCAGCTGGTGCAGTCGGGGGGAGGCGTGGTCCAGCCTGGGAGGTCCCTGAGACTCTC
CTGTGCAGCCTCTGGATTCACCTTCGGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCAGCAGTGATGTTGGTGGTTATAACTATG
TCTCCTGGTACCAACAACACCCAGGCAAAGCCCCCAAACTCATCATTTATGATGTCAATAATCGG
CCCTCAGGGGTTTCTAATCGCTTCTCTGCCTCCAAGTCTGGCAACACGGCCTCCCTGACCATCT
CTGGGCTCCAGGCTGAGGACGAGGCTGATTATTACTGCAACTCATATACAAGCGGTAGCACTTG
GGTCTTCGGCGGAGGGACCAAGCTGACCGTCCTAGGTCAGCCCAAGGCTGCCCCTCGGTCAC
TCTGTTCCCGCCCTCCTCT (SEQ ID NO:534)

YU112-G01
CAGGTGCAGCTGGTGGAGTCGGGGGGAGGCGTGGTCCAGCCTGGGAGGTCCCTGAGACTCTC
CTGTGCAGCCTCTGGGTTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAACTTTCCGGGCCCAACGGTGTGGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCATCAGTGATGTTGGTGGTTATAACTATG
TCTCCTGGTACCAACAGCACCCAGGCAAAGCCCCCAAACTCATGATTTATGATGTCACTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGGTTATTACTGCTCCTCATATGCAGGCAGCTACACTTG
GGTGTTCGGCGGAGGGACCGAGCTGACCGTCCTGAGTCAGCCCAAGGCTGCCCCTCGGTCAC
TCTGTTCCCGCCCTCCTCT (SEQ ID NO:535)

FIG. 51 (Cont.)

YU112-G06
CAGGTGCAGCTGCAGGAGTCGGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACACTGTACCTGCAAATGAACAGC
CTGAGAGCTGAGGACACGGCTGTGTATTACTGTGCGAAAATAGGAGCTACTGACCCCCTTGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGTCTGCCCTGACTCAGCCTCGCTCAGTGTCCGGGTC
TCCTGGACAGTCAGTCACCATCTCCTGCACTGGAACCATCAGTGATGTTGGTGGTTATAACTATG
TCTCCTGGTACCAACAGCACCCAGGCAAAGCCCCCAAACTCATGATTTATGATGTCACTAAGCGG
CGCTCAGGGGTCCCTGATCGCTTCTCTGGCTCCAAGTCTGGCAACACGGCCTCCTGACCATCT
CTGGGCTCCAGGCTGAGGATGAGGCTGGTTATTACTGCTCCTCATATGCAGGCGGCTACACTTG
GGTGTTCGGCGGAGGGACCGAGCTGACCGTCCTGAGTCAGCCCAAGGCTGCCCCCTCGGTCAC
TCTGTTCCCGCCCTCCTCT (SEQ ID NO:536)

YU112-G09
TAGGTCACCTTGAAGGAGTCTGGGGGAGGCGTGGTCCAGCCTGGGAGGTCCCTGAGACTCTCC
TGTGCAGCCTCTGGATTCACCTTCAGTAGCTATGGCATGCACTGGGTCCGCCAGGCTCCAGGCA
AGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAAGGGGGGAAGAGCTACTACGGATTTG
ACTACTGGGGCCAGGGAACCCTGGTCACCGTCTCCTCAGGGAGTGCATCCGCCCCAAAGCTTG
AAGAAGGTGAATTTTCAGAAGCACGCGTAGACATCCAGATGACCCAGTCTCCATCCTTCCTGTCT
GCATCTGTAGGAGACAGAGTCACCATCACTTGCCGGGCAAGTCAGATCATTAGCAGCTATTTAAA
TTGGTATCAGCAGAAACCAGGGAAAGCCCCTAAACTCCTGATCTATGCTGCATCCAGTTTGCAAA
GTGGGGTCCCATCAAGGTTCAGTGGCAGTGGATCTGGGACAGATTTCACTCTCACCATCAGCAG
TCTGCAACCTGGAAGATTTTGCAACTTACTACTGTCAACAGAGTTACAGTACCCCCACGTG (SEQ
ID NO:537)

YU112-H01
CAGGTGCAGCTGGTGGAGTCTGGGGGAGGCGTGGTCCAGCCTGGGAGGTCCCTGAGACTCTC
CTGTGCAGCCTCTGGATTCACCTTCGGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAAGGTTCGTACTACTTTGACTACTGGG
GCCAGGGAACCCTGGTCACCGTCTCCTCAGGGAGTGCATCCGCCCCAAAGCTTGAAGAAGGTG
AATTTTCAGAAGCACGCGTAGAAACGACACTCACGCAGTCTCCAGGCACCCTGTCTTTGTCTCCA
GGGGAAAGAGCCACCCTCTCCTGCAGGGCCAGTCAGAGTGTTAGCAGCAGCTACTTAGCCTGG
TACCAGCAGAAACCTGGCCAGGCTCCCAGGCTCCTCATCTATGGTGCATCCAGCAGGGCCACTG
GCATCCCAGACAGGTTCAGTGGCAGTGGGTCTGGGACAGACTTCACTCTCACCATCAGCAGTCT
GCAACCTGATGATTTTGCAACTTACTACTGTCAACAGAGTTACAGCACTCCTACGTGGACATTCG
GCCAAGGGACCAAGGTGGAAATCAAACGAACTGTGGCTGCACCATCTGTC (SEQ ID NO:538)

FIG. 51 (Cont.)

YU112-H02
CAGGTGCAGCTGGTGGAGTCTGGGGGAGGCGTGGTCCAGCCTGGGAGGTCCCTGAGACTCTC
CTGTGCAGCCTCTGGATTCACCTTCAGTAGCTATGGCATGCACTGGGTCCGCCAGGCTCCAGGC
AAGGGGCTGGAGTGGGTGGCAGTTATATCATATGATGGAAGTAATAAATACTATGCAGACTCCGT
GAAGGGCCGATTCACCATCTCCAGAGACAATTCCAAGAACACGCTGTATCTGCAAATGAACAGC
CTGAGAGCTGAGGACACGGCTGTGTATTACTGTGCGAAACTTTCCGGGCCCAACGGTGTGGACT
ACTGGGGCCAGGGAACCCTGGTCACCGTCTCCTCAGGGAGTGCATCCGCCCCAAAGCTTGAAG
AAGGTGAATTTTCAGAAGCACGCGTACAGCCTGTGCTGACTCAGCCCCGCTCAGTGTCCGGGTC
TCCTGGACAGTCAGTCACCATCTCCTGCACTGGAACCAGCAGTGATGTTGGTGGTTATAACTATG
TCTCCTGGTACCAACAACACCCAGGCAAAGCCCCCAAAGTCATGATTTATGATGTCAGTAAGCGG
CCCTCAGGGGTCCCTGATCGCTTCTCTGGCTCCAAGTCTGGCAACACGGCCTCCCTGACCATCT
CTGGGCTCCAGGCTGAGGATGAGGCTGATTATTACTGCTGCTCATATGCAGGCAGCTACACTTG
GGTGTTCGGCGGAGGGACCAAGCTGACCGTCCTAGGTCAGCCCAAGGCTGCCCCCTCGGTCAC
TCTGTTCCCGCCCTCCTCT (SEQ ID NO:539)

FIG. 51 (Cont.)

| Strategy No | Round 1 | Round 2 | soluble competition with | No of first hits (lambda sublibrary) | No of first hits (kappa sublibrary) |
|---|---|---|---|---|---|
| 1 | h-IL11 | h-IL11 | h-IL11 | 27 | 14 |
| 2 | m-IL11 | m-IL11 | m-IL11 | 103 | 36 |
| 3 | h-IL11 | m-IL11 | h-IL11/m-IL11 | 11 | 21 |

FIG. 52

| Clone | hIL11 - average signal | mIL11 - average signal | Clone | hIL11 - average signal | mIL11 - average signal |
|---|---|---|---|---|---|
| YU100-A10 | 0.4430 | 0.5400 | YU100-F07 | 0.1720 | 0.1480 |
| YU100-A11 | 0.3328 | 0.3716 | YU100-F11 | 0.3190 | 0.3950 |
| YU100-A12 | 0.3200 | 0.3883 | YU100-G01 | 0.2050 | 0.3100 |
| YU100-B01 | 0.1870 | 0.1750 | YU100-G07 | 0.2030 | 0.2060 |
| YU100-B03 | 0.2270 | 0.3210 | YU100-G08 | 0.1530 | 0.2700 |
| YU100-B06 | 0.2090 | 0.4040 | YU100-G09 | 0.8023 | 0.9846 |
| YU100-B07 | 0.1670 | 0.3540 | YU100-G10 | 0.2620 | 0.4040 |
| YU100-B08 | 0.2090 | 0.4230 | YU100-G11 | 0.4980 | 0.5070 |
| YU100-B09 | 0.2100 | 0.2930 | YU100-H01 | 0.4300 | 0.2830 |
| YU100-B12 | 0.4430 | 0.4540 | YU100-H02 | 0.3090 | 0.1880 |
| YU100-C02 | 0.3010 | 0.3330 | YU100-H04 | 0.5080 | 0.3930 |
| YU100-C04 | 0.1480 | 0.1550 | YU100-H05 | 0.1630 | 0.4610 |
| YU100-C05 | 0.2810 | 0.2350 | YU100-H06 | 0.1810 | 0.3280 |
| YU100-C10 | 0.1610 | 0.2770 | YU100-H09 | 0.4000 | 0.6680 |
| YU100-C11 | 0.1830 | 0.2670 | YU100-H11 | 0.7240 | 0.6290 |
| YU100-C12 | 0.2829 | 0.3226 | YU112-A07 | 0.4380 | 0.6120 |
| YU100-D01 | 0.2510 | 0.2060 | YU112-B06 | 0.7563 | 0.6217 |
| YU100-D02 | 0.2680 | 0.3460 | YU112-C03 | 0.5660 | 0.4450 |
| YU100-D05 | 0.2230 | 0.2840 | YU112-C05 | 0.4576 | 0.6850 |
| YU100-D07 | 0.2460 | 0.3220 | YU112-C09 | 0.5930 | 0.8980 |
| YU100-D11 | 0.4470 | 0.4750 | YU112-D08 | 0.4180 | 0.7230 |
| YU100-E01 | 0.2070 | 0.2380 | YU112-E07 | 0.7100 | 0.5610 |
| YU100-E04 | 0.3600 | 0.4720 | YU112-E08 | 0.3733 | 0.3233 |
| YU100-E05 | 0.1600 | 0.2750 | YU112-F05 | 0.8630 | 0.6010 |
| YU100-E06 | 0.1730 | 0.3090 | YU112-G01 | 0.5280 | 0.7937 |
| YU100-E07 | 0.1930 | 0.2470 | YU112-G06 | 0.6640 | 0.7620 |
| YU100-E08 | 0.2140 | 0.2510 | YU112-G09 | 0.2760 | 0.1310 |
| YU100-E09 | 0.2240 | 0.3350 | YU112-H01 | 1.2290 | 1.1750 |
| YU100-E10 | 0.3380 | 0.2970 | YU112-H02 | 0.6060 | 0.7850 |
| YU100-E11 | 0.2675 | 0.4350 | | | |
| YU100-E12 | 0.4260 | 0.5000 | | | |
| YU100-F01 | 0.4640 | 0.5280 | | | |
| YU100-F02 | 0.3610 | 0.3030 | | | |
| YU100-F05 | 0.3040 | 0.5420 | | | |
| YU100-F06 | 0.1600 | 0.4810 | | | |

FIG. 54B

|  | Affinity EC50 (ng/ml) | MMP2 production (ng/ml) (Experiment 1) | MMP2 production (ng/ml) (Experiment 2) |
|---|---|---|---|
| No TGFB1, IgG1 control (NEG) | - | 42.7 | 36.2 |
| + TGFB1, IgG1 control (POS) | - | 70.2 | 62.3 |
| YU100-C04* | 21 | 62.3 | 52.5 |
| YU100-C05* | 17 | 55.3 | 53.5 |
| YU100-C10* | 15 | 56.4 | 48.9 |
| YU100-C12* | 23 | 53.5 | 46.8 |
| YU100-E07* | 23 | 52.1 | 46.5 |
| YU100-E09* | 19 | 51.7 | 44.4 |
| YU100-E11* | 28 | 49.1 | 41.9 |
| YU100-E12* | 16 | 56.0 | 47.9 |
| YU100-F01* | 18 | 52.8 | 39.9 |
| YU100-F02* | 18 | 51.2 | 43.5 |
| YU100-G01* | 19 | 56.6 | 49.7 |
| YU100-G07* | 18 | 59.0 | 49.7 |
| YU100-G09* | 14 | 59.9 | 47.5 |
| YU100-H02* | 32 | 57.5 | 51.3 |
| YU100-H04* | 27 | 58.5 | 48.7 |
| YU100-H05* | 22 | 57.1 | 47.8 |
| YU100-H06* | 13 | 52.3 | 43.9 |
| YU100-H09* | 28 | 52.9 | 39.6 |
| YU100-H11* | 15 | 53.7 | 45.5 |
| YU112-A07 | 25 | 50.7 | 45.0 |
| YU112-B06 | 20 | 49.7 | 43.9 |
| YU112-C03 | 17 | 57.6 | 53.3 |
| YU112-C05 | 12 | 55.2 | 50.1 |
| YU112-D08 | 18 | 50.3 | 42.5 |
| YU112-F05 | 40 | 53.9 | 48.5 |
| YU112-G01 | N.D. | 47.6 | 43.8 |
| YU112-G06 | 17 | 55.0 | 47.8 |
| YU112-H01 | 20 | 51.9 | 47.7 |
| YU112-H02 | 20 | 65.3 | 58.0 |
| YU100-A10 | 23 | 52.1 | 50.1 |
| YU100-A11 | 20 | 51.6 | 45.7 |
| YU100-A12 | 23 | 59.5 | 50.4 |
| YU100-B01 | 23 | 52.5 | 40.0 |
| YU100-B03 | 25 | 47.3 | 46.8 |
| YU100-B06 | 33 | 47.6 | 49.6 |
| YU100-B07 | 23 | 55.9 | 47.4 |
| YU100-B08 | 21 | 55.3 | 40.6 |
| YU100-C02 | 14 | 54.6 | 49.4 |
| YU100-C11 | 33 | 53.8 | 44.2 |
| YU100-D02 | 22 | 49.6 | 42.2 |
| YU100-D05 | 42 | 53.3 | 48.8 |
| YU100-D11 | 38 | 51.2 | 47.2 |
| YU100-E01 | 30 | 59.3 | 51.8 |
| YU100-E04 | 36 | 50.0 | 43.5 |
| YU100-E05 | 27 | 56.3 | 50.2 |
| YU100-E06 | 24 | 54.1 | 48.2 |
| YU112-E07 | 58 | 53.5 | 49.1 |
| YU100-E08 | 32 | 48.2 | 59.7 |
| YU100-E10 | 33 | 56.1 | 47.0 |
| YU100-F07 | 41 | 53.1 | 46.6 |
| YU100-F11 | 27 | 44.5 | 37.6 |
| YU100-G08 | 28 | 42.3 | 38.0 |
| YU100-G10 | 34 | 54.0 | 45.4 |
| YU100-H01 | 53 | 48.3 | 42.2 |

FIG. 57

BSN-2E1
QVQLQESGPELVKPGASVKIPCKAS<u>GYTFTDYN</u>MDWVKQSHGKSLEWIGD<u>INPHNGGP</u>IYNQKFTG
KATLTVDKSSSTAYMELRSLTSEDTAVYYC<u>ARGELGHWYFDV</u>WGTGTTVTVSS (SEQ ID NO:541)

HC-CDR1:    GYTFTDYN (SEQ ID NO:542)
    HC-CDR2:    INPHNGGP (SEQ ID NO:543)
    HC-CDR3:    ARGELGHWYFDV (SEQ ID NO:544)

BSN-2G6
QVQLQESGPELVKPGASVKIPCKAS<u>GYTFTDYN</u>MDWVKQSHGKSLEWIGN<u>INPDNGGT</u>IYNQKFKG
KATLTVDKSSSTAYMELRSLTSEDTAVYFC<u>AREGPYGYTWFAY</u>WGQGTLDTVSA (SEQ ID NO:545)

HC-CDR1:    GYTFTDYN (SEQ ID NO:542)
    HC-CDR2:    INPDNGGT (SEQ ID NO:546)
    HC-CDR3:    AREGPYGYTWFAY (SEQ ID NO:547)

BSN-3C6
QVQLQESGPELVKPGASVKIPCKAS<u>GYTFTDYN</u>MDWVKQSHGKSLEWIGD<u>INPHNGGP</u>IYNQKFTG
KATLTVDKSSSTAYMELRSLTSEDTAVYYC<u>ARGELGHWYFDV</u>WGTGTTVTVSS (SEQ ID NO:541)

HC-CDR1:    GYTFTDYN (SEQ ID NO:542)
    HC-CDR2:    INPHNGGP (SEQ ID NO:543)
    HC-CDR3:    ARGELGHWYFDV (SEQ ID NO:544)

BSN-5A6
EVQLQQSGPELVKPGASVKIPCKAS<u>GYTFTDYN</u>MDWVKQSHGKSLEWIGN<u>INPNNGGI</u>YNQKFKGK
ATLTVDKSSSTAYMVLRSLTSEDTAVYYC<u>ARNPSLYDGYLDC</u>WGQGTTLTVSS (SEQ ID NO:548)

HC-CDR1:    GYTFTDYN (SEQ ID NO:542)
    HC-CDR2:    INPNNGGI (SEQ ID NO:549)
    HC-CDR3:    ARNPSLYDGYLDC (SEQ ID NO:550)

BSN-5B8
QVQLQQSGAELARPGTSVKLSCKAS<u>GYTFTSYG</u>ISWVKQRTGQGLEWIGE<u>IYPRSSNT</u>YYNEKFKGK
ATLTADKSSSTAYMELRSLTSEDSADYFC<u>ARANWVGYFDV</u>WGTGTTVTVSS (SEQ ID NO:551)

HC-CDR1:    GYTFTSYG (SEQ ID NO:228)
    HC-CDR2:    IYPRSSNT (SEQ ID NO:552)
    HC-CDR3:    ARANWVGYFDV (SEQ ID NO:553)

FIG. 68

BSN-2E1
NIVMTQSPKSMSMSVGERVTLTCKAS<u>ENVVTY</u>VSWYQQKPEQSPKLLIY<u>GAS</u>NRYTGVPDRFTGSG
SATDFTLTISSVQAEDLADYHC<u>GQGYSYPYT</u>FGGGTKLEIK (SEQ ID NO:554)

LC-CDR1:  ENVVTY (SEQ ID NO:555)
  LC-CDR2:  GAS (SEQ ID NO:138)
  LC-CDR3:  GQGYSYPYT (SEQ ID NO:556)

BSN-2G6
DILLTQSPAILSVSPGERVSFSCRAS<u>QSIGTS</u>IHWYQQRTNGSPRLLIK<u>YAS</u>ESISGIPSRFSGSGSGTD
FTLSINSVESEDIADYYC<u>QQSNSWPLT</u>FGAGTKLELK (SEQ ID NO:557)

LC-CDR1:  QSIGTS (SEQ ID NO:558)
  LC-CDR2:  YAS (SEQ ID NO:559)
  LC-CDR3:  QQSNSWPLT (SEQ ID NO:560)

BSN-3C6
NIVMTQSPKSMSMSVGERVTLTCKAS<u>ENVVTY</u>VSWYQQKPEQSPKLLIY<u>GAS</u>NRYTGVPDRFTGSG
SATDFTLTISSVQAEDLADYHC<u>GQGYSYPYT</u>FGGGTKLEIK (SEQ ID NO:554)

LC-CDR1:  ENVVTY (SEQ ID NO:555)
  LC-CDR2:  GAS (SEQ ID NO:138)
  LC-CDR3:  GQGYSYPYT (SEQ ID NO:556)

BSN-5A6_1
NIVMTQSPKSMSMSVGERVTLTCKAS<u>ENVVTY</u>VSWYQQKPEQSPKLLIY<u>GAS</u>NRYTGVPDRFTGSG
SATDFTLTISSVQAEDLADYHC<u>GQGYSYPYT</u>FGGGTKLEIK (SEQ ID NO:554)

LC-CDR1:  ENVVTY (SEQ ID NO:555)
  LC-CDR2:  GAS (SEQ ID NO:138)
  LC-CDR3:  GQGYSYPYT (SEQ ID NO:556)

BSN-5A6_2
DIVMSQSPSSLAVSVGEKVTMNCKSS<u>QSLLYNSSQKNY</u>LAWYQQKPGQSPKLLIY<u>WAS</u>TRESGVPD
RFTGSGSGTDFTLTISSVKAEDLAVYYC<u>QQYYSYPLT</u>FGAGTNLELK (SEQ ID NO:561)

LC-CDR1:  QSLLYNSSQKNY (SEQ ID NO:562)
  LC-CDR2:  WAS (SEQ ID NO:563)
  LC-CDR3:  QQYYSYPLT (SEQ ID NO:581)

BSN-5B8
DIVMTQSHKFMSTSVGDRVTITCKAS<u>QDVGTA</u>VAWYQQKPGQSPKLLIY<u>WAS</u>TRLTGVPDRFTGSG
SGTYFTLTINNVQSEDLADYFC<u>QQYSSYRT</u>FGGGTKLEIK (SEQ ID NO:564)

LC-CDR1:  QDVGTA (SEQ ID NO:565)
  LC-CDR2:  WAS (SEQ ID NO:563)
  LC-CDR3:  QQYSSYRT (SEQ ID NO:566)

FIG. 69

| Clone | CDR 1 | CDR 2 | CDR 3 |
|---|---|---|---|
| | Heavy Chain | | |
| BSN-2E1 and BSN-3C6 | GYTFTDYN (SEQ ID NO:542) | INPHNGGP (SEQ ID NO:543) | ARGELGHWYFDV (SEQ ID NO:544) |
| BSN-2G6 | GYTFTDYN (SEQ ID NO:542) | INPDNGGT (SEQ ID NO:546) | AREGPYGYTWFAY (SEQ ID NO:547) |
| BSN-5A6 | GYTFTDYN (SEQ ID NO:542) | INPNNGGI (SEQ ID NO:549) | ARNPSLYDGYLDC (SEQ ID NO:550) |
| BSN-5B8 | GYTFTSYG (SEQ ID NO:228) | IYPRSSNT (SEQ ID NO:552) | ARANWVGYFDV (SEQ ID NO:553) |

FIG. 70

| Clone | CDR 1 | CDR 2 | CDR 3 |
|---|---|---|---|
| | Light Chain | | |
| BSN-2E1, BSN-3C6 and BSN-5A6_1 | ENVVTY (SEQ ID NO:555) | GAS (SEQ ID NO:138) | GQGYSYPYT (SEQ ID NO:556) |
| BSN-2G6 | QSIGTS (SEQ ID NO:558) | YAS (SEQ ID NO:559) | QQSNSWPLT (SEQ ID NO:560) |
| BSN-5A6_2 | QSLLYNSSQKNY (SEQ ID NO:562) | WAS (SEQ ID NO:563) | QQYYSYPLT (SEQ ID NO:581) |
| BSN-5B8 | QDVGTA (SEQ ID NO:565) | WAS (SEQ ID NO:563) | QQYSSYRT (SEQ ID NO:566) |

FIG. 71

| Clone(s) | HC-CDR1 | Sequence family | Family Consensus |
|---|---|---|---|
| BSN-2E1 and BSN-3C6<br>BSN-2G6<br>BSN-5A6 | GYTFTDYN (SEQ ID NO:542) | mHC-CDR1-1 | GYTFTX$_{180}$YX$_{181}$ (SEQ ID NO:567)<br><br>X$_{180}$ = D or S<br>X$_{181}$ = N or G |
| BSN-5B8 | GYTFTSYG (SEQ ID NO:228) | | |

FIG. 72A

| Clone(s) | HC-CDR2 | Sequence family | Family Consensus |
|---|---|---|---|
| BSN-2E1 and BSN-3C6 | INPHNGGP (SEQ ID NO:543) | mHC-CDR2-1 | INPX$_{182}$NGGX$_{183}$ (SEQ ID NO:568)<br><br>X$_{182}$ = H, D or N<br>X$_{183}$ = P, T or I |
| BSN-2G6 | INPDNGGT (SEQ ID NO:546) | | |
| BSN-5A6 | INPNNGGI (SEQ ID NO:549) | | |
| BSN-5B8 | IYPRSSNT (SEQ ID NO:552) | mHC-CDR2-2 | IYPRSSNT (SEQ ID NO:552) |

FIG. 72B

| Clone(s) | HC-CDR3 | Sequence family | Family Consensus |
|---|---|---|---|
| BSN-2E1 and BSN-3C6 | ARGELGHWYFDV (SEQ ID NO:544) | mHC-CDR3-1 | ARGELGHWYFDV (SEQ ID NO:544) |
| BSN-2G6 | AREGPYGYTWFAY (SEQ ID NO:547) | mHC-CDR3-2 | AREGPYGYTWFAY (SEQ ID NO:547) |
| BSN-5A6 | ARNPSLYDGYLDC (SEQ ID NO:550) | mHC-CDR3-3 | ARNPSLYDGYLDC (SEQ ID NO:550) |
| BSN-5B8 | ARANWVGYFDV (SEQ ID NO:553) | mHC-CDR3-4 | ARANWVGYFDV (SEQ ID NO:553) |

FIG. 72C

| Clone(s) | LC-CDR1 | Sequence family | Family Consensus |
|---|---|---|---|
| BSN-2E1, BSN-3C6 and BSN-5A6_1 | ENVVTY (SEQ ID NO:555) | mLC-CDR1-1 | ENVVTY (SEQ ID NO:555) |
| BSN-2G6 | QSIGTS (SEQ ID NO:558) | mLC-CDR1-2 | QSIGTS (SEQ ID NO:558) |
| BSN-5A6_2 | QSLLYNSSQKNY (SEQ ID NO:562) | mLC-CDR1-3 | QSLLYNSSQKNY (SEQ ID NO:562) |
| BSN-5B8 | QDVGTA (SEQ ID NO:565) | mLC-CDR1-4 | QDVGTA (SEQ ID NO:565) |

FIG. 73A

| Clone(s) | LC-CDR2 | Sequence family | Family Consensus |
|---|---|---|---|
| BSN-2E1, BSN-3C6 and BSN-5A6_1 | GAS (SEQ ID NO:138) | mLC-CDR2-1 | $X_{184}$AS (SEQ ID NO:569)<br><br>$X_{184}$ = G, Y or W |
| BSN-2G6 | YAS (SEQ ID NO:559) | | |
| BSN-5A6_2 and BSN-5B8 | WAS (SEQ ID NO:563) | | |

FIG. 73B

| Clone(s) | LC-CDR3 | Sequence family | Family Consensus |
|---|---|---|---|
| BSN-2E1, BSN-3C6 and BSN-5A6_1 | GQGYSYPYT (SEQ ID NO:556) | mLC-CDR3-1 | $X_{185}QX_{186}X_{187}SX_{188}X_{189}X_{190}T$ (SEQ ID NO:570)<br><br>$X_{185}$ = Q or G<br>$X_{186}$ = Y, G or S<br>$X_{187}$ = Y, N or S<br>$X_{188}$ = Y or W<br>$X_{189}$ = P or absent<br>$X_{190}$ = L, Y or R |
| BSN-2G6 | QQSNSWPLT (SEQ ID NO:560) | | |
| BSN-5A6_2 | QQYYSYPLT (SEQ ID NO:581) | | |
| BSN-5B8 | QQYSSYRT (SEQ ID NO:566) | | |

FIG. 73C

BSN-2E1_VH
CAGGTCCAGCTGCAGGAGTCTGGACCTGAGCTGGTGAAGCCTGGGGCTTCAGTGAAGATACCC
TGCAAGGCTTCTGGATACACATTCACTGACTACAACATGGACTGGGTGAAGCAGAGCCATGGAA
AGAGCCTTGAGTGGATTGGAGATATTAATCCTCACAATGGTGGTCCTATCTACAACCAGAAGTTC
ACGGGCAAGGCCACATTGACTGTAGACAAGTCCTCCAGCACAGCCTACATGGAGCTCCGCAGC
CTGACATCTGAGGACACTGCAGTCTATTACTGTGCAAGAGGGGAACTGGGTCACTGGTACTTCG
ATGTCTGGGGCACAGGGACCACGGTCACCGTCTCCTCA (SEQ ID NO:571)

BSN-2E1_VL
AACATTGTAATGACCCAATCTCCCAAATCCATGTCCATGTCAGTAGGAGAGAGGGTCACCTTGAC
CTGCAAGGCCAGTGAGAATGTGGTTACTTATGTTTCCTGGTATCAACAGAAACCAGAGCAGTCTC
CTAAACTGCTGATATACGGGGCATCCAACCGGTACACTGGGGTCCCCGATCGCTTCACAGGCAG
TGGATCTGCAACAGATTTCACTCTGACCATCAGCAGTGTGCAGGCTGAAGACCTTGCAGATTATC
ACTGTGGACAGGGTTACAGCTATCCGTACACGTTCGGAGGGGGGACCAAGCTGGAAATAAAA
(SEQ ID NO:572)

BSN-2G6_VH
CAGGTCCAGCTGCAGGAGTCTGGACCTGAGCTGGTGAAGCCTGGGGCTTCAGTGAAGATACCC
TGCAAGGCTTCTGGATACACGTTCACTGACTACAACATGGACTGGGTGAAGCAGAGCCATGGAA
AGAGCCTTGAGTGGATTGGAAATATTAATCCTGACAATGGTGGTACTATCTACAACCAGAAGTTC
AAGGGCAAGGCCACATTGACTGTAGACAAGTCCTCCAGCACAGCCTACATGGAGCTCCGCAGCC
TGACATCTGAGGACACTGCAGTCTATTTCTGTGCAAGAGAGGGGCCTTATGGTTACACCTGGTTT
GCTTACTGGGGCCAAGGGACTCTGGACACTGTCTCTGCA (SEQ ID NO:573)

BSN-2G6_VL
GACATCTTGCTGACTCAGTCTCCAGCCATCCTGTCTGTGAGTCCAGGAGAAAGAGTCAGTTTCTC
CTGCAGGGCCAGTCAGAGCATTGGCACAAGCATACACTGGTATCAGCAAAGAACAAATGGTTCT
CCAAGGCTTCTCATAAAGTATGCTTCTGAGTCTATCTCTGGGATCCCTTCCAGGTTTAGTGGCAG
TGGATCAGGGACAGATTTTACTCTTAGCATCAACAGTGTGGAGTCTGAAGATATTGCAGATTATTA
CTGTCAACAAAGTAATAGCTGGCCGCTCACGTTCGGTGCTGGGACCAAGCTGGAGCTGAAA
(SEQ ID NO:574)

BSN-3C6_VH
CAGGTCCAGCTGCAGGAGTCTGGACCTGAGCTGGTGAAGCCTGGGGCTTCAGTGAAGATACCC
TGCAAGGCTTCTGGATACACATTCACTGACTACAACATGGACTGGGTGAAGCAGAGCCATGGAA
AGAGCCTTGAGTGGATTGGAGATATTAATCCTCACAATGGTGGTCCTATCTACAACCAGAAGTTC
ACGGGCAAGGCCACATTGACTGTAGACAAGTCCTCCAGCACAGCCTACATGGAGCTCCGCAGC
CTGACATCTGAGGACACTGCAGTCTATTACTGTGCAAGAGGGGAACTGGGTCACTGGTACTTCG
ATGTCTGGGGCACAGGGACCACGGTCACCGTCTCCTCA (SEQ ID NO:574)

BSN-3C6_VL
AACATTGTAATGACCCAATCTCCCAAATCCATGTCCATGTCAGTAGGAGAGAGGGTCACCTTGAC
CTGCAAGGCCAGTGAGAATGTGGTTACTTATGTTTCCTGGTATCAACAGAAACCAGAGCAGTCTC
CTAAACTGCTGATATACGGGGCATCCAACCGGTACACTGGGGTCCCCGATCGCTTCACAGGCAG
TGGATCTGCAACAGATTTCACTCTGACCATCAGCAGTGTGCAGGCTGAAGACCTTGCAGATTATC
ACTGTGGACAGGGTTACAGCTATCCGTACACGTTCGGAGGGGGGACCAAGCTGGAAATAAAA
(SEQ ID NO:575)

FIG. 74

BSN-5A6_VH
GAGGTCCAGCTGCAACAGTCTGGACCTGAACTGGTGAAGCCTGGGGCTTCAGTGAAGATACCCT
GCAAGGCTTCTGGATACACATTCACTGACTACAACATGGACTGGGTGAAGCAGAGCCATGGAAA
GAGCCTTGAGTGGATTGGAAATATTAATCCTAACAATGGTGGTATTATCTACAACCAGAAGTTCAA
GGGCAAGGCCACATTGACTGTAGACAAGTCCTCCAGCACAGCCTACATGGTACTCCGCAGCCTG
ACATCTGAGGACACTGCAGTCTATTACTGTGCAAGAAACCCAAGTCTCTATGATGGTTACCTTGA
CTGCTGGGGCCAAGGCACCACTCTCACAGTCTCCTCA (SEQ ID NO:576)

BSN-5A6_VL1
AACATTGTAATGACCCAATCTCCCAAATCCATGTCCATGTCAGTAGGAGAGAGGGTCACCTTGAC
CTGCAAGGCCAGTGAGAATGTGGTTACTTATGTTTCCTGGTATCAACAGAAACCAGAGCAGTCTC
CTAAACTGCTGATATACGGGGCATCCAACCGGTACACTGGGGTCCCCGATCGCTTCACAGGCAG
TGGATCTGCAACAGATTTCACTCTGACCATCAGCAGTGTGCAGGCTGAAGACCTTGCAGATTATC
ACTGTGGACAGGGTTACAGCTATCCGTACACGTTCGGAGGGGGGACCAAGCTGGAAATAAAA
(SEQ ID NO:577)

BSN-5A6_VL2
GACATTGTGATGTCACAGTCTCCATCCTCCCTAGCTGTGTCAGTTGGAGAGAAGGTTACTATGAA
CTGCAAGTCCAGTCAGAGCCTTTTATATAATAGCAGTCAAAAGAACTACTTGGCCTGGTACCAGC
AGAAACCAGGGCAGTCTCCTAAATTGCTGATTTACTGGGCATCCACTAGGGAATCTGGGGTCCC
TGATCGCTTCACAGGCAGTGGATCTGGGACAGATTTCACTCTCACCATCAGCAGTGTGAAGGCT
GAAGACCTGGCAGTTTATTACTGTCAGCAATATTATAGTTATCCGCTCACGTTCGGTGCTGGGAC
CAACCTGGAGCTGAAA (SEQ ID NO:578)

BSN-5B8_VH
CAGGTCCAGCTGCAGCAGTCTGGAGCTGAGCTGGCGAGGCCTGGGACTTCAGTGAAACTGTCC
TGCAAGGCTTCTGGCTACACCTTCACAAGCTATGGTATAAGCTGGGTGAAACAGAGAACTGGAC
AGGGCCTTGAGTGGATTGGAGAAATTTATCCTCGAAGTAGTAATACTTACTACAATGAGAAGTTC
AAGGGCAAGGCCACACTGACTGCAGACAAATCCTCCAGCACAGCGTACATGGAGCTCCGCAGC
CTGACATCTGAGGACTCTGCGGACTATTTCTGTGCAAGGGCTAACTGGGTAGGGTACTTCGATG
TCTGGGGCACAGGGACCACGGTCACCGTCTCCTCA (SEQ ID NO:579)

BSN-5B8_VL
GACATTGTGATGACCCAGTCTCACAAATTCATGTCCACATCAGTCGGAGACAGGGTCACCATCAC
CTGCAAGGCCAGTCAGGATGTGGGTACTGCTGTAGCCTGGTATCAACAGAAACCAGGACAATCT
CCTAAACTACTGATTTACTGGGCATCCACCCGGCTCACTGGAGTCCCTGATCGCTTCACAGGCA
GTGGATCTGGGACATATTTCACTCTCACCATTAACAATGTGCAGTCTGAAGACTTGGCAGATTATT
TCTGTCAGCAATATAGCAGCTATCGGACGTTCGGTGGAGGCACCAAGCTGGAAATCAAG (SEQ ID NO:580)

FIG. 74 (Cont.)

SEQUENCE LISTING

```
<160> NUMBER OF SEQ ID NOS: 581

<210> SEQ ID NO 1
<211> LENGTH: 107
<212> TYPE: PRT
<213> ORGANISM: Artificial Sequence
<220> FEATURE:
<223> OTHER INFORMATION: YU33-A2

<400> SEQUENCE: 1

Asp Val Val Met Thr Gln Ser Pro Ser Ser Leu Ser Ala Ser Val Gly
1               5                   10                  15

Asp Arg Val Thr Ile Thr Cys Arg Ala Ser Gln Asp Val Gly Arg Tyr
            20                  25                  30

Val Ala Trp Tyr Gln Gln Lys Val Gly Lys Val Pro Arg Leu Leu Ile
        35                  40                  45

Tyr Ala Ala Ser Ala Leu Gln Ser Gly Val Pro Ser Arg Phe Ser Gly
    50                  55                  60

Thr Ala Ser Glu Thr Ser Phe Thr Leu Thr Ile Ser Ser Leu Gln Pro
65                  70                  75                  80

Glu Asp Val Ala Ser Tyr Tyr Cys Gln Gln Tyr Arg Ser Ala Pro Leu
                85                  90                  95

Ala Phe Gly Gly Gly Thr Gly Val Glu Ile Lys
            100                 105

<210> SEQ ID NO 2
<211> LENGTH: 110
<212> TYPE: PRT
<213> ORGANISM: Artificial Sequence
<220> FEATURE:
<223> OTHER INFORMATION: YU33-B3/H3

<400> SEQUENCE: 2

Leu Pro Val Leu Thr Gln Pro His Ser Val Ser Glu Ser Pro Gly Arg
1               5                   10                  15
```

```
Thr Val Thr Ile Ser Cys Thr Arg Asn Thr Gly Asn Ile Ala Ser Asn
            20                  25                  30

Arg Val Gln Trp Tyr Gln Gln Arg Pro Ala Ser Ala Pro Thr Val Val
        35                  40                  45

Ile Tyr Asp Asn His Gln Arg Pro Ser Gly Val Pro Asp Arg Phe Ser
 50                  55                  60

Gly Ser Ile Asp Thr Ser Pro Asn Ser Ala Tyr Leu Thr Ile Ser Gly
 65                  70                  75                  80

Leu Lys Thr Glu Asp Glu Ala Asp Tyr Tyr Cys Gln Ser Tyr Asp Tyr
                85                  90                  95

Ser Ser Val Ile Phe Gly Gly Gly Thr Gln Leu Thr Val Leu
            100                 105                 110
```

<210> SEQ ID NO 3
<211> LENGTH: 110
<212> TYPE: PRT
<213> ORGANISM: Artificial Sequence
<220> FEATURE:
<223> OTHER INFORMATION: YU33-B4/YU45-G2/A3

<400> SEQUENCE: 3

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Phe Gly Leu
 65                  70                  75                  80

Gln Ala Glu Asp Glu Ala Asp Tyr Tyr Cys Ser Ser Tyr Thr Ser Ser
                85                  90                  95

Ser Ser Trp Val Phe Gly Gly Gly Thr Lys Leu Thr Val Leu
            100                 105                 110
```

<210> SEQ ID NO 4
<211> LENGTH: 110
<212> TYPE: PRT
<213> ORGANISM: Artificial Sequence
<220> FEATURE:
<223> OTHER INFORMATION: YU33-E6

<400> SEQUENCE: 4

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Glu Val Ser His Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                85                  90                  95

Asn Thr Leu Val Phe Gly Gly Gly Thr Lys Leu Thr Val Leu
```

<210> SEQ ID NO 5
<211> LENGTH: 110
<212> TYPE: PRT
<213> ORGANISM: Artificial Sequence
<220> FEATURE:
<223> OTHER INFORMATION: YU45-C11/A10

<400> SEQUENCE: 5

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
                20                  25                  30
Asn Tyr Val Ser Trp Tyr Gln Gln His Pro Gly Lys Ala Pro Lys Leu
            35                  40                  45
Met Ile Tyr Asp Val Ser Asn Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Val Val Phe Gly Gly Gly Thr Lys Leu Thr Val Leu
                100                 105                 110
```

<210> SEQ ID NO 6
<211> LENGTH: 110
<212> TYPE: PRT
<213> ORGANISM: Artificial Sequence
<220> FEATURE:
<223> OTHER INFORMATION: YU45-D11/F11

<400> SEQUENCE: 6

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Ile Gly Ala Tyr
                20                  25                  30
Asn Tyr Val Ser Trp Tyr Gln Gln His Pro Gly Lys Ala Pro Lys Leu
            35                  40                  45
Met Ile Tyr Asp Val Ser His Arg Pro Ser Gly Val Ser Asn Arg Phe
        50                  55                  60
Ser Gly Ser Lys Ser Gly Asn Ala Ala Ser Leu Thr Ile Ser Gly Val
65                  70                  75                  80
Gln Ala Glu Asp Gly Ala Asp Tyr Tyr Cys Ser Ser Tyr Thr Thr Ser
                85                  90                  95
Ser Thr Val Val Phe Gly Gly Gly Thr Gln Leu Thr Val Leu
                100                 105                 110
```

<210> SEQ ID NO 7
<211> LENGTH: 110
<212> TYPE: PRT
<213> ORGANISM: Artificial Sequence
<220> FEATURE:
<223> OTHER INFORMATION: YU45-E11/E12

<400> SEQUENCE: 7

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
                20                  25                  30
```

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Gly Ser Leu
            85                  90                  95

Ser Gly Trp Val Phe Gly Gly Gly Thr Lys Leu Thr Val Leu
            100                 105                 110

<210> SEQ ID NO 8
<211> LENGTH: 110
<212> TYPE: PRT
<213> ORGANISM: Artificial Sequence
<220> FEATURE:
<223> OTHER INFORMATION: YU45-H11/D12

<400> SEQUENCE: 8

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
            85                  90                  95

Ser Thr Trp Val Phe Gly Gly Gly Thr Lys Leu Thr Val Leu
            100                 105                 110

<210> SEQ ID NO 9
<211> LENGTH: 110
<212> TYPE: PRT
<213> ORGANISM: Artificial Sequence
<220> FEATURE:
<223> OTHER INFORMATION: YU45-A12/G10

<400> SEQUENCE: 9

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Gly Ser Leu
            85                  90                  95

Ser Gly Trp Val Phe Gly Gly Gly Thr Lys Leu Thr Val Leu
            100                 105                 110

<210> SEQ ID NO 10
<211> LENGTH: 110
<212> TYPE: PRT
<213> ORGANISM: Artificial Sequence
<220> FEATURE:
<223> OTHER INFORMATION: YU45-G1

<400> SEQUENCE: 10

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe Val Phe Gly Gly Gly Thr Lys Leu Thr Val Leu
            100                 105                 110

<210> SEQ ID NO 11
<211> LENGTH: 110
<212> TYPE: PRT
<213> ORGANISM: Artificial Sequence
<220> FEATURE:
<223> OTHER INFORMATION: YU45-C2/A7/B10

<400> SEQUENCE: 11

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Ser
                85                  90                  95

Thr Pro Tyr Val Phe Gly Thr Gly Thr Lys Val Thr Val Leu
            100                 105                 110

<210> SEQ ID NO 12
<211> LENGTH: 110
<212> TYPE: PRT
<213> ORGANISM: Artificial Sequence
<220> FEATURE:
<223> OTHER INFORMATION: YU45-D2/H2/C7/F3/C9/E1/E9/C10/G3/H9/C5/A2/A5

<400> SEQUENCE: 12

Gln Ser Ala Leu Thr Gln Pro Arg Ser Val Ser Gly Ser Pro Gly Gln
1               5                   10                  15

Ser Val Thr Ile Ser Cys Thr Gly Thr Ile Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
            50                  55                  60

Ser Gly Ser Lys Ser Gly Asn Thr Ala Ser Leu Thr Ile Ser Gly Leu
 65                  70                  75                  80

Gln Ala Glu Asp Glu Ala Gly Tyr Tyr Cys Ser Ser Tyr Ala Gly Ser
                85                  90                  95

Tyr Thr Trp Val Phe Gly Gly Gly Thr Glu Leu Thr Val Leu
                100                 105                 110

<210> SEQ ID NO 13
<211> LENGTH: 110
<212> TYPE: PRT
<213> ORGANISM: Artificial Sequence
<220> FEATURE:
<223> OTHER INFORMATION: YU45-E3

<400> SEQUENCE: 13

Gln Ser Ala Leu Thr Gln Pro Arg Ser Val Ser Gly Ser Pro Gly Gln
 1               5                  10                  15

Ser Val Thr Ile Ser Cys Thr Gly Thr Ile Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
            50                  55                  60

Ser Gly Ser Lys Ser Gly Asn Thr Ala Ser Leu Thr Ile Ser Gly Leu
 65                  70                  75                  80

Gln Ala Glu Asp Glu Ala Gly Tyr Tyr Cys Ser Ser Tyr Ala Gly Ser
                85                  90                  95

Tyr Thr Trp Val Phe Gly Gly Gly Thr Glu Leu Thr Val Leu
                100                 105                 110

<210> SEQ ID NO 14
<211> LENGTH: 110
<212> TYPE: PRT
<213> ORGANISM: Artificial Sequence
<220> FEATURE:
<223> OTHER INFORMATION: YU45-C8/E8

<400> SEQUENCE: 14

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Val Tyr Asp Val Ser Asn Arg Pro Ser Gly Val Ser Asp Arg Phe
            50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ser Tyr Thr Ser Ser
                85                  90                  95

Asn Thr Gln Val Phe Gly Gly Gly Thr Lys Leu Thr Val Leu
                100                 105                 110

<210> SEQ ID NO 15
<211> LENGTH: 110
<212> TYPE: PRT

<213> ORGANISM: Artificial Sequence
<220> FEATURE:
<223> OTHER INFORMATION: YU45-F8

<400> SEQUENCE: 15

```
Gln Pro Val Leu Thr Gln Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Leu Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Gly Val Phe Gly Gly Gly Thr Lys Leu Thr Ala Leu
            100                 105                 110
```

<210> SEQ ID NO 16
<211> LENGTH: 110
<212> TYPE: PRT
<213> ORGANISM: Artificial Sequence
<220> FEATURE:
<223> OTHER INFORMATION: YU45-G8/H6

<400> SEQUENCE: 16

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asp Tyr Val Ser Trp Tyr Gln Gln His Pro Gly Thr Ala Pro Lys Leu
        35                  40                  45

Met Ile Ser Asp Val His Asn Arg Pro Leu Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ile Thr Trp Val Phe Gly Gly Gly Thr Lys Leu Thr Val Leu
            100                 105                 110
```

<210> SEQ ID NO 17
<211> LENGTH: 110
<212> TYPE: PRT
<213> ORGANISM: Artificial Sequence
<220> FEATURE:
<223> OTHER INFORMATION: YU45-F9

<400> SEQUENCE: 17

```
Gln Ser Ala Leu Thr Gln Pro Arg Ser Val Ser Arg Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Trp Val Phe Gly Gly Gly Thr Lys Leu Thr Val Leu
                100                 105                 110

<210> SEQ ID NO 18
<211> LENGTH: 110
<212> TYPE: PRT
<213> ORGANISM: Artificial Sequence
<220> FEATURE:
<223> OTHER INFORMATION: YU45-H10

<400> SEQUENCE: 18

Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Trp Val Phe Gly Gly Gly Thr Lys Leu Thr Val Leu
                100                 105                 110

<210> SEQ ID NO 19
<211> LENGTH: 110
<212> TYPE: PRT
<213> ORGANISM: Artificial Sequence
<220> FEATURE:
<223> OTHER INFORMATION: YU46-A10

<400> SEQUENCE: 19

Gln Pro Val Leu Thr Gln Pro Pro Ser Val Ser Ala Ala Pro Gly Gln
 1               5                   10                  15

Lys Val Thr Ile Ser Cys Ser Gly Ser Ser Ser Asn Ile Gly Asn Asn
                 20                  25                  30

Leu Val Tyr Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Ala Gly Val Phe Gly Gly Gly Thr Lys Leu Thr Ala Leu
                100                 105                 110

<210> SEQ ID NO 20
<211> LENGTH: 110
<212> TYPE: PRT
<213> ORGANISM: Artificial Sequence
<220> FEATURE:
<223> OTHER INFORMATION: YU45-F2
```

<400> SEQUENCE: 20

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Val
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
            100                 105                 110

<210> SEQ ID NO 21
<211> LENGTH: 110
<212> TYPE: PRT
<213> ORGANISM: Artificial Sequence
<220> FEATURE:
<223> OTHER INFORMATION: YU45-H3

<400> SEQUENCE: 21

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110

<210> SEQ ID NO 22
<211> LENGTH: 110
<212> TYPE: PRT
<213> ORGANISM: Artificial Sequence
<220> FEATURE:
<223> OTHER INFORMATION: YU45-A1

<400> SEQUENCE: 22

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Trp Val Phe Gly Gly Gly Thr Lys Leu Thr Val Leu
            100                 105                 110

<210> SEQ ID NO 23
<211> LENGTH: 110
<212> TYPE: PRT
<213> ORGANISM: Artificial Sequence
<220> FEATURE:
<223> OTHER INFORMATION: YU45-A8/C6

<400> SEQUENCE: 23

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Gly Asn Arg Pro Ser Gly Val Ser Asn Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Gly
                85                  90                  95

Ser Thr Trp Val Phe Gly Gly Gly Thr Lys Leu Thr Val Leu
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: YU45-B5/A4

<400> SEQUENCE: 24

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65              70                  75                  80

Gln Ala Glu Asp Glu Ala Asp Tyr Tyr Cys Ser Ser Tyr Ala Gly Thr
                85                  90                  95

Asn Asn Phe Val Val Phe Gly Gly Gly Thr Lys Leu Thr Val Leu
            100                 105                 110

<210> SEQ ID NO 25
<211> LENGTH: 110
<212> TYPE: PRT
<213> ORGANISM: Artificial Sequence
<220> FEATURE:
<223> OTHER INFORMATION: YU45-C3/A6

<400> SEQUENCE: 25

-continued

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
            100                 105                 110

<210> SEQ ID NO 26
<211> LENGTH: 107
<212> TYPE: PRT
<213> ORGANISM: Artificial Sequence
<220> FEATURE:
<223> OTHER INFORMATION: YU45-D1

<400> SEQUENCE: 26

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Phe Lys
            100                 105

<210> SEQ ID NO 27
<211> LENGTH: 110
<212> TYPE: PRT
<213> ORGANISM: Artificial Sequence
<220> FEATURE:
<223> OTHER INFORMATION: YU45-D9/D3

<400> SEQUENCE: 27

Gln Ser Val Leu Thr Gln Pro Pro Ser Val Ser Ala Ala Pro Gly Gln
1               5                   10                  15

Glu Val Thr Ile Ser Cys Ser Gly Ser Ser Ser Asn Ile Gly Asn Asn
            20                  25                  30

Tyr Val Ser Trp Tyr Gln His Leu Pro Gly Thr Ala Pro Lys Leu Leu
        35                  40                  45

Ile Tyr Asp Asn Thr Glu Arg Pro Ser Gly Ile Pro Asp Arg Phe Ser
    50                  55                  60

Gly Ser Arg Ser Gly Thr Ser Val Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95
```

Ser Gly Gly Val Phe Gly Gly Gly Thr Lys Leu Thr Val Leu
            100                 105                 110

<210> SEQ ID NO 28
<211> LENGTH: 110
<212> TYPE: PRT
<213> ORGANISM: Artificial Sequence
<220> FEATURE:
<223> OTHER INFORMATION: YU45-E5

<400> SEQUENCE: 28

Gln Ser Ala Leu Thr Gln Pro Arg Ser Val Ser Gly Ser Pro Gly Gln
1               5                   10                  15

Ser Val Thr Ile Ser Cys Thr Gly Thr Ile Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Gly Tyr Tyr Cys Ser Ser Tyr Ala Gly Ser
                85                  90                  95

Tyr Thr Trp Gly Val Arg Arg Arg Asp Arg Ala Asp Arg Pro
            100                 105                 110

<210> SEQ ID NO 29
<211> LENGTH: 110
<212> TYPE: PRT
<213> ORGANISM: Artificial Sequence
<220> FEATURE:
<223> OTHER INFORMATION: YU45-G7

<400> SEQUENCE: 29

Gln Ser Val Leu Thr Gln Pro Pro Ser Val Ser Ala Ala Pro Gly Arg
1               5                   10                  15

Thr Val Thr Ile Ser Cys Ser Gly Ser Tyr Ser Asn Val Gly Ser Asn
            20                  25                  30

Leu Val Ser Trp Tyr Gln Gln Leu Pro Gly Thr Ala Pro Lys Leu Val
        35                  40                  45

Ile Tyr Glu Asp Asp Lys Arg Leu Ser Gly Ile Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ser Leu
                85                  90                  95

Lys Gly His Val Phe Gly Gly Gly Thr Gln Leu Thr Val Leu
            100                 105                 110

<210> SEQ ID NO 30
<211> LENGTH: 110
<212> TYPE: PRT
<213> ORGANISM: Artificial Sequence
<220> FEATURE:
<223> OTHER INFORMATION: YU45-B4

<400> SEQUENCE: 30

Gln Ser Val Leu Thr Gln Pro Pro Ser Ala Ser Gly Thr Pro Gly Gln
1               5                   10                  15

```
Arg Val Thr Ile Ser Cys Ser Gly Ser Ser Asn Ile Gly Ser Asn
                 20                  25                  30

Thr Val Asn Trp Tyr Gln Gln Leu Pro Gly Thr Ala Pro Lys Leu Leu
         35                  40                  45

Ile Tyr Ile Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Thr Asp Tyr Tyr Cys Ala Ala Trp Asp Asp Ser Leu
                 85                  90                  95

Asn Gly Trp Val Phe Gly Gly Gly Thr Lys Leu Thr Val Leu
                100                 105                 110
```

<210> SEQ ID NO 31
<211> LENGTH: 110
<212> TYPE: PRT
<213> ORGANISM: Artificial Sequence
<220> FEATURE:
<223> OTHER INFORMATION: YU45-H4

<400> SEQUENCE: 31

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
         35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Trp Val Phe Gly Gly Gly Thr Lys Leu Thr Ala Leu
                100                 105                 110
```

<210> SEQ ID NO 32
<211> LENGTH: 110
<212> TYPE: PRT
<213> ORGANISM: Artificial Sequence
<220> FEATURE:
<223> OTHER INFORMATION: YU45-B6

<400> SEQUENCE: 32

```
Gln Ser Ala Leu Thr Gln Pro Arg Ser Val Ser Gly Ser Pro Gly Gln
 1               5                  10                  15

Ser Val Thr Ile Ser Cys Thr Gly Thr Ser Arg Asp Val Gly Gly Tyr
                 20                  25                  30

Asn Tyr Val Ser Trp Tyr Gln Gln His Pro Gly Glu Ala Pro Lys Leu
         35                  40                  45

Met Ile Phe Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Asp Tyr
                 85                  90                  95

Tyr Thr Trp Val Phe Gly Gly Gly Thr Lys Val Thr Val Leu
                100                 105                 110
```

<210> SEQ ID NO 33
<211> LENGTH: 110
<212> TYPE: PRT
<213> ORGANISM: Artificial Sequence
<220> FEATURE:
<223> OTHER INFORMATION: YU45-D6

<400> SEQUENCE: 33

```
Gln Pro Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Leu Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Gly Val Phe Gly Gly Gly Thr Lys Leu Thr Ala Leu
            100                 105                 110
```

<210> SEQ ID NO 34
<211> LENGTH: 111
<212> TYPE: PRT
<213> ORGANISM: Artificial Sequence
<220> FEATURE:
<223> OTHER INFORMATION: YU45-E7

<400> SEQUENCE: 34

```
Leu Pro Val Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Asp Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Leu Trp Val Phe Gly Gly Gly Thr Lys Leu Thr Val Leu
            100                 105                 110
```

<210> SEQ ID NO 35
<211> LENGTH: 108
<212> TYPE: PRT
<213> ORGANISM: Artificial Sequence
<220> FEATURE:
<223> OTHER INFORMATION: YU45-F5

<400> SEQUENCE: 35

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Ile Ile Ser Ser Tyr
            20                  25                  30
```

Leu Asn Trp Tyr Gln Gln Lys Pro Gly Lys Ala Pro Lys Leu Leu Ile
              35                  40                  45

Tyr Ala Ala Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Trp Thr Phe Gly Gln Gly Thr Lys Val Glu Ile Lys
                100                 105

<210> SEQ ID NO 36
<211> LENGTH: 110
<212> TYPE: PRT
<213> ORGANISM: Artificial Sequence
<220> FEATURE:
<223> OTHER INFORMATION: YU45-H7/46-B5

<400> SEQUENCE: 36

Gln Ser Ala Leu Thr Gln Pro Pro Ser Ala Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Trp Val Phe Gly Gly Gly Thr Lys Leu Thr Val Leu
                100                 105                 110

<210> SEQ ID NO 37
<211> LENGTH: 110
<212> TYPE: PRT
<213> ORGANISM: Artificial Sequence
<220> FEATURE:
<223> OTHER INFORMATION: YU46-G1

<400> SEQUENCE: 37

Leu Pro Val Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                 20                  25                  30

Tyr Val Gln Trp Tyr Gln Gln Arg Pro Gly Ser Ser Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Arg Thr Glu Asp Glu Ala Asp Tyr Tyr Cys Gln Ser Tyr Asn Ser
                 85                  90                  95

Ser Lys Val Val Phe Gly Gly Gly Thr Lys Leu Thr Val Leu
                100                 105                 110

<210> SEQ ID NO 38

<211> LENGTH: 111
<212> TYPE: PRT
<213> ORGANISM: Artificial Sequence
<220> FEATURE:
<223> OTHER INFORMATION: YU46-A2

<400> SEQUENCE: 38

Gln Ser Ala Leu Thr Gln Pro Arg Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Glu Tyr Val Ser Trp Tyr Gln Gln His Pro Gly Lys Ala Pro Arg Leu
        35                  40                  45

Leu Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Asn Ser Tyr Thr Ser Ser
                85                  90                  95

Gly Thr Leu Val Val Phe Gly Gly Gly Thr Lys Leu Thr Val Leu
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: YU46-A8

<400> SEQUENCE: 39

Gln Ser Ala Leu Thr Gln Pro Arg Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Glu Tyr Val Ser Trp Tyr Gln Gln His Pro Gly Lys Ala Pro Arg Leu
        35                  40                  45

Leu Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Asn Ser Tyr Thr Ser Ser
                85                  90                  95

Gly Thr Leu Val Val Phe Gly Gly Gly Thr Lys Leu Thr Val Leu
            100                 105                 110

<210> SEQ ID NO 40
<211> LENGTH: 110
<212> TYPE: PRT
<213> ORGANISM: Artificial Sequence
<220> FEATURE:
<223> OTHER INFORMATION: YU46-B2

<400> SEQUENCE: 40

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
                100                 105                 110

<210> SEQ ID NO 41
<211> LENGTH: 108
<212> TYPE: PRT
<213> ORGANISM: Artificial Sequence
<220> FEATURE:
<223> OTHER INFORMATION: YU46-B6

<400> SEQUENCE: 41

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Gly Tyr Tyr Ala
                20                  25                  30

Thr Trp Tyr Gln Gln Lys Pro Gly Gln Ala Pro Val Val Val Met Tyr
            35                  40                  45

Gly Asn Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asp Ser Arg Gly Arg Ser Gly Asp His
                85                  90                  95

Trp Leu Phe Gly Gly Gly Thr Lys Leu Thr Val Leu
                100                 105

<210> SEQ ID NO 42
<211> LENGTH: 110
<212> TYPE: PRT
<213> ORGANISM: Artificial Sequence
<220> FEATURE:
<223> OTHER INFORMATION: YU46-C1

<400> SEQUENCE: 42

Gln Ala Val Leu Thr Gln Pro Pro Ser Ala Ser Gly Thr Pro Gly Gln
1               5                   10                  15

Arg Val Ser Ile Ser Cys Ser Gly Ser Ser Ser Asn Ile Gly Ser Tyr
                20                  25                  30

Tyr Val Tyr Trp Tyr Gln Gln Val Pro Gly Thr Ala Pro Lys Ile Leu
            35                  40                  45

Ile Tyr Arg Asn Asp Glu Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala His Tyr Tyr Cys Ala Thr Trp Asp Asp Gly Leu
                85                  90                  95

Ser Gly Trp Val Phe Gly Gly Gly Thr Lys Leu Thr Val Leu
                100                 105                 110

<210> SEQ ID NO 43
<211> LENGTH: 110
<212> TYPE: PRT
<213> ORGANISM: Artificial Sequence
```

<220> FEATURE:
<223> OTHER INFORMATION: YU46-D7

<400> SEQUENCE: 43

Gln Ser Val Leu Thr Gln Pro Pro Ala Ser Gly Ser Pro Gly Gln
1               5                   10                  15

Ser Val Thr Ile Ser Cys Ala Gly Thr Ser Ser Asp Val Gly Ala Tyr
            20                  25                  30

Asn Tyr Val Ala Trp Tyr Gln Gln His Pro Gly Lys Ala Pro Lys Leu
        35                  40                  45

Ile Ile Ser Glu Val Phe Arg Arg Pro Ser Gly Val Pro Asp Arg Phe
    50                  55                  60

Ser Gly Ser Lys Ser Gly Thr Thr Ala Phe Leu Thr Val Ser Gly Leu
65              70                  75                  80

Gln Ala Asp Asp Glu Ala Val Tyr Phe Cys Asn Ser Tyr Val Thr Gly
                85                  90                  95

Asn Asn Trp Ala Phe Gly Gly Gly Thr Lys Leu Thr Val Leu
            100                 105                 110

<210> SEQ ID NO 44
<211> LENGTH: 110
<212> TYPE: PRT
<213> ORGANISM: Artificial Sequence
<220> FEATURE:
<223> OTHER INFORMATION: YU46-E3

<400> SEQUENCE: 44

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 45
<211> LENGTH: 110
<212> TYPE: PRT
<213> ORGANISM: Artificial Sequence
<220> FEATURE:
<223> OTHER INFORMATION: YU46-E7

<400> SEQUENCE: 45

Gln Ser Val Leu Thr Gln Pro Pro Ala Ser Gly Thr Pro Gly Gln
1               5                   10                  15

Arg Val Thr Ile Ser Cys Ser Gly Ser Ser Ser Asn Ile Gly Tyr Asp
            20                  25                  30

Ala Val Asn Trp Tyr Gln Gln Leu Pro Gly Thr Ala Pro Lys Leu Val
        35                  40                  45

Ile Ser Asn Asp Asn Arg Arg Pro Ser Gly Val Pro Ala Arg Phe Ser
    50                  55                  60

```
Gly Ser Lys Ser Gly Thr Ser Ala Ser Leu Ala Ile Ser Gly Leu Gln
 65                  70                  75                  80

Ser Glu Asp Glu Ala Tyr Tyr Tyr Cys Ala Ala Trp Asp Asp Ser Leu
                 85                  90                  95

Ser Gly Trp Val Phe Gly Gly Gly Thr Lys Leu Thr Val Leu
            100                 105                 110

<210> SEQ ID NO 46
<211> LENGTH: 108
<212> TYPE: PRT
<213> ORGANISM: Artificial Sequence
<220> FEATURE:
<223> OTHER INFORMATION: YU46-H8

<400> SEQUENCE: 46

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ser Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Tyr Thr Phe Gly Gln Gly Thr Lys Leu Glu Ile Lys
            100                 105

<210> SEQ ID NO 47
<211> LENGTH: 110
<212> TYPE: PRT
<213> ORGANISM: Artificial Sequence
<220> FEATURE:
<223> OTHER INFORMATION: YU46-G9

<400> SEQUENCE: 47

Gln Pro Val Leu Thr Gln Pro Arg Ser Val Ser Gly Ser Pro Gly Gln
  1               5                  10                  15

Ser Val Thr Ile Ser Cys Thr Gly Thr Ser Ser Asp Val Gly Gly Tyr
                 20                  25                  30

Lys Tyr Val Ser Trp Tyr Gln Gln His Pro Gly Lys Ala Pro Glu Leu
             35                  40                  45

Ile Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Asn
                 85                  90                  95

Tyr Thr Trp Leu Phe Gly Gly Gly Thr Lys Val Thr Val Leu
            100                 105                 110

<210> SEQ ID NO 48
<211> LENGTH: 108
<212> TYPE: PRT
<213> ORGANISM: Artificial Sequence
<220> FEATURE:
<223> OTHER INFORMATION: YU46-G8
```

-continued

```
<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ser Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Tyr Thr Phe Gly Gln Gly Thr Lys Leu Glu Ile Lys
            100                 105

<210> SEQ ID NO 49
<211> LENGTH: 111
<212> TYPE: PRT
<213> ORGANISM: Artificial Sequence
<220> FEATURE:
<223> OTHER INFORMATION: YU46-B7

<400> SEQUENCE: 49

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Ser Ser Ser
                85                  90                  95

Ser Thr Leu Val Ala Phe Gly Gly Gly Thr Lys Leu Thr Val Leu
            100                 105                 110

<210> SEQ ID NO 50
<211> LENGTH: 111
<212> TYPE: PRT
<213> ORGANISM: Artificial Sequence
<220> FEATURE:
<223> OTHER INFORMATION: YU46-D3

<400> SEQUENCE: 50

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Tyr
            20                  25                  30

Lys Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
            100                 105                 110

<210> SEQ ID NO 51
<211> LENGTH: 118
<212> TYPE: PRT
<213> ORGANISM: Artificial Sequence
<220> FEATURE:
<223> OTHER INFORMATION: YU33-A2

<400> SEQUENCE: 51

Gln Leu Gln Gln Ser Gly Pro Gly Leu Val Lys Pro Ser Gln Thr Leu
1               5                   10                  15

Ser Leu Thr Cys Ala Ile Ser Gly Asp Ser Val Ser Ser Asn Ser Ala
            20                  25                  30

Ala Trp Asn Trp Ile Arg Gln Ser Pro Ser Arg Gly Leu Glu Trp Leu
        35                  40                  45

Gly Arg Thr Tyr Tyr Arg Ser Lys Trp Tyr Asn Asp Tyr Ala Val Ser
    50                  55                  60

Val Lys Ser Arg Ile Thr Ile Asn Pro Asp Thr Ser Lys Asn Gln Phe
65                  70                  75                  80

Thr Leu Gln Leu Asn Ser Val Thr Pro Asp Asp Thr Ala Val Tyr Tyr
                85                  90                  95

Cys Ala Arg Gly Thr Arg Gly Tyr Phe Asp Tyr Trp Gly Gln Gly Thr
            100                 105                 110

Leu Val Thr Val Ser Ser
        115

<210> SEQ ID NO 52
<211> LENGTH: 116
<212> TYPE: PRT
<213> ORGANISM: Artificial Sequence
<220> FEATURE:
<223> OTHER INFORMATION: YU33-B3/H3

<400> SEQUENCE: 52

Glu Val Gln Leu Val Glu Ser Gly Gly Gly Phe Val Lys Pro Gly Gly
1               5                   10                  15

Ser Leu Ser Ile Ser Cys Ala Ala Ser Gly Phe Thr Phe Ser Gly Ala
            20                  25                  30

Tyr Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Ala Phe Asp Ile Trp Gly Gln Gly Thr Met Val
            100                 105                 110

Thr Val Ser Ser
        115

<210> SEQ ID NO 53
<211> LENGTH: 118
<212> TYPE: PRT
<213> ORGANISM: Artificial Sequence

```
<220> FEATURE:
<223> OTHER INFORMATION: YU33-B4/YU45-G2/A3

<400> SEQUENCE: 53
```

| Glu | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Val | Ile | Ser | Tyr | Asp | Gly | Ser | Asn | Lys | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Ile | Gly | Ala | Thr | Asp | Pro | Leu | Asp | Tyr | Trp | Gly | Gln | Gly | Thr |
| | | | 100 | | | | | 105 | | | | | 110 | | |
| Leu | Val | Thr | Val | Ser | Ser |
| | | | | 115 | |

```
<210> SEQ ID NO 54
<211> LENGTH: 119
<212> TYPE: PRT
<213> ORGANISM: Artificial Sequence
<220> FEATURE:
<223> OTHER INFORMATION: YU33-E6

<400> SEQUENCE: 54
```

| Gln | Val | Gln | Leu | Gln | Gln | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Val | Ile | Ser | Tyr | Asp | Gly | Ser | Asp | Lys | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Val | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Asp | Leu | Ser | Gly | Leu | Pro | Ile | Ile | Asp | Tyr | Trp | Gly | Gln | Gly |
| | | | 100 | | | | | 105 | | | | | 110 | | |
| Thr | Leu | Val | Thr | Val | Ser | Ser |
| | | | | 115 | | |

```
<210> SEQ ID NO 55
<211> LENGTH: 115
<212> TYPE: PRT
<213> ORGANISM: Artificial Sequence
<220> FEATURE:
<223> OTHER INFORMATION: YU45-C11/A10

<400> SEQUENCE: 55
```

| Glu | Val | Gln | Leu | Leu | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

Ala Met His Trp Val Arg Gln Ala Pro Gly Glu Gly Leu Glu Trp Val
        35                  40                  45

Ala Val Ile Ser Tyr Asp Gly Ser Asn Lys Tyr Ala Asp Ser Val
 50                  55                  60

Lys Gly Arg Phe Thr Ile Ser Arg Asp Asn Ala Lys Asp Ser Leu Tyr
 65                  70                  75                  80

Leu Gln Met Asn Ser Leu Arg Asp Glu Asp Thr Ala Val Tyr Tyr Cys
                 85                  90                  95

Ala Arg Arg Gly Tyr Phe Asp Tyr Trp Gly Gln Gly Thr Leu Val Thr
            100                 105                 110

Val Ser Ser
        115

<210> SEQ ID NO 56
<211> LENGTH: 118
<212> TYPE: PRT
<213> ORGANISM: Artificial Sequence
<220> FEATURE:
<223> OTHER INFORMATION: YU45-D11/F11

<400> SEQUENCE: 56

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Ala Ala Ala Asp Gly Met Asp Val Trp Gly Gln Gly Thr
            100                 105                 110

Thr Val Thr Val Ser Ser
        115

<210> SEQ ID NO 57
<211> LENGTH: 123
<212> TYPE: PRT
<213> ORGANISM: Artificial Sequence
<220> FEATURE:
<223> OTHER INFORMATION: YU45-E11/E12

<400> SEQUENCE: 57

Gln Val Gln Leu Val Gln Ser Gly Gly Gly Val Val Leu Pro Gly Arg
 1               5                  10                  15

Ser Leu Arg Leu Ser Cys Ala Ala Ser Gly Phe Ser Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Thr Gly Asp Thr Ala Val Tyr Tyr Cys
                 85                  90                  95

Ala Arg Ile Thr His Asp Tyr Gly Asp Phe Ser Asp Ala Phe Asp Ile
        100                 105                 110
Trp Gly Gln Gly Thr Met Val Ala Val Ser Ser
        115                 120

<210> SEQ ID NO 58
<211> LENGTH: 119
<212> TYPE: PRT
<213> ORGANISM: Artificial Sequence
<220> FEATURE:
<223> OTHER INFORMATION: YU45-H11/D12

<400> SEQUENCE: 58

Glu Val Gln Leu Leu Glu Ser Gly Gly Gly Val Val Gln Pro Gly Arg
1               5                   10                  15
Ser Arg Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Leu Tyr Ser Gly Ser Ser Asn Phe Asp Tyr Trp Gly Gln Gly
            100                 105                 110
Thr Leu Val Thr Val Ser Ser
        115

<210> SEQ ID NO 59
<211> LENGTH: 123
<212> TYPE: PRT
<213> ORGANISM: Artificial Sequence
<220> FEATURE:
<223> OTHER INFORMATION: YU45-A12/G10

<400> SEQUENCE: 59

Gln Val Gln Leu Val Gln Ser Gly Gly Gly Val Val Leu Pro Gly Arg
1               5                   10                  15
Ser Leu Arg Leu Ser Cys Ala Ala Ser Gly Phe Thr Phe Arg Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Thr Gly Asp Thr Ala Val Tyr Tyr Cys
                85                  90                  95
Ala Arg Ile Thr His Asp Tyr Gly Asp Phe Ser Asp Ala Phe Asp Ile
            100                 105                 110
Trp Gly Gln Gly Thr Met Val Ala Val Ser Ser
        115                 120

<210> SEQ ID NO 60
<211> LENGTH: 118
<212> TYPE: PRT

```
<213> ORGANISM: Artificial Sequence
<220> FEATURE:
<223> OTHER INFORMATION: YU45-G1

<400> SEQUENCE: 60

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser
        115

<210> SEQ ID NO 61
<211> LENGTH: 115
<212> TYPE: PRT
<213> ORGANISM: Artificial Sequence
<220> FEATURE:
<223> OTHER INFORMATION: YU45-C2/A7/B10

<400> SEQUENCE: 61

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Asn Val Asp Leu Trp Gly Gln Gly Thr Leu Val Thr
            100                 105                 110

Val Ser Ser
        115

<210> SEQ ID NO 62
<211> LENGTH: 123
<212> TYPE: PRT
<213> ORGANISM: Artificial Sequence
<220> FEATURE:
<223> OTHER INFORMATION: YU45-D2/H2/C7/F3/C9/E1/E9/C10/G3/H9/C5/A2/A5

<400> SEQUENCE: 62

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
        115                 120

<210> SEQ ID NO 63
<211> LENGTH: 123
<212> TYPE: PRT
<213> ORGANISM: Artificial Sequence
<220> FEATURE:
<223> OTHER INFORMATION: YU45-E3

<400> SEQUENCE: 63

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
        115                 120

<210> SEQ ID NO 64
<211> LENGTH: 115
<212> TYPE: PRT
<213> ORGANISM: Artificial Sequence
<220> FEATURE:
<223> OTHER INFORMATION: YU45-C8/E8

<400> SEQUENCE: 64

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys

```
                    85                  90                  95

Ala Arg Arg Gly Tyr Gly Asp Tyr Trp Gly Gln Gly Thr Leu Val Thr
                100                 105                 110

Val Ser Ser
        115

<210> SEQ ID NO 65
<211> LENGTH: 124
<212> TYPE: PRT
<213> ORGANISM: Artificial Sequence
<220> FEATURE:
<223> OTHER INFORMATION: YU45-F8

<400> SEQUENCE: 65

Arg Ser Ala Ala Gly Gly Val Trp Gly Arg Gly Pro Ala Trp Glu
1               5                   10                  15

Val Pro Glu Thr Leu Leu Cys Ser Leu Trp Ile Phe Leu Lys Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Val Gly Phe Ser Ser Trp Tyr Pro Asp Leu Tyr Tyr Phe Asp
                100                 105                 110

Tyr Trp Gly Gln Gly Thr Leu Val Thr Val Ser Ser
        115                 120

<210> SEQ ID NO 66
<211> LENGTH: 119
<212> TYPE: PRT
<213> ORGANISM: Artificial Sequence
<220> FEATURE:
<223> OTHER INFORMATION: YU45-G8/H6

<400> SEQUENCE: 66

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ala Arg Gly Val Tyr Leu Phe Asp Tyr Trp Gly Gln Gly
                100                 105                 110

Thr Leu Val Thr Val Ser Ser
        115

<210> SEQ ID NO 67
<211> LENGTH: 119
```

<212> TYPE: PRT
<213> ORGANISM: Artificial Sequence
<220> FEATURE:
<223> OTHER INFORMATION: YU45-F9

<400> SEQUENCE: 67

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gln Ser Gly Glu Pro Glu Ser Asp Tyr Trp Gly Gln Gly
            100                 105                 110

Thr Leu Val Thr Val Ser Ser
        115

<210> SEQ ID NO 68
<211> LENGTH: 119
<212> TYPE: PRT
<213> ORGANISM: Artificial Sequence
<220> FEATURE:
<223> OTHER INFORMATION: YU45-H10

<400> SEQUENCE: 68

Glu Val Gln Leu Leu Glu Ser Gly Gly Gly Val Val Gln Pro Gly Arg
1               5                   10                  15

Ser Arg Arg Leu Ser Cys Ala Ala Ser Gly Phe Ser Leu Asn Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Tyr Ser Gly Ser Ser Asn Phe Asp Tyr Trp Gly Gln Gly
            100                 105                 110

Thr Leu Val Thr Val Ser Ser
        115

<210> SEQ ID NO 69
<211> LENGTH: 124
<212> TYPE: PRT
<213> ORGANISM: Artificial Sequence
<220> FEATURE:
<223> OTHER INFORMATION: YU46-A10

<400> SEQUENCE: 69

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

-continued

```
                    20                  25                  30
Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Val Gly Phe Ser Ser Trp Tyr Pro Asp Leu Tyr Tyr Phe Asp
            100                 105                 110

Tyr Trp Gly Gln Gly Thr Leu Val Thr Val Ser Ser
            115                 120
```

<210> SEQ ID NO 70
<211> LENGTH: 118
<212> TYPE: PRT
<213> ORGANISM: Artificial Sequence
<220> FEATURE:
<223> OTHER INFORMATION: YU45-F2

<400> SEQUENCE: 70

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser
            115
```

<210> SEQ ID NO 71
<211> LENGTH: 121
<212> TYPE: PRT
<213> ORGANISM: Artificial Sequence
<220> FEATURE:
<223> OTHER INFORMATION: YU45-H3

<400> SEQUENCE: 71

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Leu Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Met Val Asn Leu Tyr Tyr Gly Asp Ala Phe Asp Ile Trp Gly
            100                 105                 110

Gln Gly Thr Met Val Thr Val Ser Ser
        115                 120
```

<210> SEQ ID NO 72
<211> LENGTH: 118
<212> TYPE: PRT
<213> ORGANISM: Artificial Sequence
<220> FEATURE:
<223> OTHER INFORMATION: YU45-A1

<400> SEQUENCE: 72

```
Gln Leu Gln Leu Gln Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Val Gly Ala Thr Ala Asp Asp Tyr Trp Gly Gln Gly Thr
            100                 105                 110

Leu Val Thr Val Ser Ser
        115
```

<210> SEQ ID NO 73
<211> LENGTH: 118
<212> TYPE: PRT
<213> ORGANISM: Artificial Sequence
<220> FEATURE:
<223> OTHER INFORMATION: YU45-A8/C6

<400> SEQUENCE: 73

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser
        115
```

<210> SEQ ID NO 74

```
<211> LENGTH: 124
<212> TYPE: PRT
<213> ORGANISM: Artificial Sequence
<220> FEATURE:
<223> OTHER INFORMATION: YU45-B5/A4

<400> SEQUENCE: 74
```

Ser Glu Gln Glu Asn Cys Glu Gln Val Gln Leu Val Gln Ser Gly Ala
1               5                   10                  15

Glu Val Lys Lys Pro Gly Ser Ser Val Lys Val Ser Cys Lys Ala Ser
            20                  25                  30

Gly Gly Thr Phe Ser Ser Tyr Ala Ile Ser Trp Val Arg Gln Ala Pro
        35                  40                  45

Gly Gln Gly Leu Glu Trp Met Gly Gly Ile Ile Pro Ile Phe Gly Thr
    50                  55                  60

Ala Asn Tyr Ala Gln Lys Phe Gln Gly Arg Val Thr Ile Thr Ala Asp
65                  70                  75                  80

Glu Ser Thr Ser Thr Ala Tyr Met Glu Leu Ser Ser Leu Arg Ser Glu
                85                  90                  95

Asp Thr Ala Val Tyr Tyr Cys Ala Arg Gly Leu Ile Thr Gly Thr Thr
            100                 105                 110

Pro Trp Gly Gln Gly Thr Leu Val Thr Val Ser Ser
        115                 120

```
<210> SEQ ID NO 75
<211> LENGTH: 118
<212> TYPE: PRT
<213> ORGANISM: Artificial Sequence
<220> FEATURE:
<223> OTHER INFORMATION: YU45-C3/A6

<400> SEQUENCE: 75
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser
        115

```
<210> SEQ ID NO 76
<211> LENGTH: 126
<212> TYPE: PRT
<213> ORGANISM: Artificial Sequence
<220> FEATURE:
<223> OTHER INFORMATION: YU45-D1

<400> SEQUENCE: 76
```

Ala Gln Val Gln Leu Gln Glu Ser Gly Pro Gly Leu Val Lys Pro Ser
1               5                   10                  15

```
Gly Thr Leu Ser Leu Thr Cys Ala Val Ser Gly Gly Ser Ile Ser Ser
                20                  25                  30

Ser Asn Trp Trp Ser Trp Val Arg Gln Pro Pro Gly Lys Gly Leu Glu
        35                  40                  45

Trp Ile Gly Glu Ile Tyr His Ser Gly Ser Thr Asn Tyr Asn Pro Ser
    50                  55                  60

Leu Lys Ser Arg Val Thr Ile Ser Val Asp Lys Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gln Asn Leu Gly Gly Gly Ser Tyr Tyr Val Gly Ala
                100                 105                 110

Phe Asp Tyr Trp Gly Gln Gly Thr Leu Val Thr Val Ser Ser
            115                 120                 125

<210> SEQ ID NO 77
<211> LENGTH: 124
<212> TYPE: PRT
<213> ORGANISM: Artificial Sequence
<220> FEATURE:
<223> OTHER INFORMATION: YU45-D9/D3

<400> SEQUENCE: 77

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu His Phe Ser Gln Tyr Phe Ser Thr Ile Asp Ala Phe Asp
                100                 105                 110

Ile Trp Gly Gln Gly Thr Met Val Thr Ile Ser Ser
            115                 120

<210> SEQ ID NO 78
<211> LENGTH: 123
<212> TYPE: PRT
<213> ORGANISM: Artificial Sequence
<220> FEATURE:
<223> OTHER INFORMATION: YU45-E5

<400> SEQUENCE: 78

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
        115                 120
```

<210> SEQ ID NO 79
<211> LENGTH: 121
<212> TYPE: PRT
<213> ORGANISM: Artificial Sequence
<220> FEATURE:
<223> OTHER INFORMATION: YU45-G7

<400> SEQUENCE: 79

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Tyr Ser Ser Gly Trp Tyr Phe Asp Tyr Trp Gly
            100                 105                 110

Gln Gly Thr Leu Val Thr Val Ser Ser
        115                 120
```

<210> SEQ ID NO 80
<211> LENGTH: 131
<212> TYPE: PRT
<213> ORGANISM: Artificial Sequence
<220> FEATURE:
<223> OTHER INFORMATION: YU45-B4

<400> SEQUENCE: 80

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Gln Ser Tyr Ser Ser Trp Tyr Glu Trp Glu Pro
            100                 105                 110

Gly Arg Glu His Ala Phe Asp Ile Trp Gly Gln Gly Thr Met Val Thr
        115                 120                 125

Val Ser Ser
```

<210> SEQ ID NO 81
<211> LENGTH: 114
<212> TYPE: PRT
<213> ORGANISM: Artificial Sequence
<220> FEATURE:
<223> OTHER INFORMATION: YU45-H4

<400> SEQUENCE: 81

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Asp Asp Tyr Trp Gly Gln Gly Thr Leu Val Thr Val
            100                 105                 110

Ser Ser
```

<210> SEQ ID NO 82
<211> LENGTH: 118
<212> TYPE: PRT
<213> ORGANISM: Artificial Sequence
<220> FEATURE:
<223> OTHER INFORMATION: YU45-B6

<400> SEQUENCE: 82

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Val Asp Tyr Trp Gly Gln Gly Thr
            100                 105                 110

Leu Val Thr Val Ser Ser
        115
```

<210> SEQ ID NO 83
<211> LENGTH: 124
<212> TYPE: PRT
<213> ORGANISM: Artificial Sequence
<220> FEATURE:
<223> OTHER INFORMATION: YU45-D6

<400> SEQUENCE: 83

```
Arg Ser Ala Ala Gly Val Trp Gly Arg Gly Pro Ala Trp Glu
1               5                   10                  15

Val Pro Glu Thr Leu Leu Cys Ser Leu Trp Ile Phe Leu Lys Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Val Gly Phe Ser Ser Trp Tyr Pro Asp Leu Tyr Tyr Phe Asp
            100                 105                 110

Tyr Trp Gly Gln Gly Thr Leu Val Thr Val Ser Ser
        115                 120
```

<210> SEQ ID NO 84
<211> LENGTH: 124
<212> TYPE: PRT
<213> ORGANISM: Artificial Sequence
<220> FEATURE:
<223> OTHER INFORMATION: YU45-E7

<400> SEQUENCE: 84

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ser Gly Tyr Pro Ser Arg Tyr Tyr Tyr Gly Met Asp
            100                 105                 110

Val Trp Gly Gln Gly Thr Thr Val Thr Val Ser Ser
        115                 120
```

<210> SEQ ID NO 85
<211> LENGTH: 118
<212> TYPE: PRT
<213> ORGANISM: Artificial Sequence
<220> FEATURE:
<223> OTHER INFORMATION: YU45-F5

<400> SEQUENCE: 85

```
Val Thr Leu Lys Glu Ser Gly Gly Gly Val Val Gln Pro Gly Arg Ser
1               5                   10                  15

Leu Arg Leu Ser Cys Ala Ala Ser Gly Phe Thr Phe Ser Ser Tyr Gly
            20                  25                  30

Met His Trp Val Arg Gln Ala Pro Gly Lys Gly Leu Glu Trp Val Ala
        35                  40                  45

Val Ile Ser Tyr Asp Gly Ser Asn Lys Tyr Tyr Ala Asp Ser Val Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Gly Lys Ser Tyr Tyr Gly Phe Asp Tyr Trp Gly Gln Gly Thr
            100                 105                 110

Leu Val Thr Val Ser Ser
        115

<210> SEQ ID NO 86
<211> LENGTH: 122
<212> TYPE: PRT
<213> ORGANISM: Artificial Sequence
<220> FEATURE:
<223> OTHER INFORMATION: YU45-H7/46-B5

<400> SEQUENCE: 86

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu His Ser Gly Arg Asn Trp Gly Asp Ala Phe Asp Ile Trp
            100                 105                 110

Gly Gln Gly Thr Met Val Thr Val Ser Ser
        115                 120

<210> SEQ ID NO 87
<211> LENGTH: 126
<212> TYPE: PRT
<213> ORGANISM: Artificial Sequence
<220> FEATURE:
<223> OTHER INFORMATION: YU46-G1

<400> SEQUENCE: 87

Gln Val Leu Val Gln Ser Gly Ala Glu Val Lys Lys Pro Gly Ser Ser
1               5                   10                  15

Val Lys Val Ser Cys Lys Ala Ser Gly Gly Thr Phe Ser Ser Tyr Ala
                20                  25                  30

Ile Ser Trp Val Arg Gln Ala Pro Gly Gln Gly Leu Glu Trp Met Gly
            35                  40                  45

Gly Ile Ile Pro Ile Phe Gly Thr Ala Asn Tyr Ala Gln Lys Phe Gln
        50                  55                  60

Gly Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Gly Gly Gly Pro Tyr Tyr Asp Phe Trp Ser Gly Tyr Tyr Thr Glu
            100                 105                 110

Phe Asp Tyr Trp Gly Gln Gly Thr Leu Val Thr Val Ser Ser

<210> SEQ ID NO 88
<211> LENGTH: 121
<212> TYPE: PRT
<213> ORGANISM: Artificial Sequence
<220> FEATURE:
<223> OTHER INFORMATION: YU46-A2

<400> SEQUENCE: 88

Glu Val Gln Leu Leu Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Ser Ser Gly Trp Tyr Phe Asp Tyr Trp Gly
            100                 105                 110

Gln Gly Thr Leu Val Thr Val Ser Ser
        115                 120

<210> SEQ ID NO 89
<211> LENGTH: 121
<212> TYPE: PRT
<213> ORGANISM: Artificial Sequence
<220> FEATURE:
<223> OTHER INFORMATION: YU46-A8

<400> SEQUENCE: 89

Glu Val Gln Leu Leu Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Ser Ser Gly Trp Tyr Phe Asp Tyr Trp Gly
            100                 105                 110

Gln Gly Thr Leu Val Thr Val Ser Ser
        115                 120

<210> SEQ ID NO 90
<211> LENGTH: 120
<212> TYPE: PRT
<213> ORGANISM: Artificial Sequence
<220> FEATURE:
<223> OTHER INFORMATION: YU46-B2

<400> SEQUENCE: 90

-continued

Gly Ala Ala Gly Gly Val Trp Gly Arg Arg Gly Pro Ala Trp Glu Val
1               5                   10                  15

Pro Glu Thr Leu Leu Cys Ser Leu Trp Ile Leu Pro Ser Asp Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Ala Ala Ala Gly Arg Asp Ala Phe Asp Ile Trp Gly Gln
            100                 105                 110

Gly Thr Met Val Thr Val Ser Ser
            115                 120

<210> SEQ ID NO 91
<211> LENGTH: 123
<212> TYPE: PRT
<213> ORGANISM: Artificial Sequence
<220> FEATURE:
<223> OTHER INFORMATION: YU46-B6

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Val Ala Ala Arg Ser Tyr Tyr Tyr Tyr Met Asp Val
            100                 105                 110

Trp Gly Lys Gly Thr Thr Val Thr Val Ser Ser
            115                 120

<210> SEQ ID NO 92
<211> LENGTH: 125
<212> TYPE: PRT
<213> ORGANISM: Artificial Sequence
<220> FEATURE:
<223> OTHER INFORMATION: YU46-C1

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe

```
                    50                  55                  60
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Ala Asp Ser Ser Ala Gly Gly Pro Tyr Tyr Tyr Gly Met
                100                 105                 110

Asp Val Trp Gly Gln Gly Thr Thr Val Thr Val Ser Ser
            115                 120                 125

<210> SEQ ID NO 93
<211> LENGTH: 119
<212> TYPE: PRT
<213> ORGANISM: Artificial Sequence
<220> FEATURE:
<223> OTHER INFORMATION: YU46-D7

<400> SEQUENCE: 93

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Gly Ala Glu Asp Thr Ala Val Tyr Tyr Cys
                85                  90                  95

Ala Lys Phe Ala Arg Gly Val Tyr Leu Phe Asp Tyr Trp Gly Gln Gly
                100                 105                 110

Thr Leu Val Thr Val Ser Ser
            115

<210> SEQ ID NO 94
<211> LENGTH: 118
<212> TYPE: PRT
<213> ORGANISM: Artificial Sequence
<220> FEATURE:
<223> OTHER INFORMATION: YU46-E3

<400> SEQUENCE: 94

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile Gly Gly Tyr Asp Asp Phe Asp Tyr Trp Gly Gln Gly Thr
                100                 105                 110
```

```
Leu Val Thr Val Ser Ser
        115

<210> SEQ ID NO 95
<211> LENGTH: 124
<212> TYPE: PRT
<213> ORGANISM: Artificial Sequence
<220> FEATURE:
<223> OTHER INFORMATION: YU46-E7

<400> SEQUENCE: 95

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Asp Ser Ser Gly Thr Gln Gly Asp Ser Phe Asp
            100                 105                 110

Tyr Trp Gly Gln Gly Thr Leu Val Thr Val Ser Ser
        115                 120

<210> SEQ ID NO 96
<211> LENGTH: 116
<212> TYPE: PRT
<213> ORGANISM: Artificial Sequence
<220> FEATURE:
<223> OTHER INFORMATION: YU46-H8

<400> SEQUENCE: 96

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Tyr Tyr Phe Asp Tyr Trp Gly Gln Gly Thr Leu Val
            100                 105                 110

Thr Val Ser Ser
        115

<210> SEQ ID NO 97
<211> LENGTH: 118
<212> TYPE: PRT
<213> ORGANISM: Artificial Sequence
<220> FEATURE:
<223> OTHER INFORMATION: YU46-G9
```

<400> SEQUENCE: 97

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser
        115

<210> SEQ ID NO 98
<211> LENGTH: 116
<212> TYPE: PRT
<213> ORGANISM: Artificial Sequence
<220> FEATURE:
<223> OTHER INFORMATION: YU46-G8

<400> SEQUENCE: 98

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Tyr Tyr Phe Asp Tyr Trp Gly Gln Gly Thr Leu Val
            100                 105                 110

Thr Val Ser Ser
        115

<210> SEQ ID NO 99
<211> LENGTH: 115
<212> TYPE: PRT
<213> ORGANISM: Artificial Sequence
<220> FEATURE:
<223> OTHER INFORMATION: YU46-B7

<400> SEQUENCE: 99

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

-continued

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Val Leu Phe Asp Tyr Trp Gly Gln Gly Thr Leu Val Thr
            100                 105                 110

Val Ser Ser
        115

<210> SEQ ID NO 100
<211> LENGTH: 115
<212> TYPE: PRT
<213> ORGANISM: Artificial Sequence
<220> FEATURE:
<223> OTHER INFORMATION: YU46-D3

<400> SEQUENCE: 100

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ser Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ser Gly Val Leu Asp Tyr Trp Gly Gln Gly Thr Leu Val Thr
            100                 105                 110

Val Ser Ser
        115

<210> SEQ ID NO 101
<211> LENGTH: 6
<212> TYPE: PRT
<213> ORGANISM: Artificial Sequence
<220> FEATURE:
<223> OTHER INFORMATION: YU33-A2 LC-CDR 1

<400> SEQUENCE: 101

Gln Asp Val Gly Arg Tyr
 1               5

<210> SEQ ID NO 102
<211> LENGTH: 3
<212> TYPE: PRT
<213> ORGANISM: Artificial Sequence
<220> FEATURE:
<223> OTHER INFORMATION: YU33-A2 LC-CDR 2

<400> SEQUENCE: 102

Ala Ala Ser
 1

<210> SEQ ID NO 103
<211> LENGTH: 9
<212> TYPE: PRT

```
<213> ORGANISM: Artificial Sequence
<220> FEATURE:
<223> OTHER INFORMATION: YU33-A2 LC-CDR 3

<400> SEQUENCE: 103

Gln Gln Tyr Arg Ser Ala Pro Leu Ala
1               5

<210> SEQ ID NO 104
<211> LENGTH: 8
<212> TYPE: PRT
<213> ORGANISM: Artificial Sequence
<220> FEATURE:
<223> OTHER INFORMATION: YU33-B3/H3 LC-CDR 1

<400> SEQUENCE: 104

Thr Gly Asn Ile Ala Ser Asn Arg
1               5

<210> SEQ ID NO 105
<211> LENGTH: 3
<212> TYPE: PRT
<213> ORGANISM: Artificial Sequence
<220> FEATURE:
<223> OTHER INFORMATION: YU33-B3/H3 LC-CDR 2

<400> SEQUENCE: 105

Asp Asn His
1

<210> SEQ ID NO 106
<211> LENGTH: 9
<212> TYPE: PRT
<213> ORGANISM: Artificial Sequence
<220> FEATURE:
<223> OTHER INFORMATION: YU33-B3/H3 LC-CDR 3

<400> SEQUENCE: 106

Gln Ser Tyr Asp Tyr Ser Ser Val Ile
1               5

<210> SEQ ID NO 107
<211> LENGTH: 9
<212> TYPE: PRT
<213> ORGANISM: Artificial Sequence
<220> FEATURE:
<223> OTHER INFORMATION: YU33-B4/YU45-G2/A3 LC-CDR 1

<400> SEQUENCE: 107

Ser Ser Asp Val Gly Gly Tyr Asn Tyr
1               5

<210> SEQ ID NO 108
<211> LENGTH: 3
<212> TYPE: PRT
<213> ORGANISM: Artificial Sequence
<220> FEATURE:
<223> OTHER INFORMATION: YU33-B4/YU45-G2/A3 LC-CDR 2

<400> SEQUENCE: 108

Asp Val Ser
1

<210> SEQ ID NO 109
<211> LENGTH: 10
<212> TYPE: PRT
<213> ORGANISM: Artificial Sequence
```

<220> FEATURE:
<223> OTHER INFORMATION: YU33-B4/YU45-G2/A3 LC-CDR 3

<400> SEQUENCE: 109

Ser Ser Tyr Thr Ser Ser Ser Trp Val
1               5               10

<210> SEQ ID NO 110
<211> LENGTH: 9
<212> TYPE: PRT
<213> ORGANISM: Artificial Sequence
<220> FEATURE:
<223> OTHER INFORMATION: YU33-E6 LC-CDR 1

<400> SEQUENCE: 110

Ser Ser Asp Val Gly Ala Tyr Asn Tyr
1               5

<210> SEQ ID NO 111
<211> LENGTH: 3
<212> TYPE: PRT
<213> ORGANISM: Artificial Sequence
<220> FEATURE:
<223> OTHER INFORMATION: YU33-E6 LC-CDR 2

<400> SEQUENCE: 111

Glu Val Ser
1

<210> SEQ ID NO 112
<211> LENGTH: 10
<212> TYPE: PRT
<213> ORGANISM: Artificial Sequence
<220> FEATURE:
<223> OTHER INFORMATION: YU33-E6 LC-CDR 3

<400> SEQUENCE: 112

Ser Ser Tyr Thr Ser Ser Asn Thr Leu Val
1               5               10

<210> SEQ ID NO 113
<211> LENGTH: 10
<212> TYPE: PRT
<213> ORGANISM: Artificial Sequence
<220> FEATURE:
<223> OTHER INFORMATION: YU45-C11/A10 LC-CDR 3

<400> SEQUENCE: 113

Ser Ser Tyr Thr Ser Ser Ser Thr Val Val
1               5               10

<210> SEQ ID NO 114
<211> LENGTH: 9
<212> TYPE: PRT
<213> ORGANISM: Artificial Sequence
<220> FEATURE:
<223> OTHER INFORMATION: YU45-D11/F11 LC-CDR 1

<400> SEQUENCE: 114

Ser Ser Asp Ile Gly Ala Tyr Asn Tyr
1               5

<210> SEQ ID NO 115
<211> LENGTH: 10
<212> TYPE: PRT
<213> ORGANISM: Artificial Sequence
<220> FEATURE:

<223> OTHER INFORMATION: YU45-D11/F11 LC-CDR 3

<400> SEQUENCE: 115

Ser Ser Tyr Thr Thr Ser Ser Thr Val Val
1               5                   10

<210> SEQ ID NO 116
<211> LENGTH: 8
<212> TYPE: PRT
<213> ORGANISM: Artificial Sequence
<220> FEATURE:
<223> OTHER INFORMATION: YU45-E11/E12 LC-CDR 1

<400> SEQUENCE: 116

Ser Ser Asn Ile Gly Ser Asn Tyr
1               5

<210> SEQ ID NO 117
<211> LENGTH: 3
<212> TYPE: PRT
<213> ORGANISM: Artificial Sequence
<220> FEATURE:
<223> OTHER INFORMATION: YU45-E11/E12 LC-CDR 2

<400> SEQUENCE: 117

Arg Asn Asn
1

<210> SEQ ID NO 118
<211> LENGTH: 11
<212> TYPE: PRT
<213> ORGANISM: Artificial Sequence
<220> FEATURE:
<223> OTHER INFORMATION: YU45-E11/E12 LC-CDR 3

<400> SEQUENCE: 118

Ala Ala Trp Asp Gly Ser Leu Ser Gly Trp Val
1               5                   10

<210> SEQ ID NO 119
<211> LENGTH: 10
<212> TYPE: PRT
<213> ORGANISM: Artificial Sequence
<220> FEATURE:
<223> OTHER INFORMATION: YU45-H11/D12 LC-CDR 3

<400> SEQUENCE: 119

Ser Ser Tyr Thr Ser Ser Ser Thr Trp Val
1               5                   10

<210> SEQ ID NO 120
<211> LENGTH: 10
<212> TYPE: PRT
<213> ORGANISM: Artificial Sequence
<220> FEATURE:
<223> OTHER INFORMATION: YU45-G1 LC-CDR 3

<400> SEQUENCE: 120

Cys Ser Tyr Ala Gly Ser Tyr Thr Phe Val
1               5                   10

<210> SEQ ID NO 121
<211> LENGTH: 10
<212> TYPE: PRT
<213> ORGANISM: Artificial Sequence
<220> FEATURE:
<223> OTHER INFORMATION: YU45-C2/A7/B10 LC-LCDR 3

<400> SEQUENCE: 121

Asn Ser Tyr Thr Ser Ser Thr Pro Tyr Val
1               5                   10

<210> SEQ ID NO 122
<211> LENGTH: 9
<212> TYPE: PRT
<213> ORGANISM: Artificial Sequence
<220> FEATURE:
<223> OTHER INFORMATION: YU45-D2/H2/C7/F3/C9/E1/E9/C10/G3/H9/C5/A2/A5
      LC-CDR 1

<400> SEQUENCE: 122

Ile Ser Asp Val Gly Gly Tyr Asn Tyr
1               5

<210> SEQ ID NO 123
<211> LENGTH: 3
<212> TYPE: PRT
<213> ORGANISM: Artificial Sequence
<220> FEATURE:
<223> OTHER INFORMATION: YU45-D2/H2/C7/F3/C9/E1/E9/C10/G3/H9/C5/A2/A5
      LC-CDR 2

<400> SEQUENCE: 123

Asp Val Thr
1

<210> SEQ ID NO 124
<211> LENGTH: 10
<212> TYPE: PRT
<213> ORGANISM: Artificial Sequence
<220> FEATURE:
<223> OTHER INFORMATION: YU45-D2/H2/C7/F3/C9/E1/E9/C10/G3/H9/C5/A2/A5
      LC-CDR 3

<400> SEQUENCE: 124

Ser Ser Tyr Ala Gly Ser Tyr Thr Trp Val
1               5                   10

<210> SEQ ID NO 125
<211> LENGTH: 10
<212> TYPE: PRT
<213> ORGANISM: Artificial Sequence
<220> FEATURE:
<223> OTHER INFORMATION: YU45-C8/E8 LC-CDR 3

<400> SEQUENCE: 125

Gly Ser Tyr Thr Ser Ser Asn Thr Gln Val
1               5                   10

<210> SEQ ID NO 126
<211> LENGTH: 8
<212> TYPE: PRT
<213> ORGANISM: Artificial Sequence
<220> FEATURE:
<223> OTHER INFORMATION: YU45-F8YU45-F8 LC-CDR 1

<400> SEQUENCE: 126

Ser Ser Asn Ile Gly Asn Asn Leu
1               5

<210> SEQ ID NO 127
<211> LENGTH: 11
<212> TYPE: PRT
<213> ORGANISM: Artificial Sequence

```
<220> FEATURE:
<223> OTHER INFORMATION: YU45-F8YU45-F8 LC-CDR 3

<400> SEQUENCE: 127

Ala Ala Trp Asp Asp Ser Leu Ser Ala Gly Val
1               5                   10

<210> SEQ ID NO 128
<211> LENGTH: 9
<212> TYPE: PRT
<213> ORGANISM: Artificial Sequence
<220> FEATURE:
<223> OTHER INFORMATION: YU45-G8/H6 LC-CDR 1

<400> SEQUENCE: 128

Ser Ser Asp Val Gly Gly Tyr Asp Tyr
1               5

<210> SEQ ID NO 129
<211> LENGTH: 3
<212> TYPE: PRT
<213> ORGANISM: Artificial Sequence
<220> FEATURE:
<223> OTHER INFORMATION: YU45-G8/H6 LC-CDR 2

<400> SEQUENCE: 129

Asp Val His
1

<210> SEQ ID NO 130
<211> LENGTH: 10
<212> TYPE: PRT
<213> ORGANISM: Artificial Sequence
<220> FEATURE:
<223> OTHER INFORMATION: YU45-G8/H6 LC-CDR 3

<400> SEQUENCE: 130

Ser Ser Tyr Thr Ser Ser Ile Thr Trp Val
1               5                   10

<210> SEQ ID NO 131
<211> LENGTH: 10
<212> TYPE: PRT
<213> ORGANISM: Artificial Sequence
<220> FEATURE:
<223> OTHER INFORMATION: YU45-F9 LC-CDR 3

<400> SEQUENCE: 131

Cys Ser Tyr Ala Gly Ser Tyr Thr Trp Val
1               5                   10

<210> SEQ ID NO 132
<211> LENGTH: 10
<212> TYPE: PRT
<213> ORGANISM: Artificial Sequence
<220> FEATURE:
<223> OTHER INFORMATION: YU45-A1 LC-CDR 3

<400> SEQUENCE: 132

Gly Ser Tyr Thr Ser Ser Ser Thr Trp Val
1               5                   10

<210> SEQ ID NO 133
<211> LENGTH: 3
<212> TYPE: PRT
<213> ORGANISM: Artificial Sequence
<220> FEATURE:
```

<223> OTHER INFORMATION: YU45-A8/C6 LC-CDR 2

<400> SEQUENCE: 133

Asp Val Gly
1

<210> SEQ ID NO 134
<211> LENGTH: 10
<212> TYPE: PRT
<213> ORGANISM: Artificial Sequence
<220> FEATURE:
<223> OTHER INFORMATION: YU45-A8/C6 LC-CDR 3

<400> SEQUENCE: 134

Ser Ser Tyr Thr Ser Gly Ser Thr Trp Val
1               5                   10

<210> SEQ ID NO 135
<211> LENGTH: 3
<212> TYPE: PRT
<213> ORGANISM: Artificial Sequence
<220> FEATURE:
<223> OTHER INFORMATION: YU45-B5/A4 LC-CDR 2

<400> SEQUENCE: 135

Glu Val Asn
1

<210> SEQ ID NO 136
<211> LENGTH: 11
<212> TYPE: PRT
<213> ORGANISM: Artificial Sequence
<220> FEATURE:
<223> OTHER INFORMATION: YU45-B5/A4 LC-CDR 3

<400> SEQUENCE: 136

Ser Ser Tyr Ala Gly Thr Asn Asn Phe Val Val
1               5                   10

<210> SEQ ID NO 137
<211> LENGTH: 6
<212> TYPE: PRT
<213> ORGANISM: Artificial Sequence
<220> FEATURE:
<223> OTHER INFORMATION: YU45-D1 LC-CDR 1

<400> SEQUENCE: 137

Gln Ser Val Ser Ser Asn
1               5

<210> SEQ ID NO 138
<211> LENGTH: 3
<212> TYPE: PRT
<213> ORGANISM: Artificial Sequence
<220> FEATURE:
<223> OTHER INFORMATION: YU45-D1 LC-CDR 2

<400> SEQUENCE: 138

Gly Ala Ser
1

<210> SEQ ID NO 139
<211> LENGTH: 19
<212> TYPE: PRT
<213> ORGANISM: Artificial Sequence
<220> FEATURE:
<223> OTHER INFORMATION: YU45-D1 LC-CDR 3

<400> SEQUENCE: 139

Gln Gln Tyr Asn Asn Trp Pro Leu Thr Phe Gly Gly Gly Thr Lys Val
1               5                   10                  15

Glu Phe Lys

<210> SEQ ID NO 140
<211> LENGTH: 8
<212> TYPE: PRT
<213> ORGANISM: Artificial Sequence
<220> FEATURE:
<223> OTHER INFORMATION: YU45-D9/D3 LC-CDR 1

<400> SEQUENCE: 140

Ser Ser Asn Ile Gly Asn Asn Tyr
1               5

<210> SEQ ID NO 141
<211> LENGTH: 3
<212> TYPE: PRT
<213> ORGANISM: Artificial Sequence
<220> FEATURE:
<223> OTHER INFORMATION: YU45-D9/D3 LC-CDR 2

<400> SEQUENCE: 141

Asp Asn Thr
1

<210> SEQ ID NO 142
<211> LENGTH: 11
<212> TYPE: PRT
<213> ORGANISM: Artificial Sequence
<220> FEATURE:
<223> OTHER INFORMATION: YU45-D9/D3 LC-CDR 3

<400> SEQUENCE: 142

Gly Thr Trp Asp Ser Ser Leu Ser Gly Gly Val
1               5                   10

<210> SEQ ID NO 143
<211> LENGTH: 20
<212> TYPE: PRT
<213> ORGANISM: Artificial Sequence
<220> FEATURE:
<223> OTHER INFORMATION: YU45-E5 LC-CDR 3

<400> SEQUENCE: 143

Ser Ser Tyr Ala Gly Ser Tyr Thr Trp Gly Val Arg Arg Arg Asp Arg
1               5                   10                  15

Ala Asp Arg Pro
            20

<210> SEQ ID NO 144
<211> LENGTH: 8
<212> TYPE: PRT
<213> ORGANISM: Artificial Sequence
<220> FEATURE:
<223> OTHER INFORMATION: YU45-G7 LC-CDR 1

<400> SEQUENCE: 144

Tyr Ser Asn Val Gly Ser Asn Leu
1               5

<210> SEQ ID NO 145
<211> LENGTH: 3

```
<212> TYPE: PRT
<213> ORGANISM: Artificial Sequence
<220> FEATURE:
<223> OTHER INFORMATION: YU45-G7 LC-CDR 2

<400> SEQUENCE: 145

Glu Asp Asp
1

<210> SEQ ID NO 146
<211> LENGTH: 11
<212> TYPE: PRT
<213> ORGANISM: Artificial Sequence
<220> FEATURE:
<223> OTHER INFORMATION: YU45-G7 LC-CDR 3

<400> SEQUENCE: 146

Ala Ala Trp Asp Asp Ser Leu Lys Gly His Val
1               5                   10

<210> SEQ ID NO 147
<211> LENGTH: 8
<212> TYPE: PRT
<213> ORGANISM: Artificial Sequence
<220> FEATURE:
<223> OTHER INFORMATION: YU45-B4 LC-CDR 1

<400> SEQUENCE: 147

Ser Ser Asn Ile Gly Ser Asn Thr
1               5

<210> SEQ ID NO 148
<211> LENGTH: 3
<212> TYPE: PRT
<213> ORGANISM: Artificial Sequence
<220> FEATURE:
<223> OTHER INFORMATION: YU45-B4 LC-CDR 2

<400> SEQUENCE: 148

Ile Asn Asn
1

<210> SEQ ID NO 149
<211> LENGTH: 11
<212> TYPE: PRT
<213> ORGANISM: Artificial Sequence
<220> FEATURE:
<223> OTHER INFORMATION: YU45-B4 LC-CDR 3

<400> SEQUENCE: 149

Ala Ala Trp Asp Asp Ser Leu Asn Gly Trp Val
1               5                   10

<210> SEQ ID NO 150
<211> LENGTH: 9
<212> TYPE: PRT
<213> ORGANISM: Artificial Sequence
<220> FEATURE:
<223> OTHER INFORMATION: YU45-B6 LC-CDR 1

<400> SEQUENCE: 150

Ser Arg Asp Val Gly Gly Tyr Asn Tyr
1               5

<210> SEQ ID NO 151
<211> LENGTH: 10
<212> TYPE: PRT
```

```
<213> ORGANISM: Artificial Sequence
<220> FEATURE:
<223> OTHER INFORMATION: YU45-B6  LC-CDR 3

<400> SEQUENCE: 151

Cys Ser Tyr Ala Asp Tyr Tyr Thr Trp Val
1               5                   10

<210> SEQ ID NO 152
<211> LENGTH: 8
<212> TYPE: PRT
<213> ORGANISM: Artificial Sequence
<220> FEATURE:
<223> OTHER INFORMATION: YU45-E7 LC-CDR 1

<400> SEQUENCE: 152

Ser Gly Ser Ile Ala Ser Asn Tyr
1               5

<210> SEQ ID NO 153
<211> LENGTH: 3
<212> TYPE: PRT
<213> ORGANISM: Artificial Sequence
<220> FEATURE:
<223> OTHER INFORMATION: YU45-E7 LC-CDR 2

<400> SEQUENCE: 153

Asp Asp Asn
1

<210> SEQ ID NO 154
<211> LENGTH: 10
<212> TYPE: PRT
<213> ORGANISM: Artificial Sequence
<220> FEATURE:
<223> OTHER INFORMATION: YU45-E7 LC-CDR 3

<400> SEQUENCE: 154

Gln Ser Tyr Asp Ser Ser Asn Leu Trp Val
1               5                   10

<210> SEQ ID NO 155
<211> LENGTH: 6
<212> TYPE: PRT
<213> ORGANISM: Artificial Sequence
<220> FEATURE:
<223> OTHER INFORMATION: YU45-F5 LC-CDR 1

<400> SEQUENCE: 155

Gln Ile Ile Ser Ser Tyr
1               5

<210> SEQ ID NO 156
<211> LENGTH: 10
<212> TYPE: PRT
<213> ORGANISM: Artificial Sequence
<220> FEATURE:
<223> OTHER INFORMATION: YU45-F5 LC-CDR 3

<400> SEQUENCE: 156

Gln Gln Ser Tyr Ser Thr Pro Thr Trp Thr
1               5                   10

<210> SEQ ID NO 157
<211> LENGTH: 3
<212> TYPE: PRT
<213> ORGANISM: Artificial Sequence
```

```
<220> FEATURE:
<223> OTHER INFORMATION: YU46-G1 LC-CDR 2

<400> SEQUENCE: 157

Glu Asp Asn
1

<210> SEQ ID NO 158
<211> LENGTH: 9
<212> TYPE: PRT
<213> ORGANISM: Artificial Sequence
<220> FEATURE:
<223> OTHER INFORMATION: YU46-G1 LC-CDR 3

<400> SEQUENCE: 158

Gln Ser Tyr Asn Ser Ser Lys Val Val
1               5

<210> SEQ ID NO 159
<211> LENGTH: 9
<212> TYPE: PRT
<213> ORGANISM: Artificial Sequence
<220> FEATURE:
<223> OTHER INFORMATION: YU46-A2 LC-CDR 1

<400> SEQUENCE: 159

Ser Ser Asp Val Gly Gly Tyr Glu Tyr
1               5

<210> SEQ ID NO 160
<211> LENGTH: 11
<212> TYPE: PRT
<213> ORGANISM: Artificial Sequence
<220> FEATURE:
<223> OTHER INFORMATION: YU46-A2 LC-CDR 3

<400> SEQUENCE: 160

Asn Ser Tyr Thr Ser Ser Gly Thr Leu Val Val
1               5                   10

<210> SEQ ID NO 161
<211> LENGTH: 6
<212> TYPE: PRT
<213> ORGANISM: Artificial Sequence
<220> FEATURE:
<223> OTHER INFORMATION: YU46-B6 LC-CDR 1

<400> SEQUENCE: 161

Ser Leu Arg Gly Tyr Tyr
1               5

<210> SEQ ID NO 162
<211> LENGTH: 3
<212> TYPE: PRT
<213> ORGANISM: Artificial Sequence
<220> FEATURE:
<223> OTHER INFORMATION: YU46-B6 LC-CDR 2

<400> SEQUENCE: 162

Gly Asn Asn
1

<210> SEQ ID NO 163
<211> LENGTH: 11
<212> TYPE: PRT
<213> ORGANISM: Artificial Sequence
<220> FEATURE:
```

<223> OTHER INFORMATION: YU46-B6 LC-CDR 3

<400> SEQUENCE: 163

Asp Ser Arg Gly Arg Ser Gly Asp His Trp Leu
1               5                   10

<210> SEQ ID NO 164
<211> LENGTH: 8
<212> TYPE: PRT
<213> ORGANISM: Artificial Sequence
<220> FEATURE:
<223> OTHER INFORMATION: YU46-C1 LC-CDR 1

<400> SEQUENCE: 164

Ser Ser Asn Ile Gly Ser Tyr Tyr
1               5

<210> SEQ ID NO 165
<211> LENGTH: 3
<212> TYPE: PRT
<213> ORGANISM: Artificial Sequence
<220> FEATURE:
<223> OTHER INFORMATION: YU46-C1 LC-CDR 2

<400> SEQUENCE: 165

Arg Asn Asp
1

<210> SEQ ID NO 166
<211> LENGTH: 11
<212> TYPE: PRT
<213> ORGANISM: Artificial Sequence
<220> FEATURE:
<223> OTHER INFORMATION: YU46-C1 LC-CDR 3

<400> SEQUENCE: 166

Ala Thr Trp Asp Asp Gly Leu Ser Gly Trp Val
1               5                   10

<210> SEQ ID NO 167
<211> LENGTH: 9
<212> TYPE: PRT
<213> ORGANISM: Artificial Sequence
<220> FEATURE:
<223> OTHER INFORMATION: YU46-D7 LC-CDR 1

<400> SEQUENCE: 167

Ser Ser Asp Val Gly Ala Tyr Asn Tyr
1               5

<210> SEQ ID NO 168
<211> LENGTH: 3
<212> TYPE: PRT
<213> ORGANISM: Artificial Sequence
<220> FEATURE:
<223> OTHER INFORMATION: YU46-D7 LC-CDR 2

<400> SEQUENCE: 168

Glu Val Phe
1

<210> SEQ ID NO 169
<211> LENGTH: 10
<212> TYPE: PRT
<213> ORGANISM: Artificial Sequence
<220> FEATURE:
<223> OTHER INFORMATION: YU46-D7 LC-CDR 3

<400> SEQUENCE: 169

Asn Ser Tyr Val Thr Gly Asn Asn Trp Ala
1               5                   10

<210> SEQ ID NO 170
<211> LENGTH: 8
<212> TYPE: PRT
<213> ORGANISM: Artificial Sequence
<220> FEATURE:
<223> OTHER INFORMATION: YU46-E7 LC-CDR 1

<400> SEQUENCE: 170

Ser Ser Asn Ile Gly Tyr Asp Ala
1               5

<210> SEQ ID NO 171
<211> LENGTH: 3
<212> TYPE: PRT
<213> ORGANISM: Artificial Sequence
<220> FEATURE:
<223> OTHER INFORMATION: YU46-E7 LC-CDR 2

<400> SEQUENCE: 171

Asn Asp Asn
1

<210> SEQ ID NO 172
<211> LENGTH: 11
<212> TYPE: PRT
<213> ORGANISM: Artificial Sequence
<220> FEATURE:
<223> OTHER INFORMATION: YU46-E7 LC-CDR 3

<400> SEQUENCE: 172

Ala Ala Trp Asp Asp Ser Leu Ser Gly Trp Val
1               5                   10

<210> SEQ ID NO 173
<211> LENGTH: 6
<212> TYPE: PRT
<213> ORGANISM: Artificial Sequence
<220> FEATURE:
<223> OTHER INFORMATION: YU46-H8 LC-CDR 1

<400> SEQUENCE: 173

Gln Gly Ser Ser Ser Tyr
1               5

<210> SEQ ID NO 174
<211> LENGTH: 10
<212> TYPE: PRT
<213> ORGANISM: Artificial Sequence
<220> FEATURE:
<223> OTHER INFORMATION: YU46-H8 LC-CDR 3

<400> SEQUENCE: 174

Gln Gln Ser Tyr Ser Thr Pro Leu Tyr Thr
1               5                   10

<210> SEQ ID NO 175
<211> LENGTH: 9
<212> TYPE: PRT
<213> ORGANISM: Artificial Sequence
<220> FEATURE:
<223> OTHER INFORMATION: YU46-G9 LC-CDR 1

<400> SEQUENCE: 175

Ser Ser Asp Val Gly Gly Tyr Lys Tyr
1               5

<210> SEQ ID NO 176
<211> LENGTH: 10
<212> TYPE: PRT
<213> ORGANISM: Artificial Sequence
<220> FEATURE:
<223> OTHER INFORMATION: YU46-G9 LC-CDR 3

<400> SEQUENCE: 176

Cys Ser Tyr Ala Gly Asn Tyr Thr Trp Leu
1               5                   10

<210> SEQ ID NO 177
<211> LENGTH: 11
<212> TYPE: PRT
<213> ORGANISM: Artificial Sequence
<220> FEATURE:
<223> OTHER INFORMATION: YU46-B7 LC-CDR 3

<400> SEQUENCE: 177

Thr Ser Tyr Ser Ser Ser Ser Thr Leu Val Ala
1               5                   10

<210> SEQ ID NO 178
<211> LENGTH: 9
<212> TYPE: PRT
<213> ORGANISM: Artificial Sequence
<220> FEATURE:
<223> OTHER INFORMATION: YU46-D3 LC-CDR 1

<400> SEQUENCE: 178

Ser Ser Asp Val Gly Asn Tyr Lys Tyr
1               5

<210> SEQ ID NO 179
<211> LENGTH: 11
<212> TYPE: PRT
<213> ORGANISM: Artificial Sequence
<220> FEATURE:
<223> OTHER INFORMATION: YU46-D3 LC-CDR 3

<400> SEQUENCE: 179

Ser Ser Tyr Thr Ser Ser Ser Thr Leu Val Val
1               5                   10

<210> SEQ ID NO 180
<211> LENGTH: 9
<212> TYPE: PRT
<213> ORGANISM: Artificial Sequence
<220> FEATURE:
<223> OTHER INFORMATION: YU33-A2 LC-CDR 1

<400> SEQUENCE: 180

Val Ser Ser Asn Ser Ala Ala Trp Asn
1               5

<210> SEQ ID NO 181
<211> LENGTH: 7
<212> TYPE: PRT
<213> ORGANISM: Artificial Sequence
<220> FEATURE:
<223> OTHER INFORMATION: YU33-A2 LC-CDR 2

<400> SEQUENCE: 181

Tyr Arg Ser Lys Trp Tyr Asn
1               5

<210> SEQ ID NO 182
<211> LENGTH: 10
<212> TYPE: PRT
<213> ORGANISM: Artificial Sequence
<220> FEATURE:
<223> OTHER INFORMATION: YU33-A2 LC-CDR 3

<400> SEQUENCE: 182

Ala Arg Gly Thr Arg Gly Tyr Phe Asp Tyr
1               5                   10

<210> SEQ ID NO 183
<211> LENGTH: 8
<212> TYPE: PRT
<213> ORGANISM: Artificial Sequence
<220> FEATURE:
<223> OTHER INFORMATION: YU33-B3/H3 LC-CDR 1

<400> SEQUENCE: 183

Gly Phe Thr Phe Ser Gly Ala Tyr
1               5

<210> SEQ ID NO 184
<211> LENGTH: 8
<212> TYPE: PRT
<213> ORGANISM: Artificial Sequence
<220> FEATURE:
<223> OTHER INFORMATION: YU33-B3/H3 LC-CDR 2

<400> SEQUENCE: 184

Ile Ser Tyr Asp Gly Ser Asn Lys
1               5

<210> SEQ ID NO 185
<211> LENGTH: 9
<212> TYPE: PRT
<213> ORGANISM: Artificial Sequence
<220> FEATURE:
<223> OTHER INFORMATION: YU33-B3/H3 LC-CDR 3

<400> SEQUENCE: 185

Ala Arg Asp Leu Tyr Ala Phe Asp Ile
1               5

<210> SEQ ID NO 186
<211> LENGTH: 8
<212> TYPE: PRT
<213> ORGANISM: Artificial Sequence
<220> FEATURE:
<223> OTHER INFORMATION: YU33-B4/YU45-G2/A3 LC-CDR 1

<400> SEQUENCE: 186

Gly Phe Thr Phe Ser Ser Tyr Gly
1               5

<210> SEQ ID NO 187
<211> LENGTH: 11
<212> TYPE: PRT
<213> ORGANISM: Artificial Sequence
<220> FEATURE:
<223> OTHER INFORMATION: YU33-B4/YU45-G2/A3 LC-CDR 3

<400> SEQUENCE: 187

Ala Lys Ile Gly Ala Thr Asp Pro Leu Asp Tyr
1               5                   10

<210> SEQ ID NO 188
<211> LENGTH: 8
<212> TYPE: PRT
<213> ORGANISM: Artificial Sequence
<220> FEATURE:
<223> OTHER INFORMATION: YU33-E6 LC-CDR 2

<400> SEQUENCE: 188

Ile Ser Tyr Asp Gly Ser Asp Lys
1               5

<210> SEQ ID NO 189
<211> LENGTH: 12
<212> TYPE: PRT
<213> ORGANISM: Artificial Sequence
<220> FEATURE:
<223> OTHER INFORMATION: YU33-E6 LC-CDR 3

<400> SEQUENCE: 189

Ala Lys Asp Leu Ser Gly Leu Pro Ile Ile Asp Tyr
1               5                   10

<210> SEQ ID NO 190
<211> LENGTH: 8
<212> TYPE: PRT
<213> ORGANISM: Artificial Sequence
<220> FEATURE:
<223> OTHER INFORMATION: YU45-C11/A10 LC-CDR 1

<400> SEQUENCE: 190

Gly Phe Thr Phe Ser Ser Tyr Ala
1               5

<210> SEQ ID NO 191
<211> LENGTH: 8
<212> TYPE: PRT
<213> ORGANISM: Artificial Sequence
<220> FEATURE:
<223> OTHER INFORMATION: YU45-C11/A10 LC-CDR 2

<400> SEQUENCE: 191

Ala Arg Arg Gly Tyr Phe Asp Tyr
1               5

<210> SEQ ID NO 192
<211> LENGTH: 11
<212> TYPE: PRT
<213> ORGANISM: Artificial Sequence
<220> FEATURE:
<223> OTHER INFORMATION: YU45-C11/A10 LC-CDR 3

<400> SEQUENCE: 192

Ala Arg Ile Ala Ala Ala Asp Gly Met Asp Val
1               5                   10

<210> SEQ ID NO 193
<211> LENGTH: 8
<212> TYPE: PRT
<213> ORGANISM: Artificial Sequence
<220> FEATURE:
<223> OTHER INFORMATION: YU45-E11/E12 LC-CDR 1

<400> SEQUENCE: 193

Gly Phe Ser Phe Arg Ser Tyr Gly

```
<210> SEQ ID NO 194
<211> LENGTH: 16
<212> TYPE: PRT
<213> ORGANISM: Artificial Sequence
<220> FEATURE:
<223> OTHER INFORMATION: YU45-E11/E12 LC-CDR 3

<400> SEQUENCE: 194

Ala Arg Ile Thr His Asp Tyr Gly Asp Phe Ser Asp Ala Phe Asp Ile
1               5                   10                  15

<210> SEQ ID NO 195
<211> LENGTH: 12
<212> TYPE: PRT
<213> ORGANISM: Artificial Sequence
<220> FEATURE:
<223> OTHER INFORMATION: YU45-H11/D12 LC-CDR 3

<400> SEQUENCE: 195

Ala Lys Leu Tyr Ser Gly Ser Ser Asn Phe Asp Tyr
1               5                   10

<210> SEQ ID NO 196
<211> LENGTH: 8
<212> TYPE: PRT
<213> ORGANISM: Artificial Sequence
<220> FEATURE:
<223> OTHER INFORMATION: YU45-A12/G10 LC-CDR 1

<400> SEQUENCE: 196

Gly Phe Thr Phe Arg Ser Tyr Gly
1               5

<210> SEQ ID NO 197
<211> LENGTH: 11
<212> TYPE: PRT
<213> ORGANISM: Artificial Sequence
<220> FEATURE:
<223> OTHER INFORMATION: YU45-G1 LC-CDR 3

<400> SEQUENCE: 197

Ala Lys Leu Ser Gly Pro Asn Gly Val Asp Tyr
1               5                   10

<210> SEQ ID NO 198
<211> LENGTH: 8
<212> TYPE: PRT
<213> ORGANISM: Artificial Sequence
<220> FEATURE:
<223> OTHER INFORMATION: YU45-C2/A7/B10 LC-CDR 3

<400> SEQUENCE: 198

Ala Arg Gly Gln Asn Val Asp Leu
1               5

<210> SEQ ID NO 199
<211> LENGTH: 16
<212> TYPE: PRT
<213> ORGANISM: Artificial Sequence
<220> FEATURE:
<223> OTHER INFORMATION: YU45-D2/H2/C7/F3/C9/E1/E9/C10/G3/H9/C5/A2/A5
      LC-CDR 3

<400> SEQUENCE: 199

Ala Arg Ile Met Gly Tyr Asp Tyr Gly Asp Tyr Asp Val Val Asp Tyr
```

<210> SEQ ID NO 200
<211> LENGTH: 14
<212> TYPE: PRT
<213> ORGANISM: Artificial Sequence
<220> FEATURE:
<223> OTHER INFORMATION: YU45-G7 LC-CDR 3

<400> SEQUENCE: 200

Ala Arg Asp Val Gly Tyr Ser Ser Gly Trp Tyr Phe Asp Tyr
1               5                   10

<210> SEQ ID NO 201
<211> LENGTH: 8
<212> TYPE: PRT
<213> ORGANISM: Artificial Sequence
<220> FEATURE:
<223> OTHER INFORMATION: YU45-B4 LC-CDR 1

<400> SEQUENCE: 201

Gly Phe Ser Leu Ser Ser Tyr Gly
1               5

<210> SEQ ID NO 202
<211> LENGTH: 24
<212> TYPE: PRT
<213> ORGANISM: Artificial Sequence
<220> FEATURE:
<223> OTHER INFORMATION: YU45-B4 LC-CDR 3

<400> SEQUENCE: 202

Ala Arg Leu Ala Gln Ser Tyr Ser Ser Ser Trp Tyr Glu Trp Glu Pro
1               5                   10                  15

Gly Arg Glu His Ala Phe Asp Ile
            20

<210> SEQ ID NO 203
<211> LENGTH: 7
<212> TYPE: PRT
<213> ORGANISM: Artificial Sequence
<220> FEATURE:
<223> OTHER INFORMATION: YU45-H4 HC-CDR3 Family Consensus

<400> SEQUENCE: 203

Ala Arg Pro Asp Asp Asp Tyr
1               5

<210> SEQ ID NO 204
<211> LENGTH: 8
<212> TYPE: PRT
<213> ORGANISM: Artificial Sequence
<220> FEATURE:
<223> OTHER INFORMATION: YU45-F8 HC-CDR 1

<400> SEQUENCE: 204

Trp Ile Phe Leu Lys Ser Tyr Ala
1               5

<210> SEQ ID NO 205
<211> LENGTH: 17
<212> TYPE: PRT
<213> ORGANISM: Artificial Sequence
<220> FEATURE:
<223> OTHER INFORMATION: YU45-F8 HC-CDR 3

<400> SEQUENCE: 205

Ala Arg Val Gly Phe Ser Ser Trp Tyr Pro Asp Leu Tyr Tyr Phe Asp
1               5                   10                  15
Tyr

<210> SEQ ID NO 206
<211> LENGTH: 17
<212> TYPE: PRT
<213> ORGANISM: Artificial Sequence
<220> FEATURE:
<223> OTHER INFORMATION: YU45-E7 HC-CDR 3

<400> SEQUENCE: 206

Ala Arg Leu Tyr Ser Gly Tyr Pro Ser Arg Tyr Tyr Gly Met Asp
1               5                   10                  15
Val

<210> SEQ ID NO 207
<211> LENGTH: 12
<212> TYPE: PRT
<213> ORGANISM: Artificial Sequence
<220> FEATURE:
<223> OTHER INFORMATION: YU45-F5 HC-CDR 3

<400> SEQUENCE: 207

Ala Lys Gly Gly Lys Ser Tyr Tyr Gly Phe Asp Tyr
1               5                   10

<210> SEQ ID NO 208
<211> LENGTH: 15
<212> TYPE: PRT
<213> ORGANISM: Artificial Sequence
<220> FEATURE:
<223> OTHER INFORMATION: YU45-H7/B5 HC-CDR 3

<400> SEQUENCE: 208

Ala Arg Leu His Ser Gly Arg Asn Trp Gly Asp Ala Phe Asp Ile
1               5                   10                  15

<210> SEQ ID NO 209
<211> LENGTH: 8
<212> TYPE: PRT
<213> ORGANISM: Artificial Sequence
<220> FEATURE:
<223> OTHER INFORMATION: YU45-B5/A4 HC-CDR 1

<400> SEQUENCE: 209

Gly Gly Thr Phe Ser Ser Tyr Ala
1               5

<210> SEQ ID NO 210
<211> LENGTH: 8
<212> TYPE: PRT
<213> ORGANISM: Artificial Sequence
<220> FEATURE:
<223> OTHER INFORMATION: YU45-B5/A4 HC-CDR 2

<400> SEQUENCE: 210

Ile Ile Pro Ile Phe Gly Thr Ala
1               5

<210> SEQ ID NO 211
<211> LENGTH: 10
<212> TYPE: PRT
<213> ORGANISM: Artificial Sequence
<220> FEATURE:

<223> OTHER INFORMATION: YU45-B5/A4 HC-CDR 3

<400> SEQUENCE: 211

Ala Arg Gly Leu Ile Thr Gly Thr Thr Pro
1               5                   10

<210> SEQ ID NO 212
<211> LENGTH: 8
<212> TYPE: PRT
<213> ORGANISM: Artificial Sequence
<220> FEATURE:
<223> OTHER INFORMATION: YU45-E3 HC-CDR 1

<400> SEQUENCE: 212

Gly Phe Ser Phe Ser Ser Tyr Ala
1               5

<210> SEQ ID NO 213
<211> LENGTH: 8
<212> TYPE: PRT
<213> ORGANISM: Artificial Sequence
<220> FEATURE:
<223> OTHER INFORMATION: YU45-C8/E8 HC-CDR 3

<400> SEQUENCE: 213

Ala Arg Arg Gly Tyr Gly Asp Tyr
1               5

<210> SEQ ID NO 214
<211> LENGTH: 110
<212> TYPE: PRT
<213> ORGANISM: Artificial Sequence
<220> FEATURE:
<223> OTHER INFORMATION: YU100-H06

<400> SEQUENCE: 214

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Thr Trp Val Phe Gly Gly Gly Thr Lys Leu Thr Val Leu
            100                 105                 110

<210> SEQ ID NO 215
<211> LENGTH: 12
<212> TYPE: PRT
<213> ORGANISM: Artificial Sequence
<220> FEATURE:
<223> OTHER INFORMATION: YU45-G8/H6 HC-CDR3

<400> SEQUENCE: 215

Ala Lys Phe Ala Arg Gly Val Tyr Leu Phe Asp Tyr
1               5                   10

<210> SEQ ID NO 216

```
<211> LENGTH: 12
<212> TYPE: PRT
<213> ORGANISM: Artificial Sequence
<220> FEATURE:
<223> OTHER INFORMATION: YU45-F9 HC-CDR 3

<400> SEQUENCE: 216

Ala Arg Val Gln Ser Gly Glu Pro Glu Ser Asp Tyr
1               5                   10

<210> SEQ ID NO 217
<211> LENGTH: 8
<212> TYPE: PRT
<213> ORGANISM: Artificial Sequence
<220> FEATURE:
<223> OTHER INFORMATION: YU45-H10 HC-CDR 1

<400> SEQUENCE: 217

Gly Phe Ser Leu Asn Ser Tyr Gly
1               5

<210> SEQ ID NO 218
<211> LENGTH: 14
<212> TYPE: PRT
<213> ORGANISM: Artificial Sequence
<220> FEATURE:
<223> OTHER INFORMATION: YU45-H3 HC-CDR 3

<400> SEQUENCE: 218

Ala Arg Met Val Asn Leu Tyr Tyr Gly Asp Ala Phe Asp Ile
1               5                   10

<210> SEQ ID NO 219
<211> LENGTH: 11
<212> TYPE: PRT
<213> ORGANISM: Artificial Sequence
<220> FEATURE:
<223> OTHER INFORMATION: YU45-A1 HC-CDR 3

<400> SEQUENCE: 219

Ala Arg Leu Val Gly Ala Thr Ala Asp Asp Tyr
1               5                   10

<210> SEQ ID NO 220
<211> LENGTH: 9
<212> TYPE: PRT
<213> ORGANISM: Artificial Sequence
<220> FEATURE:
<223> OTHER INFORMATION: YU45-D1 HC-CDR 1

<400> SEQUENCE: 220

Gly Gly Ser Ile Ser Ser Ser Asn Trp
1               5

<210> SEQ ID NO 221
<211> LENGTH: 7
<212> TYPE: PRT
<213> ORGANISM: Artificial Sequence
<220> FEATURE:
<223> OTHER INFORMATION: YU45-D1 HC-CDR 2

<400> SEQUENCE: 221

Ile Tyr His Ser Gly Ser Thr
1               5

<210> SEQ ID NO 222
<211> LENGTH: 18
```

```
<212> TYPE: PRT
<213> ORGANISM: Artificial Sequence
<220> FEATURE:
<223> OTHER INFORMATION: YU45-D1 HC-CDR 3

<400> SEQUENCE: 222

Ala Arg Val Gln Asn Leu Gly Gly Gly Ser Tyr Tyr Val Gly Ala Phe
1               5                   10                  15

Asp Tyr

<210> SEQ ID NO 223
<211> LENGTH: 17
<212> TYPE: PRT
<213> ORGANISM: Artificial Sequence
<220> FEATURE:
<223> OTHER INFORMATION: YU45-D9/D3 HC-CDR 3

<400> SEQUENCE: 223

Ala Arg Leu His Phe Ser Gln Tyr Phe Ser Thr Ile Asp Ala Phe Asp
1               5                   10                  15

Ile

<210> SEQ ID NO 224
<211> LENGTH: 20
<212> TYPE: PRT
<213> ORGANISM: Artificial Sequence
<220> FEATURE:
<223> OTHER INFORMATION: YU46-G1 HC-CDR 3

<400> SEQUENCE: 224

Ala Arg Gly Gly Gly Pro Tyr Tyr Asp Phe Trp Ser Gly Tyr Tyr Thr
1               5                   10                  15

Glu Phe Asp Tyr
            20

<210> SEQ ID NO 225
<211> LENGTH: 14
<212> TYPE: PRT
<213> ORGANISM: Artificial Sequence
<220> FEATURE:
<223> OTHER INFORMATION: YU46-A2 HC-CDR 3

<400> SEQUENCE: 225

Ala Arg Asp Ser Gly Tyr Ser Ser Gly Trp Tyr Phe Asp Tyr
1               5                   10

<210> SEQ ID NO 226
<211> LENGTH: 8
<212> TYPE: PRT
<213> ORGANISM: Artificial Sequence
<220> FEATURE:
<223> OTHER INFORMATION: YU46-B2 HC-CDR 1

<400> SEQUENCE: 226

Ile Leu Pro Ser Asp Ser Tyr Ala
1               5

<210> SEQ ID NO 227
<211> LENGTH: 13
<212> TYPE: PRT
<213> ORGANISM: Artificial Sequence
<220> FEATURE:
<223> OTHER INFORMATION: YU46-B2 HC-CDR 3

<400> SEQUENCE: 227
```

Ala Arg Ile Ala Ala Ala Gly Arg Asp Ala Phe Asp Ile
1               5                   10

<210> SEQ ID NO 228
<211> LENGTH: 8
<212> TYPE: PRT
<213> ORGANISM: Artificial Sequence
<220> FEATURE:
<223> OTHER INFORMATION: YU46-B6 HC-CDR 1

<400> SEQUENCE: 228

Gly Tyr Thr Phe Thr Ser Tyr Gly
1               5

<210> SEQ ID NO 229
<211> LENGTH: 8
<212> TYPE: PRT
<213> ORGANISM: Artificial Sequence
<220> FEATURE:
<223> OTHER INFORMATION: YU46-B6 HC-CDR 2

<400> SEQUENCE: 229

Ile Ser Ala Tyr Asn Gly Asn Thr
1               5

<210> SEQ ID NO 230
<211> LENGTH: 16
<212> TYPE: PRT
<213> ORGANISM: Artificial Sequence
<220> FEATURE:
<223> OTHER INFORMATION: YU46-B6 HC-CDR 3

<400> SEQUENCE: 230

Ala Arg Val Val Ala Ala Arg Ser Tyr Tyr Tyr Tyr Met Asp Val
1               5                   10                  15

<210> SEQ ID NO 231
<211> LENGTH: 18
<212> TYPE: PRT
<213> ORGANISM: Artificial Sequence
<220> FEATURE:
<223> OTHER INFORMATION: YU46-C1 HC-CDR 3

<400> SEQUENCE: 231

Ala Arg Ala Asp Ser Ser Ala Gly Gly Gly Pro Tyr Tyr Tyr Gly Met
1               5                   10                  15

Asp Val

<210> SEQ ID NO 232
<211> LENGTH: 11
<212> TYPE: PRT
<213> ORGANISM: Artificial Sequence
<220> FEATURE:
<223> OTHER INFORMATION: YU46-E3 HC-CDR 3

<400> SEQUENCE: 232

Ala Arg Ile Gly Gly Tyr Asp Asp Phe Asp Tyr
1               5                   10

<210> SEQ ID NO 233
<211> LENGTH: 17
<212> TYPE: PRT
<213> ORGANISM: Artificial Sequence
<220> FEATURE:
<223> OTHER INFORMATION: YU46-E7 HC-CDR 3

<400> SEQUENCE: 233

Ala Arg Val Tyr Tyr Asp Ser Ser Gly Thr Gln Gly Asp Ser Phe Asp
1               5                   10                  15

Tyr

<210> SEQ ID NO 234
<211> LENGTH: 8
<212> TYPE: PRT
<213> ORGANISM: Artificial Sequence
<220> FEATURE:
<223> OTHER INFORMATION: YU46-H8 HC-CDR 1

<400> SEQUENCE: 234

Gly Phe Thr Phe Gly Ser Tyr Gly
1               5

<210> SEQ ID NO 235
<211> LENGTH: 9
<212> TYPE: PRT
<213> ORGANISM: Artificial Sequence
<220> FEATURE:
<223> OTHER INFORMATION: YU46-H8 HC-CDR 3

<400> SEQUENCE: 235

Ala Lys Gly Ser Tyr Tyr Phe Asp Tyr
1               5

<210> SEQ ID NO 236
<211> LENGTH: 8
<212> TYPE: PRT
<213> ORGANISM: Artificial Sequence
<220> FEATURE:
<223> OTHER INFORMATION: YU46-B7 HC-CDR 3

<400> SEQUENCE: 236

Ala Arg Gly Val Leu Phe Asp Tyr
1               5

<210> SEQ ID NO 237
<211> LENGTH: 8
<212> TYPE: PRT
<213> ORGANISM: Artificial Sequence
<220> FEATURE:
<223> OTHER INFORMATION: YU46-D3 HC-CDR 3

<400> SEQUENCE: 237

Ala Arg Ser Gly Val Leu Asp Tyr
1               5

<210> SEQ ID NO 238
<211> LENGTH: 8
<212> TYPE: PRT
<213> ORGANISM: Artificial Sequence
<220> FEATURE:
<223> OTHER INFORMATION: YU46-G8 HC-CDR 1

<400> SEQUENCE: 238

Gly Phe Ser Leu Gly Ser Tyr Gly
1               5

<210> SEQ ID NO 239
<211> LENGTH: 9
<212> TYPE: PRT
<213> ORGANISM: Artificial Sequence
<220> FEATURE:
<223> OTHER INFORMATION: LC-CDR1-1 Family consensus
<220> FEATURE:

```
<221> NAME/KEY: MISC_FEATURE
<222> LOCATION: (1)..(1)
<223> OTHER INFORMATION: X = S or I
<220> FEATURE:
<221> NAME/KEY: MISC_FEATURE
<222> LOCATION: (2)..(2)
<223> OTHER INFORMATION: X = S or R
<220> FEATURE:
<221> NAME/KEY: MISC_FEATURE
<222> LOCATION: (4)..(4)
<223> OTHER INFORMATION: X = V or I
<220> FEATURE:
<221> NAME/KEY: MISC_FEATURE
<222> LOCATION: (6)..(6)
<223> OTHER INFORMATION: X = G, A or N
<220> FEATURE:
<221> NAME/KEY: MISC_FEATURE
<222> LOCATION: (8)..(8)
<223> OTHER INFORMATION: X = N, E, K or D

<400> SEQUENCE: 239

Xaa Xaa Asp Xaa Gly Xaa Tyr Xaa Tyr
1               5

<210> SEQ ID NO 240
<211> LENGTH: 8
<212> TYPE: PRT
<213> ORGANISM: Artificial Sequence
<220> FEATURE:
<223> OTHER INFORMATION: LC-CDR1-2 Family consensus
<220> FEATURE:
<221> NAME/KEY: MISC_FEATURE
<222> LOCATION: (1)..(1)
<223> OTHER INFORMATION: X = S or Y
<220> FEATURE:
<221> NAME/KEY: MISC_FEATURE
<222> LOCATION: (4)..(4)
<223> OTHER INFORMATION: X = I or V
<220> FEATURE:
<221> NAME/KEY: MISC_FEATURE
<222> LOCATION: (6)..(6)
<223> OTHER INFORMATION: X = S, N or Y
<220> FEATURE:
<221> NAME/KEY: MISC_FEATURE
<222> LOCATION: (7)..(7)
<223> OTHER INFORMATION: X = N, Y or D
<220> FEATURE:
<221> NAME/KEY: MISC_FEATURE
<222> LOCATION: (8)..(8)
<223> OTHER INFORMATION: X = L, Y, T or A

<400> SEQUENCE: 240

Xaa Ser Asn Xaa Gly Xaa Xaa Xaa
1               5

<210> SEQ ID NO 241
<211> LENGTH: 6
<212> TYPE: PRT
<213> ORGANISM: Artificial Sequence
<220> FEATURE:
<223> OTHER INFORMATION: LC-CDR1-3 Family Consensus
<220> FEATURE:
<221> NAME/KEY: MISC_FEATURE
<222> LOCATION: (2)..(2)
<223> OTHER INFORMATION: X= G, S or I
<220> FEATURE:
<221> NAME/KEY: MISC_FEATURE
<222> LOCATION: (3)..(3)
<223> OTHER INFORMATION: X= S, I or V
<220> FEATURE:
<221> NAME/KEY: MISC_FEATURE
<222> LOCATION: (6)..(6)
<223> OTHER INFORMATION: X= Y or N

<400> SEQUENCE: 241
```

```
Gln Xaa Xaa Ser Ser Xaa
1               5

<210> SEQ ID NO 242
<211> LENGTH: 8
<212> TYPE: PRT
<213> ORGANISM: Artificial Sequence
<220> FEATURE:
<223> OTHER INFORMATION: LC-CDR1-4 Family consensus
<220> FEATURE:
<221> NAME/KEY: MISC_FEATURE
<222> LOCATION: (1)..(1)
<223> OTHER INFORMATION: X= S or T
<220> FEATURE:
<221> NAME/KEY: MISC_FEATURE
<222> LOCATION: (3)..(3)
<223> OTHER INFORMATION: X = S or N
<220> FEATURE:
<221> NAME/KEY: MISC_FEATURE
<222> LOCATION: (8)..(8)
<223> OTHER INFORMATION: X = Y or R

<400> SEQUENCE: 242

Xaa Gly Xaa Ile Ala Ser Asn Xaa
1               5

<210> SEQ ID NO 243
<211> LENGTH: 3
<212> TYPE: PRT
<213> ORGANISM: Artificial Sequence
<220> FEATURE:
<223> OTHER INFORMATION: LC-CDR2-1 Family consensus
<220> FEATURE:
<221> NAME/KEY: MISC_FEATURE
<222> LOCATION: (3)..(3)
<223> OTHER INFORMATION: X = S, T or G

<400> SEQUENCE: 243

Asp Val Xaa
1

<210> SEQ ID NO 244
<211> LENGTH: 3
<212> TYPE: PRT
<213> ORGANISM: Artificial Sequence
<220> FEATURE:
<223> OTHER INFORMATION: LC-CDR2-2 Family consensus
<220> FEATURE:
<221> NAME/KEY: MISC_FEATURE
<222> LOCATION: (1)..(1)
<223> OTHER INFORMATION: X = R, I or G
<220> FEATURE:
<221> NAME/KEY: MISC_FEATURE
<222> LOCATION: (3)..(3)
<223> OTHER INFORMATION: X = N or D

<400> SEQUENCE: 244

Xaa Asn Xaa
1

<210> SEQ ID NO 245
<211> LENGTH: 3
<212> TYPE: PRT
<213> ORGANISM: Artificial Sequence
<220> FEATURE:
<223> OTHER INFORMATION: LC-CDR2-3 Family consensus
<220> FEATURE:
<221> NAME/KEY: MISC_FEATURE
<222> LOCATION: (1)..(1)
<223> OTHER INFORMATION: X = A or G
```

```
<400> SEQUENCE: 245

Xaa Ala Ser
1

<210> SEQ ID NO 246
<211> LENGTH: 3
<212> TYPE: PRT
<213> ORGANISM: Artificial Sequence
<220> FEATURE:
<223> OTHER INFORMATION: LC-CDR2-4 Family consensus
<220> FEATURE:
<221> NAME/KEY: MISC_FEATURE
<222> LOCATION: (1)..(1)
<223> OTHER INFORMATION: X = E, D or N
<220> FEATURE:
<221> NAME/KEY: MISC_FEATURE
<222> LOCATION: (3)..(3)
<223> OTHER INFORMATION: X = N or D

<400> SEQUENCE: 246

Xaa Asp Xaa
1

<210> SEQ ID NO 247
<211> LENGTH: 3
<212> TYPE: PRT
<213> ORGANISM: Artificial Sequence
<220> FEATURE:
<223> OTHER INFORMATION: LC-CDR2-5 Family consensus
<220> FEATURE:
<221> NAME/KEY: MISC_FEATURE
<222> LOCATION: (3)..(3)
<223> OTHER INFORMATION: X = S, F or N

<400> SEQUENCE: 247

Glu Val Xaa
1

<210> SEQ ID NO 248
<211> LENGTH: 3
<212> TYPE: PRT
<213> ORGANISM: Artificial Sequence
<220> FEATURE:
<223> OTHER INFORMATION: LC-CDR2-6 Family consensus
<220> FEATURE:
<221> NAME/KEY: MISC_FEATURE
<222> LOCATION: (2)..(2)
<223> OTHER INFORMATION: X = N or V
<220> FEATURE:
<221> NAME/KEY: MISC_FEATURE
<222> LOCATION: (3)..(3)
<223> OTHER INFORMATION: X = H or T

<400> SEQUENCE: 248

Asp Xaa Xaa
1

<210> SEQ ID NO 249
<211> LENGTH: 11
<212> TYPE: PRT
<213> ORGANISM: Artificial Sequence
<220> FEATURE:
<223> OTHER INFORMATION: LC-CDR3-1 Family consensus
<220> FEATURE:
<221> NAME/KEY: MISC_FEATURE
<222> LOCATION: (1)..(1)
<223> OTHER INFORMATION: X = S, N or G
<220> FEATURE:
<221> NAME/KEY: MISC_FEATURE
<222> LOCATION: (5)..(5)
<223> OTHER INFORMATION: X = S or T
```

```
<220> FEATURE:
<221> NAME/KEY: MISC_FEATURE
<222> LOCATION: (6)..(6)
<223> OTHER INFORMATION: X = S or G
<220> FEATURE:
<221> NAME/KEY: MISC_FEATURE
<222> LOCATION: (7)..(7)
<223> OTHER INFORMATION: X = S, N, G or I
<220> FEATURE:
<221> NAME/KEY: MISC_FEATURE
<222> LOCATION: (8)..(8)
<223> OTHER INFORMATION: X = T or S
<220> FEATURE:
<221> NAME/KEY: MISC_FEATURE
<222> LOCATION: (9)..(9)
<223> OTHER INFORMATION: X = W, L, V or Q
<220> FEATURE:
<221> NAME/KEY: MISC_FEATURE
<222> LOCATION: (11)..(11)
<223> OTHER INFORMATION: X = absent or V

<400> SEQUENCE: 249

Xaa Ser Tyr Thr Xaa Xaa Xaa Xaa Xaa Val Xaa
1               5                   10

<210> SEQ ID NO 250
<211> LENGTH: 20
<212> TYPE: PRT
<213> ORGANISM: Artificial Sequence
<220> FEATURE:
<223> OTHER INFORMATION: LC-CDR3-2 Family consensus
<220> FEATURE:
<221> NAME/KEY: MISC_FEATURE
<222> LOCATION: (1)..(1)
<223> OTHER INFORMATION: X = C or S
<220> FEATURE:
<221> NAME/KEY: MISC_FEATURE
<222> LOCATION: (5)..(5)
<223> OTHER INFORMATION: X = G or D
<220> FEATURE:
<221> NAME/KEY: MISC_FEATURE
<222> LOCATION: (6)..(6)
<223> OTHER INFORMATION: X = S, Y, N or T
<220> FEATURE:
<221> NAME/KEY: MISC_FEATURE
<222> LOCATION: (7)..(7)
<223> OTHER INFORMATION: X = Y or N
<220> FEATURE:
<221> NAME/KEY: MISC_FEATURE
<222> LOCATION: (8)..(8)
<223> OTHER INFORMATION: X = T or N
<220> FEATURE:
<221> NAME/KEY: MISC_FEATURE
<222> LOCATION: (9)..(9)
<223> OTHER INFORMATION: X = W or F
<220> FEATURE:
<221> NAME/KEY: MISC_FEATURE
<222> LOCATION: (10)..(10)
<223> OTHER INFORMATION: X = V, G or L
<220> FEATURE:
<221> NAME/KEY: MISC_FEATURE
<222> LOCATION: (11)..(11)
<223> OTHER INFORMATION: X = absent or V
<220> FEATURE:
<221> NAME/KEY: MISC_FEATURE
<222> LOCATION: (12)..(12)
<223> OTHER INFORMATION: X = absent or R
<220> FEATURE:
<221> NAME/KEY: MISC_FEATURE
<222> LOCATION: (13)..(13)
<223> OTHER INFORMATION: X = absent or R
<220> FEATURE:
<221> NAME/KEY: MISC_FEATURE
<222> LOCATION: (14)..(14)
<223> OTHER INFORMATION: X = absent or R
<220> FEATURE:
<221> NAME/KEY: MISC_FEATURE
```

```
<222> LOCATION: (15)..(15)
<223> OTHER INFORMATION: X = absent or D
<220> FEATURE:
<221> NAME/KEY: MISC_FEATURE
<222> LOCATION: (16)..(16)
<223> OTHER INFORMATION: X = absent or R
<220> FEATURE:
<221> NAME/KEY: MISC_FEATURE
<222> LOCATION: (17)..(17)
<223> OTHER INFORMATION: X = absent or A
<220> FEATURE:
<221> NAME/KEY: MISC_FEATURE
<222> LOCATION: (18)..(18)
<223> OTHER INFORMATION: X = absent or D
<220> FEATURE:
<221> NAME/KEY: MISC_FEATURE
<222> LOCATION: (19)..(19)
<223> OTHER INFORMATION: X = absent or R
<220> FEATURE:
<221> NAME/KEY: MISC_FEATURE
<222> LOCATION: (20)..(20)
<223> OTHER INFORMATION: X = absent or P

<400> SEQUENCE: 250

Xaa Ser Tyr Ala Xaa Xaa Xaa Xaa Xaa Xaa Xaa Xaa Xaa Xaa Xaa
1               5                   10                  15

Xaa Xaa Xaa Xaa
            20

<210> SEQ ID NO 251
<211> LENGTH: 11
<212> TYPE: PRT
<213> ORGANISM: Artificial Sequence
<220> FEATURE:
<223> OTHER INFORMATION: LC-CDR3-3 Family consensus
<220> FEATURE:
<221> NAME/KEY: MISC_FEATURE
<222> LOCATION: (1)..(1)
<223> OTHER INFORMATION: X = A or G
<220> FEATURE:
<221> NAME/KEY: MISC_FEATURE
<222> LOCATION: (2)..(2)
<223> OTHER INFORMATION: X = A or T
<220> FEATURE:
<221> NAME/KEY: MISC_FEATURE
<222> LOCATION: (5)..(5)
<223> OTHER INFORMATION: X = D, G or S
<220> FEATURE:
<221> NAME/KEY: MISC_FEATURE
<222> LOCATION: (6)..(6)
<223> OTHER INFORMATION: X = S or G
<220> FEATURE:
<221> NAME/KEY: MISC_FEATURE
<222> LOCATION: (8)..(8)
<223> OTHER INFORMATION: X = S, K or N
<220> FEATURE:
<221> NAME/KEY: MISC_FEATURE
<222> LOCATION: (9)..(9)
<223> OTHER INFORMATION: X = G or A
<220> FEATURE:
<221> NAME/KEY: MISC_FEATURE
<222> LOCATION: (10)..(10)
<223> OTHER INFORMATION: X = W, G or H

<400> SEQUENCE: 251

Xaa Xaa Trp Asp Xaa Xaa Leu Xaa Xaa Xaa Val
1               5                   10

<210> SEQ ID NO 252
<211> LENGTH: 19
<212> TYPE: PRT
<213> ORGANISM: Artificial Sequence
<220> FEATURE:
<223> OTHER INFORMATION: LC-CDR3-4 Family consensus
```

```
<220> FEATURE:
<221> NAME/KEY: MISC_FEATURE
<222> LOCATION: (3)..(3)
<223> OTHER INFORMATION: X = S or Y
<220> FEATURE:
<221> NAME/KEY: MISC_FEATURE
<222> LOCATION: (4)..(4)
<223> OTHER INFORMATION: X = Y, R or N
<220> FEATURE:
<221> NAME/KEY: MISC_FEATURE
<222> LOCATION: (5)..(5)
<223> OTHER INFORMATION: X = S or N
<220> FEATURE:
<221> NAME/KEY: MISC_FEATURE
<222> LOCATION: (7)..(7)
<223> OTHER INFORMATION: X = T, A or W
<220> FEATURE:
<221> NAME/KEY: MISC_FEATURE
<222> LOCATION: (8)..(8)
<223> OTHER INFORMATION: X = L or T
<220> FEATURE:
<221> NAME/KEY: MISC_FEATURE
<222> LOCATION: (9)..(9)
<223> OTHER INFORMATION: X = Y, A, W or T
<220> FEATURE:
<221> NAME/KEY: MISC_FEATURE
<222> LOCATION: (10)..(10)
<223> OTHER INFORMATION: X = T, absent or F
<220> FEATURE:
<221> NAME/KEY: MISC_FEATURE
<222> LOCATION: (11)..(11)
<223> OTHER INFORMATION: X = absent or G
<220> FEATURE:
<221> NAME/KEY: MISC_FEATURE
<222> LOCATION: (12)..(12)
<223> OTHER INFORMATION: X = absent or G
<220> FEATURE:
<221> NAME/KEY: MISC_FEATURE
<222> LOCATION: (13)..(13)
<223> OTHER INFORMATION: X = absent or G
<220> FEATURE:
<221> NAME/KEY: MISC_FEATURE
<222> LOCATION: (14)..(14)
<223> OTHER INFORMATION: X = absent or T
<220> FEATURE:
<221> NAME/KEY: MISC_FEATURE
<222> LOCATION: (15)..(15)
<223> OTHER INFORMATION: X = absent or K
<220> FEATURE:
<221> NAME/KEY: MISC_FEATURE
<222> LOCATION: (16)..(16)
<223> OTHER INFORMATION: X = absent or V
<220> FEATURE:
<221> NAME/KEY: MISC_FEATURE
<222> LOCATION: (17)..(17)
<223> OTHER INFORMATION: X = absent or E
<220> FEATURE:
<221> NAME/KEY: MISC_FEATURE
<222> LOCATION: (18)..(18)
<223> OTHER INFORMATION: X = absent or F
<220> FEATURE:
<221> NAME/KEY: MISC_FEATURE
<222> LOCATION: (19)..(19)
<223> OTHER INFORMATION: X = absent or K

<400> SEQUENCE: 252

Gln Gln Xaa Xaa Xaa Pro Xaa Xaa Xaa Xaa Xaa Xaa Xaa Xaa Xaa
1               5                   10                  15

Xaa Xaa Xaa

<210> SEQ ID NO 253
<211> LENGTH: 10
<212> TYPE: PRT
<213> ORGANISM: Artificial Sequence
<220> FEATURE:
<223> OTHER INFORMATION: LC-CDR3-5 Family consensus
```

```
<220> FEATURE:
<221> NAME/KEY: MISC_FEATURE
<222> LOCATION: (4)..(4)
<223> OTHER INFORMATION: X = D or N
<220> FEATURE:
<221> NAME/KEY: MISC_FEATURE
<222> LOCATION: (5)..(5)
<223> OTHER INFORMATION: X = S or Y
<220> FEATURE:
<221> NAME/KEY: MISC_FEATURE
<222> LOCATION: (7)..(7)
<223> OTHER INFORMATION: X = K, S or N
<220> FEATURE:
<221> NAME/KEY: MISC_FEATURE
<222> LOCATION: (8)..(8)
<223> OTHER INFORMATION: X = V or L
<220> FEATURE:
<221> NAME/KEY: MISC_FEATURE
<222> LOCATION: (9)..(9)
<223> OTHER INFORMATION: X = I, V or W
<220> FEATURE:
<221> NAME/KEY: MISC_FEATURE
<222> LOCATION: (10)..(10)
<223> OTHER INFORMATION: X = absent or V

<400> SEQUENCE: 253

Gln Ser Tyr Xaa Xaa Ser Xaa Xaa Xaa Xaa
1               5                   10

<210> SEQ ID NO 254
<211> LENGTH: 11
<212> TYPE: PRT
<213> ORGANISM: Artificial Sequence
<220> FEATURE:
<223> OTHER INFORMATION: LC-CDR3-6 Family consensus
<220> FEATURE:
<221> NAME/KEY: MISC_FEATURE
<222> LOCATION: (1)..(1)
<223> OTHER INFORMATION: X = T or N
<220> FEATURE:
<221> NAME/KEY: MISC_FEATURE
<222> LOCATION: (4)..(4)
<223> OTHER INFORMATION: X = T or S
<220> FEATURE:
<221> NAME/KEY: MISC_FEATURE
<222> LOCATION: (7)..(7)
<223> OTHER INFORMATION: X = T or S
<220> FEATURE:
<221> NAME/KEY: MISC_FEATURE
<222> LOCATION: (8)..(8)
<223> OTHER INFORMATION: X = P or T
<220> FEATURE:
<221> NAME/KEY: MISC_FEATURE
<222> LOCATION: (9)..(9)
<223> OTHER INFORMATION: X = Y or L
<220> FEATURE:
<221> NAME/KEY: MISC_FEATURE
<222> LOCATION: (11)..(11)
<223> OTHER INFORMATION: X = absent or A

<400> SEQUENCE: 254

Xaa Ser Tyr Xaa Ser Ser Xaa Xaa Xaa Val Xaa
1               5                   10

<210> SEQ ID NO 255
<211> LENGTH: 8
<212> TYPE: PRT
<213> ORGANISM: Artificial Sequence
<220> FEATURE:
<223> OTHER INFORMATION: HC-CDR1-1 Familyl consensus
<220> FEATURE:
<221> NAME/KEY: MISC_FEATURE
<222> LOCATION: (8)..(8)
<223> OTHER INFORMATION: X = A or G
```

```
<400> SEQUENCE: 255

Gly Phe Thr Phe Ser Ser Tyr Xaa
1               5

<210> SEQ ID NO 256
<211> LENGTH: 8
<212> TYPE: PRT
<213> ORGANISM: Artificial Sequence
<220> FEATURE:
<223> OTHER INFORMATION: HC-CDR1-2 Family consensus
<220> FEATURE:
<221> NAME/KEY: MISC_FEATURE
<222> LOCATION: (2)..(2)
<223> OTHER INFORMATION: X = F or Y
<220> FEATURE:
<221> NAME/KEY: MISC_FEATURE
<222> LOCATION: (3)..(3)
<223> OTHER INFORMATION: X = S or T
<220> FEATURE:
<221> NAME/KEY: MISC_FEATURE
<222> LOCATION: (4)..(4)
<223> OTHER INFORMATION: X = L or F
<220> FEATURE:
<221> NAME/KEY: MISC_FEATURE
<222> LOCATION: (5)..(5)
<223> OTHER INFORMATION: X = G, R, T, S or N

<400> SEQUENCE: 256

Gly Xaa Xaa Xaa Xaa Ser Tyr Gly
1               5

<210> SEQ ID NO 257
<211> LENGTH: 8
<212> TYPE: PRT
<213> ORGANISM: Artificial Sequence
<220> FEATURE:
<223> OTHER INFORMATION: HC-CDR1-3 Family consensus
<220> FEATURE:
<221> NAME/KEY: MISC_FEATURE
<222> LOCATION: (1)..(1)
<223> OTHER INFORMATION: X = G or I
<220> FEATURE:
<221> NAME/KEY: MISC_FEATURE
<222> LOCATION: (2)..(2)
<223> OTHER INFORMATION: X = G, F or L
<220> FEATURE:
<221> NAME/KEY: MISC_FEATURE
<222> LOCATION: (3)..(3)
<223> OTHER INFORMATION: X = T, S or P
<220> FEATURE:
<221> NAME/KEY: MISC_FEATURE
<222> LOCATION: (4)..(4)
<223> OTHER INFORMATION: X = F or S
<220> FEATURE:
<221> NAME/KEY: MISC_FEATURE
<222> LOCATION: (5)..(5)
<223> OTHER INFORMATION: X = S or D

<400> SEQUENCE: 257

Xaa Xaa Xaa Xaa Xaa Ser Tyr Ala
1               5

<210> SEQ ID NO 258
<211> LENGTH: 8
<212> TYPE: PRT
<213> ORGANISM: Artificial Sequence
<220> FEATURE:
<223> OTHER INFORMATION: HC-CDR2-1 Family consensus
<220> FEATURE:
<221> NAME/KEY: MISC_FEATURE
<222> LOCATION: (7)..(7)
<223> OTHER INFORMATION: X = N or D
```

```
<400> SEQUENCE: 258

Ile Ser Tyr Asp Gly Ser Xaa Lys
1               5

<210> SEQ ID NO 259
<211> LENGTH: 12
<212> TYPE: PRT
<213> ORGANISM: Artificial Sequence
<220> FEATURE:
<223> OTHER INFORMATION: HC-CDR3-2 Family consensus
<220> FEATURE:
<221> NAME/KEY: MISC_FEATURE
<222> LOCATION: (3)..(3)
<223> OTHER INFORMATION: X = L, F or D
<220> FEATURE:
<221> NAME/KEY: MISC_FEATURE
<222> LOCATION: (4)..(4)
<223> OTHER INFORMATION: X =Y, A or L
<220> FEATURE:
<221> NAME/KEY: MISC_FEATURE
<222> LOCATION: (5)..(5)
<223> OTHER INFORMATION: X = S or R
<220> FEATURE:
<221> NAME/KEY: MISC_FEATURE
<222> LOCATION: (7)..(7)
<223> OTHER INFORMATION: X = S, V or L
<220> FEATURE:
<221> NAME/KEY: MISC_FEATURE
<222> LOCATION: (8)..(8)
<223> OTHER INFORMATION: X = S, Y or P
<220> FEATURE:
<221> NAME/KEY: MISC_FEATURE
<222> LOCATION: (9)..(9)
<223> OTHER INFORMATION: X = N, L or I
<220> FEATURE:
<221> NAME/KEY: MISC_FEATURE
<222> LOCATION: (10)..(10)
<223> OTHER INFORMATION: X = F or I

<400> SEQUENCE: 259

Ala Lys Xaa Xaa Xaa Gly Xaa Xaa Xaa Xaa Asp Tyr
1               5                   10

<210> SEQ ID NO 260
<211> LENGTH: 14
<212> TYPE: PRT
<213> ORGANISM: Artificial Sequence
<220> FEATURE:
<223> OTHER INFORMATION: HC-CDR3-3 Family consensus
<220> FEATURE:
<221> NAME/KEY: MISC_FEATURE
<222> LOCATION: (4)..(4)
<223> OTHER INFORMATION: X = S or V

<400> SEQUENCE: 260

Ala Arg Asp Xaa Gly Tyr Ser Ser Gly Trp Tyr Phe Asp Tyr
1               5                   10

<210> SEQ ID NO 261
<211> LENGTH: 24
<212> TYPE: PRT
<213> ORGANISM: Artificial Sequence
<220> FEATURE:
<223> OTHER INFORMATION: HC-CDR3-4 Family consensus
<220> FEATURE:
<221> NAME/KEY: MISC_FEATURE
<222> LOCATION: (4)..(4)
<223> OTHER INFORMATION: X = H or A
<220> FEATURE:
<221> NAME/KEY: MISC_FEATURE
<222> LOCATION: (5)..(5)
<223> OTHER INFORMATION: X = S, Q or F
<220> FEATURE:
```

```
<221> NAME/KEY: MISC_FEATURE
<222> LOCATION: (6)..(6)
<223> OTHER INFORMATION: X = S or G
<220> FEATURE:
<221> NAME/KEY: MISC_FEATURE
<222> LOCATION: (7)..(7)
<223> OTHER INFORMATION: X = absent or Y
<220> FEATURE:
<221> NAME/KEY: MISC_FEATURE
<222> LOCATION: (8)..(8)
<223> OTHER INFORMATION: X = absent or S
<220> FEATURE:
<221> NAME/KEY: MISC_FEATURE
<222> LOCATION: (9)..(9)
<223> OTHER INFORMATION: X = absent, R or S
<220> FEATURE:
<221> NAME/KEY: MISC_FEATURE
<222> LOCATION: (10)..(10)
<223> OTHER INFORMATION: X = Q, N or S
<220> FEATURE:
<221> NAME/KEY: MISC_FEATURE
<222> LOCATION: (11)..(11)
<223> OTHER INFORMATION: X = W or Y
<220> FEATURE:
<221> NAME/KEY: MISC_FEATURE
<222> LOCATION: (12)..(12)
<223> OTHER INFORMATION: X = absent, Y or F
<220> FEATURE:
<221> NAME/KEY: MISC_FEATURE
<222> LOCATION: (13)..(13)
<223> OTHER INFORMATION: X = absent or E
<220> FEATURE:
<221> NAME/KEY: MISC_FEATURE
<222> LOCATION: (14)..(14)
<223> OTHER INFORMATION: X = absent or W
<220> FEATURE:
<221> NAME/KEY: MISC_FEATURE
<222> LOCATION: (15)..(15)
<223> OTHER INFORMATION: X = absent or E
<220> FEATURE:
<221> NAME/KEY: MISC_FEATURE
<222> LOCATION: (16)..(16)
<223> OTHER INFORMATION: X = absent or P
<220> FEATURE:
<221> NAME/KEY: MISC_FEATURE
<222> LOCATION: (17)..(17)
<223> OTHER INFORMATION: X = absent, G or S
<220> FEATURE:
<221> NAME/KEY: MISC_FEATURE
<222> LOCATION: (18)..(18)
<223> OTHER INFORMATION: X = absent, R or T
<220> FEATURE:
<221> NAME/KEY: MISC_FEATURE
<222> LOCATION: (19)..(19)
<223> OTHER INFORMATION: X = G, E or I
<220> FEATURE:
<221> NAME/KEY: MISC_FEATURE
<222> LOCATION: (20)..(20)
<223> OTHER INFORMATION: X = D or H

<400> SEQUENCE: 261

Ala Arg Leu Xaa Xaa Xaa Xaa Xaa Xaa Xaa Xaa Xaa Xaa Xaa Xaa Xaa
1               5                   10                  15

Xaa Xaa Xaa Xaa Ala Phe Asp Ile
            20

<210> SEQ ID NO 262
<211> LENGTH: 14
<212> TYPE: PRT
<213> ORGANISM: Artificial Sequence
<220> FEATURE:
<223> OTHER INFORMATION: HC-CDR3-6 Family consensus
<220> FEATURE:
<221> NAME/KEY: MISC_FEATURE
<222> LOCATION: (4)..(4)
<223> OTHER INFORMATION: X = A or G
```

```
<220> FEATURE:
<221> NAME/KEY: MISC_FEATURE
<222> LOCATION: (5)..(5)
<223> OTHER INFORMATION: X = A or G
<220> FEATURE:
<221> NAME/KEY: MISC_FEATURE
<222> LOCATION: (6)..(6)
<223> OTHER INFORMATION: X = A or Y
<220> FEATURE:
<221> NAME/KEY: MISC_FEATURE
<222> LOCATION: (7)..(7)
<223> OTHER INFORMATION: X = D or absent
<220> FEATURE:
<221> NAME/KEY: MISC_FEATURE
<222> LOCATION: (8)..(8)
<223> OTHER INFORMATION: X = G or D
<220> FEATURE:
<221> NAME/KEY: MISC_FEATURE
<222> LOCATION: (9)..(9)
<223> OTHER INFORMATION: X = F, M or R
<220> FEATURE:
<221> NAME/KEY: MISC_FEATURE
<222> LOCATION: (11)..(11)
<223> OTHER INFORMATION: X = V, Y or A
<220> FEATURE:
<221> NAME/KEY: MISC_FEATURE
<222> LOCATION: (12)..(12)
<223> OTHER INFORMATION: X = absent or F
<220> FEATURE:
<221> NAME/KEY: MISC_FEATURE
<222> LOCATION: (13)..(13)
<223> OTHER INFORMATION: X = absent or D
<220> FEATURE:
<221> NAME/KEY: MISC_FEATURE
<222> LOCATION: (14)..(14)
<223> OTHER INFORMATION: X = absent or I

<400> SEQUENCE: 262

Ala Arg Ile Xaa Xaa Xaa Xaa Xaa Xaa Asp Xaa Xaa Xaa Xaa
1               5                   10

<210> SEQ ID NO 263
<211> LENGTH: 10
<212> TYPE: PRT
<213> ORGANISM: Artificial Sequence
<220> FEATURE:
<223> OTHER INFORMATION: HC-CDR3-8 Family consensus
<220> FEATURE:
<221> NAME/KEY: MISC_FEATURE
<222> LOCATION: (1)..(1)
<223> OTHER INFORMATION: X = absent or A
<220> FEATURE:
<221> NAME/KEY: MISC_FEATURE
<222> LOCATION: (2)..(2)
<223> OTHER INFORMATION: X = absent or R
<220> FEATURE:
<221> NAME/KEY: MISC_FEATURE
<222> LOCATION: (3)..(3)
<223> OTHER INFORMATION: X = A or G
<220> FEATURE:
<221> NAME/KEY: MISC_FEATURE
<222> LOCATION: (4)..(4)
<223> OTHER INFORMATION: X = R or T
<220> FEATURE:
<221> NAME/KEY: MISC_FEATURE
<222> LOCATION: (8)..(8)
<223> OTHER INFORMATION: X = F or G

<400> SEQUENCE: 263

Xaa Xaa Xaa Xaa Arg Gly Tyr Xaa Asp Tyr
1               5                   10

<210> SEQ ID NO 264
<211> LENGTH: 9
<212> TYPE: PRT
```

```
<213> ORGANISM: Artificial Sequence
<220> FEATURE:
<223> OTHER INFORMATION: HC-CDR3-10 Family consensus
<220> FEATURE:
<221> NAME/KEY: MISC_FEATURE
<222> LOCATION: (3)..(3)
<223> OTHER INFORMATION: X = absent or S
<220> FEATURE:
<221> NAME/KEY: MISC_FEATURE
<222> LOCATION: (7)..(7)
<223> OTHER INFORMATION: X = absent or F

<400> SEQUENCE: 264

Ala Arg Xaa Gly Val Leu Xaa Asp Tyr
1               5

<210> SEQ ID NO 265
<211> LENGTH: 1575
<212> TYPE: DNA
<213> ORGANISM: Artificial Sequence
<220> FEATURE:
<223> OTHER INFORMATION: DNA encoding IL-11:IL-11Ralpha fusion protein

<400> SEQUENCE: 265
```

| | | | | |
|---|---|---|---|---|
| gaattcccgc | cgccaccatg | ggctggtcct | gcatcatcct | gtttctggtg gccacagcca | 60 |
| ccggcgtgca | ctctccacag | gcttggggac | ctccaggcgt | gcagtatggc cagcctggca | 120 |
| gatccgtgaa | gctgtgctgt | cctggcgtga | cagctggcga | ccctgtgtcc tggttcagag | 180 |
| atggcgagcc | caagctgctg | cagggcccag | attctggact | gggccacgaa ctggtgctgg | 240 |
| cccaggccga | ttctaccgac | gagggcacct | acatctgcca | gaccctggat ggcgccctgg | 300 |
| gcggaacagt | gacactgcag | ctgggctacc | ctcccgccag | acctgtggtg tcttgtcagg | 360 |
| ccgccgacta | cgagaacttc | agctgcacat | ggtcccccag | ccagatcagc ggcctgccca | 420 |
| ccagatacct | gaccagctac | cggaagaaaa | ccgtgctggg | cgccgacagc cagagaagaa | 480 |
| gcccttctac | aggcccctgg | ccctgcctc  | aggatcctct | gggagctgcc agatgtgtgg | 540 |
| tgcacggcgc | cgagttctgg | tcccagtacc | ggatcaacgt | gaccgaagtg aacccctgg  | 600 |
| gcgcctccac | aagactgctg | gatgtgtccc | tgcagagcat | cctgcggccc gatcctccac | 660 |
| agggcctgag | agtggaaagc | gtgcccggct | accccagaag | gctgagagcc agctggacat | 720 |
| accccgcctc | ttggccttgc | cagcccccact | tcctgctgaa | gtttcggctg cagtaccggc | 780 |
| cagcccagca | ccctgcttgg | agcacagtgg | aacctgccgg | cctggaagaa gtgatcacag | 840 |
| acgccgtggc | cggactgcct | catgctgtgc | gggtgtccgc | cagagacttt ctggatgccg | 900 |
| gcacctggtc | tacctggtcc | ccagaagcct | ggggcacacc | ttctactggc ggacctgctg | 960 |
| gacagtctgg | cggaggcgga | ggaagtggcg | gaggatcagg | gggaggatct gtgcctggac | 1020 |
| ctcctccagg | acccccctaga | gtgtccccag | atcctagggc | cgagctggac tctaccgtgc | 1080 |
| tgctgaccag | atccctgctg | ccgacacaa  | ggcagctggc | tgcccagctg agagacaagt | 1140 |
| tccccgccga | cggcgaccac | aacctggata | gcctgcctac | cctggccatg tctgctggcg | 1200 |
| cactgggggc | tctgcagctg | cctggggtgc | tgactagact | gagagccgac tgctgagct  | 1260 |
| acctgcggca | tgtgcagtgg | ctgagaaggg | ctggcggcag | cagcctgaaa acctggaac  | 1320 |
| ctgagctggg | cacactgcag | gccagactgg | acagactgct | cgcagactg cagctgctga | 1380 |
| tgagcagact | ggctctgccc | cagcctcctc | ctgaccctcc | tgctcctcca ctggctcctc | 1440 |
| caagctctgc | ttggggcgga | attagagccg | cccacgccat | tctgggaggc ctgcacctga | 1500 |
| cactggattg | ggcagtgcgg | ggcctgctgc | tgctgaaaac | cagactgcac caccaccatc | 1560 | accactgata agctt                                                          1575

<210> SEQ ID NO 266
<211> LENGTH: 516
<212> TYPE: PRT
<213> ORGANISM: Artificial Sequence
<220> FEATURE:
<223> OTHER INFORMATION: Amino acid sequence of IL-11:IL-11Ralpha fusion
      protein

<400> SEQUENCE: 266

```
Met Gly Trp Ser Cys Ile Ile Leu Phe Leu Val Ala Thr Ala Thr Gly
1               5                   10                  15

Val His Ser Pro Gln Ala Trp Gly Pro Gly Val Gln Tyr Gly Gln
            20                  25                  30

Pro Gly Arg Ser Val Lys Leu Cys Cys Pro Gly Val Thr Ala Gly Asp
        35                  40                  45

Pro Val Ser Trp Phe Arg Asp Gly Glu Pro Lys Leu Leu Gln Gly Pro
    50                  55                  60

Asp Ser Gly Leu Gly His Glu Leu Val Leu Ala Gln Ala Asp Ser Thr
65                  70                  75                  80

Asp Glu Gly Thr Tyr Ile Cys Gln Thr Leu Asp Gly Ala Leu Gly Gly
                85                  90                  95

Thr Val Thr Leu Gln Leu Gly Tyr Pro Pro Ala Arg Pro Val Val Ser
            100                 105                 110

Cys Gln Ala Ala Asp Tyr Glu Asn Phe Ser Cys Thr Trp Ser Pro Ser
        115                 120                 125

Gln Ile Ser Gly Leu Pro Thr Arg Tyr Leu Thr Ser Tyr Arg Lys Lys
130                 135                 140

Thr Val Leu Gly Ala Asp Ser Gln Arg Arg Ser Pro Ser Thr Gly Pro
145                 150                 155                 160

Trp Pro Cys Pro Gln Asp Pro Leu Gly Ala Ala Arg Cys Val Val His
                165                 170                 175

Gly Ala Glu Phe Trp Ser Gln Tyr Arg Ile Asn Val Thr Glu Val Asn
            180                 185                 190

Pro Leu Gly Ala Ser Thr Arg Leu Leu Asp Val Ser Leu Gln Ser Ile
        195                 200                 205

Leu Arg Pro Asp Pro Pro Gln Gly Leu Arg Val Glu Ser Val Pro Gly
    210                 215                 220

Tyr Pro Arg Arg Leu Arg Ala Ser Trp Thr Tyr Pro Ala Ser Trp Pro
225                 230                 235                 240

Cys Gln Pro His Phe Leu Leu Lys Phe Arg Leu Gln Tyr Arg Pro Ala
                245                 250                 255

Gln His Pro Ala Trp Ser Thr Val Glu Pro Ala Gly Leu Glu Glu Val
            260                 265                 270

Ile Thr Asp Ala Val Ala Gly Leu Pro His Ala Val Arg Val Ser Ala
        275                 280                 285

Arg Asp Phe Leu Asp Ala Gly Thr Trp Ser Thr Trp Ser Pro Glu Ala
    290                 295                 300

Trp Gly Thr Pro Ser Thr Gly Pro Ala Gly Gln Ser Gly Gly Gly
305                 310                 315                 320

Gly Gly Ser Gly Gly Ser Gly Gly Ser Val Pro Gly Pro Pro
                325                 330                 335

Pro Gly Pro Pro Arg Val Ser Pro Asp Pro Arg Ala Glu Leu Asp Ser
            340                 345                 350
```

```
Thr Val Leu Leu Thr Arg Ser Leu Leu Ala Asp Thr Arg Gln Leu Ala
            355                 360                 365

Ala Gln Leu Arg Asp Lys Phe Pro Ala Asp Gly Asp His Asn Leu Asp
    370                 375                 380

Ser Leu Pro Thr Leu Ala Met Ser Ala Gly Ala Leu Gly Ala Leu Gln
385                 390                 395                 400

Leu Pro Gly Val Leu Thr Arg Leu Arg Ala Asp Leu Leu Ser Tyr Leu
                405                 410                 415

Arg His Val Gln Trp Leu Arg Arg Ala Gly Gly Ser Ser Leu Lys Thr
            420                 425                 430

Leu Glu Pro Glu Leu Gly Thr Leu Gln Ala Arg Leu Asp Arg Leu Leu
        435                 440                 445

Arg Arg Leu Gln Leu Leu Met Ser Arg Leu Ala Leu Pro Gln Pro Pro
    450                 455                 460

Pro Asp Pro Pro Ala Pro Pro Leu Ala Pro Pro Ser Ser Ala Trp Gly
465                 470                 475                 480

Gly Ile Arg Ala Ala His Ala Ile Leu Gly Gly Leu His Leu Thr Leu
                485                 490                 495

Asp Trp Ala Val Arg Gly Leu Leu Leu Leu Lys Thr Arg Leu His His
            500                 505                 510

His His His His
        515

<210> SEQ ID NO 267
<211> LENGTH: 110
<212> TYPE: PRT
<213> ORGANISM: Artificial Sequence
<220> FEATURE:
<223> OTHER INFORMATION: YU100-A10

<400> SEQUENCE: 267

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Glu Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Pro Glu Asp Glu Ala Asp Tyr Tyr Cys Ser Ser Phe Thr Thr Ser
                85                  90                  95

Ile Ala Trp Val Phe Gly Gly Gly Thr Lys Leu Thr Val Leu
            100                 105                 110

<210> SEQ ID NO 268
<211> LENGTH: 10
<212> TYPE: PRT
<213> ORGANISM: Artificial Sequence
<220> FEATURE:
<223> OTHER INFORMATION: YU100-A10 LC-CDR3

<400> SEQUENCE: 268

Ser Ser Phe Thr Thr Ser Ile Ala Trp Val
1               5                   10

<210> SEQ ID NO 269
```

<211> LENGTH: 110
<212> TYPE: PRT
<213> ORGANISM: Artificial Sequence
<220> FEATURE:
<223> OTHER INFORMATION: YU100-A11

<400> SEQUENCE: 269

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
            100                 105                 110
```

<210> SEQ ID NO 270
<211> LENGTH: 110
<212> TYPE: PRT
<213> ORGANISM: Artificial Sequence
<220> FEATURE:
<223> OTHER INFORMATION: YU100-A12

<400> SEQUENCE: 270

```
Leu Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Thr Trp Val Phe Gly Gly Gly Thr Lys Leu Thr Val Leu
            100                 105                 110
```

<210> SEQ ID NO 271
<211> LENGTH: 110
<212> TYPE: PRT
<213> ORGANISM: Artificial Sequence
<220> FEATURE:
<223> OTHER INFORMATION: YU100-B01

<400> SEQUENCE: 271

```
Gln Ser Ala Leu Thr Gln Pro Arg Ser Val Ser Gly Ser Pro Gly Gln
1               5                   10                  15

Ser Val Thr Ile Ser Cys Thr Gly Thr Asn Thr Asp Val Gly Ala Tyr
            20                  25                  30

Asn Tyr Val Ser Trp Tyr Gln Gln Tyr Pro Gly Lys Ala Pro Lys Leu
        35                  40                  45
```

```
Ile Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Ser Trp Val Phe Gly Gly Gly Thr Lys Leu Thr Val Leu
            100                 105                 110

<210> SEQ ID NO 272
<211> LENGTH: 9
<212> TYPE: PRT
<213> ORGANISM: Artificial Sequence
<220> FEATURE:
<223> OTHER INFORMATION: YU100-B01 LC-CDR1

<400> SEQUENCE: 272

Asn Thr Asp Val Gly Ala Tyr Asn Tyr
1               5

<210> SEQ ID NO 273
<211> LENGTH: 10
<212> TYPE: PRT
<213> ORGANISM: Artificial Sequence
<220> FEATURE:
<223> OTHER INFORMATION: YU100-B01 LC-CDR3

<400> SEQUENCE: 273

Cys Ser Tyr Ala Gly Ser Tyr Ser Trp Val
1               5                   10

<210> SEQ ID NO 274
<211> LENGTH: 120
<212> TYPE: PRT
<213> ORGANISM: Artificial Sequence
<220> FEATURE:
<223> OTHER INFORMATION: YU100-B03

<400> SEQUENCE: 274

Gln Ser Val Leu Thr Gln Pro Arg Ser Val Ser Gly Ser Pro Gly Arg
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Thr Leu Tyr Asp Val Val Lys Arg Pro Ser Gly Val Pro Asp Arg Tyr
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Gly
                 85                  90                  95

Tyr Thr Trp Val Phe Gly Gly Gly Thr Lys Val Thr Val Val Cys Ser
            100                 105                 110

Tyr Ala Gly Ser Tyr Ser Trp Val
            115                 120

<210> SEQ ID NO 275
<211> LENGTH: 3
<212> TYPE: PRT
<213> ORGANISM: Artificial Sequence
<220> FEATURE:
<223> OTHER INFORMATION: YU100-B03 LC-CDR2
```

<400> SEQUENCE: 275

Asp Val Val
1

<210> SEQ ID NO 276
<211> LENGTH: 10
<212> TYPE: PRT
<213> ORGANISM: Artificial Sequence
<220> FEATURE:
<223> OTHER INFORMATION: YU100-B03 LC-CDR3

<400> SEQUENCE: 276

Cys Ser Tyr Ala Gly Gly Tyr Thr Trp Val
1               5                   10

<210> SEQ ID NO 277
<211> LENGTH: 110
<212> TYPE: PRT
<213> ORGANISM: Artificial Sequence
<220> FEATURE:
<223> OTHER INFORMATION: YU100-B06

<400> SEQUENCE: 277

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Ala Gly Ser
                85                  90                  95

Tyr Thr Trp Val Phe Gly Gly Gly Thr Lys Leu Thr Val Leu
            100                 105                 110

<210> SEQ ID NO 278
<211> LENGTH: 10
<212> TYPE: PRT
<213> ORGANISM: Artificial Sequence
<220> FEATURE:
<223> OTHER INFORMATION: YU100-B06 LC-CDR3

<400> SEQUENCE: 278

Asn Ser Tyr Ala Gly Ser Tyr Thr Trp Val
1               5                   10

<210> SEQ ID NO 279
<211> LENGTH: 110
<212> TYPE: PRT
<213> ORGANISM: Artificial Sequence
<220> FEATURE:
<223> OTHER INFORMATION: YU100-B07

<400> SEQUENCE: 279

Gln Ser Ala Leu Thr Gln Pro Arg Ser Val Ser Gly Ser Pro Gly Gln
1               5                   10                  15

Ser Val Thr Met Ser Cys Thr Gly Thr Ser Arg Asp Val Gly Gly Tyr
            20                  25                  30

-continued

```
Asn Tyr Val Ser Trp Tyr Gln His Pro Gly Lys Ala Pro Lys Leu
             35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Glu Leu
 65                  70                  75                  80

Gln Ala Glu Asp Glu Ala Asp Tyr Tyr Cys Cys Ser Tyr Ala Gly Ser
                 85                  90                  95

Tyr Thr Trp Val Phe Gly Gly Thr Lys Leu Thr Val Leu
            100                 105                 110
```

<210> SEQ ID NO 280
<211> LENGTH: 110
<212> TYPE: PRT
<213> ORGANISM: Artificial Sequence
<220> FEATURE:
<223> OTHER INFORMATION: YU100-B08

<400> SEQUENCE: 280

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Val Pro Arg Leu
             35                  40                  45

Leu Ile Tyr Asp Val Ser Asn Arg Pro Ser Gly Val Ser Thr Arg Phe
 50                  55                  60

Ser Gly Ser Lys Ser Gly Asn Thr Ala Ser Leu Thr Ile Ser Gly Leu
 65                  70                  75                  80

Gln Gly Glu Asp Glu Ala Glu Tyr Tyr Cys Ser Ser Phe Thr Ser Ser
                 85                  90                  95

Thr Thr Trp Val Phe Gly Gly Gly Thr Lys Leu Thr Val Leu
            100                 105                 110
```

<210> SEQ ID NO 281
<211> LENGTH: 10
<212> TYPE: PRT
<213> ORGANISM: Artificial Sequence
<220> FEATURE:
<223> OTHER INFORMATION: YU100-B08 LC-CDR3

<400> SEQUENCE: 281

```
Ser Ser Phe Thr Ser Ser Thr Thr Trp Val
 1               5                  10
```

<210> SEQ ID NO 282
<211> LENGTH: 21
<212> TYPE: PRT
<213> ORGANISM: Artificial Sequence
<220> FEATURE:
<223> OTHER INFORMATION: YU100-B09 LC-CDR3

<400> SEQUENCE: 282

```
Ser Ser Tyr Arg Ser Gly Ser Thr Leu Gly Val Arg Arg Arg Asp Gln
 1               5                  10                  15

Ala Asp Arg Pro Arg
             20
```

<210> SEQ ID NO 283
<211> LENGTH: 110
<212> TYPE: PRT

```
<213> ORGANISM: Artificial Sequence
<220> FEATURE:
<223> OTHER INFORMATION: YU100-C02

<400> SEQUENCE: 283

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asn Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Val Trp Val Phe Gly Gly Gly Thr Lys Leu Thr Val Leu
            100                 105                 110

<210> SEQ ID NO 284
<211> LENGTH: 9
<212> TYPE: PRT
<213> ORGANISM: Artificial Sequence
<220> FEATURE:
<223> OTHER INFORMATION: YU100-C02 LC-CDR1

<400> SEQUENCE: 284

Ser Ser Asn Val Gly Gly Tyr Asn Tyr
1               5

<210> SEQ ID NO 285
<211> LENGTH: 10
<212> TYPE: PRT
<213> ORGANISM: Artificial Sequence
<220> FEATURE:
<223> OTHER INFORMATION: YU100-C02 LC-CDR3

<400> SEQUENCE: 285

Cys Ser Tyr Ala Gly Ser Tyr Val Trp Val
1               5                   10

<210> SEQ ID NO 286
<211> LENGTH: 110
<212> TYPE: PRT
<213> ORGANISM: Artificial Sequence
<220> FEATURE:
<223> OTHER INFORMATION: YU100-C04

<400> SEQUENCE: 286

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Ile Ile Tyr Asp Val Thr Lys Arg Pro Ser Gly Val Pro Asp Arg Phe
50                  55                  60

Ser Gly Ser Lys Ser Gly Asn Thr Ala Ser Leu Ala Ile Ser Gly Leu
65                  70                  75                  80

Gln Ala Glu Glu Glu Ala Asp Tyr Tyr Cys Cys Ser Tyr Ala Gly Gly
```

```
                    85                  90                  95

Tyr Thr Trp Val Phe Gly Gly Gly Thr Lys Leu Thr Val Leu
                100                 105                 110

<210> SEQ ID NO 287
<211> LENGTH: 110
<212> TYPE: PRT
<213> ORGANISM: Artificial Sequence
<220> FEATURE:
<223> OTHER INFORMATION: YU100-C05

<400> SEQUENCE: 287

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ile Ser Trp Val Phe Gly Gly Gly Thr Lys Leu Thr Val Leu
                100                 105                 110

<210> SEQ ID NO 288
<211> LENGTH: 10
<212> TYPE: PRT
<213> ORGANISM: Artificial Sequence
<220> FEATURE:
<223> OTHER INFORMATION: YU100-C05 LC-CDR3

<400> SEQUENCE: 288

Ser Ser Tyr Thr Ser Ser Ile Ser Trp Val
1               5                   10

<210> SEQ ID NO 289
<211> LENGTH: 110
<212> TYPE: PRT
<213> ORGANISM: Artificial Sequence
<220> FEATURE:
<223> OTHER INFORMATION: YU100-C10

<400> SEQUENCE: 289

Gln Ser Ala Leu Thr Gln Pro Ala Ser Val Ser Gly Ser Pro Gly Gln
1               5                   10                  15

Ser Ile Thr Ile Ser Cys Thr Gly Thr Arg Ser Asp Ile Gly Gly Tyr
            20                  25                  30

Asp Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Glu Tyr Tyr Cys Ser Ser Tyr Thr Ser Ser
                85                  90                  95

Ile Thr Trp Val Phe Gly Gly Gly Thr Lys Val Thr Val Leu
                100                 105                 110
```

<210> SEQ ID NO 290
<211> LENGTH: 9
<212> TYPE: PRT
<213> ORGANISM: Artificial Sequence
<220> FEATURE:
<223> OTHER INFORMATION: YU100-C10 LC-CDR1

<400> SEQUENCE: 290

Arg Ser Asp Ile Gly Gly Tyr Asp Tyr
1               5

<210> SEQ ID NO 291
<211> LENGTH: 3
<212> TYPE: PRT
<213> ORGANISM: Artificial Sequence
<220> FEATURE:
<223> OTHER INFORMATION: YU100-C10 LC-CDR3

<400> SEQUENCE: 291

Asp Val Asn
1

<210> SEQ ID NO 292
<211> LENGTH: 10
<212> TYPE: PRT
<213> ORGANISM: Artificial Sequence
<220> FEATURE:
<223> OTHER INFORMATION: YU100-C11 LC-CDR3

<400> SEQUENCE: 292

Ser Ser Tyr Thr Asn Ser Arg Thr Trp Val
1               5                   10

<210> SEQ ID NO 293
<211> LENGTH: 110
<212> TYPE: PRT
<213> ORGANISM: Artificial Sequence
<220> FEATURE:
<223> OTHER INFORMATION: YU100-D01

<400> SEQUENCE: 293

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Leu Ile Tyr Asp Val Asp Lys Arg Pro Ser Gly Val Pro Asp Arg Phe
    50                  55                  60

Ser Gly Ser Lys Ser Gly Arg Thr Ala Ser Leu Thr Ile Ser Gly Leu
65                  70                  75                  80

Gln Thr Glu Asp Glu Ala Lys Tyr Tyr Cys Cys Ser Tyr Ala Gly Arg
                85                  90                  95

Tyr Thr Trp Ile Phe Gly Gly Gly Thr Lys Leu Thr Val Leu
            100                 105                 110

<210> SEQ ID NO 294
<211> LENGTH: 9
<212> TYPE: PRT
<213> ORGANISM: Artificial Sequence
<220> FEATURE:
<223> OTHER INFORMATION: YU100-D01 LC-CDR1

```
<400> SEQUENCE: 294

Ser Ser Asp Val Gly Gly Tyr Asn Phe
1               5

<210> SEQ ID NO 295
<211> LENGTH: 3
<212> TYPE: PRT
<213> ORGANISM: Artificial Sequence
<220> FEATURE:
<223> OTHER INFORMATION: YU100-D01 LC-CDR2

<400> SEQUENCE: 295

Asp Val Asp
1

<210> SEQ ID NO 296
<211> LENGTH: 10
<212> TYPE: PRT
<213> ORGANISM: Artificial Sequence
<220> FEATURE:
<223> OTHER INFORMATION: YU100-D01 LC-CDR3

<400> SEQUENCE: 296

Cys Ser Tyr Ala Gly Arg Tyr Thr Trp Ile
1               5                   10

<210> SEQ ID NO 297
<211> LENGTH: 110
<212> TYPE: PRT
<213> ORGANISM: Artificial Sequence
<220> FEATURE:
<223> OTHER INFORMATION: YU100-D02

<400> SEQUENCE: 297

Gln Ser Ala Leu Thr Gln Pro Arg Ser Val Ser Gly Ser Pro Gly Gln
1               5                   10                  15

Ser Val Thr Ile Ser Cys Thr Gly Thr Ser Gly Asp Val Gly Thr Tyr
            20                  25                  30

Asn Tyr Val Ser Trp Tyr Gln Gln His Pro Gly Lys Ala Pro Lys Leu
        35                  40                  45

Met Ile Phe Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Ala Gly Ser
                85                  90                  95

Tyr Thr Trp Val Phe Gly Gly Gly Thr Lys Leu Thr Val Leu
            100                 105                 110

<210> SEQ ID NO 298
<211> LENGTH: 9
<212> TYPE: PRT
<213> ORGANISM: Artificial Sequence
<220> FEATURE:
<223> OTHER INFORMATION: YU100-D02 LC-CDR1

<400> SEQUENCE: 298

Ser Gly Asp Val Gly Thr Tyr Asn Tyr
1               5

<210> SEQ ID NO 299
<211> LENGTH: 110
<212> TYPE: PRT
```

```
<213> ORGANISM: Artificial Sequence
<220> FEATURE:
<223> OTHER INFORMATION: YU100-D05

<400> SEQUENCE: 299

Gln Ser Ala Leu Thr Gln Pro Ala Ser Val Ser Gly Ser Pro Gly Gln
1               5                   10                  15

Leu Ile Thr Ile Ser Cys Thr Gly Thr Asn Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
            100                 105                 110

<210> SEQ ID NO 300
<211> LENGTH: 9
<212> TYPE: PRT
<213> ORGANISM: Artificial Sequence
<220> FEATURE:
<223> OTHER INFORMATION: YU100-D05 LC-CDR1

<400> SEQUENCE: 300

Asn Ser Asp Val Gly Gly Tyr Asn Tyr
1               5

<210> SEQ ID NO 301
<211> LENGTH: 110
<212> TYPE: PRT
<213> ORGANISM: Artificial Sequence
<220> FEATURE:
<223> OTHER INFORMATION: YU100-D07

<400> SEQUENCE: 301

Gln Ser Ala Leu Thr Gln Pro Arg Ser Val Ser Gly Ser Pro Gly Gln
1               5                   10                  15

Ser Val Thr Ile Ser Cys Thr Gly Thr Ser Gly Asp Val Gly Thr Tyr
            20                  25                  30

Asp Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Ala Gly Ser
                85                  90                  95

Tyr Thr Trp Val Phe Gly Gly Gly Thr Lys Leu Thr Val Leu
            100                 105                 110

<210> SEQ ID NO 302
<211> LENGTH: 9
<212> TYPE: PRT
<213> ORGANISM: Artificial Sequence
<220> FEATURE:
<223> OTHER INFORMATION: YU100-D07 LC-CDR1
```

<400> SEQUENCE: 302

Ser Gly Asp Val Gly Thr Tyr Asp Tyr
1               5

<210> SEQ ID NO 303
<211> LENGTH: 110
<212> TYPE: PRT
<213> ORGANISM: Artificial Sequence
<220> FEATURE:
<223> OTHER INFORMATION: YU100-D11

<400> SEQUENCE: 303

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asn Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asn Tyr Tyr Cys Ala Ser Tyr Ala Gly Asn
                85                  90                  95

Tyr Asn Trp Val Phe Gly Gly Gly Thr Lys Leu Thr Val Leu
            100                 105                 110

<210> SEQ ID NO 304
<211> LENGTH: 10
<212> TYPE: PRT
<213> ORGANISM: Artificial Sequence
<220> FEATURE:
<223> OTHER INFORMATION: YU100-D11 LC-CDR3

<400> SEQUENCE: 304

Ala Ser Tyr Ala Gly Asn Tyr Asn Trp Val
1               5                   10

<210> SEQ ID NO 305
<211> LENGTH: 110
<212> TYPE: PRT
<213> ORGANISM: Artificial Sequence
<220> FEATURE:
<223> OTHER INFORMATION: YU100-E01

<400> SEQUENCE: 305

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Ile Gly Ala Tyr
                20                  25                  30

Asn Tyr Val Ser Trp Tyr Gln Gln His Pro Gly Lys Ala Pro Lys Leu
            35                  40                  45

Leu Ile Tyr Asp Val Asn Asn Arg Pro Ser Gly Val Ser Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Ser Trp Val Phe Gly Gly Gly Thr Lys Leu Thr Val Leu
            100                 105                 110

<210> SEQ ID NO 306
<211> LENGTH: 9
<212> TYPE: PRT
<213> ORGANISM: Artificial Sequence
<220> FEATURE:
<223> OTHER INFORMATION: YU100-E01 LC-CDR1

<400> SEQUENCE: 306

Ser Asn Asp Ile Gly Ala Tyr Asn Tyr
1               5

<210> SEQ ID NO 307
<211> LENGTH: 110
<212> TYPE: PRT
<213> ORGANISM: Artificial Sequence
<220> FEATURE:
<223> OTHER INFORMATION: YU100-E04

<400> SEQUENCE: 307

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Thr Pro Lys Leu
        35                  40                  45

Met Ile Tyr Asp Val Thr Lys Arg Pro Ser Gly Val Pro Asp His Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

His Ile Trp Val Phe Gly Gly Gly Thr Lys Leu Thr Val Leu
            100                 105                 110

<210> SEQ ID NO 308
<211> LENGTH: 10
<212> TYPE: PRT
<213> ORGANISM: Artificial Sequence
<220> FEATURE:
<223> OTHER INFORMATION: YU100-E04 LC-CDR3

<400> SEQUENCE: 308

Cys Ser Tyr Ala Gly Ser His Ile Trp Val
1               5                   10

<210> SEQ ID NO 309
<211> LENGTH: 110
<212> TYPE: PRT
<213> ORGANISM: Artificial Sequence
<220> FEATURE:
<223> OTHER INFORMATION: YU100-E05

<400> SEQUENCE: 309

Gln Ala Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Ser Trp Val Phe Gly Gly Gly Thr Lys Leu Thr Val Leu
            100                 105                 110

<210> SEQ ID NO 310
<211> LENGTH: 126
<212> TYPE: PRT
<213> ORGANISM: Artificial Sequence
<220> FEATURE:
<223> OTHER INFORMATION: YU100-E06

<400> SEQUENCE: 310

Gln Ser Ala Leu Thr Gln Pro Ala Ser Val Ser Gly Phe Pro Glu Gln
 1               5                  10                  15

Ser Ile Thr Ile Ser Cys Thr Gly Thr Ser Ser Asp Val Gly Gly Tyr
                 20                  25                  30

Asp Tyr Val Ser Trp Tyr Gln Gln His Pro Gly Lys Ala Pro Lys Leu
             35                  40                  45

Met Ile Tyr Asp Val Thr Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Pro Glu Asp Glu Ala Asp Tyr Tyr Cys Ser Ser Tyr Thr Ser Asn
                 85                  90                  95

Thr Thr Trp Val Phe Gly Gly Gly Thr Lys Leu Thr Val Leu Arg Gln
            100                 105                 110

Pro Lys Ala Ala Pro Ser Val Thr Leu Phe Pro Pro Ser Ser
            115                 120                 125

<210> SEQ ID NO 311
<211> LENGTH: 10
<212> TYPE: PRT
<213> ORGANISM: Artificial Sequence
<220> FEATURE:
<223> OTHER INFORMATION: YU100-E06 LC-CDR3

<400> SEQUENCE: 311

Ser Ser Tyr Thr Ser Asn Thr Thr Trp Val
 1               5                  10

<210> SEQ ID NO 312
<211> LENGTH: 110
<212> TYPE: PRT
<213> ORGANISM: Artificial Sequence
<220> FEATURE:
<223> OTHER INFORMATION: YU100-E07

<400> SEQUENCE: 312

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
                 20                  25                  30

Asp Tyr Val Ser Trp Tyr Gln Gln His Pro Gly Lys Ala Pro Glu Leu
             35                  40                  45

Met Ile Tyr Asp Val Thr Lys Arg Pro Ser Gly Val Ala Asp Arg Phe
 50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Arg
                85                  90                  95

Tyr Thr Trp Val Phe Gly Gly Gly Thr Lys Leu Thr Val Leu
            100                 105                 110

<210> SEQ ID NO 313
<211> LENGTH: 10
<212> TYPE: PRT
<213> ORGANISM: Artificial Sequence
<220> FEATURE:
<223> OTHER INFORMATION: YU100-E07 LC-CDR3

<400> SEQUENCE: 313

Cys Ser Tyr Ala Gly Arg Tyr Thr Trp Val
1               5                   10

<210> SEQ ID NO 314
<211> LENGTH: 110
<212> TYPE: PRT
<213> ORGANISM: Artificial Sequence
<220> FEATURE:
<223> OTHER INFORMATION: YU100-E08

<400> SEQUENCE: 314

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Arg Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asn
                85                  90                  95

Tyr Thr Trp Met Phe Gly Gly Gly Thr Lys Leu Thr Val Leu
            100                 105                 110

<210> SEQ ID NO 315
<211> LENGTH: 10
<212> TYPE: PRT
<213> ORGANISM: Artificial Sequence
<220> FEATURE:
<223> OTHER INFORMATION: YU100-E08 LC-CDR3

<400> SEQUENCE: 315

Cys Ser Tyr Ala Gly Asn Tyr Thr Trp Met
1               5                   10

<210> SEQ ID NO 316
<211> LENGTH: 110
<212> TYPE: PRT
<213> ORGANISM: Artificial Sequence
<220> FEATURE:
<223> OTHER INFORMATION: YU100-E09

<400> SEQUENCE: 316

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Asp Tyr
            20                  25                  30

Asp Tyr Val Ser Trp Tyr Gln Gln His Pro Gly Lys Ala Pro Lys Leu
        35                  40                  45

Ile Ile Tyr Asp Val Thr Lys Arg Pro Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Arg Gly Thr Lys Leu Thr Val Leu
            100                 105                 110

<210> SEQ ID NO 317
<211> LENGTH: 9
<212> TYPE: PRT
<213> ORGANISM: Artificial Sequence
<220> FEATURE:
<223> OTHER INFORMATION: YU100-E09 LC-CDR1

<400> SEQUENCE: 317

Ser Ser Asp Val Gly Asp Tyr Asp Tyr
1               5

<210> SEQ ID NO 318
<211> LENGTH: 110
<212> TYPE: PRT
<213> ORGANISM: Artificial Sequence
<220> FEATURE:
<223> OTHER INFORMATION: YU100-E10

<400> SEQUENCE: 318

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Phe Asp Val Ser Gln Arg Pro Ser Gly Val Pro Asp Arg Phe
    50                  55                  60

Ser Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
            100                 105                 110

<210> SEQ ID NO 319
<211> LENGTH: 110
<212> TYPE: PRT
<213> ORGANISM: Artificial Sequence
<220> FEATURE:
<223> OTHER INFORMATION: YU100-E12

<400> SEQUENCE: 319

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Thr Ala Pro Lys Leu

```
                35                  40                  45
Met Ile Tyr Asp Val Ser Asn Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Thr Trp Val Phe Gly Gly Gly Thr Lys Leu Thr Val Leu
            100                 105                 110

<210> SEQ ID NO 320
<211> LENGTH: 10
<212> TYPE: PRT
<213> ORGANISM: Artificial Sequence
<220> FEATURE:
<223> OTHER INFORMATION: YU100-E12 LC-CDR3

<400> SEQUENCE: 320

Ser Ser Tyr Thr Ser Ser Thr Thr Trp Val
1               5                   10

<210> SEQ ID NO 321
<211> LENGTH: 110
<212> TYPE: PRT
<213> ORGANISM: Artificial Sequence
<220> FEATURE:
<223> OTHER INFORMATION: YU100-F01

<400> SEQUENCE: 321

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ala Tyr
            20                  25                  30

Asp Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Glu Tyr Tyr Cys Ser Ser Phe Ala Thr Ser
                85                  90                  95

Ile Ser Trp Val Phe Gly Gly Gly Thr Arg Leu Thr Val Leu
            100                 105                 110

<210> SEQ ID NO 322
<211> LENGTH: 9
<212> TYPE: PRT
<213> ORGANISM: Artificial Sequence
<220> FEATURE:
<223> OTHER INFORMATION: YU100-F01 LC-CDR1

<400> SEQUENCE: 322

Gly Ser Asp Val Gly Ala Tyr Asp Tyr
1               5

<210> SEQ ID NO 323
<211> LENGTH: 110
<212> TYPE: PRT
<213> ORGANISM: Artificial Sequence
<220> FEATURE:
<223> OTHER INFORMATION: YU100-F02
```

<400> SEQUENCE: 323

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Cys Ser Tyr Ala Gly Ser
                85                  90                  95

Tyr Thr Trp Ile Phe Gly Gly Gly Thr Lys Leu Thr Val Leu
            100                 105                 110

<210> SEQ ID NO 324
<211> LENGTH: 10
<212> TYPE: PRT
<213> ORGANISM: Artificial Sequence
<220> FEATURE:
<223> OTHER INFORMATION: YU100-F02 LC-CDR3

<400> SEQUENCE: 324

Cys Ser Tyr Ala Gly Ser Tyr Thr Trp Ile
1               5                   10

<210> SEQ ID NO 325
<211> LENGTH: 110
<212> TYPE: PRT
<213> ORGANISM: Artificial Sequence
<220> FEATURE:
<223> OTHER INFORMATION: YU100-F05

<400> SEQUENCE: 325

Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asn Tyr Val Ser Trp Tyr Gln Gln His Pro Gly Thr Ala Pro Lys Leu
        35                  40                  45

Met Ile Tyr Asp Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Met Thr Val Leu
            100                 105                 110

<210> SEQ ID NO 326
<211> LENGTH: 9
<212> TYPE: PRT
<213> ORGANISM: Artificial Sequence
<220> FEATURE:
<223> OTHER INFORMATION: YU100-F05 LC-CDR1

<400> SEQUENCE: 326

Ser Ser Asp Ile Gly Gly Tyr Asn Tyr
1               5

<210> SEQ ID NO 327
<211> LENGTH: 110
<212> TYPE: PRT
<213> ORGANISM: Artificial Sequence
<220> FEATURE:
<223> OTHER INFORMATION: YU100-F06

<400> SEQUENCE: 327

Gln Ser Ala Leu Thr Gln Pro Arg Ser Val Ser Gly Ser Pro Gly Gln
1               5                   10                  15

Ser Val Thr Ile Ser Cys Thr Gly Ser Ser Asp Val Gly Gly Tyr
            20                  25                  30

Asn Phe Val Ser Trp Tyr Arg Gln His Pro Gly Glu Ala Pro Lys Leu
        35                  40                  45

Val Ile Phe Asp Val Asn Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Phe Cys Cys Ser Tyr Ala Gly Gly
                85                  90                  95

Tyr Thr Trp Val Phe Gly Gly Gly Thr Lys Val Thr Val Val
            100                 105                 110

<210> SEQ ID NO 328
<211> LENGTH: 110
<212> TYPE: PRT
<213> ORGANISM: Artificial Sequence
<220> FEATURE:
<223> OTHER INFORMATION: YU100-F07

<400> SEQUENCE: 328

Gln Ser Ala Leu Thr Gln Pro Arg Ser Val Ser Val Ser Pro Gly Gln
1               5                   10                  15

Ser Val Thr Ile Ser Cys Thr Gly Thr Ser Ser Asp Val Gly Gly Tyr
            20                  25                  30

Glu Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Gly Glu Asp Ala Ala Asp Tyr Tyr Cys Cys Ser Tyr Ala Gly Ser
                85                  90                  95

Tyr Thr Trp Val Phe Gly Gly Gly Thr Thr Val Thr Val Leu
            100                 105                 110

<210> SEQ ID NO 329
<211> LENGTH: 110
<212> TYPE: PRT
<213> ORGANISM: Artificial Sequence
<220> FEATURE:
<223> OTHER INFORMATION: YU100-F11

<400> SEQUENCE: 329

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ala Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Trp Val Phe Gly Gly Gly Thr Gln Leu Thr Val Leu
            100                 105                 110

<210> SEQ ID NO 330
<211> LENGTH: 9
<212> TYPE: PRT
<213> ORGANISM: Artificial Sequence
<220> FEATURE:
<223> OTHER INFORMATION: YU100-F11 LC-CDR1

<400> SEQUENCE: 330

Ser Ser Asp Val Ala Gly Tyr Asn Tyr
 1               5

<210> SEQ ID NO 331
<211> LENGTH: 110
<212> TYPE: PRT
<213> ORGANISM: Artificial Sequence
<220> FEATURE:
<223> OTHER INFORMATION: YU100-G01

<400> SEQUENCE: 331

Gln Ser Ala Leu Thr Gln Pro Arg Ser Val Ser Ala Ser Pro Gly Gln
 1               5                  10                  15

Ser Val Thr Ile Ser Cys Thr Gly Thr Ser Ser Asp Val Gly Ala Tyr
                 20                  25                  30

Asn Tyr Val Ser Trp Tyr Gln Gln His Pro Gly Lys Ala Pro Lys Leu
            35                  40                  45

Met Leu Tyr Asp Val Asn Lys Arg Pro Ser Gly Val Pro Asp Arg Phe
 50                  55                  60

Ser Gly Ser Lys Ser Gly Asn Thr Ala Ser Leu Thr Ile Ser Arg Leu
 65                  70                  75                  80

Gln Ala Glu Asp Glu Ala Asp Tyr Tyr Cys Cys Ser Tyr Ala Gly Ser
                 85                  90                  95

Tyr Thr Trp Val Phe Gly Gly Gly Thr Lys Leu Thr Val Leu
            100                 105                 110

<210> SEQ ID NO 332
<211> LENGTH: 110
<212> TYPE: PRT
<213> ORGANISM: Artificial Sequence
<220> FEATURE:
<223> OTHER INFORMATION: YU100-G07

<400> SEQUENCE: 332

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ala Tyr
                 20                  25                  30

Asp Tyr Val Ser Trp Tyr Gln Gln His Pro Gly Lys Ala Pro Lys Leu
            35                  40                  45

Met Ile Tyr Asp Val Thr Asn Arg Pro Ser Gly Val Ser Asn Arg Phe

```
                50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Thr Arg Ser
                 85                  90                  95

Ser Val Trp Val Phe Gly Gly Gly Thr Lys Leu Thr Val Leu
                100                 105                 110

<210> SEQ ID NO 333
<211> LENGTH: 9
<212> TYPE: PRT
<213> ORGANISM: Artificial Sequence
<220> FEATURE:
<223> OTHER INFORMATION: YU100-G07 LC-CDR1

<400> SEQUENCE: 333

Ser Ser Asp Val Gly Ala Tyr Asp Tyr
 1               5

<210> SEQ ID NO 334
<211> LENGTH: 10
<212> TYPE: PRT
<213> ORGANISM: Artificial Sequence
<220> FEATURE:
<223> OTHER INFORMATION: YU100-G07 LC-CDR3

<400> SEQUENCE: 334

Ala Ser Tyr Thr Arg Ser Ser Val Trp Val
 1               5                  10

<210> SEQ ID NO 335
<211> LENGTH: 110
<212> TYPE: PRT
<213> ORGANISM: Artificial Sequence
<220> FEATURE:
<223> OTHER INFORMATION: YU100-G08

<400> SEQUENCE: 335

Gln Ser Ala Leu Thr Gln Pro Arg Ser Val Ser Gly Ser Pro Gly Gln
 1               5                  10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
                35                  40                  45

Met Ile Phe Asp Val Asn Glu Arg Ser Ser Gly Val Pro Asp Arg Phe
             50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Arg
                 85                  90                  95

Tyr Thr Trp Met Phe Gly Gly Gly Thr Lys Val Thr Val Leu
                100                 105                 110

<210> SEQ ID NO 336
<211> LENGTH: 10
<212> TYPE: PRT
<213> ORGANISM: Artificial Sequence
<220> FEATURE:
<223> OTHER INFORMATION: YU100-G08 LC-CDR3

<400> SEQUENCE: 336

Cys Ser Tyr Ala Gly Arg Tyr Thr Trp Met
```

```
<210> SEQ ID NO 337
<211> LENGTH: 110
<212> TYPE: PRT
<213> ORGANISM: Artificial Sequence
<220> FEATURE:
<223> OTHER INFORMATION: YU100-G09

<400> SEQUENCE: 337

Gln Ser Ala Leu Thr Gln Pro Arg Ser Val Ser Gly Ser Pro Gly Gln
1               5                   10                  15

Ser Val Thr Ile Ser Cys Thr Gly Thr Ile Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Gly Tyr Tyr Cys Ser Ser Tyr Ala Gly Ser
                85                  90                  95

Tyr Thr Trp Val Phe Gly Gly Gly Thr Lys Leu Thr Val Leu
            100                 105                 110

<210> SEQ ID NO 338
<211> LENGTH: 110
<212> TYPE: PRT
<213> ORGANISM: Artificial Sequence
<220> FEATURE:
<223> OTHER INFORMATION: YU100-G10

<400> SEQUENCE: 338

Gln Ser Ala Leu Thr Gln Pro Ala Ser Val Ser Gly Ser Leu Gly Gln
1               5                   10                  15

Ser Ile Thr Met Ser Cys Thr Gly Thr Arg Arg Asp Val Gly Gly Tyr
            20                  25                  30

Asp Phe Val Ser Trp Tyr Gln Gln Tyr Pro Gly Lys Ala Pro Lys Leu
        35                  40                  45

Ile Ile Tyr Asp Val Ser Asn Arg Pro Ser Gly Val Ser Asn Arg Phe
    50                  55                  60

Thr Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Thr
                85                  90                  95

Tyr Thr Trp Val Phe Gly Gly Gly Thr Lys Val Thr Val Leu
            100                 105                 110

<210> SEQ ID NO 339
<211> LENGTH: 9
<212> TYPE: PRT
<213> ORGANISM: Artificial Sequence
<220> FEATURE:
<223> OTHER INFORMATION: YU100-G10 LC-CDR1

<400> SEQUENCE: 339

Arg Arg Asp Val Gly Gly Tyr Asp Phe
1               5

<210> SEQ ID NO 340
```

<211> LENGTH: 10
<212> TYPE: PRT
<213> ORGANISM: Artificial Sequence
<220> FEATURE:
<223> OTHER INFORMATION: YU100-G10 LC-CDR3

<400> SEQUENCE: 340

Cys Ser Tyr Ala Gly Thr Tyr Thr Trp Val
1               5                   10

<210> SEQ ID NO 341
<211> LENGTH: 110
<212> TYPE: PRT
<213> ORGANISM: Artificial Sequence
<220> FEATURE:
<223> OTHER INFORMATION: YU100-G11

<400> SEQUENCE: 341

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Thr Leu Tyr Asp Val Gly Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Gly
                85                  90                  95

Tyr Thr Trp Val Phe Gly Gly Gly Thr Lys Val Thr Val Val
            100                 105                 110

<210> SEQ ID NO 342
<211> LENGTH: 110
<212> TYPE: PRT
<213> ORGANISM: Artificial Sequence
<220> FEATURE:
<223> OTHER INFORMATION: YU100-H01

<400> SEQUENCE: 342

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
            100                 105                 110

<210> SEQ ID NO 343
<211> LENGTH: 110
<212> TYPE: PRT
<213> ORGANISM: Artificial Sequence
<220> FEATURE:

<223> OTHER INFORMATION: YU100-H02

<400> SEQUENCE: 343

Gln Ser Ala Leu Thr Gln Pro Arg Ser Val Ser Arg Ser Pro Gly Gln
1               5                   10                  15

Ser Val Thr Ile Ser Cys Thr Gly Thr Ser Ser Asp Val Gly Thr Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Phe
                85                  90                  95

Tyr Thr Trp Val Phe Gly Gly Gly Thr Lys Leu Thr Val Leu
            100                 105                 110

<210> SEQ ID NO 344
<211> LENGTH: 9
<212> TYPE: PRT
<213> ORGANISM: Artificial Sequence
<220> FEATURE:
<223> OTHER INFORMATION: YU100-H02 LC-CDR1

<400> SEQUENCE: 344

Ser Ser Asp Val Gly Thr Tyr Asn Tyr
1               5

<210> SEQ ID NO 345
<211> LENGTH: 10
<212> TYPE: PRT
<213> ORGANISM: Artificial Sequence
<220> FEATURE:
<223> OTHER INFORMATION: YU100-H02 LC-CDR3

<400> SEQUENCE: 345

Cys Ser Tyr Ala Gly Phe Tyr Thr Trp Val
1               5                   10

<210> SEQ ID NO 346
<211> LENGTH: 110
<212> TYPE: PRT
<213> ORGANISM: Artificial Sequence
<220> FEATURE:
<223> OTHER INFORMATION: YU100-H04

<400> SEQUENCE: 346

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Val Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu
              100                 105                 110

<210> SEQ ID NO 347
<211> LENGTH: 9
<212> TYPE: PRT
<213> ORGANISM: Artificial Sequence
<220> FEATURE:
<223> OTHER INFORMATION: YU100-H04 LC-CDR1

<400> SEQUENCE: 347

Ser Ser Asp Ile Gly Val Tyr Asn Tyr
1               5

<210> SEQ ID NO 348
<211> LENGTH: 110
<212> TYPE: PRT
<213> ORGANISM: Artificial Sequence
<220> FEATURE:
<223> OTHER INFORMATION: YU100-H05

<400> SEQUENCE: 348

Gln Ala Val Leu Thr Gln Pro Arg Ser Val Ser Gly Ser Pro Gly Gln
1               5                   10                  15

Ser Ile Thr Ile Ser Cys Thr Gly Thr Gly Ser Asn Val Gly Gly Tyr
                20                  25                  30

Asn Tyr Val Ser Trp Tyr Gln Gln His Pro Gly Gln Ala Pro Lys Leu
            35                  40                  45

Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Thr
                85                  90                  95

Tyr Thr Trp Val Phe Gly Gly Gly Thr Lys Leu Thr Val Leu
              100                 105                 110

<210> SEQ ID NO 349
<211> LENGTH: 9
<212> TYPE: PRT
<213> ORGANISM: Artificial Sequence
<220> FEATURE:
<223> OTHER INFORMATION: YU100-H05 LC-CDR1

<400> SEQUENCE: 349

Gly Ser Asn Val Gly Gly Tyr Asn Tyr
1               5

<210> SEQ ID NO 350
<211> LENGTH: 110
<212> TYPE: PRT
<213> ORGANISM: Artificial Sequence
<220> FEATURE:
<223> OTHER INFORMATION: YU100-H09

<400> SEQUENCE: 350

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Trp Val Phe Gly Gly Gly Thr Lys Leu Thr Val Leu
            100                 105                 110

<210> SEQ ID NO 351
<211> LENGTH: 108
<212> TYPE: PRT
<213> ORGANISM: Artificial Sequence
<220> FEATURE:
<223> OTHER INFORMATION: YU112-C03

<400> SEQUENCE: 351

Asp Ser Val Met Thr Gln Ser Pro Ser Leu Ser Ala Ser Val Gly
 1               5                  10                  15

Asp Arg Val Thr Ile Thr Cys Arg Ala Ser Gln Ala Ile Asn Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Ser Tyr Ser Thr Pro Ser
                 85                  90                  95

Trp Thr Phe Gly Gln Gly Thr Lys Val Glu Ile Lys
            100                 105

<210> SEQ ID NO 352
<211> LENGTH: 6
<212> TYPE: PRT
<213> ORGANISM: Artificial Sequence
<220> FEATURE:
<223> OTHER INFORMATION: YU112-C03 LC-CDR1

<400> SEQUENCE: 352

Gln Ala Ile Asn Ser Tyr
 1               5

<210> SEQ ID NO 353
<211> LENGTH: 110
<212> TYPE: PRT
<213> ORGANISM: Artificial Sequence
<220> FEATURE:
<223> OTHER INFORMATION: YU100-C11

<400> SEQUENCE: 353

Gln Ser Ala Leu Thr Gln Pro Ala Ser Val Ser Gly Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln Arg Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu

```
                65                  70                  75                  80
Gln Pro Asp Asp Glu Ala Asp Tyr Tyr Cys Ser Ser Tyr Thr Asn Ser
                    85                  90                  95
Arg Thr Trp Val Phe Gly Gly Gly Thr Lys Leu Thr Val Leu
            100                 105                 110
```

<210> SEQ ID NO 354
<211> LENGTH: 10
<212> TYPE: PRT
<213> ORGANISM: Artificial Sequence
<220> FEATURE:
<223> OTHER INFORMATION: YU112-C03 LC-CDR3

<400> SEQUENCE: 354

```
Gln Gln Ser Tyr Ser Thr Pro Ser Trp Thr
1               5                   10
```

<210> SEQ ID NO 355
<211> LENGTH: 109
<212> TYPE: PRT
<213> ORGANISM: Artificial Sequence
<220> FEATURE:
<223> OTHER INFORMATION: YU112-C09

<400> SEQUENCE: 355

```
Glu Thr Thr Leu Thr Gln Ser Pro Ala Thr Leu Ser Val Ser Pro Gly
1               5                   10                  15
Glu Arg Ala Thr Leu Ser Cys Arg Ala Ser Gln Ser Phe Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Arg Arg Ala Pro Gly Ile Pro Asp Arg Phe Ser
    50                  55                  60
Gly Ser Gly Ser Gly Thr Asp Phe Ser Leu Thr Ile Ser Arg Leu Glu
65                  70                  75                  80
Pro Glu Asp Phe Ala Val Tyr Tyr Cys Gln Gln Ser Ser Thr Ser Pro
                85                  90                  95
Thr Trp Ala Phe Gly Arg Gly Thr Lys Val Glu Val Lys
            100                 105
```

<210> SEQ ID NO 356
<211> LENGTH: 7
<212> TYPE: PRT
<213> ORGANISM: Artificial Sequence
<220> FEATURE:
<223> OTHER INFORMATION: YU112-C09 LC-CDR1

<400> SEQUENCE: 356

```
Gln Ser Phe Ser Ser Ser Tyr
1               5
```

<210> SEQ ID NO 357
<211> LENGTH: 10
<212> TYPE: PRT
<213> ORGANISM: Artificial Sequence
<220> FEATURE:
<223> OTHER INFORMATION: YU112-C09 LC-CDR2

<400> SEQUENCE: 357

```
Gln Gln Ser Ser Thr Ser Pro Thr Trp Ala
1               5                   10
```

-continued

```
<210> SEQ ID NO 358
<211> LENGTH: 109
<212> TYPE: PRT
<213> ORGANISM: Artificial Sequence
<220> FEATURE:
<223> OTHER INFORMATION: YU112-E07

<400> SEQUENCE: 358

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asn Ser Ala
                20                  25                  30

Tyr Leu Ala Trp Tyr Gln His Lys Pro Gly Gln Pro Arg Leu Leu
            35                  40                  45

Ile Tyr Gly Ala Ser Arg Arg Val Thr Gly Val Pro Asp Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Asp Pro
                85                  90                  95

Arg Trp Thr Phe Gly Gln Gly Thr Lys Val Glu Ile Lys
            100                 105

<210> SEQ ID NO 359
<211> LENGTH: 7
<212> TYPE: PRT
<213> ORGANISM: Artificial Sequence
<220> FEATURE:
<223> OTHER INFORMATION: YU112-E07 LC-CDR1

<400> SEQUENCE: 359

Gln Ser Val Asn Ser Ala Tyr
1               5

<210> SEQ ID NO 360
<211> LENGTH: 10
<212> TYPE: PRT
<213> ORGANISM: Artificial Sequence
<220> FEATURE:
<223> OTHER INFORMATION: YU112-E07 LC-CDR3

<400> SEQUENCE: 360

Gln Gln Ser Tyr Ser Asp Pro Arg Trp Thr
1               5                   10

<210> SEQ ID NO 361
<211> LENGTH: 110
<212> TYPE: PRT
<213> ORGANISM: Artificial Sequence
<220> FEATURE:
<223> OTHER INFORMATION: YU112-F05

<400> SEQUENCE: 361

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Ile Ile Tyr Asp Val Asn Asn Arg Pro Ser Gly Val Ser Asn Arg Phe
        50                  55                  60

Ser Ala Ser Lys Ser Gly Asn Thr Ala Ser Leu Thr Ile Ser Gly Leu
```

```
                65                  70                  75                  80
Gln Ala Glu Asp Glu Ala Asp Tyr Tyr Cys Asn Ser Tyr Thr Ser Gly
                    85                  90                  95

Ser Thr Trp Val Phe Gly Gly Gly Thr Lys Leu Thr Val Leu
            100                 105                 110

<210> SEQ ID NO 362
<211> LENGTH: 10
<212> TYPE: PRT
<213> ORGANISM: Artificial Sequence
<220> FEATURE:
<223> OTHER INFORMATION: YU112-F05 LC-CDR3

<400> SEQUENCE: 362

Asn Ser Tyr Thr Ser Gly Ser Thr Trp Val
1               5                   10

<210> SEQ ID NO 363
<211> LENGTH: 110
<212> TYPE: PRT
<213> ORGANISM: Artificial Sequence
<220> FEATURE:
<223> OTHER INFORMATION: YU112-G06

<400> SEQUENCE: 363

Gln Ser Ala Leu Thr Gln Pro Arg Ser Val Ser Gly Ser Pro Gly Gln
1               5                   10                  15

Ser Val Thr Ile Ser Cys Thr Gly Thr Ile Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Arg Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Gly Tyr Tyr Cys Ser Ser Tyr Ala Gly Gly
                85                  90                  95

Tyr Thr Trp Val Phe Gly Gly Gly Thr Glu Leu Thr Val Leu
            100                 105                 110

<210> SEQ ID NO 364
<211> LENGTH: 10
<212> TYPE: PRT
<213> ORGANISM: Artificial Sequence
<220> FEATURE:
<223> OTHER INFORMATION: YU112-G06 LC-CDR3

<400> SEQUENCE: 364

Ser Ser Tyr Ala Gly Gly Tyr Thr Trp Val
1               5                   10

<210> SEQ ID NO 365
<211> LENGTH: 97
<212> TYPE: PRT
<213> ORGANISM: Artificial Sequence
<220> FEATURE:
<223> OTHER INFORMATION: YU112-G09

<400> SEQUENCE: 365

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Ile Ile Ser Ser Tyr
```

-continued

```
                20                  25                  30
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Gly Arg Phe Cys Asn Leu Leu Leu Ser Thr Glu Leu Gln Tyr Pro His
                85                  90                  95

Val

<210> SEQ ID NO 366
<211> LENGTH: 109
<212> TYPE: PRT
<213> ORGANISM: Artificial Sequence
<220> FEATURE:
<223> OTHER INFORMATION: YU112-H01

<400> SEQUENCE: 366

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Ser Leu Gln
65                  70                  75                  80

Pro Asp Asp Phe Ala Thr Tyr Tyr Cys Gln Gln Ser Tyr Ser Thr Pro
                85                  90                  95

Thr Trp Thr Phe Gly Gln Gly Thr Lys Val Glu Ile Lys
            100                 105

<210> SEQ ID NO 367
<211> LENGTH: 7
<212> TYPE: PRT
<213> ORGANISM: Artificial Sequence
<220> FEATURE:
<223> OTHER INFORMATION: YU112-H01 LC-CDR1

<400> SEQUENCE: 367

Gln Ser Val Ser Ser Ser Tyr
1               5

<210> SEQ ID NO 368
<211> LENGTH: 118
<212> TYPE: PRT
<213> ORGANISM: Artificial Sequence
<220> FEATURE:
<223> OTHER INFORMATION: YU100-A11

<400> SEQUENCE: 368

Glu Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45
```

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
            115

<210> SEQ ID NO 369
<211> LENGTH: 118
<212> TYPE: PRT
<213> ORGANISM: Artificial Sequence
<220> FEATURE:
<223> OTHER INFORMATION: YU100-A12

<400> SEQUENCE: 369

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
            115

<210> SEQ ID NO 370
<211> LENGTH: 118
<212> TYPE: PRT
<213> ORGANISM: Artificial Sequence
<220> FEATURE:
<223> OTHER INFORMATION: YU100-B01

<400> SEQUENCE: 370

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 371
<211> LENGTH: 118
<212> TYPE: PRT
<213> ORGANISM: Artificial Sequence
<220> FEATURE:
<223> OTHER INFORMATION: YU100-B06

<400> SEQUENCE: 371

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 372
<211> LENGTH: 118
<212> TYPE: PRT
<213> ORGANISM: Artificial Sequence
<220> FEATURE:
<223> OTHER INFORMATION: YU100-B08

<400> SEQUENCE: 372

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 373
<211> LENGTH: 123
<212> TYPE: PRT
<213> ORGANISM: Artificial Sequence
<220> FEATURE:
<223> OTHER INFORMATION: YU100-B12

<400> SEQUENCE: 373

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
            115                 120

<210> SEQ ID NO 374
<211> LENGTH: 118
<212> TYPE: PRT
<213> ORGANISM: Artificial Sequence
<220> FEATURE:
<223> OTHER INFORMATION: YU100-C10

<400> SEQUENCE: 374

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Ile Thr Val Ser Ser
            115

<210> SEQ ID NO 375
<211> LENGTH: 123
<212> TYPE: PRT
<213> ORGANISM: Artificial Sequence
<220> FEATURE:
<223> OTHER INFORMATION: YU100-C12

<400> SEQUENCE: 375

Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
            115                 120
```

<210> SEQ ID NO 376
<211> LENGTH: 123
<212> TYPE: PRT
<213> ORGANISM: Artificial Sequence
<220> FEATURE:
<223> OTHER INFORMATION: YU100-D01

<400> SEQUENCE: 376

```
Gln Val Gln Leu Gln Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
            115                 120
```

<210> SEQ ID NO 377
<211> LENGTH: 118
<212> TYPE: PRT
<213> ORGANISM: Artificial Sequence
<220> FEATURE:
<223> OTHER INFORMATION: YU100-D02

<400> SEQUENCE: 377

```
Gln Val Arg Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
```

Leu Val Thr Val Ser Ser
115

<210> SEQ ID NO 378
<211> LENGTH: 118
<212> TYPE: PRT
<213> ORGANISM: Artificial Sequence
<220> FEATURE:
<223> OTHER INFORMATION: YU100-D05

<400> SEQUENCE: 378

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 379
<211> LENGTH: 123
<212> TYPE: PRT
<213> ORGANISM: Artificial Sequence
<220> FEATURE:
<223> OTHER INFORMATION: YU100-D07

<400> SEQUENCE: 379

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
        115                 120

<210> SEQ ID NO 380
<211> LENGTH: 118
<212> TYPE: PRT
<213> ORGANISM: Artificial Sequence
<220> FEATURE:

<223> OTHER INFORMATION: YU100-E07

<400> SEQUENCE: 380

Gln Val Gln Leu Gln Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
            115

<210> SEQ ID NO 381
<211> LENGTH: 8
<212> TYPE: PRT
<213> ORGANISM: Artificial Sequence
<220> FEATURE:
<223> OTHER INFORMATION: YU100-E07 LC-CDR2

<400> SEQUENCE: 381

Ile Ser Tyr Asp Gly Ser Asn Arg
1               5

<210> SEQ ID NO 382
<211> LENGTH: 123
<212> TYPE: PRT
<213> ORGANISM: Artificial Sequence
<220> FEATURE:
<223> OTHER INFORMATION: YU100-E08

<400> SEQUENCE: 382

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
            115                 120

<210> SEQ ID NO 383
<211> LENGTH: 123
<212> TYPE: PRT

<213> ORGANISM: Artificial Sequence
<220> FEATURE:
<223> OTHER INFORMATION: YU100-E09

<400> SEQUENCE: 383

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Asp Tyr
            100                 105                 110

Trp Gly Gln Gly Thr Leu Val Thr Val Ser Ser
        115                 120

<210> SEQ ID NO 384
<211> LENGTH: 123
<212> TYPE: PRT
<213> ORGANISM: Artificial Sequence
<220> FEATURE:
<223> OTHER INFORMATION: YU100-E11

<400> SEQUENCE: 384

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Asp Tyr
            100                 105                 110

Trp Gly Gln Gly Thr Leu Val Thr Val Ser Ser
        115                 120

<210> SEQ ID NO 385
<211> LENGTH: 123
<212> TYPE: PRT
<213> ORGANISM: Artificial Sequence
<220> FEATURE:
<223> OTHER INFORMATION: YU100-H02

<400> SEQUENCE: 385

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser
            115                 120

<210> SEQ ID NO 386
<211> LENGTH: 118
<212> TYPE: PRT
<213> ORGANISM: Artificial Sequence
<220> FEATURE:
<223> OTHER INFORMATION: YU112-A07

<400> SEQUENCE: 386

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Thr Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
            115

<210> SEQ ID NO 387
<211> LENGTH: 119
<212> TYPE: PRT
<213> ORGANISM: Artificial Sequence
<220> FEATURE:
<223> OTHER INFORMATION: YU112-C03

<400> SEQUENCE: 387

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                 85                  90                  95
Ala Lys Gly Gly Lys Ser Tyr Tyr Gly Phe Asp Tyr Trp Gly Gln Gly
            100                 105                 110

Thr Leu Val Thr Val Ser Ser
        115

<210> SEQ ID NO 388
<211> LENGTH: 116
<212> TYPE: PRT
<213> ORGANISM: Artificial Sequence
<220> FEATURE:
<223> OTHER INFORMATION: YU112-C09

<400> SEQUENCE: 388

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Tyr Tyr Phe Asp Tyr Trp Gly Gln Gly Thr Leu Val
            100                 105                 110

Thr Val Ser Ser
        115

<210> SEQ ID NO 389
<211> LENGTH: 118
<212> TYPE: PRT
<213> ORGANISM: Artificial Sequence
<220> FEATURE:
<223> OTHER INFORMATION: YU112-D08

<400> SEQUENCE: 389

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 390
<211> LENGTH: 118
```

```
<212> TYPE: PRT
<213> ORGANISM: Artificial Sequence
<220> FEATURE:
<223> OTHER INFORMATION: YU112-F05

<400> SEQUENCE: 390

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 391
<211> LENGTH: 118
<212> TYPE: PRT
<213> ORGANISM: Artificial Sequence
<220> FEATURE:
<223> OTHER INFORMATION: YU112-G06

<400> SEQUENCE: 391

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser
        115

<210> SEQ ID NO 392
<211> LENGTH: 116
<212> TYPE: PRT
<213> ORGANISM: Artificial Sequence
<220> FEATURE:
<223> OTHER INFORMATION: YU112-H01

<400> SEQUENCE: 392

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
```

```
                20                  25                  30
Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Tyr Tyr Phe Asp Tyr Trp Gly Gln Gly Thr Leu Val
            100                 105                 110

Thr Val Ser Ser
        115

<210> SEQ ID NO 393
<211> LENGTH: 9
<212> TYPE: PRT
<213> ORGANISM: Artificial Sequence
<220> FEATURE:
<223> OTHER INFORMATION: matLC-CDR1-1 Family consensus
<220> FEATURE:
<221> NAME/KEY: MISC_FEATURE
<222> LOCATION: (1)..(1)
<223> OTHER INFORMATION: X = S, N or I
<220> FEATURE:
<221> NAME/KEY: MISC_FEATURE
<222> LOCATION: (2)..(2)
<223> OTHER INFORMATION: X = S or R
<220> FEATURE:
<221> NAME/KEY: MISC_FEATURE
<222> LOCATION: (8)..(8)
<223> OTHER INFORMATION: X = N, E or D
<220> FEATURE:
<221> NAME/KEY: MISC_FEATURE
<222> LOCATION: (9)..(9)
<223> OTHER INFORMATION: X = Y or F

<400> SEQUENCE: 393

Xaa Xaa Asp Val Gly Gly Tyr Xaa Xaa
1               5

<210> SEQ ID NO 394
<211> LENGTH: 9
<212> TYPE: PRT
<213> ORGANISM: Artificial Sequence
<220> FEATURE:
<223> OTHER INFORMATION: matLC-CDR1-2 Family consensus
<220> FEATURE:
<221> NAME/KEY: MISC_FEATURE
<222> LOCATION: (5)..(5)
<223> OTHER INFORMATION: X = G or A
<220> FEATURE:
<221> NAME/KEY: MISC_FEATURE
<222> LOCATION: (6)..(6)
<223> OTHER INFORMATION: X = D, G or T
<220> FEATURE:
<221> NAME/KEY: MISC_FEATURE
<222> LOCATION: (8)..(8)
<223> OTHER INFORMATION: X = N or D

<400> SEQUENCE: 394

Ser Ser Asp Val Xaa Xaa Tyr Xaa Tyr
1               5

<210> SEQ ID NO 395
<211> LENGTH: 9
<212> TYPE: PRT
<213> ORGANISM: Artificial Sequence
```

```
<220> FEATURE:
<223> OTHER INFORMATION: matLC-CDR1-3 Family consensus
<220> FEATURE:
<221> NAME/KEY: MISC_FEATURE
<222> LOCATION: (1)..(1)
<223> OTHER INFORMATION: X = S or N
<220> FEATURE:
<221> NAME/KEY: MISC_FEATURE
<222> LOCATION: (2)..(2)
<223> OTHER INFORMATION: X = N, T or S
<220> FEATURE:
<221> NAME/KEY: MISC_FEATURE
<222> LOCATION: (4)..(4)
<223> OTHER INFORMATION: X = V or I

<400> SEQUENCE: 395

Xaa Xaa Asp Xaa Gly Ala Tyr Asn Tyr
1               5

<210> SEQ ID NO 396
<211> LENGTH: 9
<212> TYPE: PRT
<213> ORGANISM: Artificial Sequence
<220> FEATURE:
<223> OTHER INFORMATION: matLC-CDR1-4 Family consensus
<220> FEATURE:
<221> NAME/KEY: MISC_FEATURE
<222> LOCATION: (6)..(6)
<223> OTHER INFORMATION: X = V or G

<400> SEQUENCE: 396

Ser Ser Asp Ile Gly Xaa Tyr Asn Tyr
1               5

<210> SEQ ID NO 397
<211> LENGTH: 9
<212> TYPE: PRT
<213> ORGANISM: Artificial Sequence
<220> FEATURE:
<223> OTHER INFORMATION: matLC-CDR1-5 Family consensus
<220> FEATURE:
<221> NAME/KEY: MISC_FEATURE
<222> LOCATION: (1)..(1)
<223> OTHER INFORMATION: X = S or G

<400> SEQUENCE: 397

Xaa Ser Asp Val Gly Ala Tyr Asp Tyr
1               5

<210> SEQ ID NO 398
<211> LENGTH: 9
<212> TYPE: PRT
<213> ORGANISM: Artificial Sequence
<220> FEATURE:
<223> OTHER INFORMATION: matLC-CDR1-6 Family consensus
<220> FEATURE:
<221> NAME/KEY: MISC_FEATURE
<222> LOCATION: (8)..(8)
<223> OTHER INFORMATION: X = N or D

<400> SEQUENCE: 398

Ser Gly Asp Val Gly Thr Tyr Xaa Tyr
1               5

<210> SEQ ID NO 399
<211> LENGTH: 6
<212> TYPE: PRT
<213> ORGANISM: Artificial Sequence
<220> FEATURE:
<223> OTHER INFORMATION: matLC-CDR1-7 Family consensus
<220> FEATURE:
```

```
<221> NAME/KEY: MISC_FEATURE
<222> LOCATION: (2)..(2)
<223> OTHER INFORMATION: X = A or I
<220> FEATURE:
<221> NAME/KEY: MISC_FEATURE
<222> LOCATION: (4)..(4)
<223> OTHER INFORMATION: X = N or S

<400> SEQUENCE: 399

Gln Xaa Ile Xaa Ser Tyr
1               5

<210> SEQ ID NO 400
<211> LENGTH: 7
<212> TYPE: PRT
<213> ORGANISM: Artificial Sequence
<220> FEATURE:
<223> OTHER INFORMATION: matLC-CDR1-8 Family consensus
<220> FEATURE:
<221> NAME/KEY: MISC_FEATURE
<222> LOCATION: (3)..(3)
<223> OTHER INFORMATION: X = F or V

<400> SEQUENCE: 400

Gln Ser Xaa Ser Ser Ser Tyr
1               5

<210> SEQ ID NO 401
<211> LENGTH: 9
<212> TYPE: PRT
<213> ORGANISM: Artificial Sequence
<220> FEATURE:
<223> OTHER INFORMATION: matLC-CDR1-9 Family consensus
<220> FEATURE:
<221> NAME/KEY: MISC_FEATURE
<222> LOCATION: (2)..(2)
<223> OTHER INFORMATION: X = S or R
<220> FEATURE:
<221> NAME/KEY: MISC_FEATURE
<222> LOCATION: (4)..(4)
<223> OTHER INFORMATION: X = I or V
<220> FEATURE:
<221> NAME/KEY: MISC_FEATURE
<222> LOCATION: (9)..(9)
<223> OTHER INFORMATION: X = Y or F

<400> SEQUENCE: 401

Arg Xaa Asp Xaa Gly Gly Tyr Asp Xaa
1               5

<210> SEQ ID NO 402
<211> LENGTH: 3
<212> TYPE: PRT
<213> ORGANISM: Artificial Sequence
<220> FEATURE:
<223> OTHER INFORMATION: matLC-CDR2-1 Family consensus
<220> FEATURE:
<221> NAME/KEY: MISC_FEATURE
<222> LOCATION: (3)..(3)
<223> OTHER INFORMATION: X = S, T, N, G, V or D

<400> SEQUENCE: 402

Asp Val Xaa
1

<210> SEQ ID NO 403
<211> LENGTH: 3
<212> TYPE: PRT
<213> ORGANISM: Artificial Sequence
<220> FEATURE:
<223> OTHER INFORMATION: matLC-CDR2-2 Family consensus
```

```
<220> FEATURE:
<221> NAME/KEY: MISC_FEATURE
<222> LOCATION: (1)..(1)
<223> OTHER INFORMATION: X = A or G

<400> SEQUENCE: 403

Xaa Ala Ser
1

<210> SEQ ID NO 404
<211> LENGTH: 10
<212> TYPE: PRT
<213> ORGANISM: Artificial Sequence
<220> FEATURE:
<223> OTHER INFORMATION: matLC-CDR3-1 Family consensus
<220> FEATURE:
<221> NAME/KEY: MISC_FEATURE
<222> LOCATION: (1)..(1)
<223> OTHER INFORMATION: X = C, S, A or N
<220> FEATURE:
<221> NAME/KEY: MISC_FEATURE
<222> LOCATION: (6)..(6)
<223> OTHER INFORMATION: X = S, R, N, G, T or F
<220> FEATURE:
<221> NAME/KEY: MISC_FEATURE
<222> LOCATION: (7)..(7)
<223> OTHER INFORMATION: X = Y or H
<220> FEATURE:
<221> NAME/KEY: MISC_FEATURE
<222> LOCATION: (8)..(8)
<223> OTHER INFORMATION: X = T, N, I, S or V
<220> FEATURE:
<221> NAME/KEY: MISC_FEATURE
<222> LOCATION: (10)..(10)
<223> OTHER INFORMATION: X = V, M or I

<400> SEQUENCE: 404

Xaa Ser Tyr Ala Gly Xaa Xaa Xaa Trp Xaa
1               5                   10

<210> SEQ ID NO 405
<211> LENGTH: 10
<212> TYPE: PRT
<213> ORGANISM: Artificial Sequence
<220> FEATURE:
<223> OTHER INFORMATION: matLC-CDR3-2 Family consensus
<220> FEATURE:
<221> NAME/KEY: MISC_FEATURE
<222> LOCATION: (5)..(5)
<223> OTHER INFORMATION: X = S or N
<220> FEATURE:
<221> NAME/KEY: MISC_FEATURE
<222> LOCATION: (6)..(6)
<223> OTHER INFORMATION: X = S or N
<220> FEATURE:
<221> NAME/KEY: MISC_FEATURE
<222> LOCATION: (7)..(7)
<223> OTHER INFORMATION: X = T, I, S or R
<220> FEATURE:
<221> NAME/KEY: MISC_FEATURE
<222> LOCATION: (8)..(8)
<223> OTHER INFORMATION: X = T or S

<400> SEQUENCE: 405

Ser Ser Tyr Thr Xaa Xaa Xaa Xaa Trp Val
1               5                   10

<210> SEQ ID NO 406
<211> LENGTH: 10
<212> TYPE: PRT
<213> ORGANISM: Artificial Sequence
<220> FEATURE:
<223> OTHER INFORMATION: matLC-CDR3-3 Family consensus
```

```
<220> FEATURE:
<221> NAME/KEY: MISC_FEATURE
<222> LOCATION: (6)..(6)
<223> OTHER INFORMATION: X = T or D
<220> FEATURE:
<221> NAME/KEY: MISC_FEATURE
<222> LOCATION: (8)..(8)
<223> OTHER INFORMATION: X = S, R or T

<400> SEQUENCE: 406

Gln Gln Ser Tyr Ser Xaa Pro Xaa Trp Thr
1               5                   10

<210> SEQ ID NO 407
<211> LENGTH: 10
<212> TYPE: PRT
<213> ORGANISM: Artificial Sequence
<220> FEATURE:
<223> OTHER INFORMATION: matLC-CDR3-4 Family consensus
<220> FEATURE:
<221> NAME/KEY: MISC_FEATURE
<222> LOCATION: (4)..(4)
<223> OTHER INFORMATION: X = T or A
<220> FEATURE:
<221> NAME/KEY: MISC_FEATURE
<222> LOCATION: (5)..(5)
<223> OTHER INFORMATION: X = T or S
<220> FEATURE:
<221> NAME/KEY: MISC_FEATURE
<222> LOCATION: (7)..(7)
<223> OTHER INFORMATION: X = I or T
<220> FEATURE:
<221> NAME/KEY: MISC_FEATURE
<222> LOCATION: (8)..(8)
<223> OTHER INFORMATION: X = A or T

<400> SEQUENCE: 407

Ser Ser Phe Xaa Xaa Ser Xaa Xaa Trp Val
1               5                   10

<210> SEQ ID NO 408
<211> LENGTH: 10
<212> TYPE: PRT
<213> ORGANISM: Artificial Sequence
<220> FEATURE:
<223> OTHER INFORMATION: YU100-F01 LC-CDR3

<400> SEQUENCE: 408

Ser Ser Phe Ala Thr Ser Ile Ser Trp Val
1               5                   10

<210> SEQ ID NO 409
<211> LENGTH: 8
<212> TYPE: PRT
<213> ORGANISM: Artificial Sequence
<220> FEATURE:
<223> OTHER INFORMATION: matHC-CDR1-1 Family consensus
<220> FEATURE:
<221> NAME/KEY: MISC_FEATURE
<222> LOCATION: (5)..(5)
<223> OTHER INFORMATION: X = S or G
<220> FEATURE:
<221> NAME/KEY: MISC_FEATURE
<222> LOCATION: (8)..(8)
<223> OTHER INFORMATION: X = G or A

<400> SEQUENCE: 409

Gly Phe Thr Phe Xaa Ser Tyr Xaa
1               5

<210> SEQ ID NO 410
```

```
<211> LENGTH: 8
<212> TYPE: PRT
<213> ORGANISM: Artificial Sequence
<220> FEATURE:
<223> OTHER INFORMATION: matHC-CDR2-1 Family consensus
<220> FEATURE:
<221> NAME/KEY: MISC_FEATURE
<222> LOCATION: (8)..(8)
<223> OTHER INFORMATION: X = K or R

<400> SEQUENCE: 410

Ile Ser Tyr Asp Gly Ser Asn Xaa
1               5

<210> SEQ ID NO 411
<211> LENGTH: 12
<212> TYPE: PRT
<213> ORGANISM: Artificial Sequence
<220> FEATURE:
<223> OTHER INFORMATION: matHC-CDR3-4 Family consensus
<220> FEATURE:
<221> NAME/KEY: MISC_FEATURE
<222> LOCATION: (4)..(4)
<223> OTHER INFORMATION: X = absent or G
<220> FEATURE:
<221> NAME/KEY: MISC_FEATURE
<222> LOCATION: (5)..(5)
<223> OTHER INFORMATION: X = absent or K
<220> FEATURE:
<221> NAME/KEY: MISC_FEATURE
<222> LOCATION: (9)..(9)
<223> OTHER INFORMATION: X = absent or G

<400> SEQUENCE: 411

Ala Lys Gly Xaa Xaa Ser Tyr Tyr Xaa Phe Asp Tyr
1               5                   10

<210> SEQ ID NO 412
<211> LENGTH: 262
<212> TYPE: PRT
<213> ORGANISM: Artificial Sequence
<220> FEATURE:
<223> OTHER INFORMATION: YU100-A10

<400> SEQUENCE: 412

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Leu Pro Val Leu Thr Gln Pro Ala
    130                 135                 140

Ser Val Ser Gly Ser Pro Gly Gln Ser Ile Thr Ile Ser Cys Thr Gly
145                 150                 155                 160
```

```
Thr Ser Ser Asp Val Gly Ala Tyr Asn Tyr Val Ser Trp Tyr Gln Gln
                165                 170                 175

His Pro Gly Lys Ala Pro Glu Leu Met Ile Tyr Asp Val Ser Asn Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Pro Glu Asp Glu Ala Asp Tyr
    210                 215                 220

Tyr Cys Ser Ser Phe Thr Thr Ser Ile Ala Trp Val Phe Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 413
<211> LENGTH: 262
<212> TYPE: PRT
<213> ORGANISM: Artificial Sequence
<220> FEATURE:
<223> OTHER INFORMATION: YU100-A11

<400> SEQUENCE: 413

Glu Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Ser Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Thr Trp Val Phe Gly Gly
225                 230                 235                 240

Thr Lys Leu Thr Val Leu Gly Gln Pro Lys Ala Ala Pro Ser Val Thr
                245                 250                 255
```

Leu Phe Pro Pro Ser Ser
            260

<210> SEQ ID NO 414
<211> LENGTH: 262
<212> TYPE: PRT
<213> ORGANISM: Artificial Sequence
<220> FEATURE:
<223> OTHER INFORMATION: YU100-A12

<400> SEQUENCE: 414

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Leu Pro Val Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Ser Lys Arg
            180                 185                 190

Pro Ser Gly Val Pro Asp Arg Phe Ser Gly Ser Lys Ser Gly Asp Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Ala Gly Ser Tyr Thr Trp Val Phe Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 415
<211> LENGTH: 262
<212> TYPE: PRT
<213> ORGANISM: Artificial Sequence
<220> FEATURE:
<223> OTHER INFORMATION: YU100-B01

<400> SEQUENCE: 415

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Ile Gly Ala Thr Asp Pro Leu Asp Tyr Trp Gly Gln Gly Thr
            100                 105                 110
Leu Val Thr Val Ser Ser Gly Ser Ala Ser Ala Pro Lys Leu Glu Glu
        115                 120                 125
Gly Glu Phe Ser Glu Ala Arg Val Gln Ser Ala Leu Thr Gln Pro Arg
    130                 135                 140
Ser Val Ser Gly Ser Pro Gly Gln Ser Val Thr Ile Ser Cys Thr Gly
145                 150                 155                 160
Thr Asn Thr Asp Val Gly Ala Tyr Asn Tyr Val Ser Trp Tyr Gln Gln
                165                 170                 175
Tyr Pro Gly Lys Ala Pro Lys Leu Ile Ile Tyr Asp Val Ser Lys Arg
            180                 185                 190
Pro Ser Gly Val Pro Asp Arg Phe Ser Gly Ser Lys Ser Gly Asn Thr
        195                 200                 205
Ala Ser Leu Thr Ile Ser Gly Leu Gln Ala Glu Asp Glu Ala Asp Tyr
    210                 215                 220
Tyr Cys Cys Ser Tyr Ala Gly Ser Tyr Ser Trp Val Phe Gly Gly Gly
225                 230                 235                 240
Thr Lys Leu Thr Val Leu Gly Gln Pro Lys Ala Ala Pro Ser Val Thr
                245                 250                 255
Leu Phe Pro Pro Ser Ser
            260
```

<210> SEQ ID NO 416
<211> LENGTH: 262
<212> TYPE: PRT
<213> ORGANISM: Artificial Sequence
<220> FEATURE:
<223> OTHER INFORMATION: YU100-B03

<400> SEQUENCE: 416

```
Gln Val Gln Leu Val Gln Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Ile Gly Ala Thr Asp Pro Leu Asp Tyr Trp Gly Gln Gly Thr
            100                 105                 110
Leu Val Thr Val Ser Ser Gly Ser Ala Ser Ala Pro Lys Leu Glu Glu
```

```
                115                 120                 125
Gly Glu Phe Ser Glu Ala Arg Val Gln Ser Val Leu Thr Gln Pro Arg
            130                 135                 140
Ser Val Ser Gly Ser Pro Gly Arg Ser Val Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Leu Thr Leu Tyr Asp Val Val Lys Arg
            180                 185                 190
Pro Ser Gly Val Pro Asp Arg Tyr Ser Gly Ser Lys Ser Gly Asn Thr
            195                 200                 205
Ala Ser Leu Thr Ile Ser Gly Leu Gln Ala Glu Asp Glu Ala Asp Tyr
            210                 215                 220
Tyr Cys Cys Ser Tyr Ala Gly Gly Tyr Thr Trp Val Phe Gly Gly Gly
225                 230                 235                 240
Thr Lys Val Thr Val Gly Gln Pro Lys Ala Ala Pro Ser Val Thr
                245                 250                 255
Leu Phe Pro Pro Ser Ser
            260

<210> SEQ ID NO 417
<211> LENGTH: 262
<212> TYPE: PRT
<213> ORGANISM: Artificial Sequence
<220> FEATURE:
<223> OTHER INFORMATION: YU100-B06

<400> SEQUENCE: 417

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Ser Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Ile Gly Ala Thr Asp Pro Leu Asp Tyr Trp Gly Gln Gly Thr
            100                 105                 110
Leu Val Thr Val Ser Ser Gly Ser Ala Ser Ala Pro Lys Leu Glu Glu
        115                 120                 125
Gly Glu Phe Ser Glu Ala Arg Val Gln Ser Ala Leu Thr Gln Pro Ala
    130                 135                 140
Ser Val Ser Gly Ser Pro Gly Gln Ser Ile Thr Ile Ser Cys Thr Gly
145                 150                 155                 160
Thr Ser Ser Asp Val Gly Gly Tyr Asn Tyr Val Ser Trp Tyr Gln Gln
                165                 170                 175
His Pro Gly Lys Ala Pro Lys Leu Met Ile Tyr Asp Val Ser Lys Arg
            180                 185                 190
Pro Ser Gly Val Pro Asp Arg Phe Ser Gly Ser Lys Ser Gly Asn Thr
        195                 200                 205
Ala Ser Leu Thr Ile Ser Gly Leu Gln Ala Glu Asp Glu Ala Asp Tyr
```

```
            210                 215                 220
Tyr Cys Asn Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 418
<211> LENGTH: 262
<212> TYPE: PRT
<213> ORGANISM: Artificial Sequence
<220> FEATURE:
<223> OTHER INFORMATION: YU100-B07

<400> SEQUENCE: 418

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Met Ser Cys Thr Gly
145                 150                 155                 160

Thr Ser Arg Asp Val Gly Gly Tyr Asn Tyr Val Ser Trp Tyr Gln His
                165                 170                 175

His Pro Gly Lys Ala Pro Lys Leu Met Ile Tyr Asp Val Ser Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Glu Leu Gln Ala Glu Asp Glu Ala Asp Tyr
    210                 215                 220

Tyr Cys Cys Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 419
<211> LENGTH: 262
<212> TYPE: PRT
<213> ORGANISM: Artificial Sequence
<220> FEATURE:
<223> OTHER INFORMATION: YU100-B08
```

<400> SEQUENCE: 419

Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Val Pro Arg Leu Leu Ile Tyr Asp Val Ser Asn Arg
            180                 185                 190

Pro Ser Gly Val Ser Thr Arg Phe Ser Gly Ser Lys Ser Gly Asn Thr
        195                 200                 205

Ala Ser Leu Thr Ile Ser Gly Leu Gln Gly Glu Asp Glu Ala Glu Tyr
    210                 215                 220

Tyr Cys Ser Ser Phe Thr Ser Thr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 420
<211> LENGTH: 262
<212> TYPE: PRT
<213> ORGANISM: Artificial Sequence
<220> FEATURE:
<223> OTHER INFORMATION: YU100-B09

<400> SEQUENCE: 420

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Pro Glu Asp Glu Ala Asp Tyr
    210                 215                 220

Tyr Cys Ser Ser Tyr Arg Ser Gly Ser Thr Leu Gly Val Arg Arg Arg
225                 230                 235                 240

Asp Gln Ala Asp Arg Pro Arg Ser Ala Gln Gly Cys Pro Leu Gly His
                245                 250                 255

Ser Val Pro Ala Leu Leu
            260

<210> SEQ ID NO 421
<211> LENGTH: 267
<212> TYPE: PRT
<213> ORGANISM: Artificial Sequence
<220> FEATURE:
<223> OTHER INFORMATION: YU100-B12

<400> SEQUENCE: 421

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Gly Tyr Asn Tyr Val
                165                 170                 175
```

```
Ser Trp Tyr Gln Gln His Pro Gly Lys Ala Pro Lys Leu Met Ile Tyr
            180                 185                 190

Asp Val Ser Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Ala Glu
    210                 215                 220

Asp Glu Ala Asp Tyr Tyr Cys Cys Ser Tyr Ala Gly Ser Tyr Thr Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser
            260                 265
```

<210> SEQ ID NO 422
<211> LENGTH: 262
<212> TYPE: PRT
<213> ORGANISM: Artificial Sequence
<220> FEATURE:
<223> OTHER INFORMATION: YU100-C02

<400> SEQUENCE: 422

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asn Val Gly Gly Tyr Asn Tyr Val Ser Trp Tyr Gln Gln
                165                 170                 175

His Pro Gly Lys Ala Pro Lys Leu Met Ile Tyr Asp Val Ser Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Val Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260
```

<210> SEQ ID NO 423
<211> LENGTH: 262
<212> TYPE: PRT
<213> ORGANISM: Artificial Sequence
<220> FEATURE:
<223> OTHER INFORMATION: YU100-C04

<400> SEQUENCE: 423

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln His
                165                 170                 175

His Pro Gly Lys Ala Pro Lys Leu Ile Ile Tyr Asp Val Thr Lys Arg
            180                 185                 190

Pro Ser Gly Val Pro Asp Arg Phe Ser Gly Ser Lys Ser Gly Asn Thr
        195                 200                 205

Ala Ser Leu Ala Ile Ser Gly Leu Gln Ala Glu Glu Ala Asp Tyr
    210                 215                 220

Tyr Cys Cys Ser Tyr Ala Gly Gly Tyr Thr Trp Val Phe Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260
```

<210> SEQ ID NO 424
<211> LENGTH: 262
<212> TYPE: PRT
<213> ORGANISM: Artificial Sequence
<220> FEATURE:
<223> OTHER INFORMATION: YU100-C05

<400> SEQUENCE: 424

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45
```

```
Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Gly Ala Thr Asp Pro Leu Asp Tyr Trp Gly Gln Gly Thr
                100                 105                 110

Leu Val Thr Val Ser Ser Gly Ser Ala Ser Ala Pro Lys Leu Glu Glu
            115                 120                 125

Gly Glu Phe Ser Glu Ala Arg Val Gln Ser Ala Leu Thr Gln Pro Ala
            130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Ser Asn Arg
            180                 185                 190

Pro Ser Gly Ile Ser Asn Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
            210                 215                 220

Tyr Cys Ser Ser Tyr Thr Ser Ser Ile Ser Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 425
<211> LENGTH: 262
<212> TYPE: PRT
<213> ORGANISM: Artificial Sequence
<220> FEATURE:
<223> OTHER INFORMATION: YU100-C10

<400> SEQUENCE: 425

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Gly Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Gly Ala Thr Asp Pro Leu Asp Tyr Trp Gly Gln Gly Thr
                100                 105                 110

Leu Ile Thr Val Ser Ser Gly Ser Ala Ser Ala Pro Lys Leu Glu Glu
            115                 120                 125

Gly Glu Phe Ser Glu Ala Arg Val Gln Ser Ala Leu Thr Gln Pro Ala
            130                 135                 140
```

```
Ser Val Ser Gly Ser Pro Gln Ser Ile Thr Ile Ser Cys Thr Gly
145                 150                 155                 160

Thr Arg Ser Asp Ile Gly Gly Tyr Asp Tyr Val Ser Trp Tyr Gln Gln
                165                 170                 175

His Pro Gly Lys Ala Pro Lys Leu Met Ile Tyr Asp Val Asn Asn Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Glu Tyr
    210                 215                 220

Tyr Cys Ser Ser Tyr Thr Ser Ser Ile Thr Trp Val Phe Gly Gly Gly
225                 230                 235                 240

Thr Lys Val Thr Val Leu Gly Gln Pro Lys Ala Ala Pro Ser Val Thr
                245                 250                 255

Leu Phe Pro Pro Ser Ser
            260
```

<210> SEQ ID NO 426
<211> LENGTH: 262
<212> TYPE: PRT
<213> ORGANISM: Artificial Sequence
<220> FEATURE:
<223> OTHER INFORMATION: YU100-C11

<400> SEQUENCE: 426

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Arg Pro Gly Lys Ala Pro Lys Leu Met Ile Tyr Asp Val Ser Asn Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Pro Asp Asp Glu Ala Asp Tyr
    210                 215                 220

Tyr Cys Ser Ser Tyr Thr Asn Ser Arg Thr Trp Val Phe Gly Gly Gly
225                 230                 235                 240
```

```
Thr Lys Leu Thr Val Leu Ser Gln Pro Lys Ala Ala Pro Ser Val Thr
            245                 250                 255

Leu Phe Pro Pro Ser Ser
            260

<210> SEQ ID NO 427
<211> LENGTH: 267
<212> TYPE: PRT
<213> ORGANISM: Artificial Sequence
<220> FEATURE:
<223> OTHER INFORMATION: YU100-C12

<400> SEQUENCE: 427

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Gly Tyr Asn Tyr Val
                165                 170                 175

Ser Trp Tyr Gln Gln His Pro Gly Lys Ala Pro Lys Leu Met Ile Tyr
            180                 185                 190

Asp Val Ser Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Ala Glu
    210                 215                 220

Asp Glu Ala Asp Tyr Tyr Cys Cys Ser Tyr Ala Gly Ser Tyr Thr Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser
            260                 265

<210> SEQ ID NO 428
<211> LENGTH: 267
<212> TYPE: PRT
<213> ORGANISM: Artificial Sequence
<220> FEATURE:
<223> OTHER INFORMATION: YU100-D01

<400> SEQUENCE: 428

Gln Val Gln Leu Gln Gln Ser Gly Gly Gly Val Val Gln Pro Gly Arg
```

```
                1               5                   10                  15
            Ser Leu Arg Leu Ser Cys Ala Ala Ser Gly Phe Thr Phe Ser Ser Tyr
                            20                  25                  30

Ala Met His Trp Val Arg Gln Ala Pro Gly Lys Gly Leu Glu Trp Val
                            35                  40                  45

Ala Val Ile Ser Tyr Asp Gly Ser Asn Lys Tyr Tyr Ala Asp Ser Val
                            50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                            85                  90                  95

Ala Arg Ile Met Gly Tyr Asp Tyr Gly Asp Tyr Asp Val Val Asp Tyr
                            100                 105                 110

Trp Gly Gln Gly Thr Leu Val Thr Val Ser Ser Gly Ser Ala Ser Ala
                            115                 120                 125

Pro Lys Leu Glu Glu Gly Glu Phe Ser Glu Ala Arg Val Gln Ser Ala
                            130                 135                 140

Leu Thr Gln Pro Pro Ser Ala Ser Gly Ser Pro Gly Gln Ser Val Thr
            145                 150                 155                 160

Ile Ser Cys Thr Gly Thr Ser Ser Asp Val Gly Gly Tyr Asn Phe Val
                            165                 170                 175

Ser Trp Tyr Gln Gln His Pro Gly Lys Ala Pro Lys Leu Leu Ile Tyr
                            180                 185                 190

Asp Val Asp Lys Arg Pro Ser Gly Val Pro Asp Arg Phe Ser Gly Ser
                            195                 200                 205

Lys Ser Gly Arg Thr Ala Ser Leu Thr Ile Ser Gly Leu Gln Thr Glu
                            210                 215                 220

Asp Glu Ala Lys Tyr Tyr Cys Cys Ser Tyr Ala Gly Arg Tyr Thr Trp
            225                 230                 235                 240

Ile Phe Gly Gly Gly Thr Lys Leu Thr Val Leu Gly Gln Pro Lys Ala
                            245                 250                 255

Ala Pro Ser Val Ile Leu Phe Pro Pro Ser Ser
                            260                 265

<210> SEQ ID NO 429
<211> LENGTH: 262
<212> TYPE: PRT
<213> ORGANISM: Artificial Sequence
<220> FEATURE:
<223> OTHER INFORMATION: YU100-D02

<400> SEQUENCE: 429

Gln Val Arg Leu Val Gln Ser Gly Gly Gly Val Val Gln Pro Gly Arg
             1               5                   10                  15

Ser Leu Arg Leu Ser Cys Ala Ala Ser Gly Phe Thr Phe Ser Ser Tyr
                            20                  25                  30

Gly Met His Trp Val Arg Gln Ala Pro Gly Lys Gly Leu Glu Trp Val
                            35                  40                  45

Ala Val Ile Ser Tyr Asp Gly Ser Asn Lys Tyr Tyr Ala Asp Ser Val
                            50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                            85                  90                  95

Ala Lys Ile Gly Ala Thr Asp Pro Leu Asp Tyr Trp Gly Gln Gly Thr
```

```
                100                 105                 110
Leu Val Thr Val Ser Ser Gly Ser Ala Ser Ala Pro Lys Leu Glu Glu
            115                 120                 125

Gly Glu Phe Ser Glu Ala Arg Val Gln Ser Ala Leu Thr Gln Pro Arg
        130                 135                 140

Ser Val Ser Gly Ser Pro Gly Gln Ser Val Thr Ile Ser Cys Thr Gly
145                 150                 155                 160

Thr Ser Gly Asp Val Gly Thr Tyr Asn Tyr Val Ser Trp Tyr Gln Gln
                165                 170                 175

His Pro Gly Lys Ala Pro Lys Leu Met Ile Phe Asp Val Ser Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Asn Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260
```

```
<210> SEQ ID NO 430
<211> LENGTH: 262
<212> TYPE: PRT
<213> ORGANISM: Artificial Sequence
<220> FEATURE:
<223> OTHER INFORMATION: YU100-D05

<400> SEQUENCE: 430
```

```
Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Leu Ile Thr Ile Ser Cys Thr Gly
145                 150                 155                 160

Thr Asn Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Ser Asn Arg
            180                 185                 190

Pro Ser Gly Val Ser Asn Arg Phe Ser Gly Ser Lys Ser Gly Asn Thr
```

```
            195                 200                 205

Ala Ser Leu Thr Ile Ser Gly Leu Gln Ala Glu Asp Glu Ala Asp Tyr
210                 215                 220

Tyr Cys Cys Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
            245                 250                 255

Leu Phe Pro Pro Ser Ser
            260

<210> SEQ ID NO 431
<211> LENGTH: 267
<212> TYPE: PRT
<213> ORGANISM: Artificial Sequence
<220> FEATURE:
<223> OTHER INFORMATION: YU100-D07

<400> SEQUENCE: 431

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Gly Asp Val Gly Thr Tyr Asp Tyr Val
                165                 170                 175

Ser Trp Tyr Gln Gln His Pro Gly Lys Ala Pro Lys Leu Met Ile Tyr
            180                 185                 190

Asp Val Ser Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Ala Glu
210                 215                 220

Asp Glu Ala Asp Tyr Tyr Cys Asn Ser Tyr Ala Gly Ser Tyr Thr Trp
225                 230                 235                 240

Val Phe Gly Gly Gly Thr Lys Leu Thr Val Leu Gly Gln Pro Lys Thr
                245                 250                 255

Ala Pro Ser Val Thr Leu Phe Pro Pro Ser Ser
            260                 265

<210> SEQ ID NO 432
<211> LENGTH: 262
<212> TYPE: PRT
```

<213> ORGANISM: Artificial Sequence
<220> FEATURE:
<223> OTHER INFORMATION: YU100-D11

<400> SEQUENCE: 432

| | | | | | | | | | | | | | | |
|---|---|---|---|---|---|---|---|---|---|---|---|---|---|---|
| Gln | Val | Gln | Leu | Val | Gln | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | | 35 | | | | | 40 | | | | | 45 | | |
| Ala | Val | Ile | Ser | Tyr | Asp | Gly | Ser | Asn | Lys | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Ile | Gly | Ala | Thr | Asp | Pro | Leu | Asp | Tyr | Trp | Gly | Gln | Gly | Thr |
| | | | 100 | | | | | 105 | | | | | 110 | | |
| Leu | Val | Thr | Val | Ser | Ser | Gly | Ser | Ala | Ser | Ala | Pro | Lys | Leu | Glu | Glu |
| | | 115 | | | | | 120 | | | | | 125 | | | |
| Gly | Glu | Phe | Ser | Glu | Ala | Arg | Val | Gln | Ser | Ala | Leu | Thr | Gln | Pro | Arg |
| | 130 | | | | | 135 | | | | | 140 | | | | |
| Ser | Val | Ser | Gly | Ser | Pro | Gly | Gln | Ser | Val | Thr | Ile | Ser | Cys | Thr | Gly |
| 145 | | | | | 150 | | | | | 155 | | | | | 160 |
| Thr | Ser | Ser | Asn | Val | Gly | Gly | Tyr | Asn | Tyr | Val | Ser | Trp | Tyr | Gln | Gln |
| | | | | 165 | | | | | 170 | | | | | 175 | |
| His | Pro | Gly | Lys | Ala | Pro | Lys | Leu | Met | Ile | Tyr | Asp | Val | Ser | Lys | Arg |
| | | | 180 | | | | | 185 | | | | | 190 | | |
| Pro | Ser | Gly | Val | Pro | Asp | Arg | Phe | Ser | Gly | Ser | Lys | Ser | Gly | Asn | Thr |
| | | 195 | | | | | 200 | | | | | 205 | | | |
| Ala | Ser | Leu | Thr | Ile | Ser | Gly | Leu | Gln | Ala | Glu | Asp | Glu | Ala | Asn | Tyr |
| | 210 | | | | | 215 | | | | | 220 | | | | |
| Tyr | Cys | Ala | Ser | Tyr | Ala | Gly | Asn | Tyr | Asn | Trp | Val | Phe | Gly | Gly | Gly |
| 225 | | | | | 230 | | | | | 235 | | | | | 240 |
| Thr | Lys | Leu | Thr | Val | Leu | Gly | Gln | Pro | Lys | Ala | Ala | Pro | Ser | Val | Thr |
| | | | | 245 | | | | | 250 | | | | | 255 | |
| Leu | Phe | Pro | Pro | Ser | Ser |
| | | | | 260 | |

<210> SEQ ID NO 433
<211> LENGTH: 262
<212> TYPE: PRT
<213> ORGANISM: Artificial Sequence
<220> FEATURE:
<223> OTHER INFORMATION: YU100-E01

<400> SEQUENCE: 433

| | | | | | | | | | | | | | | | |
|---|---|---|---|---|---|---|---|---|---|---|---|---|---|---|---|
| Gln | Val | Gln | Leu | Gln | Gln | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | | 35 | | | | | 40 | | | | | 45 | | |
| Ala | Val | Ile | Ser | Tyr | Asp | Gly | Ser | Asn | Lys | Tyr | Tyr | Ala | Asp | Ser | Val |
| | 50 | | | | | 55 | | | | | 60 | | | | |

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Asn Asp Ile Gly Ala Tyr Asn Tyr Val Ser Trp Tyr Gln Gln
                165                 170                 175

His Pro Gly Lys Ala Pro Lys Leu Leu Ile Tyr Asp Val Asn Asn Arg
            180                 185                 190

Pro Ser Gly Val Ser Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Ser Trp Val Phe Gly Gly Gly
225                 230                 235                 240

Thr Lys Leu Thr Val Leu Gly Gln Pro Lys Ala Asn Pro Thr Val Thr
                245                 250                 255

Leu Phe Pro Pro Ser Ser
            260

<210> SEQ ID NO 434
<211> LENGTH: 262
<212> TYPE: PRT
<213> ORGANISM: Artificial Sequence
<220> FEATURE:
<223> OTHER INFORMATION: YU100-E04

<400> SEQUENCE: 434

Gln Val Gln Leu Gln Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160
```

Thr Ser Ser Asp Val Gly Gly Tyr Asn Tyr Val Ser Trp Tyr Gln Gln
            165                 170                 175

His Pro Gly Lys Thr Pro Lys Leu Met Ile Tyr Asp Val Thr Lys Arg
        180                 185                 190

Pro Ser Gly Val Pro Asp His Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser His Ile Trp Val Phe Gly Gly Gly
225                 230                 235                 240

Thr Lys Leu Thr Val Leu Gly Gln Pro Lys Ala Ala Pro Ser Val Thr
        245                 250                 255

Leu Phe Pro Pro Ser Ser
            260

<210> SEQ ID NO 435
<211> LENGTH: 262
<212> TYPE: PRT
<213> ORGANISM: Artificial Sequence
<220> FEATURE:
<223> OTHER INFORMATION: YU100-E05

<400> SEQUENCE: 435

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ile Gly Ala Thr Asp Pro Leu Asp Tyr Trp Gly Gln Gly Thr
        100                 105                 110

Leu Val Thr Val Ser Ser Gly Ser Ala Ser Ala Pro Lys Leu Glu Glu
    115                 120                 125

Gly Glu Phe Ser Glu Ala Arg Val Gln Ala Val Leu Thr Gln Pro Arg
130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
            165                 170                 175

His Pro Gly Lys Ala Pro Lys Leu Met Ile Tyr Asp Val Ser Lys Arg
        180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Ser Trp Val Phe Gly Gly Gly
225                 230                 235                 240

Thr Lys Leu Thr Val Leu Gly Gln Pro Lys Ala Ala Pro Ser Val Thr
        245                 250                 255

```
Leu Phe Pro Pro Ser Ser
            260

<210> SEQ ID NO 436
<211> LENGTH: 262
<212> TYPE: PRT
<213> ORGANISM: Artificial Sequence
<220> FEATURE:
<223> OTHER INFORMATION: YU100-E06

<400> SEQUENCE: 436

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Phe Pro Glu Gln Ser Ile Thr Ile Ser Cys Thr Gly
145                 150                 155                 160

Thr Ser Ser Asp Val Gly Gly Tyr Asp Tyr Val Ser Trp Tyr Gln Gln
                165                 170                 175

His Pro Gly Lys Ala Pro Lys Leu Met Ile Tyr Asp Val Thr Asn Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Pro Glu Asp Glu Ala Asp Tyr
    210                 215                 220

Tyr Cys Ser Ser Tyr Thr Ser Asn Thr Thr Trp Val Phe Gly Gly Gly
225                 230                 235                 240

Thr Lys Leu Thr Val Leu Arg Gln Pro Lys Ala Ala Pro Ser Val Thr
                245                 250                 255

Leu Phe Pro Pro Ser Ser
            260

<210> SEQ ID NO 437
<211> LENGTH: 262
<212> TYPE: PRT
<213> ORGANISM: Artificial Sequence
<220> FEATURE:
<223> OTHER INFORMATION: YU100-E07

<400> SEQUENCE: 437

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Gly Met His Trp Val Arg Gln Ala Pro Gly Lys Gly Leu Glu Trp Val
            35                  40                  45

Ala Val Ile Ser Tyr Asp Gly Ser Asn Arg Tyr Tyr Ala Asp Ser Val
        50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asp Tyr Val Ser Trp Tyr Gln Gln
                165                 170                 175

His Pro Gly Lys Ala Pro Glu Leu Met Ile Tyr Asp Val Thr Lys Arg
            180                 185                 190

Pro Ser Gly Val Ala Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Arg Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 438
<211> LENGTH: 267
<212> TYPE: PRT
<213> ORGANISM: Artificial Sequence
<220> FEATURE:
<223> OTHER INFORMATION: YU100-E08

<400> SEQUENCE: 438

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

```
Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Gly Tyr Asn Tyr Val
                165                 170                 175

Ser Trp Tyr Gln Gln His Pro Gly Lys Ala Pro Lys Leu Met Ile Tyr
                180                 185                 190

Asp Val Ser Arg Arg Pro Ser Gly Val Pro Asp Arg Phe Ser Gly Ser
                195                 200                 205

Lys Ser Gly Asn Thr Ala Ser Leu Thr Ile Ser Gly Leu Gln Ala Glu
210                 215                 220

Asp Glu Ala Asp Tyr Tyr Cys Cys Ser Tyr Ala Gly Asn Tyr Thr Trp
225                 230                 235                 240

Met Phe Gly Gly Gly Thr Lys Leu Thr Val Leu Gly Gln Pro Lys Ala
                245                 250                 255

Ala Pro Ser Val Thr Leu Phe Pro Pro Ser Ser
                260                 265

<210> SEQ ID NO 439
<211> LENGTH: 267
<212> TYPE: PRT
<213> ORGANISM: Artificial Sequence
<220> FEATURE:
<223> OTHER INFORMATION: YU100-E09

<400> SEQUENCE: 439

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
                100                 105                 110

Trp Gly Gln Gly Thr Leu Val Thr Val Ser Ser Gly Ser Ala Ser Ala
            115                 120                 125

Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Asp Tyr Asp Tyr Val
                165                 170                 175

Ser Trp Tyr Gln Gln His Pro Gly Lys Ala Pro Lys Leu Ile Ile Tyr
                180                 185                 190

Asp Val Thr Lys Arg Pro Ser Gly Ile Pro Asp Arg Phe Ser Gly Ser
                195                 200                 205

Lys Ser Gly Asn Thr Ala Ser Leu Thr Ile Ser Gly Leu Gln Ala Glu
210                 215                 220
```

Asp Glu Ala Asp Tyr Tyr Cys Cys Ser Tyr Ala Gly Ser Tyr Thr Trp
225                 230                 235                 240

Val Phe Gly Arg Gly Thr Lys Leu Thr Val Leu Gly Gln Pro Lys Ala
            245                 250                 255

Ala Pro Ser Val Thr Leu Phe Pro Pro Ser Thr
        260                 265

<210> SEQ ID NO 440
<211> LENGTH: 262
<212> TYPE: PRT
<213> ORGANISM: Artificial Sequence
<220> FEATURE:
<223> OTHER INFORMATION: YU100-E10

<400> SEQUENCE: 440

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Phe Asp Val Ser Gln Arg
            180                 185                 190

Pro Ser Gly Val Pro Asp Arg Phe Ser Ala Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 441
<211> LENGTH: 267
<212> TYPE: PRT
<213> ORGANISM: Artificial Sequence
<220> FEATURE:
<223> OTHER INFORMATION: YU100-E11

<400> SEQUENCE: 441

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Gly Tyr Asn Tyr Val
                165                 170                 175

Ser Trp Tyr Gln Gln His Pro Gly Lys Ala Pro Lys Leu Met Ile Tyr
            180                 185                 190

Asp Val Ser Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Ala Glu
    210                 215                 220

Asp Glu Ala Asp Tyr Tyr Cys Cys Ser Tyr Ala Gly Ser Tyr Thr Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser
            260                 265

<210> SEQ ID NO 442
<211> LENGTH: 262
<212> TYPE: PRT
<213> ORGANISM: Artificial Sequence
<220> FEATURE:
<223> OTHER INFORMATION: YU100-E12

<400> SEQUENCE: 442

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Thr Ala Pro Lys Leu Met Ile Tyr Asp Val Ser Asn Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Thr Ser Ser Thr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 443
<211> LENGTH: 262
<212> TYPE: PRT
<213> ORGANISM: Artificial Sequence
<220> FEATURE:
<223> OTHER INFORMATION: YU100-F01

<400> SEQUENCE: 443

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Gly Ser Asp Val Gly Ala Tyr Asp Tyr Val Ser Trp Tyr Gln Gln
                165                 170                 175

His Pro Gly Lys Ala Pro Lys Leu Met Ile Tyr Asp Val Asn Asn Arg
```

```
            180                 185                 190
Pro Ser Gly Val Ser Asn Arg Phe Ser Gly Ser Lys Ser Gly Asn Thr
            195                 200                 205

Ala Ser Leu Thr Ile Ser Gly Leu Gln Ala Glu Asp Glu Ala Glu Tyr
            210                 215                 220

Tyr Cys Ser Ser Phe Ala Thr Ser Ile Ser Trp Val Phe Gly Gly Gly
225                 230                 235                 240

Thr Arg Leu Thr Val Leu Gly Gln Pro Lys Ala Ala Pro Ser Val Thr
                    245                 250                 255

Leu Phe Pro Pro Ser Ser
            260
```

<210> SEQ ID NO 444
<211> LENGTH: 262
<212> TYPE: PRT
<213> ORGANISM: Artificial Sequence
<220> FEATURE:
<223> OTHER INFORMATION: YU100-F02

<400> SEQUENCE: 444

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Asp Glu Ala Asp Tyr
            210                 215                 220

Tyr Cys Cys Ser Tyr Ala Gly Ser Tyr Thr Trp Ile Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260
```

```
<210> SEQ ID NO 445
<211> LENGTH: 262
<212> TYPE: PRT
<213> ORGANISM: Artificial Sequence
<220> FEATURE:
<223> OTHER INFORMATION: YU100-F05

<400> SEQUENCE: 445

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ala Val Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Ile Gly Gly Tyr Asn Tyr Val Ser Trp Tyr Gln Gln
                165                 170                 175

His Pro Gly Thr Ala Pro Lys Leu Met Ile Tyr Asp Val Ser Ser Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Thr Trp Val Phe Gly Gly Gly
225                 230                 235                 240

Thr Lys Met Thr Val Leu Gly Gln Pro Lys Ala Ala Pro Ser Val Thr
                245                 250                 255

Leu Phe Pro Pro Ser Ser
            260

<210> SEQ ID NO 446
<211> LENGTH: 267
<212> TYPE: PRT
<213> ORGANISM: Artificial Sequence
<220> FEATURE:
<223> OTHER INFORMATION: YU100-F06

<400> SEQUENCE: 446

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
            115                 120                 125

Pro Lys Leu Glu Glu Gly Glu Phe Ser Glu Ala Arg Val Gln Ser Ala
            130                 135                 140

Leu Thr Gln Pro Arg Ser Val Ser Gly Ser Pro Gly Gln Ser Val Thr
145                 150                 155                 160

Ile Ser Cys Thr Gly Ser Ser Asp Val Gly Gly Tyr Asn Phe Val
                165                 170                 175

Ser Trp Tyr Arg Gln His Pro Gly Glu Ala Pro Lys Leu Val Ile Phe
            180                 185                 190

Asp Val Asn Lys Arg Pro Ser Gly Val Pro Asp Arg Phe Ser Gly Ser
            195                 200                 205

Lys Ser Gly Asn Thr Ala Ser Leu Thr Ile Ser Gly Leu Gln Thr Glu
210                 215                 220

Asp Glu Ala Asp Tyr Phe Cys Cys Ser Tyr Ala Gly Tyr Thr Trp
225                 230                 235                 240

Val Phe Gly Gly Gly Thr Lys Val Thr Val Val Gly Gln Pro Lys Ala
                245                 250                 255

Ala Pro Ser Val Thr Leu Phe Pro Pro Ser Ser
            260                 265

<210> SEQ ID NO 447
<211> LENGTH: 267
<212> TYPE: PRT
<213> ORGANISM: Artificial Sequence
<220> FEATURE:
<223> OTHER INFORMATION: YU100-F07

<400> SEQUENCE: 447

Gln Val Gln Leu Val Glu Ser Gly Gly Gly Val Val Gln Pro Gly Arg
 1                   5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
            115                 120                 125

Pro Lys Leu Glu Glu Gly Glu Phe Ser Glu Ala Arg Val Gln Ser Ala
            130                 135                 140
```

Leu Thr Gln Pro Arg Ser Val Ser Val Ser Pro Gly Gln Ser Val Thr
145                 150                 155                 160

Ile Ser Cys Thr Gly Thr Ser Ser Asp Val Gly Gly Tyr Glu Tyr Val
                165                 170                 175

Ser Trp Tyr Gln Gln His Pro Gly Lys Ala Pro Lys Leu Met Ile Tyr
            180                 185                 190

Asp Val Thr Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Gly Glu
210                 215                 220

Asp Ala Ala Asp Tyr Tyr Cys Cys Ser Tyr Ala Gly Ser Tyr Thr Trp
225                 230                 235                 240

Val Phe Gly Gly Gly Thr Thr Val Thr Val Leu Gly Gln Pro Lys Ala
                245                 250                 255

Ala Pro Ser Val Thr Leu Phe Pro Pro Ser Ser
                260                 265

<210> SEQ ID NO 448
<211> LENGTH: 262
<212> TYPE: PRT
<213> ORGANISM: Artificial Sequence
<220> FEATURE:
<223> OTHER INFORMATION: YU100-F11

<400> SEQUENCE: 448

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
130                 135                 140

Ser Val Ser Gly Ser Pro Gly Gln Ser Ile Thr Ile Ser Cys Thr Gly
145                 150                 155                 160

Ser Ser Ser Asp Val Ala Gly Tyr Asn Tyr Val Ser Trp Tyr Gln Gln
                165                 170                 175

His Pro Gly Lys Ala Pro Lys Leu Met Ile Tyr Asp Val Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
210                 215                 220

Tyr Cys Cys Ser Tyr Ala Gly Ser Tyr Thr Trp Val Phe Gly Gly Gly
225                 230                 235                 240

Thr Gln Leu Thr Val Leu Gly Gln Pro Lys Ala Ala Pro Ser Val Thr
            245                 250                 255

Leu Phe Pro Pro Ser Ser
            260

<210> SEQ ID NO 449
<211> LENGTH: 262
<212> TYPE: PRT
<213> ORGANISM: Artificial Sequence
<220> FEATURE:
<223> OTHER INFORMATION: YU100-G01

<400> SEQUENCE: 449

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Ala Ser Pro Gly Gln Ser Val Thr Ile Ser Cys Thr Gly
145                 150                 155                 160

Thr Ser Ser Asp Val Gly Ala Tyr Asn Tyr Val Ser Trp Tyr Gln Gln
                165                 170                 175

His Pro Gly Lys Ala Pro Lys Leu Met Leu Tyr Asp Val Asn Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Arg Leu Gln Ala Glu Asp Glu Ala Asp Tyr
    210                 215                 220

Tyr Cys Cys Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 450
<211> LENGTH: 262
<212> TYPE: PRT
<213> ORGANISM: Artificial Sequence
<220> FEATURE:
<223> OTHER INFORMATION: YU100-G07

<400> SEQUENCE: 450

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Ala Tyr Asp Tyr Val Ser Trp Tyr Gln Gln
                165                 170                 175

His Pro Gly Lys Ala Pro Lys Leu Met Ile Tyr Asp Val Thr Asn Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ala Ser Tyr Thr Arg Ser Ser Val Trp Val Phe Gly Gly Gly
225                 230                 235                 240

Thr Lys Leu Thr Val Leu Gly Gln Pro Lys Ala Ala Ser Ser Val Thr
                245                 250                 255

Leu Phe Pro Pro Ser Ser
            260

<210> SEQ ID NO 451
<211> LENGTH: 262
<212> TYPE: PRT
<213> ORGANISM: Artificial Sequence
<220> FEATURE:
<223> OTHER INFORMATION: YU100-G08

<400> SEQUENCE: 451

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

```
Leu Val Thr Val Ser Ser Gly Ser Ala Ser Ala Pro Lys Leu Glu Glu
            115                 120                 125

Gly Glu Phe Ser Glu Ala Arg Val Gln Ser Ala Leu Thr Gln Pro Arg
        130                 135                 140

Ser Val Ser Gly Ser Pro Gly Gln Ser Val Thr Leu Ser Cys Thr Gly
145                 150                 155                 160

Thr Ser Ser Asp Val Gly Gly Tyr Asn Tyr Val Ser Trp Tyr Gln His
                165                 170                 175

Tyr Pro Gly Lys Ala Pro Lys Leu Met Ile Phe Asp Val Asn Glu Arg
                180                 185                 190

Ser Ser Gly Val Pro Asp Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
            210                 215                 220

Tyr Cys Cys Ser Tyr Ala Gly Arg Tyr Thr Trp Met Phe Gly Gly Gly
225                 230                 235                 240

Thr Lys Val Thr Val Leu Gly Gln Pro Lys Ala Ala Pro Ser Val Thr
                245                 250                 255

Leu Phe Pro Pro Ser Ser
            260

<210> SEQ ID NO 452
<211> LENGTH: 262
<212> TYPE: PRT
<213> ORGANISM: Artificial Sequence
<220> FEATURE:
<223> OTHER INFORMATION: YU100-G09

<400> SEQUENCE: 452

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
            115                 120                 125

Gly Glu Phe Ser Glu Ala Arg Val Gln Ser Ala Leu Thr Gln Pro Arg
        130                 135                 140

Ser Val Ser Gly Ser Pro Gly Gln Ser Val Thr Ile Ser Cys Thr Gly
145                 150                 155                 160

Thr Ile Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Thr Lys Arg
                180                 185                 190

Pro Ser Gly Val Pro Asp Arg Phe Ser Gly Ser Lys Ser Gly Asn Thr
            195                 200                 205
```

```
Ala Ser Leu Thr Ile Ser Gly Leu Gln Ala Glu Asp Glu Ala Gly Tyr
        210                 215                 220

Tyr Cys Ser Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260
```

<210> SEQ ID NO 453
<211> LENGTH: 262
<212> TYPE: PRT
<213> ORGANISM: Artificial Sequence
<220> FEATURE:
<223> OTHER INFORMATION: YU100-G10

<400> SEQUENCE: 453

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Leu Gly Gln Ser Ile Thr Met Ser Cys Thr Gly
145                 150                 155                 160

Thr Arg Arg Asp Val Gly Gly Tyr Asp Phe Val Ser Trp Tyr Gln Gln
                165                 170                 175

Tyr Pro Gly Lys Ala Pro Lys Leu Ile Ile Tyr Asp Val Ser Asn Arg
            180                 185                 190

Pro Ser Gly Val Ser Asn Arg Phe Thr Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Thr Tyr Thr Trp Val Phe Gly Gly Gly
225                 230                 235                 240

Thr Lys Val Thr Val Leu Gly Gln Pro Lys Ala Ala Pro Ser Val Thr
                245                 250                 255

Leu Phe Pro Pro Ser Ser
            260
```

<210> SEQ ID NO 454
<211> LENGTH: 267
<212> TYPE: PRT
<213> ORGANISM: Artificial Sequence

<220> FEATURE:
<223> OTHER INFORMATION: YU100-G11

<400> SEQUENCE: 454

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Gly Tyr Asn Tyr Val
                165                 170                 175

Ser Trp Tyr Gln Gln His Pro Gly Lys Ala Pro Lys Leu Thr Leu Tyr
            180                 185                 190

Asp Val Gly Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Ala Glu
    210                 215                 220

Asp Glu Ala Asp Tyr Tyr Cys Cys Ser Tyr Ala Gly Gly Tyr Thr Trp
225                 230                 235                 240

Val Phe Gly Gly Gly Thr Lys Val Thr Val Gly Gln Pro Lys Ala
                245                 250                 255

Ala Pro Ser Val Thr Leu Phe Pro Pro Ser Ser
            260                 265

<210> SEQ ID NO 455
<211> LENGTH: 267
<212> TYPE: PRT
<213> ORGANISM: Artificial Sequence
<220> FEATURE:
<223> OTHER INFORMATION: YU100-H01

<400> SEQUENCE: 455

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr

-continued

```
                65                  70                  75                  80
Leu Gln Met Asn Ser Leu Arg Ala Glu Asp Thr Ala Val Tyr Tyr Cys
                    85                  90                  95

Ala Arg Ile Met Gly Tyr Asp Tyr Gly Asp Tyr Asp Val Val Asp Tyr
                100                 105                 110

Trp Gly Gln Gly Thr Leu Val Thr Val Ser Ser Gly Ser Ala Ser Ala
                115                 120                 125

Pro Lys Leu Glu Glu Gly Glu Phe Ser Glu Ala Arg Val Gln Ser Ala
                130                 135                 140

Leu Thr Gln Pro Arg Ser Val Ser Gly Ser Pro Gly Gln Ser Val Thr
145                 150                 155                 160

Ile Ser Cys Thr Gly Thr Ser Ser Asp Val Gly Ala Tyr Asn Tyr Val
                165                 170                 175

Ser Trp Tyr Gln Gln His Pro Gly Lys Ala Pro Lys Leu Met Ile Tyr
                180                 185                 190

Asp Val Ser Glu Arg Pro Ser Gly Val Pro Asp Arg Phe Ser Gly Ser
                195                 200                 205

Lys Ser Gly Asn Thr Ala Ser Leu Thr Ile Ser Gly Leu Gln Ala Glu
                210                 215                 220

Asp Glu Ala Asp Tyr Tyr Cys Cys Ser Tyr Ala Gly Ser Tyr Thr Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser
                260                 265
```

<210> SEQ ID NO 456
<211> LENGTH: 267
<212> TYPE: PRT
<213> ORGANISM: Artificial Sequence
<220> FEATURE:
<223> OTHER INFORMATION: YU100-H02

<400> SEQUENCE: 456

```
Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Ile Met Gly Tyr Asp Tyr Gly Asp Tyr Asp Val Val Asp Tyr
                100                 105                 110

Trp Gly Gln Gly Thr Leu Val Thr Val Ser Ser Gly Ser Ala Ser Ala
                115                 120                 125

Pro Lys Leu Glu Glu Gly Glu Phe Ser Glu Ala Arg Val Gln Ser Ala
                130                 135                 140

Leu Thr Gln Pro Arg Ser Val Ser Arg Ser Pro Gly Gln Ser Val Thr
145                 150                 155                 160

Ile Ser Cys Thr Gly Thr Ser Ser Asp Val Gly Thr Tyr Asn Tyr Val
```

```
                    165                 170                 175
Ser Trp Tyr Gln Gln His Pro Gly Lys Ala Pro Lys Leu Met Ile Tyr
            180                 185                 190

Asp Val Ser Lys Arg Pro Ser Gly Val Pro Asp Arg Phe Ser Gly Ser
        195                 200                 205

Lys Ser Gly Asn Thr Ala Ser Leu Thr Ile Ser Gly Leu Gln Ala Glu
    210                 215                 220

Asp Glu Ala Asp Tyr Tyr Cys Cys Ser Tyr Ala Gly Ser Tyr Thr Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser
                260                 265

<210> SEQ ID NO 457
<211> LENGTH: 267
<212> TYPE: PRT
<213> ORGANISM: Artificial Sequence
<220> FEATURE:
<223> OTHER INFORMATION: YU100-H04

<400> SEQUENCE: 457

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ile Met Gly Tyr Asp Tyr Gly Asp Tyr Asp Val Val Asp Tyr
        100                 105                 110

Trp Gly Gln Gly Thr Leu Val Thr Val Ser Ser Gly Ser Ala Ser Ala
    115                 120                 125

Pro Lys Leu Glu Glu Gly Glu Phe Ser Glu Ala Arg Val Gln Ser Ala
130                 135                 140

Leu Thr Gln Pro Ala Ser Val Ser Gly Ser Pro Gly Gln Ser Ile Thr
145                 150                 155                 160

Ile Ser Cys Thr Gly Thr Ser Ser Asp Ile Gly Val Tyr Asn Tyr Val
            165                 170                 175

Ser Trp Tyr Gln Gln His Pro Gly Lys Ala Pro Lys Leu Met Ile Tyr
        180                 185                 190

Asp Val Ser Lys Arg Pro Ser Gly Val Pro Asp Arg Phe Ser Gly Ser
    195                 200                 205

Lys Ser Gly Asn Thr Ala Ser Leu Thr Ile Ser Gly Leu Gln Ala Glu
    210                 215                 220

Asp Glu Ala Asp Tyr Tyr Cys Cys Ser Tyr Ala Gly Ser Tyr Thr Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser
```

<210> SEQ ID NO 458
<211> LENGTH: 262
<212> TYPE: PRT
<213> ORGANISM: Artificial Sequence
<220> FEATURE:
<223> OTHER INFORMATION: YU100-H05

<400> SEQUENCE: 458

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ala Val Leu Thr Gln Pro Arg
    130                 135                 140

Ser Val Ser Gly Ser Pro Gly Gln Ser Ile Thr Ile Ser Cys Thr Gly
145                 150                 155                 160

Thr Gly Ser Asn Val Gly Gly Tyr Asn Tyr Val Ser Trp Tyr Gln Gln
                165                 170                 175

His Pro Gly Gln Ala Pro Lys Leu Met Ile Tyr Asp Val Ser Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Thr Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260
```

<210> SEQ ID NO 459
<211> LENGTH: 262
<212> TYPE: PRT
<213> ORGANISM: Artificial Sequence
<220> FEATURE:
<223> OTHER INFORMATION: YU100-H06

<400> SEQUENCE: 459

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Ile Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 460
<211> LENGTH: 267
<212> TYPE: PRT
<213> ORGANISM: Artificial Sequence
<220> FEATURE:
<223> OTHER INFORMATION: YU100-H09

<400> SEQUENCE: 460

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Ala
            130                 135                 140

Leu Thr Gln Pro Ala Ser Val Ser Gly Ser Pro Gly Gln Ser Ile Thr
145                 150                 155                 160

Ile Ser Cys Thr Gly Thr Ser Ser Asp Val Gly Gly Tyr Asn Tyr Val
                165                 170                 175

Ser Trp Tyr Gln Gln His Pro Gly Lys Ala Pro Lys Leu Met Ile Tyr
            180                 185                 190

Asp Val Ser Asn Arg Pro Ser Gly Val Ser Asn Arg Phe Ser Gly Ser
                195                 200                 205

Lys Ser Gly Asn Thr Ala Ser Leu Thr Ile Ser Gly Leu Gln Ala Glu
210                 215                 220

Asp Glu Ala Asp Tyr Tyr Cys Cys Ser Tyr Ala Gly Ser Tyr Thr Trp
225                 230                 235                 240

Val Phe Gly Gly Gly Thr Lys Leu Thr Val Leu Gly Gln Pro Lys Ala
                245                 250                 255

Ala Pro Ser Val Thr Leu Phe Pro Pro Ser Ser
            260                 265

<210> SEQ ID NO 461
<211> LENGTH: 262
<212> TYPE: PRT
<213> ORGANISM: Artificial Sequence
<220> FEATURE:
<223> OTHER INFORMATION: YU100-H11

<400> SEQUENCE: 461

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Ser Asn Arg
            180                 185                 190

Pro Ser Gly Val Ser Asn Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Thr Trp Val Phe Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 462
<211> LENGTH: 262
<212> TYPE: PRT
<213> ORGANISM: Artificial Sequence
<220> FEATURE:
<223> OTHER INFORMATION: YU112-A07

<400> SEQUENCE: 462

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ile Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Gly Tyr
    210                 215                 220

Tyr Cys Ser Ser Tyr Ala Gly Ser Tyr Thr Trp Val Phe Gly Gly Gly
225                 230                 235                 240

Thr Glu Leu Thr Val Leu Ser Gln Pro Lys Ala Ala Pro Ser Val Thr
                245                 250                 255

Leu Phe Pro Pro Ser Ser
            260

<210> SEQ ID NO 463
<211> LENGTH: 262
<212> TYPE: PRT
<213> ORGANISM: Artificial Sequence
<220> FEATURE:
<223> OTHER INFORMATION: YU112-B06

<400> SEQUENCE: 463

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
            115                 120                 125

Gly Glu Phe Ser Glu Ala Arg Val Gln Ser Ala Leu Thr Gln Pro Ala
130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Ser Asn Arg
            180                 185                 190

Pro Ser Gly Val Ser Asn Arg Phe Ser Gly Ser Lys Ser Gly Asn Thr
            195                 200                 205

Ala Ser Leu Thr Ile Phe Gly Leu Gln Ala Glu Asp Glu Ala Asp Tyr
210                 215                 220

Tyr Cys Ser Ser Tyr Thr Ser Ser Ser Trp Val Phe Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 464
<211> LENGTH: 253
<212> TYPE: PRT
<213> ORGANISM: Artificial Sequence
<220> FEATURE:
<223> OTHER INFORMATION: YU112-C03

<400> SEQUENCE: 464

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Gly Gly Lys Ser Tyr Tyr Gly Phe Asp Tyr Trp Gly Gln Gly
                100                 105                 110

Thr Leu Val Thr Val Ser Ser Gly Ala Ser Ala Pro Lys Leu Glu
            115                 120                 125

Glu Gly Glu Phe Ser Glu Ala Arg Val Asp Ser Val Met Thr Gln Ser
130                 135                 140

Pro Ser Ser Leu Ser Ala Ser Val Gly Asp Arg Val Thr Ile Thr Cys
145                 150                 155                 160

Arg Ala Ser Gln Ala Ile Asn Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Gly Leu Gln Pro Glu Asp Phe Ala Thr Tyr Tyr
    210                 215                 220

Cys Gln Gln Ser Tyr Ser Thr Pro Ser Trp Thr Phe Gly Gln Gly Thr
225                 230                 235                 240

Lys Val Glu Ile Lys Arg Thr Val Ala Ala Pro Ser Val
                245                 250
```

<210> SEQ ID NO 465
<211> LENGTH: 267
<212> TYPE: PRT
<213> ORGANISM: Artificial Sequence
<220> FEATURE:
<223> OTHER INFORMATION: YU112-C05

<400> SEQUENCE: 465

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Val Asp Tyr
            100                 105                 110

Trp Gly Gln Gly Thr Leu Val Thr Val Ser Ser Gly Ser Ala Ser Ala
        115                 120                 125

Pro Lys Leu Glu Glu Gly Glu Phe Ser Glu Ala Arg Val Gln Ser Ala
    130                 135                 140

Leu Thr Gln Pro Arg Ser Val Ser Gly Ser Pro Gly Gln Ser Val Thr
145                 150                 155                 160

Ile Ser Cys Thr Gly Thr Ile Ser Asp Val Gly Gly Tyr Asn Tyr Val
                165                 170                 175

Ser Trp Tyr Gln Gln His Pro Gly Lys Ala Pro Lys Leu Met Ile Tyr
            180                 185                 190

Asp Val Thr Lys Arg Pro Ser Gly Val Pro Asp Arg Phe Ser Gly Ser
        195                 200                 205
```

```
Lys Ser Gly Asn Thr Ala Ser Leu Thr Ile Ser Gly Leu Gln Ala Glu
            210                 215                 220

Asp Glu Ala Gly Tyr Tyr Cys Ser Ser Tyr Ala Gly Ser Tyr Thr Trp
225                 230                 235                 240

Val Phe Gly Gly Gly Thr Glu Leu Thr Val Leu Ser Gln Pro Lys Ala
                245                 250                 255

Ala Pro Ser Val Thr Leu Phe Pro Pro Ser Ser
            260                 265

<210> SEQ ID NO 466
<211> LENGTH: 251
<212> TYPE: PRT
<213> ORGANISM: Artificial Sequence
<220> FEATURE:
<223> OTHER INFORMATION: YU112-C09

<400> SEQUENCE: 466

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Tyr Tyr Phe Asp Tyr Trp Gly Gln Gly Thr Leu Val
            100                 105                 110

Thr Val Ser Ser Gly Ser Ala Ser Ala Pro Lys Leu Glu Glu Gly Glu
        115                 120                 125

Phe Ser Glu Ala Arg Val Glu Thr Thr Leu Thr Gln Ser Pro Ala Thr
    130                 135                 140

Leu Ser Val Ser Pro Gly Glu Arg Ala Thr Leu Ser Cys Arg Ala Ser
145                 150                 155                 160

Gln Ser Phe Ser Ser Tyr Leu Ala Trp Tyr Gln Gln Lys Pro Gly
                165                 170                 175

Gln Ala Pro Arg Leu Leu Ile Tyr Gly Ala Ser Arg Arg Ala Pro Gly
            180                 185                 190

Ile Pro Asp Arg Phe Ser Gly Ser Gly Ser Gly Thr Asp Phe Ser Leu
    195                 200                 205

Thr Ile Ser Arg Leu Glu Pro Glu Asp Phe Ala Val Tyr Tyr Cys Gln
            210                 215                 220

Gln Ser Ser Thr Ser Pro Thr Trp Ala Phe Gly Arg Gly Thr Lys Val
225                 230                 235                 240

Glu Val Lys Arg Thr Val Ala Ala Pro Ser Val
                245                 250

<210> SEQ ID NO 467
<211> LENGTH: 262
<212> TYPE: PRT
<213> ORGANISM: Artificial Sequence
<220> FEATURE:
<223> OTHER INFORMATION: YU112-D08
```

-continued

<400> SEQUENCE: 467

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ile Gly Ala Thr Asp Pro Leu Asp Tyr Trp Gly Gln Gly Thr
        100                 105                 110

Leu Val Thr Val Ser Ser Gly Ser Ala Ser Ala Pro Lys Leu Glu Glu
    115                 120                 125

Gly Glu Phe Ser Glu Ala Arg Val Gln Ser Ala Leu Thr Gln Pro Arg
130                 135                 140

Ser Val Ser Gly Ser Pro Gly Gln Ser Val Thr Ile Ser Cys Thr Gly
145                 150                 155                 160

Thr Ile Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Gly Tyr
    210                 215                 220

Tyr Cys Ser Ser Tyr Ala Gly Ser Tyr Thr Trp Val Phe Gly Gly Gly
225                 230                 235                 240

Thr Glu Leu Thr Val Leu Ser Gln Pro Lys Ala Ala Pro Ser Val Thr
                245                 250                 255

Leu Phe Pro Pro Ser Ser
            260

<210> SEQ ID NO 468
<211> LENGTH: 251
<212> TYPE: PRT
<213> ORGANISM: Artificial Sequence
<220> FEATURE:
<223> OTHER INFORMATION: YU112-E07

<400> SEQUENCE: 468

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                        85                  90                  95
Ala Lys Gly Ser Tyr Tyr Phe Asp Tyr Trp Gly Gln Gly Thr Leu Val
                100                 105                 110

Thr Val Ser Ser Gly Ser Ala Ser Ala Pro Lys Leu Glu Glu Gly Glu
            115                 120                 125

Phe Ser Glu Ala Arg Val Glu Ile Val Met Thr Gln Ser Pro Asp Ser
        130                 135                 140

Leu Ala Val Ser Leu Gly Glu Arg Ala Thr Ile Asn Cys Lys Ser Ser
145                 150                 155                 160

Gln Ser Val Asn Ser Ala Tyr Leu Ala Trp Tyr Gln His Lys Pro Gly
                165                 170                 175

Gln Pro Pro Arg Leu Leu Ile Tyr Gly Ala Ser Arg Arg Val Thr Gly
            180                 185                 190

Val Pro Asp Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
210                 215                 220

Gln Ser Tyr Ser Asp Pro Arg Trp Thr Phe Gly Gln Gly Thr Lys Val
225                 230                 235                 240

Glu Ile Lys Arg Thr Val Ala Ala Pro Ser Val
                245                 250
```

<210> SEQ ID NO 469
<211> LENGTH: 252
<212> TYPE: PRT
<213> ORGANISM: Artificial Sequence
<220> FEATURE:
<223> OTHER INFORMATION: YU112-E08

<400> SEQUENCE: 469

```
Val Thr Leu Lys Glu Ser Gly Gly Gly Val Val Gln Pro Gly Arg Ser
1               5                   10                  15

Leu Arg Leu Ser Cys Ala Ala Ser Gly Phe Thr Phe Ser Ser Tyr Gly
            20                  25                  30

Met His Trp Val Arg Gln Ala Pro Gly Lys Gly Leu Glu Trp Val Ala
        35                  40                  45

Val Ile Ser Tyr Asp Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Gly Lys Ser Tyr Tyr Gly Phe Asp Tyr Trp Gly Gln Gly Thr
                100                 105                 110

Leu Val Thr Val Ser Ser Gly Ser Ala Ser Ala Pro Lys Leu Glu Glu
            115                 120                 125

Gly Glu Phe Ser Glu Ala Arg Val Asp Ile Gln Met Thr Gln Ser Pro
        130                 135                 140

Ser Phe Leu Ser Ala Ser Val Gly Asp Arg Val Thr Ile Thr Cys Arg
145                 150                 155                 160

Ala Ser Gln Ile Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
```

```
                195                 200                 205
Leu Thr Ile Ser Ser Leu Gln Pro Glu Asp Phe Ala Thr Tyr Tyr Cys
    210                 215                 220

Gln Gln Ser Tyr Ser Thr Pro Thr Trp Thr Phe Gly Gln Gly Thr Lys
225                 230                 235                 240

Val Glu Ile Lys Arg Thr Val Ala Ala Pro Ser Val
                245                 250

<210> SEQ ID NO 470
<211> LENGTH: 262
<212> TYPE: PRT
<213> ORGANISM: Artificial Sequence
<220> FEATURE:
<223> OTHER INFORMATION: YU112-F05

<400> SEQUENCE: 470

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Gly Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Leu Ile Ile Tyr Asp Val Asn Asn Arg
            180                 185                 190

Pro Ser Gly Val Ser Asn Arg Phe Ser Ala Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Asn Ser Tyr Thr Ser Gly Ser Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 471
<211> LENGTH: 262
<212> TYPE: PRT
<213> ORGANISM: Artificial Sequence
<220> FEATURE:
<223> OTHER INFORMATION: YU112-G01
```

-continued

```
<400> SEQUENCE: 471

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ile Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Gly Tyr
    210                 215                 220

Tyr Cys Ser Ser Tyr Ala Gly Ser Tyr Thr Trp Val Phe Gly Gly Gly
225                 230                 235                 240

Thr Glu Leu Thr Val Leu Ser Gln Pro Lys Ala Ala Pro Ser Val Thr
                245                 250                 255

Leu Phe Pro Pro Ser Ser
            260

<210> SEQ ID NO 472
<211> LENGTH: 262
<212> TYPE: PRT
<213> ORGANISM: Artificial Sequence
<220> FEATURE:
<223> OTHER INFORMATION: YU112-G06

<400> SEQUENCE: 472

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Ser Ala Leu Thr Gln Pro Arg
    130                 135                 140

Ser Val Ser Gly Ser Pro Gly Gln Ser Val Thr Ile Ser Cys Thr Gly
145                 150                 155                 160

Thr Ile Ser Asp Val Gly Gly Tyr Asn Tyr Val Ser Trp Tyr Gln Gln
                165                 170                 175

His Pro Gly Lys Ala Pro Lys Leu Met Ile Tyr Asp Val Thr Lys Arg
            180                 185                 190

Arg Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Gly Tyr
    210                 215                 220

Tyr Cys Ser Ser Tyr Ala Gly Gly Tyr Thr Trp Val Phe Gly Gly Gly
225                 230                 235                 240

Thr Glu Leu Thr Val Leu Ser Gln Pro Lys Ala Ala Pro Ser Val Thr
                245                 250                 255

Leu Phe Pro Pro Ser Ser
            260

<210> SEQ ID NO 473
<211> LENGTH: 233
<212> TYPE: PRT
<213> ORGANISM: Artificial Sequence
<220> FEATURE:
<223> OTHER INFORMATION: YU112-G09

<400> SEQUENCE: 473

Val Thr Leu Lys Glu Ser Gly Gly Val Val Gln Pro Gly Arg Ser
1               5                   10                  15

Leu Arg Leu Ser Cys Ala Ala Ser Gly Phe Thr Phe Ser Ser Tyr Gly
            20                  25                  30

Met His Trp Val Arg Gln Ala Pro Gly Lys Gly Leu Glu Trp Val Ala
        35                  40                  45

Val Ile Ser Tyr Asp Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Gly Lys Ser Tyr Tyr Gly Phe Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Asp Ile Gln Met Thr Gln Ser Pro
    130                 135                 140

Ser Phe Leu Ser Ala Ser Val Gly Asp Arg Val Thr Ile Thr Cys Arg
145                 150                 155                 160

Ala Ser Gln Ile Ile Ser Ser Tyr Leu Asn Trp Tyr Gln Gln Lys Pro
                165                 170                 175
```

```
Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Gly Arg Phe Cys Asn Leu Leu Leu
    210                 215                 220

Ser Thr Glu Leu Gln Tyr Pro His Val
225                 230
```

<210> SEQ ID NO 474
<211> LENGTH: 251
<212> TYPE: PRT
<213> ORGANISM: Artificial Sequence
<220> FEATURE:
<223> OTHER INFORMATION: YU112-H01

<400> SEQUENCE: 474

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Tyr Tyr Phe Asp Tyr Trp Gly Gln Gly Thr Leu Val
            100                 105                 110

Thr Val Ser Ser Gly Ser Ala Ser Ala Pro Lys Leu Glu Glu Gly Glu
        115                 120                 125

Phe Ser Glu Ala Arg Val Glu Thr Thr Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Gln Ser Val Ser Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
        195                 200                 205

Thr Ile Ser Ser Leu Gln Pro Asp Asp Phe Ala Thr Tyr Tyr Cys Gln
    210                 215                 220

Gln Ser Tyr Ser Thr Pro Thr Trp Thr Phe Gly Gln Gly Thr Lys Val
225                 230                 235                 240

Glu Ile Lys Arg Thr Val Ala Ala Pro Ser Val
                245                 250
```

<210> SEQ ID NO 475
<211> LENGTH: 262
<212> TYPE: PRT
<213> ORGANISM: Artificial Sequence
<220> FEATURE:
<223> OTHER INFORMATION: YU112-H02

<400> SEQUENCE: 475

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Gln Pro Val Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

His Pro Gly Lys Ala Pro Lys Val Met Ile Tyr Asp Val Ser Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Cys Ser Tyr Ala Gly Ser Tyr Thr Trp Val Phe Gly Gly Gly
225                 230                 235                 240

Thr Lys Leu Thr Val Leu Gly Gln Pro Lys Ala Ala Pro Ser Val Thr
                245                 250                 255

Leu Phe Pro Pro Ser Ser
            260

<210> SEQ ID NO 476
<211> LENGTH: 786
<212> TYPE: DNA
<213> ORGANISM: Artificial Sequence
<220> FEATURE:
<223> OTHER INFORMATION: YU100-A10

<400> SEQUENCE: 476
gaggtgcagc tggtggagtc tgggggaggc gtggtccagc ctggagggtc cctgagactc        60
tcctgtgcag cctctggatt caccttcagt agctatggca tgcactgggt ccgccaggct       120
ccaggcaagg ggctggagtg ggtggcagtt atatcatatg atggaagtaa taatactat        180 gcagactccg tgaagggccg attcaccatc tccagagaca attccaagaa cacgctgtac       240
ctgcaaatga acagcctgag agctgaggac acggctgtgt attactgtgc aaaatagga       300 gctactgacc cccttgacta ctggggccag ggaaccctgg tcaccgtctc ctcagggagt       360
gcatccgccc caaagcttga agaaggtgaa ttttcagaag cacgcgtact gcctgtgctg       420
actcagcccg cctccgtgtc tgggtctcct ggacagtcga tcaccatctc tgcactgga        480 accagcagtg acgttggtgc ttataactat gtctcctggt accaacaaca cccaggcaaa       540

```
gcccccgaac tcatgattta tgatgtcagt aatcggccct ccggggtttc taatcgcttc    600
tctggctcca agtctggcaa cacggcctcc ctgaccatct ctgggctcca gcctgaggac    660
gaggctgatt attactgcag ctcatttacg accagcatcg cttgggtgtt cggcggaggg    720
accaagctga ccgtcctagg tcagcccaag gctgcccct cggtcactct gttcccgccc    780
tcctct                                                              786
```

<210> SEQ ID NO 477
<211> LENGTH: 786
<212> TYPE: DNA
<213> ORGANISM: Artificial Sequence
<220> FEATURE:
<223> OTHER INFORMATION: YU100-A11

<400> SEQUENCE: 477

```
gaggtgcagc tgcagcagtc gggggggggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtac   240
ctgcaaatga acagcctgag agctgaggac acggctgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtaca gtctgccctg   420
actcagcctc gctcagtgtc cgggtctcct ggacagtcag tcaccatctc ctgcactgga   480
accagcagtg atgttggtgg ttataactat gtctcctggt accaacagca cccaggcaaa   540 gccccaaac tcatgattta tgatgtcagt aagcggccct caggggtccc tgatcgcttc   600
tctggctcca agtctggcaa cacggcctcc ctgaccatct ctgggctcca ggctgaggat   660
gaggctgatt attactgctg ctcatatgca ggcagctaca cttgggtatt cggcggaggg   720
accaagctga ccgtcctagg tcagcccaag gctgcccct cggtcactct gttcccaccc    780
tcctct                                                              786
```

<210> SEQ ID NO 478
<211> LENGTH: 786
<212> TYPE: DNA
<213> ORGANISM: Artificial Sequence
<220> FEATURE:
<223> OTHER INFORMATION: YU100-A12

<400> SEQUENCE: 478

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtac   240
ctgcaaatga acagcctgag agctgaggac acggctgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtact gcctgtgctg   420
actcagcccc gctcagtgtc cgggtctcct ggacagtcag tcaccatctc ctgcactgga   480
accagcagtg atgttggtgg ttataactat gtctcctggt accaacagca cccaggcaaa   540
gcccccaaac tcatgattta tgatgtcagt aagcggccct caggggtccc tgatcgcttc   600
```

| | |
|---|---:|
| tctggctcca agtctggcga cacggcctcc ctgaccatct ctgggctcca ggctgaggat | 660 |
| gaggctgatt attactgttc ctcatatgca ggcagctaca cttgggtgtt cggcggaggg | 720 |
| accaagctga ccgtcctagg tcagcccaag gctgccccct cggtcactct gttcccgccc | 780 |
| tcctct | 786 |

<210> SEQ ID NO 479
<211> LENGTH: 786
<212> TYPE: DNA
<213> ORGANISM: Artificial Sequence
<220> FEATURE:
<223> OTHER INFORMATION: YU100-B01

<400> SEQUENCE: 479

| | |
|---|---:|
| caggtgcagc tggtgcagtc ggggggaggc gtggtccagc ctgggaggtc cctgagactc | 60 |
| tcctgtgcag cctctggatt caccttcagt agctatggca tgcactgggt ccgccaggct | 120 |
| ccaggcaagg gctggagtg gtggcagtt atatcatatg atggaagtaa taaatactat | 180 |
| gcagactccg tgaagggccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc caaagcttga agaaggtgaa ttttcagaag cacgcgtaca gtctgccctg | 420 |
| actcagcctc gctcagtgtc cgggtctcct ggacagtcag tcaccatctc ctgcactgga | 480 |
| accaacactg atgttggtgc ttataactat gtctcctggt accaacagta cccaggcaaa | 540 |
| gccccaaac tcatcattta tgatgtcagt aagcggccct caggggtccc tgatcgcttc | 600 |
| tctggctcca agtctggcaa cacggcctcc ctgaccatct ctgggctcca ggctgaggat | 660 |
| gaggctgatt attactgctg ctcatatgca ggcagctact cttgggtgtt cggcggaggg | 720 |
| accaagctga ccgtcctagg tcagcccaag gctgccccct cggtcactct gttcccgccg | 780 |
| tcctct | 786 |

<210> SEQ ID NO 480
<211> LENGTH: 786
<212> TYPE: DNA
<213> ORGANISM: Artificial Sequence
<220> FEATURE:
<223> OTHER INFORMATION: YU100-B03

<400> SEQUENCE: 480

| | |
|---|---:|
| caggtgcagc tggtgcagtc tggggaggc gtggtccagc ctgggaggtc cctgagactc | 60 |
| tcctgtgcag cctctggatt caccttcagt agctatggca tgcactgggt ccgccaggct | 120 |
| ccaggcaagg gctggagtg gtggcagtt atatcatatg atggaagtaa taaatactat | 180 |
| gcagactccg tgaagggccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc caaagcttga agaaggtgaa ttttcagaag cacgcgtaca gtctgtgctg | 420 |
| actcagcccc gctcagtgtc cgggtctcct gggcggtcag tcaccatctc atgcactgga | 480 |
| accagcagtg atgttggtgg ttataactat gtctcctggt accaacagca cccaggcaag | 540 |
| gccccaaac tcacactta tgatgtcgtt aagcggccct caggggtccc tgatcgctac | 600 |
| tctggctcca agtctggcaa cacggcctcc ctgaccatct ctgggctcca ggctgaggat | 660 |
| gaggccgatt attactgctg ctcatatgca ggcggctaca cttgggtgtt cggcggaggg | 720 |

```
accaaggtga ccgtcgttgg tcagcccaag gctgccccct cggtcactct gttcccaccc    780
tcctct                                                              786
```

<210> SEQ ID NO 481
<211> LENGTH: 786
<212> TYPE: DNA
<213> ORGANISM: Artificial Sequence
<220> FEATURE:
<223> OTHER INFORMATION: YU100-B06

<400> SEQUENCE: 481

```
caggtgcagc tggtggagtc gggggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagagccg attcaccatc tccagagaca attccaagaa cacgctgtac   240
ctgcaaatga acagcctgag agctgaggac acggctgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtaca gtctgccctg   420
actcagcctg cctccgtgtc tgggtctcct ggacagtcga tcaccatctc ctgcactgga   480
accagtagtg acgttggtgg ttataactat gtctcctggt accaacagca cccaggcaaa   540
gcccccaaac tcatgattta tgatgtcagt aagcggccct caggggtccc tgatcgcttc   600
tctggctcca agtctggcaa cacggcctcc ctgaccatct ctgggctcca ggctgaggat   660
gaggctgatt attactgcaa ctcatatgca ggcagctaca cttgggtgtt cggcggaggg   720
accaagctga ccgtcctagg tcagcccaag gctgccccct cggtcactct gttcccaccc   780
tcctct                                                              786
```

<210> SEQ ID NO 482
<211> LENGTH: 786
<212> TYPE: DNA
<213> ORGANISM: Artificial Sequence
<220> FEATURE:
<223> OTHER INFORMATION: YU100-B07

<400> SEQUENCE: 482

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatacg atggaagtaa taaatactat   180
gcagactccg tgaagggccg attcaccatc tccagagaca attccaagaa cacgctgtac   240
ctgcaaatga acagcctgag agctgaggac acggctgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtaca gtctgccctg   420
actcagcctc gctcagtgtc cgggtctcct ggacagtcag tcaccatgtc ctgcactgga   480
accagcagag atgttggtgg ttataattat gtctcctggt accaacatca cccaggcaaa   540
gcccccaaac tcatgattta tgatgtcagt aagcggccct caggggtccc tgatcgcttc   600
tctggctcca agtctggcaa cacggcctcc ctgaccatct ctgagctcca ggctgaggat   660
gaggctgatt attactgttg ctcatatgca ggcagctaca cttgggtgtt cggcggaggg   720
accaagctga ccgtcctagg tcagcccaag gctgccccct cggtcactct gttcccaccc   780
```

```
tcctct                                                             786

<210> SEQ ID NO 483
<211> LENGTH: 786
<212> TYPE: DNA
<213> ORGANISM: Artificial Sequence
<220> FEATURE:
<223> OTHER INFORMATION: YU100-B08

<400> SEQUENCE: 483
gaggtgcagc tggtgcagtc tggggggaggc gtggtccagc ctggggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtac   240
ctgcaaatga acagcctgag agctgaggac acggctgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtaca gtctgccctg   420
actcagcctg cctccgtgtc tgggtctcct ggcagtcga tcaccatctc ctgcactgga   480
accagcagtg acgttggtgg ttataactat gtctcctggt accaacaaca cccaggcaaa   540
gtccccagac tcttgattta tgatgtcagt aaccggccct caggggtttc tactcgcttc   600
tctggctcca agtctggcaa cacggcctcc ctgaccatct ctgggctcca gggtgaggac   660
gaggctgagt attactgcag ttcatttacg agtagtacca cttgggtgtt cggcggaggg   720
accaagctga ccgtcctggg tcagcccaag gctgccccct cggtcactct gttcccaccg   780
tcctct                                                             786

<210> SEQ ID NO 484
<211> LENGTH: 787
<212> TYPE: DNA
<213> ORGANISM: Artificial Sequence
<220> FEATURE:
<223> OTHER INFORMATION: YU100-B09

<400> SEQUENCE: 484
caggtgcagc tggtgcagtc tggggggaggc gtggtccagc ctggggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtac   240
ctgcaaatga acagcctgag agctgaggac acggctgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtaca gtctgccctg   420
actcagcctg cctccgtgtc tgggtctcct ggacagtcga tcaccatctc ctgcactgga   480
accagcagtg acgttggtgg ttataactat gtctcctggt accaacaaca cccaggcaaa   540
gccccaaac ttatgattta tgatgtcagt gatcggccct caggggtttc taatcgcttc   600
tctggctcca agtctggcaa cacggcctcc ctgaccatct ctgggctcca gcctgaggac   660
gaggctgatt attactgcag ttcatataga agcggcagca ctttgggtgt tcggcggagg   720
gaccaagctg accgtcctag gtcagcccaa ggctgccccc tcggtcactc tgttcccgcc   780
ctcctct                                                            787
```

<210> SEQ ID NO 485
<211> LENGTH: 801
<212> TYPE: DNA
<213> ORGANISM: Artificial Sequence
<220> FEATURE:
<223> OTHER INFORMATION: YU100-B12

<400> SEQUENCE: 485

```
caggtgcagc tggtggagtc tgggggaggc gtggtccagc ctggagggtc cctgagactc    60
tcctgtgcag cctctggatt caccttcagt agctatgcta tgcactgggt ccgccaggct   120
ccaggcaagg ggctggagtg ggtggcagtt atatcatatg atggaagcaa taaatactac   180
gcagactccg tgaaggaccg attcaccatc tccagagaca attccaagaa cacgctgtat   240
ctgcaaatga acagcctgag agctgaggac acggctgtgt attactgtgc gagaatcatg   300
ggctatgact acggtgacta cgacgtagtt gactactggg gccagggaac cctggtcacc   360
gtctcctcag ggagtgcatc cgccccaaag cttgaagaag tgaattttc agaagcacgc   420
gtacagtctg ccctgactca gcctcgctca gtgtccgggt ctcctggaca gtcagtcacc   480
atctcctgca ctggaaccag cagtgatgtt ggtggttata actatgtctc tggtaccaa    540
cagcacccag gcaaagcccc caaactcatg atttatgatg tcagtaagcg gccctcaggg   600
gtccctgatc gcttctctgg ctccaagtct ggcaacacgg cctccctgac catctctggg   660
ctccaggctg aggatgaggc tgattattac tgctgctcat atgcaggcag ctacacttgg   720
gtgttcggcg agggaccaa gctgaccgtc ctaggtcagc ccaaggctgc cccctcggtc   780
actctgttcc caccctcctc t                                             801
```

<210> SEQ ID NO 486
<211> LENGTH: 786
<212> TYPE: DNA
<213> ORGANISM: Artificial Sequence
<220> FEATURE:
<223> OTHER INFORMATION: YU100-C02

<400> SEQUENCE: 486

```
caggtgcagc tggtggagtc gggggggaggc gtggtccagc ctggagggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtac   240
ctgcaaatga acagcctgag agctgaggac acggccgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtaca gtctgccctg   420
actcagcctc gctcagtgtc cgggtctcct ggacagtcag tcaccatctc ctgcactgga   480
accagcagta atgttggtgg ttataactat gtctcctggt accaacagca cccaggcaaa   540
gcccccaaac tcatgattta tgatgtcagt aagcggccct caggggtccc tgatcgcttc   600
agtggctcca gtctggcaa cacggcctcc ctgaccatct ctgggctcca ggctgaggat   660
gaggctgatt attactgctg ctcatatgca ggcagctacg tttgggtgtt cggcggaggg   720
accaagctga ccgtcctcgg tcagcccaag gctgccccct cggtcactct gttcccgccg   780
tcctct                                                              786
```

<210> SEQ ID NO 487
<211> LENGTH: 786
<212> TYPE: DNA

<213> ORGANISM: Artificial Sequence
<220> FEATURE:
<223> OTHER INFORMATION: YU100-C04

<400> SEQUENCE: 487

```
caggtgcagc tggtggagtc gggggaggc gtggtccagc ctgggaggtc cctgagactc      60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtac    240
ctgcaaatga acagcttgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctc gctcagtgtc cgggtctcct ggacagtcag tcaccatctc ctgcactgga    480
accagcagtg atgttggtgg ttataactat gtctcctggt accaacacca cccaggcaaa    540
gcccccaaac tcataattta tgatgtcact aagcggccct caggggtccc tgatcgcttc    600
tctggctcca agtctggcaa cacggcctcc ctggccatct ctgggctcca ggctgaggaa    660
gaggctgatt attactgctg ctcatatgca ggcgggtaca cttgggtgtt cggcggaggg    720
accaagctga ccgtcctagg tcagcccaag gctgccccct cggtcactct gttcccgccg    780
tcctct                                                               786
```

<210> SEQ ID NO 488
<211> LENGTH: 786
<212> TYPE: DNA
<213> ORGANISM: Artificial Sequence
<220> FEATURE:
<223> OTHER INFORMATION: YU100-C05

<400> SEQUENCE: 488

```
caggtgcagc tggtggagtc tgggggaggc gtggtccagc ctgggaggtc cctgagactc      60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctg cctccgtgtc tgggtctcct ggacagtcga tcaccatctc ctgcactgga    480
accagcagtg acgttggggg ttataattat gtctcctggt atcaacaaca cccaggcaaa    540
gcccccaaac tcatgattta tgatgtcagt aatcggccct cagggatttc taatcgcttc    600
tctggctcca agtctggcaa cacggcctcc ctgaccatct ctgggctcca ggctgaggac    660
gaggctgatt attactgcag ctcatacaca agcagcattt cttgggtgtt cggcggaggg    720
accaaactga ccgtcctagg tcagcccaag gctgccccct cggtcactct gttcccgccc    780
tcctct                                                               786
```

<210> SEQ ID NO 489
<211> LENGTH: 786
<212> TYPE: DNA
<213> ORGANISM: Artificial Sequence
<220> FEATURE:
<223> OTHER INFORMATION: YU100-C10

<400> SEQUENCE: 489

```
caggtgcagc tggtggagtc ggggggaggc gtggtccagc ctggagggtc cctgagactc    60
tcctgtgcag cctctggatt caccttcggt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaaatagga   300
gctactgacc cccttgacta ctggggccag ggaaccctga tcaccgtctc ctcagggagt   360
gcatccgccc caaagcttga agaaggtgaa ttttcagaag cacgcgtaca gtctgccctg   420
actcagcctg cctccgtgtc tgggtctcct ggacagtcga tcaccatctc ctgcactgga   480
acccgcagtg acattggtgg ttatgactat gtctcctggt atcaacagca cccaggcaaa   540
gccccccaaac tcatgattta tgacgtcaat aatcggccct caggggtttc taatcgcttc   600
tctggctcca gtctggcaa cacggcctcc ctgaccatct ctgggctcca ggctgaggac   660
gaggctgagt attactgctc ctcatataca agcagcatca cttgggtgtt cggcggaggg   720
accaaggtga ccgtcctagg tcagcccaag gctgccccct cggtcactct gttcccaccc   780
tcctct                                                             786
```

<210> SEQ ID NO 490
<211> LENGTH: 786
<212> TYPE: DNA
<213> ORGANISM: Artificial Sequence
<220> FEATURE:
<223> OTHER INFORMATION: YU100-C11

<400> SEQUENCE: 490

```
caggtgcagc tggtgcagtc tgggggaggc gtggtccagc ctggagggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtac   240
ctgcaaatga acagcctgag agctgaggac acggctgtgt attactgtgc gaaaatagga   300
gctactgacc cccttgacta ctggggccag ggaaccctgg tcaccgtctc ctcagggagt   360
gcatccgccc caaagcttga agaaggtgaa ttttcagaag cacgcgtaca gtctgccctg   420
actcagcctg cctccgtgtc tgggtctcct ggacagtcga tcaccatctc ctgcactgga   480
accagcagtg acgttggtgg ttataactat gtctcctggt accaacagcg cccaggcaag   540
gccccccaaac tcatgattta tgatgtcagt aatcggccct caggggtttc taatcgcttc   600
tctggctcca gtctggcaa cacggcctcc ctgaccatct ctgggctcca gctgacgac   660
gaggctgatt attactgcag ctcatataca aacagcagga cttgggtgtt cggcggaggg   720
accaagttga ccgtcctaag tcagcccaag gctgccccct cggtcactct gttcccaccg   780
tcctct                                                             786
```

<210> SEQ ID NO 491
<211> LENGTH: 801
<212> TYPE: DNA
<213> ORGANISM: Artificial Sequence
<220> FEATURE:
<223> OTHER INFORMATION: YU100-C12

<400> SEQUENCE: 491

```
gaggtgcagc tggtgcagtc tgggggaggc gtggtccagc ctgggaggtc cctgagactc      60
tcctgtgcag cctctggatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gagaatcatg     300
ggctatgact acggtgacta cgacgtagtt gactactggg gccagggaac cctggtcacc     360
gtctcctcag ggagtgcatc cgccccaaag cttgaagaag gtgaattttc agaagcacgc     420
gtacagtctg ccctgactca gcctcgctca gtgtccgggt ctcctggaca gtcagtcacc     480
atctcctgca ctggaaccag cagtgatgtt ggtggttata actatgtctc ctggtaccaa     540
cagcacccag gcaaagcccc caaactcatg atttatgatg tcagtaagcg gccctcaggg     600
gtccctgatc gcttctctgg ctccaagtct ggcaacacgg cctccctgac catctctggg     660
ctccaggctg aggatgaggc tgattattac tgctgctcat atgcaggcag ctacacttgg     720
gtgttcggcg gagggaccaa gctgaccgtc ctaggtcagc ccaaggctgc cccctcggtc     780
actctgttcc caccgtcctc t                                                801

<210> SEQ ID NO 492
<211> LENGTH: 801
<212> TYPE: DNA
<213> ORGANISM: Artificial Sequence
<220> FEATURE:
<223> OTHER INFORMATION: YU100-D01

<400> SEQUENCE: 492
caggtgcagc tgcagcagtc gggggggaggc gtggtccagc ctgggaggtc cctgagactc     60
tcctgtgcag cctctggatt caccttcagt agctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagaatcatg    300
ggctatgact acggtgacta cgacgtagtt gactactggg gccagggaac cctggtcacc    360
gtctcctcag ggagtgcatc cgccccaaag cttgaagaag gtgaattttc agaagcacgc    420
gtacagtctg ccctgactca gcctccctcc gcgtccgggt ctcctggaca gtcagtcacc    480
atctcctgca ctggaaccag cagtgatgtc ggtggttaca actttgtctc ctggtatcaa    540
caacaccccg gcaaagcccc caaactcttg atttatgatg tcgataagcg gccctcaggg    600
gtccctgatc gcttctctgg ctccaagtct ggcagaacgg cctccctgac catctctggg    660
ctccagactg aggatgaggc taatatttat tgctgctcat atgcaggcag gtacacttgg    720
atattcggcg gagggaccaa gctgaccgtc ctcggtcagc ccaaggctgc cccctcggtc    780
attctgttcc caccgtcctc t                                              801

<210> SEQ ID NO 493
<211> LENGTH: 786
<212> TYPE: DNA
<213> ORGANISM: Artificial Sequence
<220> FEATURE:
<223> OTHER INFORMATION: YU100-D02

<400> SEQUENCE: 493
caggtgcggc tggtgcagtc tgggggaggc gtggtccagc ctgggaggtc cctgagactc     60
tcctgtgcag cctctggatt caccttcagt agctatggca tgcactgggt ccgccaggct   120
```

```
ccaggcaagg ggctggagtg ggtggcagtt atatcatatg atggaagtaa taaatactat    180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctc gctcagtgtc cgggtctcct ggacagtcag tcaccatctc ctgcactgga    480
accagcggtg atgttggtac ttataactat gtctcctggt accaacaaca cccaggcaaa    540
gcccccaaac tcatgatttt tgatgtcagt aagcggccct caggggtccc tgatcgcttc    600
tctggctcca agtctggcaa cacggcctcc ctgaccatct ctgggctcca ggctgaggat    660
gaggctgatt attactgcaa ctcatatgca ggcagctaca cttgggtgtt cggcggaggg    720
accaagctga ccgtcctagg tcagcccaag gctgccccct cggtcactct gttcccaccc    780
tcctct                                                                786

<210> SEQ ID NO 494
<211> LENGTH: 786
<212> TYPE: DNA
<213> ORGANISM: Artificial Sequence
<220> FEATURE:
<223> OTHER INFORMATION: YU100-D05

<400> SEQUENCE: 494
caggtgcagc tgcagcagtc tggggggaggc gtggtccagc ctgggaggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctc cctccgtgtc tgggtctcct ggacagttga tcaccatctc ctgcactgga    480
accaacagtg acgttggtgg ttataactat gtctcctggt accaacaaca cccaggcaaa    540
gcccccaaac tcatgattta tgatgtcagt aatcggccct caggggtttc taatcgcttc    600
tctggctcca agtctggcaa cacggcctcc ctgaccatct ctgggctcca ggctgaggat    660
gaggctgatt attactgctg ctcatatgca ggcagctaca cttgggtgtt cggcggaggg    720
accaagctga ccgtcctagg tcagcccaag gctgccccct cggtcactct gttcccaccg    780
tcctct                                                                786

<210> SEQ ID NO 495
<211> LENGTH: 801
<212> TYPE: DNA
<213> ORGANISM: Artificial Sequence
<220> FEATURE:
<223> OTHER INFORMATION: YU100-D07

<400> SEQUENCE: 495
caggtgcagc tggtggagtc tggggggaggc gtggtccagc ctgggaggtc cctgagactc     60
tcctgtgcag cctctggatt caccttcagt agctatgcta tgcactgggt ccgccaggct    120
ccaggcaagg ggctggagtg ggtggcagtt atatcatatg atggaagcaa taaatactac    180
```

-continued

```
gcagactccg tgaagggccg actcaccatc tccagagaca attccaagaa cacgctgtat    240
ctgcaaatga acagcctgag agctgaggac acggctgtgt attactgtgc gagaatcatg    300
ggctatgact acggtgacta cgacgtagtt gactactggg gccagggaac cctggtcacc    360
gtctcctcag ggagtgcatc cgccccaaag cttgaagaag tgaatttttc agaagcacgc    420
gtacagtctg ccctgactca gcctcgctca gtgtccgggt ctcctggaca gtcagtcacc    480
atctcctgca ctggaaccag cggtgatgtt ggtacttatg actatgtctc ctggtaccaa    540
cagcacccag gcaaagcccc caaactcatg atttatgatg tcagtaagcg gccctcaggg    600
gtccctgatc gcttctctgg ctccaagtct ggcaacacgg cctccctgac catctctggg    660
ctccaggctg aggatgaggc tgattattac tgcaactcat atgcaggcag ctacacttgg    720
gtgttcggcg agggaccaa gctgaccgtc ctaggtcagc ccaagactgc cccctcggtc    780
actctgttcc cgccctcctc t                                                801

<210> SEQ ID NO 496
<211> LENGTH: 786
<212> TYPE: DNA
<213> ORGANISM: Artificial Sequence
<220> FEATURE:
<223> OTHER INFORMATION: YU100-D11

<400> SEQUENCE: 496
caggtgcagc tggtgcagtc tgggggaggc gtggtccagc ctgggaggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctc gctcagtgtc cgggtctcct ggacagtcag tcaccatctc ctgcactgga    480
accagcagta atgttggtgg ttataactat gtctcctggt accaacagca cccaggcaaa    540
gcccccaaac tcatgattta tgatgtcagt aagcggccct caggggtccc tgatcgcttc    600
tctggctcca gtctggcaa cacggcctcc ctgaccatct ctgggctcca ggctgaagat    660
gaggctaatt attactgcgc ctcatatgca ggcaactaca attgggtgtt cggcggaggg    720
accaagctga ccgtccttgg tcagcccaag ctgccccct cggtcactct gttcccaccc    780
tcctct                                                              786

<210> SEQ ID NO 497
<211> LENGTH: 786
<212> TYPE: DNA
<213> ORGANISM: Artificial Sequence
<220> FEATURE:
<223> OTHER INFORMATION: YU100-E01

<400> SEQUENCE: 497
caggtgcagc tgcagcagtc tgggggaggc gtggtccagc ctgggaggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtac    240
ctgcaaatga acagcctgag agctgaggac acggctgtgt attactgtgc gaaaatagga    300
```

| gctactgacc cccttgacta ctggggccag ggaaccctgg tcaccgtctc ctcagggagt | 360 |
| gcatccgccc caaagcttga agaaggtgaa ttttcagaag cacgcgtaca gtctgccctg | 420 |
| actcagcctg cctccgtgtc tgggtctcct ggacagtcga tcaccatctc ctgcactgga | 480 |
| accagcaatg acataggtgc ttataactat gtctcctggt accaacaaca cccaggcaaa | 540 |
| gcccccaaac tcctgattta tgatgtcaat aatcggccct cagggggttc tgatcgcttc | 600 |
| tctggctcca agtctggcaa cacggcctcc ctgaccatct ctgggctcca ggctgaggat | 660 |
| gaggctgatt attactgctg ctcatatgca ggcagctact cttgggtgtt cggcggaggg | 720 |
| accaaactga ccgtcctagg tcagcccaag gccaaccccc ctgtcactct gttcccaccc | 780 |
| tcctct | 786 |

<210> SEQ ID NO 498
<211> LENGTH: 786
<212> TYPE: DNA
<213> ORGANISM: Artificial Sequence
<220> FEATURE:
<223> OTHER INFORMATION: YU100-E04

<400> SEQUENCE: 498

| caggtgcagc tgcagcagtc tgggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa taaatactat | 180 |
| gcagactccg tgaagggccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc caaagcttga agaaggtgaa ttttcagaag cacgcgtaca gtctgccctg | 420 |
| actcagcctc gctcagtgtc cgggtctcct ggacagtcag tcaccatctc ctgcactgga | 480 |
| accagcagtg atgttggtgg ttataactat gtctcctggt accaacaaca cccaggcaaa | 540 |
| accccccaaac tcatgattta tgatgtcact aagcggccct cagggggtccc tgatcacttc | 600 |
| tctggctcca agtctggcaa cacggcctcc ctgaccatct ctgggctcca ggctgaggat | 660 |
| gaggctgatt attactgctg ctcatatgca ggcagtcaca tttgggtgtt cggcggaggg | 720 |
| accaagttga ccgtcctagg tcagcccaag gctgccccct cggtcactct gttcccgccc | 780 |
| tcctct | 786 |

<210> SEQ ID NO 499
<211> LENGTH: 786
<212> TYPE: DNA
<213> ORGANISM: Artificial Sequence
<220> FEATURE:
<223> OTHER INFORMATION: YU100-E05

<400> SEQUENCE: 499

| gaggtgcagc tggtgcagtc gggggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa taaatactat | 180 |
| gcagactccg tgaagggccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |

| | |
|---|---|
| gcatccgccc caaagcttga agaaggtgaa ttttcagaag cacgcgtaca ggctgtgctg | 420 |
| actcagcctc gctcagtgtc cgggtctcct ggacagtcag tcaccatctc ctgcactgga | 480 |
| accagcagtg atgttggtgg ttataactat gtctcctggt accaacagca cccaggcaaa | 540 |
| gcccccaaac tcatgattta tgatgtcagt aagcggccct caggggtccc tgatcgcttc | 600 |
| tctggctcca agtctggcaa cacggcctcc ctgaccatct ctgggctcca ggctgaggat | 660 |
| gaggctgatt attactgctg ctcatatgca ggcagctact cctgggtgtt cggcggaggg | 720 |
| accaagctga ccgtcctagg tcagcccaag gctgccccct cggtcactct gttcccgccc | 780 |
| tcctct | 786 |

<210> SEQ ID NO 500
<211> LENGTH: 786
<212> TYPE: DNA
<213> ORGANISM: Artificial Sequence
<220> FEATURE:
<223> OTHER INFORMATION: YU100-E06

<400> SEQUENCE: 500

| | |
|---|---|
| caggtgcagc tggtggagtc tggggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa taaatactat | 180 |
| gcagactccg tgaagggccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc caaagcttga agaaggtgaa ttttcagaag cacgcgtaca gtctgccctg | 420 |
| actcagcctg cctccgtgtc tgggtttcct gaacagtcga tcaccatctc ctgcactgga | 480 |
| accagcagtg acgttggtgg ttatgactat gtctcctggt accaacaaca cccaggcaaa | 540 |
| gcccccaaac tcatgattta tgatgtcact aatcggccct caggggtttc taatcgcttc | 600 |
| tctggctcca agtctggcaa cacggcctcc ctgaccatct ctggcctcca acctgaggac | 660 |
| gaggctgatt attattgcag ctcatatacr agcaacacca cttgggtgtt cggcggaggg | 720 |
| accaagctga ccgtcctacg tcagcccaag gctgccccct cggtcactct gttcccaccg | 780 |
| tcctct | 786 |

<210> SEQ ID NO 501
<211> LENGTH: 786
<212> TYPE: DNA
<213> ORGANISM: Artificial Sequence
<220> FEATURE:
<223> OTHER INFORMATION: YU100-E07

<400> SEQUENCE: 501

| | |
|---|---|
| caggtgcagc tgcaggagtc gggggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa tagatactat | 180 |
| gcagactccg tgaagggccg attcgccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc caaagcttga agaaggtgaa ttttcagaag cacgcgtaca gtctgccctg | 420 |
| actcagcctc gctcagtgtc cgggtctcct ggacagtcag tcaccatctc ctgcactgga | 480 |

```
accagcagtg atgttggtgg ttatgactat gtctcctggt accaacagca cccaggcaaa    540
gcccccgaac tcatgattta tgatgtcact aagcggccct caggggtcgc tgatcgcttc    600
tctggctcca agtctggcaa cacggcctcc ctgaccatct ctgggctcca ggctgaggat    660
gaggctgatt attactgctg ctcatatgca ggcaggtaca cttgggtgtt cggcggaggg    720
accaagctga ccgtcctagg tcagcccaag ctgccccct cggtcactct gttcccaccc    780
tcctct                                                               786

<210> SEQ ID NO 502
<211> LENGTH: 801
<212> TYPE: DNA
<213> ORGANISM: Artificial Sequence
<220> FEATURE:
<223> OTHER INFORMATION: YU100-E08

<400> SEQUENCE: 502
caggtgcagc tggtgcagtc tggggggaggc gtggtccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gagaatcatg   300
ggctatgact acggtgacta cgacgtagtt gactactggg gccagggaac cctggtcacc   360
gtctcctcag ggagtgcatc cgccccaaag cttgaagaag gtgaattttc agaagcacgc   420
gtacagtctg ccctgactca gcctcgctca gtgtccgggt ctcctggaca gtcagtcacc   480
atctcctgca ctggaaccag cagtgatgtt ggtggttata actatgtctc ctggtaccaa   540
cagcacccag gcaaagcccc caaactcatg atttatgatg tcagtaggcg gccctcaggg   600
gtccctgatc gcttctctgg ctccaagtct ggcaacacgg cctccctgac catctctggg   660
ctccaggctg aggatgaggc tgattattac tgctgctcat atgcaggcaa ttacacttgg   720
atgttcggcg agggaccaa gctgaccgtc ctaggtcagc ccaaggctgc cccctcggtc   780
actctgttcc caccgtcctc t                                              801

<210> SEQ ID NO 503
<211> LENGTH: 801
<212> TYPE: DNA
<213> ORGANISM: Artificial Sequence
<220> FEATURE:
<223> OTHER INFORMATION: YU100-E09

<400> SEQUENCE: 503
caggtgcagc tggtggagtc ggggggaggc gtggtccagc ctgggaggtc cctgagactc    60
tcctgtgcag cctctgggtt caccttcagt agctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gagaatcatg   300
ggctatgact acggtgacta cgacgtagtt gactactggg gccagggaac cctggtcacc   360
gtctcctcag ggagtgcatc cgccccaaag cttgaagaag gtgaattttc agaagcacgc   420
gtacagtctg ccctgactca gcctcgctca gtgtccgggt ctcctggaca gtcagtcacc   480
atctcctgca ctggaaccag cagtgatgtt ggtggattat actatgtctc ctggtaccaa   540
```

| | |
|---|---|
| caacacccag gcaaagcccc caaactcatt atttatgatg tcactaaacg gccctcaggg | 600 |
| atccctgatc gcttctctgg ctccaagtct ggcaacacgg cctccctgac catctctggg | 660 |
| ctccaggctg aggatgaggc tgattattac tgctgctcat atgcaggcag ttacacttgg | 720 |
| gtgttcggca gagggaccaa gctgaccgtc ctaggtcagc ccaaggctgc cccctcggtc | 780 |
| actctgttcc caccctccac t | 801 |

<210> SEQ ID NO 504
<211> LENGTH: 786
<212> TYPE: DNA
<213> ORGANISM: Artificial Sequence
<220> FEATURE:
<223> OTHER INFORMATION: YU100-E10

<400> SEQUENCE: 504

| | |
|---|---|
| caggtgcagc tggtgcagtc tgggggaggc gtggtccagc ctggagggtc cctgagactc | 60 |
| tcctgtgcag cctctggatt caccttcagt agctatggca tgcactgggt ccgccaggct | 120 |
| ccaggcaagg ggctggagtg gtggcagtt atatcatatg atggaagtaa taaatactat | 180 |
| gcagactccg tgaagggccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc aaagcttga agaaggtgaa ttttcagaag cacgcgtaca gtctgccctg | 420 |
| actcagcctc gctcagtgtc cgggtctcct ggacagtcag tcaccatctc ctgcactgga | 480 |
| accagcagtg atgttggtgg ttataactat gtctcctggt accaacaaca cccaggcaaa | 540 |
| gcccccaaac tcatgatttt tgatgtcagt cagcggccct caggggtccc tgatcgcttc | 600 |
| tctgcctcca gtccggcaa cacggcctcc ctgaccatct ctgggctcca ggctgaggat | 660 |
| gaggctgatt attactgctg ctcatatgca ggcagctaca cttgggtgtt cggcggaggg | 720 |
| accaagctga ccgtcctagg tcagcccaag gctgccccct cggtcactct gttcccaccc | 780 |
| tcctct | 786 |

<210> SEQ ID NO 505
<211> LENGTH: 801
<212> TYPE: DNA
<213> ORGANISM: Artificial Sequence
<220> FEATURE:
<223> OTHER INFORMATION: YU100-E11

<400> SEQUENCE: 505

| | |
|---|---|
| caggtgcagc tggtggagtc gggggaggc gtggtccagc ctggagggtc cctgagactc | 60 |
| tcctgtgcag cctctggatt caccttcagt agctatggca tgcactgggt ccgccaggct | 120 |
| ccaggcaagg ggctggagtg gtggcagtt atatcatatg atggaagtaa taaatactat | 180 |
| gcagactccg tgaagggccg attcaccatc tccagagaca attccaagaa cacgctgtat | 240 |
| ctgcaaatga acagcctgag agctgaggac acggctgtgt attactgtgc gagaatcatg | 300 |
| ggctatgact acggtgacta cgacgtagtt gactactggg gccagggaac cctggtcacc | 360 |
| gtctcctcag ggagtgcatc cgccccaaag cttgaagaag tgaattttc agaagcacgc | 420 |
| gtacagtctg ccctgactca gcctcgctca gtgtccgggt ctcctggaca gtcagtcacc | 480 |
| atctcctgca ctggaaccag cagtgatgtt ggtggttata actatgtctc ctggtaccaa | 540 |
| cagcacccag gcaaagcccc caaactcatg atttatgatg tcagtaagcg gccctcaggg | 600 |
| gtccctgatc gcttctctgg ctccaagtct ggcaacacgg cctccctgac catctctggg | 660 |

```
ctccaggctg aggatgaggc tgattattac tgctgctcat atgcaggcag ctacacttgg    720
gtgttcggcg gagggaccaa gctgaccgtc ctaggtcagc ccaaggctgc ccctcggtc     780 actctgttcc caccctcctc t                                              801
```

<210> SEQ ID NO 506
<211> LENGTH: 786
<212> TYPE: DNA
<213> ORGANISM: Artificial Sequence
<220> FEATURE:
<223> OTHER INFORMATION: YU100-E12

<400> SEQUENCE: 506

```
caggtgcagc tggtggagtc gggggaggc gtggtccagc ctgggaggtc cctgagactc     60
tcctgtgcag cctctggatt caccttcagt agctatggca tgcactgggt ccgccaggct    120
ccaggcaagg gctggagtg gtggcagtt atatcatatg atggaagtaa taaatactat      180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctg cctccgtgtc tgggtctcct ggacagtcga tcaccatctc tgcactgga    480 accagcagtg acgttggtgg ttataactat gtctcctggt accaacagca cccaggcaca    540
gcccccaaac tcatgattta tgatgtcagt aatcggccct caggggtttc taatcgcttc    600
tctggctcca agtctggcaa cacggcctcc ctgaccatct ctgggctcca ggctgaggac    660
gaggctgatt attactgcag ctcatatca agcagcacca cttgggtgtt cggcggaggg    720
accaagctga ccgtcctagg tcagcccaag gctgccccct cggtcactct gttcccgccc    780
tcctct                                                              786
```

<210> SEQ ID NO 507
<211> LENGTH: 786
<212> TYPE: DNA
<213> ORGANISM: Artificial Sequence
<220> FEATURE:
<223> OTHER INFORMATION: YU100-F01

<400> SEQUENCE: 507

```
caggtgcagc tggtgcagtc tgggggaggc gtggtccagc ctgggaggtc cctgagactc    60
tcctgtgcag cctctggatt caccttcagt agctatggca tgcactgggt ccgccaggct    120
ccaggcaagg gctggagtg gtggcagtt atatcatatg atggaagtaa taaatactat      180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctg cctccgtgtc tgggtctcct ggacagtcga tcaccatctc tgcactgga    480 accggcagtg acgttggtgc ttatgactat gtctcctggt accaacaaca cccaggcaaa    540
gcccccaaac tcatgattta tgatgtcaat aatcggccct caggagtttc taatcgcttc    600
tctggctcca agtctggcaa cacggcctcc ctgaccatct ctgggctcca agctgaggac    660
gaggctgaat attactgcag ttcatttgca actagcattt cttgggtgtt cggcggaggg    720
```

```
accagactga ccgtcctagg tcagcccaag gctgccccct cggtcactct gttcccgccc    780
tcctct                                                               786
```

<210> SEQ ID NO 508
<211> LENGTH: 786
<212> TYPE: DNA
<213> ORGANISM: Artificial Sequence
<220> FEATURE:
<223> OTHER INFORMATION: YU100-F02

<400> SEQUENCE: 508

```
gaggtgcagc tggtggagtc gggggggaggc gtggtccagc ctgggaggtc cctgagactc     60
tcctgtgcag cctctggatt caccttcagt agctatggca tgcactgggt ccgccaggct    120
ccaggcaagg gctggagtg gtggcagtt atatcatatg atggaagtaa taaatactat     180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctc gctcagtgtc cgggtctcct ggacagtcag tcaccatctc ctgcactgga    480
accagcagtg atgttggtgg ttataactat gtctcctggt accaacagca cccaggcaaa    540
gcccccaaac tcatgattta tgatgtcact aagcggccct caggggtccc tgatcgcttc    600
tctggctcca agtctggcaa cacggcctcc ctgaccatct ctgggctcca ggctgacgat    660
gaggctgatt attactgctg ctcatatgca ggcagctaca cttggatatt cggcggaggg    720
accaagctga ccgtcctagg tcagcccaag gctgccccct cggtcactct gttcccaccc    780
tcctct                                                               786
```

<210> SEQ ID NO 509
<211> LENGTH: 786
<212> TYPE: DNA
<213> ORGANISM: Artificial Sequence
<220> FEATURE:
<223> OTHER INFORMATION: YU100-F05

<400> SEQUENCE: 509

```
caggtgcagc tgcagcagtc gggggggaggc gtggtccagc ctgggaggtc cctgagactc     60
tcctgtgcag cctctggatt caccttcagt agctatggca tgcactgggt ccgccaggct    120
ccaggcaagg gctggagtg gtggcagtt atatcatatg atggaagtaa taaatactat     180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca ggccgtgctg    420
actcagcccg cctccgtgtc tgggtctcct ggacagtcga tcaccatttc ctgcactgga    480
accagcagtg acattggtgg ttataactat gtctcctggt accagcaaca cccaggcaca    540
gcccccaaac tcatgattta tgatgtcagt agtcggccct caggggtttc taatcgcttc    600
tctggctcca agtctggcaa cacggcctcc ctgaccatct ctgggctcca ggctgaggac    660
gaggctgatt attactgctg ctcatatgca ggcagttaca cttgggtgtt cggcggaggg    720
accaagatga ccgtcctggg tcagcccaag gctgccccct cggtcactct gttcccaccc    780
tcctct                                                               786
```

<210> SEQ ID NO 510
<211> LENGTH: 801
<212> TYPE: DNA
<213> ORGANISM: Artificial Sequence
<220> FEATURE:
<223> OTHER INFORMATION: YU100-F06

<400> SEQUENCE: 510

```
caggtgcagc tggtggagtc tggggaggc gtggtccagc ctgggaggtc cctgagactc      60
tcctgtgcag cctctggatt caccttcagt agctatggca tgcactgggt ccgccaggct     120
ccaggcaagg gctggagtg gtggcagtt atatcatatg atggaagcaa taaatactac      180
gcagactccg tgaagggccg attcaccatc tccagagaca attccaagaa cacgctgtat     240
ctgcaaatga acagcctgag agctgaggac acggctgtgt attactgtgc gagaatcatg     300
ggctatgact acgtgactac cgacgtagtt gactactggg gccagggaac cctggtcacc     360
gtctcctcag ggagtgcatc cgccccaaag cttgaagaag gtgaattttc agaagcacgc     420
gtacagtctg ccctgactca gcctcgctca gtgtccgggt ctcctggaca gtcagtcacc     480
atctcctgca ctggatccag cagtgatgtt ggtggttata actttgtctc ctggtaccga     540
caacacccag gcgaagcccc caaactcgtg attttgatg tcaataagcg cccctcaggg      600
gtccctgatc gcttctctgg ctccaagtct ggcaacacgg cctccctgac catctcaggg     660
ctgcaaactg aggatgaggc tgattatttc tgctgctcat atgcaggcgg ctacacttgg     720
gtgttcggcg agggaccaa ggtgaccgtc gttggtcagc ccaaggctgc cccctcggtc      780
actctgttcc caccctcctc t                                              801
```

<210> SEQ ID NO 511
<211> LENGTH: 801
<212> TYPE: DNA
<213> ORGANISM: Artificial Sequence
<220> FEATURE:
<223> OTHER INFORMATION: YU100-F07

<400> SEQUENCE: 511

```
caggtgcagc tggtggagtc gggggaggc gtggtccagc ctgggaggtc cctgagactc      60
tcctgtgcag cctctggatt caccttcagt agctatgcta tgcactgggt ccgccaggct     120
ccaggcaagg gctggagtg gtggcagtt atatcatatg atggaagcaa taaatactac      180
gcagactccg tgaagggccg attcaccatc tccagagaca attccaagaa cacgctgtat     240
ctgcaaatga acagcctgag agctgaggac acggctgtgt attactgtgc gagaatcatg     300
ggctatgact acgtgactac cgacgtagtt gactactggg gccagggaac cctggtcacc     360
gtctcctcag ggagtgcatc cgccccaaag cttgaagaag gtgaattttc agaagcacgc     420
gtacagtctg ccctgactca gcctcgctca gtgtccgtgt ctcctggaca gtcagtcacc     480
atctcctgca ctggaaccag cagtgacgtt ggcggttatg aatatgtctc ctggtaccaa     540
caacacccag gcaaagcccc caaactcatg atttatgatg tcactaagag gccctcaggg     600
gtccctgatc gcttctctgg ctccaagtct ggcaacacgg cctccctgac catctctggg     660
ctccagggtg aagatgcggc tgattattac tgctgttcat atgcaggctc ttacacttgg     720
gtattcggcg aggcaccac ggtgaccgtc ctaggtcagc ccaaggctgc cccctcggtc      780
actctgttcc caccgtcctc t                                              801
```

<210> SEQ ID NO 512

```
<211> LENGTH: 786
<212> TYPE: DNA
<213> ORGANISM: Artificial Sequence
<220> FEATURE:
<223> OTHER INFORMATION: YU100-F11

<400> SEQUENCE: 512
caggtgcagc tggtggagtc tgggggaggc gtggtccagc ctggaggtc cctgagactc      60
tcctgtgcag cctctggatt caccttcagt agctatggca tgcactggt ccgccaggct     120
ccaggcaagg gctggagtg gtggcagtt atatcatatg atggaagtaa taaatactat     180
gcagactccg tgaagggccg attcaccatc tccagacaca attccaagaa cacgctgtac     240
ctgcaaatga acagcctgag agctgaggac acggctgtgt attactgtgc gaaaatagga     300
gctactgacc cccttgacta ctggggccag ggaaccctgg tcaccgtctc ctcagggagt     360
gcatccgccc caaagcttga agaaggtgaa ttttcagaag cacgcgtaca gtctgccctg     420
actcagcctg cctccgtgtc tgggtctcct ggacagtcga tcaccatctc ctgcactggg     480
agcagtagtg acgttgctgg ttataactat gtctcctggt accaacagca cccaggcaaa     540
gccccccaaac tcatgattta tgatgtcact aagcggccct caggggtccc tgatcgcttc     600
tctggctcca agtctggcaa cacggcctcc ctgaccatct ctgggctcca ggctgaggat     660
gaggctgatt attactgctg ctcatatgca ggcagttaca cttgggtttt cggcggaggg     720
acccagctga ccgtcctagg tcagcccaag gctgccccct cggtcactct gttcccgccg     780
tcctct                                                               786

<210> SEQ ID NO 513
<211> LENGTH: 786
<212> TYPE: DNA
<213> ORGANISM: Artificial Sequence
<220> FEATURE:
<223> OTHER INFORMATION: YU100-G01

<400> SEQUENCE: 513
caggtgcagc tggtgcagtc tgggggaggc gtggtccagc ctggaggtc cctgagactc      60
tcctgtgcag cctctggatt caccttcagt agctatggca tgcactggt ccgccaggct     120
ccaggcaagg gctggagtg gtggcagtt atatcatatg atggaagtaa taaatactat     180
gcagactccg tgaagggccg attcaccatc tccagacaca attccaagaa cacgctgtac     240
ctgcaaatga acagcctgag agctgaggac acggctgtgt attactgtgc gaaaatagga     300
gctactgacc cccttgacta ctggggccag ggaaccctgg tcaccgtctc ctcagggagt     360
gcatccgccc caaagcttga agaaggtgaa ttttcagaag cacgcgtaca gtctgccctg     420
actcagcctc gctcagtgtc cgcgtctcct ggacagtcag tcaccatctc ctgcactgga     480
accagcagtg atgttggtgc ttataactat gtctcctggt accaacaaca ccccggcaaa     540
gccccccaaac tcatgcttta tgatgtcaat aagcggccct caggggtccc tgatcgcttc     600
tctggctcca agtctggcaa cacggcctcc ctgaccatct ctaggctcca ggctgaggat     660
gaggctgatt attactgctg ctcatatgca ggcagctaca cttgggtgtt cggcggaggg     720
accaagctga ccgtcctagg tcagcccaag gctgccccct cggtcactct gttcccgccc     780
tcctct                                                               786

<210> SEQ ID NO 514
<211> LENGTH: 786
<212> TYPE: DNA
<213> ORGANISM: Artificial Sequence
```

<220> FEATURE:
<223> OTHER INFORMATION: YU100-G07

<400> SEQUENCE: 514

| caggtgcagc | tggtggagtc | tgggggaggc | gtggtccagc | ctgggaggtc | cctgagactc | 60 |
| tcctgtgcag | cctctggatt | caccttcagt | agctatggca | tgcactgggt | ccgccaggct | 120 |
| ccaggcaagg | ggctggagtg | ggtggcagtt | atatcatatg | atggaagtaa | taaatactat | 180 |
| gcagactccg | tgaagggccg | attcaccatc | tccagagaca | attccaagaa | cacgctgtac | 240 |
| ctgcaaatga | acagcctgag | agctgaggac | acggctgtgt | attactgtgc | gaaaatagga | 300 |
| gctactgacc | cccttgacta | ctggggccag | ggaaccctgg | tcaccgtctc | ctcagggagt | 360 |
| gcatccgccc | aaagcttga | agaaggtgaa | ttttcagaag | cacgcgtaca | gtctgccctg | 420 |
| actcagcctg | cctccgtgtc | tgggtctcct | ggacagtcga | tcaccatctc | ctgcactgga | 480 |
| accagcagtg | acgttggtgc | ttatgactat | gtctcctggt | atcaacaaca | cccaggcaaa | 540 |
| gcccccaaac | tcatgattta | tgatgtcact | aatcggccct | caggggtttc | taatcgcttc | 600 |
| tctggctcca | agtctggcaa | cacggcctcc | ctgaccatct | ctgggctcca | ggctgaggac | 660 |
| gaggctgatt | attactgcgc | tcatacaca | cgcagcagcg | tttgggtgtt | cggcggaggg | 720 |
| accaaactga | ccgtcttagg | tcagcccaag | gctgcctcct | cggtcactct | gttcccaccc | 780 |
| tcctct |  |  |  |  |  | 786 |

<210> SEQ ID NO 515
<211> LENGTH: 786
<212> TYPE: DNA
<213> ORGANISM: Artificial Sequence
<220> FEATURE:
<223> OTHER INFORMATION: YU100-G08

<400> SEQUENCE: 515

| caggtgcagc | tggtgcagtc | tgggggaggc | gtggtccagc | ctgggaggtc | cctgagactc | 60 |
| tcctgtgcag | cctctggatt | caccttcagt | agctatggca | tgcactgggt | ccgccaggct | 120 |
| ccaggcaagg | ggctggagtg | ggtggcagtt | atatcatatg | atggaagtaa | taaatactat | 180 |
| gcagactccg | tgaagggccg | attcaccatc | tccagagaca | attccaagaa | cacgctgtac | 240 |
| ctgcaaatga | acagcctgag | agctgaggac | acggctgtgt | attactgtgc | gaaaatagga | 300 |
| gctactgacc | cccttgacta | ctggggccag | ggaaccctgg | tcaccgtctc | ctcagggagt | 360 |
| gcatccgccc | aaagcttga | agaaggtgaa | ttttcagaag | cacgcgtaca | gtctgccctg | 420 |
| actcagcctc | gctcagtgtc | cgggtctcct | ggacagtcag | tcaccctctc | ctgtactgga | 480 |
| accagcagtg | atgttggtgg | ttataactat | gtctcctggt | accaacacta | cccaggcaaa | 540 |
| gcccccaaac | tcatgatttt | tgatgtcaat | gagcggtcct | caggagtccc | tgatcgcttc | 600 |
| tctggctcca | agtctggcaa | cacggcctcc | ctgaccatct | ctgggctcca | ggctgaggat | 660 |
| gaggctgatt | attactgctg | ctcatatgca | ggcaggtaca | cttggatgtt | cggcggaggg | 720 |
| accaaagtga | ccgtcctagg | tcagcccaag | gctgccccct | cggtcactct | gttcccgccc | 780 |
| tcctct |  |  |  |  |  | 786 |

<210> SEQ ID NO 516
<211> LENGTH: 786
<212> TYPE: DNA
<213> ORGANISM: Artificial Sequence
<220> FEATURE:
<223> OTHER INFORMATION: YU100-G09

<400> SEQUENCE: 516

```
gaggtgcagc tggtggagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg gtggcagtt atatcatatg atggaagtaa taaatactat     180
gcagactccg tgaagggccg attcaccatc tccagagaca attccaagaa cacgctgtac     240
ctgcaaatga acagcctgag agctgaggac acggctgtgt attactgtgc gaaaatagga     300
gctactgacc cccttgacta ctggggccag ggaaccctgg tcaccgtctc ctcagggagt     360
gcatccgccc caaagcttga agaaggtgaa ttttcagaag cacgcgtaca gtctgccctg     420
actcagcctc gctcagtgtc cgggtctcct ggacagtcag tcaccatctc ctgcactgga     480
accatcagtg atgttggtgg ttataactat gtctcctggt accaacagca cccaggcaaa     540
gcccccaaac tcatgattta tgatgtcact aagcggccct caggggtccc tgatcgcttc     600
tctggctcca agtctggcaa cacggcctcc ctgaccatct ctgggctcca ggctgaggat     660
gaggctggtt attactgctc ctcatatgca ggcagctaca cttgggtgtt cggcggaggg     720
accaagctga ccgtcctagg tcagcccaag gctgccccct cggtcactct gttcccaccc     780
tcctct                                                                786

<210> SEQ ID NO 517
<211> LENGTH: 786
<212> TYPE: DNA
<213> ORGANISM: Artificial Sequence
<220> FEATURE:
<223> OTHER INFORMATION: YU100-G10

<400> SEQUENCE: 517
caggtgcagc tggtgcagtc gggggaggc gtggtccagc ctgggaggtc cctgagactc      60
tcctgtgcag cctctggatt caccttcagt agctatggca tgcactgggt ccgccaggct     120
ccaggtaagg ggctggagtg gtggcagtt atatcatatg atggaagtaa taaatactat     180
gcagactccg tgaagggccg attcaccatc tccagagaca attccaagaa cacgctgtac     240
ctgcaaatga acagcctgag agctgaggac acggctgtgt attactgtgc gaaaatagga     300
gctactgacc cccttgacta ctggggccag ggaaccctgg tcaccgtctc ctcagggagt     360
gcatccgccc caaagcttga agaaggtgaa ttttcagaag cacgcgtaca gtctgccctg     420
actcagcctg cctccgtgtc tgggtctctt ggacagtcga tcaccatgtc ctgcactgga     480
accagaagag acgttggtgg ttatgacttt gtctcctggt accaacagta ccccggcaaa     540
gcccccaagc tcatcattta cgatgtcagc aatcggccct cggggttttc taatcgcttc     600
actggctcca agtctggcaa cacggcctcc ctgaccatct ctgggctcca ggctgaggat     660
gaggctgatt attactgctg ctcatatgca ggcacctaca cttgggtgtt cggcggaggg     720
accaaggtga ccgtcctagg tcagcccaag gctgccccct cggtcactct gttcccgccc     780
tcctct                                                                786

<210> SEQ ID NO 518
<211> LENGTH: 801
<212> TYPE: DNA
<213> ORGANISM: Artificial Sequence
<220> FEATURE:
<223> OTHER INFORMATION: YU100-G11

<400> SEQUENCE: 518
caggtgcagc tggtggagtc tgggggaggc gtggtccagc ctgggaggtc cctgagactc      60
```

```
tcctgtgcag cctctggatt caccttcagt agctatggca tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagaatcatg    300
ggctatgact acggtgacta cgacgtagtt gactactggg gccagggaac cctggtcacc    360
gtctcctcag ggagtgcatc cgccccaaag cttgaagaag gtgaattttc agaagcacgc    420
gtacagtctg ccctgactca gcctcgctca gtgtccgggt ctcctgggca gtcagtcacc    480
atctcatgca ctggaaccag cagtgatgtt ggtggttata actatgtctc ctggtaccaa    540
cagcacccag gcaaggcccc caaactcacg ctttatgatg tcggtaagcg cccctcaggg    600
gtccctgatc gcttctctgg ctccaagtct ggcaacacgg cctccctgac catctctggg    660
ctccaggctg aggatgaggc tgattattac tgctgctcat atgcaggcgg ctacacttgg    720
gtgttcggcg agggaccaa ggtgaccgtc gtaggtcagc ccaaggctgc cccctcggtc    780
actctgttcc caccctcctc t                                              801

<210> SEQ ID NO 519
<211> LENGTH: 801
<212> TYPE: DNA
<213> ORGANISM: Artificial Sequence
<220> FEATURE:
<223> OTHER INFORMATION: YU100-H01

<400> SEQUENCE: 519
caggtgcagc tggtgcagtc ggggggaggc gtggtccagc ctgggaggtc cctgagactc     60
tcctgtgcag cctctggatt caccttcagt agctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagaatcatg    300
ggctatgact acggtgacta cgacgtagtt gactactggg gccagggaac cctggtcacc    360
gtctcctcag ggagtgcatc cgccccaaag cttgaagaag gtgaattttc agaagcacgc    420
gtacagtctg ccctgactca gcctcgctca gtgtccgggt ctcctggaca gtcagtcacc    480
atctcctgca ctggaaccag cagtgatgtt ggtgcttata actatgtctc ctggtaccag    540
cagcacccag gcaaagcccc caaactcatg atttatgatg tcagtgagcg cccctcaggg    600
gtccctgatc gcttctctgg ctccaagtct ggcaacacgg cctccctgac catctctggg    660
ctccaggctg aggatgaggc tgattattac tgctgctcat atgcaggcag ctacacttgg    720
gtgttcggcg agggaccaa gctgaccgtc ctaggtcagc ccaaggctgc cccctcggtc    780
actctgttcc caccgtcctc t                                              801

<210> SEQ ID NO 520
<211> LENGTH: 801
<212> TYPE: DNA
<213> ORGANISM: Artificial Sequence
<220> FEATURE:
<223> OTHER INFORMATION: YU100-H02

<400> SEQUENCE: 520
caggtgcagc tgcagcagtc tggggggaggc gtggtccagc ctgggaggtc cctgagactc     60
tcctgtgcag cctctggatt caccttcagt agctatggca tgcactgggt ccgccaggct    120
```

| | |
|---|---|
| ccaggcaagg ggctggagtg ggtggcagtt atatcatatg atggaagtaa taaatactat | 180 |
| gcagactccg tgaagggccg attcaccatc tccagagaca attccaagaa cacgctgtat | 240 |
| ctgcaaatga acagcctgag agctgaggac acggctgtgt attactgtgc gagaatcatg | 300 |
| ggctatgact acggtgacta cgacgtagtt gactactggg gccagggaac cctggtcacc | 360 |
| gtctcctcag ggagtgcatc cgccccaaag cttgaagaag gtgaattttc agaagcacgc | 420 |
| gtacagtctg ccctgactca gcctcgctca gtgtccaggt ctcctggaca gtcagtcacc | 480 |
| atctcctgca ctggaaccag cagtgatgtt ggtacttata actatgtctc ctggtaccaa | 540 |
| cagcacccag gcaaagcccc caaactcatg atttatgatg tcagtaagcg gccctcaggg | 600 |
| gtccctgatc gcttctctgg ctccaagtct ggcaacacgg cctccctgac catctctggg | 660 |
| ctccaggctg aggatgaggc tgattattac tgctgctcat atgcaggctt ctacacttgg | 720 |
| gtgttcggcg agggaccaa gctgaccgtc ctaggtcagc ccaaggctgc cccctcggtc | 780 |
| actctgttcc caccgtcctc t | 801 |

<210> SEQ ID NO 521
<211> LENGTH: 801
<212> TYPE: DNA
<213> ORGANISM: Artificial Sequence
<220> FEATURE:
<223> OTHER INFORMATION: YU100-H04

<400> SEQUENCE: 521

| | |
|---|---|
| caggtgcagc tggtggagtc tgggggaggc gtggtccagc ctgggaggtc cctgagactc | 60 |
| tcctgtgcag cctctggatt caccttcagt agctatgcta tgcactgggt ccgccaggct | 120 |
| ccaggcaagg ggctggagtg ggtggcagtt atatcatatg atggaagcaa taaatactac | 180 |
| gcagactccg tgaagggccg attcaccatc tccagagaca attccaagaa cacgctgtat | 240 |
| ctgcaaatga acagcctgag agctgaggac acggctgtgt attactgtgc gagaatcatg | 300 |
| ggctatgact acggtgacta cgacgtagtt gactactggg gccagggaac cctggtcacc | 360 |
| gtctcctcag ggagtgcatc cgccccaaag cttgaagaag gtgaattttc agaagcacgc | 420 |
| gtacagtctg ccctgactca gcctgcctcc gtgtctgggt ctcctggaca gtcgatcacc | 480 |
| atctcctgca cgggaaccag cagtgacatt ggtgtttata actatgtctc ctggtaccaa | 540 |
| cagcacccag gcaaagcccc caaactcatg atttatgatg tcagtaagcg gccctcaggg | 600 |
| gtccctgatc gcttctctgg ctccaagtct ggcaacacgg cctccctgac catctctggg | 660 |
| ctccaggctg aggatgaggc tgattattac tgctgctcat atgcgggcag ctacacctgg | 720 |
| gtgttcggcg agggaccaa gctgaccgtc ctaggtcagc ccaaggctgc cccctcggtc | 780 |
| actctgttcc cgccctcctc t | 801 |

<210> SEQ ID NO 522
<211> LENGTH: 786
<212> TYPE: DNA
<213> ORGANISM: Artificial Sequence
<220> FEATURE:
<223> OTHER INFORMATION: YU100-H05

<400> SEQUENCE: 522

| | |
|---|---|
| caggtgcagc tggtggagtc tgggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa taaatactat | 180 |
| gcagactccg tgaagggccg attcaccatc tccagagaca attccaagaa cacgctgtac | 240 |

```
ctgcaaatga acagcctgag agctgaggac acggctgtgt attactgtgc gaaaatagga      300
gctactgacc cccttgacta ctggggccag ggaaccctgg tcaccgtctc ctcagggagt      360
gcatccgccc caaagcttga agaaggtgaa ttttcagaag cacgcgtaca ggctgtgctg      420
actcagcctc gctcagtgtc cgggtctcct ggacagtcaa tcaccatctc ctgcactgga      480
accggcagta atgttggtgg ttataactat gtctcctggt atcaacaaca cccaggccaa      540 gccccaaac tcatgattta tgatgtcagt aagaggccct caggggtccc tgatcgcttc       600
tctggctcca agtctggcaa cacggcctcc ctgaccatct ctgggctcca ggctgaggat      660
gaggctgatt attattgctg ctcatatgca ggcacctaca cttgggtgtt cggcggaggg      720
accaagctga ccgtcctagg tcagcccaag gctgcccct cggtcactct gttcccaccc       780
tcctct                                                                 786
```

<210> SEQ ID NO 523
<211> LENGTH: 786
<212> TYPE: DNA
<213> ORGANISM: Artificial Sequence
<220> FEATURE:
<223> OTHER INFORMATION: YU100-H06
<220> FEATURE:
<221> NAME/KEY: misc_feature
<222> LOCATION: (405)..(405)
<223> OTHER INFORMATION: n is a, c, g, or t

<400> SEQUENCE: 523

```
caggtgcagc tggtggagtc tggggggaggc gtggtccagc ctgggaggtc cctgagactc      60
tcctgtgcag cctctggatt caccttcagt agctatggca tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtac      240
ctgcaaatga acagcctgag agctgaggac acggctgtgt attactgtgc gaaaatagga      300
gctactgacc cccttgacta ctggggccag ggaaccctgg tcaccgtctc ctcagggagt      360
gcatccgccc caaagcttga agaaggtgaa ttttcagaag cacgnataca gtctgccctg      420
actcagcctc gctcagtgtc cgggtctcct ggacagtcag tcaccatctc ctgcactgga      480
accagcagtg atgttggtgg ttataactat gtctcctggt accaacagca cccaggcaaa      540 gccccaaat tgatgattta tgatgtcact aagcggccct caggggtccc tgatcgcttc       600
tctggctcca agtctggcaa cacggcctcc ctgaccatct ctgggctcca ggctgaagat      660
gaggctgatt attattgctc ctcatatgca ggcagctaca cttgggtgtt cggcggaggg      720
accaagctga ccgtcctagg tcagcccaag gctgcccct cggtcactct gttcccaccc       780
tcctct                                                                 786
```

<210> SEQ ID NO 524
<211> LENGTH: 801
<212> TYPE: DNA
<213> ORGANISM: Artificial Sequence
<220> FEATURE:
<223> OTHER INFORMATION: YU100-H09

<400> SEQUENCE: 524

```
caggtgcagc tggtgcagtc gggggaggc gtggtccagc ctgggaggtc cctgagactc       60
tcctgtgcag cctctggatt caccttcagt agctatgcta tgcactgggt ccgccaggct      120
ccaggcaagg ggctggagtg ggtggcagtt atatcatatg atggaagcaa taaatactac      180
```

| | |
|---|---|
| gcagactccg tgaagggccg attcaccatc tccagagaca attccaagaa cacgctgtat | 240 |
| ctgcaaatga acagcctgag agctgaggac acggctgtgt attactgtgc gagaatcatg | 300 |
| ggctatgact acggtgacta cgacgtagtt gattactggg gccagggaac cctggtcacc | 360 |
| gtctcctcag ggagtgcatc cgccccaaag cttgaagaag gtgaattttc agaagcacgc | 420 |
| gtacagtctg ccctgactca gcctgcctcc gtgtctgggt ctcctggaca gtcgatcacc | 480 |
| atctcctgca ctggaaccag cagtgacgtt ggtggttata actatgtctc ctggtaccaa | 540 |
| cagcacccag gcaaagcccc caaactcatg atttatgatg tcagtaatcg gccctcaggg | 600 |
| gtttctaatc gcttctctgg ctccaagtct ggcaacacgg cctccctgac catctctggg | 660 |
| ctccaggctg aggacgaggc tgattattac tgctgttcat atgcaggcag ctacacttgg | 720 |
| gtgttcggcg agggaccaa gctgaccgtc ctaggtcagc ccaaggctgc cccctcggtc | 780 |
| actctgttcc cgccgtcctc t | 801 |

<210> SEQ ID NO 525
<211> LENGTH: 786
<212> TYPE: DNA
<213> ORGANISM: Artificial Sequence
<220> FEATURE:
<223> OTHER INFORMATION: YU100-H11

<400> SEQUENCE: 525

| | |
|---|---|
| caggtgcagc tggtgcagtc tggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa taaatactat | 180 |
| gcagactccg tgaagggccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc caaagcttga agaaggtgaa ttttcagaag cacgcgtaca gtctgccctg | 420 |
| actcagcctg cctccgtgtc tgggtctcct ggacagtcga tcaccatctc ctgcactgga | 480 |
| accagcagtg acgttggtgg ttataactat gtctcctggt accaacaaca cccaggcaaa | 540 |
| gcccccaaac tcatgattta tgatgtcagt aatcggccct caggggtttc taatcgcttc | 600 |
| tctggctcca gtctggcaa cacgcctcc ctgaccatct ctgggctcca ggctgaggat | 660 |
| gaggctgatt attactgctg ctcatatgca ggcagctaca cttgggtgtt cggcggaggg | 720 |
| accaagctga ccgtcctagg tcagcccaag ctgcccccct cggtcactct gttcccaccc | 780 |
| tcctct | 786 |

<210> SEQ ID NO 526
<211> LENGTH: 786
<212> TYPE: DNA
<213> ORGANISM: Artificial Sequence
<220> FEATURE:
<223> OTHER INFORMATION: YU112-A07

<400> SEQUENCE: 526

| | |
|---|---|
| caggtgcagc tggtggagtc tggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa taaatactat | 180 |
| acagactccg tgaagggccg attcaccatc tccagagaca attccaagaa cacgctgtac | 240 |
| ctgcaaatga acagcctgag agctgaggac acggctgtgt attactgtgc gaaaatagga | 300 |

```
gctactgacc cccttgacta ctggggccag ggaaccctgg tcaccgtctc ctcagggagt      360
gcatccgccc caaagcttga agaaggtgaa ttttcagaag cacgcgtaca gtctgccctg      420
actcagcctc gctcagtgtc cgggtctcct ggacagtcag tcaccatctc ctgcactgga      480
accatcagtg atgttggtgg ttataactat gtctcctggt accaacagca cccaggcaaa      540 gccccaaac tcatgattta tgatgtcact aagcggccct caggggtccc tgatcgcttc       600
tctggctcca agtctggcaa cacggcctcc ctgaccatct ctgggctcca ggctgaggat      660
gaggctggtt attactgctc ctcatatgca ggcagctaca cttgggtgtt cggcggaggg      720
accgagctga ccgtcctgag tcagcccaag ctgcccct cggtcactct gttcccgccc        780
tcctct                                                                 786
```

<210> SEQ ID NO 527
<211> LENGTH: 786
<212> TYPE: DNA
<213> ORGANISM: Artificial Sequence
<220> FEATURE:
<223> OTHER INFORMATION: YU112-B06

<400> SEQUENCE: 527

```
caggtgcagc tggtggagtc gggggggaggc gtggtccagc ctgggaggtc cctgagactc      60
tcctgtgcag cctctggatt caccttcagt agctatggca tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtac      240
ctgcaaatga acagcctgag agctgaggac acggctgtgt attactgtgc gaaaatagga      300
gctactgacc cccttgacta ctggggccag ggaaccctgg tcaccgtctc ctcagggagt      360
gcatccgccc caaagcttga agaaggtgaa ttttcagaag cacgcgtaca gtctgccctg      420
actcagcctg cctccgtgtc tgggtctcct ggacagtcga tcaccatctc ctgcactgga      480
accagcagtg acgttggtgg ttataactat gtctcctggt accaacagca cccaggcaaa      540 gccccaaac tcatgattta tgatgtcagt aatcggccct caggggtttc taatcgcttc       600
tctggctcca agtctggcaa cacggcctcc ctgaccatct ttgggctcca ggctgaggac      660
gaggctgatt attactgcag ctcatataca agcagtagca gttgggtgtt cggcggaggg      720
accaagctga ccgtcctagg tcagcccaag ctgcccct cggtcactct gttcccgccc        780
tcctct                                                                 786
```

<210> SEQ ID NO 528
<211> LENGTH: 759
<212> TYPE: DNA
<213> ORGANISM: Artificial Sequence
<220> FEATURE:
<223> OTHER INFORMATION: YU112-C03

<400> SEQUENCE: 528

```
caggtgcagc tggtggagtc tgggggaggc gtggtccagc ctgggaggtc cctgagactc      60
tcctgtgcag cctctggatt caccttcagt agctatggca tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtat      240
ctgcaaatga acagcctgag agctgaggac acggctgtgt attactgtgc gaaaggggga      300
aagagctact acggatttga ctactggggc cagggaaccc tggtcaccgt ctcctcaggg      360
```

| | |
|---|---|
| agtgcatccg cccaaagct tgaagaaggt gaattttcag aagcacgcgt agacagcgtg | 420 |
| atgacccagt ctccatcctc cctgtctgca tctgtagggg acagagtcac catcacttgc | 480 |
| cgggcaagtc aggccattaa cagctattta aattggtatc agcagaaacc agggaaagcc | 540 |
| cctaagctcc tgatctatgc tgcatccagt ttgcagagtg ggtcccatc aaggttcagt | 600 |
| ggcagtggat ctgggacaga tttcactctc accatcagcg gtctgcaacc tgaagatttt | 660 |
| gcaacttact actgtcaaca gagttacagt accccttcgt ggacgttcgg ccaagggacc | 720 |
| aaggtggaaa tcaaacgaac tgtggctgca ccatctgtc | 759 |

<210> SEQ ID NO 529
<211> LENGTH: 801
<212> TYPE: DNA
<213> ORGANISM: Artificial Sequence
<220> FEATURE:
<223> OTHER INFORMATION: YU112-C05

<400> SEQUENCE: 529

| | |
|---|---|
| gaggtgcagc tggtggagtc tgggggaggc gtggtccagc ctgggaggtc cctgagactc | 60 |
| tcctgtgcag cctctggatt caccttcagt agctatgcta tgcactgggt ccgccaggct | 120 |
| ccaggcaagg ggctggagtg ggtggcagtt atatcatatg atggaagcaa taaatactac | 180 |
| gcagactccg tgaagggccg attcaccatc tccagagaca attccaagaa cacgctgtat | 240 |
| ctgcaaatga acagcctgag agctgaggac acggctgtgt attactgtgc gagaatcatg | 300 |
| ggctatgact acggtgacta cgacgtagtt gactactggg gccagggaac cctggtcacc | 360 |
| gtctcctcag ggagtgcatc cgccccaaag cttgaagaag tgaattttc agaagcacgc | 420 |
| gtacagtctg ccctgactca gcctcgctca gtgtccgggt ctcctggaca gtcagtcacc | 480 |
| atctcctgca ctggaaccat cagtgatgtt ggtggttata actatgtctc ctggtaccaa | 540 |
| cagcacccag gcaaagcccc caaactcatg atttatgatg tcactaagcg gccctcaggg | 600 |
| gtccctgatc gcttctctgg ctccaagtct ggcaacacgg cctccctgac catctctggg | 660 |
| ctccaggctg aggatgaggc tggttattac tgctcctcat atgcaggcag ctacacttgg | 720 |
| gtgttcggcg agggaccga gctgaccgtc ctgagtcagc ccaaggctgc cccctcggtc | 780 |
| actctgttcc cgccctcctc t | 801 |

<210> SEQ ID NO 530
<211> LENGTH: 753
<212> TYPE: DNA
<213> ORGANISM: Artificial Sequence
<220> FEATURE:
<223> OTHER INFORMATION: YU112-C09

<400> SEQUENCE: 530

| | |
|---|---|
| caggtgcagc tggtgcagtc tggggggaggc gtggtccagc ctgggaggtc cctgagactc | 60 |
| tcctgtgcag cctctggatt caccttcggt agctatggca tgcactgggt ccgccaggct | 120 |
| ccaggcaagg ggctggagtg ggtggcagtt atatcatatg atggaagtaa taaatactat | 180 |
| gcagactccg tgaagggccg attcaccatc tccagagaca attccaagaa cacgctgtat | 240 |
| ctgcaaatga acagcctgag agctgaggac acggctgtgt attactgtgc gaaaggttcg | 300 |
| tactactttg actactgggg ccagggaacc ctggtcaccg tctcctcagg gagtgcatcc | 360 |
| gccccaaagc ttgaagaagg tgaattttca gaagcacgcg tagaaacgac actcacgcag | 420 |
| tctccagcca ccctgtctgt gtctccaggg gaaagagcca cctcctctg cagggccagt | 480 |
| cagagtttta gcagcagcta cttagcctgg taccagcaga aacctggcca ggctcccagg | 540 |

| | |
|---|---|
| ctcctcatct atggtgcatc cagaagagcc cctggcatcc cagacaggtt cagtggcagt | 600 |
| gggtctggga cagacttcag tctcaccatc agcagactgg agcctgaaga ttttgcagtg | 660 |
| tattactgtc agcagtctag cacctcaccc acgtgggcgt tcggccgagg gaccaaggtg | 720 |
| gaagtcaaac gaactgtggc tgcaccatct gtc | 753 |

<210> SEQ ID NO 531
<211> LENGTH: 786
<212> TYPE: DNA
<213> ORGANISM: Artificial Sequence
<220> FEATURE:
<223> OTHER INFORMATION: YU112-D08

<400> SEQUENCE: 531

| | |
|---|---|
| caggtgcagc tggtggagtc tggggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg atggaagtaa taaatactat | 180 |
| gcagactccg tgagggcccg attcaccatc tccagagaca attccaagaa cacgctgtac | 240 |
| ctgcaaatga acagcctgag agctgaggac acggctgtgt attactgtgc gaaaatagga | 300 |
| gctactgacc cccttgacta ctggggccag ggaaccctgg tcaccgtctc ctcagggagt | 360 |
| gcatccgccc caaagcttga agaaggtgaa ttttcagaag cacgcgtaca gtctgccctg | 420 |
| actcagcctc gctcagtgtc cgggtctcct ggacagtcag tcaccatctc ctgcactgga | 480 |
| accatcagtg atgttggtgg ttataactat gtctcctggt accaacagca cccaggcaaa | 540 |
| gcccccaaac tcatgattta tgatgtcact aagcggccct caggggtccc tgatcgcttc | 600 |
| tctggctcca agtctggcaa cacggcctcc ctgaccatct ctgggctcca ggctgaggat | 660 |
| gaggctggtt attactgctc ctcatatgca ggcagctaca cttgggtgtt cggcggaggg | 720 |
| accgagctga ccgtcctgag tcagcccaag gctgccccct cggtcactct gttcccgccc | 780 |
| tcctct | 786 |

<210> SEQ ID NO 532
<211> LENGTH: 753
<212> TYPE: DNA
<213> ORGANISM: Artificial Sequence
<220> FEATURE:
<223> OTHER INFORMATION: YU112-E07

<400> SEQUENCE: 532

| | |
|---|---|
| caggtgcagc tggtgcagtc ggggggaggc gtggtccagc ctgggaggtc cctgagactc | 60 |
| tcctgtgcag cctctggatt caccttcggt agctatggca tgcactgggt ccgccaggct | 120 |
| ccaggcaagg ggctggagtg ggtggcagtt atatcatatg atggaagtaa taaatactat | 180 |
| gcagactccg tgaagggccg attcaccatc tccagagaca attccaagaa cacgctgtat | 240 |
| ctgcaaatga acagcctgag agctgaggac acggctgtgt attactgtgc gaaaggttcg | 300 |
| tactactttg actactgggg ccagggaacc ctggtcaccg tctcctcagg gagtgcatcc | 360 |
| gccccaaagc ttgaagaagg tgaattttca gaagcacgcg tagaaattgt gatgactcag | 420 |
| tctccagact ccctggctgt gtctctgggc gagagggcca ccatcaactg caagtccagc | 480 |
| cagagtgtta acagcgccta cttagcctgg taccagcaca aacctggcca gcctcccaga | 540 |
| ctcctcattt atggtgcatc tcgcaggtc actggcgtcc cagacaggtt cagtggcagt | 600 |
| gggtctggga cagacttcac tctcaccatc agcagtctgc aaccagaaga ttttgcaact | 660 |

```
tactactgtc aacagagtta cagtgaccct cggtggacgt tcggccaagg gaccaaggtg    720
gaaatcaaac gaactgtggc tgcaccatct gtc                                 753
```

<210> SEQ ID NO 533
<211> LENGTH: 759
<212> TYPE: DNA
<213> ORGANISM: Artificial Sequence
<220> FEATURE:
<223> OTHER INFORMATION: YU112-E08

<400> SEQUENCE: 533

```
taggtcacct tgaaggagtc tggggggaggc gtggtccagc ctgggaggtc cctgagactc    60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaaggggggg    300 aagagctact acggatttga ctactgggggc cagggaaccc tggtcaccgt ctcctcaggg    360
agtgcatccg ccccaaagct tgaagaaggt gaattttcag aagcacgcgt agacatccag    420
atgacccagt ctccatcctt cctgtctgca tctgtaggag acagagtcac catcacttgc    480
cgggcaagtc agatcattag cagctattta aattggtatc agcagaaacc agggaaagcc    540
cctaaactcc tgatctatgc tgcatccagt ttgcaaagtg ggtcccatc aaggttcagt    600 ggcagtggat ctgggacaga tttcactctc accatcagca gtctgcaacc tgaagatttt    660
gcaacttact actgtcaaca gagttacagt accccccacgt ggacgttcgg ccaagggacc    720
aaggtggaaa tcaaacgaac tgtggctgca ccatctgtc                           759
```

<210> SEQ ID NO 534
<211> LENGTH: 786
<212> TYPE: DNA
<213> ORGANISM: Artificial Sequence
<220> FEATURE:
<223> OTHER INFORMATION: YU112-F05

<400> SEQUENCE: 534

```
gaggtgcagc tggtgcagtc gggggggaggc gtggtccagc ctgggaggtc cctgagactc    60
tcctgtgcag cctctggatt caccttcggt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtac    240
ctgcaaatga acagcctgag agctgaggac acggctgtgt attactgtgc gaaaatagga    300
gctactgacc cccttgacta ctgggggccag ggaaccctgg tcaccgtctc ctcagggagt    360
gcatccgccc caaagcttga agaaggtgaa ttttcagaag cacgcgtaca gtctgccctg    420
actcagcctc gctcagtgtc cgggtctcct ggacagtcag tcaccatctc ctgcactgga    480
accagcagtg atgttggtgg ttataactat gtctcctggt accaacaaca cccaggcaaa    540 gccccccaaac tcatcattta tgatgtcaat aatcggccct caggggtttc taatcgcttc    600
tctgcctcca gtctggcaa cacggcctcc ctgaccatct ctgggctcca ggctgaggac    660
gaggctgatt attactgcaa ctcatataca agcggtagca cttgggtctt cggcggaggg    720
accaagctga ccgtcctagg tcagcccaag gctgccccct cggtcactct gttcccgccc    780
tcctct                                                               786
```

<210> SEQ ID NO 535
<211> LENGTH: 786
<212> TYPE: DNA
<213> ORGANISM: Artificial Sequence
<220> FEATURE:
<223> OTHER INFORMATION: YU112-G01

<400> SEQUENCE: 535

```
caggtgcagc tggtggagtc ggggggaggc gtggtccagc ctggaggtc cctgagactc      60
tcctgtgcag cctctgggtt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaactttcc    300
gggcccaacg tgtggacta ctggggccag ggaaccctgg tcaccgtctc ctcagggagt    360
gcatccgccc caaagcttga agaaggtgaa ttttcagaag cacgcgtaca gtctgccctg    420
actcagcctc gctcagtgtc cgggtctcct ggacagtcag tcaccatctc ctgcactgga    480
accatcagtg atgttggtgg ttataactat gtctcctggt accaacagca cccaggcaaa    540
gcccccaaac tcatgattta tgatgtcact aagcggccct caggggtccc tgatcgcttc    600
tctggctcca agtctggcaa cacggcctcc ctgaccatct ctgggctcca ggctgaggat    660
gaggctggtt attactgctc ctcatatgca ggcagctaca cttgggtgtt cggcggaggg    720
accgagctga ccgtcctgag tcagcccaag gctgccccct cggtcactct gttcccgccc    780
tcctct                                                                786
```

<210> SEQ ID NO 536
<211> LENGTH: 786
<212> TYPE: DNA
<213> ORGANISM: Artificial Sequence
<220> FEATURE:
<223> OTHER INFORMATION: YU112-G06

<400> SEQUENCE: 536

```
caggtgcagc tgcaggagtc ggggggaggc gtggtccagc ctggaggtc cctgagactc      60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacactgtac    240
ctgcaaatga acagcctgag agctgaggac acggctgtgt attactgtgc gaaaatagga    300
gctactgacc cccttgacta ctggggccag ggaaccctgg tcaccgtctc ctcagggagt    360
gcatccgccc caaagcttga agaaggtgaa ttttcagaag cacgcgtaca gtctgccctg    420
actcagcctc gctcagtgtc cgggtctcct ggacagtcag tcaccatctc ctgcactgga    480
accatcagtg atgttggtgg ttataactat gtctcctggt accaacagca cccaggcaaa    540
gcccccaaac tcatgattta tgatgtcact aagcggcgct caggggtccc tgatcgcttc    600
tctggctcca agtctggcaa cacggcctcc ctgaccatct ctgggctcca ggctgaggat    660
gaggctggtt attactgctc ctcatatgca ggcggctaca cttgggtgtt cggcggaggg    720
accgagctga ccgtcctgag tcagcccaag gctgccccct cggtcactct gttcccgccc    780
tcctct                                                                786
```

<210> SEQ ID NO 537
<211> LENGTH: 702
<212> TYPE: DNA

<213> ORGANISM: Artificial Sequence
<220> FEATURE:
<223> OTHER INFORMATION: YU112-G09

<400> SEQUENCE: 537

| | | | | | |
|---|---|---|---|---|---|
| taggtcacct | tgaaggagtc | tgggggaggc | gtggtccagc | ctgggaggtc | cctgagactc | 60 |
| tcctgtgcag | cctctggatt | caccttcagt | agctatggca | tgcactgggt | ccgccaggct | 120 |
| ccaggcaagg | ggctggagtg | ggtggcagtt | atatcatatg | atggaagtaa | taaatactat | 180 |
| gcagactccg | tgaagggccg | attcaccatc | tccagagaca | attccaagaa | cacgctgtat | 240 |
| ctgcaaatga | acagcctgag | agctgaggac | acggctgtgt | attactgtgc | gaaaggggg | 300 |
| aagagctact | acggatttga | ctactgggc | cagggaaccc | tggtcaccgt | ctcctcaggg | 360 |
| agtgcatccg | ccccaaagct | tgaagaaggt | gaattttcag | aagcacgcgt | agacatccag | 420 |
| atgacccagt | ctccatcctt | cctgtctgca | tctgtaggag | acagagtcac | catcacttgc | 480 |
| cgggcaagtc | agatcattag | cagctattta | aattggtatc | agcagaaacc | agggaaagcc | 540 |
| cctaaactcc | tgatctatgc | tgcatccagt | ttgcaaagtg | gggtcccatc | aaggttcagt | 600 |
| ggcagtggat | ctgggacaga | tttcactctc | accatcagca | gtctgcaacc | tgaagatttt | 660 |
| gcaacttac | tactgtcaac | agagttacag | taccccacg | tg | | 702 |

<210> SEQ ID NO 538
<211> LENGTH: 753
<212> TYPE: DNA
<213> ORGANISM: Artificial Sequence
<220> FEATURE:
<223> OTHER INFORMATION: YU112-H01

<400> SEQUENCE: 538

| | | | | | |
|---|---|---|---|---|---|
| caggtgcagc | tggtggagtc | tgggggaggc | gtggtccagc | ctgggaggtc | cctgagactc | 60 |
| tcctgtgcag | cctctggatt | caccttcggt | agctatggca | tgcactgggt | ccgccaggct | 120 |
| ccaggcaagg | ggctggagtg | ggtggcagtt | atatcatatg | atggaagtaa | taaatactat | 180 |
| gcagactccg | tgaagggccg | attcaccatc | tccagagaca | attccaagaa | cacgctgtat | 240 |
| ctgcaaatga | acagcctgag | agctgaggac | acggctgtgt | attactgtgc | gaaaggttcg | 300 |
| tactactttg | actactgggg | ccagggaacc | ctggtcaccg | tctcctcagg | gagtgcatcc | 360 |
| gccccaaagc | ttgaagaagg | tgaattttca | gaagcacgcg | tagaaacgac | actcacgcag | 420 |
| tctccaggca | ccctgtcttt | gtctccaggg | gaaagagcca | ccctctcctg | cagggccagt | 480 |
| cagagtgtta | gcagcagcta | cttagcctgg | taccagcaga | aacctggcca | ggctcccagg | 540 |
| ctcctcatct | atggtgcatc | cagcagggcc | actggcatcc | cagacaggtt | cagtggcagt | 600 |
| gggtctggga | cagacttcac | tctcaccatc | agcagtctgc | aacctgatga | ttttgcaact | 660 |
| tactactgtc | aacagagtta | cagcactcct | acgtggacat | tcggccaagg | gaccaaggtg | 720 |
| gaaatcaaac | gaactgtggc | tgcaccatct | gtc | | | 753 |

<210> SEQ ID NO 539
<211> LENGTH: 786
<212> TYPE: DNA
<213> ORGANISM: Artificial Sequence
<220> FEATURE:
<223> OTHER INFORMATION: YU112-H02

<400> SEQUENCE: 539

| | | | | | |
|---|---|---|---|---|---|
| caggtgcagc | tggtggagtc | tgggggaggc | gtggtccagc | ctgggaggtc | cctgagactc | 60 |
| tcctgtgcag | cctctggatt | caccttcagt | agctatggca | tgcactgggt | ccgccaggct | 120 |

```
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaactttcc    300
gggcccaacg tgtgtgacta ctggggccag ggaaccctgg tcaccgtctc ctcagggagt    360
gcatccgccc caaagcttga agaaggtgaa ttttcagaag cacgcgtaca gcctgtgctg    420
actcagcccc gctcagtgtc cgggtctcct ggacagtcag tcaccatctc ctgcactgga    480
accagcagtg atgttggtgg ttataactat gtctcctggt accaacaaca cccaggcaaa    540 gccccccaaag tcatgattta tgatgtcagt aagcggccct cagggcgtccc tgatcgcttc    600 tctggctcca agtctggcaa cacggcctcc ctgaccatct ctgggctcca ggctgaggat    660
gaggctgatt attactgctg ctcatatgca ggcagctaca cttgggtgtt cggcggaggg    720
accaagctga ccgtcctagg tcagcccaag gctgccccct cggtcactct gttcccgccc    780
tcctct    786
```

<210> SEQ ID NO 540
<211> LENGTH: 111
<212> TYPE: PRT
<213> ORGANISM: Artificial Sequence
<220> FEATURE:
<223> OTHER INFORMATION: YU100-B09

<400> SEQUENCE: 540

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Pro Glu Asp Glu Ala Asp Tyr Tyr Cys Ser Ser Tyr Arg Ser Gly
                85                  90                  95

Ser Thr Leu Gly Val Arg Arg Asp Gln Ala Asp Arg Pro Arg
            100                 105                 110
```

<210> SEQ ID NO 541
<211> LENGTH: 119
<212> TYPE: PRT
<213> ORGANISM: Artificial Sequence
<220> FEATURE:
<223> OTHER INFORMATION: BSN-2E1

<400> SEQUENCE: 541

```
Gln Val Gln Leu Gln Glu Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro His Asn Gly Gly Pro Ile Tyr Asn Gln Lys Phe
    50                  55                  60

Thr Gly Lys Ala Thr Leu Thr Val Asp Lys Ser Ser Ser Thr Ala Tyr
```

```
                65                  70                  75                  80
Met Glu Leu Arg Ser Leu Thr Ser Asp Thr Ala Val Tyr Tyr Cys
                    85                  90                  95

Ala Arg Gly Glu Leu Gly His Trp Tyr Phe Asp Val Trp Gly Thr Gly
            100                 105                 110

Thr Thr Val Thr Val Ser Ser
        115

<210> SEQ ID NO 542
<211> LENGTH: 8
<212> TYPE: PRT
<213> ORGANISM: Artificial Sequence
<220> FEATURE:
<223> OTHER INFORMATION: BSN-2E1 HC-CDR1

<400> SEQUENCE: 542

Gly Tyr Thr Phe Thr Asp Tyr Asn
1               5

<210> SEQ ID NO 543
<211> LENGTH: 8
<212> TYPE: PRT
<213> ORGANISM: Artificial Sequence
<220> FEATURE:
<223> OTHER INFORMATION: BSN-2E1 HC-CDR2

<400> SEQUENCE: 543

Ile Asn Pro His Asn Gly Gly Pro
1               5

<210> SEQ ID NO 544
<211> LENGTH: 12
<212> TYPE: PRT
<213> ORGANISM: Artificial Sequence
<220> FEATURE:
<223> OTHER INFORMATION: BSN-2E1 HC-CDR3

<400> SEQUENCE: 544

Ala Arg Gly Glu Leu Gly His Trp Tyr Phe Asp Val
1               5                   10

<210> SEQ ID NO 545
<211> LENGTH: 120
<212> TYPE: PRT
<213> ORGANISM: Artificial Sequence
<220> FEATURE:
<223> OTHER INFORMATION: BSN-2G6

<400> SEQUENCE: 545

Gln Val Gln Leu Gln Glu Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asn Ile Asn Pro Asp Asn Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Phe Cys
                85                  90                  95

Ala Arg Glu Gly Pro Tyr Gly Tyr Thr Trp Phe Ala Tyr Trp Gly Gln
```

Gly Thr Leu Asp Thr Val Ser Ala
        115                 120

<210> SEQ ID NO 546
<211> LENGTH: 8
<212> TYPE: PRT
<213> ORGANISM: Artificial Sequence
<220> FEATURE:
<223> OTHER INFORMATION: BSN-2G6 HC-CDR2

<400> SEQUENCE: 546

Ile Asn Pro Asp Asn Gly Gly Thr
1               5

<210> SEQ ID NO 547
<211> LENGTH: 13
<212> TYPE: PRT
<213> ORGANISM: Artificial Sequence
<220> FEATURE:
<223> OTHER INFORMATION: BSN-2G6 HC-CDR3

<400> SEQUENCE: 547

Ala Arg Glu Gly Pro Tyr Gly Tyr Thr Trp Phe Ala Tyr
1               5                   10

<210> SEQ ID NO 548
<211> LENGTH: 120
<212> TYPE: PRT
<213> ORGANISM: Artificial Sequence
<220> FEATURE:
<223> OTHER INFORMATION: BSN-5A6

<400> SEQUENCE: 548

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asn Ile Asn Pro Asn Asn Gly Gly Ile Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Val Leu Arg Ser Leu Thr Ser Glu Asp Thr Ala Val Tyr Tyr Cys
                85                  90                  95

Ala Arg Asn Pro Ser Leu Tyr Asp Gly Tyr Leu Asp Cys Trp Gly Gln
            100                 105                 110

Gly Thr Thr Leu Thr Val Ser Ser
        115                 120

<210> SEQ ID NO 549
<211> LENGTH: 8
<212> TYPE: PRT
<213> ORGANISM: Artificial Sequence
<220> FEATURE:
<223> OTHER INFORMATION: BSN-5A6 HC-CDR2

<400> SEQUENCE: 549

Ile Asn Pro Asn Asn Gly Gly Ile
1               5

```
<210> SEQ ID NO 550
<211> LENGTH: 13
<212> TYPE: PRT
<213> ORGANISM: Artificial Sequence
<220> FEATURE:
<223> OTHER INFORMATION: BSN-5A6 HC-CDR3

<400> SEQUENCE: 550

Ala Arg Asn Pro Ser Leu Tyr Asp Gly Tyr Leu Asp Cys
1               5                   10

<210> SEQ ID NO 551
<211> LENGTH: 118
<212> TYPE: PRT
<213> ORGANISM: Artificial Sequence
<220> FEATURE:
<223> OTHER INFORMATION: BSN-5B8

<400> SEQUENCE: 551

Gln Val Gln Leu Gln Gln Ser Gly Ala Glu Leu Ala Arg Pro Gly Thr
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Ser Asn Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Asp Tyr Phe Cys
                85                  90                  95

Ala Arg Ala Asn Trp Val Gly Tyr Phe Asp Val Trp Gly Thr Gly Thr
            100                 105                 110

Thr Val Thr Val Ser Ser
        115

<210> SEQ ID NO 552
<211> LENGTH: 8
<212> TYPE: PRT
<213> ORGANISM: Artificial Sequence
<220> FEATURE:
<223> OTHER INFORMATION: BSN-5B8 HC-CDR2

<400> SEQUENCE: 552

Ile Tyr Pro Arg Ser Ser Asn Thr
1               5

<210> SEQ ID NO 553
<211> LENGTH: 11
<212> TYPE: PRT
<213> ORGANISM: Artificial Sequence
<220> FEATURE:
<223> OTHER INFORMATION: BSN-5B8 HC-CDR3

<400> SEQUENCE: 553

Ala Arg Ala Asn Trp Val Gly Tyr Phe Asp Val
1               5                   10

<210> SEQ ID NO 554
<211> LENGTH: 107
<212> TYPE: PRT
<213> ORGANISM: Artificial Sequence
<220> FEATURE:
<223> OTHER INFORMATION: BSN-2E1
```

<400> SEQUENCE: 554

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 555
<211> LENGTH: 6
<212> TYPE: PRT
<213> ORGANISM: Artificial Sequence
<220> FEATURE:
<223> OTHER INFORMATION: BSN-2E1 LC-CDR1

<400> SEQUENCE: 555

Glu Asn Val Val Thr Tyr
1               5

<210> SEQ ID NO 556
<211> LENGTH: 9
<212> TYPE: PRT
<213> ORGANISM: Artificial Sequence
<220> FEATURE:
<223> OTHER INFORMATION: BSN-2E1 LC-CDR3

<400> SEQUENCE: 556

Gly Gln Gly Tyr Ser Tyr Pro Tyr Thr
1               5

<210> SEQ ID NO 557
<211> LENGTH: 107
<212> TYPE: PRT
<213> ORGANISM: Artificial Sequence
<220> FEATURE:
<223> OTHER INFORMATION: BSN-2G6

<400> SEQUENCE: 557

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Leu
                85                  90                  95

Thr Phe Gly Ala Gly Thr Lys Leu Glu Leu Lys 100               105

<210> SEQ ID NO 558
<211> LENGTH: 6
<212> TYPE: PRT
<213> ORGANISM: Artificial Sequence
<220> FEATURE:
<223> OTHER INFORMATION: BSN-2G6 LC-CDR1

<400> SEQUENCE: 558

Gln Ser Ile Gly Thr Ser
1               5

<210> SEQ ID NO 559
<211> LENGTH: 3
<212> TYPE: PRT
<213> ORGANISM: Artificial Sequence
<220> FEATURE:
<223> OTHER INFORMATION: BSN-2G6 LC-CDR2

<400> SEQUENCE: 559

Tyr Ala Ser
1

<210> SEQ ID NO 560
<211> LENGTH: 9
<212> TYPE: PRT
<213> ORGANISM: Artificial Sequence
<220> FEATURE:
<223> OTHER INFORMATION: BSN-2G6 LC-CDR3

<400> SEQUENCE: 560

Gln Gln Ser Asn Ser Trp Pro Leu Thr
1               5

<210> SEQ ID NO 561
<211> LENGTH: 113
<212> TYPE: PRT
<213> ORGANISM: Artificial Sequence
<220> FEATURE:
<223> OTHER INFORMATION: BSN-5A6_2

<400> SEQUENCE: 561

Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Leu Tyr Asn
                20                  25                  30

Ser Ser Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Asn Leu Glu Leu
                100                 105                 110

Lys

<210> SEQ ID NO 562
<211> LENGTH: 12
<212> TYPE: PRT
<213> ORGANISM: Artificial Sequence

<220> FEATURE:
<223> OTHER INFORMATION: BSN-5A6_2 LC-CDR1

<400> SEQUENCE: 562

Gln Ser Leu Leu Tyr Asn Ser Ser Gln Lys Asn Tyr
1               5                   10

<210> SEQ ID NO 563
<211> LENGTH: 3
<212> TYPE: PRT
<213> ORGANISM: Artificial Sequence
<220> FEATURE:
<223> OTHER INFORMATION: BSN-5A6_2 LC-CDR2

<400> SEQUENCE: 563

Trp Ala Ser
1

<210> SEQ ID NO 564
<211> LENGTH: 106
<212> TYPE: PRT
<213> ORGANISM: Artificial Sequence
<220> FEATURE:
<223> OTHER INFORMATION: BSN-5B8

<400> SEQUENCE: 564

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg Leu Thr Gly Val Pro Asp Arg Phe Thr Gly
    50                  55                  60

Ser Gly Ser Gly Thr Tyr Phe Thr Leu Thr Ile Asn Asn Val Gln Ser
65                  70                  75                  80

Glu Asp Leu Ala Asp Tyr Phe Cys Gln Gln Tyr Ser Ser Tyr Arg Thr
                85                  90                  95

Phe Gly Gly Gly Thr Lys Leu Glu Ile Lys
            100                 105

<210> SEQ ID NO 565
<211> LENGTH: 6
<212> TYPE: PRT
<213> ORGANISM: Artificial Sequence
<220> FEATURE:
<223> OTHER INFORMATION: BSN-5B8 LC-CDR1

<400> SEQUENCE: 565

Gln Asp Val Gly Thr Ala
1               5

<210> SEQ ID NO 566
<211> LENGTH: 8
<212> TYPE: PRT
<213> ORGANISM: Artificial Sequence
<220> FEATURE:
<223> OTHER INFORMATION: BSN-5B8 LC-CDR3

<400> SEQUENCE: 566

Gln Gln Tyr Ser Ser Tyr Arg Thr
1               5

```
<210> SEQ ID NO 567
<211> LENGTH: 8
<212> TYPE: PRT
<213> ORGANISM: Artificial Sequence
<220> FEATURE:
<223> OTHER INFORMATION: mHC-CDR1-1 family consensus
<220> FEATURE:
<221> NAME/KEY: MISC_FEATURE
<222> LOCATION: (6)..(6)
<223> OTHER INFORMATION: Xaa = D or S
<220> FEATURE:
<221> NAME/KEY: MISC_FEATURE
<222> LOCATION: (8)..(8)
<223> OTHER INFORMATION: Xaa = N or G

<400> SEQUENCE: 567

Gly Tyr Thr Phe Thr Xaa Tyr Xaa
1               5

<210> SEQ ID NO 568
<211> LENGTH: 8
<212> TYPE: PRT
<213> ORGANISM: Artificial Sequence
<220> FEATURE:
<223> OTHER INFORMATION: mHC-CDR2-1 family consensus
<220> FEATURE:
<221> NAME/KEY: MISC_FEATURE
<222> LOCATION: (4)..(4)
<223> OTHER INFORMATION: Xaa = H, D or N
<220> FEATURE:
<221> NAME/KEY: MISC_FEATURE
<222> LOCATION: (8)..(8)
<223> OTHER INFORMATION: Xaa = P, T or I

<400> SEQUENCE: 568

Ile Asn Pro Xaa Asn Gly Gly Xaa
1               5

<210> SEQ ID NO 569
<211> LENGTH: 3
<212> TYPE: PRT
<213> ORGANISM: Artificial Sequence
<220> FEATURE:
<223> OTHER INFORMATION: mLC-CDR2-1 family consensus
<220> FEATURE:
<221> NAME/KEY: MISC_FEATURE
<222> LOCATION: (1)..(1)
<223> OTHER INFORMATION: Xaa = G, Y or W

<400> SEQUENCE: 569

Xaa Ala Ser
1

<210> SEQ ID NO 570
<211> LENGTH: 9
<212> TYPE: PRT
<213> ORGANISM: Artificial Sequence
<220> FEATURE:
<223> OTHER INFORMATION: mLC-CDR3-1 family consensus
<220> FEATURE:
<221> NAME/KEY: MISC_FEATURE
<222> LOCATION: (1)..(1)
<223> OTHER INFORMATION: Xaa = Q or G
<220> FEATURE:
<221> NAME/KEY: MISC_FEATURE
<222> LOCATION: (3)..(3)
<223> OTHER INFORMATION: Xaa = Y, G or S
<220> FEATURE:
<221> NAME/KEY: MISC_FEATURE
<222> LOCATION: (4)..(4)
<223> OTHER INFORMATION: Xaa = Y, N or S
<220> FEATURE:
<221> NAME/KEY: MISC_FEATURE
```

```
<222> LOCATION: (6)..(6)
<223> OTHER INFORMATION: Xaa = Y or W
<220> FEATURE:
<221> NAME/KEY: MISC_FEATURE
<222> LOCATION: (7)..(7)
<223> OTHER INFORMATION: Xaa = P or absent
<220> FEATURE:
<221> NAME/KEY: MISC_FEATURE
<222> LOCATION: (8)..(8)
<223> OTHER INFORMATION: Xaa = L, Y or R

<400> SEQUENCE: 570

Xaa Gln Xaa Xaa Ser Xaa Xaa Xaa Thr
 1               5

<210> SEQ ID NO 571
<211> LENGTH: 357
<212> TYPE: DNA
<213> ORGANISM: Artificial Sequence
<220> FEATURE:
<223> OTHER INFORMATION: BSN-2E1_VH

<400> SEQUENCE: 571
caggtccagc tgcaggagtc tggacctgag ctggtgaagc ctggggcttc agtgaagata      60
ccctgcaagg cttctggata cacattcact gactacaaca tggactgggt gaagcagagc     120
catggaaaga gccttgagtg gattggagat attaatcctc acaatggtgg tcctatctac     180
aaccagaagt tcacgggcaa ggccacattg actgtagaca gtcctccag cacagcctac      240 atggagctcc gcagcctgac atctgaggac actgcagtct attactgtgc aagaggggaa     300
ctgggtcact ggtacttcga tgtctggggc acagggacca cggtcaccgt ctcctca        357

<210> SEQ ID NO 572
<211> LENGTH: 321
<212> TYPE: DNA
<213> ORGANISM: Artificial Sequence
<220> FEATURE:
<223> OTHER INFORMATION: BSN-2E1_VL

<400> SEQUENCE: 572
aacattgtaa tgacccaatc tcccaaatcc atgtccatgt cagtaggaga gagggtcacc      60
ttgacctgca aggccagtga aaatgtggtt acttatgttt cctggtatca acagaaacca     120
gagcagtctc ctaaactgct gatatacggg gcatccaacc ggtacactgg ggtcccccgat    180 cgcttcacag gcagtggatc tgcaacagat ttcactctga ccatcagcag tgtgcaggct    240
gaagaccttg cagattatca ctgtggacag ggttacagct atccgtacac gttcggaggg     300
gggaccaagc tggaaataaa a                                              321

<210> SEQ ID NO 573
<211> LENGTH: 360
<212> TYPE: DNA
<213> ORGANISM: Artificial Sequence
<220> FEATURE:
<223> OTHER INFORMATION: BSN-2G6_VH

<400> SEQUENCE: 573
caggtccagc tgcaggagtc tggacctgag ctggtgaagc ctggggcttc agtgaagata      60
ccctgcaagg cttctggata cacgttcact gactacaaca tggactgggt gaagcagagc     120
catggaaaga gccttgagtg gattggaaat attaatcctg acaatggtgg tactatctac     180
aaccagaagt tcaagggcaa ggccacattg actgtagaca gtcctccag cacagcctac      240 atggagctcc gcagcctgac atctgaggac actgcagtct atttctgtgc aagagagggg     300
```

```
ccttatggtt acacctggtt tgcttactgg ggccaaggga ctctggacac tgtctctgca    360
```

<210> SEQ ID NO 574
<211> LENGTH: 321
<212> TYPE: DNA
<213> ORGANISM: Artificial Sequence
<220> FEATURE:
<223> OTHER INFORMATION: BSN-2G6_VL

<400> SEQUENCE: 574

```
gacatcttgc tgactcagtc tccagccatc ctgtctgtga gtccaggaga aagagtcagt     60
ttctcctgca gggccagtca gagcattggc acaagcatac actggtatca gcaaagaaca    120
aatggttctc caaggcttct cataaagtat gcttctgagt ctatctctgg atcccttcc    180
aggtttagtg gcagtggatc aggacagat tttactctta gcatcaacag tgtggagtct    240
gaagatattg cagattatta ctgtcaacaa agtaatagct ggccgctcac gttcggtgct    300
gggaccaagc tggagctgaa a                                               321
```

<210> SEQ ID NO 575
<211> LENGTH: 321
<212> TYPE: DNA
<213> ORGANISM: Artificial Sequence
<220> FEATURE:
<223> OTHER INFORMATION: BSN-3C6_VL

<400> SEQUENCE: 575

```
aacattgtaa tgacccaatc tcccaaatcc atgtccatgt cagtaggaga gagggtcacc     60
ttgacctgca aggccagtga aatgtggtt acttatgttt cctggtatca acagaaacca    120
gagcagtctc ctaaactgct gatatacggg gcatccaacc ggtacactgg ggtcccccgat   180
cgcttcacag gcagtggatc tgcaacagat ttcactctga ccatcagcag tgtgcaggct    240
gaagaccttg cagattatca ctgtggacag ggttacagct atccgtacac gttcggaggg    300
gggaccaagc tggaaataaa a                                               321
```

<210> SEQ ID NO 576
<211> LENGTH: 360
<212> TYPE: DNA
<213> ORGANISM: Artificial Sequence
<220> FEATURE:
<223> OTHER INFORMATION: BSN-5A6_VH

<400> SEQUENCE: 576

```
gaggtccagc tgcaacagtc tggacctgaa ctggtgaagc ctggggcttc agtgaagata     60
ccctgcaagg cttctggata cacattcact gactacaaca tggactgggt gaagcagagc    120
catggaaaga gccttgagtg gattggaaat attaatccta caatggtgg tattatctac    180
aaccagaagt tcaagggcaa ggccacattg actgtagaca gtcctccag cacagcctac    240
atggtactcc gcagcctgac atctgaggac actgcagtct attactgtgc aagaaaccca    300
agtctctatg atggttacct tgactgctgg ggccaaggca ccactctcac agtctcctca    360
```

<210> SEQ ID NO 577
<211> LENGTH: 321
<212> TYPE: DNA
<213> ORGANISM: Artificial Sequence
<220> FEATURE:
<223> OTHER INFORMATION: BSN-5A6_VL1

<400> SEQUENCE: 577

```
aacattgtaa tgacccaatc tcccaaatcc atgtccatgt cagtaggaga gagggtcacc    60
ttgacctgca aggccagtga aatgtgtt  acttatgttt cctggtatca acagaaacca   120
gagcagtctc ctaaactgct gatatacggg gcatccaacc ggtacactgg ggtccccgat   180
cgcttcacag gcagtggatc tgcaacagat ttcactctga ccatcagcag tgtgcaggct   240
gaagaccttg cagattatca ctgtggacag ggttacagct atccgtacac gttcggaggg   300
gggaccaagc tggaaataaa a                                              321

<210> SEQ ID NO 578
<211> LENGTH: 339
<212> TYPE: DNA
<213> ORGANISM: Artificial Sequence
<220> FEATURE:
<223> OTHER INFORMATION: BSN-5A6_VL2

<400> SEQUENCE: 578
gacattgtga tgtcacagtc tccatcctcc ctagctgtgt cagttggaga gaaggttact    60
atgaactgca agtccagtca gagccttta tataatagca gtcaaaagaa ctacttggcc    120
tggtaccagc agaaaccagg gcagtctcct aaattgctga tttactgggc atccactagg   180
gaatctgggg tccctgatcg cttcacaggc agtggatctg gacagattt cactctcacc   240 atcagcagtg tgaaggctga agacctggca gtttattact gtcagcaata ttatagttat   300
ccgctcacgt tcggtgctgg gaccaacctg gagctgaaa                          339

<210> SEQ ID NO 579
<211> LENGTH: 354
<212> TYPE: DNA
<213> ORGANISM: Artificial Sequence
<220> FEATURE:
<223> OTHER INFORMATION: BSN-5B8_VH

<400> SEQUENCE: 579
caggtccagc tgcagcagtc tggagctgag ctggcgaggc ctgggacttc agtgaaactg    60
tcctgcaagg cttctggcta caccttcaca agctatggta aagctgggt gaaacagaga    120 actggacagg gccttgagtg gattggagaa atttatcctc gaagtagtaa tacttactac   180
aatgagaagt tcaagggcaa ggccacactg actgcagaca aatcctccag cacagcgtac   240
atggagctcc gcagcctgac atctgaggac tctgcggact attttctgtgc aagggctaac   300 tgggtagggt acttcgatgt ctggggcaca gggaccacgg tcaccgtctc ctca         354

<210> SEQ ID NO 580
<211> LENGTH: 318
<212> TYPE: DNA
<213> ORGANISM: Artificial Sequence
<220> FEATURE:
<223> OTHER INFORMATION: BSN-5B8_VL

<400> SEQUENCE: 580
gacattgtga tgacccagtc tcacaaattc atgtccacat cagtcggaga cagggtcacc    60
atcacctgca aggccagtca ggatgtgggt actgctgtag cctggtatca acagaaacca   120
ggacaatctc ctaaactact gatttactgg gcatccaccc ggctcactgg agtccctgat   180
cgcttcacag gcagtggatc tgggacatat ttcactctca ccattaacaa tgtgcagtct   240
gaagacttgg cagattattt ctgtcagcaa tatagcagct atcggacgtt cggtggaggc   300
accaagctgg aaatcaag                                                  318
```

```
<210> SEQ ID NO 581
<211> LENGTH: 9
<212> TYPE: PRT
<213> ORGANISM: Artificial Sequence
<220> FEATURE:
<223> OTHER INFORMATION: BSN-5A6_2 LC-CDR3

<400> SEQUENCE: 581

Gln Gln Tyr Tyr Ser Tyr Pro Leu Thr
1               5
```

IL-11 ANTIBODIES

CROSS-REFERENCE TO RELATED APPLICATIONS

The present application is a continuation of U.S. patent application Ser. No. 15/843,173, filed on Dec. 15, 2017, which claims priority under 35 USC § 119(a)-(d) to United Kingdom Application No. 1709535.7, filed Jun. 15, 2017 and United Kingdom Application No. 1621446.2, filed Dec. 16, 2016, the entire contents of each of which are incorporated by reference herein.

FIELD OF THE INVENTION

The present invention relates to antibodies that bind to interleukin 11 (IL-11).

BACKGROUND TO THE INVENTION

Many fatal and incurable diseases are caused by organ failure due to excessive and maladaptive fibrosis (Rockey et al., 2015 Journal of Infectious Diseases 214, jiw176). Fibrotic disorders include both rare, genetically-driven diseases such as scleroderma, idiopathic pulmonary fibrosis and hypertrophic cardiomyopathy, dilated cardiomyopathy (DCM), and common diseases like atrial fibrillation, ventricular fibrillation, non-alcoholic fatty liver disease and diabetic kidney disease. Due to the significant impact on world-wide morbidity and mortality, there is a need to develop therapeutics to inhibit the fibrotic response (Nanthakumar et al., 2015 Nat Rev Drug Discov 14, 693-720).

A major hallmark of fibrosis is the pathologic activation of resident fibroblasts that drives their transition from a quiescent state to proliferating, secretory and contractile myofibroblasts (Hinz et al., 2010 Am J Pathology 170, 1807-1816). Stimuli such as mechanical stress and pro-fibrotic cytokines can activate fibroblasts. The TGFβ1 pathway is considered to be of central importance for the fibrotic response (Leask and Abraham, 2004 The FASEB Journal 18, 816-827) and its inhibition is a therapeutic strategy that is under investigation (Gourdie et al., 2016 Nature Reviews Drug Discovery 15, 620-638). However, direct inhibition of multi-functional TGFβ1 is associated with severe side effects such as inflammation and cancer susceptibility.

SUMMARY OF THE INVENTION

In one aspect, the present invention provides an antibody or antigen binding fragment, optionally isolated, which is capable of binding to IL-11, wherein the antibody or antigen binding fragment is a fully human antibody or antigen binding fragment and is capable of inhibiting IL-11 trans signalling.

In another aspect, the present invention provides an antibody or antigen binding fragment, optionally isolated, which is capable of binding to IL-11, comprising the amino acid sequences i) to vi):

i) LC-CDR1:

$X_1X_2DX_3GX_4YX_5Y$; (SEQ ID NO: 239)

$X_6SNX_7GX_8X_9X_{10}$; (SEQ ID NO: 240)

$QX_{11}X_{12}SSX_{13}$; (SEQ ID NO: 241)

$X_{14}GX_{15}IASNX_{16}$; (SEQ ID NO: 242)

QDVGRY; (SEQ ID NO: 101)
or

SLRGYY; (SEQ ID NO: 161)

ii) LC-CDR2:

$DVX_{17}$; (SEQ ID NO: 243)

$X_{18}NX_{19}$; (SEQ ID NO: 244)

$X_{20}AS$; (SEQ ID NO: 245)

$X_{21}DX_{22}$; (SEQ ID NO: 246)

$EVX_{23}$; (SEQ ID NO: 247)
or $DX_{24}X_{25}$; (SEQ ID NO: 248)

iii) LC-CDR3:

$X_{26}SYTX_{27}X_{28}X_{29}X_{30}X_{31}VX_{32}$; (SEQ ID NO: 249)

$X_{33}SYAX_{34}X_{35}X_{36}X_{37}X_{38}X_{39}X_{40}X_{41}X_{42}X_{43}X_{44}X_{45}X_{46}X_{47}X_{48}X_{49}$; (SEQ ID NO: 250)

$X_{50}X_{51}WDX_{52}X_{53}LX_{54}X_{55}X_{56}V$; (SEQ ID NO: 251)

$QQX_{57}X_{58}X_{59}PX_{60}X_{61}X_{62}X_{63}X_{64}X_{65}X_{66}X_{67}X_{68}X_{69}X_{70}X_{71}X_{72}$; (SEQ ID NO: 252)

$QSYX_{73}X_{74}SX_{75}X_{76}X_{77}X_{78}$; (SEQ ID NO: 253)

$X_{79}SYX_{80}SSX_{81}X_{82}X_{83}VX_{84}$; (SEQ ID NO: 254)

NSYVTGNNWA; (SEQ ID NO: 169)
or

DSRGRSGDHWL; (SEQ ID NO: 163)

iv) HC-CDR1:

$GFTFSSYX_{85}$; (SEQ ID NO: 255)

$GX_{86}X_{87}X_{88}X_{89}5YG$; (SEQ ID NO: 256)

$X_{90}X_{91}X_{92}X_{93}X_{94}SYA$; (SEQ ID NO: 257)

WIFLKSYA; (SEQ ID NO: 204)

VSSNSAAWN; (SEQ ID NO: 180)

GGSISSSNW; (SEQ ID NO: 220)
or

GFTFSGAY; (SEQ ID NO: 183)

-continued v) HC-CDR2:

ISYDGSX$_{95}$K;  (SEQ ID NO: 258)

IIPIFGTA;  (SEQ ID NO: 210)

YRSKWYN;  (SEQ ID NO: 181)

ISAYNGNT;  (SEQ ID NO: 229)
or

IYHSGST;  (SEQ ID NO: 221)

vi) HC-CDR3:

AKLSGPNGVDY;  (SEQ ID NO: 197)

AKX$_{96}$X$_{97}$X$_{98}$GX$_{99}$X$_{100}$X$_{101}$X$_{102}$DY;  (SEQ ID NO: 259)

ARDX$_{103}$GYSSGWYFDY;  (SEQ ID NO: 260)

ARLX$_{104}$X$_{105}$X$_{106}$X$_{107}$X$_{108}$X$_{109}$X$_{100}$X$_{111}$X$_{112}$X$_{113}$X$_{114}$X$_{115}$X$_{116}$X$_{117}$X$_{118}$X$_{119}$X$_{120}$AFDI;  (SEQ ID NO: 261)

ARIMGYDYGDYDVVDY;  (SEQ ID NO: 199)

ARIX$_{121}$X$_{122}$X$_{123}$X$_{124}$X$_{125}$X$_{126}$DX$_{127}$X$_{128}$X$_{129}$X$_{130}$;  (SEQ ID NO: 262)

ARVGFSSWYPDLYYFDY;  (SEQ ID NO: 205)

X$_{131}$X$_{132}$X$_{133}$X$_{134}$RGYX$_{135}$DY;  (SEQ ID NO: 263)

ARITHDYGDFSDAFDI;  (SEQ ID NO: 194)

ARX$_{136}$GVLX$_{137}$DY;  (SEQ ID NO: 264)

AKGSYYFDY;  (SEQ ID NO: 235)

ARLYSGYPSRYYYGMDV;  (SEQ ID NO: 206)

ARVQSGEPESDY;  (SEQ ID NO: 216)

AKIGATDPLDY;  (SEQ ID NO: 187)

ARDLYAFDI;  (SEQ ID NO: 185)

ARPDDDY;  (SEQ ID NO: 203)

AKGGKSYYGFDY;  (SEQ ID NO: 207)

ARADSSAGGGPYYYGMDV;  (SEQ ID NO: 231)

ARVYYDSSGTQGDSFDY;  (SEQ ID NO: 233)

ARVVAAARSYYYYMDV;  (SEQ ID NO: 230)

ARGGGPYYDFWSGYYTEFDY;  (SEQ ID NO: 224)

ARMVNLYYGDAFDI;  (SEQ ID NO: 218)

ARGLITGTTP;  (SEQ ID NO: 211)

ARGQNVDL;  (SEQ ID NO: 198)

ARVQNLGGGSYYVGAFDY;  (SEQ ID NO: 222)
or

ARLVGATADDY;  (SEQ ID NO: 219)

or a variant thereof in which one or two or three amino acids in one or more of the sequences i) to vi) are replaced with another amino acid;

wherein $X_1$=S or I, $X_2$=S or R, $X_3$=V or I, $X_4$=G, A or N, $X_5$=N, E, K or D, $X_6$=S or Y, $X_7$=I or V, $X_8$=S, N or Y, $X_9$=N, Y or D, $X_{10}$=L, Y, T or A, $X_{11}$=G, S or I, $X_{12}$=S, I or V, $X_{13}$=Y or N, $X_{14}$=S or T, $X_{15}$=S or N, $X_{16}$=Y or R, $X_{17}$=S, T or G, $X_{18}$=R, I or G, $X_{19}$=N or D, $X_{20}$=A or G, $X_{21}$=E, D or N, $X_{22}$=N or D, $X_{23}$=S, F or N, $X_{24}$=N or V, $X_{25}$=H or T, $X_{26}$=S, N or G, $X_{27}$=S or T, $X_{28}$=S or G, $X_{29}$=S, N, G or I, $X_{30}$=T or S, $X_{31}$=W, L, V or Q, $X_{32}$=absent or V, $X_{33}$=C or S, $X_{34}$=G or D, $X_{35}$=S, Y, N or T, $X_{36}$=Y or N, $X_{37}$=T or N, $X_{38}$=W or F, $X_{39}$=V, G or L, $X_{40}$=absent or V, $X_{41}$=absent or R, $X_{42}$=absent or R, $X_{43}$=absent or R, $X_{44}$=absent or D, $X_{45}$=absent or R, $X_{46}$=absent or A, $X_{47}$=absent or D, $X_{48}$=absent or R, $X_{49}$=absent or P, $X_{50}$=A or G, $X_{51}$=A or T, $X_{52}$=D, G or S, $X_{53}$=S or G, $X_{54}$=S, K or N, $X_{55}$=G or A, $X_{56}$=W, G or H, $X_{57}$=S or Y, $X_{58}$=Y, R or N, $X_{59}$=S or N, $X_{60}$=T, A or W, $X_{61}$=L or T, $X_{62}$=Y, A, W or T, $X_{63}$=T, absent or F, $X_{64}$=absent or G, $X_{65}$=absent or G, $X_{66}$=absent or G, $X_{67}$=absent or T, $X_{68}$=absent or K, $X_{69}$=absent or V, $X_{70}$=absent or E, $X_{71}$=absent or F, $X_{72}$=absent or K, $X_{73}$=D or N, $X_{74}$=S or Y, $X_{75}$=K, S or N, $X_{76}$=V or L, $X_{77}$=I, V or W, $X_{78}$=absent or V, $X_{79}$=T or N, $X_{80}$=T or S, $X_{81}$=T or S, $X_{82}$=P or T, $X_{83}$=Y or L, $X_{84}$=absent or A, $X_{85}$=A or G, $X_{86}$=F or Y, $X_{87}$=S or T, $X_{88}$=L or F, $X_{89}$=G, R, T, S or N, $X_{90}$=G or I, $X_{91}$=G, F or L, $X_{92}$=T, S or P, $X_{93}$=F or S, $X_{94}$=S or D, $X_{95}$=N or D, $X_{96}$=L, F or D, $X_{97}$=Y, A or L, $X_{98}$=S or R, $X_{99}$=S, V or L, $X_{100}$=S, Y or P, $X_{101}$=N, L or I, $X_{102}$=F or I, $X_{103}$=S or V, $X_{104}$=H or A, $X_{105}$=S, Q or F, $X_{106}$=S or G, $X_{107}$=absent or Y, $X_{108}$=absent or S, $X_{109}$=absent, R or S, $X_{110}$=Q, N or S, $X_{111}$=W or Y, $X_{112}$=absent, Y or F, $X_{113}$=absent or E, $X_{114}$=absent or W, $X_{115}$=absent or E, $X_{116}$=absent or P, $X_{117}$=absent, G or S, $X_{118}$=absent, R or T, $X_{119}$=G, E or I, $X_{120}$=D or H, $X_{121}$=A or G, $X_{122}$=A or G, $X_{123}$=A or Y, $X_{124}$=D or absent, $X_{125}$=G or D, $X_{126}$=F, M or R, $X_{127}$=V, Y or A, $X_{128}$=absent or F, $X_{129}$=absent or D, $X_{130}$=absent or I, $X_{131}$=absent or A, $X_{132}$=absent or R, $X_{133}$=A or G, $X_{134}$=R or T, $X_{135}$=F or G, $X_{136}$=absent or S, $X_{137}$=absent or F.

In some embodiments, HC-CDR1 is one of VSSN-SAAWN (SEQ ID NO:180), GFTFSGAY (SEQ ID NO:183), GFTFSSYG (SEQ ID NO:186), GFTFSSYA (SEQ ID NO:190), GFSFRSYG (SEQ ID NO:193), GFTFRSYG (SEQ ID NO:196), GFSFSSYA (SEQ ID NO:212), WIFLKSYA (SEQ ID NO:204), GGTFSSYA (SEQ ID NO:209), GGSIS-SSNW (SEQ ID NO:220), GFSLSSYG (SEQ ID NO:201), GGTFSSYA (SEQ ID NO:209), ILPSDSYA (SEQ ID NO:226), GYTFTSYG (SEQ ID NO:228), GFTFGSYG (SEQ ID NO:234) or GFSLGSYG (SEQ ID NO:238).

In some embodiments, HC-CDR2 is one of YRSKWYN (SEQ ID NO:181), ISYDGSNK (SEQ ID NO:184), ISYDGSDK (SEQ ID NO:188), IIPIFGTA (SEQ ID NO:210), IYHSGST (SEQ ID NO:221), or ISAYNGNT (SEQ ID NO:229).

In some embodiments, HC-CDR3 is one of ARGTRGYFDY (SEQ ID NO:182), ARDLYAFDI (SEQ ID NO:185), AKIGATDPLDY (SEQ ID NO:187), AKDLSGLPIIDY (SEQ ID NO:189), ARRGYFDY (SEQ ID NO:191), ARIAAADGMDV (SEQ ID NO:192), ARITHDYGDFSDAFDI (SEQ ID NO:194), AKLYSGSSNFDY (SEQ ID NO:195), AKLSGPNGVDY (SEQ ID NO:197), ARGQNVDL (SEQ ID NO:198), ARIMGYDYGDYDVVDY (SEQ ID NO:199), ARRGYGDY (SEQ ID NO:213), ARVGFSSWYPDLYYFDY (SEQ ID NO:205), AKFARGVYLFDY (SEQ ID NO:215), ARVQSGEPESDY (SEQ ID NO:216), ARMVNLYYGDAFDI (SEQ ID NO:218), ARLVGATADDY (SEQ ID NO:219), AKLSGPNGVDY (SEQ ID NO:197), ARGLITGTTP (SEQ ID NO:211), ARVQNLGGGSYYVGAFDY (SEQ ID NO:222), ARLHFSQYFSTIDAFDI (SEQ ID NO:223), ARDVGYSSGWYFDY (SEQ ID NO:200), ARLAQSYSSSWYEWEPGREHAFDI (SEQ ID NO:202), ARPDDDY (SEQ ID NO:203) AKLSGPNGVDY (SEQ ID NO:197), ARLYSGYPSRYYYGMDV (SEQ ID NO:206), AKGGKSYYGFDY (SEQ ID NO:207), ARLHSGRNWGDAFDI (SEQ ID NO:208), ARGGGPYYDFWSGYYTEFDY (SEQ ID NO:224), ARDSGYSSGWYFDY (SEQ ID NO:225), ARIAAAGRDAFDI (SEQ ID NO:227), ARVVAAARSYYYYMDV (SEQ ID NO:230), ARADSSAGGGPYYYGMDV (SEQ ID NO:231), ARIGGYDDFDY (SEQ ID NO:232), ARVYYDSSGTQGDSFDY (SEQ ID NO:233), AKGSYYFDY (SEQ ID NO:235), ARGVLFDY (SEQ ID NO:236) or ARSGVLDY (SEQ ID NO:237).

In some embodiments, LC-CDR1 is one of QDVGRY (SEQ ID NO:101), TGNIASNR (SEQ ID NO:104), SSDVGGYNY (SEQ ID NO:107), SSDVGAYNY (SEQ ID NO:110), SSDIGAYNY (SEQ ID NO:114), SSNIGSNY (SEQ ID NO:116), ISDVGGYNY (SEQ ID NO:122), SSNIGNNL (SEQ ID NO:126), SSDVGGYDY (SEQ ID NO:128), QSVSSN (SEQ ID NO:137), SSNIGNNY (SEQ ID NO:140), YSNVGSNL (SEQ ID NO:144), SSNIGSNT (SEQ ID NO:147), SRDVGGYNY (SEQ ID NO:150), SGSIASNY (SEQ ID NO:152), QIISSY (SEQ ID NO:155), SSDVGGYEY (SEQ ID NO:159), SLRGYY (SEQ ID NO:161), SSNIGSYY (SEQ ID NO:164), SSDVGAYNY (SEQ ID NO:167), SSNIGYDA (SEQ ID NO:170), QGSSSY (SEQ ID NO:173), SSDVGGYKY (SEQ ID NO:175) or SSDVGNYKY (SEQ ID NO:178).

In some embodiments, LC-CDR2 is one of AAS (SEQ ID NO:102), DNH (SEQ ID NO:105), DVS (SEQ ID NO:108), EVS (SEQ ID NO:111), RNN (SEQ ID NO:117), DVT (SEQ ID NO:123), DVH (SEQ ID NO:129), DVG (SEQ ID NO:133), EVN (SEQ ID NO:135), DVT (SEQ ID NO:123), GAS (SEQ ID NO:138), DNT (SEQ ID NO:141), EDD (SEQ ID NO:145), INN (SEQ ID NO:148), DDN (SEQ ID NO:153), EDN (SEQ ID NO:157), GNN (SEQ ID NO:162), RND (SEQ ID NO:165), EVF (SEQ ID NO:168) or NDN (SEQ ID NO:171).

In some embodiments, LC-CDR3 is one of QQYRSAPLA (SEQ ID NO:103), QSYDYSSVI (SEQ ID NO:106), SSYTSSSSWV (SEQ ID NO:109), SSYTSSNTLV (SEQ ID NO:112), SSYTSSSTVV (SEQ ID NO:113), SSYTTSSTVV (SEQ ID NO:115), AAWDGSLSGWV (SEQ ID NO:118), SSYTSSSTWV (SEQ ID NO:119), CSYAGSYTFV (SEQ ID NO:120), NSYTSSTPYV (SEQ ID NO:121), SSYAGSYTWV (SEQ ID NO:124), GSYTSSNTQV (SEQ ID NO:125), AAWDDSLSAGV (SEQ ID NO:127), SSYTSSITWV (SEQ ID NO:130), CSYAGSYTWV (SEQ ID NO:131), GSYTSSSTWV (SEQ ID NO:132), SSYTSGSTWV (SEQ ID NO:134), SSYAGTNNFVV (SEQ ID NO:136), QQYNNWPLTFGGGTKVEFK (SEQ ID NO:139), GTWDSSLSGGV (SEQ ID NO:142), SSYAGSYTWGVRRRDRADRP (SEQ ID NO:143), AAWDDSLKGHV (SEQ ID NO:146), AAWDDSLNGWV (SEQ ID NO:149), CSYADYYTWV (SEQ ID NO:151), QSYDSSNLWV (SEQ ID NO:154), QQSYSTPTWT (SEQ ID NO:156), QSYNSSKVV (SEQ ID NO:158), NSYTSSGTLVV (SEQ ID NO:160), DSRGRSGDHWL (SEQ ID NO:163), ATWDDGLSGWV (SEQ ID NO:166), NSYVTGNNWA (SEQ ID NO:169), AAWDDSLSGWV (SEQ ID NO:172), QQSYSTPLYT (SEQ ID NO:174), CSYAGNYTWL (SEQ ID NO:176), TSYSSSSTLVA (SEQ ID NO:177) or SSYTSSSTLVV (SEQ ID NO:179).

In some embodiments, the antibody or antigen binding fragment has at least one heavy chain variable region incorporating the following CDRs:

```
HC-CDR1:
                                    (SEQ ID NO: 180)
VSSNSAAWN

HC-CDR2:
                                    (SEQ ID NO: 181)
YRSKWYN

HC-CDR3:
                                    (SEQ ID NO: 182)
ARGTRGYFDY;
or

HC-CDR1:
                                    (SEQ ID NO: 183)
GFTFSGAY

HC-CDR2:
                                    (SEQ ID NO: 184)
ISYDGSNK

HC-CDR3:
                                    (SEQ ID NO: 185)
ARDLYAFDI;
or

HC-CDR1:
                                    (SEQ ID NO: 186)
GFTFSSYG

HC-CDR2:
                                    (SEQ ID NO: 184)
ISYDGSNK

HC-CDR3:
                                    (SEQ ID NO: 187)
AKIGATDPLDY;
or

HC-CDR1:
                                    (SEQ ID NO: 186)
GFTFSSYG

HC-CDR2:
                                    (SEQ ID NO: 188)
ISYDGSDK
```

-continued

HC-CDR3:
(SEQ ID NO: 189)
AKDLSGLPIIDY;
or

HC-CDR1:
(SEQ ID NO: 190)
GFTFSSYA

HC-CDR2:
(SEQ ID NO: 184)
ISYDGSNK

HC-CDR3:
(SEQ ID NO: 191)
ARRGYFDY;
or

HC-CDR1:
(SEQ ID NO: 186)
GFTFSSYG

HC-CDR2:
(SEQ ID NO: 184)
ISYDGSNK

HC-CDR3:
(SEQ ID NO: 192)
ARIAAADGMDV;
or

HC-CDR1:
(SEQ ID NO: 193)
GFSFRSYG

HC-CDR2:
(SEQ ID NO: 184)
ISYDGSNK

HC-CDR3:
(SEQ ID NO: 194)
ARITHDYGDFSDAFDI;
or

HC-CDR1:
(SEQ ID NO: 186)
GFTFSSYG

HC-CDR2:
(SEQ ID NO: 184)
ISYDGSNK

HC-CDR3:
(SEQ ID NO: 195)
AKLYSGSSNFDY;
or

HC-CDR1:
(SEQ ID NO: 196)
GFTFRSYG

HC-CDR2:
(SEQ ID NO: 184)
ISYDGSNK

HC-CDR3:
(SEQ ID NO: 194)
ARITHDYGDFSDAFDI;
or

HC-CDR1:
(SEQ ID NO: 186)
GFTFSSYG

HC-CDR2:
(SEQ ID NO: 184)
ISYDGSNK

HC-CDR3:
(SEQ ID NO: 197)
AKLSGPNGVDY;

or

HC-CDR1:
(SEQ ID NO: 190)
GFTFSSYA

HC-CDR2:
(SEQ ID NO: 184)
ISYDGSNK

HC-CDR3:
(SEQ ID NO: 198)
ARGQNVDL;
or

HC-CDR1:
(SEQ ID NO: 190)
GFTFSSYA

HC-CDR2:
(SEQ ID NO: 184)
ISYDGSNK

HC-CDR3:
(SEQ ID NO: 199)
ARIMGYDYGDYDVVDY;
or

HC-CDR1:
(SEQ ID NO: 212)
GFSFSSYA

HC-CDR2:
(SEQ ID NO: 184)
ISYDGSNK

HC-CDR3:
(SEQ ID NO: 199)
ARIMGYDYGDYDVVDY;
or

HC-CDR1:
(SEQ ID NO: 186)
GFTFSSYG

HC-CDR2:
(SEQ ID NO: 184)
ISYDGSNK

HC-CDR3:
(SEQ ID NO: 213)
ARRGYGDY;
or

HC-CDR1:
(SEQ ID NO: 204)
WIFLKSYA

HC-CDR2:
(SEQ ID NO: 184)
ISYDGSNK

HC-CDR3:
(SEQ ID NO: 205)
ARVGFSSWYPDLYYFDY;
or

HC-CDR1:
(SEQ ID NO: 186)
GFTFSSYG

HC-CDR2:
(SEQ ID NO: 184)
ISYDGSNK

HC-CDR3:
(SEQ ID NO: 215)
AKFARGVYLFDY;
or

HC-CDR1:
GFTFSSYA (SEQ ID NO: 190)

HC-CDR2:
ISYDGSNK (SEQ ID NO: 184)

HC-CDR3:
ARVQSGEPESDY; (SEQ ID NO: 216)
or

HC-CDR1:
GFSLNSYG (SEQ ID NO: 217)

HC-CDR2:
ISYDGSNK (SEQ ID NO: 184)

HC-CDR3:
AKLYSGSSNFDY; (SEQ ID NO: 195)
or

HC-CDR1:
GFTFSSYA (SEQ ID NO: 190)

HC-CDR2:
ISYDGSNK (SEQ ID NO: 184)

HC-CDR3:
ARVGFSSWYPDLYYFDY; (SEQ ID NO: 205)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
GFTFSSYA (SEQ ID NO: 190)

HC-CDR2:
ISYDGSNK (SEQ ID NO: 184)

HC-CDR3:
ARMVNLYYGDAFDI; (SEQ ID NO: 218)
or

HC-CDR1:
GFTFSSYA (SEQ ID NO: 190)

HC-CDR2:
ISYDGSNK (SEQ ID NO: 184)

HC-CDR3:
ARLVGATADDY; (SEQ ID NO: 219)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
GGTFSSYA (SEQ ID NO: 209)

HC-CDR2:
IIPIFGTA (SEQ ID NO: 210)

HC-CDR3:
ARGLITGTTP; (SEQ ID NO: 211)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
GGSISSSNW (SEQ ID NO: 220)

HC-CDR2:
IYHSGST (SEQ ID NO: 221)

HC-CDR3:
ARVQNLGGGSYYVGAFDY; (SEQ ID NO: 222)
or

HC-CDR1:
GFTFSSYG (SEQ ID NO: 186)

HC-CDR2:
ISYDGSNK (SEQ ID NO: 184)

HC-CDR3:
ARLHFSQYFSTIDAFDI; (SEQ ID NO: 223)
or

HC-CDR1:
GFTFSSYA (SEQ ID NO: 190)

HC-CDR2:
ISYDGSNK (SEQ ID NO: 184)

HC-CDR3:
ARIMGYDYGDYDVVDY; (SEQ ID NO: 199)
or

HC-CDR1:
GFTFSSYA (SEQ ID NO: 190)

HC-CDR2:
ISYDGSNK (SEQ ID NO: 184)

HC-CDR3:
ARDVGYSSGWYFDY; (SEQ ID NO: 200)
or

HC-CDR1:
GFSLSSYG (SEQ ID NO: 201)

HC-CDR2:
ISYDGSNK (SEQ ID NO: 184)

HC-CDR3:
ARLAQSYSSSWYEWEPGREHAFDI; (SEQ ID NO: 202)
or

HC-CDR1:
GFTFSSYA (SEQ ID NO: 190)

HC-CDR2:
ISYDGSNK (SEQ ID NO: 184)

HC-CDR3:
ARPDDDY; (SEQ ID NO: 203)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
WIFLKSYA (SEQ ID NO: 204)

HC-CDR2:
ISYDGSNK (SEQ ID NO: 184)

HC-CDR3:
ARVGFSSWYPDLYYFDY; (SEQ ID NO: 205)
or

HC-CDR1:
GFTFSSYA (SEQ ID NO: 190)

HC-CDR2:
ISYDGSNK (SEQ ID NO: 184)

HC-CDR3:
ARLYSGYPSRYYYGMDV; (SEQ ID NO: 206)
or

HC-CDR1:
GFTFSSYG (SEQ ID NO: 186)

HC-CDR2:
ISYDGSNK (SEQ ID NO: 184)

HC-CDR3:
AKGGKSYYGFDY; (SEQ ID NO: 207)
or

HC-CDR1:
GFTFSSYA (SEQ ID NO: 190)

HC-CDR2:
ISYDGSNK (SEQ ID NO: 184)

HC-CDR3:
ARLHSGRNWGDAFDI; (SEQ ID NO: 208)
or

HC-CDR1:
GGTFSSYA (SEQ ID NO: 209)

HC-CDR2:
IIPIFGTA (SEQ ID NO: 210)

HC-CDR3:
ARGGGPYYDFWSGYYTEFDY; (SEQ ID NO: 224)
or

HC-CDR1:
GFTFSSYA (SEQ ID NO: 190)

HC-CDR2:
ISYDGSNK (SEQ ID NO: 184)

HC-CDR3:
ARDSGYSSGWYFDY; (SEQ ID NO: 225)
or

HC-CDR1:
GFTFSSYA (SEQ ID NO: 190)

HC-CDR2:
ISYDGSNK (SEQ ID NO: 184)

HC-CDR3:
ARDSGYSSGWYFDY; (SEQ ID NO: 225)
or

HC-CDR1:
ILPSDSYA (SEQ ID NO: 226)

HC-CDR2:
ISYDGSNK (SEQ ID NO: 184)

HC-CDR3:
ARIAAAGRDAFDI; (SEQ ID NO: 227)
or

HC-CDR1: GYTFTSYG (SEQ ID NO: 228)

HC-CDR2: ISAYNGNT (SEQ ID NO: 229)

HC-CDR3: ARVVAAARSYYYYMDV; (SEQ ID NO: 230)
or

HC-CDR1: GGTFSSYA (SEQ ID NO: 209)

HC-CDR2: IIPIFGTA (SEQ ID NO: 210)

HC-CDR3: ARADSSAGGGPYYYGMDV; (SEQ ID NO: 231)
or

HC-CDR1: GFTFSSYG (SEQ ID NO: 186)

HC-CDR2: ISYDGSNK (SEQ ID NO: 184)

HC-CDR3: AKFARGVYLFDY; (SEQ ID NO: 215)
or

HC-CDR1: GFTFSSYG (SEQ ID NO: 186)

HC-CDR2: ISYDGSNK (SEQ ID NO: 184)

HC-CDR3: ARIGGYDDFDY; (SEQ ID NO: 232)
or

HC-CDR1: GFTFSSYA (SEQ ID NO: 190)

HC-CDR2: ISYDGSNK (SEQ ID NO: 184)

HC-CDR3: ARVYYDSSGTQGDSFDY; (SEQ ID NO: 233)
or

HC-CDR1: GFTFGSYG (SEQ ID NO: 234)

HC-CDR2: ISYDGSNK (SEQ ID NO: 184)

HC-CDR3: AKGSYYFDY; (SEQ ID NO: 235)
or

HC-CDR1: GFTFSSYG (SEQ ID NO: 186)

HC-CDR2: ISYDGSNK (SEQ ID NO: 184)

HC-CDR3: AKLSGPNGVDY; (SEQ ID NO: 197)
or

HC-CDR1: GFSLGSYG (SEQ ID NO: 238)

HC-CDR2: ISYDGSNK (SEQ ID NO: 184)

HC-CDR3: AKGSYYFDY; (SEQ ID NO: 235)
or

HC-CDR1: GFTFSSYA (SEQ ID NO: 190)

HC-CDR2: ISYDGSNK (SEQ ID NO: 184)

HC-CDR3: ARGVLFDY; (SEQ ID NO: 236)
or

HC-CDR1: GFTFSSYA (SEQ ID NO: 190)

HC-CDR2: ISYDGSNK (SEQ ID NO: 184)

HC-CDR3: ARSGVLDY. (SEQ ID NO: 237)

In some embodiments, the antibody or antigen binding fragment has at least one light chain variable region incorporating the following CDRs:

LC-CDR1: QDVGRY (SEQ ID NO: 101)

LC-CDR2: AAS (SEQ ID NO: 102)

LC-CDR3: QQYRSAPLA; (SEQ ID NO: 103)
or

LC-CDR1: TGNIASNR (SEQ ID NO: 104)

LC-CDR2: DNH (SEQ ID NO: 105)

LC-CDR3:                                (SEQ ID NO: 106)
QSYDYSSVI;
or

LC-CDR1:                                (SEQ ID NO: 107)
SSDVGGYNY

LC-CDR2:                                (SEQ ID NO: 108)
DVS

LC-CDR3:                                (SEQ ID NO: 109)
SSYTSSSSWV;
or

LC-CDR1:                                (SEQ ID NO: 110)
SSDVGAYNY

LC-CDR2:                                (SEQ ID NO: 111)
EVS

LC-CDR3:                                (SEQ ID NO: 112)
SSYTSSNTLV;
or

LC-CDR1:                                (SEQ ID NO: 107)
SSDVGGYNY

LC-CDR2:                                (SEQ ID NO: 108)
DVS

LC-CDR3:                                (SEQ ID NO: 113)
SSYTSSSTVV;
or

LC-CDR1:                                (SEQ ID NO: 114)
SSDIGAYNY

LC-CDR2:                                (SEQ ID NO: 108)
DVS

LC-CDR3:                                (SEQ ID NO: 115)
SSYTTSSTVV;
or

LC-CDR1:                                (SEQ ID NO: 116)
SSNIGSNY

LC-CDR2:                                (SEQ ID NO: 117)
RNN

LC-CDR3:                                (SEQ ID NO: 118)
AAWDGSLSGWV;
or

LC-CDR1:                                (SEQ ID NO: 107)
SSDVGGYNY

LC-CDR2:                                (SEQ ID NO: 108)
DVS

LC-CDR3:                                (SEQ ID NO: 119)
SSYTSSSTWV;
or

LC-CDR1:                                (SEQ ID NO: 116)
SSNIGSNY

LC-CDR2:                                (SEQ ID NO: 117)
RNN

LC-CDR3:                                (SEQ ID NO: 118)
AAWDGSLSGWV;
or

LC-CDR1:                                (SEQ ID NO: 107)
SSDVGGYNY

LC-CDR2:                                (SEQ ID NO: 108)
DVS

LC-CDR3:                                (SEQ ID NO: 120)
CSYAGSYTFV;
or

LC-CDR1:                                (SEQ ID NO: 107)
SSDVGGYNY

LC-CDR2:                                (SEQ ID NO: 108)
DVS

LC-CDR3:                                (SEQ ID NO: 121)
NSYTSSTPYV;
or

LC-CDR1:                                (SEQ ID NO: 122)
ISDVGGYNY

LC-CDR2:                                (SEQ ID NO: 123)
DVT

LC-CDR3:                                (SEQ ID NO: 124)
SSYAGSYTWV;
or

LC-CDR1:                                (SEQ ID NO: 122)
ISDVGGYNY

LC-CDR2:                                (SEQ ID NO: 123)
DVT

LC-CDR3:                                (SEQ ID NO: 124)
SSYAGSYTWV;
or

LC-CDR1:                                (SEQ ID NO: 107)
SSDVGGYNY

LC-CDR2:                                (SEQ ID NO: 108)
DVS

LC-CDR3:
GSYTSSNTQV;
or
(SEQ ID NO: 125)

LC-CDR1:
SSNIGNNL
(SEQ ID NO: 126)

LC-CDR2:
RNN
(SEQ ID NO: 117)

LC-CDR3:
AAWDDSLSAGV;
or
(SEQ ID NO: 127)

LC-CDR1:
SSDVGGYDY
(SEQ ID NO: 128)

LC-CDR2:
DVH
(SEQ ID NO: 129)

LC-CDR3:
SSYTSSITWV;
or
(SEQ ID NO: 130)

LC-CDR1:
SSDVGGYNY
(SEQ ID NO: 107)

LC-CDR2:
DVS
(SEQ ID NO: 108)

LC-CDR3:
CSYAGSYTWV;
or
(SEQ ID NO: 131)

LC-CDR1:
SSDVGGYNY
(SEQ ID NO: 107)

LC-CDR2:
DVS
(SEQ ID NO: 108)

LC-CDR3:
SSYTSSSTWV;
or
(SEQ ID NO: 119)

LC-CDR1:
SSNIGNNL
(SEQ ID NO: 126)

LC-CDR2:
RNN
(SEQ ID NO: 117)

LC-CDR3:
AAWDDSLSAGV;
or
(SEQ ID NO: 127)

LC-CDR1:
SSDVGGYNY
(SEQ ID NO: 107)

LC-CDR2:
DVS
(SEQ ID NO: 108)

LC-CDR3:
CSYAGSYTWV;
or
(SEQ ID NO: 131)

LC-CDR1:
SSDVGGYNY
(SEQ ID NO: 107)

LC-CDR2:
DVS
(SEQ ID NO: 108)

LC-CDR3:
SSYTSSSTWV;
or
(SEQ ID NO: 113)

LC-CDR1:
SSDVGGYNY
(SEQ ID NO: 107)

LC-CDR2:
DVS
(SEQ ID NO: 108)

LC-CDR3:
GSYTSSSTWV;
or
(SEQ ID NO: 132)

LC-CDR1:
SSDVGGYNY
(SEQ ID NO: 107)

LC-CDR2:
DVG
(SEQ ID NO: 133)

LC-CDR3:
SSYTSGSTWV;
or
(SEQ ID NO: 134)

LC-CDR1:
SSDVGGYNY
(SEQ ID NO:107)

LC-CDR2:
EVN
(SEQ ID NO:135)

LC-CDR3:
SSYAGTNNFVV;
or
(SEQ ID NO:136)

LC-CDR1:
SSDVGGYNY
(SEQ ID NO: 107)

LC-CDR2:
DVT
(SEQ ID NO: 123)

LC-CDR3:
CSYAGSYTWV;
or
(SEQ ID NO: 131)

LC-CDR1:
QSVSSN
(SEQ ID NO: 137)

LC-CDR2:
GAS
(SEQ ID NO: 138)

-continued

LC-CDR3:
(SEQ ID NO: 139)
QQYNNWPLTFGGGTKVEFK;
or

LC-CDR1:
(SEQ ID NO: 140)
SSNIGNNY

LC-CDR2:
(SEQ ID NO: 141)
DNT

LC-CDR3:
(SEQ ID NO: 142);
GTWDSSLSGGV
or

LC-CDR1:
(SEQ ID NO: 122)
ISDVGGYNY

LC-CDR2:
(SEQ ID NO: 123)
DVT

LC-CDR3:
(SEQ ID NO: 143)
SSYAGSYTWGVRRRDRADRP;
or

LC-CDR1:
(SEQ ID NO: 144)
YSNVGSNL

LC-CDR2:
(SEQ ID NO: 145)
EDD

LC-CDR3:
(SEQ ID NO: 146)
AAWDDSLKGHV;
or

LC-CDR1:
(SEQ ID NO: 147)
SSNIGSNT

LC-CDR2:
(SEQ ID NO: 148)
INN

LC-CDR3:
(SEQ ID NO: 149)
AAWDDSLNGWV;
or

LC-CDR1:
(SEQ ID NO: 107)
SSDVGGYNY

LC-CDR2:
(SEQ ID NO: 108)
DVS

LC-CDR3:
(SEQ ID NO: 131)
CSYAGSYTWV;
or

LC-CDR1:
(SEQ ID NO: 150)
SRDVGGYNY

LC-CDR2:
(SEQ ID NO: 108)
DVS

LC-CDR3:
(SEQ ID NO: 151)
CSYADYYTWV;
or

LC-CDR1:
(SEQ ID NO: 126)
SSNIGNNL

LC-CDR2:
(SEQ ID NO: 117)
RNN

LC-CDR3:
(SEQ ID NO: 127)
AAWDDSLSAGV;
or

LC-CDR1:
(SEQ ID NO: 152)
SGSIASNY

LC-CDR2:
(SEQ ID NO: 153)
DDN

LC-CDR3:
(SEQ ID NO: 154)
QSYDSSNLWV;
or

LC-CDR1:
(SEQ ID NO: 155)
QIISSY

LC-CDR2:
(SEQ ID NO: 102)
AAS

LC-CDR3:
(SEQ ID NO: 156)
QQSYSTPTWT;
or

LC-CDR1:
(SEQ ID NO: 107)
SSDVGGYNY

LC-CDR2:
(SEQ ID NO: 108)
DVS

LC-CDR3:
(SEQ ID NO: 119)
SSYTSSSTWV;
or

LC-CDR1:
(SEQ ID NO: 152)
SGSIASNY

LC-CDR2:
(SEQ ID NO: 157)
EDN

LC-CDR3:
(SEQ ID NO: 158)
QSYNSSKVV;
or

LC-CDR1:
(SEQ ID NO: 159)
SSDVGGYEY

LC-CDR2:
(SEQ ID NO: 108)
DVS

LC-CDR3: (SEQ ID NO: 160)
NSYTSSGTLVV;
or

LC-CDR1: (SEQ ID NO: 159)
SSDVGGYEY

LC-CDR2: (SEQ ID NO: 108)
DVS

LC-CDR3: (SEQ ID NO: 160)
NSYTSSGTLVV;
or

LC-CDR1: (SEQ ID NO: 107)
SSDVGGYNY

LC-CDR2: (SEQ ID NO: 108)
DVS

LC-CDR3: (SEQ ID NO: 131)
CSYAGSYTWV;
or

LC-CDR1: (SEQ ID NO: 161)
SLRGYY

LC-CDR2: (SEQ ID NO: 162)
GNN

LC-CDR3: (SEQ ID NO: 163)
DSRGRSGDHWL;
or

LC-CDR1: (SEQ ID NO: 164)
SSNIGSYY

LC-CDR2: (SEQ ID NO: 165)
RND

LC-CDR3: (SEQ ID NO: 166)
ATWDDGLSGWV;
or

LC-CDR1: (SEQ ID NO: 110)
SSDVGAYNY

LC-CDR2: (SEQ ID NO: 168)
EVF

LC-CDR3: (SEQ ID NO: 169)
NSYVTGNNWA;
or

LC-CDR1: (SEQ ID NO: 107)
SSDVGGYNY

LC-CDR2: (SEQ ID NO: 108)
DVS

LC-CDR3: (SEQ ID NO: 119)
SSYTSSSTWV;
or

LC-CDR1: (SEQ ID NO: 170)
SSNIGYDA

LC-CDR2: (SEQ ID NO: 171)
NDN

LC-CDR3: (SEQ ID NO: 172)
AAWDDSLSGWV;
or

LC-CDR1: (SEQ ID NO: 173)
QGSSSY

LC-CDR2: (SEQ ID NO: 102)
AAS

LC-CDR3: (SEQ ID NO: 174)
QQSYSTPLYT;
or

LC-CDR1: (SEQ ID NO: 175)
SSDVGGYKY

LC-CDR2: (SEQ ID NO: 108)
DVS

LC-CDR3: (SEQ ID NO: 176)
CSYAGNYTWL;
or

LC-CDR1: (SEQ ID NO: 173)
QGSSSY

LC-CDR2: (SEQ ID NO: 102)
AAS

LC-CDR3: (SEQ ID NO: 174)
QQSYSTPLYT;
or

LC-CDR1: (SEQ ID NO: 107)
SSDVGGYNY

LC-CDR2: (SEQ ID NO: 108)
DVS

LC-CDR3: (SEQ ID NO: 177)
TSYSSSSTLVA;
or

LC-CDR1: (SEQ ID NO: 178)
SSDVGNYKY

LC-CDR2: (SEQ ID NO: 108)
DVS

LC-CDR3:

SSYTSSSTLVV. (SEQ ID NO: 179)

In another aspect, the present invention provides an antibody or antigen binding fragment, optionally isolated, which is capable of binding to IL-11, having at least one heavy chain variable region incorporating the following CDRs:

HC-CDR1:

VSSNSAAWN (SEQ ID NO: 180)

HC-CDR2:

YRSKWYN (SEQ ID NO: 181)

HC-CDR3:

ARGTRGYFDY; (SEQ ID NO: 182)
or

HC-CDR1:

GFTFSGAY (SEQ ID NO: 183)

HC-CDR2:

ISYDGSNK (SEQ ID NO: 184)

HC-CDR3:

ARDLYAFDI; (SEQ ID NO: 185)
or

HC-CDR1:

GFTFSSYG (SEQ ID NO: 186)

HC-CDR2:

ISYDGSNK (SEQ ID NO: 184)

HC-CDR3:

AKIGATDPLDY; (SEQ ID NO: 187)
or

HC-CDR1:

GFTFSSYG (SEQ ID NO: 186)

HC-CDR2:

ISYDGSDK (SEQ ID NO: 188)

HC-CDR3:

AKDLSGLPIIDY; (SEQ ID NO: 189)
or

HC-CDR1:

GFTFSSYA (SEQ ID NO: 190)

HC-CDR2:

ISYDGSNK (SEQ ID NO: 184)

HC-CDR3:

ARRGYFDY; (SEQ ID NO: 191)
or

HC-CDR1:

GFTFSSYG (SEQ ID NO: 186)

HC-CDR2:

ISYDGSNK (SEQ ID NO: 184)

HC-CDR3:

ARIAAADGMDV; (SEQ ID NO: 192)
or

HC-CDR1:

GFSFRSYG (SEQ ID NO: 193)

HC-CDR2:

ISYDGSNK (SEQ ID NO: 184)

HC-CDR3:

ARITHDYGDFSDAFDI; (SEQ ID NO: 194)
or

HC-CDR1:

GFTFSSYG (SEQ ID NO: 186)

HC-CDR2:

ISYDGSNK (SEQ ID NO: 184)

HC-CDR3:

AKLYSGSSNFDY; (SEQ ID NO: 195)
or

HC-CDR1:

GFTFRSYG (SEQ ID NO: 196)

HC-CDR2:

ISYDGSNK (SEQ ID NO: 184)

HC-CDR3:

ARITHDYGDFSDAFDI; (SEQ ID NO: 194)
or

HC-CDR1:

GFTFSSYG (SEQ ID NO: 186)

HC-CDR2:

ISYDGSNK (SEQ ID NO: 184)

HC-CDR3:

AKLSGPNGVDY; (SEQ ID NO: 197)
or

HC-CDR1:

GFTFSSYA (SEQ ID NO: 190)

HC-CDR2:

ISYDGSNK (SEQ ID NO: 184)

HC-CDR3:

ARGQNVDL; (SEQ ID NO: 198)
or

HC-CDR1:
GFTFSSYA (SEQ ID NO: 190)

HC-CDR2:
ISYDGSNK (SEQ ID NO: 184)

HC-CDR3:
ARIMGYDYGDYDVVDY; (SEQ ID NO: 199)
or

HC-CDR1:
GFSFSSYA (SEQ ID NO: 212)

HC-CDR2:
ISYDGSNK (SEQ ID NO: 184)

HC-CDR3:
ARIMGYDYGDYDVVDY; (SEQ ID NO: 199)
or

HC-CDR1:
GFTFSSYG (SEQ ID NO: 186)

HC-CDR2:
ISYDGSNK (SEQ ID NO: 184)

HC-CDR3:
ARRGYGDY; (SEQ ID NO: 213)
or

HC-CDR1:
WIFLKSYA (SEQ ID NO: 204)

HC-CDR2:
ISYDGSNK (SEQ ID NO: 184)

HC-CDR3:
ARVGFSSWYPDLYYFDY; (SEQ ID NO: 205)
or

HC-CDR1:
GFTFSSYG (SEQ ID NO: 186)

HC-CDR2:
ISYDGSNK (SEQ ID NO: 184)

HC-CDR3:
AKFARGVYLFDY; (SEQ ID NO: 215)
or

HC-CDR1:
GFTFSSYA (SEQ ID NO: 190)

HC-CDR2:
ISYDGSNK (SEQ ID NO: 184)

HC-CDR3:
ARVQSGEPESDY; (SEQ ID NO: 216)
or

HC-CDR1:
GFSLNSYG (SEQ ID NO: 217)

HC-CDR2:
ISYDGSNK (SEQ ID NO: 184)

HC-CDR3:
AKLYSGSSNFDY; (SEQ ID NO: 195)
or

HC-CDR1:
GFTFSSYA (SEQ ID NO: 190)

HC-CDR2:
ISYDGSNK (SEQ ID NO: 184)

HC-CDR3:
ARVGFSSWYPDLYYFDY; (SEQ ID NO: 205)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
GFTFSSYA (SEQ ID NO: 190)

HC-CDR2:
ISYDGSNK (SEQ ID NO: 184)

HC-CDR3:
ARMVNLYYGDAFDI; (SEQ ID NO: 218)
or

HC-CDR1:
GFTFSSYA (SEQ ID NO: 190)

HC-CDR2:
ISYDGSNK (SEQ ID NO: 184)

HC-CDR3:
ARLVGATADDY; (SEQ ID NO: 219)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
GGTFSSYA (SEQ ID NO: 209)

HC-CDR2:
IIPIFGTA (SEQ ID NO: 210)

HC-CDR3:
ARGLITGTTP; (SEQ ID NO: 211)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
GGSISSSNW (SEQ ID NO: 220)

HC-CDR2:
IYHSGST (SEQ ID NO: 221)

HC-CDR3:
ARVQNLGGGSYYVGAFDY; (SEQ ID NO: 222)
or

HC-CDR1:
GFTFSSYG (SEQ ID NO: 186)

HC-CDR2:
ISYDGSNK (SEQ ID NO: 184)

HC-CDR3:
ARLHFSQYFSTIDAFDI; (SEQ ID NO: 223)
or

HC-CDR1:
GFTFSSYA (SEQ ID NO: 190)

HC-CDR2:
ISYDGSNK (SEQ ID NO: 184)

HC-CDR3:
ARIMGYDYGDYDVVDY; (SEQ ID NO: 199)
or

HC-CDR1:
GFTFSSYA (SEQ ID NO: 190)

HC-CDR2:
ISYDGSNK (SEQ ID NO: 184)

HC-CDR3:
ARDVGYSSGWYFDY; (SEQ ID NO: 200)
or

HC-CDR1:
GFSLSSYG (SEQ ID NO: 201)

HC-CDR2:
ISYDGSNK (SEQ ID NO: 184)

HC-CDR3:
ARLAQSYSSSWYEWEPGREHAFDI; (SEQ ID NO: 202)
or

HC-CDR1:
GFTFSSYA (SEQ ID NO: 190)

HC-CDR2:
ISYDGSNK (SEQ ID NO: 184)

HC-CDR3:
ARPDDDY; (SEQ ID NO: 203)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
WIFLKSYA (SEQ ID NO: 204)

HC-CDR2:
ISYDGSNK (SEQ ID NO: 184)

HC-CDR3:
ARVGFSSWYPDLYYFDY; (SEQ ID NO: 205)
or

HC-CDR1:
GFTFSSYA (SEQ ID NO: 190)

HC-CDR2:
ISYDGSNK (SEQ ID NO: 184)

HC-CDR3:
ARLYSGYPSRYYYGMDV; (SEQ ID NO: 206)
or

HC-CDR1:
GFTFSSYG (SEQ ID NO: 186)

HC-CDR2:
ISYDGSNK (SEQ ID NO: 184)

HC-CDR3:
AKGGKSYYGFDY; (SEQ ID NO: 207)
or

HC-CDR1:
GFTFSSYA (SEQ ID NO: 190)

HC-CDR2:
ISYDGSNK (SEQ ID NO: 184)

HC-CDR3:
ARLHSGRNWGDAFDI; (SEQ ID NO: 208)
or

HC-CDR1:
GGTFSSYA (SEQ ID NO: 209)

HC-CDR2:
IIPIFGTA (SEQ ID NO: 210)

HC-CDR3:
ARGGGPYYDFWSGYYTEFDY; (SEQ ID NO: 224)
or

HC-CDR1:
GFTFSSYA (SEQ ID NO: 190)

HC-CDR2:
ISYDGSNK (SEQ ID NO: 184)

HC-CDR3:
ARDSGYSSGWYFDY; (SEQ ID NO: 225)
or

HC-CDR1:
GFTFSSYA (SEQ ID NO: 190)

HC-CDR2:
ISYDGSNK (SEQ ID NO: 184)

HC-CDR3:
ARDSGYSSGWYFDY; (SEQ ID NO: 225)
or

HC-CDR1:
ILPSDSYA (SEQ ID NO: 226)

HC-CDR2:
ISYDGSNK (SEQ ID NO: 184)

HC-CDR3:
ARIAAAGRDAFDI; (SEQ ID NO: 227)
or

HC-CDR1:
GYTFTSYG (SEQ ID NO: 228)

HC-CDR2:
ISAYNGNT (SEQ ID NO: 229)

HC-CDR3:
ARVVAAARSYYYYMDV; (SEQ ID NO: 230)
or

HC-CDR1:
GGTFSSYA (SEQ ID NO: 209)

HC-CDR2:
IIPIFGTA (SEQ ID NO: 210)

HC-CDR3:
ARADSSAGGGPYYYGMDV; (SEQ ID NO: 231)
or

HC-CDR1:
GFTFSSYG (SEQ ID NO: 186)

HC-CDR2:
ISYDGSNK (SEQ ID NO: 184)

HC-CDR3:
AKFARGVYLFDY; (SEQ ID NO: 215)
or

HC-CDR1:
GFTFSSYG (SEQ ID NO: 186)

HC-CDR2:
ISYDGSNK (SEQ ID NO: 184)

HC-CDR3:
ARIGGYDDFDY; (SEQ ID NO: 232)
or

HC-CDR1:
GFTFSSYA (SEQ ID NO: 190)

HC-CDR2:
ISYDGSNK (SEQ ID NO: 184)

HC-CDR3:
ARVYYDSSGTQGDSFDY; (SEQ ID NO: 233)
or

HC-CDR1:
GFTFGSYG (SEQ ID NO: 234)

HC-CDR2:
ISYDGSNK (SEQ ID NO: 184)

HC-CDR3:
AKGSYYFDY; (SEQ ID NO: 235)
or

HC-CDR1:
GFTFSSYG (SEQ ID NO: 186)

HC-CDR2:
ISYDGSNK (SEQ ID NO: 184)

HC-CDR3:
AKLSGPNGVDY; (SEQ ID NO: 197)
or

HC-CDR1:
GFSLGSYG (SEQ ID NO: 238)

HC-CDR2:
ISYDGSNK (SEQ ID NO: 184)

-continued

HC-CDR3:
AKGSYYFDY; (SEQ ID NO: 235)
or

HC-CDR1:
GFTFSSYA (SEQ ID NO: 190)

HC-CDR2:
ISYDGSNK (SEQ ID NO: 184)

HC-CDR3:
ARGVLFDY; (SEQ ID NO: 236)
or

HC-CDR1:
GFTFSSYA (SEQ ID NO: 190)

HC-CDR2:
ISYDGSNK (SEQ ID NO: 184)

HC-CDR3:
ARSGVLDY; (SEQ ID NO: 237)

and
having at least one light chain variable region arrived at following light chain shuffling.

In another aspect, the present invention provides an antibody or antigen binding fragment, optionally isolated, which is capable of binding to IL-11, comprising a light chain and a heavy chain variable region sequence, wherein:

the light chain comprises a LC-CDR1, LC-CDR2, LC-CDR3, having at least 85% overall sequence identity to LC-CDR1: one of $X_1X_2DX_3GX_4YX_3Y$ (SEQ ID NO:239), $X_6SNX_7GX_8X_9X_{10}$ (SEQ ID NO:240), $QX_{11}X_{12}SSX_{13}$ (SEQ ID NO:241), $X_{14}GX_{15}IASNX_{16}$ (SEQ ID NO:242), QDVGRY (SEQ ID NO:101), or SLRGYY (SEQ ID NO:161); LC-CDR2: one of $DVX_{17}$ (SEQ ID NO:243), $X_{18}NX_{19}$ (SEQ ID NO:244), $X_{20}AS$ (SEQ ID NO:245), $X_{21}DX_{22}$ (SEQ ID NO:246), $EVX_{23}$ (SEQ ID NO:247), or $DX_{24}X_{25}$ (SEQ ID NO:248); LC-CDR3: one of $X_{26}SYTX_{27}X_{28}X_{29}X_{30}X_{31}VX_{32}$ (SEQ ID NO:249), $X_{33}SYAX_{34}X_{35}X_{36}X_{37}X_{38}X_{39}X_{40}X_{41}X_{42}X_{43}X_{44}X_{45}X_{46}X_{47}X_{48}X_{49}$ (SEQ ID NO:250), $X_{50}X_{51}WDX_{52}X_{53}LX_{54}X_{55}X_{56}V$ (SEQ ID NO:251), $QQX_{57}X_{58}X_{59}PX_{60}X_{61}X_{62}X_{63}X_{64}X_{65}X_{66}X_{67}X_{68}X_{69}X_{70}X_{71}X_{72}$ (SEQ ID NO:252), $QSYX_{73}X_{74}SX_{75}X_{76}X_{77}X_{78}$ (SEQ ID NO:253), $X_{79}SYX_{80}SSX_{81}X_{82}X_{83}VX_{84}$ (SEQ ID NO:254), NSYVTGNNWA (SEQ ID NO:169), or DSRGRSGDHWL (SEQ ID NO:163); and the heavy chain comprises a HC-CDR1, HC-CDR2, HC-CDR3, having at least 85% overall sequence identity to HC-CDR1: one of $GFTFSSYX_{85}$ (SEQ ID NO:255), $GX_{86}X_{87}X_{88}X_{89}SYG$ (SEQ ID NO:256), $X_{90}X_{91}X_{92}X_{93}X_{94}SYA$ (SEQ ID NO:257), WIFLKSYA (SEQ ID NO:204), VSSNSAAWN (SEQ ID NO:180), GGSISSSNW (SEQ ID NO:220), or GFTFSGAY (SEQ ID NO:183); HC-CDR2: one of $ISYDGSX_{95}K$ (SEQ ID NO:258), IIPIFGTA (SEQ ID NO:210), YRSKWYN (SEQ ID NO:181), ISAYNGNT (SEQ ID NO:229), or IYHSGST (SEQ ID NO:221); HC-CDR3: one of AKLSGPNGVDY (SEQ ID NO:197), $AKX_{96}X_{97}X_{95}GX_{99}X_{100}X_{101}X_{102}DY$ (SEQ ID NO:259), $ARDX_{103}GYSSGWYFDY$ (SEQ ID NO:260), $ARLX_{104}X_{105}X_{106}X_{107}X_{108}X_{109}X_{110}X_{111}X_{112}X_{113}X_{114}X_{115}X_{116}X_{117}X_{118}X_{119}X_{120}AFDI$ (SEQ ID NO:261), ARIMGYDYGDYDVVDY (SEQ ID NO:199), $ARIX_{121}X_{122}X_{123}X_{124}X_{125}X_{126}DX_{127}X_{128}X_{129}X_{130}$ (SEQ ID NO:262), ARVGFSSWYPDLYYFDY (SEQ ID NO:205), $X_{131}X_{132}X_{133}X_{134}RGYX_{135}DY$ (SEQ ID NO:263), ARITHDYGDFSDAFDI (SEQ ID NO:194), $ARX_{136}GVLX_{137}DY$ (SEQ ID NO:264), AKGSYYFDY (SEQ ID NO:235), ARLYSGYPSRYYYGMDV (SEQ ID NO:206), ARVQSGEPESDY (SEQ ID NO:216), AKIGATDPLDY (SEQ ID NO:187), ARDLYAFDI (SEQ ID NO:185), ARPDDDY (SEQ ID NO:203), AKGGKSYYGFDY (SEQ ID NO:207), ARADSSAGGGPYYYGMDV (SEQ ID NO:231), ARVYYDSSGTQGDSFDY (SEQ ID NO:233), ARVVAAARSYYYYMDV (SEQ ID NO:230), ARGGGPYYDFWSGYYTEFDY (SEQ ID NO:224), ARMVNLYYGDAFDI (SEQ ID NO:218), ARGLITGTTP (SEQ ID NO:211), ARGQNVDL (SEQ ID NO:198), ARVQNLGGGSYYVGAFDY (SEQ ID NO:222), or ARLVGATADDY (SEQ ID NO:219);

wherein $X_1$=S or I, $X_2$=S or R, $X_3$=V or I, $X_4$=G, A or N, $X_5$=N, E, K or D, $X_6$=S or Y, $X_7$=I or V, $X_8$=S, N or Y, $X_9$=N, Y or D, $X_{10}$=L, Y, T or A, $X_{11}$=G, S or I, $X_{12}$=S, I or V, $X_{13}$=Y or N, $X_{14}$=S or T, $X_{15}$=S or N, $X_{16}$=Y or R, $X_{17}$=S, T or G, $X_{18}$=R, I or G, $X_{19}$=N or D, $X_{20}$=A or G, $X_{21}$=E, D or N, $X_{22}$=N or D, $X_{23}$=S, For N, $X_{24}$=N or V, $X_{25}$=H or T, $X_{26}$=S, N or G, $X_{27}$=S or T, $X_{28}$=S or G, $X_{29}$=S, N, G or I, $X_{30}$=T or S, $X_{31}$=W, L, V or Q, $X_{32}$=absent or V, $X_{33}$=C or S, $X_{34}$=G or D, $X_{35}$=S, Y, N or T, $X_{36}$=Y or N, $X_{37}$=T or N, $X_{38}$=W or F, $X_{39}$=V, G or L, $X_{40}$=absent or V, $X_{41}$=absent or R, $X_{42}$=absent or R, $X_{43}$=absent or R, $X_{44}$=absent or D, $X_{45}$=absent or R, $X_{46}$=absent or A, $X_{47}$=absent or D, $X_{48}$=absent or R, $X_{49}$=absent or P, $X_{50}$=A or G, $X_{51}$=A or T, $X_{52}$=D, G or S, $X_{53}$=S or G, $X_{54}$=S, K or N, $X_{55}$=G or A, $X_{56}$=W, G or H, $X_{57}$=S or Y, $X_{58}$=Y, R or N, $X_{59}$=S or N, $X_{60}$=T, A or W, $X_{61}$=L or T, $X_{62}$=Y, A, W or T, $X_{63}$=T, absent or F, $X_{64}$=absent or G, $X_{65}$=absent or G, $X_{66}$=absent or G, $X_{67}$=absent or T, $X_{68}$=absent or K, $X_{69}$=absent or V, $X_{70}$=absent or E, $X_{71}$=absent or F, $X_{72}$=absent or K, $X_{73}$=D or N, $X_{74}$=S or Y, $X_{75}$=K, S or N, $X_{76}$=V or L, $X_{77}$=I, V or W, $X_{78}$=absent or V, $X_{79}$=T or N, $X_{80}$=T or S, $X_{81}$=T or S, $X_{82}$=P or T, $X_{83}$=Y or L, $X_{84}$=absent or A, $X_{85}$=A or G, $X_{86}$=F or Y, $X_{87}$=S or T, $X_{88}$=L or F, $X_{89}$=G, R, T, S or N, $X_{90}$=G or I, $X_{91}$=G, For L, $X_{92}$=T, S or P, $X_{93}$=F or S, $X_{94}$=S or D, $X_{95}$=N or D, $X_{96}$=L, For D, $X_{97}$=Y, A or L, $X_{98}$=S or R, $X_{99}$=S, V or L, $X_{100}$=S, Y or P, $X_{101}$=N, L or I, $X_{102}$=F or I, $X_{103}$=S or V, $X_{104}$=H or A, $X_{105}$=S, Q or F, $X_{106}$=S or G, $X_{107}$=absent or Y, $X_{108}$=absent or S, $X_{109}$=absent, R or S, $X_{110}$=Q, N or S, $X_{111}$=W or Y, $X_{112}$=absent, Y or F, $X_{113}$=absent or E, $X_{114}$=absent or W, $X_{115}$=absent or E, $X_{116}$=absent or P, $X_{117}$=absent, G or S, $X_{118}$=absent, R or T, $X_{119}$=G, E or I, $X_{120}$=D or H, $X_{121}$=A or G, $X_{122}$=A or G, $X_{123}$=A or Y, $X_{124}$=D or absent, $X_{125}$=G or D, $X_{126}$=F, M or R, $X_{127}$=V, Y or A, $X_{128}$=absent or F, $X_{129}$=absent or D, $X_{130}$=absent or I, $X_{131}$=absent or A, $X_{132}$=absent or R, $X_{133}$=A or G, $X_{134}$=R or T, $X_{135}$=F or G, $X_{136}$=absent or S, $X_{137}$=absent or F.

In another aspect, the present invention provides an antibody or antigen binding fragment, optionally isolated, which is capable of binding to IL-11, comprising a light chain and a heavy chain variable region sequence, wherein:

the light chain sequence has at least 85% sequence identity to the light chain sequence of one of SEQ ID NOs:1 to 50, and;

the heavy chain sequence has at least 85% sequence identity to the heavy chain sequence of one of SEQ ID NOs:51 to 100.

In another aspect, the present invention provides an antibody or antigen binding fragment, optionally isolated, which is capable of binding to IL-11, which is capable of inhibiting IL-11 trans signalling, optionally wherein the antibody or antigen binding fragment is an antibody or antigen binding fragment according to the present invention.

In some embodiments in accordance with the various aspects of the present invention, the antibody or antigen binding fragment is conjugated to a drug moiety or a detectable moiety.

In another aspect, the present invention provides a complex, optionally an in vitro complex and/or optionally isolated, comprising an antibody or antigen binding fragment according to the present invention bound to IL-11.

In another aspect, the present invention provides a composition comprising the antibody or antigen binding fragment according to the present invention, and at least one pharmaceutically-acceptable carrier.

In another aspect, the present invention provides an isolated nucleic acid encoding the antibody or antigen binding fragment according to the present invention.

In some embodiments, the nucleic acid comprises a sequence having at least 60%, 70%, 80%, 90%, 95%, or greater sequence identity to one of SEQ ID NOs:476 to 539, or an equivalent sequence as a result of codon degeneracy. In some embodiments, the nucleic acid comprises a sequence having at least 60%, 70%, 80%, 90%, 95%, or greater sequence identity to one of SEQ ID NOs:571 to 580, or an equivalent sequence as a result of codon degeneracy.

In another aspect, the present invention provides a vector comprising the nucleic acid according to the present invention.

In another aspect, the present invention provides a host cell comprising the vector according to the present invention.

In another aspect, the present invention provides a method for making an antibody or antigen binding fragment according to the present invention, comprising culturing the host cell according to the present invention under conditions suitable for the expression of the antibody or antigen binding fragment, and recovering the antibody or antigen binding fragment.

In another aspect, the present invention provides an antibody, antigen binding fragment, or composition according to the present invention for use in therapy, or in a method of medical treatment.

In another aspect, the present invention provides an antibody, antigen binding fragment, or composition according to the present invention for use in the treatment or prevention of fibrosis, or a disease/disorder characterised by fibrosis.

In another aspect, the present invention provides an antibody, antigen binding fragment, or composition according to the present invention for use in the treatment of a cancer.

In another aspect, the present invention provides the use of an antibody, antigen binding fragment, or composition according to the present invention in the manufacture of a medicament for use in the treatment or prevention of fibrosis or a disease/disorder characterised by fibrosis.

In another aspect, the present invention provides the use of an antibody, antigen binding fragment, or composition according to the present invention in the manufacture of a medicament for use in the treatment or prevention of a cancer.

In another aspect, the present invention provides a method of treating fibrosis comprising administering an antibody, antigen binding fragment, or composition according to the present invention to a subject suffering from fibrosis or a disease/disorder characterised by fibrosis.

In another aspect, the present invention provides a method of treating cancer comprising administering an antibody, antigen binding fragment, or composition according to the present invention to a subject suffering from a cancer.

In another aspect, the present invention provides an antibody or antigen binding fragment for use in a method of treating a disease in which IL-11 mediated signalling is implicated in the pathology of the disease, wherein the antibody or antigen binding fragment is capable of inhibiting IL-11 trans signalling.

In another aspect, the present invention provides the use of an antibody or antigen binding fragment in the manufacture of a medicament for use in the treatment of a disease in which IL-11 mediated signalling is implicated in the pathology of the disease, wherein the antibody or antigen binding fragment is capable of inhibiting IL-11 trans signalling.

In another aspect, the present invention provides a method of treating a disease in which IL-11 mediated signalling is implicated in the pathology of the disease, comprising administering an antibody or antigen binding fragment to a subject suffering from the disease, wherein the antibody or antigen binding fragment is capable of inhibiting IL-11 trans signalling.

In another aspect, the present invention provides a method comprising contacting a sample containing, or suspected to contain, IL-11 with an antibody or antigen binding fragment according to the present invention and detecting the formation of a complex of the antibody or antigen binding fragment with IL-11.

In another aspect, the present invention provides a method of diagnosing a disease or condition in a subject, the method comprising contacting, in vitro, a sample from the subject with an antibody or antigen binding fragment according to the present invention and detecting the formation of a complex of the antibody or antigen binding fragment with IL-11.

In another aspect, the present invention provides a method of selecting or stratifying a subject for treatment with an IL-11-targeted agent, the method comprising contacting, in vitro, a sample from the subject with the antibody or antigen binding fragment according to the present invention and detecting the formation of a complex of the antibody or antigen binding fragment with IL-11.

In another aspect, the present invention provides the use of an antibody or antigen binding fragment according to the present invention for the detection of IL-11 in vitro or in vivo.

In another aspect, the present invention provides the use of an antibody or antigen binding fragment according to the present invention as an in vitro or in vivo diagnostic or prognostic agent.

In another aspect, the present invention provides an antibody or antigen binding fragment, optionally isolated, which is capable of binding to IL-11, comprising the amino acid sequences i) to vi):

i) LC-CDR1:

$X_{138}X_{139}DVGGYX_{140}X_{141}$, (SEQ ID NO: 393)

$SSDVX_{142}X_{143}YX_{144}Y$, (SEQ ID NO: 394)

$X_{145}X_{146}DX_{147}GAYNY$, (SEQ ID NO: 395)

$SSDIGX_{148}YNY$, (SEQ ID NO: 396)

$X_{149}SDVGAYDY$, (SEQ ID NO: 397)

$SGDVGTYX_{150}Y$, (SEQ ID NO: 398)

$QX_{151}IX_{152}SY$, (SEQ ID NO: 399)

$QSX_{153}SSSY$, (SEQ ID NO: 400)

$RX_{154}DX_{155}GGYDX_{156}$, (SEQ ID NO: 401)

SSNVGGYNY, (SEQ ID NO: 284)

GSNVGGYNY
or (SEQ ID NO: 349)

QSVNSAY; (SEQ ID NO: 359)

ii) LC-CDR2:

$DVX_{157}$
or (SEQ ID NO: 402)

$X_{158}AS$; (SEQ ID NO: 403)

iii) LC-CDR3:

$X_{159}SYAGX_{160}X_{161}X_{162}WX_{163}$, (SEQ ID NO: 404)

$SSYTX_{164}X_{165}X_{166}X_{167}WV$, (SEQ ID NO: 405)

$QQSYSX_{168}PX_{169}WT$, (SEQ ID NO: 406)

$SSFX_{170}X_{171}SX_{172}X_{173}WV$, (SEQ ID NO: 407)

NSYTSGSTWV, (SEQ ID NO: 362)

ASYTRSSVWV, (SEQ ID NO: 334)

QQSSTSPTWA,
or (SEQ ID NO: 357)

SSYRSGSTLGVRRRDQADRPR; (SEQ ID NO: 282)

iv) HC-CDR1:

$GFTFX_{174}SYX_{175}$; (SEQ ID NO: 409)

v) HC-CDR2:

$ISYDGSNX_{176}$; (SEQ ID NO: 410)

vi) HC-CDR3:

AKIGATDPLDY, (SEQ ID NO: 187)

ARIMGYDYGDYDVVDY, (SEQ ID NO: 199)

AKLSGPNGVDY
or (SEQ ID NO: 197)

$AKGX_{177}X_{178}SYYX_{179}FDY$; (SEQ ID NO: 411)

or a variant thereof in which one or two or three amino acids in one or more of the sequences i) to vi) are replaced with another amino acid;

wherein $X_{138}$=S, N or I, $X_{139}$=S or R, $X_{140}$=N, E or D, $X_{141}$=Y or F, $X_{142}$=G or A, $X_{143}$=D, G or T, $X_{144}$=N or D, $X_{145}$=S or N, $X_{146}$=N, T or S, $X_{147}$=V or I, $X_{148}$=V or G, $X_{149}$=S or G, $X_{150}$=N or D, $X_{151}$=A or I, $X_{152}$=N or S, $X_{153}$=F or V, $X_{154}$=S or R, $X_{155}$=I or V, $X_{156}$=Y or F, $X_{157}$=S, T, N, G, V or D, $X_{158}$=A or G, $X_{159}$=C, S, A or N, $X_{160}$=S, R, N, G, T or F, $X_{161}$=Y or H, $X_{162}$=T, N, I, S or V, $X_{163}$=V, M or I, $X_{164}$=S or N, $X_{165}$=S or N, $X_{166}$=T, I, S P, $X_{167}$=T or S, $X_{168}$=T or D, $X_{169}$=S, R or T, $X_{170}$=T or A, $X_{171}$=T or S, $X_{172}$=I or T, $X_{173}$=A or T, $X_{174}$=S or G, $X_{175}$=G or A, $X_{176}$=K or R, $X_{177}$=absent or G, $X_{178}$=absent or K, and $X_{179}$=absent or G.

In some embodiments HC-CDR1 is one of GFTFSSYG (SEQ ID NO:186), GFTFSSYA (SEQ ID NO:190) or GFTFGSYG (SEQ ID NO:234).

In some embodiments HC-CDR2 is one of ISYDGSNK (SEQ ID NO:184) or ISYDGSNR (SEQ ID NO:381).

In some embodiments HC-CDR3 is one of AKIGATDPLDY (SEQ ID NO:187), ARIMGYDYGDYDVVDY (SEQ ID NO:199), AKGGKSYYGFDY (SEQ ID NO:207), AKGSYYFDY (SEQ ID NO:235) or AKLSGPNGVDY (SEQ ID NO:197).

In some embodiments LC-CDR1 is one of SSDVGGYNF (SEQ ID NO:294), SSDVGGYEY (SEQ ID NO:159), SRDVGGYNY (SEQ ID NO:150), NSDVGGYNY (SEQ ID NO:300), SSDVGGYDY (SEQ ID NO:128), SSDVGGYNY (SEQ ID NO:107), ISDVGGYNY (SEQ ID NO:122), SSDVGDYDY (SEQ ID NO:317), SSDVAGYNY (SEQ ID NO:330), SSDVGTYNY (SEQ ID NO:344), NTDVGAYNY (SEQ ID NO:272), SNDIGAYNY (SEQ ID NO:306), SSDVGAYNY (SEQ ID NO:110), SSDIGVYNY (SEQ ID NO:347), SSDIGGYNY (SEQ ID NO:326), SSDVGAYDY (SEQ ID NO:333), GSDVGAYDY (SEQ ID NO:322), SGDVGTYNY (SEQ ID NO:298), SGDVGTYDY (SEQ ID NO:302), QAINSY (SEQ ID NO:352), QIISSY (SEQ ID NO:155), QSFSSSY (SEQ ID NO:356), QSVSSSY (SEQ ID NO:367), RSDIGGYDY (SEQ ID NO:290), RRDVGGYDF (SEQ ID NO:339), SSNVGGYNY (SEQ ID NO:284), GSNVGGYNY (SEQ ID NO:349) or QSVNSAY (SEQ ID NO:359).

In some embodiments LC-CDR2 is one of DVS (SEQ ID NO:108), DVV (SEQ ID NO:275), DVT (SEQ ID NO:123), DVD (SEQ ID NO:295), DVN (SEQ ID NO:291), DVG (SEQ ID NO:133), AAS (SEQ ID NO:102) or GAS (SEQ ID NO:138).

In some embodiments LC-CDR3 is one of CSYAGSYTWV (SEQ ID NO:131), SSYAGSYTWV (SEQ ID NO:124), CSYAGSYSWV (SEQ ID NO:273), CSYAGGYTWV (SEQ ID NO:276), NSYAGSYTWV (SEQ ID NO:278), CSYAGSYVWV (SEQ ID NO:285), CSYAGRYTWI (SEQ ID NO:296), CSYAGRYTWM (SEQ ID NO:336), CSYAGTYTWV (SEQ ID NO:340), CSYAGFYTWV (SEQ ID NO:345), CSYAGSHIWV (SEQ ID NO:308), CSYAGRYTWV (SEQ ID NO:313), CSYAGNYTWM (SEQ ID NO:315), CSYAGSYTWI (SEQ ID NO:324), ASYAGNYNWV (SEQ ID NO:304), SSYAGGYTWV (SEQ ID NO:364), SSYTNSRTWV (SEQ ID NO:292), SSYTSNTTWV (SEQ ID NO:311), SSYTSNTTWV (SEQ ID NO:320), SSYTSSSSWV (SEQ ID NO:109), SSYTSSISWV (SEQ ID NO:288), SSYTSSITWV (SEQ ID NO:130), QQSYSTPSWT (SEQ ID NO:354), QQSYSDPRWT (SEQ ID NO:360), QQSYSTPTWT (SEQ ID NO:156), SSFTTSIAWV (SEQ ID NO:268), SSFTSSTTWV (SEQ ID NO:281), SSFATSISWV (SEQ ID NO: 408), NSYTSGSTWV (SEQ ID NO:362), ASYTRSSVWV (SEQ ID NO:334), QQSSTSPTWA (SEQ ID NO:357) or SSYRSGSTLGVRRRDQADRPR (SEQ ID NO:282).

In some embodiments the antibody or antigen binding fragment has at least one heavy chain variable region incorporating the following CDRs:

HC-CDR1:
GFTFSSYG (SEQ ID NO: 186)

HC-CDR2:
ISYDGSNK (SEQ ID NO: 184)

HC-CDR3:
AKIGATDPLDY; (SEQ ID NO: 187)
or

HC-CDR1:
GFTFSSYA (SEQ ID NO: 190)

HC-CDR2:
ISYDGSNK (SEQ ID NO: 184)

HC-CDR3:
ARIMGYDYGDYDVVDY; (SEQ ID NO: 199)
or

HC-CDR1:
GFTFGSYG (SEQ ID NO: 234)

HC-CDR2:
ISYDGSNK (SEQ ID NO: 184)

HC-CDR3:
AKIGATDPLDY; (SEQ ID NO: 187)
or

HC-CDR1:
GFTFSSYG (SEQ ID NO: 186)

HC-CDR2:
ISYDGSNR (SEQ ID NO: 381)

HC-CDR3:
AKIGATDPLDY; (SEQ ID NO: 187)
or

HC-CDR1:
GFTFSSYG (SEQ ID NO: 186)

HC-CDR2:
ISYDGSNK (SEQ ID NO: 184)

HC-CDR3:
ARIMGYDYGDYDVVDY; (SEQ ID NO: 199)
or

HC-CDR1:
GFTFSSYG (SEQ ID NO: 186)

HC-CDR2:
ISYDGSNK (SEQ ID NO: 184)

HC-CDR3:
AKGGKSYYGFDY; (SEQ ID NO: 207)
or

HC-CDR1:
GFTFGSYG (SEQ ID NO: 234)

HC-CDR2:
ISYDGSNK (SEQ ID NO: 184)

HC-CDR3:
AKGSYYFDY; (SEQ ID NO: 235)
or

HC-CDR1:
GFTFSSYG (SEQ ID NO: 186)

HC-CDR2:
ISYDGSNK (SEQ ID NO: 184)

HC-CDR3:
AKLSGPNGVDY. (SEQ ID NO: 197)

In some embodiments the antibody or antigen binding fragment has at least one light chain variable region incorporating the following CDRs:

LC-CDR1:
SSDVGAYNY (SEQ ID NO: 110)

LC-CDR2:
DVS (SEQ ID NO: 108)

LC-CDR3:
SSFTTSIAWV; (SEQ ID NO: 268)
or

LC-CDR1:
SSDVGGYNY (SEQ ID NO: 107)

LC-CDR2:
DVS (SEQ ID NO: 108)

LC-CDR3:
CSYAGSYTWV; (SEQ ID NO: 131)
or

LC-CDR1:
SSDVGGYNY (SEQ ID NO: 107)

LC-CDR2:
DVS (SEQ ID NO: 108)

LC-CDR3:
SSYAGSYTWV; (SEQ ID NO: 124)
or

LC-CDR1:
NTDVGAYNY (SEQ ID NO: 272)

LC-CDR2:
DVS (SEQ ID NO: 108)

LC-CDR3:
CSYAGSYSWV; (SEQ ID NO: 273)
or

LC-CDR1:
SSDVGGYNY (SEQ ID NO: 107)

LC-CDR2:
DVV (SEQ ID NO: 275)

LC-CDR3:
CSYAGGYTWV; (SEQ ID NO: 276)
or

LC-CDR1:
SSDVGGYNY (SEQ ID NO: 107)

LC-CDR2:
DVS (SEQ ID NO: 108)

LC-CDR3:
NSYAGSYTWV; (SEQ ID NO: 278)
or

LC-CDR1:
SRDVGGYNY (SEQ ID NO: 150)

LC-CDR2:
DVS (SEQ ID NO: 108)

LC-CDR3:
CSYAGSYTWV; (SEQ ID NO: 131)
or

LC-CDR1:
SSDVGGYNY (SEQ ID NO: 107)

LC-CDR2:
DVS (SEQ ID NO: 108)

LC-CDR3:
SSFTSSTTWV; (SEQ ID NO: 281)
or

LC-CDR1:
SSDVGGYNY (SEQ ID NO: 107)

LC-CDR2:
DVS (SEQ ID NO: 108)

LC-CDR3:
SSYRSGSTLGVRRRDQADRPR; (SEQ ID NO: 282)
or

LC-CDR1:
SSNVGGYNY (SEQ ID NO: 284)

LC-CDR2:
DVS (SEQ ID NO: 108)

LC-CDR3:
CSYAGSYVWV; (SEQ ID NO: 285)
or

LC-CDR1:
SSDVGGYNY (SEQ ID NO: 107)

LC-CDR2:
DVT (SEQ ID NO: 123)

LC-CDR3:
CSYAGGYTWV; (SEQ ID NO: 276)
or

LC-CDR1:
SSDVGGYNY (SEQ ID NO: 107)

LC-CDR2:
DVS (SEQ ID NO: 108)

LC-CDR3:
SSYTSSISWV; (SEQ ID NO: 288)
or

LC-CDR1:
RSDIGGYDY (SEQ ID NO: 290)

LC-CDR2:
DVN (SEQ ID NO: 291)

LC-CDR3:
SSYTSSITWV; (SEQ ID NO: 130)
or

LC-CDR1:
SSDVGGYNY (SEQ ID NO: 107)

LC-CDR2:
DVS (SEQ ID NO: 108)

LC-CDR3:
SSYTNSRTWV; (SEQ ID NO: 292)
or

LC-CDR1:
SSDVGGYNF (SEQ ID NO: 294)

LC-CDR2:
DVD (SEQ ID NO: 295)

LC-CDR3:
CSYAGRYTWI; (SEQ ID NO: 296)
or

LC-CDR1:
SGDVGTYNY (SEQ ID NO: 298)

LC-CDR2:
DVS (SEQ ID NO: 108)

LC-CDR3:
NSYAGSYTWV; (SEQ ID NO: 278)
or

LC-CDR1:
NSDVGGYNY (SEQ ID NO: 300)

LC-CDR2:
DVS (SEQ ID NO: 108)

LC-CDR3:
CSYAGSYTWV; (SEQ ID NO: 131)
or

LC-CDR1:
SGDVGTYDY (SEQ ID NO: 302)

LC-CDR2:
DVS (SEQ ID NO: 108)

LC-CDR3:
NSYAGSYTWV; (SEQ ID NO: 278)
or

LC-CDR1:
SSNVGGYNY (SEQ ID NO: 284)

LC-CDR2:
DVS (SEQ ID NO: 108)

LC-CDR3:
ASYAGNYNWV; (SEQ ID NO: 304)
or

LC-CDR1:
SNDIGAYNY (SEQ ID NO: 306)

LC-CDR2:
DVN (SEQ ID NO: 291)

LC-CDR3:
CSYAGSYSWV; (SEQ ID NO: 273)
or

LC-CDR1:
SSDVGGYNY (SEQ ID NO: 107)

LC-CDR2:
DVT (SEQ ID NO: 123)

LC-CDR3:
CSYAGSHIWV; (SEQ ID NO: 308)
or

LC-CDR1:
SSDVGGYNY (SEQ ID NO: 107)

LC-CDR2:
DVS (SEQ ID NO: 108)

LC-CDR3:
CSYAGSYSWV; (SEQ ID NO: 273)
or

LC-CDR1:
SSDVGGYDY (SEQ ID NO: 128)

LC-CDR2:
DVT (SEQ ID NO: 123)

LC-CDR3:
SSYTSNTTWV; (SEQ ID NO: 311)
or

LC-CDR1:
SSDVGGYDY (SEQ ID NO: 128)

LC-CDR2:
DVT (SEQ ID NO: 123)

LC-CDR3:
CSYAGRYTWV; (SEQ ID NO: 313)
or

LC-CDR1:
SSDVGGYNY (SEQ ID NO: 107)

LC-CDR2:
DVS (SEQ ID NO: 108)

LC-CDR3:
CSYAGNYTWM; (SEQ ID NO: 315)
or

LC-CDR1:
SSDVGDYDY (SEQ ID NO: 317)

LC-CDR2:
DVT (SEQ ID NO: 123)

LC-CDR3:
CSYAGSYTWV; (SEQ ID NO: 131)
or

LC-CDR1:
SSDVGGYNY (SEQ ID NO: 107)

LC-CDR2:
DVS (SEQ ID NO: 108)

```
LC-CDR3:
                              (SEQ ID NO: 320)
SSYTSSTTWV;
or

LC-CDR1:
                              (SEQ ID NO: 322)
GSDVGAYDY

LC-CDR2:
                              (SEQ ID NO: 291)
DVN

LC-CDR3:
                              (SEQ ID NO: 408)
SSFATSISWV;
or

LC-CDR1:
                              (SEQ ID NO: 107)
SSDVGGYNY

LC-CDR2:
                              (SEQ ID NO: 123)
DVT

LC-CDR3:
                              (SEQ ID NO: 324)
CSYAGSYTWI;
or

LC-CDR1:
                              (SEQ ID NO: 326)
SSDIGGYNY

LC-CDR2:
                              (SEQ ID NO: 108)
DVS

LC-CDR3:
                              (SEQ ID NO: 131)
CSYAGSYTWV;
or

LC-CDR1:
                              (SEQ ID NO: 294)
SSDVGGYNF

LC-CDR2:
                              (SEQ ID NO: 291)
DVN

LC-CDR3:
                              (SEQ ID NO: 276)
CSYAGGYTWV;
or

LC-CDR1:
                              (SEQ ID NO: 159)
SSDVGGYEY

LC-CDR2:
                              (SEQ ID NO: 123)
DVT

LC-CDR3:
                              (SEQ ID NO: 131)
CSYAGSYTWV;
or

LC-CDR1:
                              (SEQ ID NO: 330)
SSDVAGYNY

LC-CDR2:
                              (SEQ ID NO: 123)
DVT

LC-CDR3:
                              (SEQ ID NO: 131)
CSYAGSYTWV;
or

LC-CDR1:
                              (SEQ ID NO: 110)
SSDVGAYNY

LC-CDR2:
                              (SEQ ID NO: 291)
DVN

LC-CDR3:
                              (SEQ ID NO: 131)
CSYAGSYTWV;
or

LC-CDR1:
                              (SEQ ID NO: 333)
SSDVGAYDY

LC-CDR2:
                              (SEQ ID NO: 123)
DVT

LC-CDR3:
                              (SEQ ID NO: 334)
ASYTRSSVWV;
or

LC-CDR1:
                              (SEQ ID NO: 107)
SSDVGGYNY

LC-CDR2:
                              (SEQ ID NO: 291)
DVN

LC-CDR3:
                              (SEQ ID NO: 336)
CSYAGRYTWM;
or

LC-CDR1:
                              (SEQ ID NO: 122)
ISDVGGYNY

LC-CDR2:
                              (SEQ ID NO: 123)
DVT

LC-CDR3:
                              (SEQ ID NO: 124)
SSYAGSYTWV;
or

LC-CDR1:
                              (SEQ ID NO: 339)
RRDVGGYDF

LC-CDR2:
                              (SEQ ID NO: 108)
DVS

LC-CDR3:
                              (SEQ ID NO: 340)
CSYAGTYTWV;
or

LC-CDR1:
                              (SEQ ID NO: 107)
SSDVGGYNY

LC-CDR2:
                              (SEQ ID NO: 133)
DVG
```

LC-CDR3:                                (SEQ ID NO: 276)
CSYAGGYTWV;
or

LC-CDR1:                                (SEQ ID NO: 110)
SSDVGAYNY

LC-CDR2:                                (SEQ ID NO: 108)
DVS

LC-CDR3:                                (SEQ ID NO: 131)
CSYAGSYTWV;
or

LC-CDR1:                                (SEQ ID NO: 344)
SSDVGTYNY

LC-CDR2:                                (SEQ ID NO: 108)
DVS

LC-CDR3:                                (SEQ ID NO: 345)
CSYAGFYTWV;
or

LC-CDR1:                                (SEQ ID NO: 347)
SSDIGVYNY

LC-CDR2:                                (SEQ ID NO: 108)
DVS

LC-CDR3:                                (SEQ ID NO: 131)
CSYAGSYTWV;
or

LC-CDR1:                                (SEQ ID NO: 349)
GSNVGGYNY

LC-CDR2:                                (SEQ ID NO: 108)
DVS

LC-CDR3:                                (SEQ ID NO: 340)
CSYAGTYTWV;
or

LC-CDR1:                                (SEQ ID NO: 107)
SSDVGGYNY

LC-CDR2:                                (SEQ ID NO: 123)
DVT

LC-CDR3:                                (SEQ ID NO: 124)
SSYAGSYTWV;
or

LC-CDR1:                                (SEQ ID NO: 107)
SSDVGGYNY

LC-CDR2:                                (SEQ ID NO: 108)
DVS

LC-CDR3:                                (SEQ ID NO: 109)
SSYTSSSSWV;
or

LC-CDR1:                                (SEQ ID NO: 352)
QAINSY

LC-CDR2:                                (SEQ ID NO: 102)
AAS

LC-CDR3:                                (SEQ ID NO: 354)
QQSYSTPSWT;
or

LC-CDR1:                                (SEQ ID NO: 356)
QSFSSSY

LC-CDR2:                                (SEQ ID NO: 138)
GAS

LC-CDR3:                                (SEQ ID NO: 357)
QQSSTSPTWA;
or

LC-CDR1:                                (SEQ ID NO: 359)
QSVNSAY

LC-CDR2:                                (SEQ ID NO: 138)
GAS

LC-CDR3:                                (SEQ ID NO: 360)
QQSYSDPRWT;
or

LC-CDR1:                                (SEQ ID NO: 155)
QIISSY

LC-CDR2:                                (SEQ ID NO: 102)
AAS

LC-CDR3:                                (SEQ ID NO: 156)
QQSYSTPTWT;
or

LC-CDR1:                                (SEQ ID NO: 107)
SSDVGGYNY

LC-CDR2:                                (SEQ ID NO: 291)
DVN

LC-CDR3:                                (SEQ ID NO: 362)
NSYTSGSTWV;
or

LC-CDR1:                                (SEQ ID NO: 122)
ISDVGGYNY

LC-CDR2:                                (SEQ ID NO: 123)
DVT

```
LC-CDR3:
                                           (SEQ ID NO: 364)
SSYAGGYTWV;
or

LC-CDR1:
                                           (SEQ ID NO: 155)
QIISSY

LC-CDR2:
                                           (SEQ ID NO: 102)
AAS;
or

LC-CDR1:
                                           (SEQ ID NO: 367)
QSVSSSY

LC-CDR2:
                                           (SEQ ID NO: 138)
GAS

LC-CDR3:
                                           (SEQ ID NO: 156)
QQSYSTPTWT.
```

In another aspect, the present invention provides an antibody or antigen binding fragment, optionally isolated, which is capable of binding to IL-11, comprising a light chain and a heavy chain variable region sequence, wherein:
the light chain comprises a LC-CDR1, LC-CDR2, LC-CDR3, having at least 85% overall sequence identity to LC-CDR1: one of $X_{138}X_{139}DVGGYX_{140}X_{141}$ (SEQ ID NO:393), $SSDVX_{142}X_{143}YX_{144}Y$ (SEQ ID NO:394), $X_{145}X_{146}DX_{147}GAYNY$ (SEQ ID NO:395), $SSDIGX_{148}YNY$ (SEQ ID NO:396), $X_{149}SDVGAYDY$ (SEQ ID NO:397), $SGDVGTYX_{150}Y$ (SEQ ID NO:398), $QX_{151}IX_{152}SY$ (SEQ ID NO:399), $QSX_{153}SSSY$ (SEQ ID NO:400), $RX_{154}DX_{155}GGYDX_{156}$ (SEQ ID NO:401), SSNVGGYNY (SEQ ID NO:284), GSNVGGYNY (SEQ ID NO:214) or QSVNSAY (SEQ ID NO:359); LC-CDR2: one of $DVX_{157}$ (SEQ ID NO:402) or $X_{158}AS$ (SEQ ID NO:403); LC-CDR3: one of $X_{159}SYAGX_{160}X_{161}X_{162}WX_{163}$ (SEQ ID NO:404), $SSYTX_{164}X_{165}X_{166}X_{167}WV$ (SEQ ID NO:405), $QQSYSX_{168}PX_{169}WT$ (SEQ ID NO:406), $SSFX_{170}X_{171}SX_{172}X_{173}WV$ (SEQ ID NO:407), NSYTSGSTWV (SEQ ID NO:362), ASYTRSSVWV (SEQ ID NO:334), QQSSTSPTWA (SEQ ID NO:357), or SSYRSGSTLGVRRRDQADRPR (SEQ ID NO:282); and
the heavy chain comprises a HC-CDR1, HC-CDR2, HC-CDR3, having at least 85% overall sequence identity to HC-CDR1: $GFTFX_{174}SYX_{175}$ (SEQ ID NO:409); HC-CDR2: $ISYDGSNX_{176}$ (SEQ ID NO:410); HC-CDR3: AKIGATDPLDY (SEQ ID NO:187), ARIMGYDYGDYDVVDY (SEQ ID NO:199), AKLSGPNGVDY (SEQ ID NO:197) or $AKGX_{177}X_{178}SYYX_{179}FDY$ (SEQ ID NO:411);
wherein $X_{138}$=S, N or I, $X_{139}$=S or R, $X_{140}$=N, E or D, $X_{141}$=Y or F, $X_{142}$=G or A, $X_{143}$=D, G or T, $X_{144}$=N or D, $X_{145}$=S or N, $X_{146}$=N, T or S, $X_{147}$=V or I, $X_{148}$=V or G, $X_{149}$=S or G, $X_{150}$=N or D, $X_{151}$=A or I, $X_{152}$=N or S, $X_{153}$=F or V, $X_{154}$=S or R, $X_{155}$=I or V, $X_{156}$=Y or F, $X_{157}$=S, T, N, G, V or D, $X_{158}$=A or G, $X_{159}$=C, S, A or N, $X_{160}$=S, R, N, G, T or F, $X_{161}$=Y or H, $X_{162}$=T, N, I, S or V, $X_{163}$=V, M or I, $X_{164}$=S or N, $X_{165}$=S or N, $X_{166}$=T, I, S R, $X_{167}$=T or S, $X_{168}$=T or D, $X_{169}$=S, R or T, $X_{170}$=T or A, $X_{171}$=T or S, $X_{172}$=I or T, $X_{173}$=A or T, $X_{174}$=S or G, $X_{175}$=G or A, $X_{176}$=K or R, $X_{177}$=absent or G, $X_{178}$=absent or K, and $X_{179}$=absent or G.

In another aspect, the present invention provides an antibody or antigen binding fragment, optionally isolated, which is capable of binding to IL-11, comprising a light chain and a heavy chain variable region sequence, wherein:
the light chain sequence has at least 85% sequence identity to the light chain sequence of one of SEQ ID NOs: 267, 269, 270, 271, 274, 277, 279, 280, 540, 283, 286, 287, 289, 353, 293, 297, 299, 301, 303, 305, 307, 309, 310, 312, 314, 316, 318, 319, 321, 323, 325, 327, 328, 329, 331, 332, 335, 337, 338, 341, 342, 343, 346, 348, 214, 350, 13, 3, 351, 355, 358, 35, 361, 363, 365, 366, or 20; and
the heavy chain sequence has at least 85% sequence identity to the heavy chain sequence of one of SEQ ID NOs: 53, 368, 369, 370, 371, 372, 373, 374, 375, 376, 377, 378, 379, 380, 382, 383, 384, 385, 386, 387, 388, 389, 85, 390, 73, 391, or 392.

In another aspect, the present invention provides an antibody or antigen binding fragment, optionally isolated, which is capable of binding to IL-11, comprising an amino acid sequence having at least 85% sequence identity to the sequence of one of SEQ ID NOs: 412 to 475.

In another aspect, the present invention provides an antibody or antigen binding fragment, optionally isolated, which is capable of binding to IL-11, comprising the amino acid sequences i) to vi):

```
i) LC-CDR1:
                                           (SEQ ID NO: 555)
ENVVTY, (SEQ ID NO: 558)
QSIGTS, (SEQ ID NO: 562)
QSLLYNSSQKNY
or (SEQ ID NO: 565)
QDVGTA;

ii) LC-CDR2:
                                           (SEQ ID NO: 569)
X184AS;

iii) LC-CDR3:
                                           (SEQ ID NO: 570)
X185QX186X187SX188X189X190T;

iv) HC-CDR1:
                                           (SEQ ID NO: 567)
GYTFTX180YX181;

v) HC-CDR2:
                                           (SEQ ID NO: 568)
INPX182NGGX183
or (SEQ ID NO: 552)
IYPRSSNT;

vi) HC-CDR3:
                                           (SEQ ID NO: 544)
ARGELGHWYFDV, (SEQ ID NO: 547)
AREGPYGYTWFAY, (SEQ ID NO: 550)
ARNPSLYDGYLDC
or (SEQ ID NO: 553)
ARANWVGYFDV;
``` or a variant thereof in which one or two or three amino acids in one or more of the sequences i) to vi) are replaced with another amino acid;

wherein $X_{180}$=D or S, $X_{181}$=N or G, $X_{182}$=H, D or N, $X_{183}$=P, T or I, $X_{184}$=G, Y or W, $X_{185}$=Q or G $X_{186}$=Y, G or S, $X_{187}$=Y, N or S, $X_{188}$=Y or W, $X_{189}$=P or absent, and $X_{190}$=L, Y or R.

In some embodiments HC-CDR1 is one of GYTFTDYN (SEQ ID NO:542) or GYTFTSYG (SEQ ID NO:228).

In some embodiments HC-CDR2 is one of INPHNGGP (SEQ ID NO:543), INPDNGGT (SEQ ID NO:546), INPNNGGI (SEQ ID NO:549) or IYPRSSNT (SEQ ID NO:552).

In some embodiments HC-CDR3 is one of ARGELGHWYFDV (SEQ ID NO:544), AREGPYGYTWFAY (SEQ ID NO:547), ARNPSLYDGYLDC (SEQ ID NO:550) or ARANWVGYFDV (SEQ ID NO:553).

In some embodiments LC-CDR1 is one of ENVVTY (SEQ ID NO:555), QSIGTS (SEQ ID NO:558), QSLLYNSSQKNY (SEQ ID NO:562) or QDVGTA (SEQ ID NO:565).

In some embodiments LC-CDR2 is one of GAS (SEQ ID NO:138), YAS (SEQ ID NO:559) or WAS (SEQ ID NO:563).

In some embodiments LC-CDR3 is one of GQGYSYPYT (SEQ ID NO:556), QQSNSWPLT (SEQ ID NO:560), QQYYSYPLT (SEQ ID NO:563) or QQYSSYRT (SEQ ID NO:566).

In some embodiments the antibody or antigen binding fragment has at least one heavy chain variable region incorporating the following CDRs:

HC-CDR1:
(SEQ ID NO: 542)
GYTFTDYN

HC-CDR2:
(SEQ ID NO: 543)
INPHNGGP

HC-CDR3:
(SEQ ID NO: 544)
ARGELGHWYFDV;
or

HC-CDR1:
(SEQ ID NO: 542)
GYTFTDYN

HC-CDR2:
(SEQ ID NO: 546)
INPDNGGT

HC-CDR3:
(SEQ ID NO: 547)
AREGPYGYTWFAY;
or

HC-CDR1:
(SEQ ID NO: 542)
GYTFTDYN

HC-CDR2:
(SEQ ID NO: 549)
INPNNGGI

HC-CDR3:
(SEQ ID NO: 550)
ARNPSLYDGYLDC;
or

HC-CDR1:
(SEQ ID NO: 228)
GYTFTSYG

HC-CDR2:
(SEQ ID NO: 552)
IYPRSSNT

HC-CDR3:
(SEQ ID NO: 553)
ARANWVGYFDV.

In some embodiments the antibody or antigen binding fragment has at least one heavy chain variable region incorporating the following CDRs:

LC-CDR1:
(SEQ ID NO: 555)
ENVVTY

LC-CDR2:
(SEQ ID NO: 138)
GAS

LC-CDR3:
(SEQ ID NO: 556)
GQGYSYPYT;
or

LC-CDR1:
(SEQ ID NO: 558)
QSIGTS

LC-CDR2:
(SEQ ID NO: 559)
YAS

LC-CDR3:
(SEQ ID NO: 560)
QQSNSWPLT;
or

LC-CDR1:
(SEQ ID NO: 562)
QSLLYNSSQKNY

LC-CDR2:
(SEQ ID NO: 563)
WAS

LC-CDR3:
(SEQ ID NO: 581)
QQYYSYPLT;
or

LC-CDR1:
(SEQ ID NO: 565)
QDVGTA

LC-CDR2:
(SEQ ID NO: 563)
WAS

LC-CDR3:
(SEQ ID NO: 566)
QQYSSYRT.

In another aspect, the present invention provides an antibody or antigen binding fragment, optionally isolated, which is capable of binding to IL-11, comprising a light chain and a heavy chain variable region sequence, wherein:
the light chain comprises a LC-CDR1, LC-CDR2, LC-CDR3, having at least 85% overall sequence identity to LC-CDR1: one of ENVVTY (SEQ ID NO:555), QSIGTS (SEQ ID NO:558), QSLLYNSSQKNY (SEQ ID NO:562) or QDVGTA (SEQ ID NO:565); LC-CDR2: $X_{184}$AS (SEQ ID NO:569); LC-CDR3: $X_{185}QX_{186}X_{187}SX_{188}X_{189}X_{190}T$ (SEQ ID NO:570); and the heavy chain comprises a HC-CDR1, HC-CDR2, HC-CDR3, having at least 85% overall sequence identity to HC-CDR1: GYTFTX$_{180}$YX$_{181}$ (SEQ ID NO:567); HC-CDR2: one of INPX$_{182}$NGGX$_{183}$ (SEQ ID NO:568) or IYPRSSNT (SEQ ID NO:552); HC-CDR3: one of ARGELGHWYFDV (SEQ ID NO:544), AREGPYGYTWFAY (SEQ ID NO:547), ARNPSLYDGYLDC (SEQ ID NO:550) or ARANWVGYFDV (SEQ ID NO:553);

wherein X$_{180}$=D or S, X$_{181}$=N or G, X$_{182}$=H, D or N, X$_{183}$=P, T or I, X$_{184}$=G, Y or W, X$_{185}$=Q or G X$_{186}$=Y, G or S, X$_{187}$=Y, N or S, X$_{188}$=Y or W, X$_{189}$=P or absent, and X$_{190}$=L, Y or R.

In another aspect, the present invention provides an antibody or antigen binding fragment, optionally isolated, which is capable of binding to IL-11, comprising a light chain and a heavy chain variable region sequence, wherein:
the light chain sequence has at least 85% sequence identity to the light chain sequence of one of SEQ ID NOs:554, 557, 561 or 564; and
the heavy chain sequence has at least 85% sequence identity to the heavy chain sequence of one of SEQ ID NOs:541, 545, 548 or 551.

DESCRIPTION

The present invention relates to antibodies with specificity for interleukin-11 (IL-11). The present disclosure describes the identification of IL-11/IL-11R signalling as a key mediator of fibrosis, and the generation and functional characterisation of anti-IL-11 antibodies. Therapeutic and diagnostic uses of the antibodies is also described.

IL-11 and IL-11 Mediated Signalling

The antibodies and fragments of the present invention bind to interleukin 11. Interleukin 11 (IL-11), also known as adipogenesis inhibitory factor, is a pleiotropic cytokine and a member of the IL-6 family of cytokines that includes IL-6, IL-11, IL-27, IL-31, oncostatin M (OSM), leukemia inhibitory factor (LIF), cardiotrophin-1 (CT-1), cardiotrophin-like cytokine (CLC), ciliary neurotrophic factor (CNTF) and neuropoetin (NP-1).

IL-11 is transcribed with a canonical signal peptide that ensures efficient secretion from cells. The immature form of human IL-11 is a 199 amino acid polypeptide whereas the mature form of IL-11 encodes a protein of 178 amino acid residues (Garbers and Scheller, Biol. Chem. 2013; 394(9): 1145-1161). The human IL-11 amino acid sequence is available under UniProt accession no. P20809 (P20809.1 GI:124294). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species.

In some embodiments, the IL-11 is mammalian IL-11 (e.g. cynomolgous, human and/or rodent (e.g. rat and/or murine) IL-11). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 100, 110, 120, 130, 140, 150, 160, 170, 180, 190 or 195 amino acids.

IL-11 signals through a homodimer of the ubiquitously expressed β-receptor glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual IL-11 α-receptor (IL-11Rα), which does not directly participate in signal transduction, although the initial cytokine binding event to the α-receptor leads to the final complex formation with the β-receptors. IL-11 activates a downstream signalling pathway, which is predominantly the mitogen-activated protein kinase (MAPK)-cascade and the Janus kinase/signal transducer and activator of transcription (Jak/STAT) pathway (Garbers and Scheller, supra).

Human IL-11Rα is a 422 amino acid polypeptide (Genbank accession no. NP_001136256.1 GI:218505839) and shares ~85% nucleotide and amino acid sequence identity with the murine IL-11Rα (Du and Williams, Blood Vol, 89, No, 11, Jun. 1, 1997). Two isoforms of IL-11Rα have been reported, which differ in the cytoplasmic domain (Du and Williams, supra). In some embodiments as used herein, the IL-11Rα may be IL-11Rα isoform 1 or IL-11Rα isoform 2.

The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signalling pathway.

IL-11Rα binds its ligand with a low affinity (Kd~10 nmol/L) and alone is insufficient to transduce a biological signal. The generation of a high affinity receptor (Kd~400 to 800 pmol/L) capable of signal transduction requires co-expression of the IL-11Rα and gp130 (Curtis et al (Blood 1997 Dec. 1; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and MAPK and/or Jak/STAT signalling as described above.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11Rα) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R.

Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be a very important component of IL-11 mediated signalling, and may even be the most common form of IL-11 mediated signalling, because whilst the expression of IL-11Rα is restricted to a relatively small subset of cell types, gp130 is expressed on a wide range of cell types.

As used herein, 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα.

In this specification an IL-11 receptor (IL-11R) refers to a polypeptide capable of binding IL-11 and inducing signal transduction in cells expressing gp130. An IL-11 receptor may be from any species and includes isoforms, fragments, variants or homologues of an IL-11 receptor from any species. In preferred embodiments the species is human (*Homo sapiens*). In some embodiments the IL-11 receptor may be IL-11Rα. Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

TGFβ1 has been shown to induce IL-11 expression in fibroblasts (Elias et al., 1994 J. Immunol. 152, 2421-2429).

IL-11 has been proposed to function mainly as a thrombopoietic growth factor, which underpinned the use of recombinant IL-11 (Neumega (Oprelvekin)) as a therapeutic agent to increase platelet count.

The role of IL-11 in fibrosis is not clear. The majority of studies suggest an anti-fibrotic function for IL-11 in the heart (Obana et al., 2010 Circulation 121, 684-691; Obana et al., 2012 Heart and Circulatory Physiology 303, H569-77) and kidney (Ham et al., 2013 Anesthesiology 119, 1389-1401; Stangou et al., 2011 J. Nephrol. 24, 106-111). Kurahara et al., J. Smooth Muscle Res. 2016; 52: 78-92 describes IL-11 as an anti-fibrotic cytokine, and suggests that IL-11 suppresses αSMA expression.

IL-11 has also been suggested to be an anti-inflammatory factor in several tissues and chronic inflammatory diseases (Trepicchio and Dorner, 1998 Expert Opin Investig Drugs 7, 1501-1504; Zhu et al., 2015 PLoS ONE 10, e0126296). These studies suggest that the observed secretion of IL-11 in response to TGFβ1 is a protective mechanism.

On the other hand, it has been suggested that IL-11 signalling may be involved in pathology of diseases of the lung. Inhibition of IL-11 either via antibodies or a mutated recombinant IL-11 in a model of tuberculosis revealed a positive feedback loop in vivo and diminished histopathology of the lung (Kapina et al., 2011 PLoS ONE 6, e21878; Shepelkova et al., 2016 Journal of Infectious Diseases 214, jiw176), fibrosis of the murine airway has been associated with IL-11 expression (Tang et al., 1996 The Journal of Clinical Investigation 98, 2845-2853). When the pro-fibrotic function of IL-13 in lung tissue was investigated in IL-11 RA –/– mice, IL-11 signalling was implicated in the mechanism (Chen et al., 2005 J. Immunol. 174, 2305-2313).

IL-11 was also found to be elevated in the airway of patients with severe asthma (Minshall et al., 2000 Respiratory Research 14, 1-14), is overexpressed in the lungs of IPF patients (Lindahl et al., 2013 Respiratory Research 14, 1-14) and is elevated in skin lesions in atopic dermatitis patients (Toda et al., 2003 J Allergy Clin Immun 111, 875-881). It is uncertain whether these associations are due to increased IL-11 gene/protein expression as a response to disease processes, or whether IL-11 is an effector of disease processes.

Antibodies and Antigen-Binding Fragments

Antibodies and antigen-binding fragments according to the present invention bind to IL-11 (interleukin 11). In some embodiments, the antibody/fragment binds to human IL-11. In some embodiments, the antibody/fragment binds to non-human primate IL-11. In some embodiments, the antibody/fragment binds to murine IL-11.

By "antibody" we include fragments and derivatives thereof, or a synthetic antibody or synthetic antibody fragment. As used herein, an antibody is a polypeptide capable of binding specifically to the relevant target molecule (i.e. the antigen for which the antibody is specific). Antibodies according to the present invention may be provided in isolated form.

In view of contemporary techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Antigen binding fragments of antibodies, such as Fab and Fab$_2$ fragments may also be used/provided as can genetically engineered antibodies and antibody fragments. The variable heavy (V$_H$) and variable light (V$_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sd. USA 81, 6851-6855).

In some embodiments, the antibody/fragment is a fully human antibody/fragment. A fully human antibody/fragment is encoded by human nucleic acid sequence(s). Fully human antibodies/fragments are devoid of non-human amino acid sequences.

The two most commonly employed techniques to the production of fully human antibodies are (i) phage display, in which human antibody genes are expressed in phage display libraries, and (ii) production of antibodies in transgenic mice engineered to have human antibody genes (described in Park and Smolen Advances in Protein Chemistry (2001) 56: 369-421). Briefly, in the human antibody gene-phage display technique, genes encoding the VH and VL chains are generated by PCR amplification and cloning from "naive" human lymphocytes, and assembled into a library from which they can be expressed either as disulfide-linked Fab fragments or as single-chain Fv (scFv) fragments. The Fab- or scFv-encoding genes are fused to a surface coat protein of filamentous bacteriophage and Fab or scFv capable of binding to the target of interest can then be identified by screening the library with antigen. Molecular evolution or affinity maturation procedures can be employed to enhance the affinity of the Fab/scFv fragment. In the transgenic mouse technique, mice in which the endogenous murine Ig gene loci have been replaced by homologous recombination with their human homologues are immunized with antigen, and monoclonal antibody is prepared by conventional hybridoma technology, to yield fully human monoclonal antibody.

In some embodiments, the antibody/fragment according to the present invention is a murine antibody/fragment. The antibody/fragment may be prepared by phage display using a human nave antibody gene library.

In some embodiments, the antibody/fragment is a mouse/human chimeric antibody/fragment (e.g., an antibody/antigen binding fragment comprising murine variable domains and human constant regions). In some embodiments, the antibody/fragment is a humanised antibody/fragment (e.g., an antibody/antigen binding fragment comprising murine CDRs and human framework and constant regions).

A mouse/human chimeric antibody/antigen binding fragment can be prepared from a mouse monoclonal antibody by the process of chimerisation, e.g. as described in Human Monoclonal Antibodies: Methods and Protocols, Michael Steinitz (Editor), Methods in Molecular Biology 1060, Springer Protocols, Humana Press (2014), in Chapter 8 thereof, in particular section 3 of Chapter 8.

A humanised antibody/antigen binding fragment can be prepared from a mouse antibody by the process of chimerisation, e.g. as described in Human Monoclonal Antibodies: Methods and Protocols, Michael Steinitz (Editor), Methods in Molecular Biology 1060, Springer Protocols, Humana Press (2014), in Chapter 7 thereof, in particular section 3.1 of Chapter 7 entitled 'Antibody Humanization'.

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the V$_H$ and V$_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the V$_H$ and V$_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

The present invention provides an antibody or antigen binding fragment which is capable of binding to IL-11. In some embodiments, the antibody or antigen binding fragment may be isolated.

An antigen-binding fragment according to the present invention may be any fragment of a polypeptide which is capable of binding to an antigen.

In some embodiments, an antigen binding fragment comprises at least three light chain CDRs (i.e. LC-CDR1, LC-CDR2 and LC-CDR3; also referred to herein as LC-CDRs 1-3) and three heavy chain CDRs (i.e. HC-CDR1, HC-CDR2 and HC-CDR3; also referred to herein as HC-CDRs 1-3) which together define the antigen binding region of an antibody or antigen binding fragment. In some embodiments, an antigen binding fragment may comprise the light chain variable domain and heavy chain variable domain of an antibody or antigen binding fragment. In some embodiments, an antigen binding fragment may comprise the light chain polypeptide and heavy chain polypeptide of an antibody or antigen binding fragment.

The present invention also provides a chimeric antigen receptor (CAR) capable of binding to IL-11, comprising one or more antigen binding fragments or polypeptides according to the present invention. Chimeric Antigen Receptors (CARs) are recombinant receptors that provide both antigen-binding and T cell activating functions. CAR structure and engineering is reviewed, for example, in Dotti et al., Immunol Rev (2014) 257(1), hereby incorporated by reference in its entirety. Antigen-binding fragments according to the present invention are provided herein as the antigen-binding domain of a chimeric antigen receptor (CAR). In some embodiments, the CAR comprises a VL domain and a VH domain according to any embodiment of an antibody, antigen binding fragment or polypeptide described herein. CARs may be combined with costimulatory ligands, chimeric costimulatory receptors or cytokines to further enhance T cell potency, specificity and safety (Sadelain et al., The basic principles of chimeric antigen receptor (CAR) design. Cancer Discov. 2013 April; 3(4): 388-398. doi:10.1158/2159-8290.CD-12-0548, specifically incorporated herein by reference). Also provided is a cell comprising a CAR according to the invention. The CAR according to the present invention may be used to generate T cells. Engineering of CARs into T cells may be performed during culture, in vitro, for transduction and expansion, such as happens during expansion of T cells for adoptive T cell therapy.

Also provided in the present invention are bispecific antibodies and bispecific antigen binding fragments comprising an antibody or antigen binding fragment according to the present invention. The bispecific antibodies or bispecific antigen binding fragments may comprise (i) an antibody or antigen binding fragment according to the present invention, and (ii) an antibody or antigen binding fragment specific for a target other than IL-11.

Bispecific antibodies/fragments may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tandAbs, tandem scFv (taFv), tandem dAb/VHH, triple body, triple head, Fab-scFv, or F(ab')$_2$-scFv$_2$), a bispecific Fc and C$_H$3 fusion protein (e.g. a taFv-Fc, Di-diabody, scDb-C$_H$3, scFv-Fc-scFv, HCAb-VHH, scFv-kih-Fc, or scFv-kih-C$_H$3), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers. Other methods include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16. Bispecific antibodies and bispecific antigen binding fragments can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339, the entire contents of both of which are hereby incorporated by reference.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

The present invention provides antibodies described herein which have further undergone the process of chain shuffling, e.g. light chain shuffling and/or heavy chain shuffling. Chain shuffling to improve antibody affinity is described in detail in Marks, Antibody Affinity Maturation by Chain Shuffling, Antibody Engineering Methods and Protocols, Humana Press (2004) Vol. 248, pp 327-343, which is hereby incorporated by reference in its entirety—in particular, light chain shuffling is described in detail at sections 3.1 and 3.2 thereof. In light chain shuffling, heavy chain variable regions of antibodies are combined with a repertoire of light chain variable region partners to identify new VL/VH combinations having high affinity for the target protein of interest. In this way, the antibody/fragment is optimised for very high binding affinity.

In some aspects, the antibody/fragment of the present invention comprises the CDRs (i.e. CDRs 1-3) of the VH and/or VL domains of an IL-11-binding antibody clone described herein, or a variant thereof. In some embodiments, the antibody/fragment of the present invention comprises HC-CDRs 1-3 of an IL-11-binding antibody clone described herein, or a variant thereof. In some embodiments, the antibody/fragment of the present invention comprises LC-CDRs 1-3 of an IL-11-binding antibody clone described herein, or a variant thereof.

HC-CDRs 1-3 and LC-CDRs 1-3 of the antibody clones of the present disclosure are defined according to VBASE2, as described in Retter et al., Nucl. Acids Res. (2005) 33 (suppl 1): D671-D674, which is hereby incorporated by reference in its entirety.

As used herein, a variant of a CDR may comprise e.g. 1 or 2 or 3 substitutions in the amino acid sequence of the CDR. As used herein, a variant of a VL or VH domain may comprise e.g. 1, 2, 3, 4, 5, 6, 7, 8, 9 or 10 substitutions in the amino acid sequence of the domain.

In some embodiments, the antibody/fragment of the present invention comprises HC-CDRs 1-3 of an IL-11-binding antibody clone described herein, or a variant thereof, and LC-CDRs 1-3 of an IL-11-binding antibody clone described herein, or a variant thereof.

In some aspects, the antibody/fragment of the present invention comprises the CDRs of the VH and/or VL domains of an IL-11-binding antibody clone described herein, or a variant thereof. In some aspects, the antibody/fragment of the present invention comprises the VH and/or VL domains of an IL-11-binding antibody clone described herein, or a variant thereof.

In some aspects, the antibody/fragment of the present invention comprises the CDRs of the VH and/or VL domains of a clone, or a variant thereof, selected from YU33-A2, YU33-B3/H3, YU33-B4/YU45-G2/A3, YU33-E3, YU33-E6, YU45-C11/A10, YU45-D11/F11, YU45-E11/E12, YU45-H11/D12, YU45-A12/G10, YU45-G1, YU45-B2, YU45-C2/A7/B10, YU45-D2/H2/C7/F3/C9/E1/E9/C10/G3/H9/C5/A2/A5, YU45-B3, YU45-E3, YU45-C8/E8, YU45-F8, YU45-G8/H6, YU45-H8, YU45-F9, YU45-H10, YU46-A10, YU45-F2, YU45-H3, YU45-A1, YU45-A8/C6, YU45-B5/A4, YU45-03/A6, YU45-D1, YU45-D9/D3, YU45-E5, YU45-G7, YU45-B4, YU45-H4, YU45-B6, YU45-D6, YU45-E7, YU45-F5, YU45-H7/B5, YU45-B8, YU45-C1, YU46-G1, YU46-A2, YU46-A8, YU46-B2, YU46-B6, YU46-C1, YU46-D7, YU46-E3, YU46-E7, YU46-H8, YU46-G9, YU46-G8, YU46-B7 or YU46-D3; e.g. selected from YU45-C11/A10, YU45-G1, YU45-E3, YU45-F8, YU45-F9, YU45-H10, YU45-F2, YU45-H3, YU45-G7, YU45-B6, YU45-C1, YU46-B6, YU46-E3, YU46-G8 or YU46-D3; or selected from YU33-B4/YU45-

G2/A3, YU45-H11/D12, YU45-G1, YU45-D2/H2/C7/F3/ C9/E1/E9/C10/G3/H9/C5/A2/A5, YU45-B3, YU45-F8, YU45-H10, YU46-A10, YU45-A8/C6, YU45-D9/D3, YU45-B6, YU45-C1, YU46-A8, YU46-C1, YU46-H8, YU46-G8 or YU46-D3; or selected from YU33-B4/YU45-G2/A3, YU45-E3, YU45-F2, YU45-F5, YU46-A8 or YU46-G8.

In some aspects, the antibody/fragment of the present invention comprises the VH and/or VL domains of a clone, or a variant thereof, selected from YU33-A2, YU33-B3/H3, YU33-B4/YU45-G2/A3, YU33-E3, YU33-E6, YU45-C11/A10, YU45-D11/F11, YU45-E11/E12, YU45-H11/D12, YU45-A12/G10, YU45-G1, YU45-B2, YU45-C2/A7/B10, YU45-D2/H2/C7/F3/C9/E1/E9/C10/G3/H9/C5/A2/A5, YU45-B3, YU45-E3, YU45-C8/E8, YU45-F8, YU45-G8/H6, YU45-H8, YU45-F9, YU45-H10, YU46-A10, YU45-F2, YU45-H3, YU45-A1, YU45-A8/C6, YU45-B5/A4, YU45-O3/A6, YU45-D1, YU45-D9/D3, YU45-E5, YU45-G7, YU45-B4, YU45-H4, YU45-B6, YU45-D6, YU45-E7, YU45-F5, YU45-H7/B5, YU45-B8, YU45-C1, YU46-G1, YU46-A2, YU46-A8, YU46-B2, YU46-B6, YU46-C1, YU46-D7, YU46-E3, YU46-E7, YU46-H8, YU46-G9, YU46-G8, YU46-B7 or YU46-D3; e.g. selected from YU45-C11/A10, YU45-G1, YU45-E3, YU45-F8, YU45-F9, YU45-H10, YU45-F2, YU45-H3, YU45-G7, YU45-B6, YU45-C1, YU46-B6, YU46-E3, YU46-G8 or YU46-D3; or selected from YU33-B4/YU45-G2/A3, YU45-H11/D12, YU45-G1, YU45-D2/H2/C7/F3/C9/E1/E9/C10/G3/H9/C5/A2/A5, YU45-B3, YU45-F8, YU45-H10, YU46-A10, YU45-A8/C6, YU45-D9/D3, YU45-B6, YU45-C1, YU46-A8, YU46-C1, YU46-H8, YU46-G8 or YU46-D3; or selected from YU33-B4/YU45-G2/A3, YU45-E3, YU45-F2, YU45-F5, YU46-A8 or YU46-G8.

In some aspects, the antibody/fragment of the present invention comprises the CDRs of the VH and/or VL domains of a clone, or a variant thereof, selected from BSN-1H2, BSN-1H7, BSN-2E1, BSN-2F5, BSN-2G6, BSN-3C6, BSN-3C11, BSN-5A6, BSN-5B8, BSN-5F6, BSN-6F3, BSN-7D4, BSN-7E4, BSN-7F9, BSN-8C4 or BSN-8H11, e.g. selected from one of BSN-2E1, BSN-2G6, BSN-3C6, BSN-5A6 or BSN-5B8; or selected from one of BSN-2G6, BSN-3C6, BSN-5B8 or BSN-7D4; or BSN-3C6.

In some aspects, the antibody/fragment of the present invention comprises the VH and/or VL domains of a clone, or a variant thereof, selected from BSN-1H2, BSN-1H7, BSN-2E1, BSN-2F5, BSN-2G6, BSN-3C6, BSN-3C11, BSN-5A6, BSN-5B8, BSN-5F6, BSN-6F3, BSN-7D4, BSN-7E4, BSN-7F9, BSN-8C4 or BSN-8H11, e.g. selected from one of BSN-2E1, BSN-2G6, BSN-3C6, BSN-5A6 or BSN-5B8; or selected from one of BSN-2G6, BSN-3C6, BSN-5B8 or BSN-7D4; or BSN-3C6.

In some aspects, the antibody/fragment of the present invention comprises HC-CDRs 1-3 of the VH domain of an IL-11-binding antibody clone described herein, or a variant thereof. In some aspects, the antibody/fragment of the present invention comprises the VH domain of a clone, or a variant thereof.

In some aspects, the antibody/fragment of the present invention comprises LC-CDRs 1-3 of the VL domain of an IL-11-binding antibody clone described herein, or a variant thereof. In some aspects, the antibody/fragment of the present invention comprises the VL domain of a clone, or a variant thereof.

In some embodiments the antibody/fragment of the present invention comprises HC-CDRs 1-3 of the VH domain, or the VH domain, of an IL-11-binding antibody clone selected from YU33-A2, YU33-B3/H3, YU33-B4/YU45-G2/A3, YU33-E3, YU33-E6, YU45-C11/A10, YU45-D11/F11, YU45-E11/E12, YU45-H11/D12, YU45-A12/G10, YU45-G1, YU45-B2, YU45-C2/A7/B10, YU45-D2/H2/C7/F3/C9/E1/E9/C10/G3/H9/C5/A2/A5, YU45-B3, YU45-E3, YU45-C8/E8, YU45-F8, YU45-G8/H6, YU45-H8, YU45-F9, YU45-H10, YU46-A10, YU45-F2, YU45-H3, YU45-A1, YU45-A8/C6, YU45-B5/A4, YU45-O3/A6, YU45-D1, YU45-D9/D3, YU45-E5, YU45-G7, YU45-B4, YU45-H4, YU45-B6, YU45-D6, YU45-E7, YU45-F5, YU45-H7/B5, YU45-B8, YU45-C1, YU46-G1, YU46-A2, YU46-A8, YU46-B2, YU46-B6, YU46-C1, YU46-D7, YU46-E3, YU46-E7, YU46-H8, YU46-G9, YU46-G8, YU46-B7 or YU46-D3; e.g. selected from YU45-C11/A10, YU45-G1, YU45-E3, YU45-F8, YU45-F9, YU45-H10, YU45-F2, YU45-H3, YU45-G7, YU45-B6, YU45-C1, YU46-B6, YU46-E3, YU46-G8 or YU46-D3; or selected from YU33-B4/YU45-G2/A3, YU45-H11/D12, YU45-G1, YU45-D2/H2/C7/F3/C9/E1/E9/C10/G3/H9/C5/A2/A5, YU45-B3, YU45-F8, YU45-H10, YU46-A10, YU45-A8/C6, YU45-D9/D3, YU45-B6, YU45-C1, YU46-A8, YU46-C1, YU46-H8, YU46-G8 or YU46-D3; or selected from YU33-B4/YU45-G2/A3, YU45-E3, YU45-F2, YU45-F5, YU46-A8 or YU46-G8. In some embodiments, the antibody/fragment comprises a VL domain which is arrived at following light chain shuffling.

In some embodiments the antibody/fragment of the present invention comprises LC-CDRs 1-3 of the VL domain, or the VL domain, of an IL-11-binding antibody clone selected from YU33-A2, YU33-B3/H3, YU33-B4/YU45-G2/A3, YU33-E3, YU33-E6, YU45-C11/A10, YU45-D11/F11, YU45-E11/E12, YU45-H11/D12, YU45-A12/G10, YU45-G1, YU45-B2, YU45-C2/A7/B10, YU45-D2/H2/C7/F3/C9/E1/E9/C10/G3/H9/C5/A2/A5, YU45-B3, YU45-E3, YU45-C8/E8, YU45-F8, YU45-G8/H6, YU45-H8, YU45-F9, YU45-H10, YU46-A10, YU45-F2, YU45-H3, YU45-A1, YU45-A8/C6, YU45-B5/A4, YU45-O3/A6, YU45-D1, YU45-D9/D3, YU45-E5, YU45-G7, YU45-B4, YU45-H4, YU45-B6, YU45-D6, YU45-E7, YU45-F5, YU45-H7/B5, YU45-B8, YU45-C1, YU46-G1, YU46-A2, YU46-A8, YU46-B2, YU46-B6, YU46-C1, YU46-D7, YU46-E3, YU46-E7, YU46-H8, YU46-G9, YU46-G8, YU46-B7 or YU46-D3; e.g. selected from YU45-C11/A10, YU45-G1, YU45-E3, YU45-F8, YU45-F9, YU45-H10, YU45-F2, YU45-H3, YU45-G7, YU45-B6, YU45-C1, YU46-B6, YU46-E3, YU46-G8 or YU46-D3; or selected from YU33-B4/YU45-G2/A3, YU45-H11/D12, YU45-G1, YU45-D2/H2/C7/F3/C9/E1/E9/C10/G3/H9/C5/A2/A5, YU45-B3, YU45-F8, YU45-H10, YU46-A10, YU45-A8/C6, YU45-D9/D3, YU45-B6, YU45-C1, YU46-A8, YU46-C1, YU46-H8, YU46-G8 or YU46-D3; or selected from YU33-B4/YU45-G2/A3, YU45-E3, YU45-F2, YU45-F5, YU46-A8 or YU46-G8. In some embodiments, the antibody/fragment comprises a VH domain which is arrived at following heavy chain shuffling.

The amino acid sequences of the VL domains of the human anti-human IL-11-binding antibody clones YU33-A2, YU33-B3/H3, YU33-B4/YU45-G2/A3, YU33-E3, YU33-E6, YU45-C11/A10, YU45-D11/F11, YU45-E11/E12, YU45-H11/D12, YU45-A12/G10, YU45-G1, YU45-B2, YU45-C2/A7/B10, YU45-D2/H2/C7/F3/C9/E1/E9/C10/G3/H9/C5/A2/A5, YU45-B3, YU45-E3, YU45-C8/E8, YU45-F8, YU45-G8/H6, YU45-H8, YU45-F9, YU45-H10, YU46-A10, YU45-F2, YU45-H3, YU45-A1, YU45-A8/C6, YU45-B5/A4, YU45-O3/A6, YU45-D1, YU45-D9/D3, YU45-E5, YU45-G7, YU45-B4, YU45-H4, YU45-B6, YU45-D6, YU45-E7, YU45-F5, YU45-H7/B5, YU45-B8, YU45-C1, YU46-G1, YU46-A2, YU46-A8, YU46-B2, YU46-B6, YU46-C1, YU46-D7, YU46-E3, YU46-E7, YU46-H8, YU46-G9, YU46-G8, YU46-B7 and YU46-D3 are shown in FIG. 15, as are the LC-CDRs 1-3, defined using VBASE2 (described in Retter et al., Nucl. Acids Res. (2005) 33 (suppl 1): D671-D674). The amino acid sequences of the VH domains for these human anti-human IL-11-binding antibody clones are shown in FIG. 16, as are the HC-CDRs 1-3, defined using VBASE2.

In some aspects, the antibody/fragment of the present invention comprises the CDRs of the VH and/or VL domains of a clone, or a variant thereof, selected from YU100-A10, YU100-A11, YU100-A12, YU100-B01, YU100-B03, YU100-B06, YU100-B07, YU100-B08, YU100-B09, YU100-B12, YU100-C02, YU100-C04, YU100-C05, YU100-C10, YU100-C11, YU100-C12, YU100-D01, YU100-D02, YU100-D05, YU100-D07, YU100-D11, YU100-E01, YU100-E04, YU100-E05, YU100-E06, YU100-E07, YU100-E08, YU100-E09, YU100-E10, YU100-E11, YU100-E12, YU100-F01, YU100-F02, YU100-F05, YU100-F06, YU100-F07, YU100-F11, YU100-G01, YU100-G07, YU100-G08, YU100-G09, YU100-G10, YU100-G11, YU100-H01, YU100-H02, YU100-H04, YU100-H05, YU100-H06, YU100-H09, YU100-H11, YU112-A07, YU112-B06, YU112-C03, YU112-C05, YU112-C09, YU112-D08, YU112-E07, YU112-E08, YU112-F05, YU112-G01, YU112-G06, YU112-G09, YU112-H01 or YU112-H02. The amino acid sequences of the VL domains and LC-CDRs 1-3 (defined using VBASE2) for these human anti-human IL-11-binding antibody clones are shown in FIG. 44, and the amino acid sequences of the VH domains and HC-CDRs 1-3 (defined using VBASE2) for these human anti-human IL-11-binding antibody clones are shown in FIG. 45.

Antibodies according to the present invention may comprise VL and/or VH chains comprising an amino acid sequence that has a high percentage sequence identity to one or more of the VL and/or VH amino acid sequences described herein. For example, antibodies according to the present invention include antibodies that bind IL-11 and have a VL chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VL chain amino acid sequence of one of SEQ ID NOs:1 to 50. Antibodies according to the present invention include antibodies that bind IL-11 and have VH chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VH chain amino acid sequence of one of SEQ ID NOs:51 to 100.

Antibodies according to the present invention include antibodies that bind IL-11 and have a VL chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VL chain amino acid sequence of one of SEQ ID NOs: 267, 269, 270, 271, 274, 277, 279, 280, 540, 283, 286, 287, 289, 353, 293, 297, 299, 301, 303, 305, 307, 309, 310, 312, 314, 316, 318, 319, 321, 323, 325, 327, 328, 329, 331, 332, 335, 337, 338, 341, 342, 343, 346, 348, 214, 350, 13, 3, 351, 355, 358, 35, 361, 363, 365, 366, or 20. Antibodies according to the present invention include antibodies that bind IL-11 and have VH chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VH chain amino acid sequence of one of SEQ ID NOs: 53, 368, 369, 370, 371, 372, 373, 374, 375, 376, 377, 378, 379, 380, 382, 383, 384, 385, 386, 387, 388, 389, 85, 390, 73, 391, or 392.

In some embodiments the antibody/fragment of the present invention comprises HC-CDRs 1-3 of the VH domain, or the VH domain, of an IL-11-binding antibody clone selected from BSN-2E1, BSN-3C6, BSN-5A6_1 BSN-2G6, BSN-5A6_2 or BSN-5B8; e.g. BSN-3C6.

In some embodiments the antibody/fragment of the present invention comprises LC-CDRs 1-3 of the VL domain, or the VL domain, of an IL-11-binding antibody clone selected from BSN-2E1, BSN-3C6, BSN-5A6_1 BSN-2G6, BSN-5A6_2 or BSN-5B8; e.g. BSN-3C6.

The amino acid sequences of the VH domains of the anti-human IL-11-binding antibody clones BSN-2E1, BSN-3C6, BSN-5A6_1 BSN-2G6, BSN-5A6_2 and BSN-5B8 are shown in FIG. 68, as are the HC-CDRs 1-3, defined using VBASE2 (described in Retter et al., Nucl. Acids Res. (2005) 33 (suppl 1): D671-D674). The amino acid sequences of the VL domains for these anti-human IL-11-binding antibody clones are shown in FIG. 69, as are the LC-CDRs 1-3, defined using VBASE2.

In some aspects, the antibody/fragment of the present invention comprises the CDRs of the VH and/or VL domains of a clone, or a variant thereof, selected from BSN-2E1, BSN-3C6, BSN-5A6_1 BSN-2G6, BSN-5A6_2 or BSN-5B8; e.g. BSN-3C6.

Antibodies according to the present invention include antibodies that bind IL-11 and have a VL chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VL chain amino acid sequence of one of SEQ ID NOs:554, 557, 561 or 564. Antibodies according to the present invention include antibodies that bind IL-11 and have VH chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VH chain amino acid sequence of one of SEQ ID NOs: 541, 545, 548 or 551.

The light and heavy chain CDRs disclosed herein may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Le:franc (2001) "The Immunoglobulin FactsBook", Academic Press, incorporated herein by reference.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, radiolabels and binding moieties. Labelling may be by conjugation to the antibody/fragment. The antigen binding molecule may be directly labelled with a detectable label or it may be indirectly labelled. In some embodiments, the label may be selected from: a radio-nucleotide, positron-emitting radionuclide (e.g. for positron emission tomography (PET)), MRI contrast agent or fluorescent label.

Antibodies and antigen binding fragments according to the present invention may be conjugated to a drug moiety, e.g. a cytotoxic small molecule. Such conjugates are useful for the targeted killing of cells expressing the antigen molecule.

Also provided by the present invention are isolated heavy chain variable region polypeptides, and isolated light chain variable region polypeptides.

In some aspects an isolated heavy chain variable region polypeptide is provided, comprising the HC-CDRs 1-3 of any one of the anti-IL-11 antibody clones described herein. In some aspects an isolated heavy chain variable region polypeptide is provided, comprising an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100% sequence identity to the amino acid sequence of the heavy chain variable region of any one of the anti-IL-11 antibody clones described herein.

In some aspects an isolated light chain variable region polypeptide is provided, comprising the LC-CDRs 1-3 of any one of the anti-IL-11 antibody clones described herein. In some aspects an isolated light chain variable region polypeptide is provided, comprising an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100% sequence identity to the amino acid sequence of the light chain variable region of any one of the anti-IL-11 antibody clones described herein.

Antibodies according to the present invention include antibodies that bind IL-11 and comprise an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of one of SEQ ID NOs: 412 to 475.

Functional Properties of the Antibodies/Fragments

The IL-11 antibodies and fragments of the present invention may be characterised by reference to certain functional properties. In particular, an IL-11 antibody or antigen binding fragment according to the present invention may possess one or more of the following properties:

a) Specific binding to IL-11 (e.g. human IL-11 and/or mouse IL-11);
b) Binding to IL-11 (e.g. human IL-11) with an affinity of binding of EC50=less than 1000 ng/ml, e.g. as determined by ELISA;
c) Inhibition of interaction between IL-11 and IL-11Rα;
d) Inhibition of interaction between IL-11 and gp130;
e) Inhibition of interaction between IL-11 and IL-11Rα:gp130 receptor complex;
f) Inhibition of interaction between IL-11:IL-11Rα complex and gp130;
g) Inhibition of signalling mediated by IL-11;
h) Inhibition of signalling mediated by binding of IL-11 to IL-11Rα:gp130 receptor complex;
i) Inhibition of signalling mediated by binding of IL-11:IL-11Rα complex to gp130 (i.e. IL-11 trans signalling);
j) Inhibition of fibroblast proliferation;
k) Inhibition of myofibroblast generation from fibroblasts;
l) Inhibition of a pathological process mediated by IL-11;
m) Inhibition of fibrosis;
n) Inhibition of gene or protein expression in fibroblasts of one or more of collagen, fibronectin, periostin, IL-6, IL-11, αSMA, TIMP1, MMP2, e.g. following stimulation with a profibrotic factor;
o) Inhibition of extracellular matrix production by fibroblasts
p) Inhibition of proliferation and/or survival of cells of a cancer;
q) Inhibition of tumour growth.

Herein, 'inhibition' refers to a reduction, decrease or lessening relative to a control condition. For example, inhibition of a process by an antibody/fragment refers to a reduction, decrease or lessening of the extent/degree of that process in the absence of the antibody/fragment, and/or in the presence of an appropriate control antibody/fragment.

Inhibition may herein also be referred to as neutralisation or antagonism. That is, an IL-11 binding antibody/fragment which is capable of inhibiting a function or process (e.g. interaction, signalling or other activity mediated by IL-11 or an IL-11-containing complex) may be said to be a 'neutralising' or 'antagonist' antibody/fragment with respect to the relevant function or process. For example, antibody/fragment which is capable of inhibiting IL-11 mediated signalling may be referred to as an antibody/fragment which is capable of neutralising IL-11 mediated signalling, or may be referred to as an antagonist of IL-11 mediated signalling.

The skilled person is able to identify an appropriate control condition for a given assay. For example, a control antibody/fragment may be an antibody/fragment directed against a target protein which is known not to have a role involved in the property being investigated in the assay. A control antibody/fragment may be of the same isotype as the anti-IL-11 antibody/fragment being analysed, and may e.g. have the same constant regions.

An antibody/fragment that specifically binds to a target molecule preferably binds the target with greater affinity, and/or with greater duration than it binds to other, non-target molecules. In some embodiments the present antibodies/fragments may bind with greater affinity to IL-11 than to one or more members of the IL-6 cytokine family. In some embodiments the present antibodies/fragments may bind with greater affinity to IL-11 than to one or more of IL-6, leukemia inhibitory factor (LIF), oncostatin M (OSM), cardiotrophin-1 (CT-1), ciliary neurotrophic factor (CNTF), and cardiotrophin-like cytokine (CLC).

In some embodiments, the extent of binding of an antibody to an non-target is less than about 10% of the binding of the antibody to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the anti-IL-11 antibody/fragment of the present invention binds to IL-11 with a $K_D$ that is at least 0.1 order of magnitude (i.e. $0.1 \times 10^n$, where n is an integer representing the order of magnitude) greater than the $K_D$ towards another, non-target molecule. This may optionally be one of at least 0.2, 0.3, 0.4, 0.5, 0.6, 0.7, 0.8, 0.9, 1.0, 1.5, or 2.0.

Binding affinity of an antibody or antigen-binding fragment for its target is often described in terms of its dissociation constant ($K_D$). Binding affinity can be measured by methods known in the art, such as by ELISA, Surface Plasmon Resonance (SPR; see e.g. Hearty et al., Methods Mol Biol (2012) 907:411-442; or Rich et al., Anal Biochem. 2008 Feb. 1; 373(1):112-20), Bio-Layer Interferometry (see e.g. Lad et al., (2015) J Biomol Screen 20(4): 498-507; or Concepcion et al., Comb Chem High Throughput Screen. 2009 September; 12(8):791-800), MicroScale Thermophoresis (MST) analysis (see e.g. Jerabek-Willemsen et al., Assay Drug Dev Technol. 2011 August; 9(4): 342-353), or by a radiolabelled antigen binding assay (RIA) performed with the Fab version of the antibody and antigen molecule.

In some embodiments, the antibody/fragment according to the present invention binds to IL-11 with a $K_D$ of 5 µM or less, preferably one of ≤1 µM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM≤3 nM, ≤2 nM, ≤1 nM, ≤500 pM.

In some embodiments, the antibody/fragment according to the present invention binds to IL-11 with an affinity of binding (e.g. as determined by ELISA) of EC50=1000 ng/ml or less, preferably one of ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, 10 ng/ml, ≤7.5 ng/ml, ≤5 ng/ml, ≤2.5 ng/ml, or ≤1 ng/ml.

Affinity of binding to IL-11 by an antibody/fragment may be analysed in vitro by ELISA assay. Suitable assays are well known in the art and can be performed by the skilled person, for example, as described in Antibody Engineering, vol. 1 ($2^{nd}$ Edn), Springer Protocols, Springer (2010), Part V, pp 657-665. For example, the affinity of binding to IL-11 by an antibody/fragment may be analysed according to the methodology described herein in the experimental examples.

The ability of an antibody/fragment to inhibit interaction between two proteins can be determined for example by analysis of interaction in the presence of, or following incubation of one or both of the interaction partners with, the antibody/fragment. An example of a suitable assay to determine whether a given antibody/fragment is capable of inhibiting interaction between two interaction partners is a competition ELISA assay.

An antibody/fragment which is capable of inhibiting a given interaction (e.g. between IL-11 and IL-11Rα, or between IL-11 and gp130, or between IL-11 and IL-11Rα:gp130, or between IL-11:IL-11Rα and gp130) is identified by the observation of a reduction/decrease in the level of interaction between the interaction partners in the presence of or following incubation of one or both of the interaction partners with the antibody/fragment, as compared to the level of interaction in the absence of the antibody/fragment (or in the presence of an appropriate control antibody/fragment). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the antibody/fragment may be labelled or used in conjunction with a detectable entity for the purposes of detecting and/or measuring the level of interaction.

Ability of an antibody/fragment to inhibit interaction between two binding partners can also be determined by analysis of the downstream functional consequences of such interaction, e.g. receptor signalling. For example, downstream functional consequences of interaction between IL-11 and IL-11Rα:gp130 or between IL-11:IL-11Rα and gp130 may include proliferation of fibroblasts, myofibroblast generation from fibroblasts, or gene or protein expression of one or more of collagen, fibronectin, periostin, IL-6, IL-11, αSMA, TIMP1, MMP2.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antibody/fragment, the fibroblasts may be cardiac fibroblasts (e.g. atrial fibroblasts), skin fibroblasts, lung fibroblasts, kidney fibroblasts or liver fibroblasts. Fibroblasts may be characterised by gene or protein expression of one or more of COL1A, ACTA2, prolyl-4-hydroxylase, MAS516, and FSP1.

Gene expression can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

In some embodiments, the antibody/fragment according to the present invention may inhibit protein expression of one or more markers of fibrosis, e.g. protein expression of one or more of collagen, fibronectin, periostin, IL-6, IL-11, αSMA, TIMP1, MMP2.

The ability of an antibody/fragment to inhibit interaction between IL-11 and IL-11Rα:gp130 can, for example, be analysed by stimulating fibroblasts with TGFβ1, incubating the cells in the presence of the antibody/fragment and analysing the proportion of cells having αSMA-positive phenotype after a defined period of time. In such example, inhibition of interaction between IL-11 and IL-11Rα:gp130 can be identified by observation of a lower proportion of cells having an αSMA-positive phenotype as compared to positive control condition in which cells are treated with TGFβ1 in the absence of the antibody/fragment (or in the presence of an appropriate control antibody/fragment), or in the presence of an appropriate control antibody/fragment.

Such assays are also suitable for analysing the ability of antibody/fragment to inhibit IL-11-mediated signalling.

In some embodiments, the antibody/fragment according to the present invention is capable of inhibiting interaction between IL-11 and IL-11Rα to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα in the absence of the antibody/fragment (or in the presence of an appropriate control antibody/fragment). In some embodiments, the antibody/fragment according to the present invention is capable of inhibiting interaction between IL-11 and IL-11Rα to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα in the absence of the antibody/fragment (or in the presence of an appropriate control antibody/fragment).

In some embodiments, the antibody/fragment according to the present invention is capable of inhibiting interaction between IL-11 and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and gp130 in the absence of the antibody/fragment (or in the presence of an appropriate control antibody/fragment). In some embodiments, the antibody/fragment according to the present invention is capable of inhibiting interaction between IL-11 and gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and gp130 in the absence of the antibody/fragment (or in the presence of an appropriate control antibody/fragment).

In some embodiments, the antibody/fragment according to the present invention is capable of inhibiting interaction between IL-11 and IL-11Rα:gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα:gp130 in the absence of the antibody/fragment (or in the presence of an appropriate control antibody/fragment). In some embodiments, the antibody/fragment according to the present invention is capable of inhibiting interaction between IL-11 and IL-11Rα:gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα:gp130 in the absence of the antibody/fragment (or in the presence of an appropriate control antibody/fragment).

In some embodiments, the antibody/fragment according to the present invention is capable of inhibiting interaction between IL-11:IL-11Rα complex and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the antibody/fragment (or in the presence of an appropriate control antibody/fragment). In some embodiments, the antibody/fragment is capable of inhibiting interaction between IL-11:IL-11Rα complex and gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11:IL-11Rα complex and gp130 in the absence of the antibody/fragment.

Inhibition of IL-11 mediated signalling can also be analysed using $^3$H-thymidine incorporation and/or Ba/F3 cell proliferation assays such as those described in e.g. Curtis et al. Blood, 1997, 90(11) and Karpovich et al. Mol. Hum. Reprod. 2003 9(2): 75-80. Ba/F3 cells co-express IL-11Rα and gp130.

As used herein, IL-11 mediated signalling and/or processes mediated by IL-11 includes signalling mediated by fragments of IL-11 and polypeptide complexes comprising IL-11 or fragments thereof. IL-11 mediated signalling may be signalling mediated by human IL-11 and/or mouse IL-11. Signalling mediated by IL-11 may occur following binding of IL-11 or an IL-11 containing complex to a receptor to which IL-11 or said complex binds.

In some embodiments, antibodies and fragments according to the present invention are capable of inhibiting the biological activity of IL-11 or an IL-11-containing complex. In some embodiments, the antibody/fragment binds to IL-11 or the IL-11-containing complex in a region which is important for binding to a receptor for the IL-11 or IL-11-containing complex, e.g. gp130 or IL-11Rα, and thereby disrupts binding to and/or signalling through the receptor.

In some embodiments, the antibody/fragment according to the present invention is an antagonist of one or more signalling pathways which are activated by signal transduction through receptors comprising IL-11Rα and/or gp130, e.g. IL-11Rα:gp130. In some embodiments, the antibody/fragment is capable of inhibiting signalling through one or more immune receptor complexes comprising IL-11Rα and/or gp130, e.g. IL-11Rα:gp130.

In some embodiments, the antibody/fragment according to the present invention is capable of inhibiting IL-11-mediated signalling to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the antibody/fragment (or in the presence of an appropriate control antibody/fragment). In some embodiments, the antibody/fragment is capable of reducing IL-11 mediated signalling to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the antibody/fragment (or in the presence of an appropriate control antibody/fragment).

In some embodiments, the IL-11 mediated signalling may be signalling mediated by binding of IL-11 to IL-11Rα:gp130 receptor. Such signalling can be analysed e.g. by treating cells expressing IL-11Rα and gp130 with IL-11, or by stimulating IL-11 production in cells which express IL-11Rα and gp130.

The $IC_{50}$ for antibody/fragment for inhibition of IL-11 mediated signalling may be determined, e.g. by culturing Ba/F3 cells expressing IL-11Rα and gp130 in the presence of human IL-11 and the IL-11 binding agent, and measuring $^3$H-thymidine incorporation into DNA.

In some embodiments, the antibody/fragment of the present invention may exhibit an $IC_{50}$ of 10 µg/ml or less, preferably one of ≤5 µg/ml, ≤4 µg/ml, ≤3.5 µg/ml, ≤3 µg/ml, ≤2 µg/ml, ≤1 µg/ml, ≤0.9 µg/ml, ≤0.8 µg/ml, ≤0.7 µg/ml, ≤0.6 µg/ml, or ≤0.5 µg/ml in such an assay.

In some embodiments, the IL-11 mediated signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment, and IL-11. In some embodiments, the soluble IL-11Rα is a soluble (secreted) isoform of IL-11Rα, or is the liberated product of proteolytic cleavage of the extracellular domain of cell membrane bound IL-11Rα.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα (e.g. hyper IL-11 as described herein).

In some embodiments, the antibody/fragment according to the present invention is capable of inhibiting signalling mediated by binding of IL-11:IL-11Rα complex to gp130, and is also capable of inhibiting signalling mediated by binding of IL-11 to IL-11Rα:gp130 receptor.

In some embodiments, the antibody/fragment is capable of inhibiting fibroblast proliferation. Proliferation of fibroblasts can be determined by analysing cell division over a period of time. Cell division for a given population of fibroblasts can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells (e.g. proliferating fibroblasts) may also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antibody/fragment, the fibroblasts may be cardiac fibroblasts (e.g. atrial fibroblasts), skin fibroblasts, lung fibroblasts, kidney fibroblasts or liver fibroblasts.

In some embodiments, the antibody/fragment according to the present invention is capable of inhibiting fibroblast proliferation to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibroblast proliferation in the absence of the antibody/fragment (or in the presence of an appropriate control antibody/fragment). In some embodiments, the antibody/fragment is capable of reducing fibroblast proliferation to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibroblast proliferation in the absence of the antibody/fragment (or in the presence of an appropriate control antibody/fragment).

In some embodiments, the antibody/fragment according to the present invention is capable of inhibiting a pathological process mediated by IL-11, e.g. following stimulation with a profibrotic factor (e.g. TGFβ1). Pathological processes mediated by IL-11 include fibrosis, and can be evaluated either in vitro or in vivo.

In some embodiments, the antibody/fragment according to the present invention is capable of inhibiting fibrosis. Fibrosis may be of a particular tissue or several tissues, e.g. liver, lung, kidney, heart, blood vessel, eye, skin, pancreas, spleen, bowel (e.g. large or small intestine), brain, or bone marrow. Fibrosis may be measured by means well known to the skilled person, for example by analysing gene or protein expression of one or more myofibroblast markers and/or gene or protein expression of one or more markers of fibrosis in a given tissue or tissues.

Myofibroblast markers may include one or more of increased αSMA, vimentin, palladin, cofilin or desmin. Markers of fibrosis include increased level of collagen, fibronectin, periostin, IL-6, IL-11, αSMA, TIMP1 and MMP2, extracellular matrix components, number/proportion of myofibroblasts, and organ weight.

Inhibition of fibrosis can be measured in vitro or in vivo. For example, whether an antibody/fragment is capable of inhibiting fibrosis in a given tissue can be analysed in vitro by treating fibroblasts derived from that tissue with a profibrotic stimulus, and then analysing whether the antibody can reduce myofibroblast generation from the fibroblasts (or e.g. some other marker of fibrosis). Whether an antibody/fragment is capable of inhibiting fibrosis can be analysed in vivo, for example, by administering the antibody/fragment to a subject (e.g. a subject that has been exposed to a profibrotic stimulus), and analysing tissue(s) for one or more markers of fibrosis.

In some embodiments, the antibody/fragment according to the present invention is capable of inhibiting fibrosis to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibrosis in the absence of the antibody/fragment (or in the presence of an appropriate control antibody/fragment). In some embodiments, the antibody/fragment is capable of reducing fibrosis to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibrosis in the absence of the antibody/fragment (or in the presence of an appropriate control antibody/fragment).

In some embodiments, the antibody/fragment according to the present invention is capable of inhibiting myofibroblast generation from fibroblasts, e.g. following exposure of the fibroblasts to profibrotic factor. Myofibroblast generation from fibroblasts can be investigated by analysis for myofibroblast markers. A profibrotic factor according to the present disclosure may be e.g. TGFβ1, IL-11, IL-13, PDGF, ET-1, oncostatin M (OSM) or ANG2 (AngII).

In some embodiments, the antibody/fragment is capable of inhibiting gene or protein expression in fibroblasts, or fibroblast-derived cells (e.g. myofibroblasts), of one or more of collagen, fibronectin, periostin, IL-6, IL-11, αSMA, TIMP1, MMP2, e.g. following stimulation with a profibrotic factor. In some embodiments, the antibody/fragment is capable of inhibiting gene or protein expression in fibroblasts, or fibroblast-derived cells (e.g. myofibroblasts), of one or more extracellular matrix components, e.g. following stimulation with a profibrotic factor.

In the experimental examples herein, myofibroblast generation from fibroblasts is analysed by measuring αSMA protein expression levels using Operetta High-Content Imaging System following stimulation of the fibroblasts with TGFβ1.

In some embodiments, the antibody/fragment according to the present invention is capable of inhibiting myofibroblast generation from fibroblasts to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of myofibroblast generation from fibroblasts in the absence of the antibody/fragment (or in the presence of an appropriate control antibody/fragment). In some embodiments, the antibody/fragment is capable of reducing myofibroblast generation from fibroblasts to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of myofibroblast generation from fibroblasts in the absence of the antibody/fragment (or in the presence of an appropriate control antibody/fragment).

In some embodiments, the antibody/fragment according to the present invention is capable of inhibiting gene or protein expression in fibroblasts of one or more of collagen, fibronectin, periostin, IL-6, IL-11, αSMA, TIMP1, MMP2, e.g. following stimulation with a profibrotic factor (e.g. TGFβ1). In some embodiments, the antibody/fragment according to the present invention is capable of inhibiting gene or protein expression to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of gene or protein expression in the absence of the antibody/fragment (or in the presence of an appropriate control antibody/fragment). In some embodiments, the antibody/fragment is capable of reducing gene or protein expression to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of gene or protein expression in the absence of the antibody/fragment (or in the presence of an appropriate control antibody/fragment).

In some embodiments, the antibody/fragment according to the present invention is capable of inhibiting extracellular matrix production by fibroblasts, e.g. following stimulation with a profibrotic factor (e.g. TGFβ1). Extracellular matrix production can be evaluated, for example, by measuring the level of an extracellular matrix component. Extracellular matrix components according to the present invention include e.g. proteoglycan, heparan sulphate, chondroitin sulphate, keratan sulphate, hyaluronic acid, collagen, periostin, fibronectin, vitronectin, elastin, fibronectin, laminin, nidogen, gelatin and aggrecan.

In some embodiments, the antibody/fragment according to the present invention is capable of inhibiting extracellular matrix production by fibroblasts to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of extracellular matrix production by fibroblasts in the absence of the antibody/fragment (or in the presence of an appropriate control antibody/fragment). In some embodiments, the antibody/fragment is capable of reducing extracellular matrix production by fibroblasts to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of extracellular matrix production in the absence of the antibody/fragment (or in the presence of an appropriate control antibody/fragment).

In some embodiments, the antibody/fragment according to the present invention is capable of inhibiting proliferation and/or survival of cells of a cancer. The skilled person is able to determine whether an antibody/fragment is capable of inhibiting proliferation and/or survival of cells of a cancer for example by analysing the effect of the antibody/fragment on cells of the cancer. For example, proliferation of cells can be measured as described herein, e.g. by $^3$H thymidine incorporation or CFSE dilution assays. Cell survival can be analysed by measuring cells for markers of cell viability/cell death following treatment with the antibody/fragment.

In some embodiments, the antibody/fragment according to the present invention is capable of inhibiting proliferation and/or survival of cells of a cancer to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of proliferation and/or survival of cells of a cancer in the absence of the antibody/fragment (or in the presence of an appropriate control antibody/fragment). In some embodiments, the antibody/fragment is capable of reducing proliferation and/or survival of cells of a cancer to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of proliferation and/or survival of cells of a cancer in the absence of the antibody/fragment (or in the presence of an appropriate control antibody/fragment).

In some embodiments, the antibody/fragment according to the present invention is capable of inhibiting tumour growth to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of tumour growth in the absence of the antibody/fragment (or in the presence of an appropriate control antibody/fragment). In some embodiments, the antibody/fragment is capable of reducing tumour growth to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of tumour growth in the absence of the antibody/fragment (or in the presence of an appropriate control antibody/fragment).

In some embodiments, the antibody/fragment according to the present invention has one or more improved properties as compared to a prior art anti-IL-11 antibody/fragment. In some embodiments the prior art anti-IL-11 antibody/antigen binding fragment may be, or may comprise the CDRs and/or VL and VH sequences of, monoclonal mouse anti-human IL-11 antibody clone #22626; Catalog No. MAB218 (R&D Systems, MN, USA).

In some embodiments, the antibody/fragment of the present invention displays one or more of the following properties as compared to a prior art antibody/antigen binding fragment (e.g. monoclonal mouse antibody clone #22626; Catalog No. MAB218):

(i) binds to IL-11 with greater specificity relative to one or more of IL-6, LIF, OSM, CT-1, CNTF, and CLC (i.e. reduced cross-reactivity for proteins of the IL-6 cytokine family other than IL-11);

(ii) binds to IL-11 (e.g. human IL-11) with greater affinity (e.g. has lower EC50 as determined by ELISA);

(iii) inhibits interaction between IL-11 and IL-11Rα to a greater extent;

(iv) inhibits interaction between IL-11 and gp130 to a greater extent;
(v) inhibits interaction between IL-11 and IL-11Rα:gp130 receptor complex to a greater extent;
(vi) inhibits interaction between IL-11:IL-11Rα complex and gp130 to a greater extent;
(vii) inhibits signalling mediated by IL-11 to a greater extent;
(viii) inhibits signalling mediated by binding of IL-11 to IL-11Rα:gp130 receptor complex to a greater extent;
(ix) inhibits signalling mediated by binding of IL-11:IL-11Rα complex to gp130 (i.e. IL-11 trans signalling) to a greater extent;
(x) inhibits fibroblast proliferation to a greater extent;
(xi) inhibits myofibroblast generation from fibroblasts to a greater extent;
(xii) inhibits a pathological process mediated by IL-11 to a greater extent;
(xiii) inhibits fibrosis to a greater extent;
(xiv) inhibits gene or protein expression in fibroblasts of one or more of collagen, fibronectin, periostin, IL-6, IL-11, αSMA, TIMP1, MMP2, e.g. following stimulation with a profibrotic factor to a greater extent;
(xv) inhibits extracellular matrix production by fibroblasts to a greater extent;
(xvi) inhibits proliferation and/or survival of cells of a cancer to a greater extent; or
(xvii) inhibits tumour growth to a greater extent.

In some embodiments, "greater specificity" or "greater affinity" or "inhibition to a greater extent" herein is, respectively, a level of specificity, affinity or inhibition which is greater than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥2.1 times, ≥2.2 times, ≥2.3 times, ≥2.4 times, ≥2.5 times, ≥2.6 times, ≥2.7 times, ≥2.8 times, ≥2.9 times, ≥3 times, ≥3.5 times, ≥4 times, ≥4.5 times, ≥5 times, ≥6 times, ≥7 times, ≥8 times, ≥9 times, ≥10 times, ≥15 times, ≥20 times, ≥25 times, ≥30 times, ≥35 times, ≥40 times, ≥45 times, ≥50 times, ≥60 times, ≥70 times, ≥80 times, ≥90 times, ≥100 times, ≥200 times, ≥300 times, ≥400 times, ≥500 times, ≥600 times, ≥700 times, ≥800 times, ≥900 times, ≥1000 times the specificity or affinity or level of inhibition displayed by the prior art antibody/antigen binding fragment in a comparable assay.

Therapeutic Applications

Antibodies and antigen binding fragments according to the present invention and compositions comprising such agents may be provided for use in methods of medical treatment or prevent of a disease/disorder, or alleviation of the symptoms of a disease/disorder. The antibodies/fragments of the present invention may be administered to subjects having a disease/condition in need of treatment, and/or to subjects at risk of such developing or contracting the disease/disorder.

Treatment, prevention or alleviation of fibrosis according to the present invention may be of fibrosis that is associated with an upregulation of IL-11 and/or IL-11Rα, e.g. an upregulation of IL-11 and/or IL-11Rα in cells or tissue in which the disease/disorder occurs or may occur, or upregulation of extracellular IL-11 or IL-11Rα. In some embodiments, IL-11 or IL-11R expression is locally or systemically upregulated in the subject.

Treatment or alleviation of a disease/disorder may be effective to prevent progression of the disease/disorder, e.g. to prevent worsening of the condition or to slow the rate of development. In some embodiments treatment or alleviation may lead to an improvement in the disease/disorder, e.g. a reduction in the symptoms of the disease/disorder or reduction in some other correlate of the severity/activity of the disease/disorder.

Prevention of a disease/disorder may refer to prevention of a worsening of the condition or prevention of the development of the disease/disorder, e.g. preventing an early stage disease/disorder developing to a later, chronic, stage.

The antibodies/fragments of the present invention are preferably able to bind to and inhibit the biological activity of IL-11 and IL-11-containing molecules/complexes (e.g. IL-11:IL-11Rα complex). Accordingly, the antibodies/fragments of the present invention find use in the treatment or prevention of diseases and disorders in which IL-11 is implicated in the pathology of the disease/disorder. That is, the antibodies/fragments of the present invention find use in the treatment or prevention of diseases and disorders associated with IL-11/IL-11R signalling.

In some embodiments, the disease/disorder may be associated with increased IL-11, IL-11Rα and/or gp130 gene or protein expression, e.g. as compared to the control (i.e. non-diseased) state. In some embodiments, the disease/disorder may be associated with an increased level of IL-11-mediated signalling as compared to the control state. In some embodiments, the disease/disorder may be associated with an increased level of signalling through ERK and/or STAT3 pathways as compared to the control state. In some embodiments, the increased expression/activity of IL-11, IL-11Rα and/or gp130, and/or the increased level of IL-11-mediated signalling, may be observed in effector cells of the disease/disorder (e.g. for a cancer, the cancerous cells). In some embodiments, the increased expression/activity of IL-11, IL-11Rα and/or gp130, and/or the increased level of IL-11-mediated signalling, may be observed in cells other than the effector cells.

Signalling through ERK can be measured e.g. using an assay for ERK phosphorylation such as an assay described in Assay Guidance Manual: Phospho-ERK Assays, Kim E. Garbison, Beverly A. Heinz, Mary E. Lajiness, Jeffrey R. Weidner, and G. Sitta Sittampalam, Eli Lilly & Company, Sittampalam G S, Coussens N P, Nelson H, et al., editors Bethesda (Md.): Eli Lilly & Company and the National Center for Advancing Translational Sciences; 2004. Signalling through STAT3 can be measured e.g. using an assay for phosphorylation of STAT3, such as the Phospho-STAT3 (Tyr705) Cellular Assay Kit (Cisbio Assays).

In some embodiments, the treatment is of a disease/disorder for which a reduction in IL-11 mediated signalling is therapeutic. In some embodiments, the treatment is of a disease/disorder associated with excess ERK and/or STAT3 signalling. In some embodiments, the treatment is of a disease/disorder associated with excess proliferation or hyperactivation of fibroblasts, or associated with an excess of myofibroblasts.

In some embodiments, the treatment may be aimed at preventing or treating a disease/disorder by decreasing the number or proportion of myofibroblasts or αSMA-positive fibroblasts.

In some embodiments, the disease/disorder may be fibrosis, a fibrotic condition, or a disease/disorder characterised by fibrosis. As used herein, "fibrosis" refers to the formation of excess fibrous connective tissue as a result of the excess deposition of extracellular matrix components, for example collagen. Fibrous connective tissue is characterised by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location in the absence of fibrosis, e.g. under normal, non-pathological conditions. As used herein, "excess deposition of extracellular matrix components" refers to a level of deposition of one or more extracellular matrix components which is greater than the level of deposition in the absence of fibrosis, e.g. under normal, non-pathological conditions.

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety. The main cellular effectors of fibrosis are myofibroblasts, which produce a collagen-rich extracellular matrix.

In response to tissue injury, damaged cells and leukocytes produce pro-fibrotic factors such as TGFβ, IL-13 and PDGF, which activate fibroblasts to αSMA-expressing myofibroblasts, and recruit myofibroblasts to the site of injury. Myofibroblasts produce a large amount of extracellular matrix, and are important mediators in aiding contracture and closure of the wound. However, under conditions of persistent infection or during chronic inflammation there can be overactivation and recruitment of myofibroblasts, and thus over-production of extracellular matrix components, resulting in the formation of excess fibrous connective tissue.

In some embodiments fibrosis may be triggered by pathological conditions, e.g. conditions, infections or disease states that lead to production of pro-fibrotic factors such as TGFβ1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (Daba et al., Saudi Med J 2004 June; 25(6): 700-6). Environmental injury/stimuli may include exposure to asbestos fibres or silica.

Fibrosis can occur in many tissues of the body. For example, fibrosis can occur in the lung, liver (e.g. cirrhosis), kidney, heart, blood vessels, eye, skin, pancreas, spleen, bowel (e.g. large or small intestine), brain, and bone marrow. Fibrosis may also occur in multiple organs at once.

In embodiments herein, fibrosis may involve an organ of the gastrointestinal system, e.g. of the liver, small intestine, large intestine, or pancreas. In some embodiments, fibrosis may involve an organ of the respiratory system, e.g. the lungs. In embodiments, fibrosis may involve an organ of the cardiovascular system, e.g. of the heart or blood vessels. In some embodiments, fibrosis may involve the skin. In some embodiments, fibrosis may involve an organ of the nervous system, e.g. the brain. In some embodiments, fibrosis may involve an organ of the urinary system, e.g. the kidneys. In some embodiments, fibrosis may involve an organ of the musculoskeletal system, e.g. muscle tissue.

In some preferred embodiments, the fibrosis is cardiac or myocardial fibrosis, hepatic fibrosis, or renal fibrosis. In some embodiments cardiac or myocardial fibrosis is associated with dysfunction of the musculature or electrical properties of the heart, or thickening of the walls or valves of the heart. In some embodiments fibrosis is of the atrium and/or ventricles of the heart. Treatment or prevention of atrial or ventricular fibrosis may help reduce risk or onset of atrial fibrillation, ventricular fibrillation, or myocardial infarction.

In some preferred embodiments hepatic fibrosis is associated with chronic liver disease or liver cirrhosis. In some preferred embodiments renal fibrosis is associated with chronic kidney disease.

Diseases/disorders characterised by fibrosis in accordance with the present invention include but are not limited to: respiratory conditions such as pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, ADS associated pulmonary hypertension, sarcoidosis, tumor stroma in lung disease, and asthma; chronic liver disease, primary biliary cirrhosis (PBC), schistosomal liver disease, liver cirrhosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Chron's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus); progressive systemic sclerosis (PSS); chronic graft versus host disease; diseases/disorders of the eye and associated processes, such as Grave's ophthalmopathy, epiretinal fibrosis (e.g. diabetic retinopathy (DR)), glaucoma, subretinal fibrosis (e.g. associated with macular degeneration (e.g. wet age-related macular degeneration (AMD))), macular edema, drusen formation, post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

It will be appreciated that many of the diseases/conditions listed above are interrelated. For example, fibrosis of the ventricle may occur post myocardial infarction, and is associated with DCM, HCM and myocarditis.

In particular embodiments, the disease/disorder may be one of pulmonary fibrosis, atrial fibrillation, ventricular fibrillation, hypertrophic cardiomyopathy (HCM), dilated cardiomyopathy (DCM), non-alcoholic steatohepatitis (NASH), cirrhosis, chronic kidney disease, scleroderma, systemic sclerosis, keloid, cystic fibrosis, Chron's disease, post-surgical fibrosis or retinal fibrosis, e.g. associated with wet age-related macular degeneration (AMD).

Fibrosis can lead directly or indirectly to, and/or increase susceptibility to development of, diseases/disorders. For example, more than 80% of hepatocellular carcinomas (HCCs) develop in fibrotic or cirrhotic livers (Affo et al. 2016, Annu Rev Pathol.), suggesting an important role for liver fibrosis in the premalignant environment (PME) of the liver.

Accordingly, the antibodies/fragments of the present invention find use in methods for the treatment and prevention of diseases/disorders associated with fibrosis, and/or for which fibrosis is a risk factor. In some embodiments, the disease/disorder associated with fibrosis, or for which fibrosis is a risk factor, is a cancer, e.g. cancer of the liver (e.g. hepatocellular carcinoma).

IL-11 is also implicated in the pathology of other diseases/disorders, and the antibodies and fragments of the present invention accordingly find use in methods to treat, prevent and/or alleviate the symptoms of these diseases/disorders also.

IL-11 has been implicated in the development and progression of various cancers. Studies suggest that IL-11 is important for promoting chronic gastric inflammation and associated gastric, colonic, hepatocellular and breast cancer tumorogenesis through excessive activation of STAT3 (Ernst M, et al. J Clin Invest. (2008); 118:1727-1738), that IL-11 may promote tumorigenesis by triggering the JAK-STAT intracellular signalling pathway, and may also promote metastasis via signalling through the PI3K-AKT-mTORC1 pathway (Xu et al., Cancer Letters (2016) 373(2): 156-163). Through STAT3, IL-11 promotes survival, proliferation, invasion angiogenesis and metastasis, the IL-11/GP130/JAK/STAT3 signalling axis may be rate-limiting for the progression of gastrointestinal tumors, and elevated IL-11 expression is associated with poor prognosis of breast cancer patients (Johnstone et al., Cytokine & Growth Reviews (2015) 26(5): 489-498). IL-11 has also been shown to influence breast cancer stem cell dynamics and tumor heterogeneity (Johnstone et al., Cytokine & Growth Reviews (2015) 26(5); 489-498). Recently, IL-11 signalling has been implicated in chemoresistance of lung adenocarcinoma; cancer associated fibroblasts were found to upregulate IL-11, and confer chemoresistance to lung cancer coils through activation of the IL-11/IL-11R/STAT3 anti-apoptotic signalling pathway (Tao et al. 2016, Sci Rep. 6; 6:38408). IL-11 signalling may promote the fibroblast-to-myofibroblast transition and extracellular matrix production by fibroblasts in the premalignant environment (PME) and tumour micro-environment (TME).

In some embodiments, the antibodies/fragments of the present invention are provided for use in methods to treat/prevent a cancer. In some embodiments, the cancer may be a cancer which leads directly or indirectly to inflammation and/or fibrosis.

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue.

In some embodiments, the antibodies/fragments of the present invention are provided for use in methods to treat/prevent a cancer, e.g. an epithelial cell cancer, breast cancer, gastrointestinal cancer (e.g. esophageal cancer, stomach cancer, pancreatic cancer, liver cancer (e.g. HOC), gallbladder cancer, colorectal cancer, anal cancer, gastrointestinal carcinoid tumor), and lung cancer (e.g. non-small cell lung cancer (NSCLC) or small cell lung cancer (SCLC))). In some embodiments, the cancer is a cancer for which acute and/or chronic inflammation is a risk factor. In some embodiments, the cancer is a cancer for which a disease/disorder characterised by fibrosis (e.g. as described herein) is a risk factor.

In some embodiments, the cancer may be associated with increased IL-11, IL-11Rα and/or gp130 gene or protein expression. For example, cells of the cancer may have increased expression of IL-11, IL-11Rα and/or gp130 as compared to comparable, non-cancerous cells, or may be associated with increased expression of IL-11, IL-11Rα and/or gp130 by other cells (e.g. non-cancerous cells) as compared to the level of expression by comparable cells in the absence of a cancer (e.g. in a healthy control subject). In some embodiments, cells of the cancer may be determined to have an increased level of signalling through ERK and/or STAT3 pathways as compared to comparable non-cancerous cells.

In some embodiments, the cancer may be associated with a mutation in IL-11, IL-11Rα and/or gp130. In some embodiments, such mutation may be associated with increased level of gene or protein expression, or may be associated with an increased level of IL-11/IL-11R signalling relative to the level of expression/signalling observed in the absence of the mutation.

IL-11 has also been implicated in diseases/disorders characterised by inflammation. Intra-articular injection of IL-11 has been shown to cause joint inflammation (Wong et al., Cytokine (2005) 29:72-76), and IL-11 has been shown to be proinflammatory at sites of IL-13-mediated tissue inflammation (Chen et al., J Immunol (2005) 174:2305-2313). IL-11 expression has also been observed to be significantly increased in chronic skin lesions in atopic dermatitis, and is known to be involved in bronchial inflammation (Toda et al., J Allergy Clin Immunol (2003) 111:875-881). IL-11-mediated signalling is implicated in inflammatory bowel disease (IBD) and asthma (Putoczki and Ernst, J Leuko Biol (2010) 88(6)1109-1117). IL-11 has also been identified as a risk factor for multiple sclerosis; IL-11 is elevated in the cerebrospinal fluid of patients with clinically isolated syndrome (CIS) as compared to control subjects, and serum levels of IL-11 are higher during relapses for patients with relapsing-remitting multiple sclerosis, and IL-11 may promote differentiation of CD4+ T cells to a $T_H17$ phenotype $T_H17$ cells are important cells in the pathogenesis of multiple sclerosis (Zhang et al., Oncotarget (2015) 6(32): 32297-32298).

In some embodiments, the antibodies/fragments of the present invention are provided for use in methods to treat/prevent a disease/disorder characterised by inflammation. In some embodiments, a disease or disorder characterised by inflammation may be a disease/disorder which leads directly or indirectly to a cancer and/or fibrosis. Diseases characterised by inflammation include e.g. allergic inflammation such as allergic asthma and bronchial inflammation, atopic dermatitis, allergic rhinitis and ocular allergic diseases, and autoimmune diseases such as multiple sclerosis, systemic lupus erythematosus, rheumatoid arthritis, chronic active hepatitis, type 1 diabetes mellitus, celiac disease, Grave's disease, uveitis, pemphigus, psoriasis, Crohn's disease, ulcerative colitis, inflammatory bowel disease, anaemia and autoimmune thyroiditis.

In some embodiments, the antibodies/fragments of the present invention are provided for use in methods to treat/prevent a disease/disorder associated with infection, in particular where infection leads directly or indirectly to fibrosis, cancer or inflammation. A disease associated with infection may be a disease which is caused or exacerbated by infection with the relevant infectious agent, or may be a disease for which infection with the relevant infectious agent is a risk factor.

An infection may be any infection or infectious disease, e.g. bacterial, viral, fungal, or parasitic infection. In particular embodiments, the disease/disorder may be associated with a viral infection. In some embodiments it may be particularly desirable to treat chronic/persistent infections, e.g. where such infections are associated with inflammation, cancer and/or fibrosis.

The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori* and *Mycobacterium tuberculosis* infection of the lung. Examples of viral infections include infection with EBV, HPV, HIV, hepatitis B or hepatitis C.

The treatment may involve ameliorating, treating, or preventing the disease/disorder by inhibiting the biological activity of IL-11 or an IL-11-containing complex. Such methods may include the administration of the antibodies/fragments/compositions according to the present invention to bind to and inhibit the biological activity of IL-11 or an IL-11-containing complex. Herein, inhibiting the biological activity of IL-11 or an IL-11-containing complex may be referred to as 'neutralising'.

Methods of treatment may optionally include the co-administration of biological adjuvants (e.g., interleukins, cytokines, Bacillus Comette-Guerin, monophosphoryl lipid A, etc.) in combination with conventional therapies for treating cancer such as treatment with an agent for treating cancer (e.g. chemotherapy), radiation, or surgery. Methods of medical treatment may also involve in vivo, ex vivo, and adoptive immunotherapies, including those using autologous and/or heterologous cells or immortalized cell lines.

The treatment may be aimed at prevention of a disease/disorder associated with overactive/elevated IL-11 mediated signalling. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of the disease or disorder.

Administration of an antibody, antigen binding fragment or polypeptide is preferably in a "therapeutically effective amount", this being sufficient to show benefit to the individual. The actual amount administered, and rate and time-course of administration, will depend on the nature and severity of the disease being treated.

Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Antibodies and antigen binding fragments according to the present invention may be formulated as pharmaceutical compositions or medicaments for clinical use and may comprise a pharmaceutically acceptable carrier, diluent, excipient or adjuvant.

The composition may be formulated for topical, parenteral, systemic, intracavitary, intravenous, intra-arterial, intramuscular, intrathecal, intraocular, intraconjunctival, intratumoral, subcutaneous, oral or transdermal routes of administration which may include injection or infusion. Suitable formulations may comprise the antibody/fragment in a sterile or isotonic medium. Medicaments and pharmaceutical compositions may be formulated in fluid, including gel, form. Fluid formulations may be formulated for administration by injection or via catheter to a selected region of the human or animal body.

In accordance with the present invention methods are also provided for the production of pharmaceutically useful compositions, such methods of production may comprise one or more steps selected from: isolating an antibody or antigen binding fragment as described herein; and/or mixing an isolated antibody or antigen binding fragment as described herein with a pharmaceutically acceptable carrier, adjuvant, excipient or diluent.

For example, a further aspect of the present invention relates to a method of formulating or producing a medicament or pharmaceutical composition for use in a method of medical treatment, the method comprising formulating a pharmaceutical composition or medicament by mixing an antibody or antigen binding fragment as described herein with a pharmaceutically acceptable carrier, adjuvant, excipient or diluent.

Methods of Detection

Antibodies, or antigen binding fragments, described herein may be used in methods that involve the binding of the antibody or antigen binding fragment to IL-11. Such methods may involve detection of the bound complex of antibody, or antigen binding fragment, and IL-11. As such, in one embodiment a method is provided, the method comprising contacting a sample containing, or suspected to contain, IL-11 with an antibody or antigen binding fragment as described herein and detecting the formation of a complex of antibody, or antigen binding fragment, and IL-11.

Suitable method formats are well known in the art, including immunoassays such as sandwich assays, e.g. ELISA. The method may involve labelling the antibody/antigen binding fragment or IL-11, or both, with a detectable label, e.g. fluorescent, luminescent or radio-label. IL-11 expression may be measured by immunohistochemistry (IHC), for example of a tissue sample obtained by biopsy. In some embodiments, the label may be selected from: a radio-nucleotide, positron-emitting radionuclide (e.g. for positron emission tomography (PET)), MRI contrast agent or fluorescent label.

Analysis in vitro or in vivo of processes mediated by IL-11 may involve analysis by positron emission tomography (PET), magnetic resonance imaging (MRI), or fluorescence imaging, e.g. by detection of appropriately labelled species.

Methods of this kind may provide the basis of a method of diagnosis of a disease or condition requiring detection and or quantitation of IL-11 or an IL-11-containing complex. Such methods may be performed in vitro on a subject sample, or following processing of a subject sample. Once the sample is collected, the subject is not required to be present for the in vitro method of diagnosis to be performed and therefore the method may be one which is not practised on the human or animal body.

Such methods may involve determining the amount of IL-11 or IL-11-containing complex present in a subject sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

The level of IL-11 or IL-11-containing complex present in a subject sample may be indicative that a subject may respond to treatment with an anti-IL-11 antibody/fragment, e.g. an anti-IL-11 antibody/fragment or composition according to the present invention. The presence of a high level of IL-11 or IL-11-containing complex in a sample may be used to select a subject for treatment with an anti-IL-11 antibody/fragment or composition described herein. The antibodies of the present invention may therefore be used to select a subject for treatment with anti-IL-11 therapy.

Detection in a sample of IL-11 or IL-11-containing complex may be used for the purpose of diagnosis of an infectious disease, autoimmune disorder or a cancerous condition in the subject, diagnosis of a predisposition to an infectious disease, autoimmune disorder or a cancerous condition or for providing a prognosis (prognosticating) of an infectious disease, autoimmune disorder or a cancerous condition. The diagnosis or prognosis may relate to an existing (previously diagnosed) infectious, inflammatory or autoimmune disease/disorder or cancerous condition.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/disorder (e.g. tissue or tissues in which symptoms of the disease manifest, or which are involved in the pathogenesis of the disease/disorder).

Methods according to the present invention may preferably be performed in vitro. The term "in vitro" is intended to encompass experiments with cells in culture whereas the term "in vivo" is intended to encompass experiments with and/or treatment of intact multi-cellular organisms.

Combination Therapies

Antibodies, antigen binding fragments and compositions according to the present invention may be administered alone or in combination with other treatments. Administration of such combination may be simultaneous or sequential, depending on the disease/disorder to be treated. The other treatment with which the antibody/fragment or composition is administered may be aimed at treating or preventing the disease/disorder. In some embodiments, the other treatment with which the antibody/fragment or composition is administered may be aimed at treating or preventing e.g. infection, inflammation and/or cancer.

Simultaneous administration refers to administration of the antibody, antigen binding fragment or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment or polypeptide or therapeutic agent followed after a given time interval by separate administration of the other agent. It is not required that the two agents are administered by the same route, although this is the case in some embodiments. The time interval may be any time interval.

In some embodiments, treatment with an antibody, antigen binding fragment or composition of the present invention may be accompanied by an agent for treating or preventing infection (e.g. an antibiotic, anti-viral, anti-fungal or anti-parasitic agent). In some embodiments, treatment with an antibody, antigen binding fragment or composition of the present invention may be accompanied by an agent for treating or preventing inflammation (e.g. a non-steroidal anti-inflammatory drug (NSAID). In some embodiments, treatment with an antibody, antigen binding fragment or composition of the present invention may be accompanied by radiotherapy (i.e. treatment with ionising radiation, e.g. X-rays or γ-rays) and/or an agent for treating or preventing cancer (e.g. a chemotherapeutic agent). In some embodiments, the antibody, antigen binding fragment or composition of the present invention may be administered as part of a combination treatment with an immunotherapy.

A treatment may involve administration of more than one drug. A drug may be administered alone or in combination with other treatments, either simultaneously or sequentially dependent upon the condition to be treated.

Routes of Administration

Antibodies, antigen binding fragments, medicaments and pharmaceutical compositions according to aspects of the present invention may be formulated for administration by a number of routes, including but not limited to, parenteral, intravenous, intra-arterial, intraocular, intraconjunctival, intramuscular, subcutaneous, intradermal, intratumoral injection or infusion, and oral administration. Antibodies, antigen binding fragments, polypeptides and other therapeutic agents, may be formulated in fluid or solid form. Fluid formulations may be formulated for administration by injection or infusion to a selected region of the human or animal body.

Kits

In some aspects of the present invention a kit of parts is provided. In some embodiments the kit may have at least one container having a predetermined quantity of the antibody, fragment, or composition. The kit may provide the antibody/fragment in the form of a medicament or pharmaceutical composition, and may be provided together with instructions for administration to a subject in order to treat a specified disease/disorder. The antibody, fragment or composition may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

In some embodiments the subject may be at risk of developing/contracting a disease or disorder.

Protein Expression

Molecular biology techniques suitable for producing the proteins (e.g. the antibodies/fragments) according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing polypeptides according to the invention. The cell may be a prokaryote or eukaryote. Suitable prokaryotic cells include *E. coli*. Examples of eukaryotic cells include a yeast cell, a plant cell, insect cell or a mammalian cell (e.g. Chinese Hamster Ovary (CHO) cells). In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides from cell culture known in the art may be used. In order to isolate a polypeptide of interest from a culture, it may be necessary to first separate the cultured cells from media containing the polypeptide of interest. If the polypeptide of interest is secreted from the cells, the cells may be separated from the culture media that contains the secreted polypeptide by centrifugation. If the polypeptide of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide of interest.

It may then be desirable to isolate the polypeptide of interest from the supernatant or culture medium, which may contain other protein and non-protein components. A common approach to separating polypeptide components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures, in which:

(FIG. 2A) PECAM1, (FIG. 2B) MYH6 (FIG. 2C) TNNT2, (FIG. 2D) COL1A2, and (FIG. 2E) ACTA2.

(FIG. 3A and FIG. 3B) Graphs showing fold change in gene expression in fibrosis; IL-11 is the most upregulated gene in response to TGFβ1 treatment. (FIG. 3C) IL-11 secretion by fibroblasts in response to stimulation with TGFβ1. (FIG. 3D) Comparison of IL-11 gene expression in tissues of healthy individuals and in atrial fibroblasts, with or without TGFβ1 stimulation. (FIG. 3E) Correspondence of fold change in IL-11 expression as determined by RNA-seq vs. qPCR.

(FIG. 4A) TGFβ1, ET-1, AngII, PDGF, OSM and IL-13 induce IL-11 secretion, and IL-11 also induces IL-11 expression in a positive feedback loop. (FIG. 4B) Graph showing that the ELISA only detects native IL-11 secreted from cells, and does not detect recombinant IL-11 used for the IL-11 stimulation condition. (FIG. 4C) and (FIG. 4D) Cells were stimulated with recombinant IL-11, IL-11 RNA was measured and the native IL-11 protein level was measured in the cell culture supernatant by ELISA at the indicated time points.

(FIG. 5A) myofibroblast generation and ECM production by primary atrial fibroblasts following stimulation with TGFβ1 or IL-11, as measured by fluorescence microscopy following staining for a α-SMA, collagen or periostin. (FIG. 5B) Collagen content of cell culture supernatant as determined by Sirius Red staining. Secretion of the fibrosis markers (FIG. 5C) IL-6, (FIG. 5D) TIMP1 and (FIG. 5E) MMP2 as measured by ELISA. (FIG. 5F) Activation of murine fibroblasts by stimulation with human or mouse recombinant IL-11. * $P<0.05$,  $P<0.01$, * $P<0.001$, **** $P<0.0001$ [Mean±SD, Dunnett].

(FIG. 6A) Mouse fibroblasts from different tissues of origin can be activated by IL-11 and display increased ECM production. [Mean±SD, Dunnett]. Injection of mice with recombinant IL-11 or AngII results in (FIG. 6B) an increase in organ weight [Mean±SEM], and (FIG. 6C) an increase in collagen content (as determined by HPA assay). * $P<0.05$,  $P<0.01$, * $P<0.001$, **** $P<0.0001$ [Mean±SD, Dunnett].

(FIG. 7A) myofibroblast generation and ECM production by primary atrial fibroblasts, with or without stimulation with TGFβ1, and in the presence/absence of neutralising anti-IL-11 antibody or isotype control IgG, as measured by fluorescence microscopy following staining for (FIG. 7A) α-SMA, (FIG. 7B) EdU or (FIG. 7C) Periostin. (FIGS. 7D to 7F) Secretion of the fibrosis markers (FIG. 7D) IL-6, (FIG. 7E) TIMP1, and (FIG. 7F) MMP2 was analysed by ELISA. Fluorescence was normalized to the control group without stimulation. [Mean±SD, Dunnett]* $P<0.05$,  $P<0.01$, * $P<0.001$ or **** $P<0.0001$.

(FIG. 10A) Percentage of myofibroblasts as determined by analysis αSMA content, (FIG. 10B) Percentage proliferating cells as determined by staining for EdU, (FIG. 10C) Collagen content and (FIG. 10D) ECM production as measured by detection of periostin [Mean±SD].

(FIG. 12A) Collagen content, as measured by hydroxyproline assay. (FIG. 12B) Collagen (Col1A2) expression. (FIG. 12C) αSMA (ACTA2) expression. (FIG. 12D) Fibronectin (Fn1) expression.

(FIG. 14A) Fold changes in gene expression in fibroblasts following stimulation with TGFβ1, IL-11 or TGFβ1 and IL-11. (FIG. 14B) Fold changes in gene expression in fibroblasts obtained from IL-11RA+/+ and IL-11RA−/− mice following stimulation with TGFβ1.

FIG. 15. Light chain variable domain sequences for human anti-IL-11 antibody clones. CDRs are underlined and shown separately.

FIG. 16. Heavy chain variable domain sequences for human anti-IL-11 antibody clones. CDRs are underlined and shown separately.

FIG. 17. Table showing light chain CDR sequences for human anti-IL-11 antibody clones.

FIG. 18. Table showing heavy chain CDR sequences for human anti-IL-11 antibody clones.

FIGS. 19A to 19C. Tables showing light chain CDR sequences for human anti-IL-11 antibody clones and consensus sequences, for (FIG. 19A) LC-CDR1, (FIG. 19B) LC-CDR2 and (FIG. 19C) LC-CDR3.

FIGS. 20A to 20C. Tables showing heavy chain CDR sequences for human anti-IL-11 antibody clones and consensus sequences, for (FIG. 20A) HC-CDR1, (FIG. 20B) HC-CDR2 and (FIG. 20C) HC-CDR3.

FIG. 21. Table summarising panning strategies used to identify human anti-human IL-11 antibodies capable of binding to both human IL-11 and mouse IL-11.

FIG. 23. Table summarising the 56 human anti-human IL-11 antibody clones.

(FIG. 24A) Bar chart showing fold change in proportion of αSMA-positive cells relative to unstimulated cells (=1). (FIG. 24B) Bar chart showing the percentage of αSMA-positive cells (activated fibroblasts).

FIG. 27. Table summarising the fold-change data of FIGS. 24 to 26 for the 56 human anti-IL-11 antibodies. Antibody candidates numbered 1 to 56 correspond to clone designations as indicated in FIG. 23. Industry standard is monoclonal mouse anti-IL-11 IgG2A; Clone #22626; Catalog No. MAB218; R&D Systems, MN, USA.

(FIG. 28A) ELISA for clones YU45-A3, YU45-A10, YU45-D11, YU45-E11, YU45-D12 and YU33-A2(IgG). (FIG. 28B) ELISA for clones YU45-G1, YU45-B2, YU45-A5, YU45-E3, YU45-F8 and YU33-H3(IgG). (FIG. 28C) ELISA for clones YU45-G8, YU45-F9, YU45-H10, YU45-F2, YU45-H3 and YU33-E3(IgG). (FIG. 28D) ELISA for clones YU45-A8, YU45-B5, YU45-D9, YU45-G7, YU45-B6 and YU45-F9. (FIG. 28E) ELISA for clones YU45-F5, YU46-B5, YU45-C1, YU46-A8, YU46-B6 and YU45-F9. (FIG. 28F) ELISA for clones YU46-E3, YU46-G8, YU46-D3, YU45-B6, YU45-C1 and YU45-F9.

FIG. 29. Table summarising $EC_{50}$ values determined for binding of human anti-IL-11 antibodies to IL-11 as determined by ELISA analysis.

FIGS. 36A and 36B. Table and bar chart showing binding of mouse-anti-IL-11 antibodies to human IL-11, as determined by iQue analysis (FIG. 36A) Table summarising the results of the experiments. (FIG. 36B) Bar chart showing strength of binding relative to the positive control anti-FLAG antibody (100%); numbers correspond to the clones as indicated in FIG. 35.

(FIG. 38A) Eye sections of IL-11RA+/+(WT) and IL-11 RA−/− (KO) animals 7 days after filtration surgery. (FIG. 38B) Maturation of collagen fibres as evaluated by picro-sirius red/polarization light technique (Szendröi et al. 1984, Acta Morphol Hung 32, 47-55); more fibrosis is observed in WT mice than KO mice.

(FIG. 42A) and (FIG. 42B) present the results of two different experiments.

FIG. 44. Light chain variable domain sequences for human anti-IL-11 antibody clones after light chain shuffling. CDRs are underlined and shown separately.

FIG. 45. Heavy chain variable domain sequences for human anti-IL-11 antibody clones after light chain shuffling. CDRs are underlined and shown separately.

FIG. 46. Table showing light chain CDR sequences for human anti-IL-11 antibody clones after light chain shuffling.

FIG. 47. Table showing heavy chain CDR sequences for human anti-IL-11 antibody clones after light chain shuffling.

FIGS. 48A to 48C. Tables showing light chain CDR sequences for human anti-IL-11 antibody clones after light chain shuffling, and consensus sequences, for (FIG. 48A) LC-CDR1, (FIG. 48B) LC-CDR2 and (FIG. 48C) LC-CDR3.

FIGS. 49A to 49C. Tables showing heavy chain CDR sequences for human anti-IL-11 antibody clones after light chain shuffling, and consensus sequences, for (FIG. 49A) HC-CDR1, (FIG. 49B) HC-CDR2 and (FIG. 49C) HC-CDR3.

FIG. 50. Single-chain variable antibody fragment (ScFv) amino acid sequences for human anti-IL-11 antibody clones after light chain shuffling.

FIG. 51. Nucleotide sequences encoding scFv for human anti-IL-11 antibody clones after light chain shuffling.

FIG. 52. Table summarising panning strategies used to identify human anti-human IL-11 antibodies capable of binding to both human IL-11 and mouse IL-11, after light chain shuffling.

FIGS. 54A and 54B. Bar chart (FIG. 54A) and Table (FIG. 54B) showing binding signal to human IL-11 and mouse IL-11 as determined by ELISA assay for the 64 unique light chain-shuffled human anti-IL-11 antibodies.

FIGS. 56A and 56B show the results of two separate experiments. Cells were cultured in the presence of TGFβ1 (5 ng/ml) for 24 hours, in the presence of the indicated light chain shuffled anti-IL-11 antibodies, or in the presence of human IgG1 isotype control. Basal MMP2 secretion by the cells in culture was measured by culture in the absence of TGFβ1, in the presence of human IgG1 isotype control. Horizontal lines show basal MMP2 secretion by cardiac atrial human fibroblasts cultured for 24 hours in the presence of human IgG1 isotype control antibody in the absence of TGFβ1 (NEG); and MMP2 secretion by cardiac atrial human fibroblasts cultured for 24 hours in the presence of 5 ng/ml TGFβ and the human IgG1 isotype control antibody (POS).

FIG. 57. Table summarising the results of FIGS. 55 and 56 relating to functional characterisation of the indicated light-chain shuffled anti-IL-11 antibody clones. N.D.=not determined.

(FIG. 58A) Images of Masson's Trichrome stained kidney sections. Fibrotic areas containing collagen appear darker as compared to healthy areas that appear lighter. (FIG. 58B) Graphs showing semi-quantitative analysis of collagen area expressed as a percentage (%) of the total kidney area (graph). ***, P<0.001 compared to FA+IgG, ANOVA.

(FIG. 61A) Mice were treated by sham operation or ureteric obstruction of one ureter. Mice received IgG, anti-IL-11 antibody (20 mg/kg on surgical days −1, 1, 3, 5) and injured kidneys (UUO IgG, IL-11) or contralateral (Con) uninjured kidneys (Con IgG, IL-11) were harvested on day 7 post surgery. (FIG. 61B) Semi-quantitative assessment of tubular injury was determined by histological analysis of casts, tubular atrophy or tubular expansion blinded to experimental conditions (Tubular injury score: 0, none; 1, minimal; 2, mild; 3, moderate; 4, severe). *, P<0.05 compared to UUO IgG, ANOVA.

(FIG. 65A) Bar chart showing quantification of the fibrosis areas in control (IgG) or anti-IL11 (IL11) treated mice. (FIG. 65B) representative images showing staining of fibrotic areas in control antibody treated eyes (IGG, top panel) or anti-IL11 treated eyes (IL11, bottom panel).

(FIG. 66A) Schematic representation of experimental procedures for different treatment groups. Groups 1 and 2 were treated with bleomycin (BLM), and either anti-IL-11 antibody (Group 1) or IgG control antibody (Group 2). Group 3 were injected with vehicle (PBS) only and do not develop fibrosis. (FIG. 66B) Images showing Masson's trichrome staining of skin section at equal distances from the injection site. Dermal thickness is indicated by the black bar. (FIG. 66C) Bar chart showing the results of analysis of dermal thickness (blinded for treatment groups). Average dermal thickness was determined from the bottom of epithelial layer to top of dermal white adipose tissue layer across 40 fields of view per sample. Each point indicates an animal. P value was calculated using an unpaired two-tailed t-test.

FIG. 68. Heavy chain variable domain sequences for mouse anti-IL-11 antibody clones. CDRs are underlined and shown separately.

FIG. 69. Light chain variable domain sequences for mouse anti-IL-11 antibody clones. CDRs are underlined and shown separately.

FIG. 70. Table showing heavy chain CDR sequences for mouse anti-IL-11 antibody clones.

FIG. 71. Table showing light chain CDR sequences for mouse anti-IL-11 antibody clones.

FIGS. 72A to 72C. Tables showing heavy chain CDR sequences for mouse anti-IL-11 antibody clones, and consensus sequences, for (FIG. 72A) HC-CDR1, (FIG. 72B) HC-CDR2 and (FIG. 72C) HC-CDR3.

FIGS. 73A to 73C. Tables showing light chain CDR sequences for mouse anti-IL-11 antibody clones, and consensus sequences, for (FIG. 73A) LC-CDR1, (FIG. 73B) LC-CDR2 and (FIG. 73C) LC-CDR3.

FIG. 74. Nucleotide sequences encoding mouse anti-IL-11 antibody clone heavy chains and light chains.

EXAMPLES

In the following Examples, the inventors identify a role for IL-11/IL-11R signalling in fibrosis in a variety of tissues, and described the generation of anti-human IL-11 antibodies, and in vitro and in vivo functional characterisation of the antibodies.

Example 1: A Role for IL-11 in Fibrosis 1.1 IL-11 is Upregulated in Fibrosis

Figure 1:
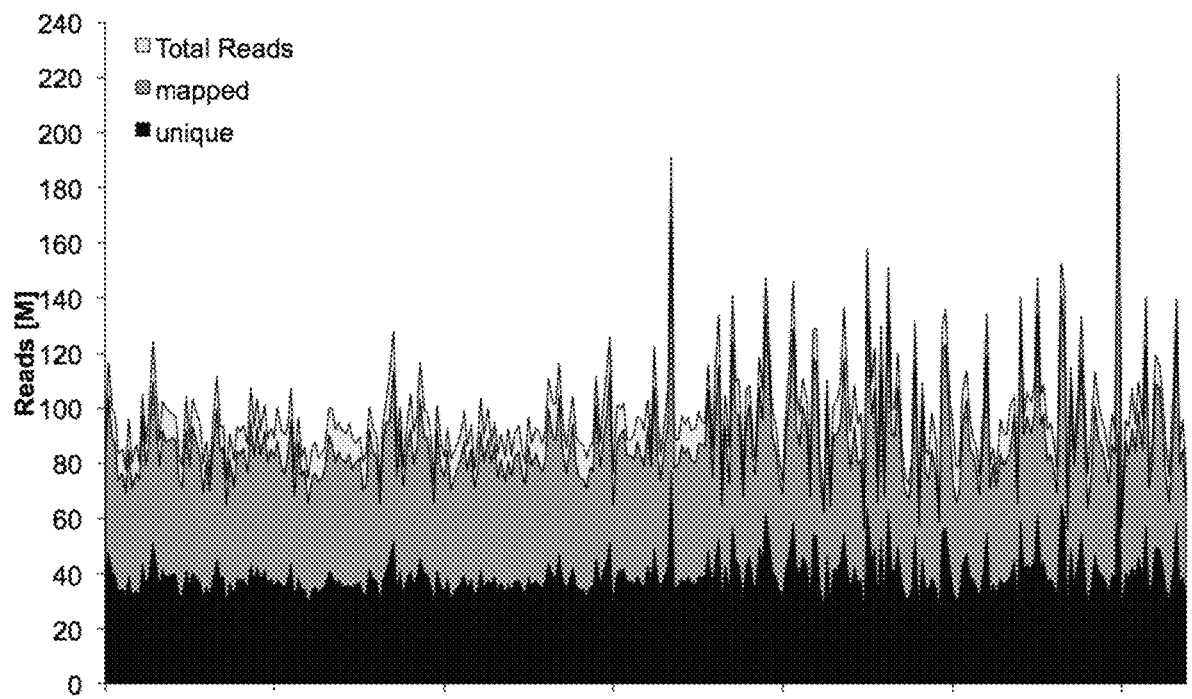
FIG. 1. Graph showing read depth for whole transcriptome sequencing of human atrial fibroblasts from 160 individuals with and without stimulation with TGFβ1.
Figure 2A:
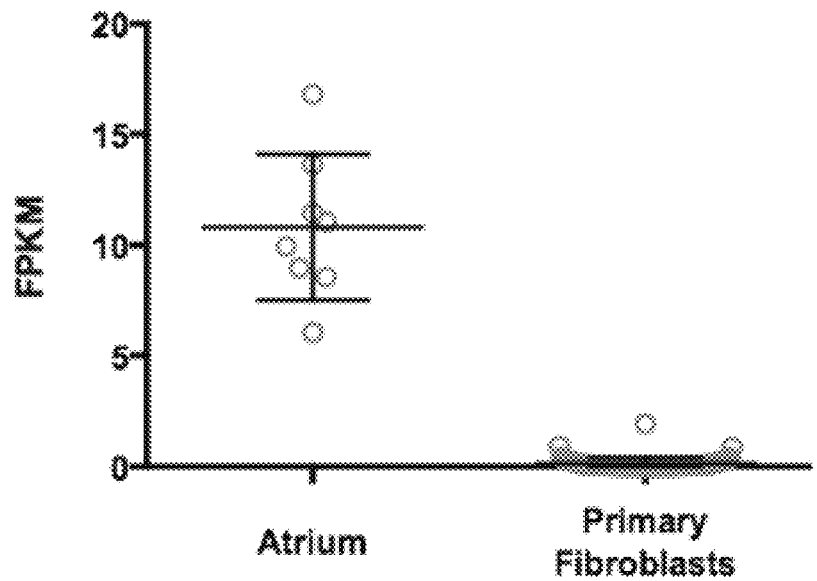
FIGS. 2A to 2E. Graphs showing expression of endothelial, cardiomyocyte and fibroblast marker genes as determined by RNA-seq of the tissue of origin (human atrial tissues samples, n=8) and primary, unstimulated fibroblast cultures.
Figure 2B:
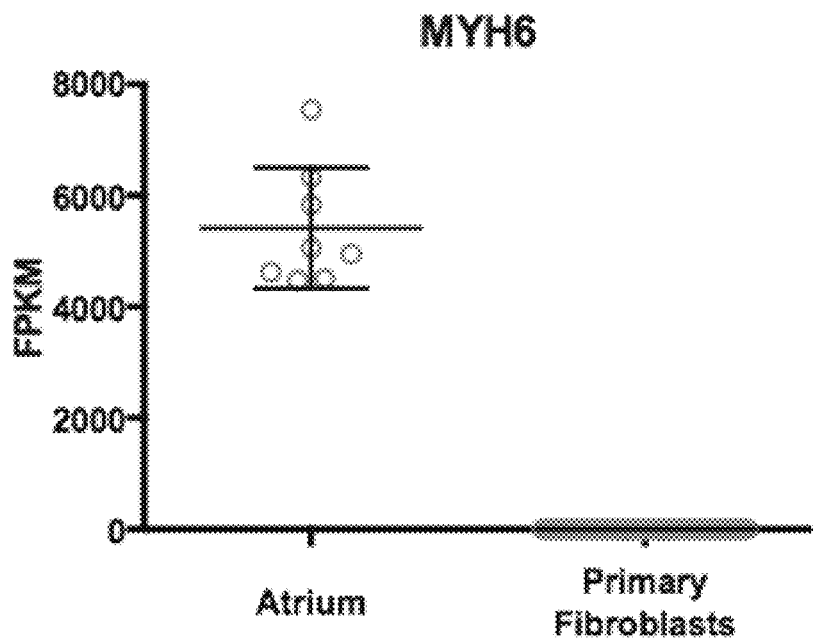
Figure 2C:
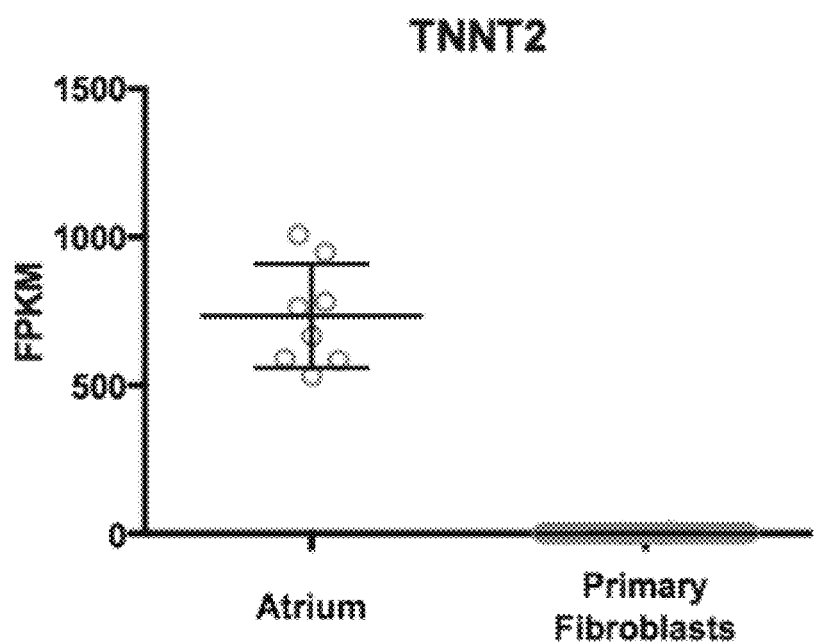
Figure 2D:
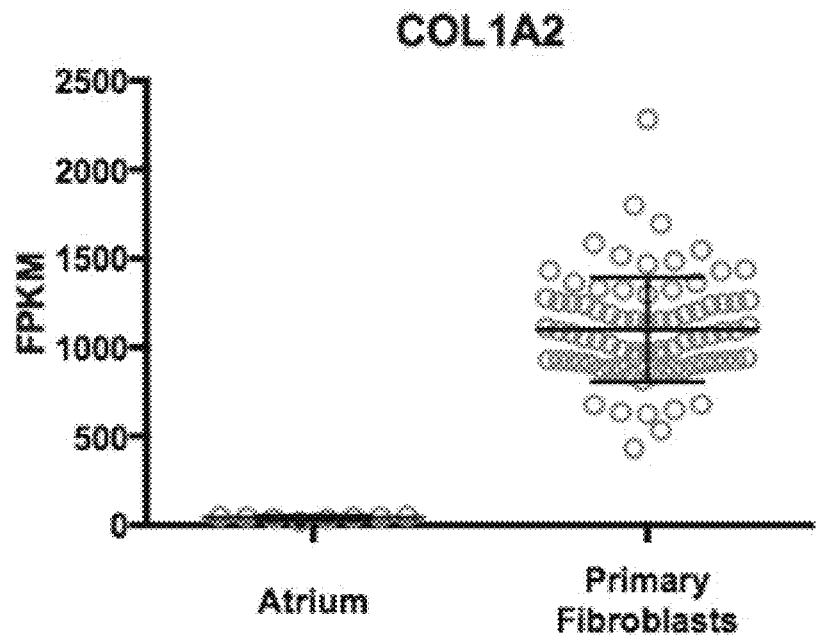
Figure 2E:
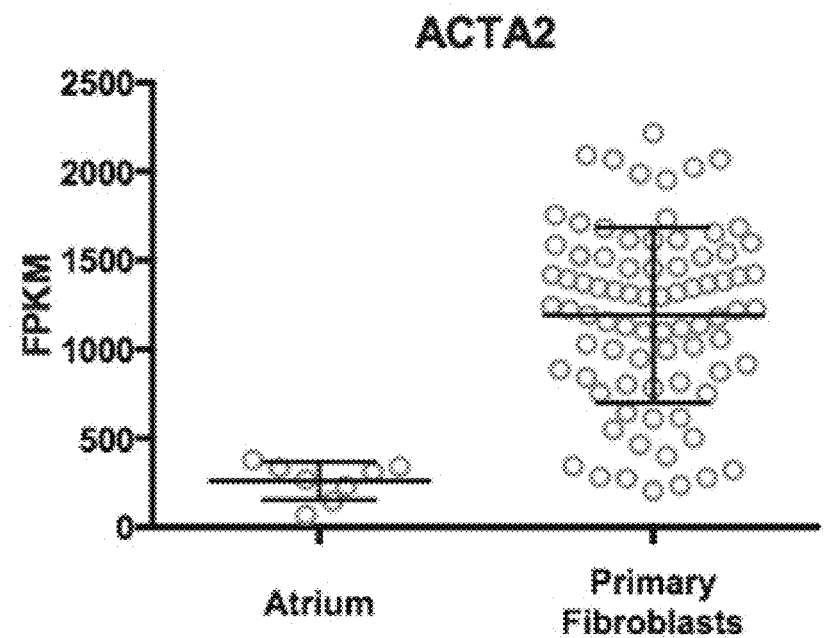

To understand the molecular processes underlying the transition of fibroblasts to activated myofibroblasts, atrial tissue was obtained from more than 200 patients that underwent cardiac bypass surgery at the National Heart Centre Singapore. Cells were cultured in vitro at low passage (passage<4), and either not stimulated or stimulated with TGFβ1 for 24 h. We subsequently performed high-throughput RNA sequencing (RNA-seq) analysis of unstimulated fibroblasts and cells stimulated with the prototypic profibrotic stimulus TGFβ1 across 160 individuals; average read depth was ~70M reads per sample (paired-end 100 bp; FIG. 1).

To ensure the purity of the atrial fibroblast cell cultures, we analysed expression of endothelial cell, cardiomyocyte and fibroblast cell type marker genes from the atrium (Hsu et al., 2012 Circulation Cardiovasc Genetics 5, 327-335) in the RNA-seq dataset.

The results are shown in FIGS. 2A to 2E, and confirm the purity of the atrial fibroblast cultures.

Gene expression was assessed by RNA-seq of the tissue of origin (human atrial tissues samples, n=8) and primary, unstimulated fibroblast cultures. No/very low expression of the endothelial cell marker PECAM1 (FIG. 2A), and the cardiomyocyte markers MYH6 (FIG. 2B) and TNNT2 (FIG. 2C) was detected in the fibroblast cell culture samples. Markers for fibroblasts COL1A2 (FIG. 2D) and ACTA2 (FIG. 2E) were highly expressed compared to the tissue of origin.

Next, the RNA-seq data was analysed to identify genes whose expression was increased or decreased upon stimulation with TGFβ1, and this information was integrated with the large RNA-seq dataset across 35+ human tissues provided by the GTEx project (The GTEx Consortium, 2015 Science 348, 648-660). This enabled the identification of gene expression signatures that were specific to the fibroblast-myofibroblast transition.

Figure 3A:
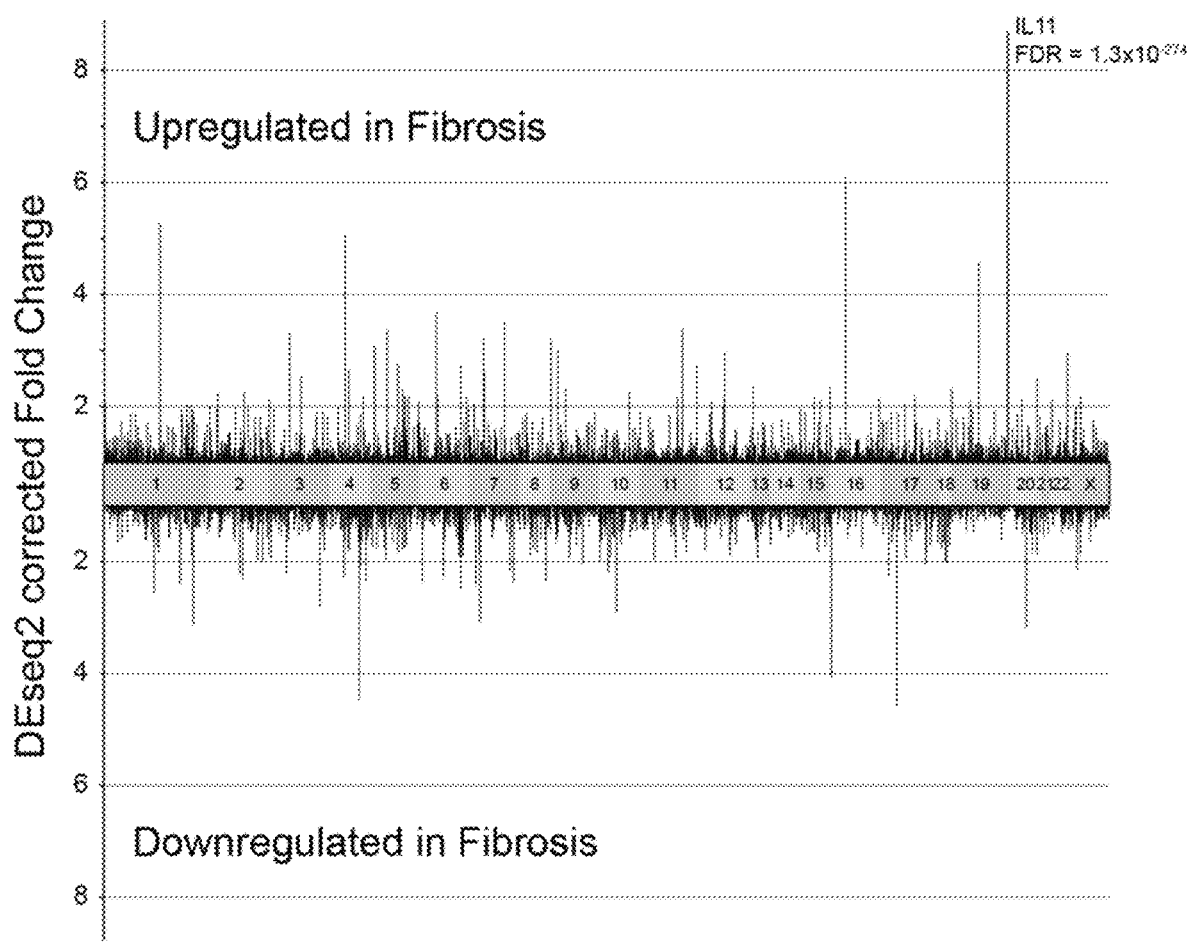
FIGS. 3A to 3E. Graphs showing upregulation of IL-11 expression in fibroblasts in response to stimulation with TGFβ1.
Figure 3B:
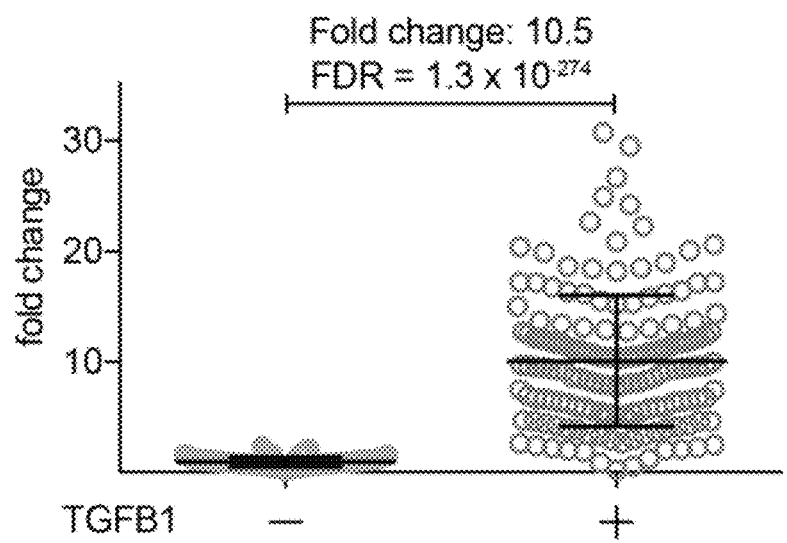

The results are shown in FIGS. 3A to 3E. Across the 10000+ genes expressed in the fibroblasts, IL-11 was the most strongly upregulated gene in response to stimulation with TGFβ1, and on average across the 160 individuals was upregulated more than 10-fold (FIG. 3B).

Figure 3C:
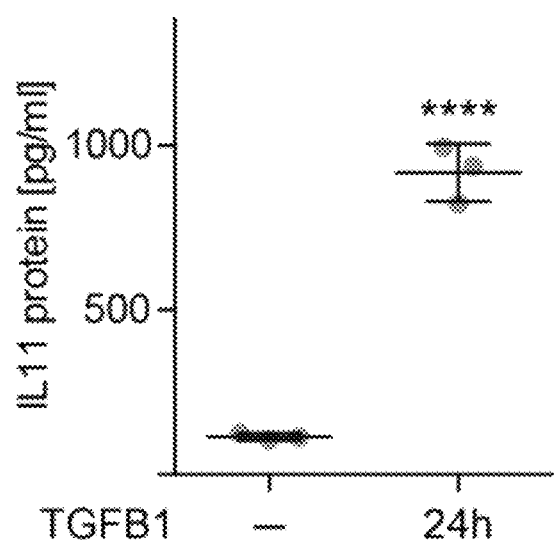
Figure 3D:
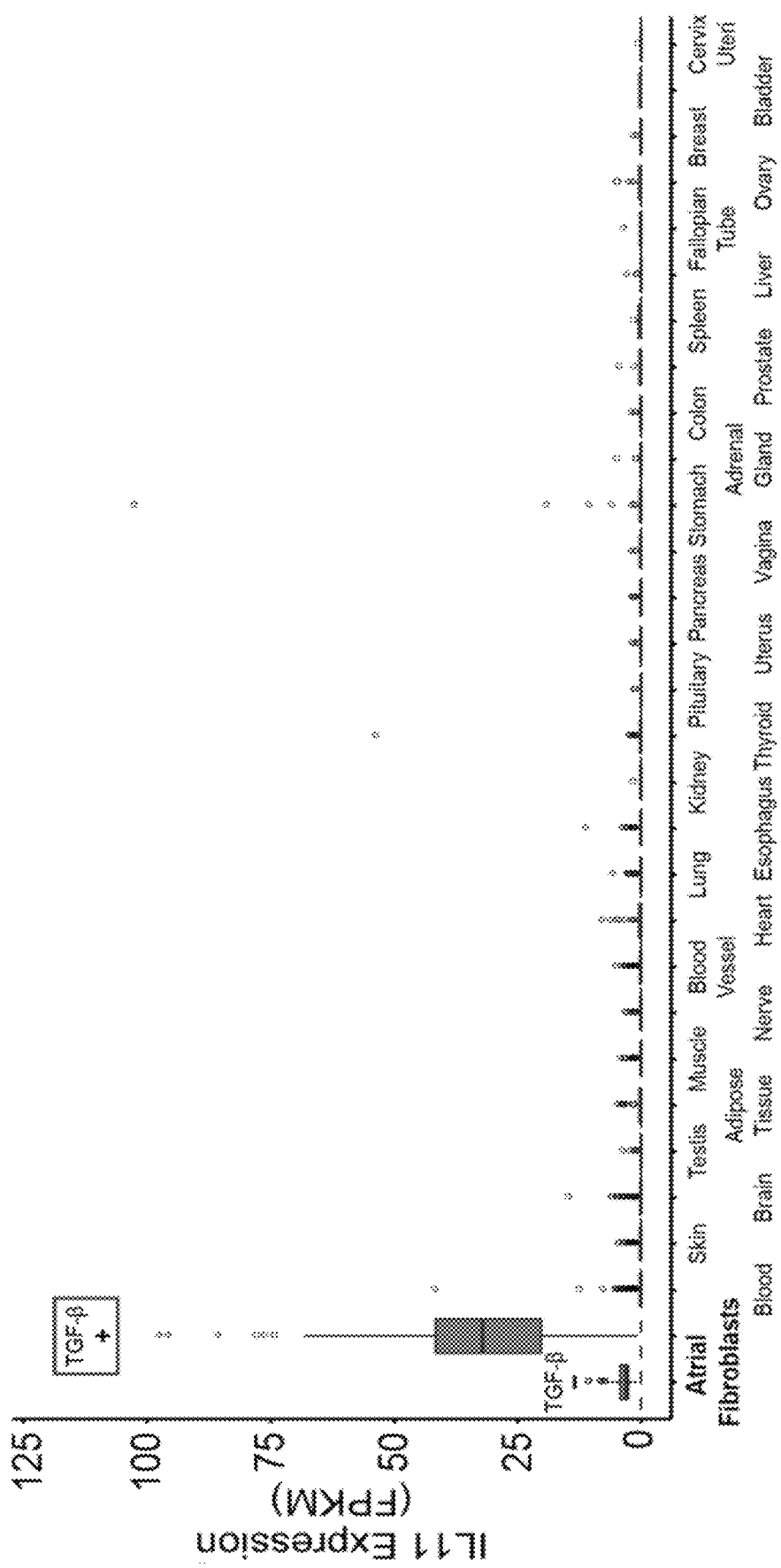
Figure 3E:
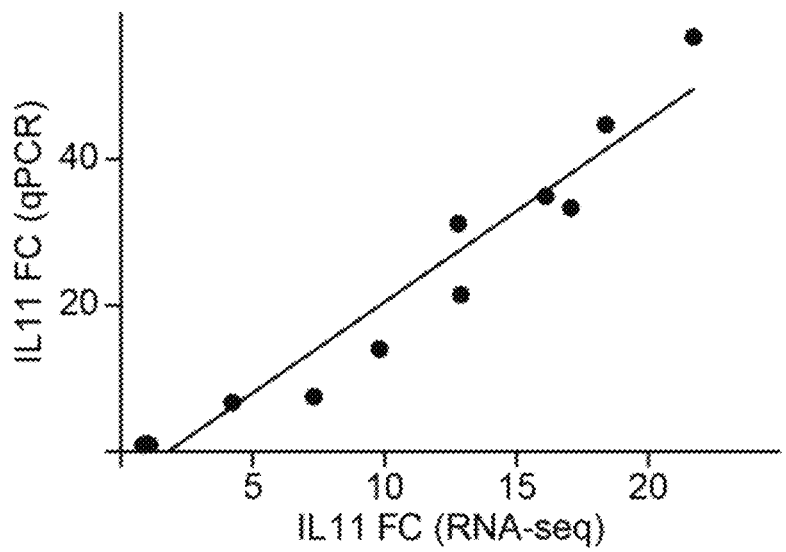

Upregulation of IL-11 expression was confirmed by ELISA analysis of the cell culture supernatant of TGFβ1 stimulated fibroblasts (FIG. 3C). As compared to the level of expression level of IL-11 in other tissues of healthy individuals, this response was observed to be highly specific to activated fibroblasts (FIG. 3D). Various fold changes of IL-11 RNA expression were also confirmed by qPCR analysis (FIG. 3E).

Next, fibroblasts were cultured in vitro and stimulated with several other known pro-fibrotic factors: ET-1, ANGII, PDGF, OSM and IL-13, and also with human recombinant IL-11. For analysing upregulation of IL-11 produced in response to stimulation with IL-11, it was confirmed that the ELISA was only able to detect native IL-11 secreted from cells and does not detect recombinant IL-11 used for the stimulations (FIG. 4B).

Figure 4A:
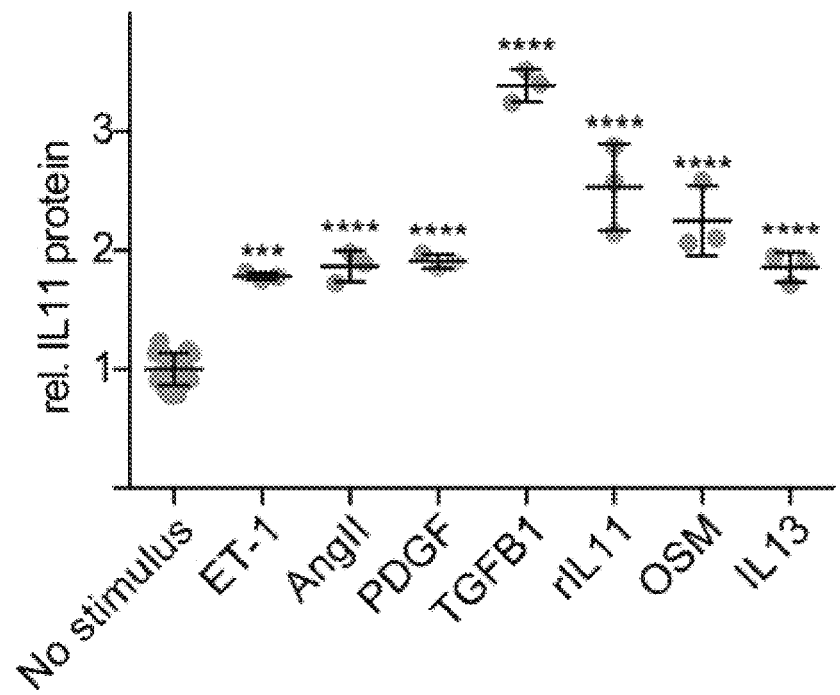
FIGS. 4A to 4D. Graphs showing induction of IL-11 secretion in primary fibroblasts by various profibrotic cytokines, as determined by ELISA.
Figure 4B:
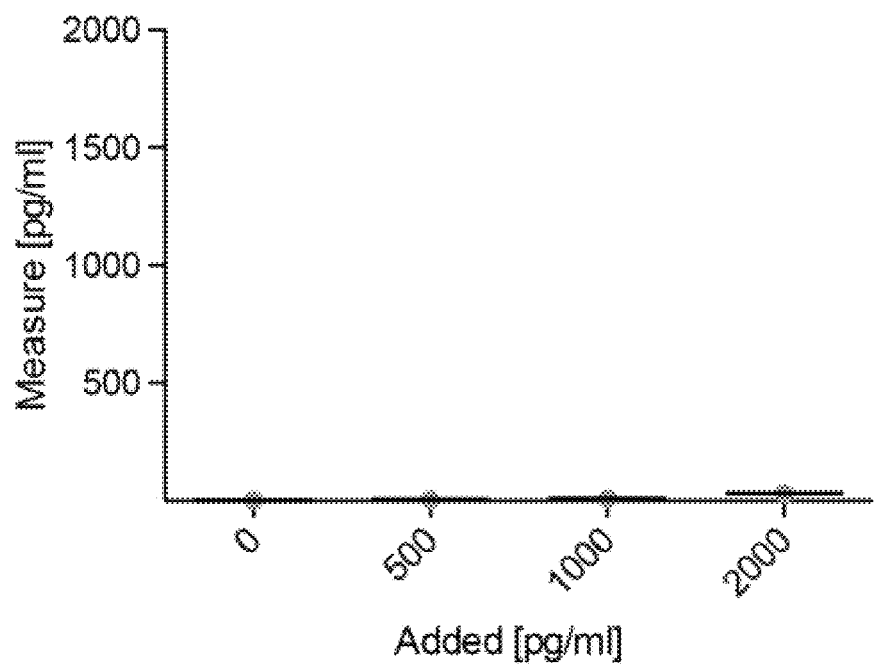
Figure 4C:
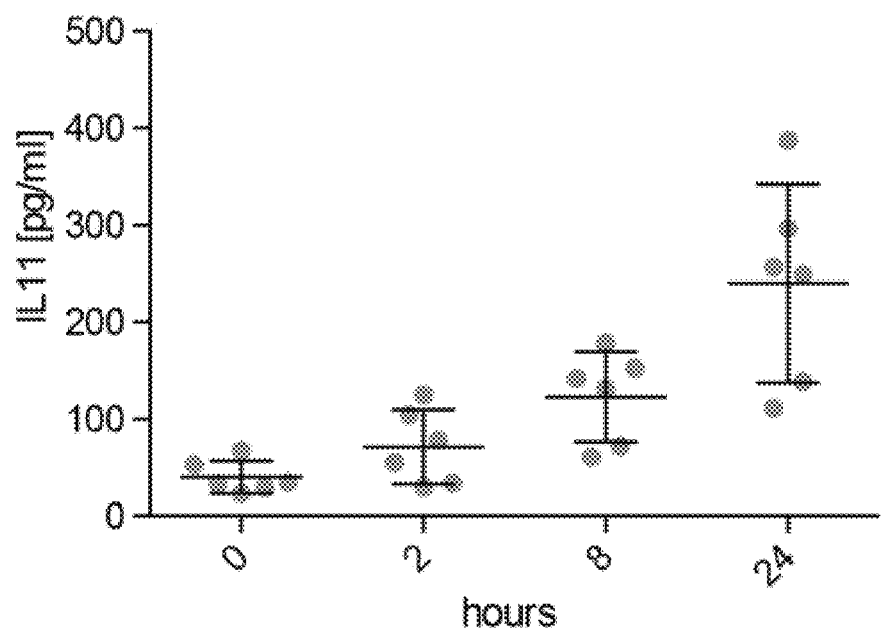

The results are shown in FIG. 4A. Each factor was found to significantly induce IL-11 secretion from fibroblasts. IL-11 is shown to act in an autocrine loop in fibroblasts, which can result in an upregulation of IL-11 protein as much as 100-fold after 72 hours (FIG. 4D).

Interestingly, this autocrine loop for IL-11 is similar to the autocrine production of IL-6. IL-6 is from the same cytokine family and also signals via the gp130 receptor (Garbers and Scheller, 2013 Biol Chem 394, 1145-1161), which is proposed to ensure the continued survival and growth of lung and breast cancer cells (Grivennikov and Karin, 2008 Cancer Cell 13, 7-9).

Figure 4D:
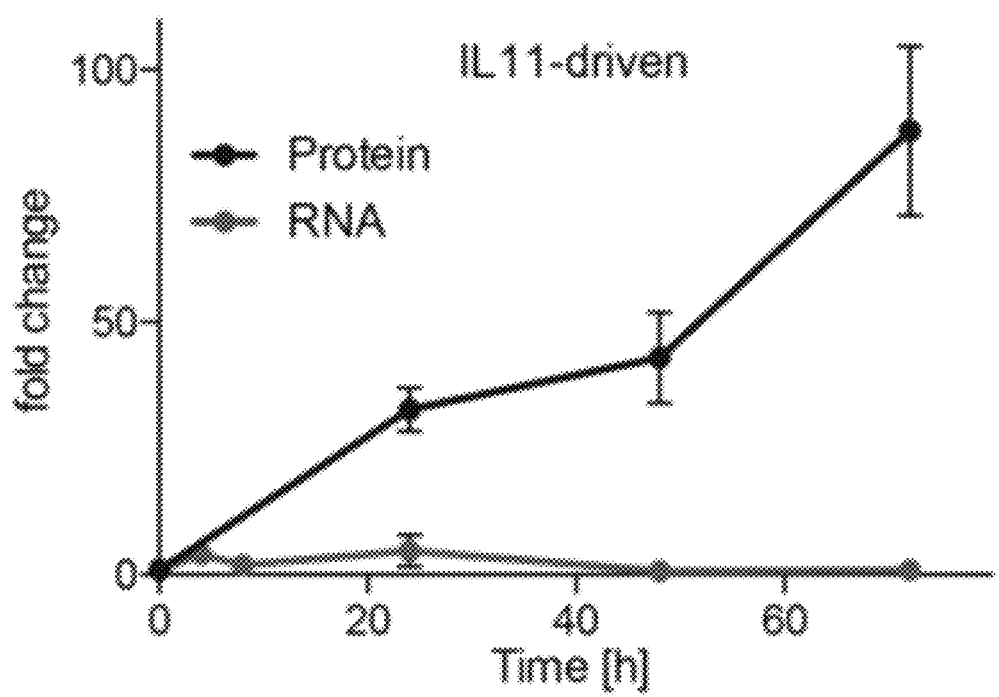

No increase in IL-11 RNA level was detected in response to stimulation with IL-11 (FIG. 4D). Unlike TGFβ1, which increases IL-11 expression at both the RNA and protein level, therefore IL-11 seems to upregulate IL-11 expression only at the post-transcriptional level.

1.2 IL-11 has a Profibrotic Role in Fibrosis of Heart Tissue

To explore whether the autocrine production of IL-11 is pro- or anti-fibrotic, fibroblasts were cultured in vitro with recombinant IL-11, and the fraction of myofibroblasts (αSMA-positive cells) and extracellular matrix production was analysed.

The expression of αSMA, collagen and periostin was monitored with the Operetta High-Content Imaging System in an automated, high-throughput fashion. In parallel, secretion of fibrosis marker proteins such as MMP2, TIMP1 and IL-6 was analysed by ELISA assays, and the levels of collagen were confirmed by calorimetric Sirius Red analysis of the cell culture supernatant.

Briefly, atrial fibroblasts derived from 3 individuals were incubated in 2 wells each for 24 h without stimulation, with TGFβ1 (5 ng/ml), or with IL-11 (5 ng/ml). Following incubation, cells were stained to analyse α-SMA content to estimate the fraction of myofibroblasts, and for collagen and periostin to estimate ECM production. Fluorescence was measured in 7 fields per well. The supernatant of 2 wells per individual was also assessed for collagen content by Sirius Red staining. The signal was normalized to the control group without stimulation. Secretion of the fibrosis markers IL-6, TIMP1 and MMP2 was analysed via ELISA.

Figure 5A:
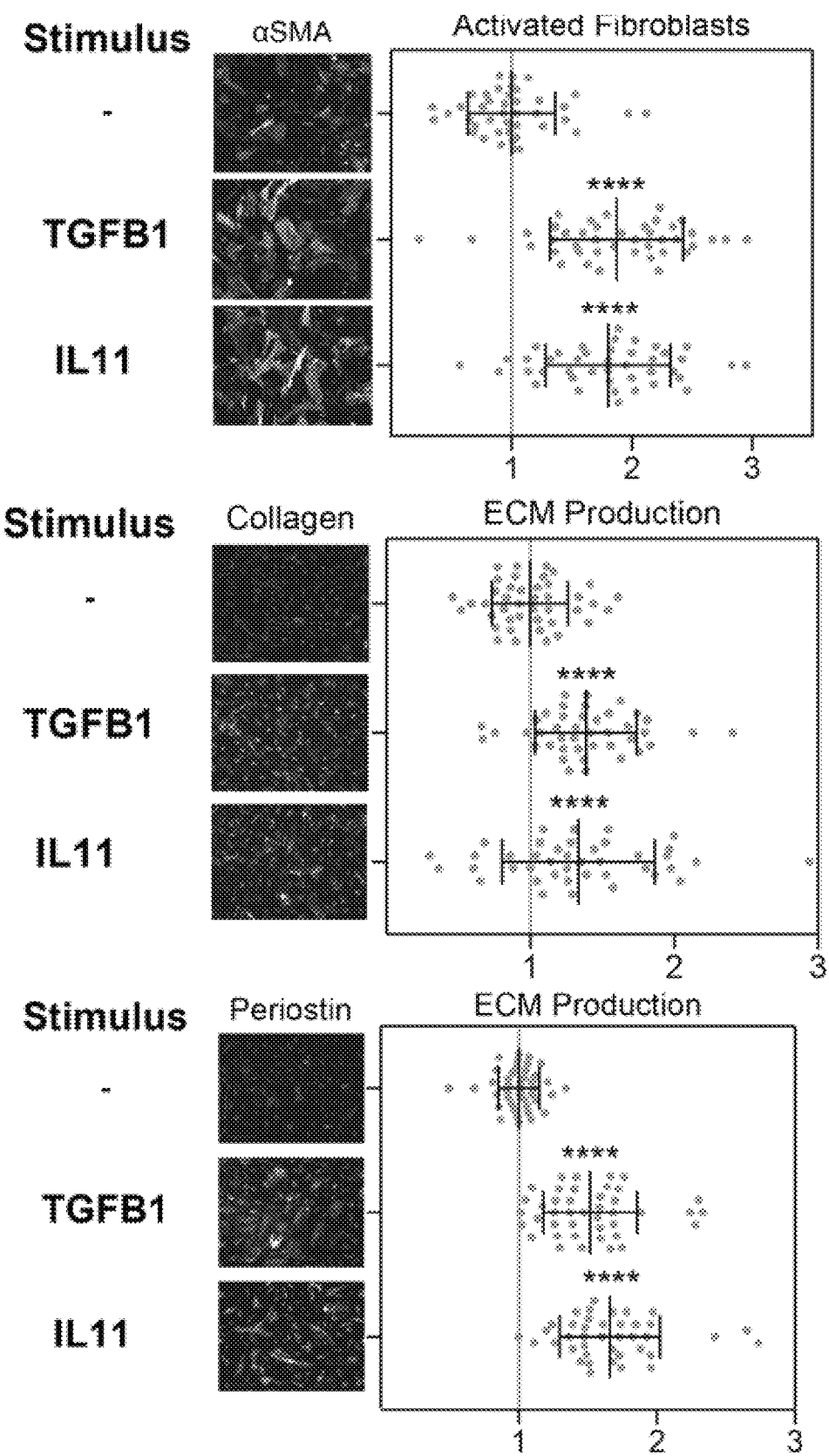
FIGS. 5A to 5F. Graphs and images showing myofibroblast generation from, and production of ECM and cytokine expression by, atrial fibroblasts in response to stimulation with TGFβ1 or IL-11.
Figure 5B:
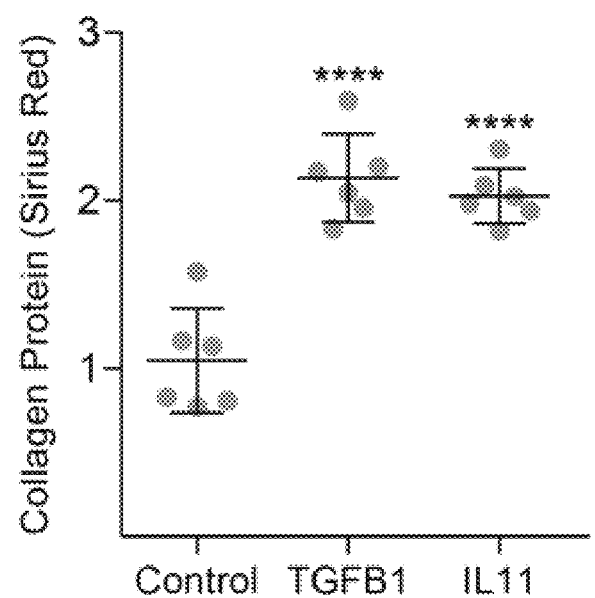
Figure 5C:
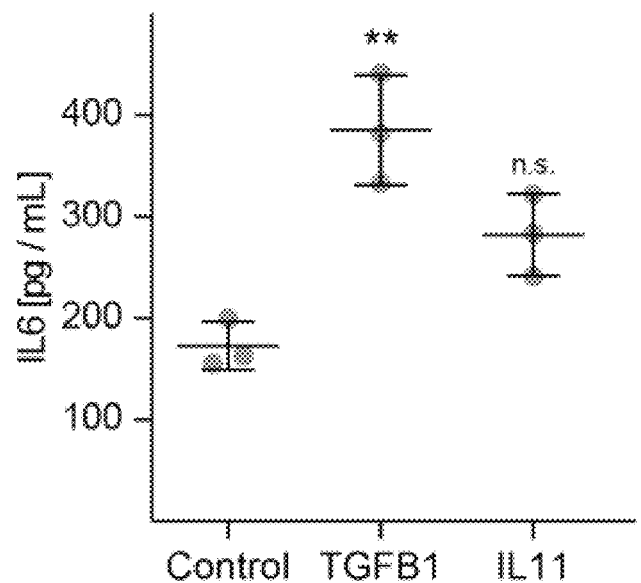
Figure 5D:
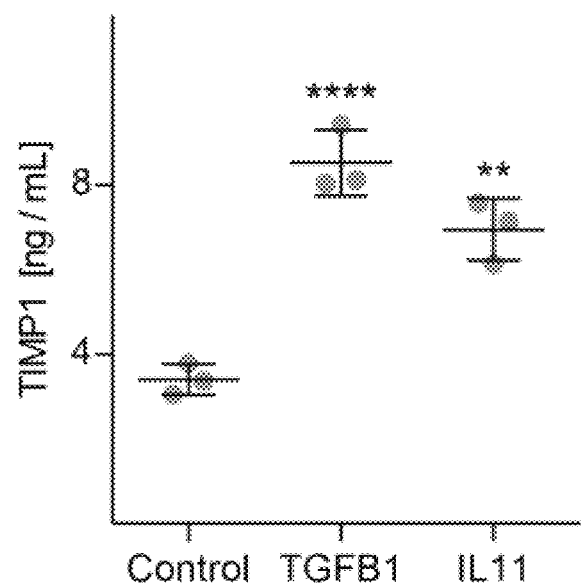
Figure 5E:
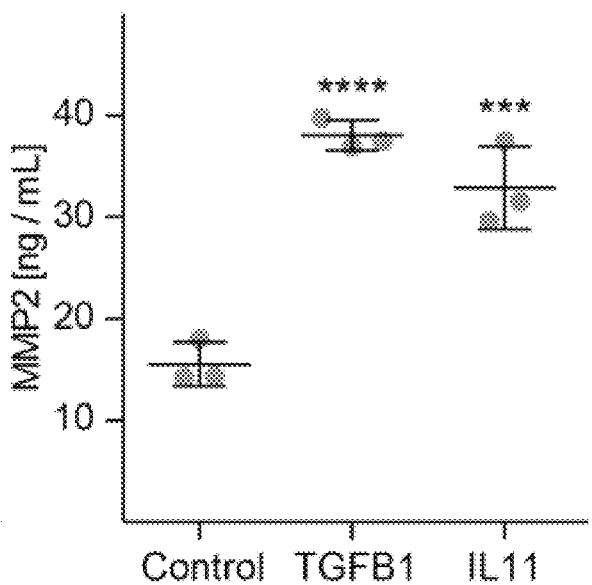

The results are shown in FIGS. 5A to 5F. TGFβ1 activated fibroblasts and increased ECM production (FIG. 5A). Unexpectedly, and in contrast with the anti-fibrotic role described for IL-11 in heart tissue in the scientific literature, recombinant IL-11 caused an increase in the fraction of myofibroblasts in fibroblast cultures, and also promoted the production of extracellular matrix proteins collagen and periostin to the same extent as TGFβ1 (FIG. 5A). Both of IL-11 and TGFβ1 cytokines also significantly increased the secretion of pro-fibrotic markers IL-6, TIMP1 and MMP2 (FIGS. 5B to 5E), and to a similar level.

The inventors hypothesized that the contradiction between the present finding that IL-11 is profibrotic in heart tissue and the antifibrotic role described in the literature might be related to the use of human IL-11 in rodents in those previous studies (Obana et al., 2010, 2012; Stangou et al., 2011; Trepicchio and Dorner, 1998).

Figure 5F:
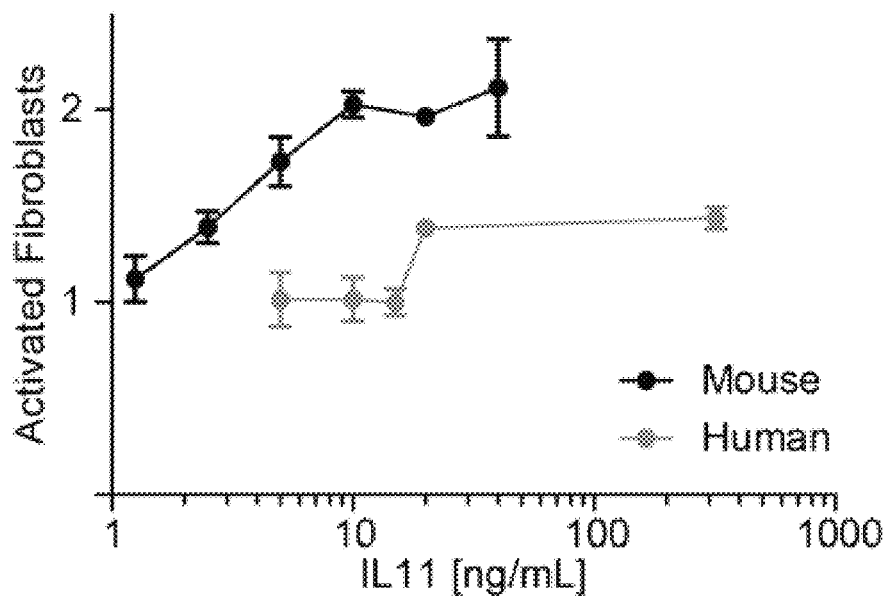

To investigate this hypothesis, serial dilutions of both human and mouse IL-11 were performed, and the activation of human atrial fibroblasts was monitored (FIG. 5F). No activation of fibroblasts was observed at low concentrations of human IL-11 on mouse cells, suggesting that previous insights into IL-11 function may in part be due to IL-11-non-specific observations.

1.3 IL-11 has a Profibrotic Role in Fibrosis of a Variety of Tissues

To test whether the profibrotic action of IL-11 was specific to atrial fibroblasts, human fibroblasts derived from several different tissues (heart, lung, skin, kidney and liver) were cultured in vitro, stimulated with human IL-11, and fibroblast activation and ECM production was analysed as described above. Increased fibroblast activation and production of ECM was observed as compared to non-stimulated cultures in fibroblasts derived from each of the tissues analysed.

1.3.1 Liver Fibrosis

To test whether IL-11 signalling is important in liver fibrosis, human primary liver fibroblasts (Cell Biologics, Cat #: H-6019) were cultured at low passage in wells of 96-well plates and either not stimulated, stimulated with TGFβ1 (5 ng/ml, 24 h), IL-11 (5 ng/ml, 24 h) or incubated with both TGFβ1 (5 ng/ml) and a neutralising IL-11 antibody (2 μg/ml), or TGFβ1 (5 ng/ml) and an Isotype control antibody. Fibroblast activation (αSMA positive cells), cell proliferation (EdU positive cells) and ECM production (Periostin and Collagen) was analysed using the Operetta platform.

The results of the experiments with primary human liver fibroblasts are shown in FIGS. 39A to 39D. IL-11 was found to activate liver fibroblasts, and IL-11 signalling was found to be necessary for the profibrotic action of TGFβ1 in liver fibroblasts. Both activation and proliferation of fibroblasts was inhibited by neutralising anti-IL-11 antibody.

1.3.2 Skin Fibrosis

To test whether IL-11 signalling is important in skin fibrosis, primary mouse skin fibroblasts were cultured at low passage in wells of 96-well plates and either not stimulated, stimulated with TGFβ1 (5 ng/ml, 24 h) or incubated for 24 h with both TGFβ1 (5 ng/ml) and a neutralising IL-11 antibody (2 μg/ml). Fibroblast activation (αSMA positive cells) was then analysed using the Operetta platform.

Figure 40:
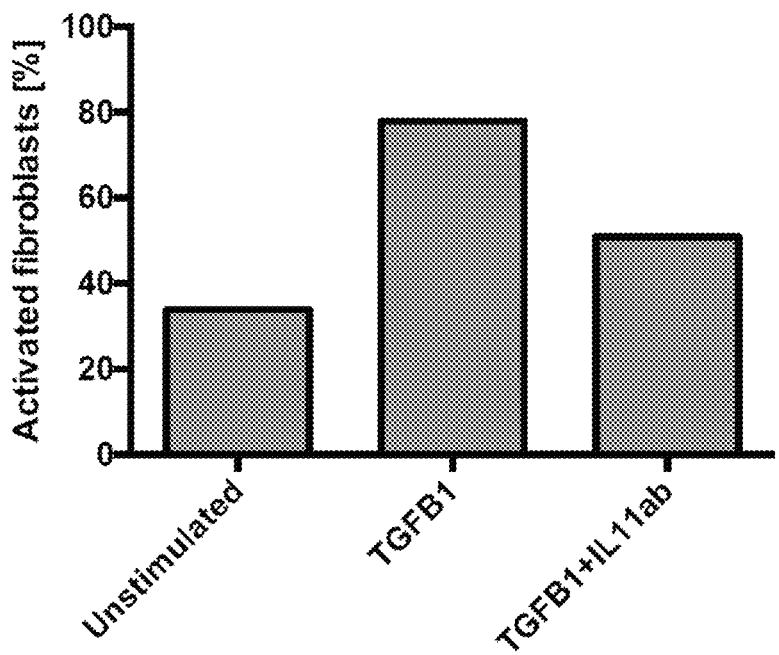
FIG. 40. Bar chart showing that IL-11 is required for the pro-fibrotic effects of TGFβ1 in skin fibroblasts. Activation of mouse skin fibroblasts, with or without stimulation with TGFβ1, and in the presence/absence of neutralising anti-IL-11 antibody, as measured by analysis of the percentage of α-SMA positive cells (activated fibroblasts).

The results are shown in FIG. 40. TGFβ1-mediated activation of skin fibroblasts was inhibited by neutralising anti-IL-11 antibody.

1.3.3 Fibrosis in Multiple Organs

Next, mouse recombinant IL-11 was injected (100 μg/kg, 3 days/week, 28 days) into mice to test whether IL-11 can drive global tissue fibrosis in vivo.

Figure 6A:
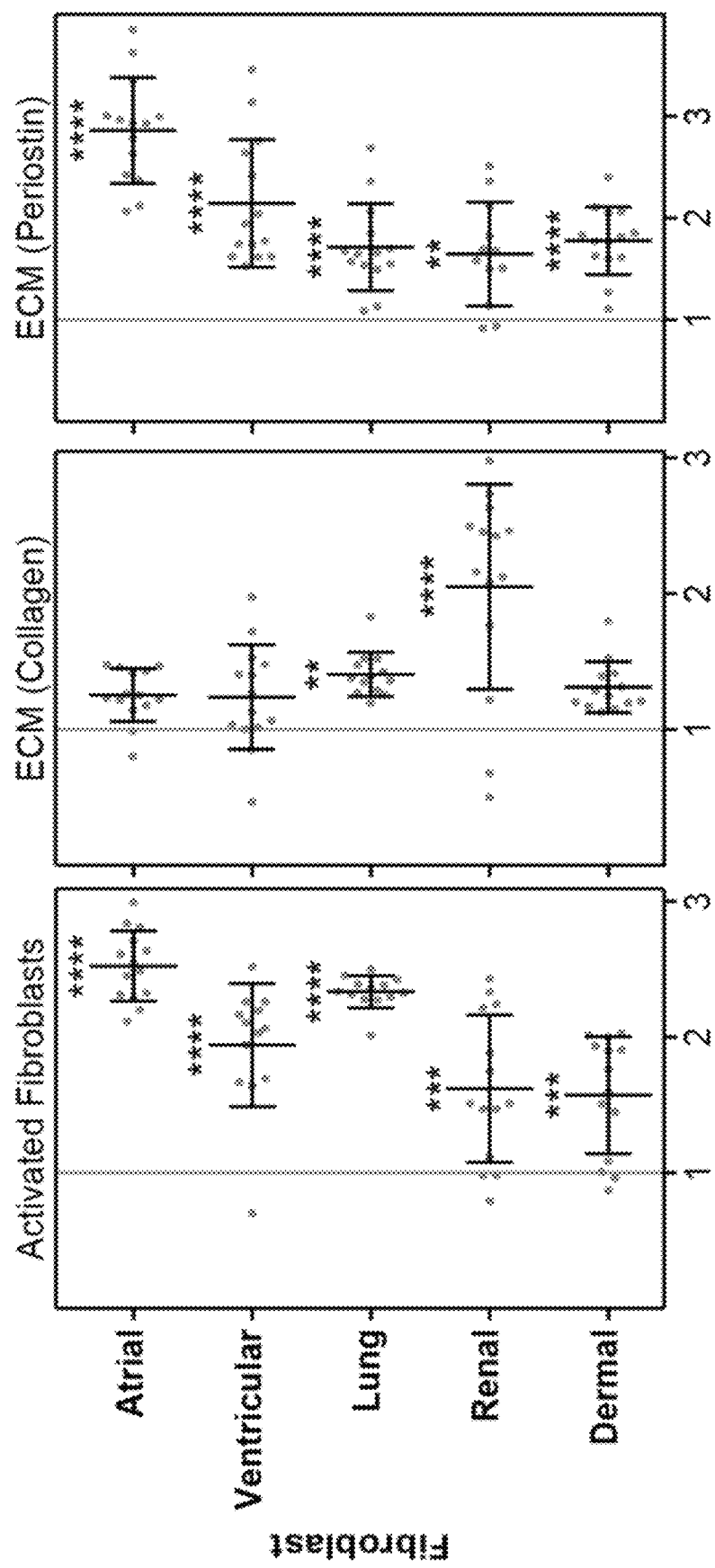
FIGS. 6A to 6C. Graphs showing the profibrotic effect of IL-11.
Figure 6B:
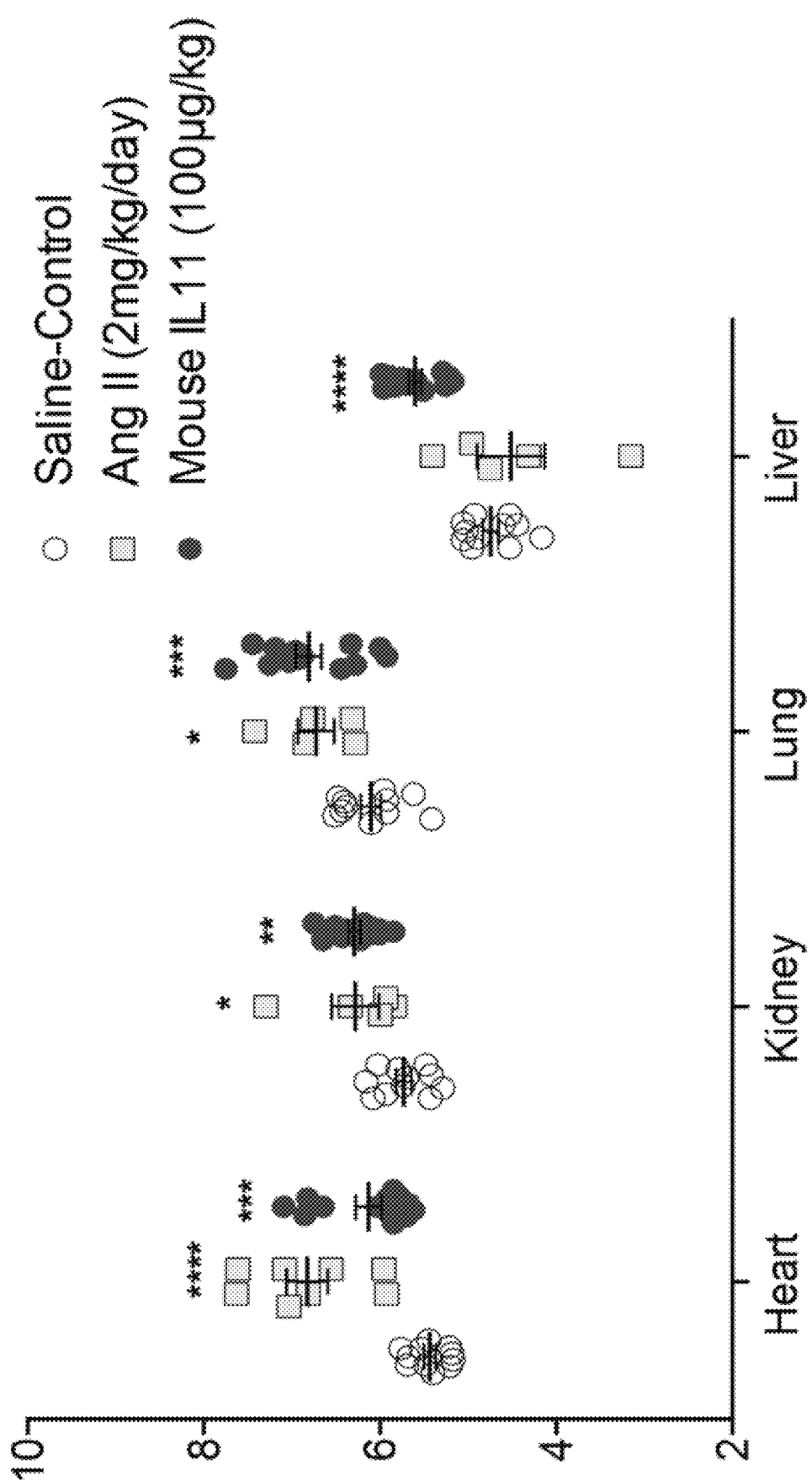
Figure 6C:
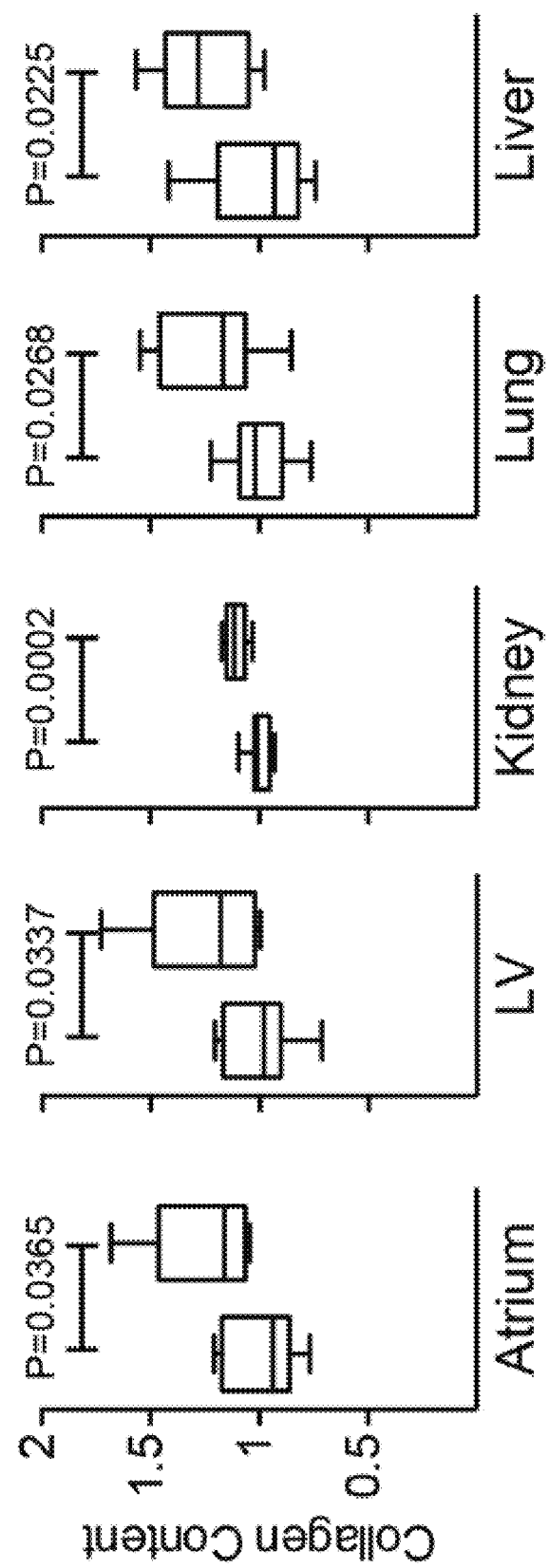
Figure 7A:
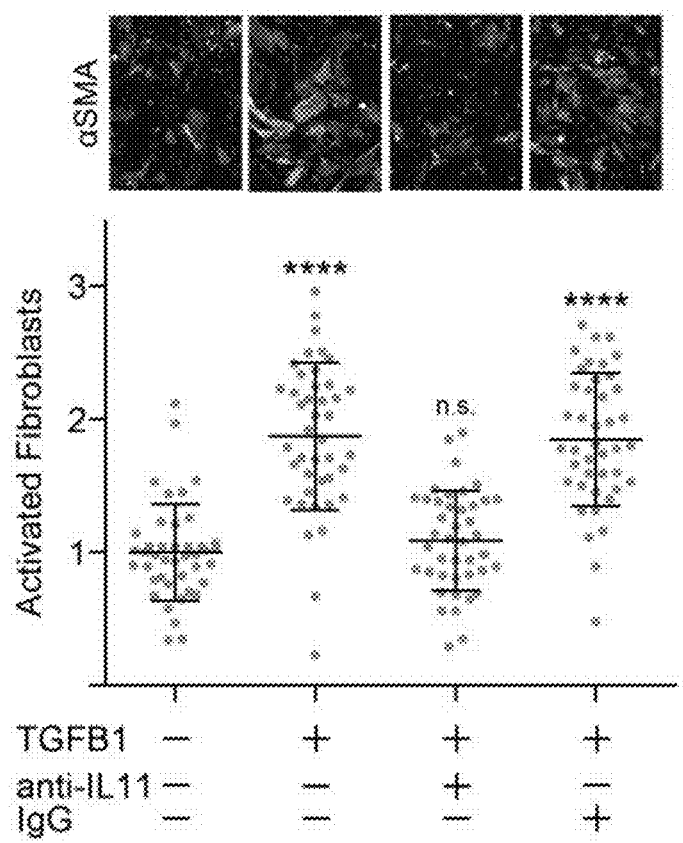
FIGS. 7A to 7F. Graphs and images showing that IL-11 is required the pro-fibrotic effects of TGFβ1 on fibroblasts.
Figure 7B:
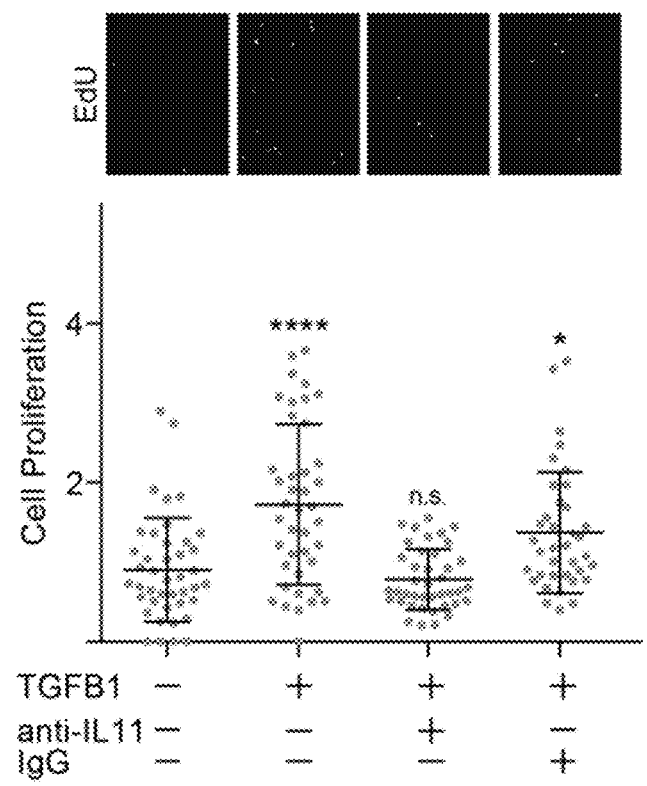
Figure 7C:
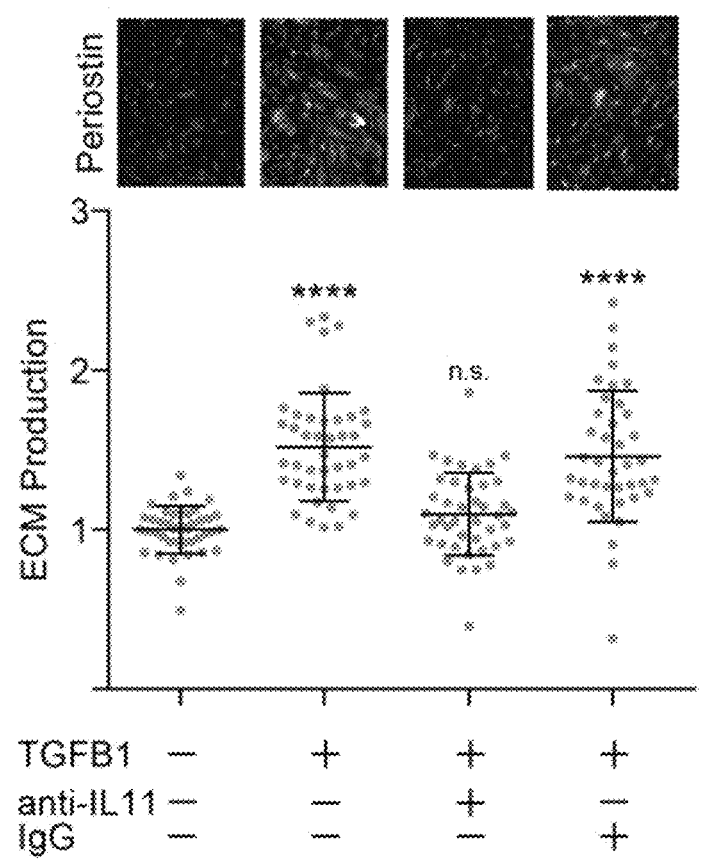
Figure 7D:
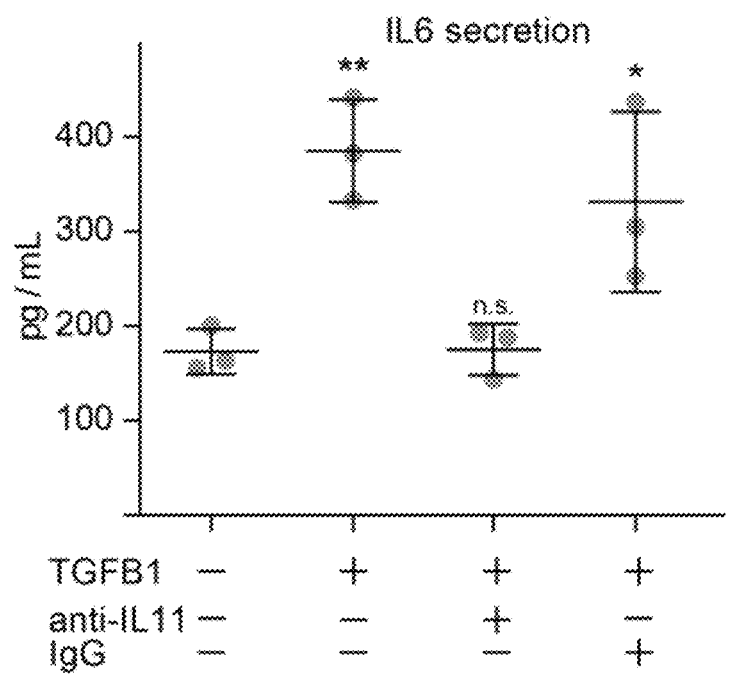
Figure 7E:
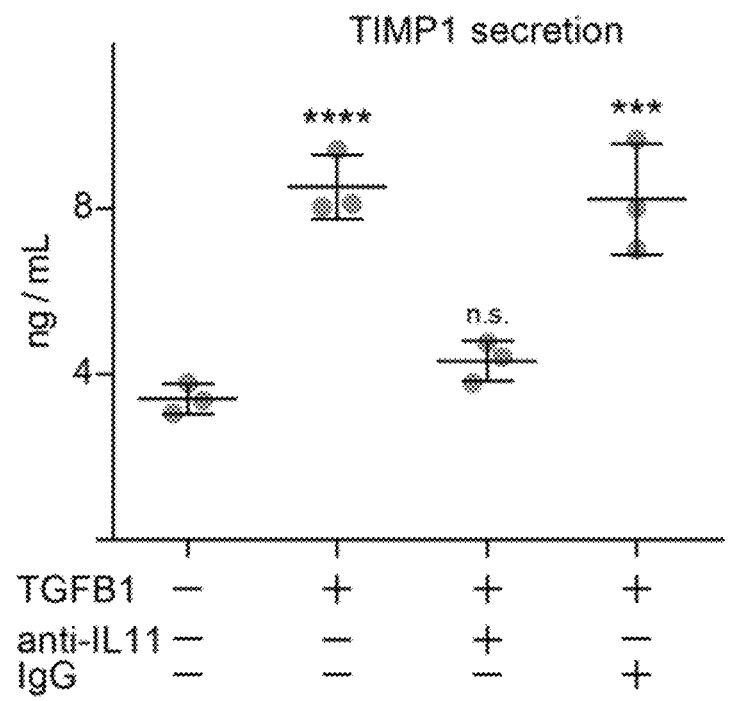
Figure 7F:
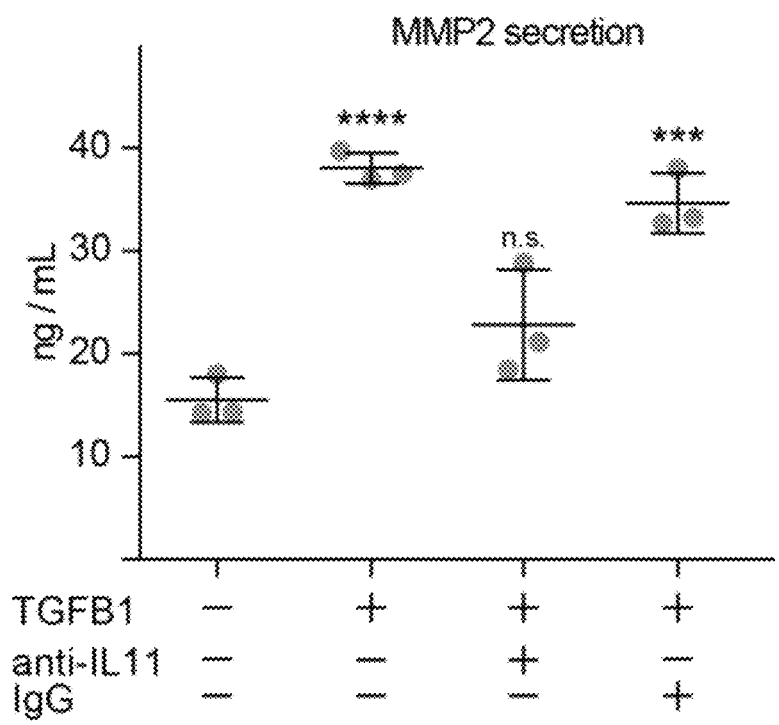

The results are shown in FIGS. 6A to 6C. Compared to injection of AngII (a cytokine that causes an elevation in blood pressure and hypertrophy of the heart), IL-11 also increased the heart weight but also kidney, lung and liver weight indexed to body weight (FIG. 6B). Assessing collagen content in these issues by hydroxyproline assay revealed an upregulation of collagen production in these tissues, indicating fibrosis as the likely cause for the increase in organ weight (FIG. 6C). Expression of fibrosis marker genes ACTA2 (=αSMA), Col1a1, Col3a1, Fn1, Mmp2 and Timp1 was also detected by qPCR analysis of RNA isolated from heart, kidney, lung and liver tissues of these animals Example 2: Therapeutic Potential of IL-11/IL-11R Antagonism 2.1 Inhibition of the Fibrotic Response Using Neutralising Antagonists of IL-11/IL-11R Next it was investigated whether the autocrine loop of IL-11 secretion was required for the pro-fibrotic effect of TGFβ1 on fibroblasts.

IL-11 was inhibited using a commercially available neutralizing antibody (Monoclonal Mouse IgG2A; Clone #22626; Catalog No. MAB218; R&D Systems, MN, USA). Fibroblasts were treated with TGFβ1 in the presence or absence of the antibody, and fibroblast activation, the proportion of proliferating cells and ECM production and markers of the fibrotic response were measured.

Briefly, atrial fibroblasts derived from 3 individuals were incubated for 24 h with TGFβ1 (5 ng/ml) or TGFβ1 in the presence of neutralising anti-IL-11 antibody or isotype control antibody. Following incubation, cells were stained for αSMA to determine the fraction of myofibroblasts, the proportion of proliferating cells was determined by analysing the cells for EdU incorporation, and periostin was measured to determine ECM production. Fluorescence was measured with the Operetta platform for 14 fields across 2 wells for each individual. Secretion of the fibrosis markers IL-6, TIMP1 and MMP2 was also analysed by ELISA. Fluorescence was normalized to the control group without stimulation.

The results are shown in FIGS. 7A to 7F. IL-11 inhibition was found to ameliorate TGFβ1-induced fibrosis, and it was shown that IL-11 is essential for the pro-fibrotic effect of TGFβ1. Inhibition of IL-11 was found to 'rescue' the TGFβ1 phenotype at the protein level.

Collagen production was also analysed. Cardiac fibroblasts derived from 3 individuals were incubated for 24 h with TGFβ1 (5 ng/ml) or TGFβ1 and a neutralizing IL-11 antibody. Following incubation the cells were stained for collagen using the Operetta assay and florescence was quantified as described above. Secreted collagen levels in the cell culture supernatant were assessed by Sirius Red staining.

Figure 8A:
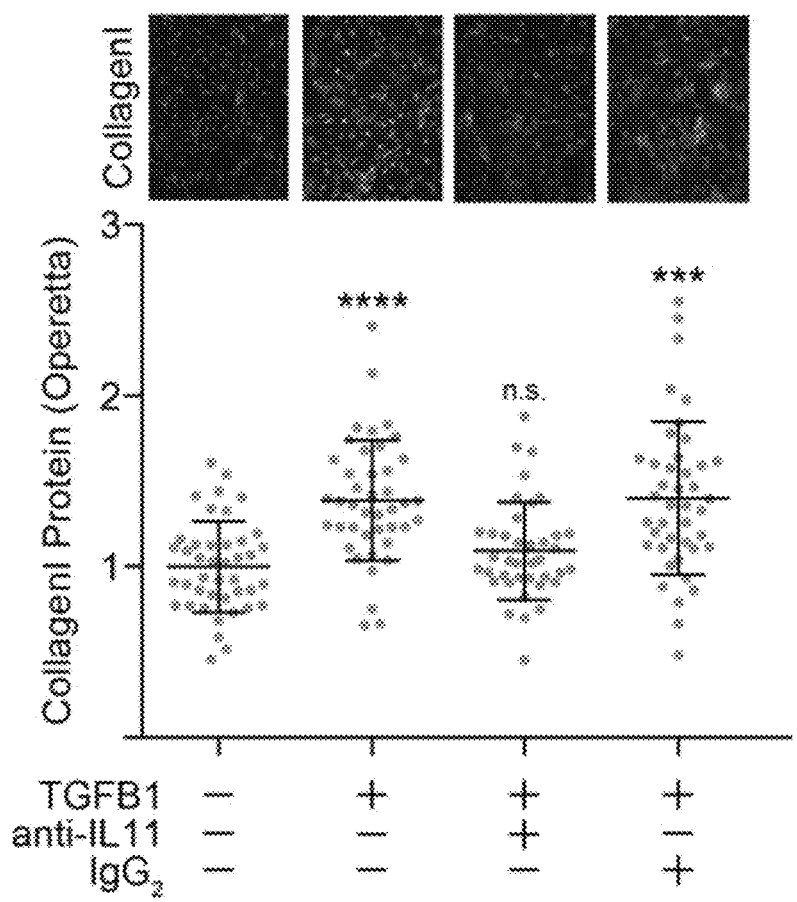
FIGS. 8A and 8B. Graphs and images showing the effect of neutralisation of IL-11 on collagen production triggered by TGFβ1. Collagen production by cardiac fibroblasts with or without stimulation with TGFβ1, and in the presence/absence of neutralising anti-IL-11 antibody or isotype control IgG, as determined by (FIG. 8A) Operetta assay or (FIG. 8B) Sirius Red staining. [Mean±SD, Dunnett]* $P<0.05$,  $P<0.01$, * $P<0.001$ or **** $P<0.0001$.
Figure 8B:
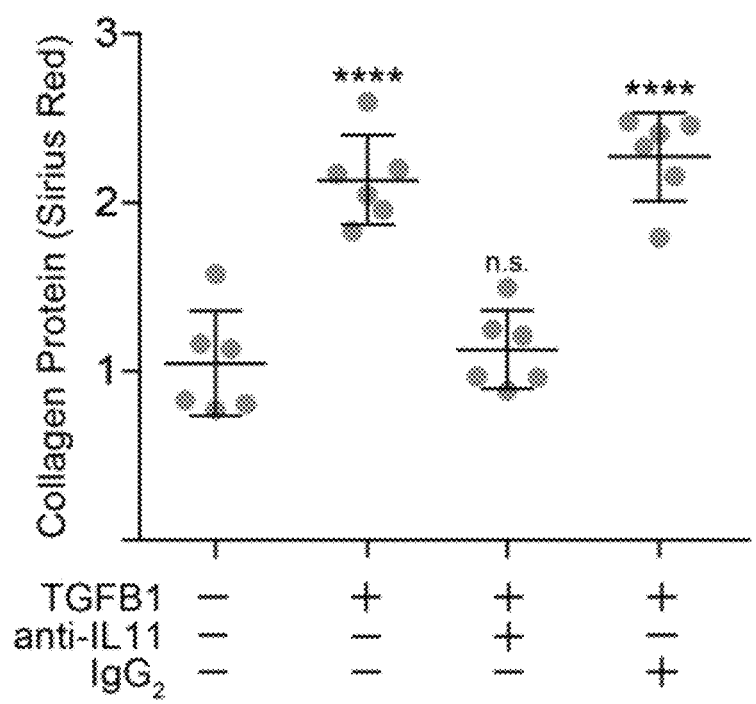

The results are shown in FIGS. 8A and 8B, and confirm the anti-fibrotic effect of inhibition of IL-11 using a neutralising antibody.

Next, the ability of several other IL-11/IL-11R antagonists to inhibit fibrosis was analysed in vitro using the atrial fibroblast, TGFβ1-induced myofibroblast transition assay described herein above.

Briefly, human atrial fibroblasts cells were cultured in vitro, stimulated for 24 h with TGFβ1 (5 ng/ml) or left unstimulated, in the presence/absence of: (i) neutralising anti-IL-11 antibody, (ii) a IL-11RA-gp130 fusion protein (iii) neutralising anti-IL-11RA antibody, (iv) treatment with siRNA directed against IL-11 or (v) treatment with siRNA directed against IL-11RA. The proportion of activated fibroblasts (myofibroblasts) was analysed by evaluating αSMA content as described above.

Figure 9:
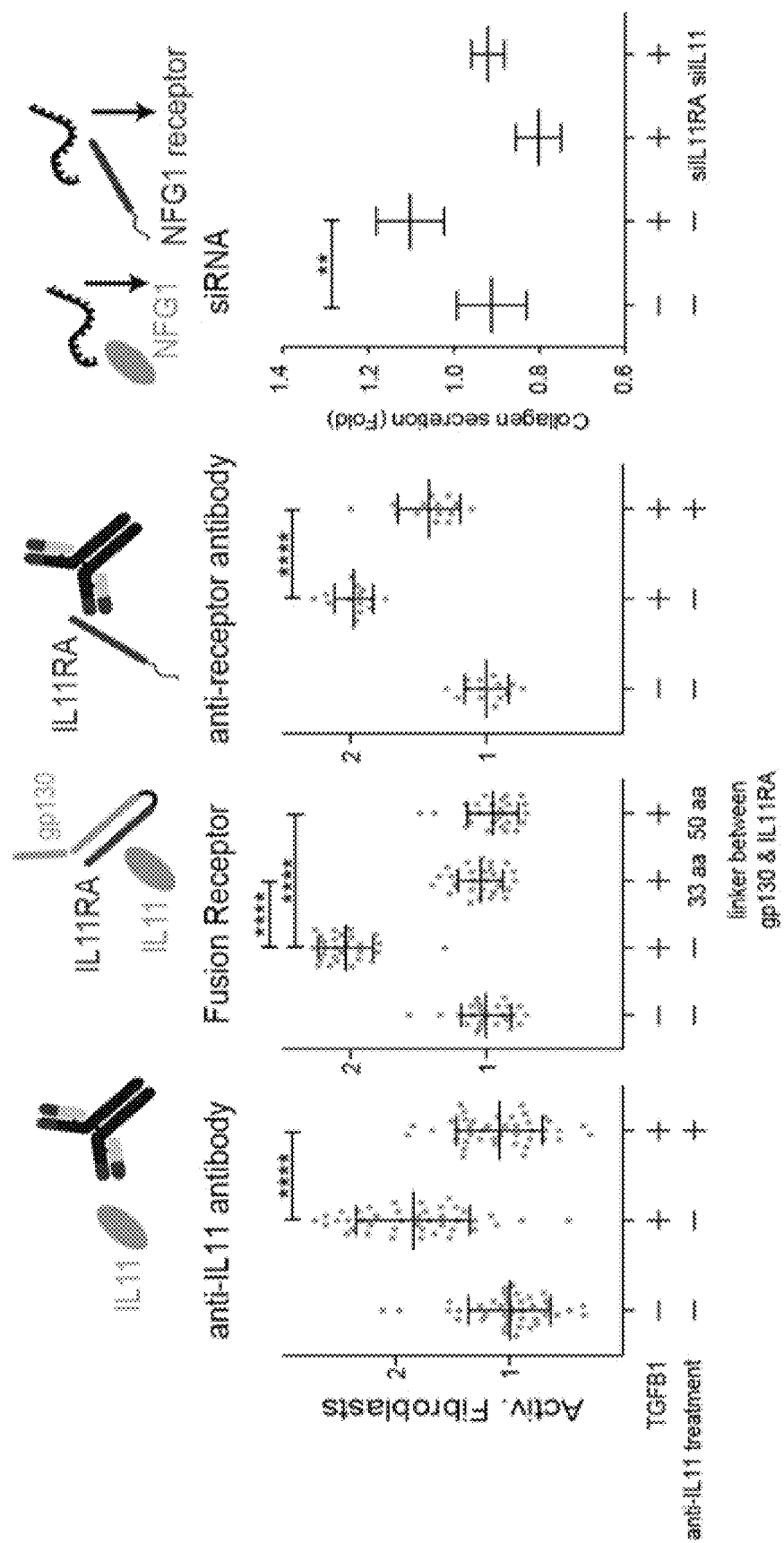
FIG. 9. Graphs showing the ability of various IL-11 and IL-11Rα antagonists to inhibit fibrosis. Human atrial fibroblasts were treated with neutralizing antibody against IL-11, neutralizing antibody against IL-11Rα, decoy IL-11 receptor molecule that binds to IL-11, siRNA that downregulates IL-11 expression or siRNA that downregulates IL-11RA expression and the effect on the TGFβ1-driven pro-fibrotic response in fibroblasts in vitro was analysed. [Mean±SD, Dunnett]* $P<0.05$,  $P<0.01$, * $P<0.001$ or **** $P<0.0001$.
Figure 10A:
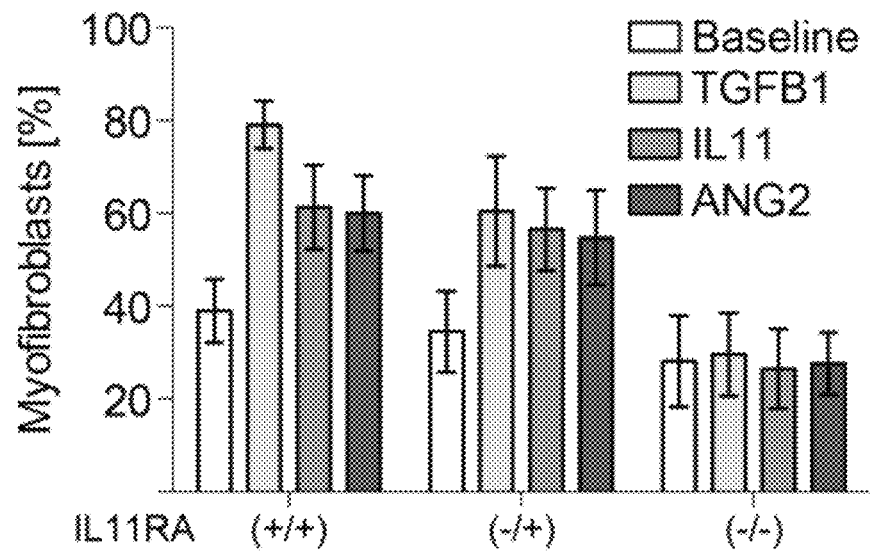
FIGS. 10A to 10D. Bar charts showing the response of fibroblasts from IL-11-RA knockout mice to pro-fibrotic treatment. Fibroblasts derived from IL-11RA WT (+/+), Heterozygous (+/−) and Homozygous null (−/−) mice were incubated for 24 h with TGFβ1, IL-11 or AngII (5 ng/ml).
Figure 10B:
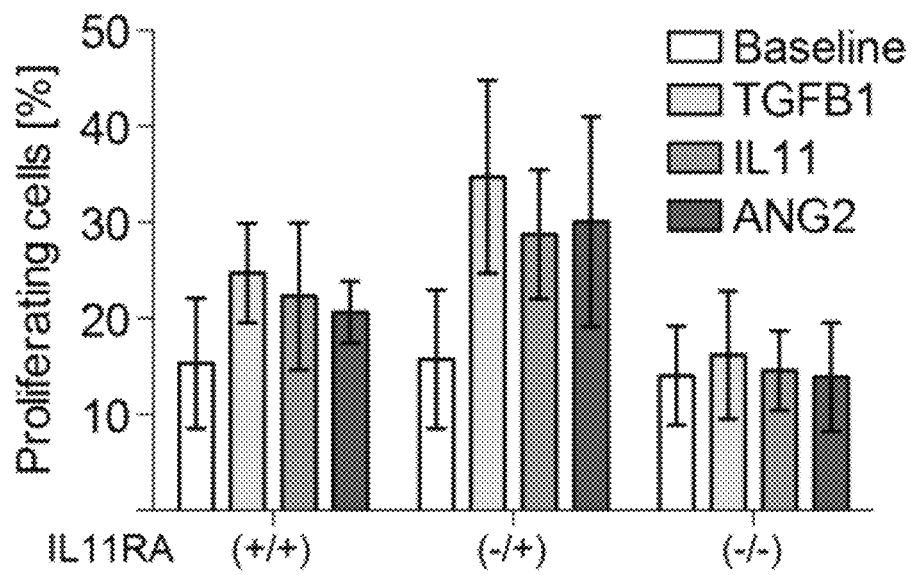
Figure 10C:
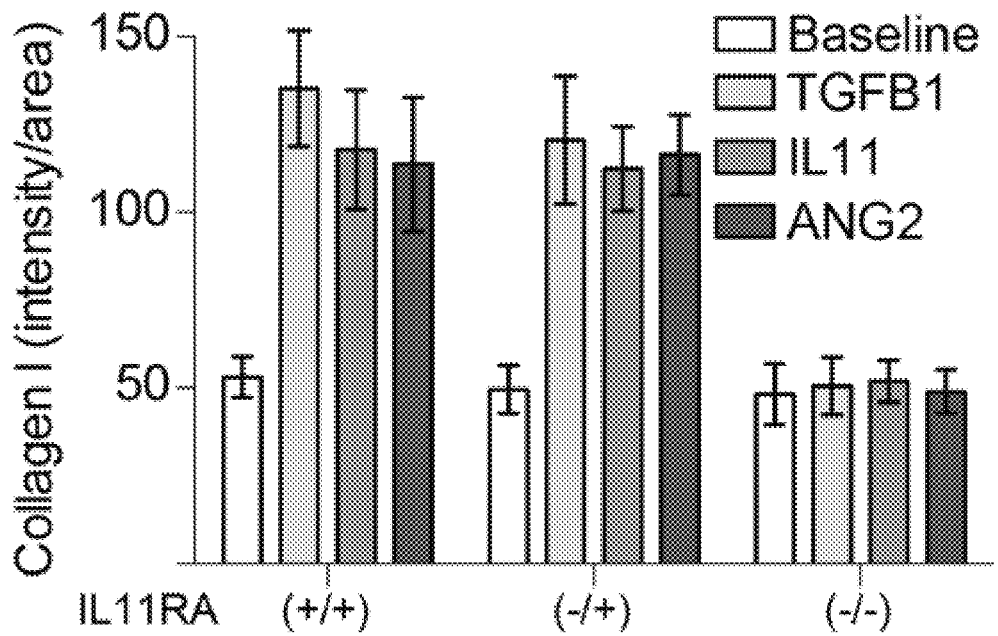
Figure 10D:
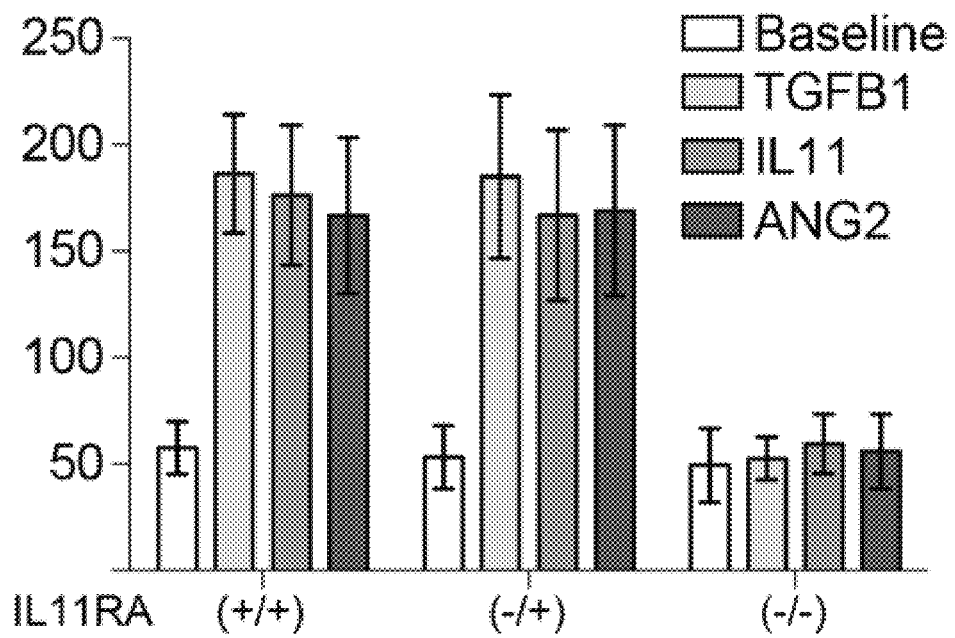

The results are shown in FIG. 9. Each of the antagonists of IL-11/IL-11R signalling was found to be able to abrogate TGFβ1-mediated profibrotic response.

Example 3: In Vivo Confirmation of a Profibrotic Role for IL-11/IL-11R Signalling 3.1 In Vitro Studies Using Cells Derived from IL-11RA Gene Knock-Out Mice All mice were bred and housed in the same room and provided food and water ad libitum. Mice lacking functional alleles for IL-11Rα (IL-11RA1 KO mice) were on C57Bl/6 genetic background. Mice were of 9-11 weeks of age and the weight of animals did not differ significantly.

To further confirm the anti-fibrotic effect of inhibition of IL-11 signalling, primary fibroblasts were generated from IL-11RA gene knock-out mice and incubated with primary fibroblast cells harvested from IL-11RA+/+ (i.e. wildtype), IL-11RA+/− (i.e. heterozygous knockout) and IL-11RA−/− (i.e. homozygous knockout) animals with TGFβ1, IL-11 or AngII. Activation and proliferation of fibroblasts and ECM production was analysed.

Fibroblasts derived from IL-11RA+/+, IL-11RA+/− and IL-11RA−/− mice were incubated for 24 hours with TGFβ1, IL-11 or AngII (5 ng/ml). Following incubation, cells were stained for αSMA content to estimate the fraction of myofibroblasts, for EdU to identify the fraction of proliferating cells, and for collagen and periostin to estimate ECM production. Fluorescence was measured using the Operetta platform.

The results are shown in FIGS. 10A to 10D. IL-11RA−/− mice were found not to respond to pro-fibrotic stimuli. These results suggested that IL-11 signalling is also required for AngII-induced fibrosis.

Next, it was investigated whether this was also true for other pro-fibrotic cytokines.

Briefly, fibroblasts were cultured in vitro in the presence/absence of various different pro-fibrotic factors (ANG2, ET-1 or PDGF), and in the presence/absence of neutralising anti-IL-11 antibody or pan anti-TGFβ antibody. After 24 hours, collagen production by the cells was determined by analysis using the Operetta system as described above, and myofibroblast generation was determined by analysis of αSMA expression as described above.

Figure 11A:
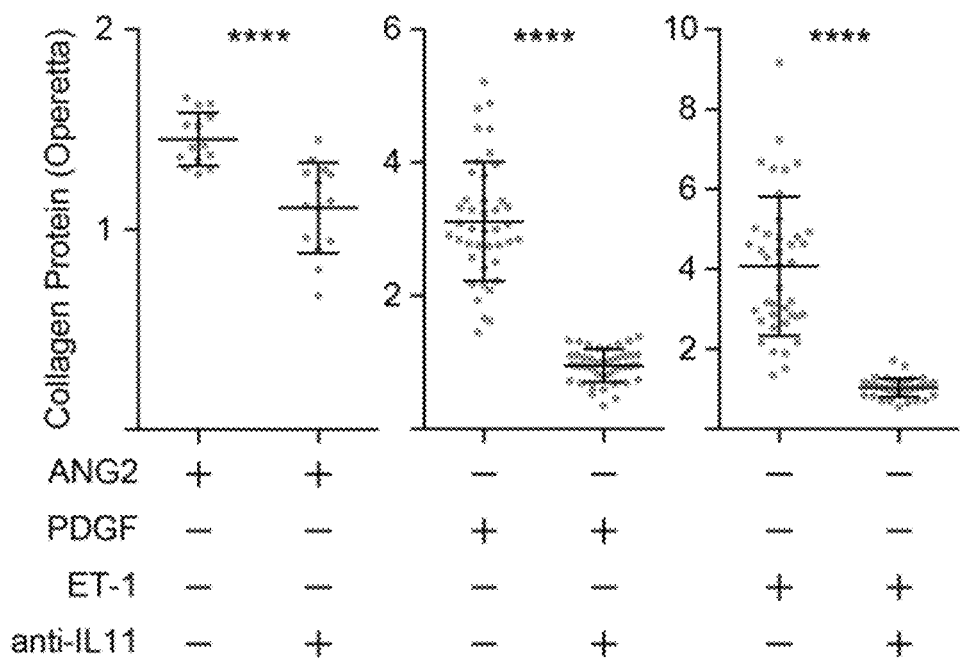
FIGS. 11A and 11B. Graphs showing the effect of IL-11 neutralisation on fibrosis in response to various pro-fibrotic stimuli. Fibroblasts were cultured in vitro in the presence/absence of various different pro-fibrotic factors, and in the presence/absence of neutralising anti-IL-11 antibody or pan anti-TGFβ antibody (FIG. 11A) Collagen production and (FIG. 11B) myofibroblast generation as determined by analysis of αSMA expression. [Mean±SD, Dunnett] * $P<0.05$,  $P<0.01$, * $P<0.001$ or **** $P<0.0001$.
Figure 11B:
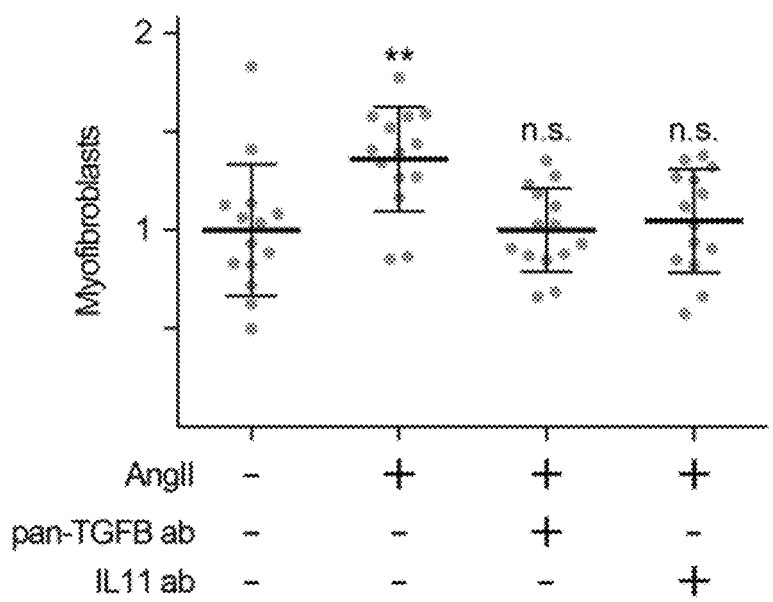
Figure 12A:
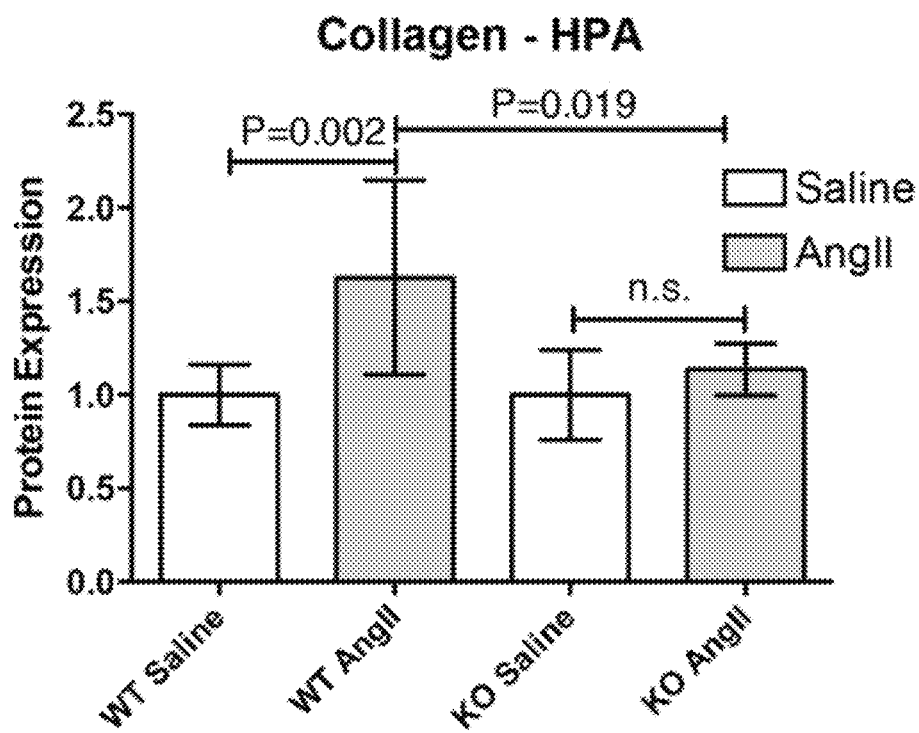
FIGS. 12A to 12D. Bar charts showing expression of markers of fibrosis in the atrium and heart of WT and IL-11RA (−/−) animals following treatment with AngII treatment.
Figure 12B:
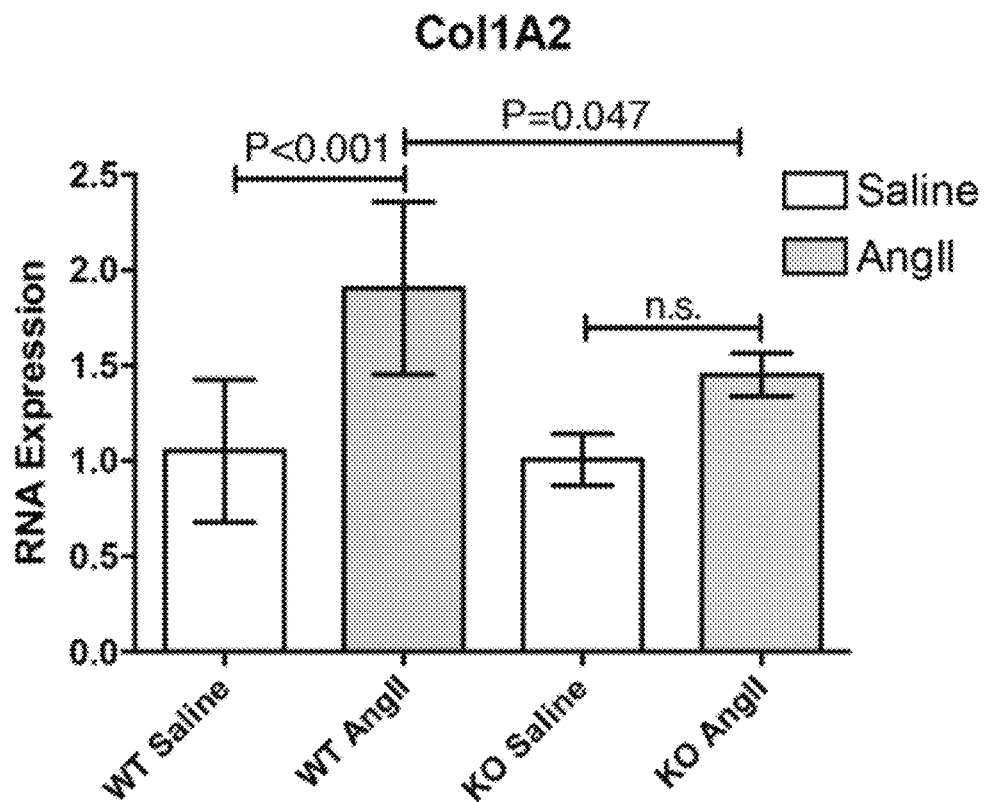
Figure 12C:
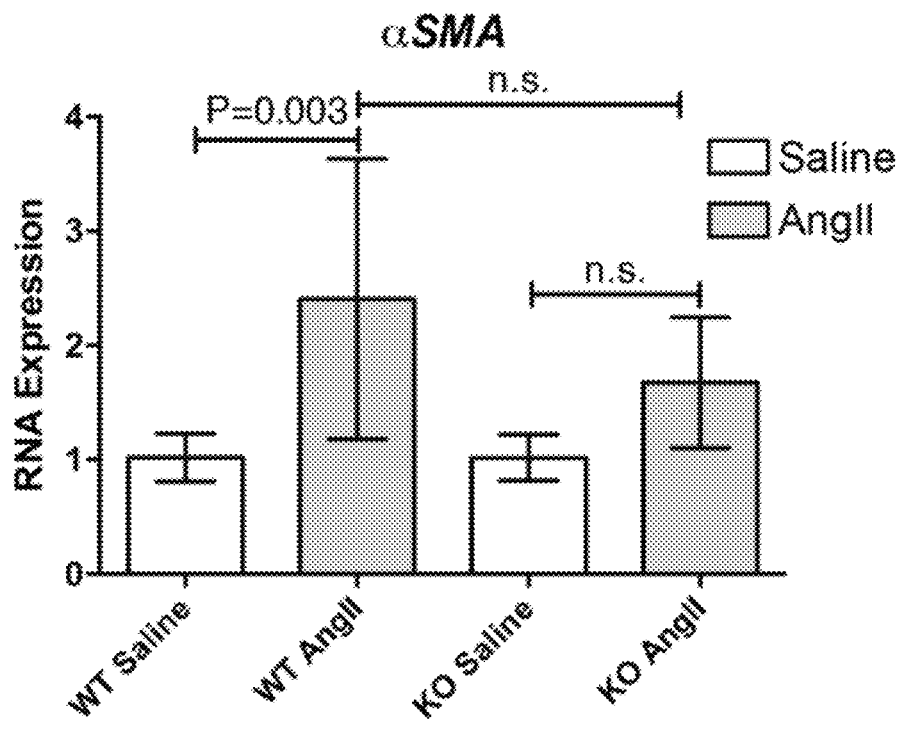
Figure 12D:
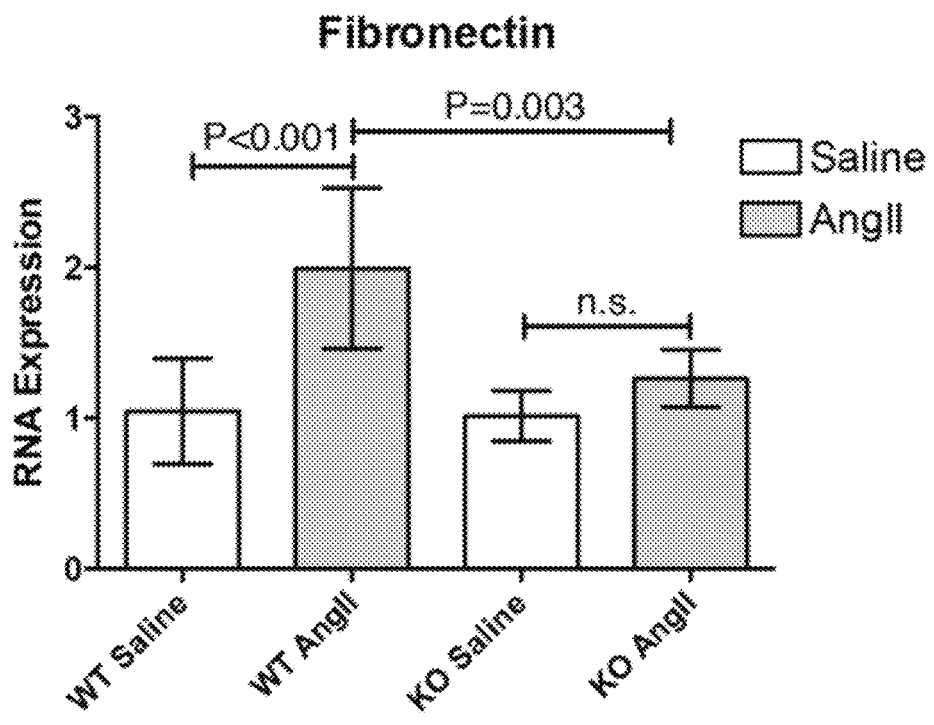

The results are shown in FIGS. 11A and 11B. IL-11 was found to be required for fibrosis downstream of various profibrotic stimuli, and was thus identified as a central mediator of fibrosis induced by a variety of different profibrotic factors.

In a further experiment, the role of IL-11 signalling was investigated in lung fibrosis, using an in vitro scratch assay of migration of lung fibroblasts. In response to pro-fibrotic stimuli, fibroblasts are activated and migrate within the fibrotic niche in the body. The migration rate of cells is a measure of cell-cell and cell-matrix interactions and a model for wound healing in vivo (Liang et al., 2007; Nat Protoc. 2(2):329-33).

Fibroblasts derived from lung tissue from both wild type (WT) and also homozygous IL-11RA (−/−) knockout mice were grown at low passage on a plastic surface until they formed a uniform cell monolayer. A scratch was then created in the cell layer, and cell migration close to the scratch was monitored, either in the absence of stimulation, or in the presence of TGFβ1 or IL-11. Images captured at images at the two time points of immediately after creating the scratch and at 24 h were used to determine the area covered by cells, and the rate of migration was compared between WT and KO fibroblasts. Cell migration (area in the scratch covered by cells after 24 h) was normalized to the migration rate of WT cells without stimulus.

Figure 41:
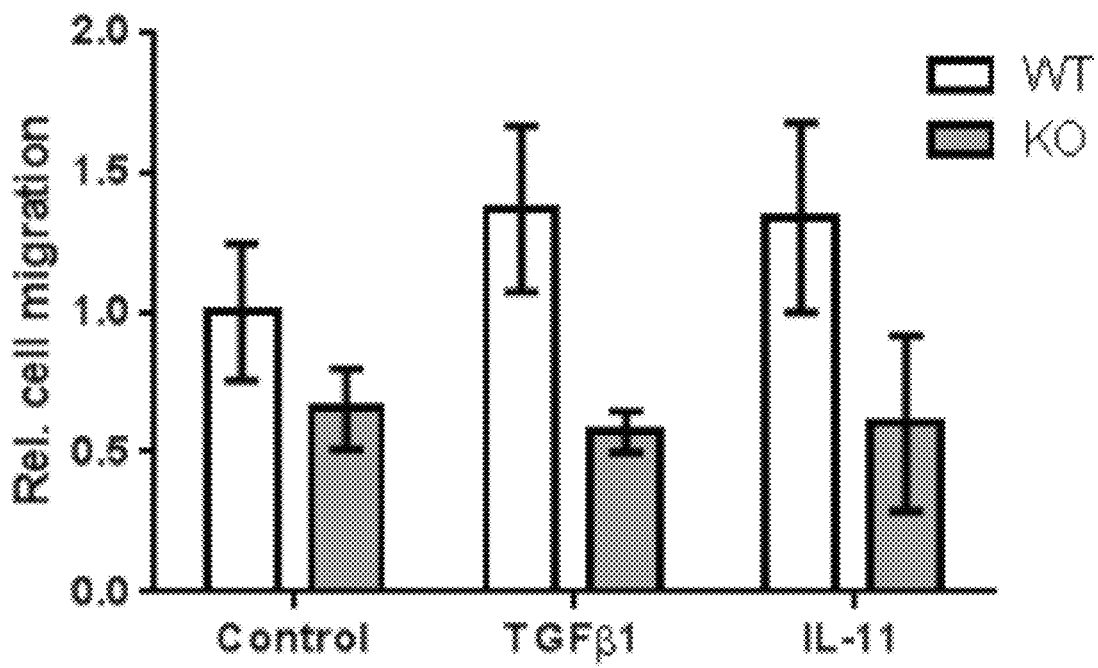
FIG. 41. Bar chart showing lung fibroblast cell migration with and without IL-11 signalling. Migration of lung fibroblasts from IL-11RA+/+(WT) and IL-11RA−/− (KO) animals was analysed in an in vitro scratch assay without stimulus, or in the presence of TGFβ1 or IL-11.

The results are shown in FIG. 41. Lung fibroblasts derived from WT mice were shown to migrate faster in the presence of TGFβ1 and IL-11, indicating a pro-fibrotic effect of both cytokines in lung fibroblasts. Cells lacking IL-11 signalling derived from KO mice migrated more slowly as compared to WT cells. They also did not migrate faster in the presence of TGFβ1. The scratch assay revealed that lung fibroblasts lacking IL-11 signalling have a decrease cell migration rate both in the presence of TGFβ1 or IL-11, and at baseline. Thus, inhibition of IL-11 signalling is anti-fibrotic in the lung.

3.2 Heart Fibrosis

The efficacy of IL-11 inhibition to treat fibrotic disorders was investigated in vivo. A mouse model for cardiac fibrosis, in which fibrosis is induced by treatment with AngII, was used to investigate whether IL-11RA −/− mice were protected from cardiac fibrosis.

Briefly, a pump was implanted, and wildtype (WT) IL-11RA(+/+) and knockout (KO) IL-11RA(−/−) mice were treated with AngII (2 mg/kg/day) for 28 days. At the end of the experiment, collagen content was assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

The results are shown in FIGS. 12A to 12D. The IL-11RA−/− mice were found to be protected from the profibrotic effects of AngII.

3.3 Kidney Fibrosis

A mouse model for kidney fibrosis was established in wildtype (WT) IL-11RA(+/+) and knockout (KO) IL-11RA(−/−) mice by intraperitoneal injection of folic acid (180 mg/kg) in vehicle (0.3M NaHCO$_3$); control mice were administered vehicle alone.

Kidneys were removed 28 days post-injection, weighed and either fixed in 10% neutral-buffered formalin for Masson's trichrome and Sirius staining or snap-frozen for collagen assay, RNA, and protein studies.

Total RNA was extracted from the snap-frozen kidney using TRIZOL™ reagent (Invitrogen) and QIAGEN TISSUELYZER™ method followed by RNEASY™ column (Qiagen) purification. The cDNA was prepared using ISCRIPT™ cDNA synthesis kit, in which each reaction contained 1 μg of total RNA, as per the manufacturer's instructions. Quantitative RT-PCR gene expression analysis was performed on triplicate samples with either TAQMAN™ (Applied Biosystems) or fast SYBR™ green (Qiagen) technology using STEPONEPLUS™ (Applied Biosystem) over 40 cycles. Expression data were normalized to GAPDH mRNA expression level and we used the 2-ΔΔCt method to calculate the fold-change. The snap-frozen kidneys were subjected to acid hydrolysis by heating in 6M HCl at a concentration of 50 mg/ml (95° C., 20 hours). The amount of total collagen in the hydrolysate was quantified based on the colorimetric detection of hydroxyproline using QUICKZYME™ Total Collagen assay kit (Quickzyme Biosciences) as per the manufacturer's instructions.

Figure 37:
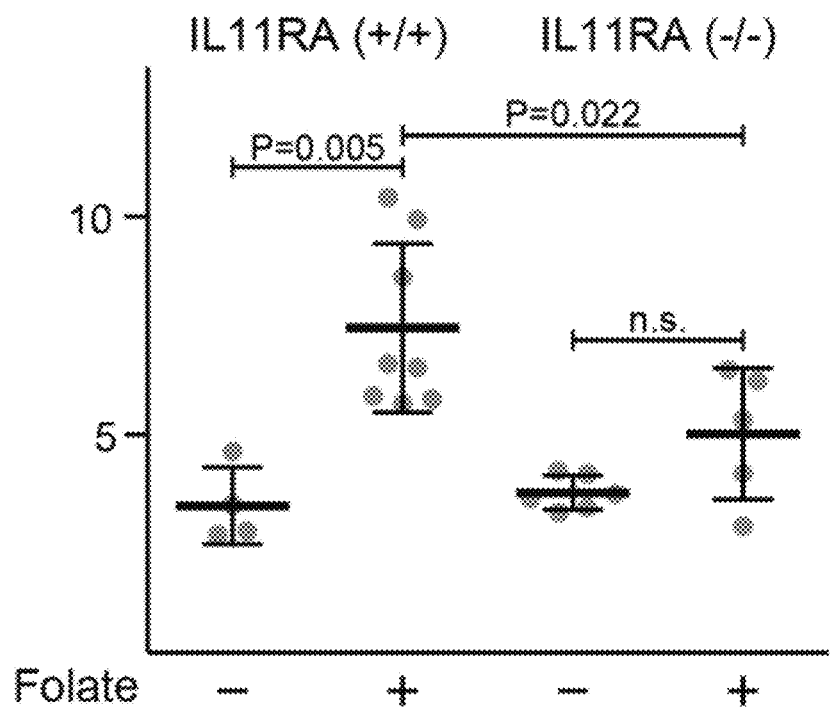
FIG. 37. Graphs showing the effect of IL-11RA knockout on folate-induced kidney fibrosis as measured by collagen content in kidney tissue.

The results of the analysis are shown in FIG. 37. Folate-induced kidney fibrosis is shown to be dependent on IL-11 mediated signalling. A significant increase in collagen content in kidney tissue was observed in IL-11 RA+/+ mice, indicative of kidney fibrosis. No significant increase in collagen content was observed in IL-11 RA −/− mice. Animals deficient for IL-11 signalling had significantly less collagen deposition in kidneys after toxic injury as compared to wild type animals.

3.4 Lung Fibrosis

Figure 13A:
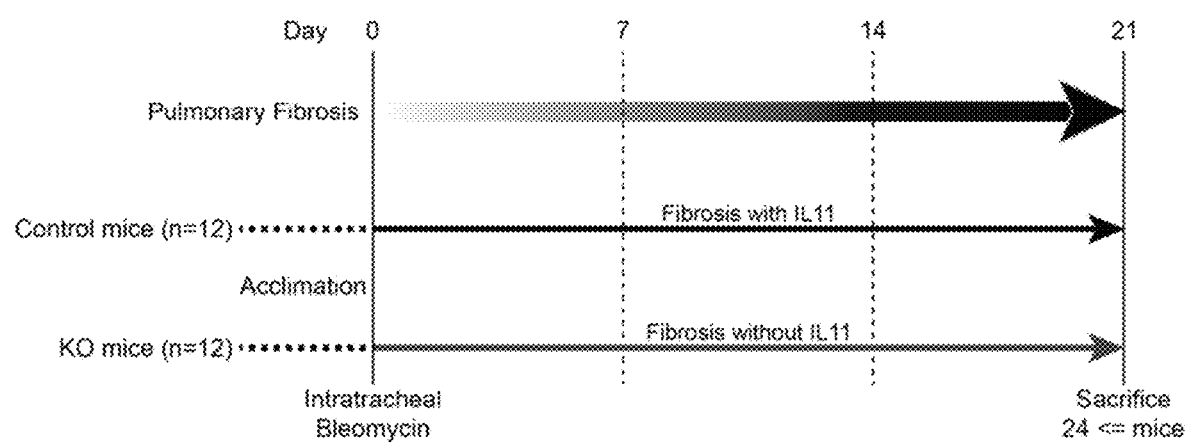
FIGS. 13A to 13C. Schematics of the experimental procedures for analysing fibrosis in (FIG. 13A) lung, (FIG. 13B) skin and (FIG. 13C) eye for IL-11RA −/− mice as compared to IL-11RA +/+ mice.
Figure 13B:
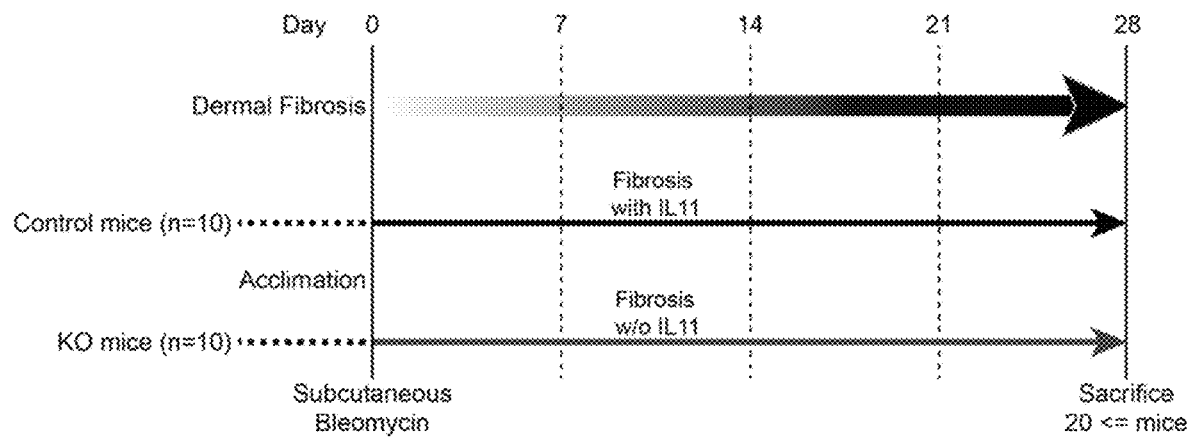
Figure 13C:
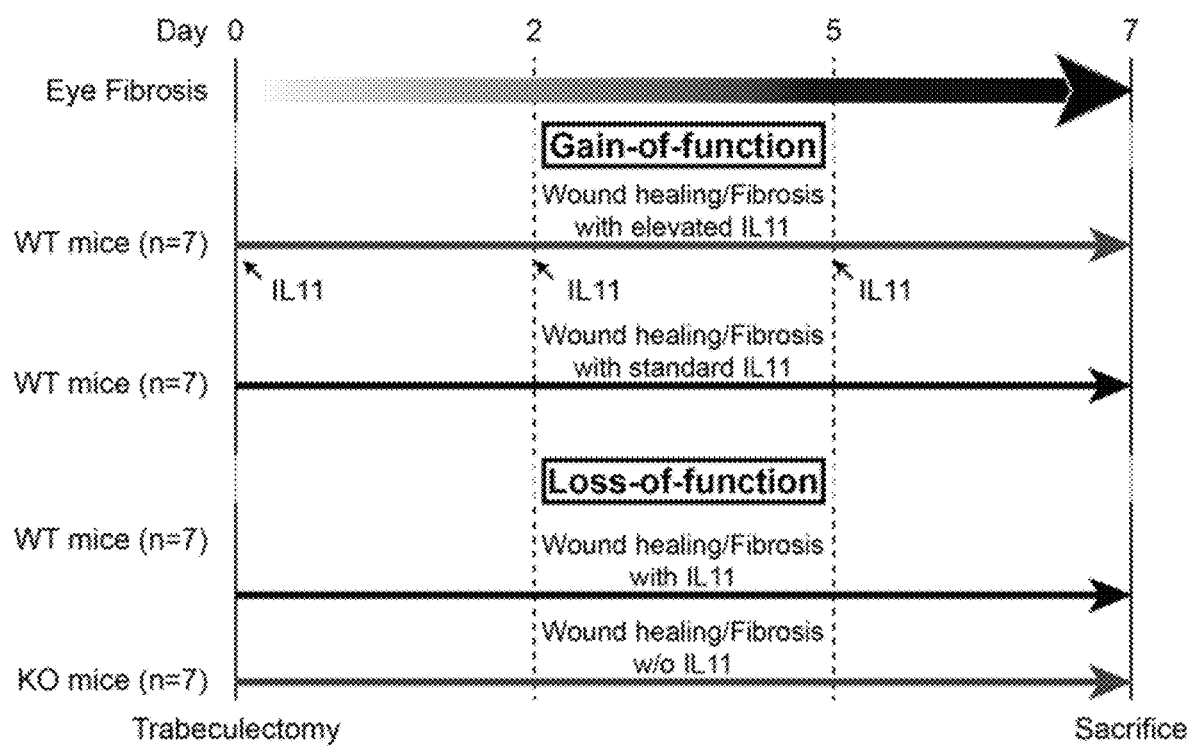

IL-11 is confirmed as a key mediator of fibrosis in the lung, skin and eye in further in vivo models using the IL-11RA −/− knockout mice. Schematics of the experiments are shown in FIGS. 13A to 13C.

To analyse pulmonary fibrosis, IL-11RA −/− mice and IL-11RA+/+ mice are treated by intratracheal administration of bleomycin on day 0 to establish a fibrotic response in the lung (pulmonary fibrosis). Fibrosis of the lung develops by 21 days, at which point animals are sacrificed and analysed for differences in fibrosis markers between animals with and without IL-11 signalling. IL-11RA −/− mice have a reduced fibrotic response in lung tissue as compared to IL-11RA+/+ mice, as evidenced by reduced expression of markers of fibrosis.

3.5 Skin Fibrosis

To analyse fibrosis of the skin, IL-11RA −/− mice and IL-11RA+/+ mice are treated by subcutaneous administration of bleomycin on day 0 to establish a fibrotic response in the skin. Fibrosis of the skin develops by 28 days, at which point animals are sacrificed and analysed for differences in fibrosis markers between animals with and without IL-11 signalling. IL-11RA −/− mice have a reduced fibrotic response in skin tissue as compared to IL-11RA+/+ mice, as evidenced by reduced expression of markers of fibrosis.

3.6 Eye Fibrosis

To analyse fibrosis in the eye, IL-11RA −/− mice and IL-11RA+/+ mice underwent trabeculectomy (filtration surgery) on day 0 to initiate a wound healing response in the eye. This mouse model of glaucoma filtration surgery has been shown to be an efficient model to evaluate the wound healing response in the eye (Khaw et al. 2001, Curr Opin Ophthalmol 12, 143-148; Seet et al. 2011, Mol. Med. 17, 557-567) and has successfully shown the beneficial effect of fibrotic modulators in vivo (Mead et al. 2003, Invest. Ophthalmol. Vis. Sci. 44, 3394-3401; Wong et al. 2003 Invest. Ophthalmol. Vis. Sci. 44, 1097-1103; Wong et al. 2005, Invest. Ophthalmol. Vis. Sci. 46, 2018-2022).

Briefly, the conjunctiva was dissected to expose the underlying sclera, after which an incision was made through the sclera into the anterior chamber of the eye using a 30-gauge needle. The created fistula allowed aqueous humor to exit into and underneath the conjunctiva. The dissected conjunctiva was then secured and closed at the limbus by a 10-0 (0.2 metric) Ethilon black monofilament nylon scleral suture. Fucithalmic ointment was instilled at the end of the procedure. The surgery was performed under anaesthesia by intraperitoneal injection of a 0.1 ml ketamine/xylazine mixture, as well as topical application of one drop per eye of 1% xylocaine. Fucithalmic ointment was instilled post-surgery to prevent infection. Surgery was performed with 70% propyl alcohol sterilized surgical scissors and forceps and sterile needles.

The accumulated fluid underneath the sutured conjunctiva was observed as a conjunctival bleb. Mice were euthanized on day 7 post-surgery for analyses. For qualitative immunehistological analyses, eyes from mice will be harvested by enucleation and then sectioned. Maturation of collagen fibres was evaluated with using the picro-sirius red/polarization light technique (Szendroi et al. 1984, Acta Morphol Hung 32, 47-55); orange-red indicated mature collagen, and yellow/green indicated newly formed immature collagen.

Figure 38A:
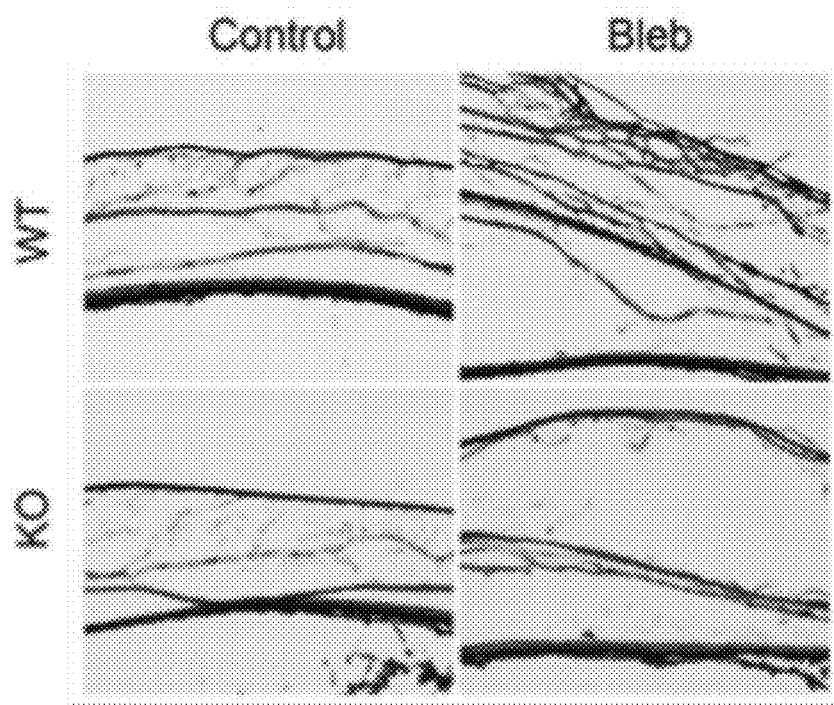
FIGS. 38A and 38B. Photographs showing the effect of IL-11RA knockout on wound healing and fibrosis in the eye following trabeculectomy (filtration surgery).
Figure 38B:
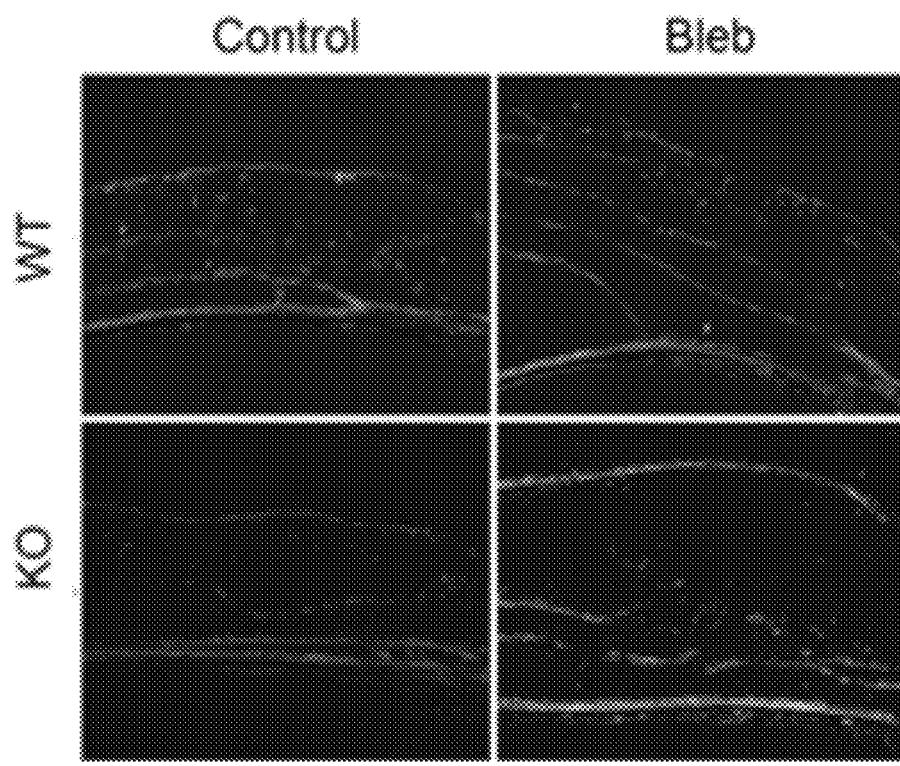
Figure 39A:
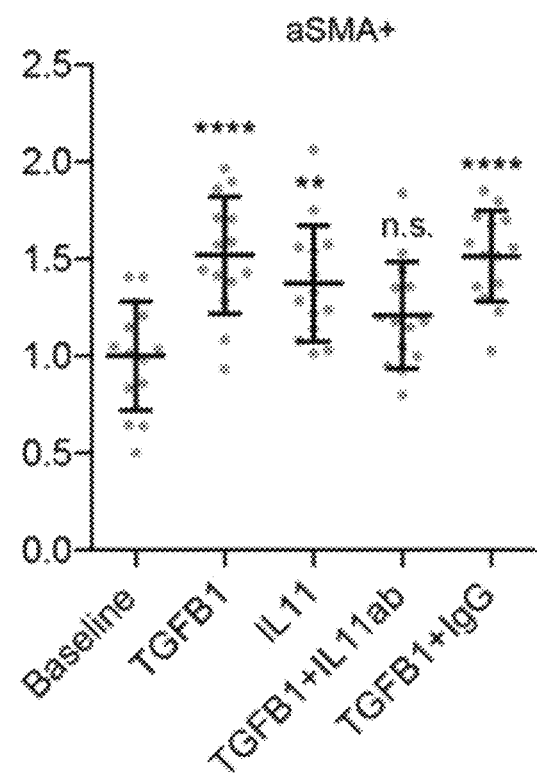
FIGS. 39A to 39D. Graphs showing that IL-11 is required the pro-fibrotic effects of TGFβ1 in liver fibroblasts. Activation and proliferation of primary human liver fibroblasts, with or without stimulation with TGFβ1, and in the presence/absence of neutralising anti-IL-11 antibody or isotype control IgG, as measured by analysis of the proportion of (FIG. 39A) α-SMA positive cells, and (FIG. 39B) EdU positive cells, (FIG. 39C) Collagen positive cells and (FIG. 39D) Periostin positive cells as compared to the unstimulated cells (Baseline). [Mean±SD, Dunnett]* P<0.05,  P<0.01, * P<0.001 or **** P<0.0001.
Figure 39B:
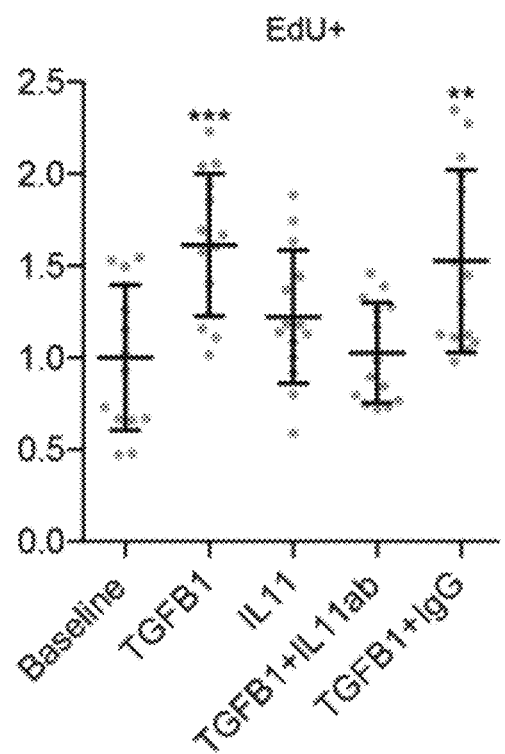
Figure 39C:
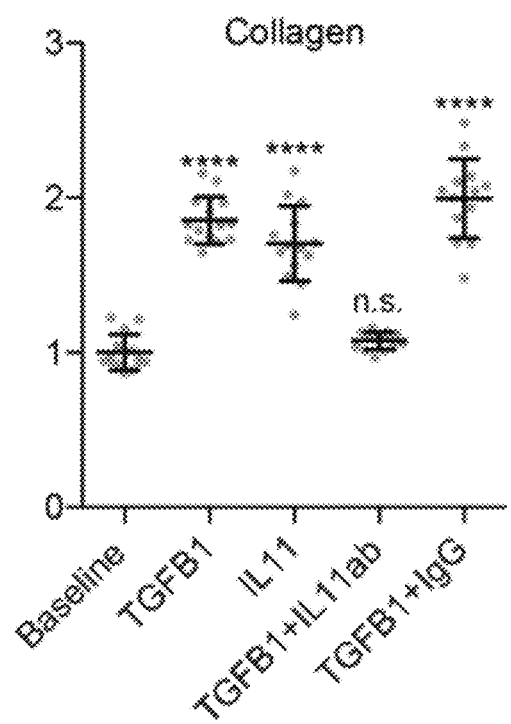
Figure 39D:
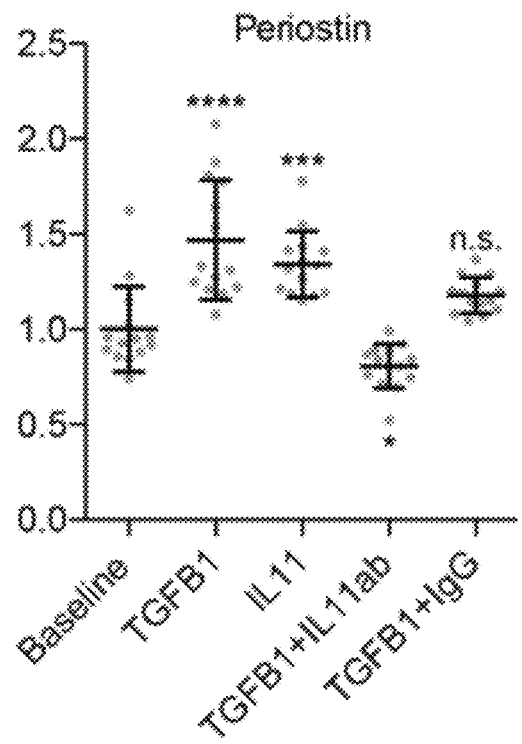

The results of the experiment are shown in FIGS. 38A and 38B. IL-11RA −/− mice were found to have a reduced fibrotic response in eye tissue as compared to IL-11RA+/+ mice.

3.7 Other Tissues

The effect of IL-11RA knockout on fibrosis is also analysed in mouse models of fibrosis for other tissues, such as the liver, bowel, and is also analysed in a model relevant to multiorgan (i.e. systemic) fibrosis. The fibrotic response is measured and compared between the IL-11RA −/− mice and IL-11RA+/+ mice. IL-11RA −/− mice have a reduced fibrotic response as compared to IL-11RA+/+ mice, as evidenced by reduced expression of markers of fibrosis.

Example 4: Analysis of the Molecular Mechanisms Underlying IL-11-Mediated Induction of Fibrosis The canonical mode of action of IL-11 is thought to be regulation of RNA expression via STAT3-mediated transcription (Zhu et al., 2015 PLoS ONE 10, e0126296), and also through activation of ERK.

STAT3 activation is observed following stimulation with IL-11. However, when fibroblasts are incubated with TGFβ1, only activation of the canonical SMACK pathway and ERK pathways is seen, and activation of STAT3 is not observed, even in spite of the fact that IL-11 is secreted in response to TGFβ1. Only ERK activation is common to both TGFβ1 and IL-11 signal transduction.

Cross-talk between TGFβ1 and IL-6 signalling has previously been described, wherein TGFβ1 blocks the activation of STAT3 by IL-6 (Walia et al., 2003 FASEB J. 17, 2130-2132). Given the close relationship between IL-6 and IL-11, similar cross-talk may be observed for IL-11 mediated signalling.

The inventors investigated by RNA-seq analysis whether regulation of RNA abundance was the underlying mechanism for the increased expression of fibrosis marker proteins in response to IL-11, which would suggest STAT3 as the underlying signalling pathway for IL-11 mediated profibrotic processes. Fibroblasts were incubated for 24 hours either without stimulus, or in the presence of TGFβ1, IL-11 or TGFβ1 and IL-11.

Figure 14A:
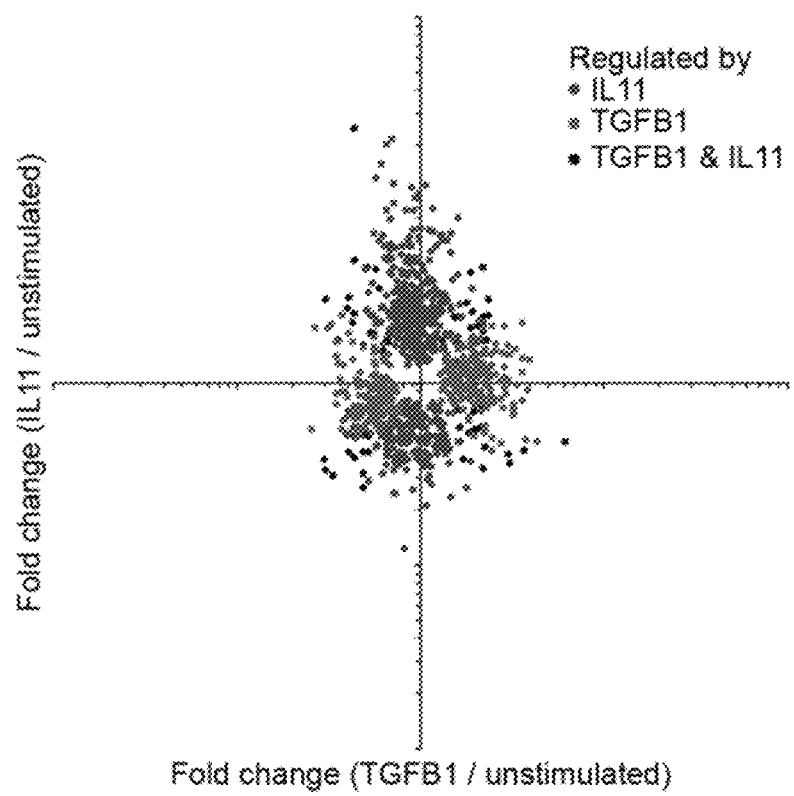
FIGS. 14A and 14B. Scatterplots showing fold change in gene expression.
Figure 14B:
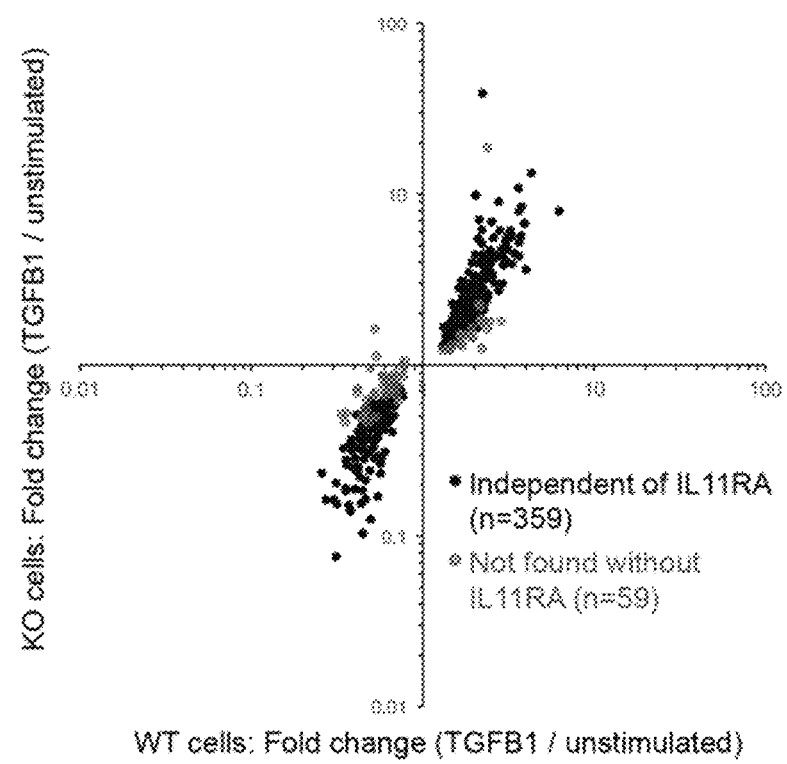

The results are shown in FIG. 14A. TGFβ1 induced the expression of collagen, ACTA2 (αSMA) and other fibrosis marker at the RNA level. However, IL-11 did not regulate the expression of these genes, but a different set of genes.

Gene ontology analysis suggests that a pro-fibrotic effect in fibroblasts is driven by IL-11-regulated RNA expression. Both TGFβ1 and IL-11 regulate an almost completely different set of genes on the RNA level.

Whilst TGFβ1 increases IL-11 secretion, the target genes of IL-11 are not regulated when both TGFβ1 and IL-11 are present. This suggests that TGFβ1 upregulates IL-11 and simultaneously blocks the canonical IL-11-driven regulation of RNA expression via STAT3, similar to what is known about the interaction of TGFβ1 and IL-6 pathways (Walia et al., 2003 FASEB J. 17, 2130-2132).

We also analysed whether RNA expression differences induced by TGFβ1 are dependent on IL-11 signalling, by analysing changes in RNA expression in fibroblasts obtained from IL-11RA −/− mice as compared to IL-11RA+1+ mice. RNA expression regulated by TGFβ1 is still observed when IL-11RA knockout cells were stimulated with TGFβ1, and RNA levels of αSMA, collagen etc. were still upregulated in the absence of IL-11 signalling (in IL-11RA −/− fibroblasts). When the pro-fibrotic effect of IL-11 and the anti-fibrotic effect of IL-11 inhibition was investigated in vitro, reduced expression of markers of fibrosis was only observed at the protein level, not at the transcriptional level as determined by qPCR.

The activation of non-canonical pathways (e.g. ERK signal transduction) is known to be crucial for the profibrotic action of TGFβ1 (Guo and Wang, 2008 Cell Res 19, 71-88). It is likely that non-canonical pathways are likely to be important for signalling for all known pro-fibrotic cytokines, and that IL-11 is a post-transcriptional regulator which is essential for fibrosis.

Example 5: Human Anti-Human IL-11 Antibodies

Fully human anti-human IL-11 antibodies were developed via phage display.

Recombinant human IL-11 (Cat. No. Z03108-1) and recombinant murine IL-11 (Cat. No. Z03052-1) were obtained from GenScript (NJ, USA). Recombinant human IL-11 was expressed in CHO cells, both as an Fc-tagged version and a tag-free version. Tag-free murine IL-11 was expressed in HEK293 cells.

IL-11 bioactivity of recombinant human IL-11 and mouse IL-11 was confirmed by in vitro analysis using primary fibroblast cell cultures.

Recombinant, biotinylated human IL-11 and murine IL-11 were also prepared by biotinylation of the recombinant human IL-11 and murine IL-11 molecules, according to standard methods.

Antibodies capable of binding to both human IL-11 and murine IL-11 (i.e. cross-reactive antibodies) were identified by phage display using a human nave library by panning using biotinylated and non-biotinylated recombinant human and murine IL-11, based on 16 different panning strategies as summarised in FIG. 21.

The phage display identified 175 scFv binders, as 'first hits'. Sequence analysis of the CDR sequences from these 175 scFv identified 86 unique scFv.

The soluble scFv were produced by recombinant expression in E. coli, and analysed for their ability to bind to human IL-11 and murine IL-11 by ELISA. Briefly, the respective antigen was coated to wells of an ELISA plate, the cell culture supernatant containing the respective scFv was added at a 1:2 dilution, and binding was detected.

Figure 22:
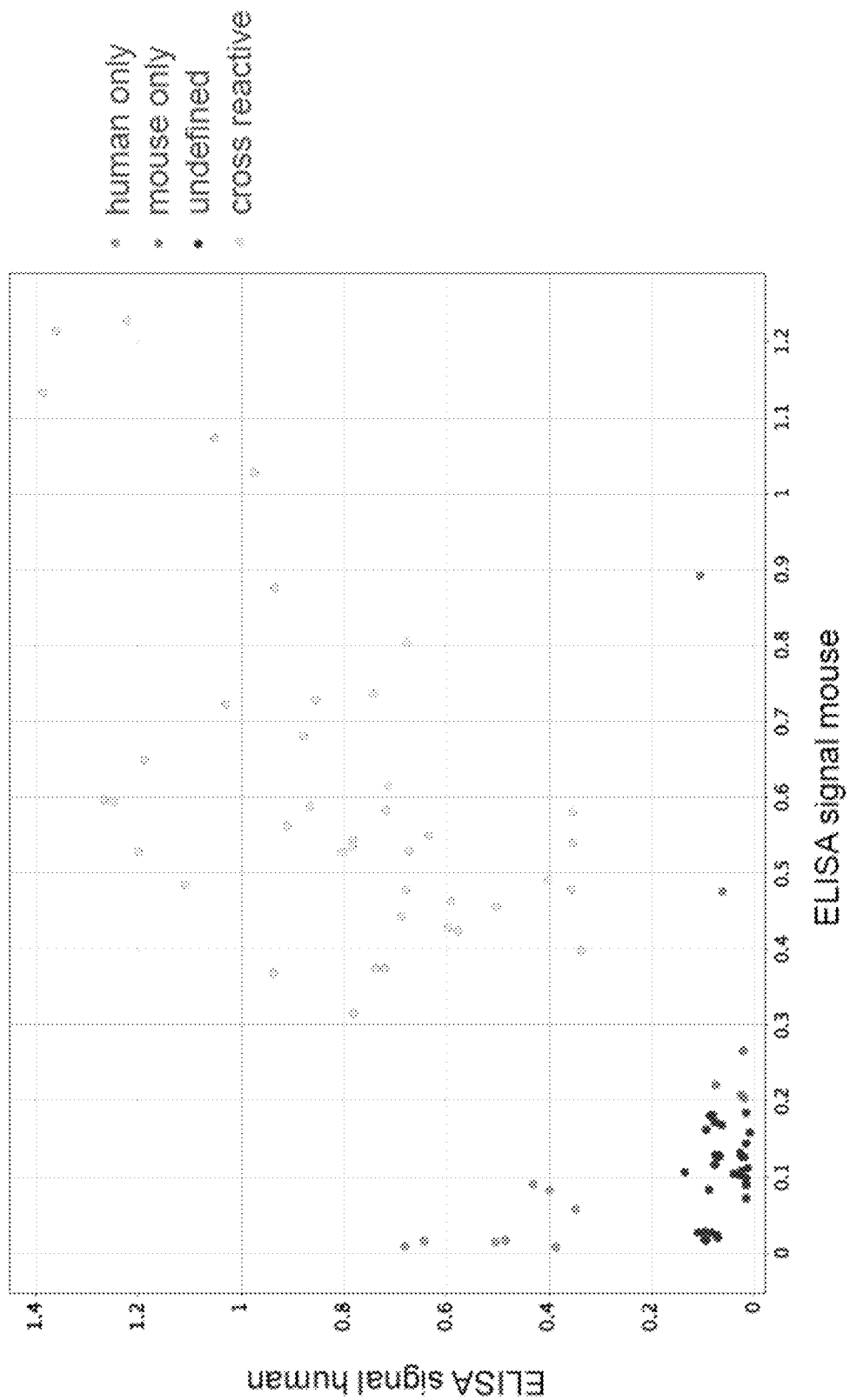
FIG. 22. Scatterplot showing strength of binding signal to human IL-11 and mouse IL-11 as determined by ELISA assay for 86 human anti-IL-11 antibody candidates.

The results of the ELISA analysis of binding to human IL-11 and murine IL-11 are shown in FIG. 22. The analysis revealed:

8 scFV capable of binding only to human IL-11;
6 scFv capable of binding to murine IL-11 only;
32 scFv displaying only weak binding to human/murine IL-11, with a high signal to noise ratio, and;
40 scFv having cross-reactivity for both human IL-11 and murine IL-11.

From these 86 scFV, 56 candidates were selected for further functional characterisation. For further analyses, the scFV were cloned into scFV-Fc format in *E. coli*.

The antibody clone designations are shown in FIG. 23.

The amino acid sequence information for the antibodies is shown in FIGS. 15 to 20.

The VH and VL sequences of the antibodies were cloned into expression vectors for the generation of scFv-Fc (human IgG1) antibodies. The vectors were transiently expressed in mammalian cells cultured in serum-free media, and isolated by protein A purification.

Example 6: Functional Characterisation of Human Anti-Human Antibodies

The antibodies described in Example 5 were analysed in in vitro assays for their ability to (i) inhibit human IL-11-mediated signalling, (ii) inhibit mouse IL-11-mediated signalling, and (iii) inhibit IL-11 trans signalling, by IL-11 in complex with IL-11RA. The affinity of the antibodies for human IL-11 was also analysed by ELISA.

6.1 Ability to Inhibit Human IL-11 Mediated Signalling

To investigate ability to neutralise human IL-11-mediated signalling, cardiac atrial human fibroblasts were cultured in wells of 96-well plates in the presence of TGFβ1 (5 ng/ml) for 24 hours, in the presence or absence of the anti-IL-11 antibodies. TGFβ1 promotes the expression of IL-11, which in turn drives the transition of quiescent fibroblasts to activated, αSMA-positive fibroblasts. It has previously been shown that neutralising IL-11 prevents TGFβ1-induced transition to activated, αSMA-positive fibroblasts.

Expression of αSMA was analysed with the Operetta High-Content Imaging System in an automated high-throughput fashion.

In non-stimulated cultures, ~29.7% (=1) of the fibroblasts were αSMA-positive, activated fibroblasts at the end of the 24 hour culture period, whilst ~52% (=1.81) of fibroblasts were αSMA-positive in cultures that were stimulated with TGFβ1 in the absence of anti-IL-11 antibodies.

Anti-IL-11 antibodies (2 μg/ml) were added to fibroblast cultures that were stimulated with TGFβ1, and at the end of the 24 hour culture period, the percentage of αSMA-positive fibroblasts was determined. The percentages were normalised based on the percentage of αSMA-positive fibroblasts observed in cultures of fibroblasts which had not been stimulated with TGFβ1.

Figure 24A:
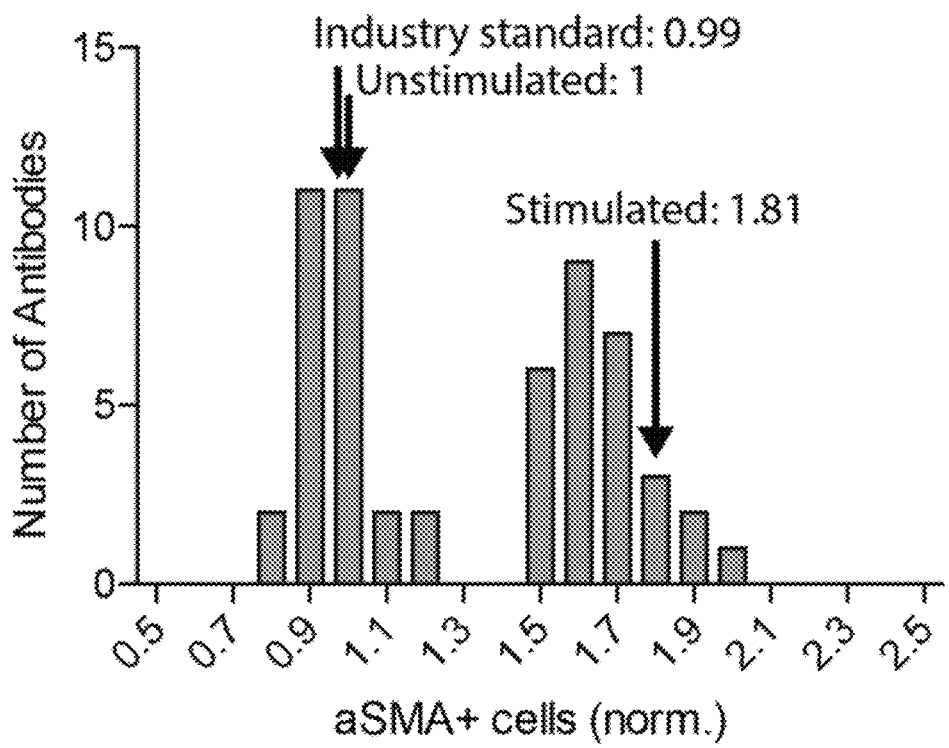
FIGS. 24A and 24B. Bar charts showing inhibition by the human anti-IL-11 antibodies of signalling mediated by IL-11 in vitro in human atrial fibroblasts, as determined by fold change in the percentage of αSMA positive cells as compared to control (unstimulated) fibroblasts, following stimulation with TGFβ1, in the presence of the human anti-IL-11 antibodies.
Figure 24B:
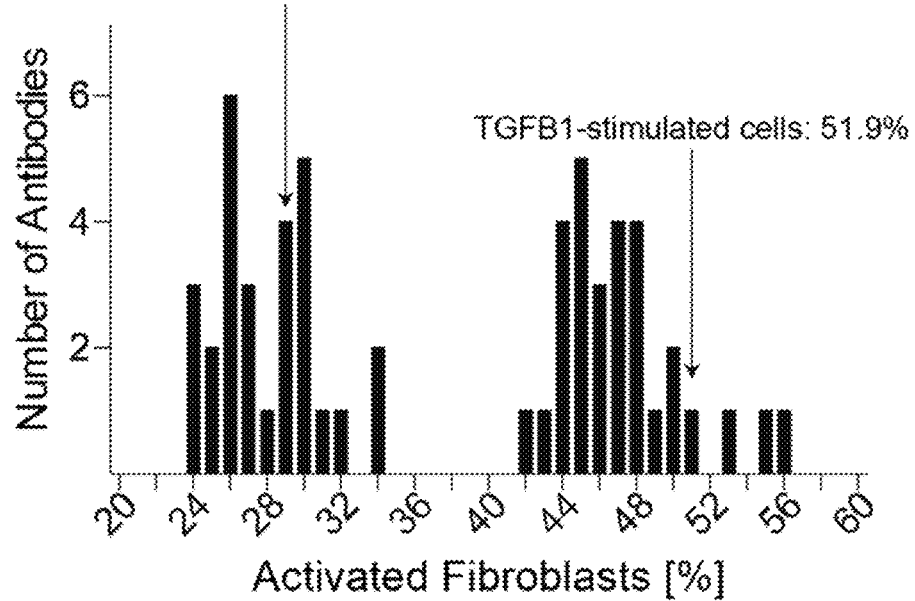

The results of the experiments are shown in FIGS. 24A, 24B and 27. 28 of the antibodies were demonstrated to be capable of neutralising signalling mediated by human IL-11.

A commercial monoclonal mouse anti-IL-11 antibody (Monoclonal Mouse IgG2A; Clone #22626; Catalog No. MAB218; R&D Systems, MN, USA) was also analysed for ability to inhibit signalling by human IL-11 in the experiments. This antibody was found to be able to reduce the percentage of activated fibroblasts to 28.3% (=0.99).

Several of the clones neutralised signalling by human IL-11 to a greater extent than the commercially available mouse anti-IL-11 antibody (industry standard): YU45-C11/A10 (#6), YU45-G1 (#11), YU45-E3 (#16), YU45-F8 (#18), YU45-F9 (#21), YU45-H10 (#22), YU45-F2 (#24), YU45-H3 (#25), YU45-G7 (#33), YU45-B6 (#36), YU45-C1 (#42), YU46-B6 (#47), YU46-E3 (#50), YU46-G8 (#54) and YU46-D3 (#56).

6.2 Ability to Inhibit Mouse IL-11 Mediated Signalling

The ability of the human antibodies to inhibit mouse IL-11-mediated signalling was also investigated, following the same procedure as described in section 6.1 above, but using mouse atrial fibroblasts instead of human atrial fibroblasts.

After 24 hours in culture, about 31.8% (=1) of non-stimulated cells in culture were activated fibroblasts. Stimulation with TGFβ1 resulted in a ~2-fold increase in the percentage of activated fibroblasts (68.8%=2.16) as compared to non-stimulated cultures.

Figure 25A:
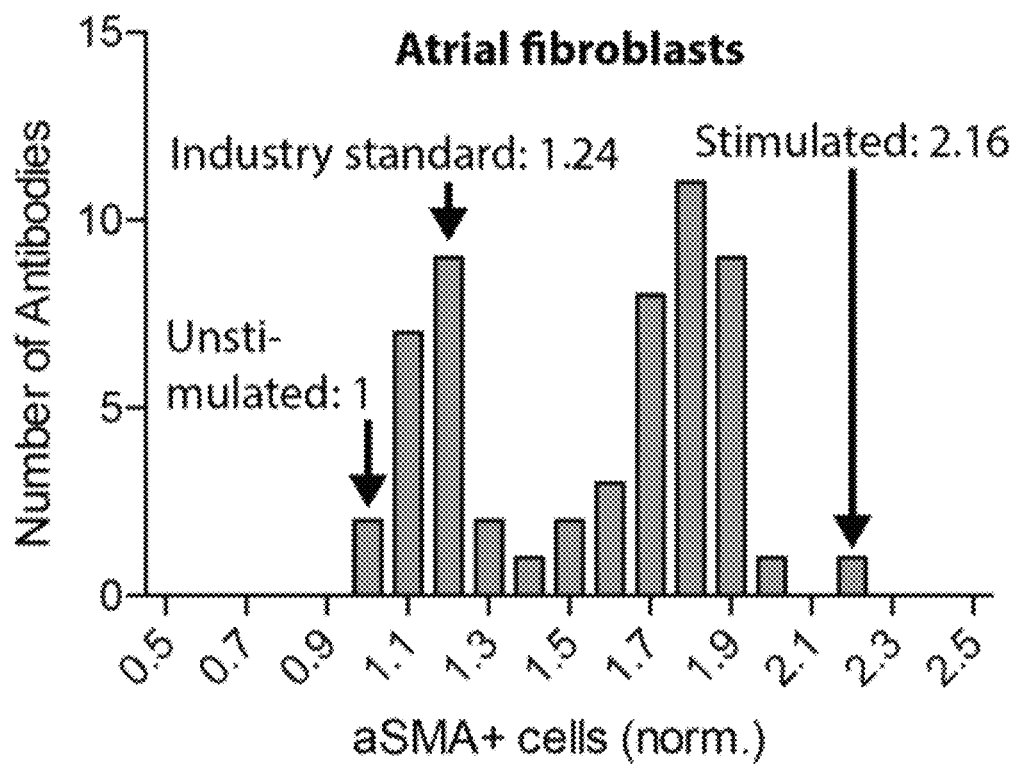
FIGS. 25A and 25B. Bar chart showing inhibition by the human anti-IL-11 antibodies of signalling mediated by IL-11 in vitro in (FIG. 25A) mouse atrial fibroblasts and (FIG. 25B) mouse dermal fibroblasts, as determined by fold change in the percentage of αSMA positive cells as compared to control (unstimulated) fibroblasts, following stimulation with TGFβ1, in the presence of the human anti-IL-11 antibodies.
Figure 25B:
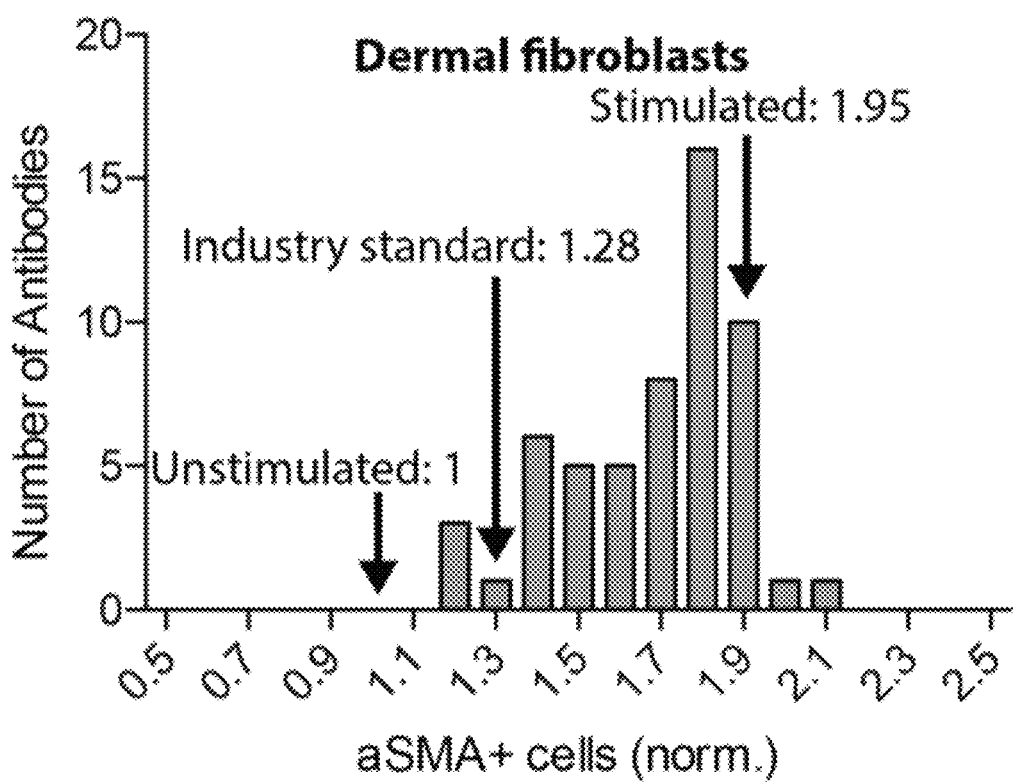

The results of the experiments are shown in FIGS. 25 and 27. The antibodies were demonstrated to be capable of neutralising signalling mediated by mouse IL-11. Monoclonal Mouse IgG2A clone #22626, catalog No. MAB218 anti-IL-11 antibody was also analysed for ability to inhibit signalling by mouse IL-11. This antibody was found to be able to reduce the percentage of activated fibroblasts to 39.4% (=1.24).

Several of the clones neutralised signalling by IL-11 in mouse atrial fibroblasts to a greater extent than the commercially available mouse anti-IL-11 antibody (industry standard): YU33-B4/YU45-G2/A3 (#3), YU45-H11/D12 (#9), YU45-G1 (#11), YU45-D2/H2/C7/F3/C9/E1/E9/C10/G3/H9/C5/A2/A5 (#14), YU45-B3 (#15), YU45-F8 (#18), YU45-H10 (#22), YU46-A10 (#23), YU45-A8/C6 (#27), YU45-D9/D3 (#31), YU45-B6 (#36), YU45-C1 (#42), YU46-A8 (#45), YU46-C1 (#48), YU46-H8 (#52), YU46-G8 (#54) and YU46-D3 (#56).

The ability of the human antibodies to inhibit mouse IL-11-mediated signalling was also investigated using mouse skin fibroblasts.

The results of the experiments are shown in FIG. 27. The antibodies were demonstrated to be capable of neutralising signalling mediated by mouse IL-11.

Several of the clones neutralised signalling by IL-11 in mouse skin fibroblasts to a greater extent than the commercially available mouse anti-IL-11 antibody (industry standard): YU45-B6 (#36), YU45-C1 (#42), and YU46-H8 (#52).

6.3 Ability to Inhibit IL-11 Trans Signalling, by IL-11 in Complex with IL-11RA

Trans signalling is recognised as a major aspect of IL-6 signalling, where a complex of IL-6 and soluble IL-6Rα can activate cells that express gp130, but lack the IL-6 receptor (Hunter and Jones, 2015 Nature Immunology 16, 448-457).

It has recently been suggested that trans signalling by a complex of IL-11 and soluble IL-11RA is also important for IL-11 biology (Lokau et al., Cell Reports (2016) 14, 1761-1773). Using a recombinant fusion protein of IL-11 and IL-11Rα (as described in Pflanz et al., Febs Lett (1999) 450: 117-122), anti-IL-11 antibodies were screened for the ability to inhibit trans signalling mediated by IL-11:IL-11Rα complex.

Importantly, antibodies which are capable of inhibiting both classical IL-11 mediated signalling and IL-11 trans signalling by IL-11:IL-11Rα complex are able to inhibit all known modes of IL-11/IL-11R signalling.

The IL-11:IL-11Rα fusion protein (hereafter referred to as hyper IL-11) consists of the extracellular domain of the IL-11 receptor alpha (IL-11Rα) linked to IL-11.

Figure 42A:
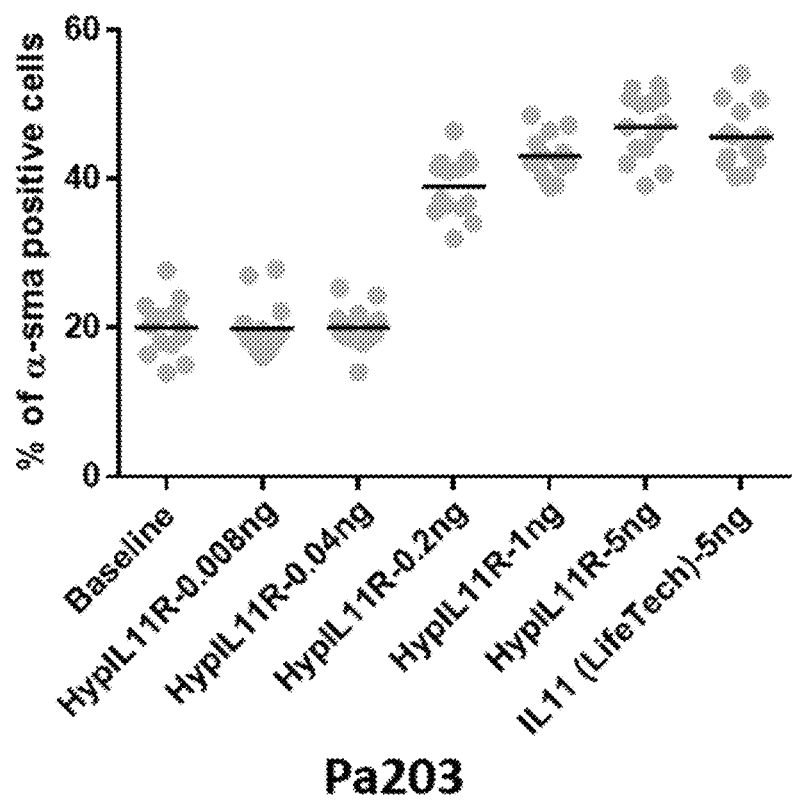
FIGS. 42A and 42B. Graphs showing fibroblast activation in response to hyper IL-11. Cells were stimulated with the indicated amount (in ng/ml) of hyper IL-11 or recombinant IL-11, and fibroblast activation was measured by analysis of the percentage of α-SMA positive cells.
Figure 42B:
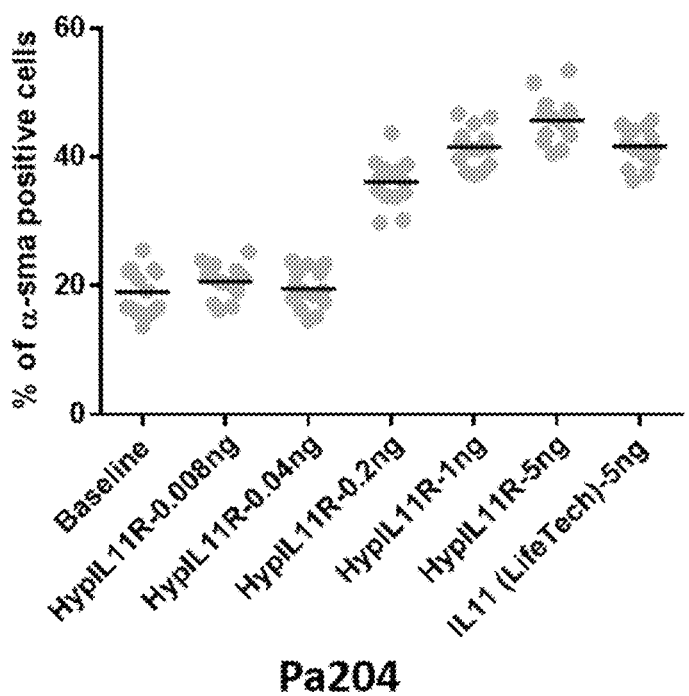

Hyper IL-11 was found to be a more potent activator of human fibroblasts than recombinant IL-11 protein. Briefly, in two separate experiments human fibroblasts were cultured without stimulation (Baseline), in the presence of different amounts of hyper IL-11 (0.008 ng/ml, 0.04 ng/ml, 0.2 ng/ml, 1 ng/ml and 5 ng/ml), or 5 ng/ml recombinant human IL-11 obtained from a commercial source, and fibroblast activation was analysed by determining the percentage of αSMA-positive cells as described herein. The results are shown in (FIGS. 42A and 42B). Hyper-IL-11 activated fibroblasts in a dose-dependent fashion, and was a more potent activator than IL-11.

The IL-11:IL-11Rα fusion protein was prepared as follows:
DNA encoding IL-11:IL-11Rα fusion protein (i.e. SEQ ID NO:265) was cloned into pTT5 vector, and transfected into 293-6E cells in culture in serum-free FREE-STYLE™ 293 Expression Medium (Thermo Fisher Scientific).
Cells were maintained in Erlenmeyer Flasks (Corning Inc.) at 37° C. with 5% $CO_2$ on an orbital shaker (VWR Scientific).
Cell culture supernatants were collected on day 6 were used for purification.
Cell culture supernatant was loaded onto an affinity purification column.
After washing and elution with appropriate buffer, the eluted fractions were pooled and buffer exchanged to final formulation buffer.
The purified IL-11:IL-11Rα fusion protein was analyzed by SDS-PAGE, Western blot to confirm molecular weight and purity.

```
DNA encoding IL-11:IL-11Rα fusion protein (SEQ ID
NO: 265):
GAATTCCCGCCGCCACCATGGGCTGGTCCTGCATCATCCTGTTTCTGGTGG

CCACAGCCACCGGCGTGCACTCTCCACAGGCTTGGGGACCTCCAGGCGTGC

AGTATGGCCAGCCTGGCAGATCCGTGAAGCTGTGCTGTCCTGGCGTGACAG

CTGGCGACCCTGTGTCCTGGTTCAGAGATGGCGAGCCCAAGCTGCTGCAGG

GCCCAGATTCTGGACTGGGCCACGAACTGGTGCTGGCCCAGGCCGATTCTA

CCGACGAGGGCACCTACATCTGCCAGACCCTGGATGGCGCCCTGGGCGGAA

CAGTGACACTGCAGCTGGGCTACCCTCCCGCCAGACCTGTGGTGTCTTGTC

AGGCCGCCGACTACGAGAACTTCAGCTGCACATGGTCCCCCAGCCAGATCA

GCGGCCTGCCCACCAGATACCTGACCAGCTACCGGAAGAAAACCGTGCTGG

GCGCCGACAGCCAGAGAAGAAGCCCTTCTACAGGCCCTGGCCCTGCCCTC

AGGATCCTCTGGGAGCTGCCAGATGTGTGGTGCACGGCGCCGAGTTCTGGT

CCCAGTACCGGATCAACGTGACCGAAGTGAACCCCCTGGGCGCCTCCACAA

GACTGCTGGATGTGTCCCTGCAGAGCATCCTGCGGCCCGATCCTCCACAGG

GCCTGAGAGTGGAAAGCGTGCCCGGCTACCCCAGAAGGCTGAGAGCCAGCT

GGACATACCCCGCCTCTTGGCCTTGCCAGCCCCACTTCCTGCTGAAGTTTC

GGCTGCAGTACCGGCCAGCCCAGCACCCTGCTTGGAGCACAGTGGAACCTG

CCGGCCTGGAAGAAGTGATCACAGACGCCGTGGCCGGACTGCCTCATGCTG
```

-continued
```
TGCGGGTGTCCGCCAGAGACTTTCTGGATGCCGGCACCTGGTCTACCTGGT

CCCCAGAAGCCTGGGGCACACCTTCTACTGGCGGACCTGCTGGACAGTCTG

GCGGAGGCGGAGGAAGTGGCGGAGGATCAGGGGGAGGATCTGTGCCTGGAC

CTCCTCCAGGACCCCCTAGAGTGTCCCCAGATCCTAGGGCCGAGCTGGACT

CTACCGTGCTGCTGACCAGATCCCTGCTGGCCGACACAAGGCAGCTGGCTG

CCCAGCTGAGAGACAAGTTCCCCGCCGACGGCGACCACAACCTGGATAGCC

TGCCTACCCTGGCCATGTCTGCTGGCGCACTGGGGGCTCTGCAGCTGCCTG

GGGTGCTGACTAGACTGAGAGCCGACCTGCTGAGCTACCTGCGGCATGTGC

AGTGGCTGAGAAGGGCTGGCGGCAGCAGCCTGAAAACCCTGGAACCTGAGC

TGGGCACACTGCAGGCCAGACTGGACAGACTGCTGCGCAGACTGCAGCTGC

TGATGAGCAGACTGGCTCTGCCCCAGCCTCCTCCTGACCCTCCTGCTCCTC

CACTGGCTCCTCCAAGCTCTGCTTGGGGCGGAATTAGAGCCGCCCACGCCA

TTCTGGGAGGCCTGCACCTGACACTGGATTGGGCAGTGCGGGCCTGCTGC

TGCTGAAAACCAGACTGCACCACCACCATCACCACTGATAAGCTT
```

Amino acid sequence of IL-11:IL-11Rα fusion protein (SEQ ID NO: 266):
```
MGWSCIILFLVATATGVHSPQAWGPPGVQYGQPGRSVKLCCPGVTAGDPVS

WFRDGEPKLLQGPDSGLGHELVLAQADSTDEGTYICQTLDGALGGTVTLQL

GYPPARPVVSCQAADYENFSCTWSPSQISGLPTRYLTSYRKKTVLGADSQR

RSPSTGPWPCPQDPLGAARCVVHGAEFWSQYRINVTEVNPLGASTRLLDVS

LQSILRPDPPQGLRVESVPGYPRRLRASWTYPASWPCQPHFLLKFRLQYRP

AQHPAWSTVEPAGLEEVITDAVAGLPHAVRVSARDFLDAGTWSTVVSPEAW

GTPSTGGPAGQSGGGGSGGGSGGGSVPGPPPGPPRVSPDPRAELDSTVLL

TRSLLADTRQLAAQLRDKFPADGDHNLDSLPTLAMSAGALGALQLPGVLTR

LRADLLSYLRHVQWLRRAGGSSLKTLEPELGTLQARLDRLLRRLQLLMSRL

ALPQPPPDPPAPPLAPPSSAWGGIRAAHAILGGLHLTLDWAVRGLLLLKTR

LHHHHHH
```

Figure 43:
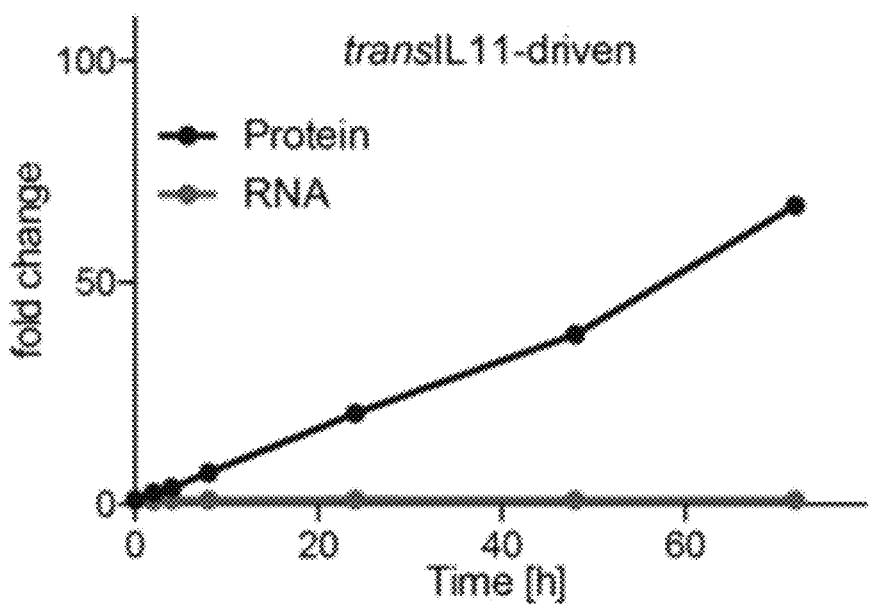
FIG. 43. Graph showing induction of IL-11 secretion in primary fibroblasts by hyper IL-11. Cells were stimulated with hyper IL-11, and IL-11 RNA and native IL-11 protein levels were measured in the cell culture supernatant by ELISA at the indicated time points.

Fibroblasts cultured in vitro and stimulated with hyper IL-11 were shown to upregulate IL-11 protein expression, as determined by ELISA (FIG. 43). Interestingly, an increase in IL-11 RNA level was not detected in response to stimulation with hyper IL-11. Unlike TGFβ1, which increases IL-11 expression at both the RNA and the protein level, hyper IL-11 seems to upregulate IL-11 expression only post-transcriptionally, at the protein level.

The ability of the human antibodies to inhibit signalling mediated by hyper IL-11 was investigated.

Human atrial fibroblasts derived from 3 individuals were incubated for 24 h with hyper IL-11 (0.2 ng/ml) in the presence of neutralising anti-IL-11 antibody or isotype control antibody. Following incubation, cells were stained for αSMA to determine the fraction of myofibroblasts.

After 24 hours in culture, about 26.5.% (=1) of non-stimulated cells in culture were activated fibroblasts. Stimulation with hyper IL-11 resulted in a ~2-fold increase in the percentage of activated fibroblasts (56.4%=2.13) as compared to non-stimulated cultures.

Figure 26:
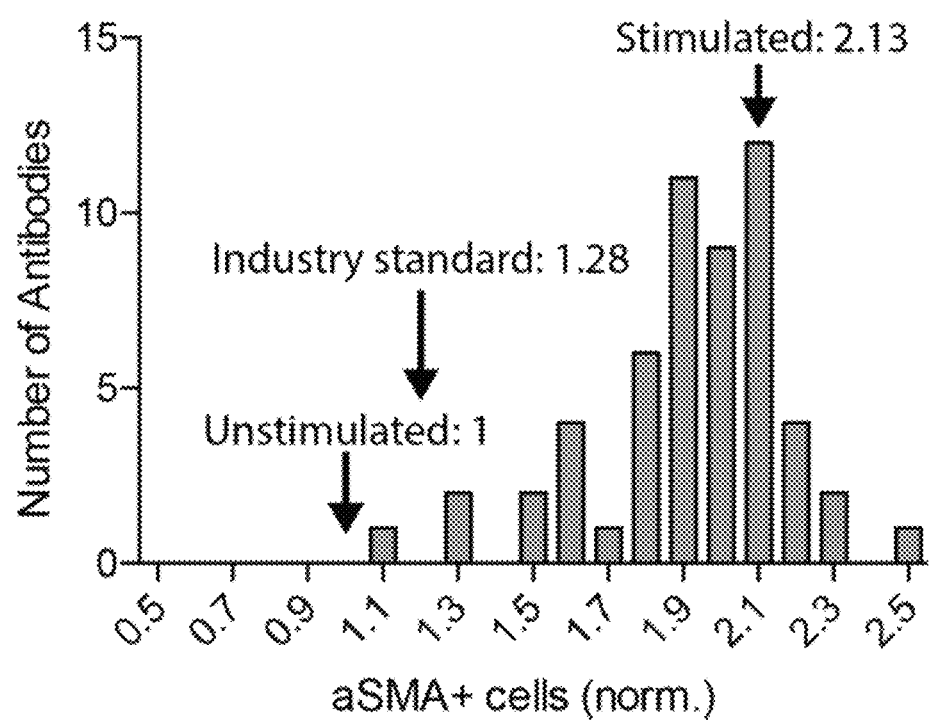
FIG. 26. Bar chart showing inhibition by the human anti-IL-11 antibodies of IL-11 trans signalling mediated by hyper IL-11 in vitro in human atrial fibroblasts, as determined by fold change in the percentage of αSMA positive cells as compared to control (unstimulated) fibroblasts, following stimulation with hyper IL-11, in the presence of the human anti-IL-11 antibodies.
Figure 28A:
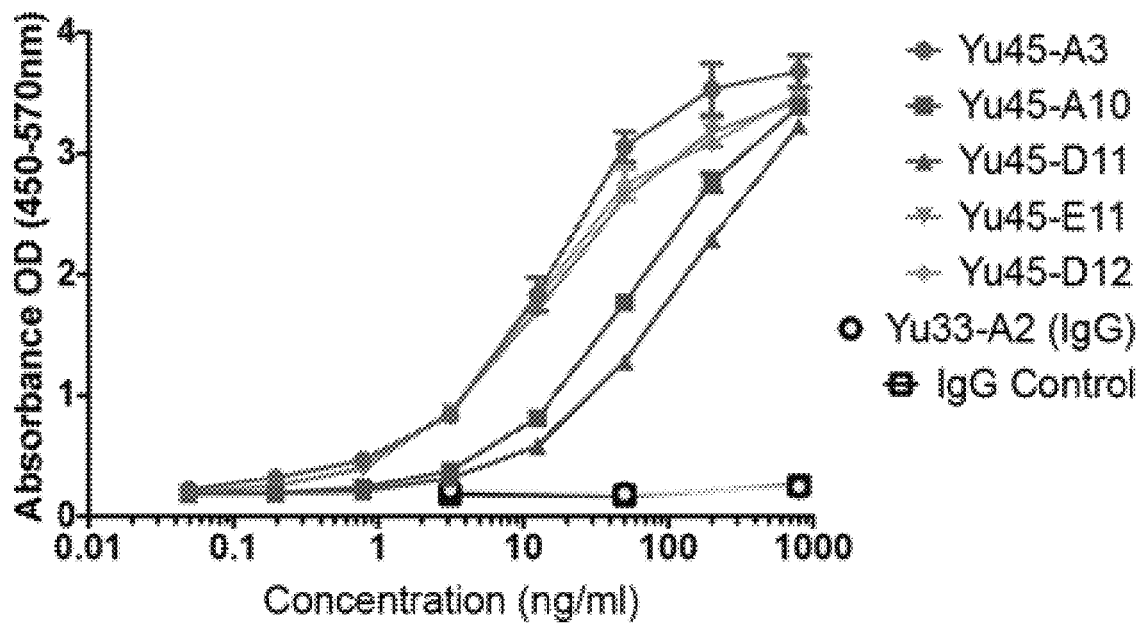
FIGS. 28A to 28F. Graphs showing binding of human anti-IL-11 antibodies to human IL-11 as determined by ELISA analysis.
Figure 28B:
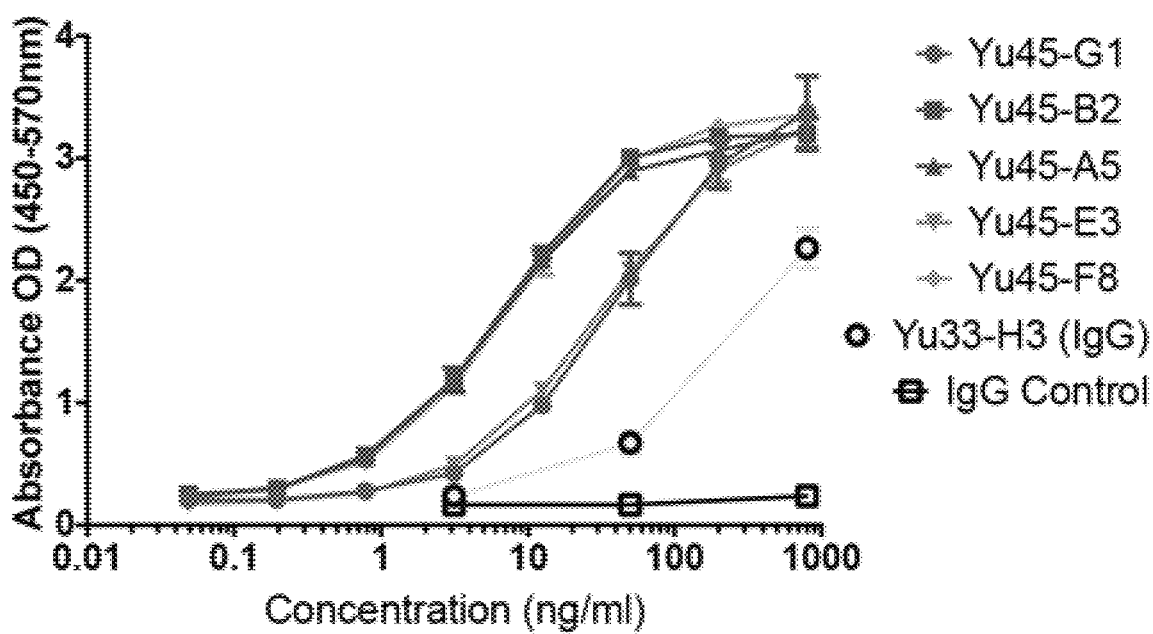
Figure 28C:
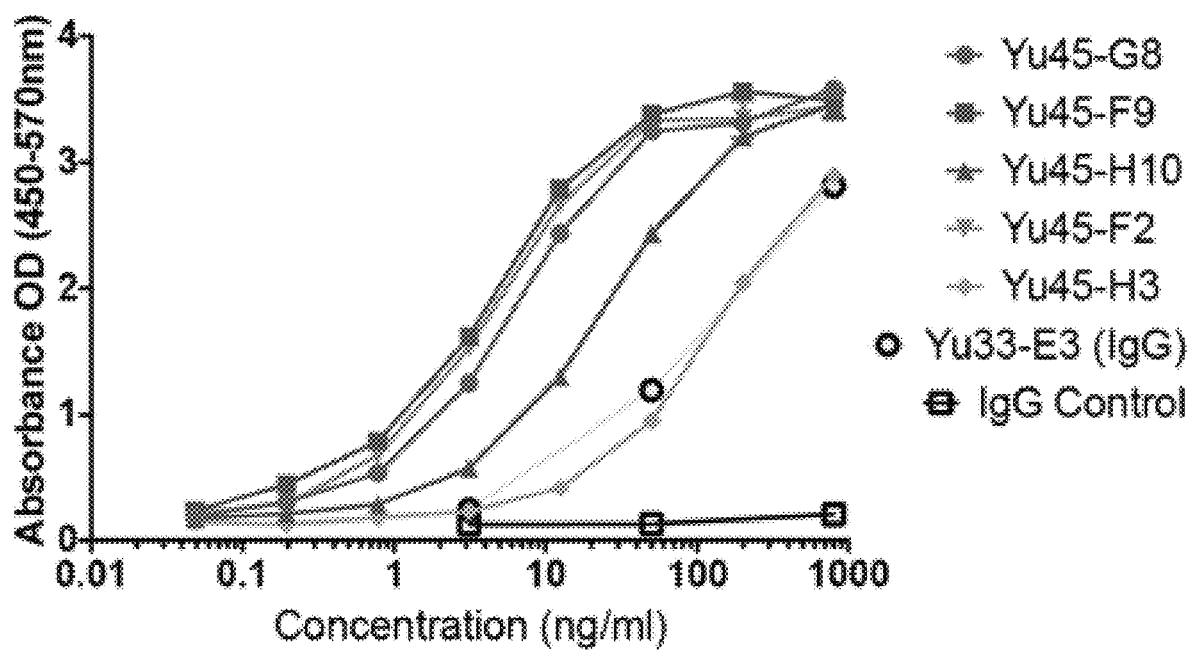
Figure 28D:
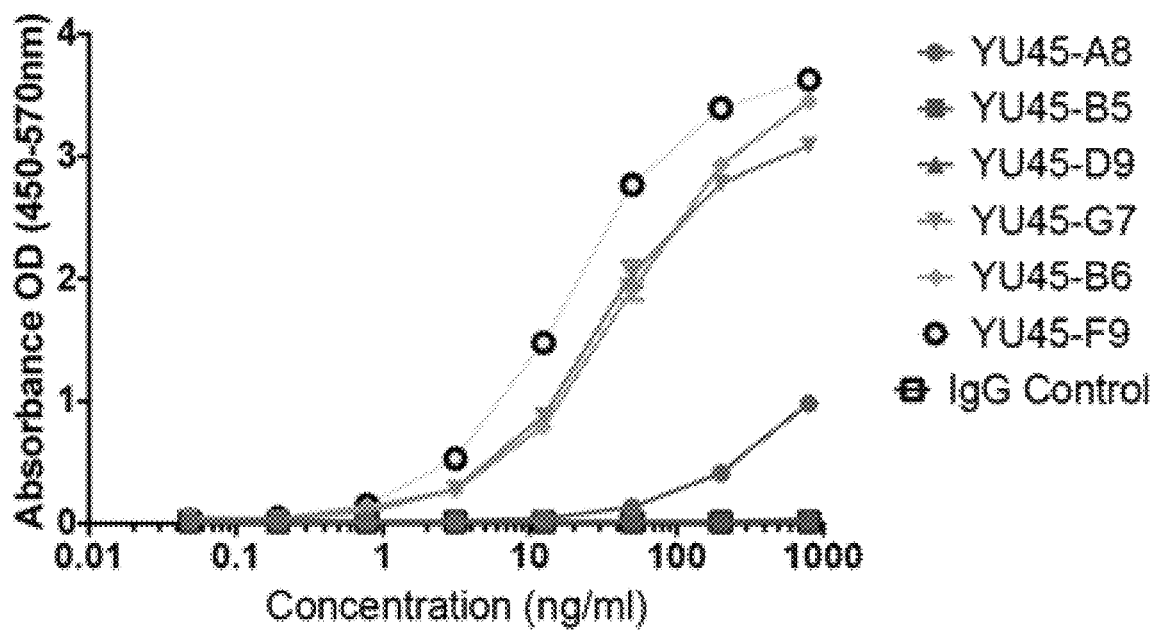
Figure 28E:
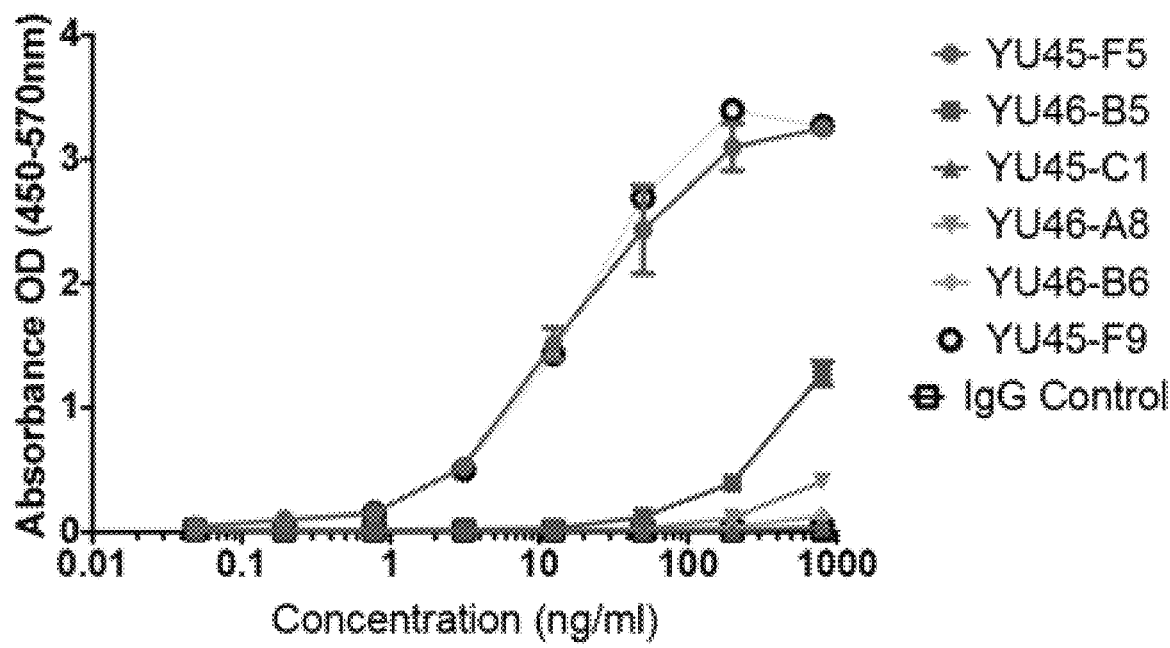
Figure 28F:
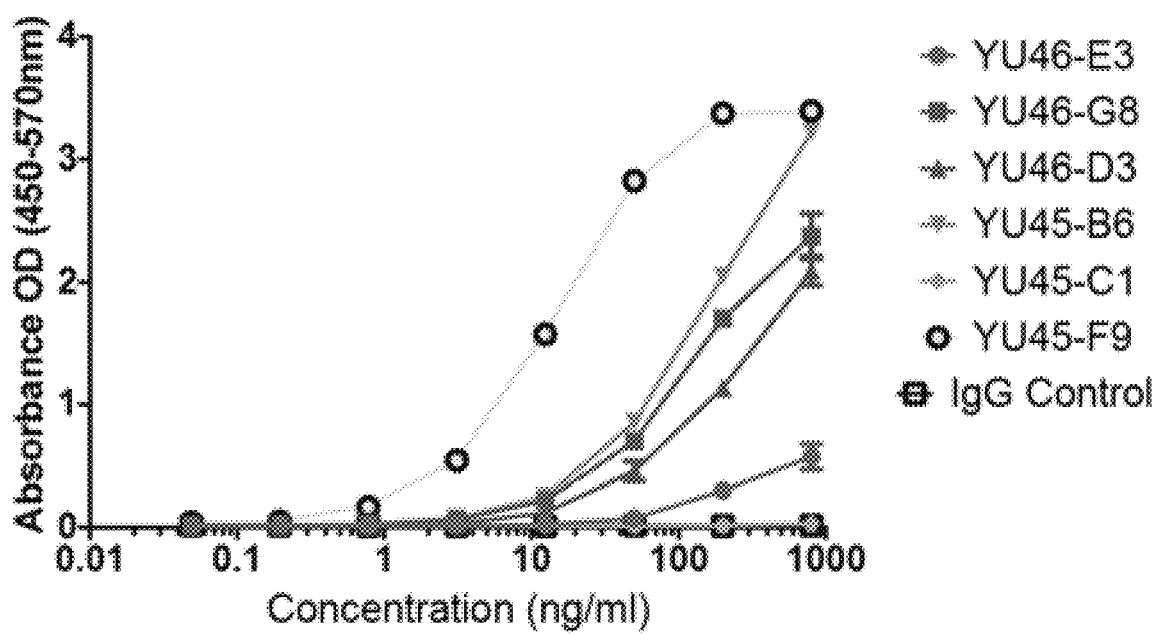

The results of the experiments are shown in FIGS. 26 and 27. The antibodies were demonstrated to be capable of neutralising signalling mediated by hyper IL-11 (i.e. IL-11 trans signalling).

Monoclonal Mouse IgG2A clone #22626, catalog No. MAB218 anti-IL-11 antibody was also analysed for ability to inhibit signalling by hyper IL-11. This antibody was found to be able to reduce the percentage of activated fibroblasts to 33.8% (=1.28).

Clone YU33-B4/YU45-G2/A3 (#3) neutralised IL-11 trans signalling by hyper IL-11 to a greater extent than the commercially available mouse anti-IL-11 antibody (industry standard).

The results of the experimental procedures described in hereinabove identified antibody clones which possess functional properties which are relevant for their pre-clinical and clinical development of antibodies capable of inhibiting IL-11/IL-11-R signalling.

Clones YU33-B4/YU45-G2/A3 (#3), YU45-E3 (#16), YU45-F2 (#24), YU45-F5 (#39), YU46-A8 (#45) and YU46-G8 (#54) were identified as particularly promising candidates, showing good ability to inhibit signalling by both human and mouse IL-11, and good inhibition of IL-11 trans signalling.

6.4 Analysis of Antibody Affinity for Human IL-11

The human anti-human IL-11 antibodies were analysed for their affinity of binding to human IL-11 by ELISA assay.

Recombinant human IL-11 was obtained from Genscript and Horseradish peroxidase (HRP)-conjugated anti-human IgG (Fc-specific) antibody was obtained from Sigma. Corning 96-well ELISA plates were obtained from Sigma. Pierce 3,3',5,5'-tetramethylbenzidine (TMB) ELISA substrate kit was obtained from Life Technologies (0.4 g/mL TMB solution, 0.02% hydrogen peroxide in citric acid buffer). Bovine serum albumin and sulphuric acid was obtained from Sigma. Wash buffer comprised 0.05% Tween-20 in phosphate buffered saline (PBS-T). ScFv-Fc antibodies were generated as described in Example 5. Purified mouse and human IgG controls were purchased from Life Technologies. Tecan Infinite 200 PRO NanoQuant was used to measure absorbance.

Criss-cross serial dilution analysis was performed as described by Hornbeck et al., (2015) Curr Protoc Immunol 110, 2.1.1-23) to determine the optimal concentration of coating antigen, primary and secondary antibodies.

An indirect ELISA was performed to assess the binding affinity of primary ScFv-Fc antibodies at 50% of effective concentration (EC50) as previously described (Unverdorben et al., (2016) MAbs 8, 120-128.). ELISA plates were coated with 1 µg/mL of recombinant human IL-11 overnight at 4° C. and remaining binding sites were blocked with 2% BSA in PBS. ScFv-Fc antibodies were diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-antibody binding was performed with 15.625 ng/mL of HRP-conjugated anti-human IgG (Fc-specific) antibody. Following 2 hours of incubation with the detection antibody, 100 µl of TMB substrate was added for 15 mins and chromogenic reaction stopped with 100 µl of 2 M H2SO4. Absorbance reading was measured at 450 nm with reference wavelength correction at 570 nm. Data were fitted with Graph Pad Prism software with log transformation of antibody concentrations followed by non-linear regression analysis with the asymmetrical (five-parameter) logistic dose-response curve to determine individual EC50 values.

The same materials and procedures as described above were performed to determine the affinity of binding for the murine monoclonal anti-IL-11 antibodies, with the exception that HRP-conjugated anti-mouse IgG (H&L) was used instead of HRP-conjugated anti-human IgG.

The same materials and procedures as described above were performed to determine the affinity of binding for the human monoclonal anti-IL-11 antibodies and murine monoclonal anti-IL-11 antibodies to recombinant murine IL-11 obtained from Genscript.

The results of the ELISA assays are shown in FIG. 28A to 28F, and were used to determine $EC_{50}$ values for the antibodies which are shown in FIG. 29.

6.5 Ability to Inhibit Human IL-11 Mediated Signalling in a Variety of Tissues

Ability of the antibodies to neutralise IL-11-mediated signalling and trans signalling in fibroblasts obtained from a variety of different tissues is investigated, essentially as described in sections 6.1 and 6.3 except that instead of cardiac atrial human fibroblasts, human fibroblasts derived from liver, lung, kidney, eye, skin, pancreas, spleen, bowel, brain, and bone marrow are used for the experiments.

Anti-IL-11 antibodies are demonstrated to be capable of neutralising signalling in fibroblasts derived from the various different tissues, as determined by observation of a relative decrease in the proportion of αSMA-positive fibroblasts at the end of the 24 h culture period in the presence of the anti-IL-11 antibodies as compared to culture in the absence of the antibodies.

Example 7: Light Chain Shuffling of Human Anti-Human IL-11 Antibodies

Human IL-11 antibodies are affinity-matured by light chain shuffling to obtain antibodies having improved affinity for IL-11.

Chain shuffling to improve antibody affinity is a well-known technique in the field of antibody technology, and is described in detail in Marks, Antibody Affinity Maturation by Chain Shuffling, Antibody Engineering Methods and Protocols, Humana Press (2004) Vol. 248, pp 327-343, incorporated by reference herein. In particular, Light chain shuffling is described in detail at sections 3.1 and 3.2 thereof.

The heavy chain variable regions of the human anti-human IL-11 antibodies are combined with a repertoire of light chain variable region partners to identify new VL/VH combinations having high affinity for IL-11.

Figures 30, 31:
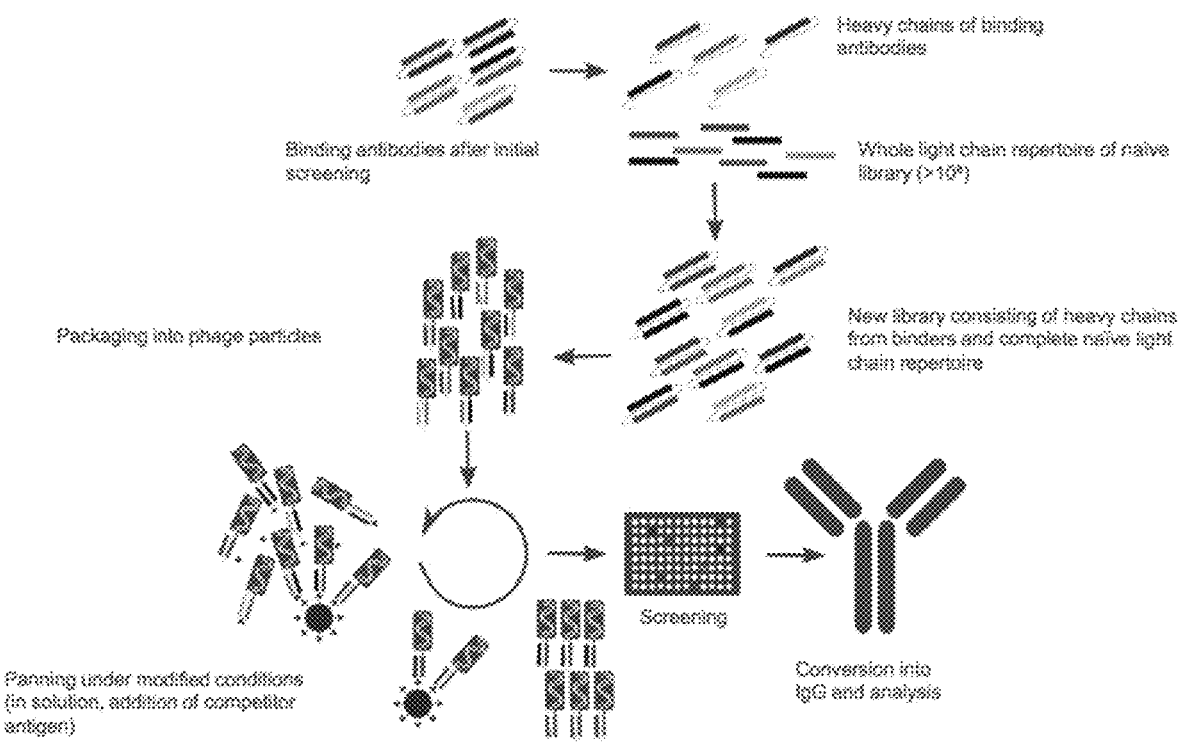
FIG. 30. Schematic representation of the process of antibody light chain shuffling.
FIG. 31. Table summarising the 16 mouse anti-human IL-11 antibody clones.

A schematic representation of light chain shuffling is shown in FIG. 30. Briefly, nucleic acid encoding the VH domain for an antibody is cloned into a phage display vector comprising a repertoire of VL chains, and scFv comprising new VH/VL combinations are analysed for binding to human IL-11 by ELISA.

The scFv having VH/VL combinations displaying the strongest binding affinity for IL-11 are then analysed for cross-reactivity against murine IL-11.

The VH/VL sequences of the scFv are then cloned into expression vectors for the generation of scFv-Fc (human IgG1) antibodies, the vectors are transiently expressed in mammalian cells cultured in serum-free media, and isolated by protein A purification.

Example 8: Mouse Monoclonal Anti-Human IL-11 Antibodies

Mouse monoclonal antibodies directed against human IL-11 protein were also generated, as follows.

cDNA encoding the amino acid for human IL-11 was cloned into expression plasmids (Aldevron GmbH, Freiburg, Germany).

Mice were immunised by intradermal application of DNA-coated gold-particles using a hand-held device for particle-bombardment ("gene gun"). Serum samples were collected from mice after a series of immunisations, and tested in flow cytometry on HEK cells which had been transiently transfected with human IL-11 expression plasmids (cell surface expression of human IL-11 by transiently transfected HEK cells was confirmed with anti-tag antibodies recognising a tag added to the N-terminus of the IL-11 protein).

Antibody-producing cells were isolated from the mice and fused with mouse myeloma cells (Ag8) according to standard procedures.

Hybridomas producing antibodies specific for IL-11 were identified by screening for ability to bind to IL-11 expressing HEK cells by flow cytometry.

Cell pellets of positive hybridomas cells were prepared using an RNA protection agent (RNAlater, cat. #AM7020 by ThermoFisher Scientific) and further processed for sequencing of the variable domains of the antibodies.

In total, 16 mouse monoclonal anti-human IL-11 antibodies were prepared (FIG. 31).

Example 9: Functional Characterisation of Mouse Monoclonal Anti-Human IL-11 Antibodies 9.1 Ability to Inhibit Human IL-11 Mediated Signalling The ability of the murine monoclonal anti-human IL-11 antibodies to inhibit signalling mediated by human IL-11 was investigated using the same assay as described in Example 6.1 above.

Figure 32:
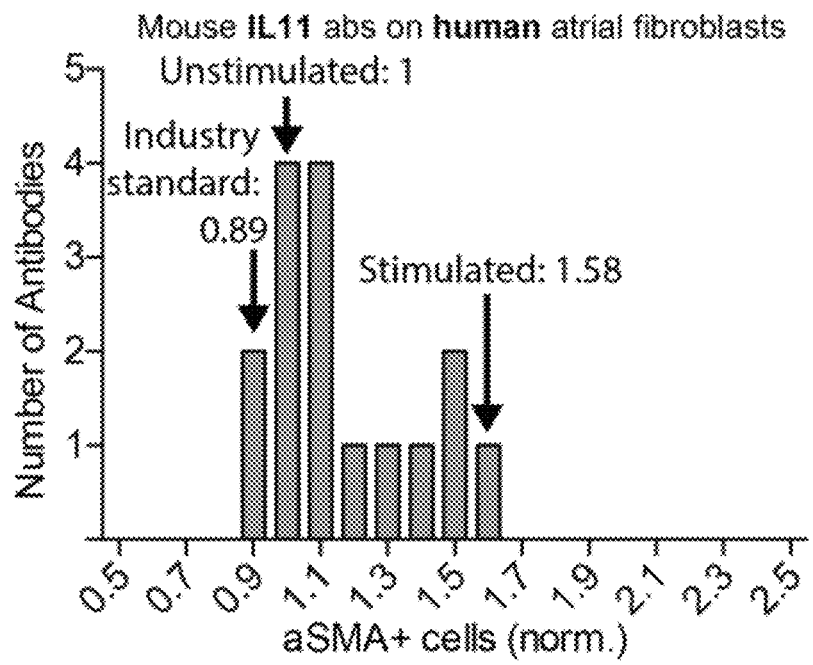
FIG. 32. Bar chart showing inhibition by the mouse anti-IL-11 antibodies of signalling mediated by IL-11 in vitro in human atrial fibroblasts, as determined by fold change in the percentage of αSMA positive cells as compared to control (unstimulated) fibroblasts, following stimulation with TGFβ1, in the presence of the mouse anti-IL-11 antibodies.
Figures 34, 35:
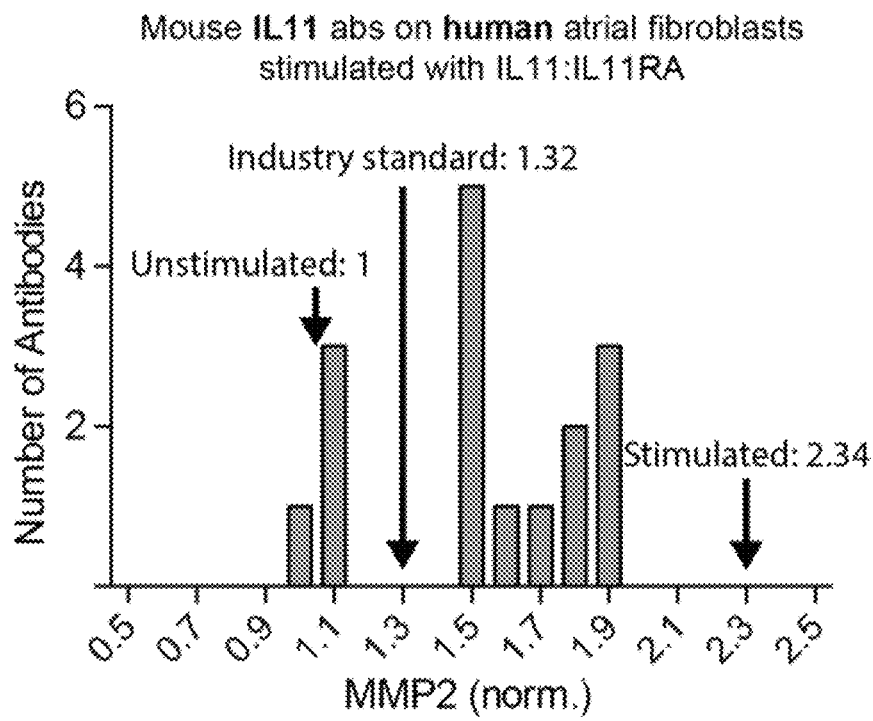
FIG. 34. Bar chart showing inhibition by the mouse anti-IL-11 antibodies of IL-11 trans signalling mediated by hyper IL-11 in vitro in human atrial fibroblasts, as determined by fold change in the amount of MMP2 in the cell culture supernatant as compared to control (unstimulated) fibroblasts, following stimulation with hyper IL-11, in the presence of the mouse anti-IL-11 antibodies.
FIG. 35. Table summarising the fold-change data of FIGS. 32 to 34 for the 16 mouse anti-IL-11 antibodies. Antibody candidates numbered 1 to 16 correspond to clone designations as indicated in FIG. 31. Industry standard is monoclonal mouse anti-IL-11 IgG2A; Clone #22626; Catalog No. MAB218; R&D Systems, MN, USA.

The results of the Experiments are shown in FIGS. 32 and 35. The antibodies were demonstrated to be capable of neutralising signalling mediated by human IL-11.

A commercial monoclonal mouse anti-IL-11 antibody (Monoclonal Mouse IgG2A; Clone #22626; Catalog No. MAB218; R&D Systems, MN, USA) was also analysed for ability to inhibit signalling by human IL-11 in the experiments. This antibody was found to be able to reduce the percentage of activated fibroblasts to 0.89 times.

Clone A7 (BSN-3C11) was found to neutralise signalling by human IL-11 to a greater extent than the commercially available mouse anti-IL-11 antibody (industry standard).

9.2 Ability to Inhibit Mouse IL-11 Mediated Signalling

The ability of the murine monoclonal anti-human IL-11 antibodies to inhibit signalling mediated by murine IL-11 was investigated using the same assay as described in Example 6.2 above, but using mouse atrial fibroblasts instead of mouse dermal fibroblasts.

Figure 33:
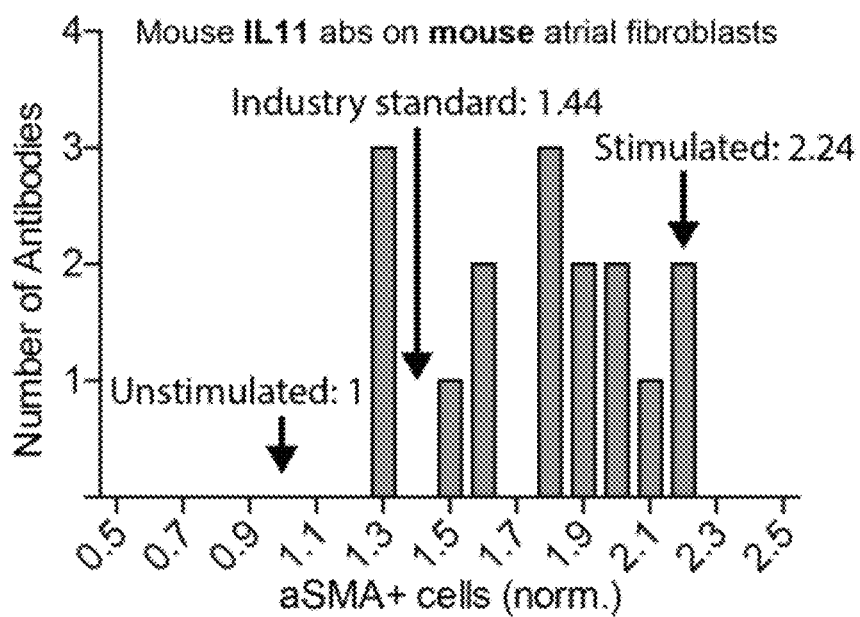
FIG. 33. Bar chart showing inhibition by the mouse anti-IL-11 antibodies of signalling mediated by IL-11 in vitro in mouse atrial fibroblasts, as determined by fold change in the percentage of αSMA positive cells as compared to control (unstimulated) fibroblasts, following stimulation with TGFβ1, in the presence of the mouse anti-IL-11 antibodies.

The results of the Experiments are shown in FIGS. 33 and 35. The antibodies were demonstrated to be capable of neutralising signalling mediated by murine IL-11.

A commercial monoclonal mouse anti-IL-11 antibody (Monoclonal Mouse IgG2A; Clone #22626; Catalog No. MAB218; R&D Systems, MN, USA) was also analysed for ability to inhibit signalling by human IL-11 in the experiments. This antibody was found to be able to reduce the percentage of activated fibroblasts to 43.0% (=1.44).

Several of the clones neutralised signalling by murine IL-11 to a greater extent than the commercially available mouse anti-IL-11 antibody (industry standard): A3 (BSN-2E1), A5 (BSN-2G6) and A6 (BSN-3C6).

9.3 Ability of Mouse Anti-IL-11 Antibodies to Inhibit IL-11 Trans Signalling, by IL-11 in Complex with IL-11RA The ability of the mouse anti-IL-11 antibodies to inhibit signalling mediated by hyper IL-11 was investigated.

Human atrial fibroblasts were incubated for 24 h with hyper IL-11 (0.2 ng/ml) in the presence of anti-IL-11 antibodies (2 μg/ml) or isotype control antibody. Following incubation, cell culture supernatant was analysed for MMP2. Stimulation with hyper IL-11 results in an increase in the secretion of MMP2 as compared to non-stimulated cultures.

The results of the experiments are shown in FIGS. 34 and 35. The mouse anti-IL-11 antibodies were found to be capable of neutralising signalling mediated by hyper IL-11 (i.e. IL-11 trans signalling), and several were found to be capable of inhibiting trans signalling to a greater extent than the commercial monoclonal mouse anti-IL-11 antibody (Monoclonal Mouse IgG2A; Clone #22626; Catalog No. MAB218; R&D Systems, MN, USA): BSN-2G6 (A5), BSN-3C6 (A6), BSN-5B8 (A9) and BSN-7D4 (A12).

Clone BSN-3C6 (A6) was identified as a particularly promising candidate for further development (highlighted in FIG. 35), showing good ability to inhibit both human IL-11 and mouse IL-11 mediated signalling, and good inhibition of IL-11 trans signalling.

9.4 Screening for Ability of Mouse Anti-IL-11 Antibodies to Bind IL-11

The mouse hybridomas producing anti-human IL-11 antibodies were sub-cloned, and cell culture supernatant from the subcloned hybridomas was analysed by "mix-and-measure" iQue assay for (i) ability to bind to human IL-11, and (ii) cross reactivity for antigen other than IL-11.

Briefly, labelled control cells (not expressing IL-11 at the cell surface) and unlabelled target cells expressing human IL-11 at their surface (following transient transfection with a plasmid encoding a FLAG-tagged human IL-11) were mixed together with the cell culture supernatant (containing mouse-anti-IL-11 antibodies) and secondary detection antibodies (fluorescently-labelled anti-mouse IgG antibody).

The cells were then analysed using the HTFC Screening System (iQue) for the two labels (i.e. the cell label and the label on the secondary antibody). Detection of the secondary antibody on the unlabelled, IL-11 expressing cells indicated ability of the mouse-anti-IL-11 antibodies to bind to IL-11. Detection of the secondary antibody on the labelled, control cells indicated cross-reactivity of the mouse-anti-IL-11 antibodies for target other than IL-11.

As a positive control condition, labelled and unlabelled cells were incubated with a mouse anti-FLAG tag antibody as the primary antibody.

The results are shown in FIGS. 36A and 36B. The majority of the subcloned hybridomas expressed antibody which was able to bind to human IL-11, and which recognised this target with high specificity.

Clones BSN-2G6, BSN-5B8 and BSN-7F9 displayed some binding to cells not expressing IL-11, and so may have cross-reactivity for target(s) other than IL-11. Antibody produced by subcloned BSN-3C11 was found not to bind to human IL-11.

13 of the 16 antibodies displayed stronger signal for binding to IL-11 than signal for the positive control anti-tag antibody for the tag, indicating that these antibodies bind to IL-11 with high affinity.

Example 10: Chimeric and Humanised Versions of the Mouse Anti-Human IL-11 Antibodies Mouse/human chimeric and humanised versions of the mouse monoclonal anti-human IL-11 antibodies of Example 8 are prepared according to standard methods.

10.1 Mouse/Human Chimeric Antibodies

Mouse/human chimeric antibodies are prepared from the mouse monoclonal anti-human IL-11 antibodies as described in Human Monoclonal Antibodies: Methods and Protocols, Michael Steinitz (Editor), Methods in Molecular Biology 1060, Springer Protocols, Humana Press (2014), in Chapter 8 thereof.

Briefly, the DNA sequences encoding the VH and VL of hybridomas producing the mouse anti-human IL-11 antibodies are determined, and combined with DNA sequence encoding human immunoglobulin constant regions to produce a mouse/human chimeric antibody sequence, from which a chimeric mouse/human antibody is expressed in mammalian cells.

10.2 Humanised Antibodies

Humanised antibodies are prepared from the mouse monoclonal anti-human IL-11 antibodies as described in Human Monoclonal Antibodies: Methods and Protocols, Michael Steinitz (Editor), Methods in Molecular Biology 1060, Springer Protocols, Humana Press (2014), in Chapter 7 thereof, in particular at section 3.1 of Chapter 7 entitled 'Antibody Humanization'.

Briefly, the DNA sequences encoding the VH and VL of hybridomas producing the mouse anti-human IL-11 antibodies are determined, and inserted into DNA sequence encoding human antibody variable region framework regions and immunoglobulin constant regions, to produce a humanised antibody sequence, from which a humanised antibody is expressed in mammalian cells.

Example 11: Further Biochemical Analysis of Anti-IL-11 Antibodies

The antibodies described above are subjected to further biochemical analysis.

The antibodies are analysed by BIAcore, Biolayer interferometry (BLI) and MicroScale Thermophoresis (MST) analysis to determine the affinity of binding to human IL-11 and mouse IL-11.

BIAcore determination of antibody affinity by surface plasmon resonance (SPR) analysis is performed as described in Rich et al., Anal Biochem. 2008 Feb. 1; 373(1):112-20.

Biolayer interferometry analysis of antibody affinity is performed as described in Concepcion et al., Comb Chem High Throughput Screen. 2009 September; 12(8):791-800.

MicroScale Thermophoresis analysis of antibody affinity is performed as described in Jerabek-Willemsen et al., Assay Drug Dev Technol. 2011 August; 9(4): 342-353.

Aggregation of the antibodies is analysed by size exclusion chromatography (SEC), as described in Iacob et al., J Pharm Sci. 2013 December; 102(12): 4315-4329.

Hydophobicity of the antibodies is analysed by Hydrophobic interaction chromatography (HIC) as described in Haverick et al., MAbs. 2014 July-August; 6(4):852-8.

The melting temperature of the antibodies is analysed by Differential scanning fluorimetry (DSF) as described in Menzen and Friess, J Pharm Sci. 2013 February; 102(2): 415-28.

Example 12: Inhibition of Fibrosis In Vivo Using Anti-IL-11 Antibodies

The therapeutic utility of the anti-human IL-11 antibodies is demonstrated in in vivo mouse models of fibrosis for various different tissues. The mice used in the experiments are wildtype (i.e. IL-11RA+/+) mice.

12.1 Heart Fibrosis

A pump is implanted, and mice are treated with AngII (2 mg/kg/day) for 28 days.

Neutralising anti-IL-11 antibodies, or control antibodies, are administered to different groups of mice by intravenous injection. At the end of the experiment, collagen content is assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

Mice treated with neutralising anti-IL-11 antibodies have a reduced fibrotic response in heart tissue as compared to mice treated with control antibodies, as evidenced by reduced expression of markers of fibrosis.

12.2 Kidney Fibrosis

A mouse model for kidney fibrosis is established, in which fibrosis is induced by intraperitoneal injection of folic acid (180 mg/kg) in vehicle (0.3M $NaHCO_3$); control mice were administered vehicle alone.

Neutralising anti-IL-11 antibodies, or control antibodies, are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using TRIZOL™ reagent (Invitrogen) and QIAGEN TISSUE-LYZER™ method followed by RNEASY™ column (Qiagen) purification. The cDNA is prepared using ISCRIPT™ cDNA synthesis kit, in which each reaction contained 1 μg of total RNA, as per the manufacturer's instructions. Quantitative RT-PCR gene expression analysis is performed on triplicate samples with either TAQMAN™ (Applied Biosystems) or fast SYBR™ green (Qiagen) technology using STEPONEPLUS™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using QUICKZYME™ Total Collagen assay kit (Quickzyme Biosciences) as per the manufacturer's instructions.

Mice treated with neutralising anti-IL-11 antibodies have a reduced fibrotic response in kidney tissue as compared to mice treated with control antibodies, as evidenced by reduced expression of markers of fibrosis.

12.3 Lung Fibrosis

Mice are treated by intratracheal administration of bleomycin on day 0 to establish a fibrotic response in the lung (pulmonary fibrosis).

Neutralising anti-IL-11 antibodies, or control antibodies, are administered to different groups of mice by intravenous injection. Mice are sacrificed at day 21, and analysed for differences in fibrosis markers.

Mice treated with neutralising anti-IL-11 antibodies have a reduced fibrotic response in lung tissue as compared to mice treated with control antibodies, as evidenced by reduced expression of markers of fibrosis.

12.4 Skin Fibrosis

Mice are treated by subcutaneous administration of bleomycin on day 0 to establish a fibrotic response in the skin.

Neutralising anti-IL-11 antibodies, or control antibodies, are administered to different groups of mice by intravenous injection. Mice are sacrificed at day 21, and analysed for differences in fibrosis markers.

Mice treated with neutralising anti-IL-11 antibodies have a reduced fibrotic response in skin tissue as compared to mice treated with control antibodies, as evidenced by reduced expression of markers of fibrosis.

12.5 Eye Fibrosis

Mice undergo trabeculectomy procedure as described in Example 3.6 above to initiate a wound healing response in the eye.

Neutralising anti-IL-11 antibodies, or control antibodies, are administered to different groups of mice by intravenous injection, and fibrosis is monitored in the eye tissue.

Mice treated with neutralising anti-IL-11 antibodies have a reduced fibrotic response in eye tissue as compared to mice treated with control antibodies, as evidenced by reduced expression of markers of fibrosis.

12.6 Other Tissues

The effect of treatment with neutralising anti-IL-11 antibodies on fibrosis is also analysed in mouse models of fibrosis for other tissues, such as the liver, kidney, bowel, and is also analysed in a model relevant to multiorgan (i.e. systemic) fibrosis.

The fibrotic response is measured and compared between mice treated with neutralising anti-IL-11 antibodies and mice treated with control antibodies. Mice treated with neutralising anti-IL-11 antibodies have a reduced fibrotic response as compared to mice treated with control antibodies, as evidenced by reduced expression of markers of fibrosis.

Example 13: Treatment of Cancer In Vivo Using Anti-IL-11 Antibodies

The effect of treatment with neutralising anti-IL-11 antibodies on cancer is analysed in mouse models of cancer.

Models of breast, lung, and gastrointestinal cancers are established in mice, the mice are treated by administration of neutralising anti-IL-11 antibodies, or control antibodies, and the development/progression of cancer is monitored.

An anti-cancer effect is observed for the neutralising anti-IL-11 antibodies, as evidenced by reduced symptoms of cancer and/or increased survival as compared to mice treated with control antibodies.

Example 14: Treatment of AMD Using Anti-IL-11 Antibodies

The effect of treatment with neutralising anti-IL-11 antibodies is investigated in wet age-related macular degeneration (AMD).

Neutralising anti-IL-11 antibody is administered to subjects having wet AMD. In some treatment conditions, subjects are administered with VEGF antagonist therapy (e.g. ranibizumab, bevacizumab, pegaptanib, brolucizumab or aflibercept), PDGF antagonist therapy (e.g. pegpleranib), or are treated by laser coagulation therapy in addition to treatment with anti-IL-11 antibody.

A reduction in wet AMD pathology and/or improvement in the symptoms of wet AMD is observed in subjects treated with anti-IL-11 antibody as compared to subjects not treated with anti-IL-11 antibody.

Example 15: Light Chain Shuffled Antibodies

Light chain shuffling was performed as represented schematically in FIG. 30.

The heavy chains of the following IL-11-binding antibody clones were used for light chain shuffling: YU45-E03, YU45-F02, YU45-F05, YU45-G02, YU46-A08, YU46-G08.

Variable regions of the heavy chains were amplified by PCR, and the resulting amplicons were pooled and cloned into phagemid vectors (phagemids) each containing a specific VL chain, and representing nave lambda and kappa light chain library repertoires. The VH and VL containing phagemids were used to produce a new library of antibody-phages, which was used to select clones displaying binding to IL-11 under stringent conditions (i.e. antigen limitation, large number washing steps).

Antibodies capable of binding to both human IL-11 and murine IL-11 (i.e. cross-reactive antibodies) were identified by phage display by panning using biotinylated and non-biotinylated recombinant human and murine IL-11, based on the panning strategy shown in FIG. 52.

Figure 53:
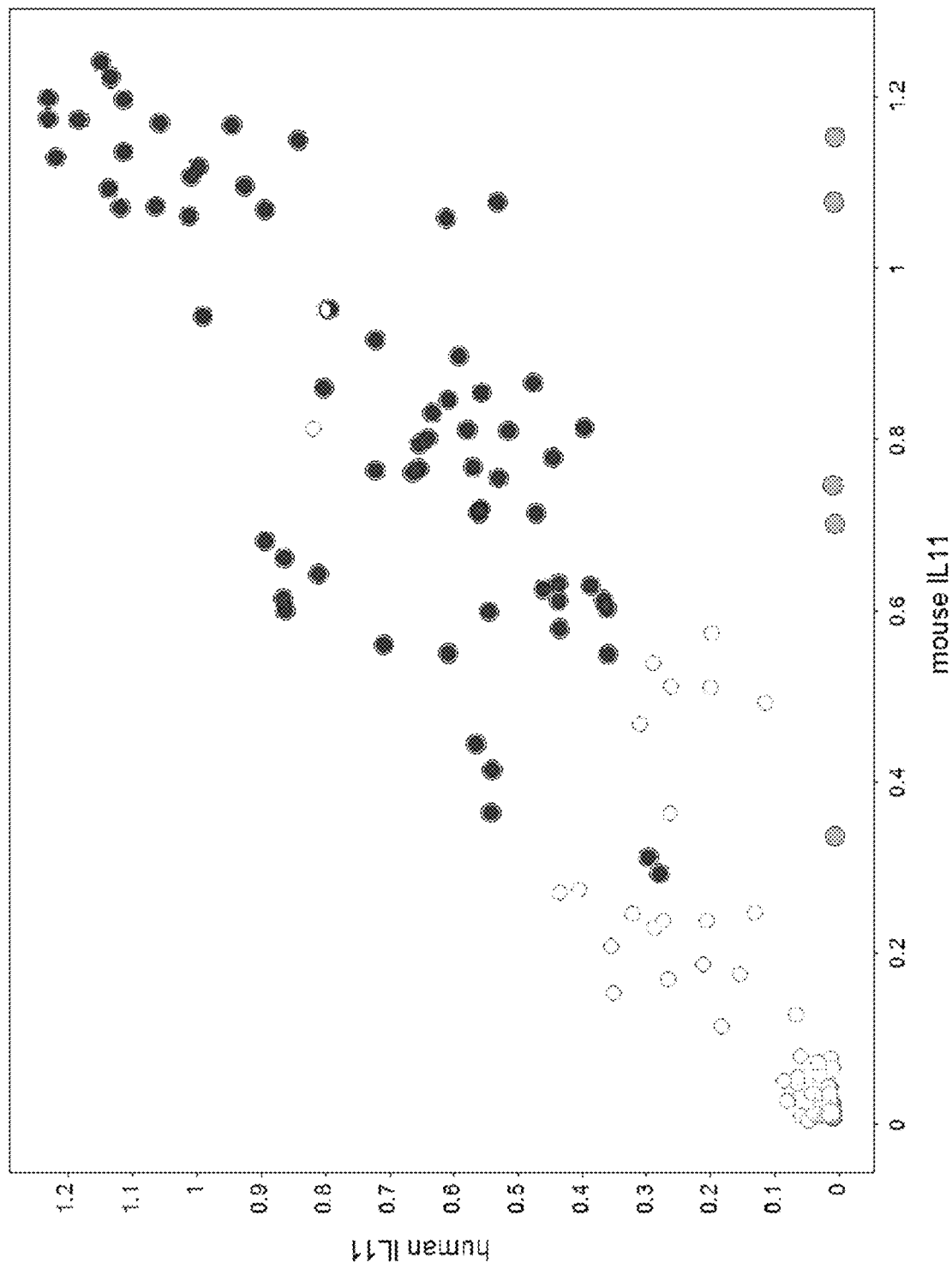
FIG. 53. Scatterplot showing binding signal to human IL-11 and mouse IL-11 as determined by ELISA assay for light chain-shuffled human anti-IL-11 antibodies. 66 antibodies displaying cross-reactive binding to human IL-11 and mouse IL-11 were identified (black circles). Antibodies displaying binding to mouse IL-11 only are indicated by grey circles.

The analysis identified 66 cross-reactive antibodies (FIG. 53). Sequence analysis identified 64 unique antibody clones, the amino acid sequences of which are shown in FIG. 50, and the nucleotide sequences of which are shown in FIG. 51.

Figure 54A:
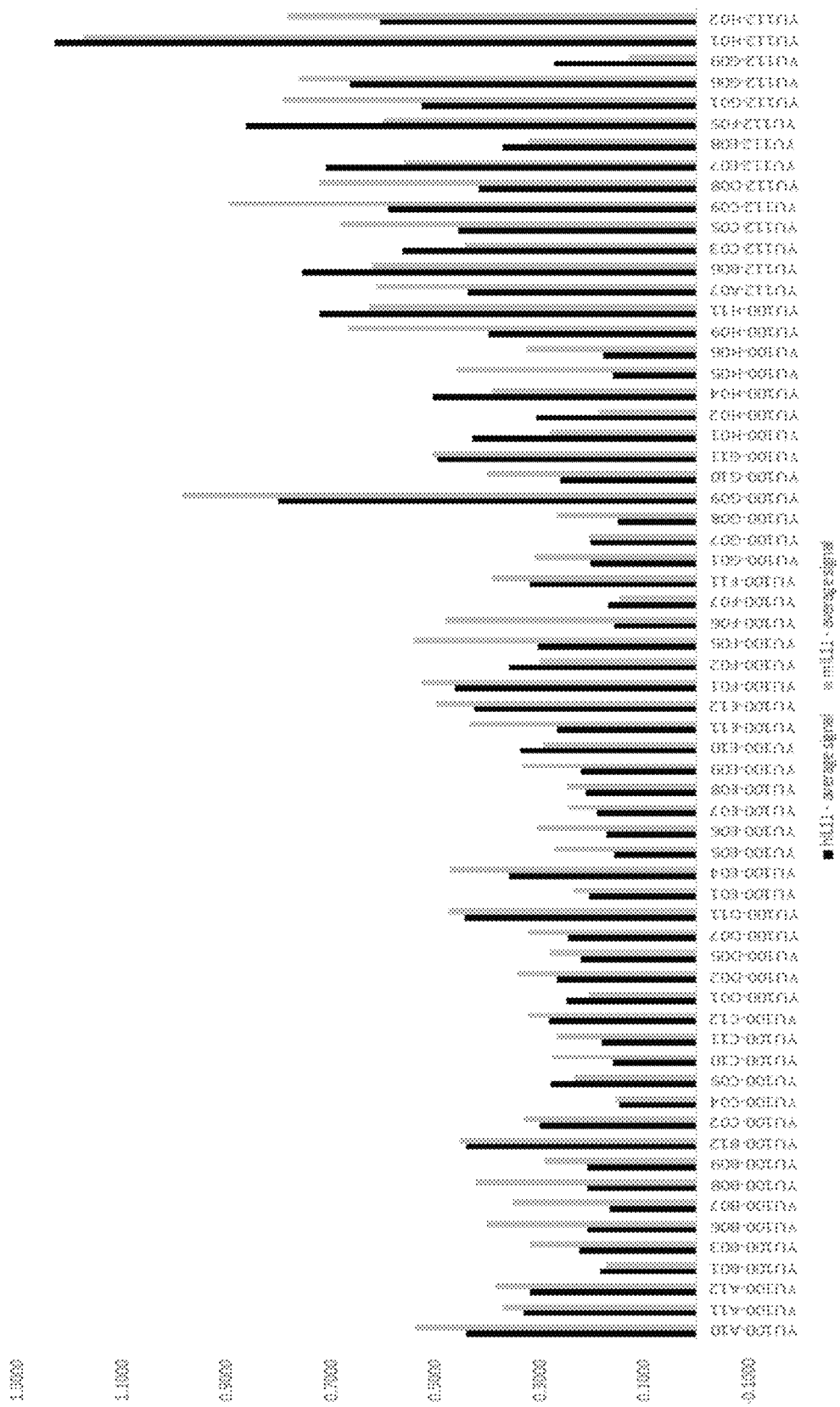

The 64 antibody clones were analysed for binding signal to human IL-11 and murine IL-11 in an ELISA assay. The results are shown in FIGS. 54A and 54B.

Example 16: Functional Characterisation of the Light Chain Shuffled Antibodies 54 of the light chain shuffled antibodies were analysed for their ability to bind IL-11 and inhibit IL-11 mediated signalling.

16.1 Binding to Human IL-11

The light chain shuffled anti-IL-11 antibodies were analysed to determine the EC50 for binding to human IL-11 by ELISA according to standard methods. Briefly, wells of microtiter plates were coated with recombinant human IL-11 (100 ng/well), scFv-Fc comprising the VH and VL domains of the clones were added in a dilution series and antibody binding was detected using a polyclonal antibody detection system.

Figure 55:
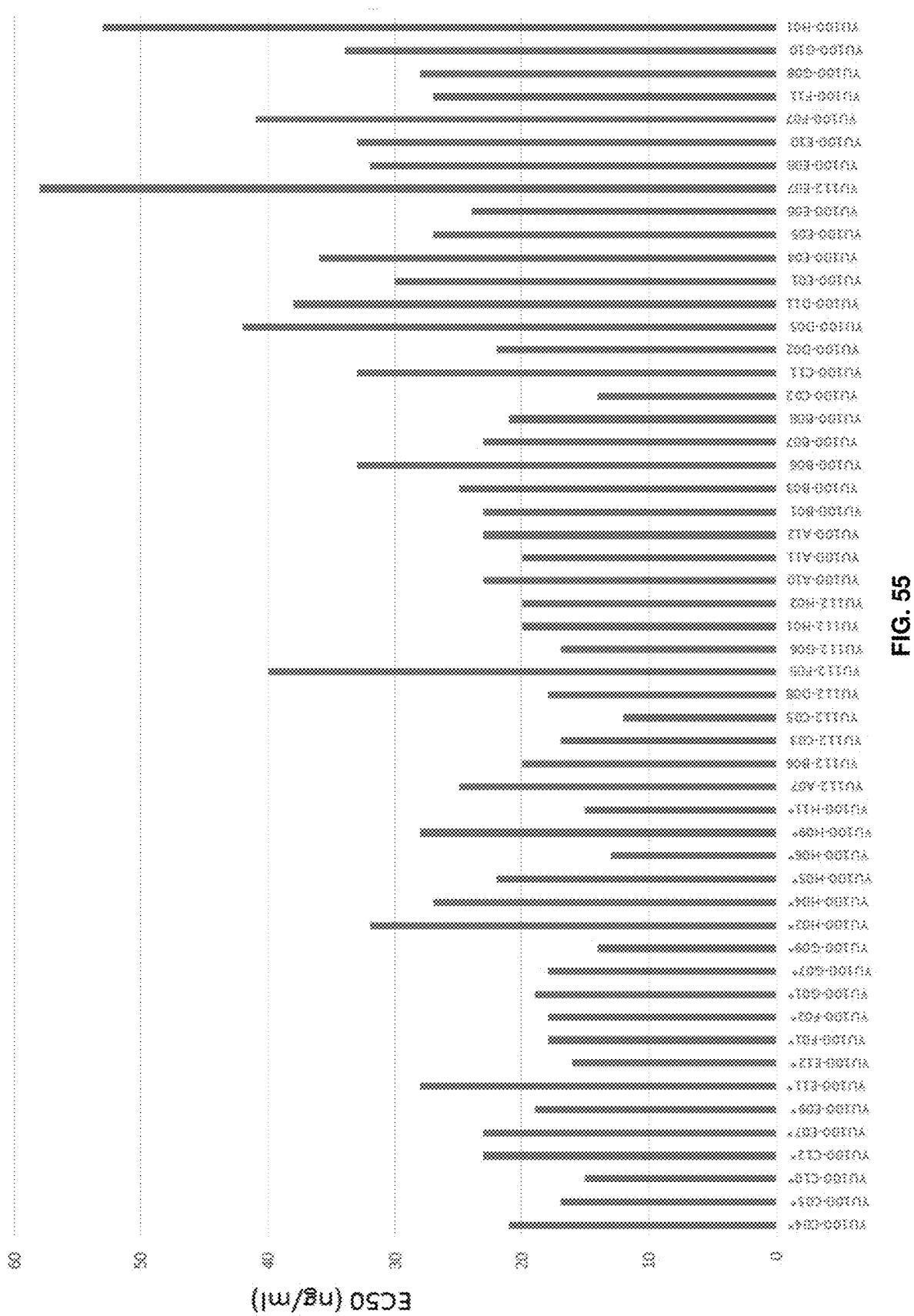
FIG. 55. Bar chart showing EC50 values in ng/ml for binding of the indicated light-chain shuffled anti-IL-11 antibodies to human IL-11, as determined by ELISA.

The results of the ELISA assays were used to calculate EC50 values (ng/ml) for the light chain shuffled antibody clones, and these are shown in FIG. 55.

16.2 Ability to Inhibit Human IL-11 Mediated Signalling

To investigate the ability of light chain shuffled antibody clones to neutralise human IL-11-mediated signalling, cardiac atrial human fibroblasts were cultured in wells of 96-well plates in the presence of TGFβ1 (5 ng/ml) for 24 hours, in the presence of anti-IL-11 antibodies in scFv-human IgG1-Fc format, or in the presence of human IgG1 isotype control antibody, at a final concentration of 2 mg/ml. Levels of the pro-fibrotic marker MMP2 in the cell culture supernatant were then measured by ELISA. Basal MMP2 secretion by the cells in culture was measured by culture in the absence of TGFβ1, in the presence of human IgG1 isotype control (2 mg/ml).

Figure 56A:
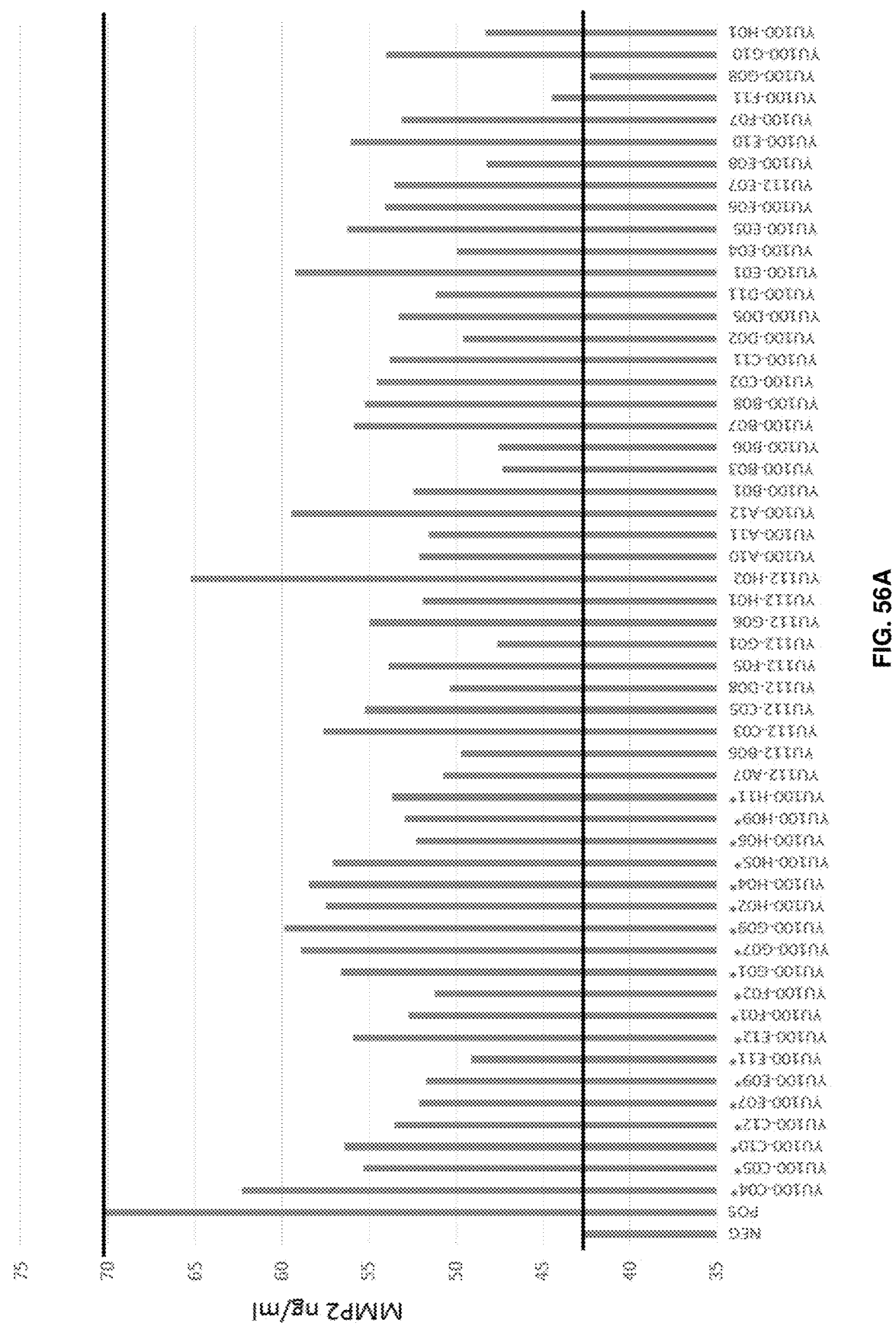
FIGS. 56A and 56B. Bar chart showing the effect of anti-IL-11 antibodies on MMP2 secretion by human cardiac atrial fibroblasts in response to TGFβ1.
Figure 56B:
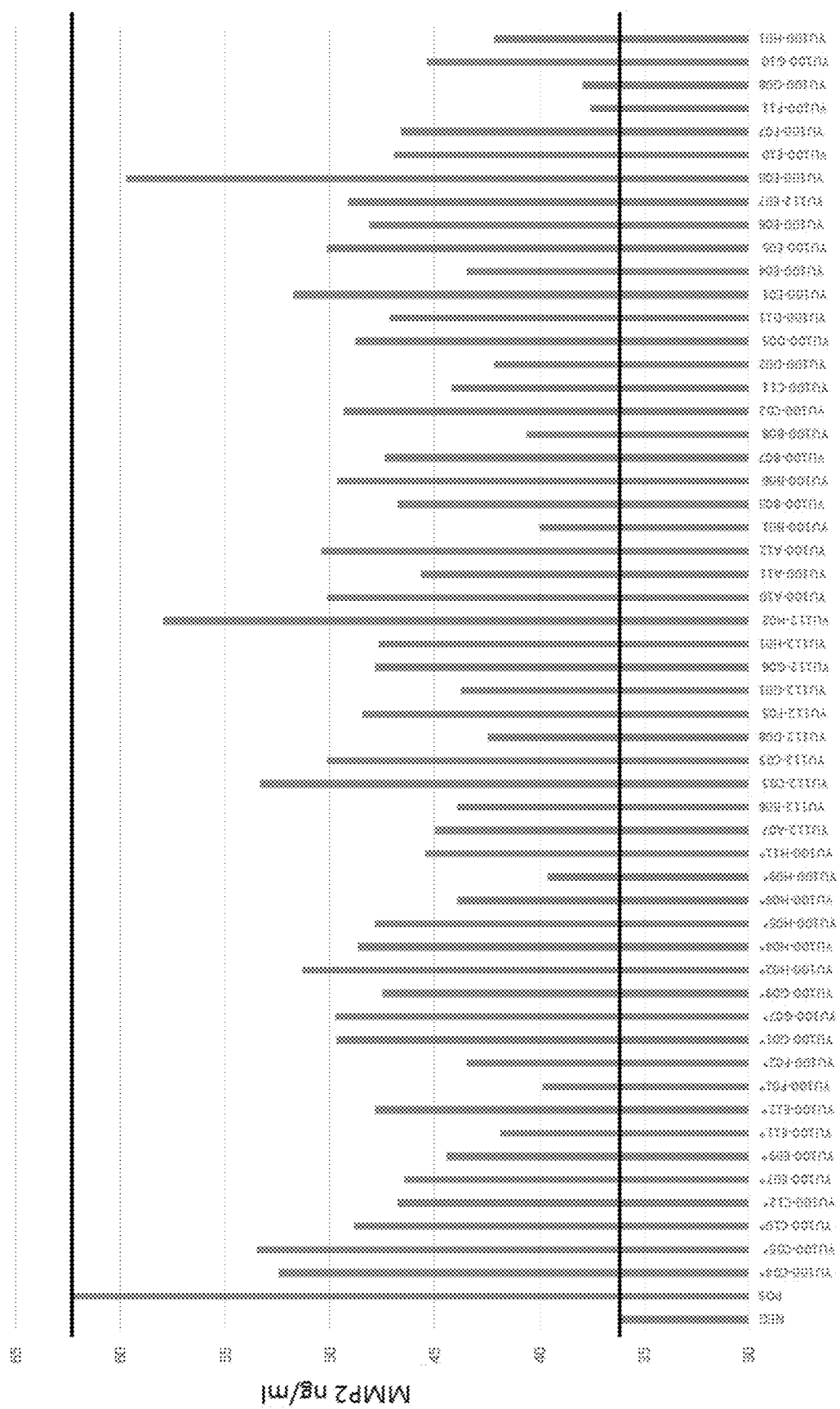

The results of two separate experiments are shown in FIGS. 56A and 56B. Horizontal lines in the bar charts represent the basal MMP2 secretion by cardiac atrial human fibroblasts cultured for 24 hours in the presence of human IgG1 isotype control antibody in the absence of TGFβ1 stimulation ('NEG' in FIGS. 56A and 56B), and MMP2 secretion by cardiac atrial human fibroblasts cultured for 24 hours in the presence of 5 ng/ml TGFβ and the human IgG1 isotype control antibody ('POS' in FIGS. 56A and 56B).

The light chain shuffled anti-IL-11 antibodies were shown to be able to bind to human IL-11, and to inhibit IL-11 mediated signalling.

Example 17: Inhibition of Kidney Fibrosis Using Anti-IL-11 Antibodies 10-12 week old littermate mice of similar weight had kidney fibrosis induced by intraperitoneal (i.p.) injection of folic acid (180 mg kg$^{-1}$) in vehicle (0.3 M NaHCO$_3$); control mice were administered vehicle alone.

Anti-IL11 antibody clone BSN-3C6 was administered one day after folic acid treatment and then 3 times per week at a dose of 20 mg/kg. Mice were euthanized 28 days post-injection.

The mouse plasma levels of urea and creatinine were quantified using urea assay kit (ab83362, Abcam) and creatinine assay kit (ab65340, Abcam), respectively according to the manufacturer's instructions. The amount of total collagen in the kidney was quantified on the basis of colourimetric detection of hydroxyproline using a QUICKZYME™ Total Collagen assay kit (Quickzyme Biosciences). All colourimetric assays were performed according to the manufacturer's instructions.

Tissues were paraffin-embedded, and kidneys were sectioned at 3 μm. For paraffin sections, tissues were fixed for 24 h, at room temperature in 10% neutral-buffered formalin (Sigma-Aldrich), dehydrated and embedded in paraffin. For cryosections, freshly dissected organs were embedded with Tissue-Tek Optimal Cutting Temperature compound (VWR International). Cryomoulds were then frozen in a metal beaker with isopentane cooled in liquid nitrogen and sections were stored in 80° C. Total collagen was stained with Masson's trichrome stain kit (HT15, Sigma-Aldrich) according to the manufacturer's instructions. Images of the sections were captured and blue-stained fibrotic areas were semi-quantitatively determined with ImageJ software (version 1.49). For immunohistochemistry, the tissue sections were incubated with anti-ACTA2 antibody (ab5694, Abcam). Primary antibody staining was visualized using an IMMPRESS™ HRP Anti-Rabbit IgG Polymer Detection kit (Vector Laboratories) with IMMPACT™ DAB Peroxidase Substrate (Vector Laboratories) as the chromogen. The sections were then counterstained with Mayer's haematoxylin (Merck).

Figure 58A:
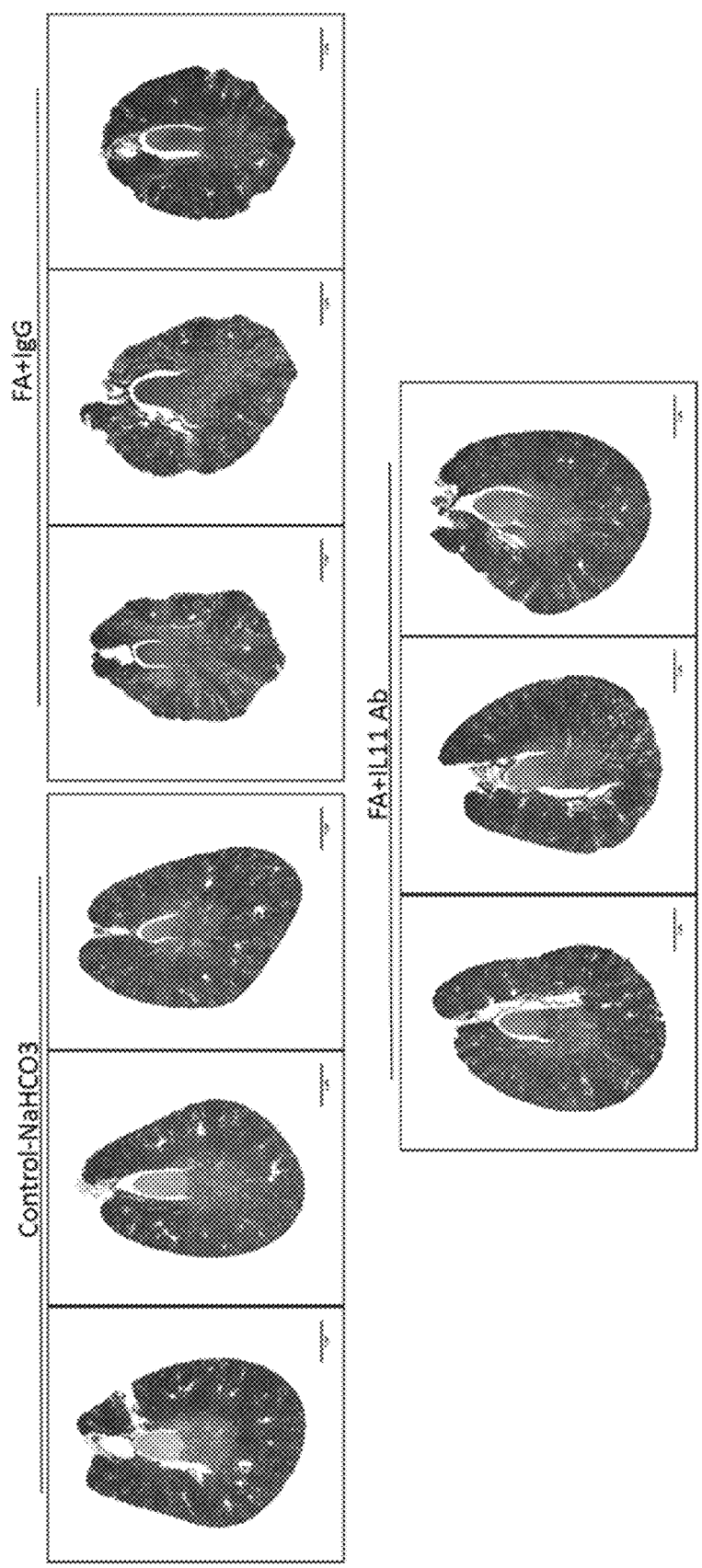
FIGS. 58A and 58B. Images and graph showing the results of histological analysis of kidney sections from mice subjected to different treatments in a mouse model of kidney fibrosis. Kidney fibrosis was induced by intraperitoneal (IP) injection of folic acid (FA, 180 mg/kg) in vehicle (0.3M NaHCO$_3$) mice; control mice were administered vehicle alone. Mice were administered isotype control IgG2 (20 mg/kg, 3× per week, intraperitoneal), anti-IL-11 antibody (20 mg/kg, 3× per week, intraperitoneally) from day 1 post folic acid injury and for the duration of the experiment. Animals were sacrificed 28 days after folic acid-induced kidney damage and analysed for fibrosis histologically using Masson's Trichrome stain.
Figure 58B:
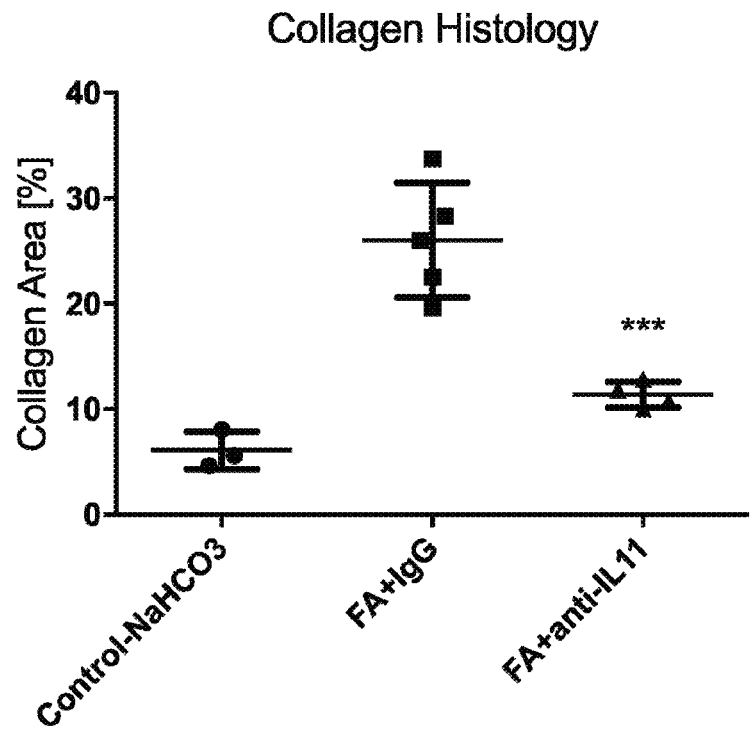

FIGS. 58A and 58B show that mice treated with anti-IL11 antibody were found to have significantly reduced staining for collagen, indicating that anti-IL-11 antibody treatment had inhibited kidney fibrosis.

Figure 59:
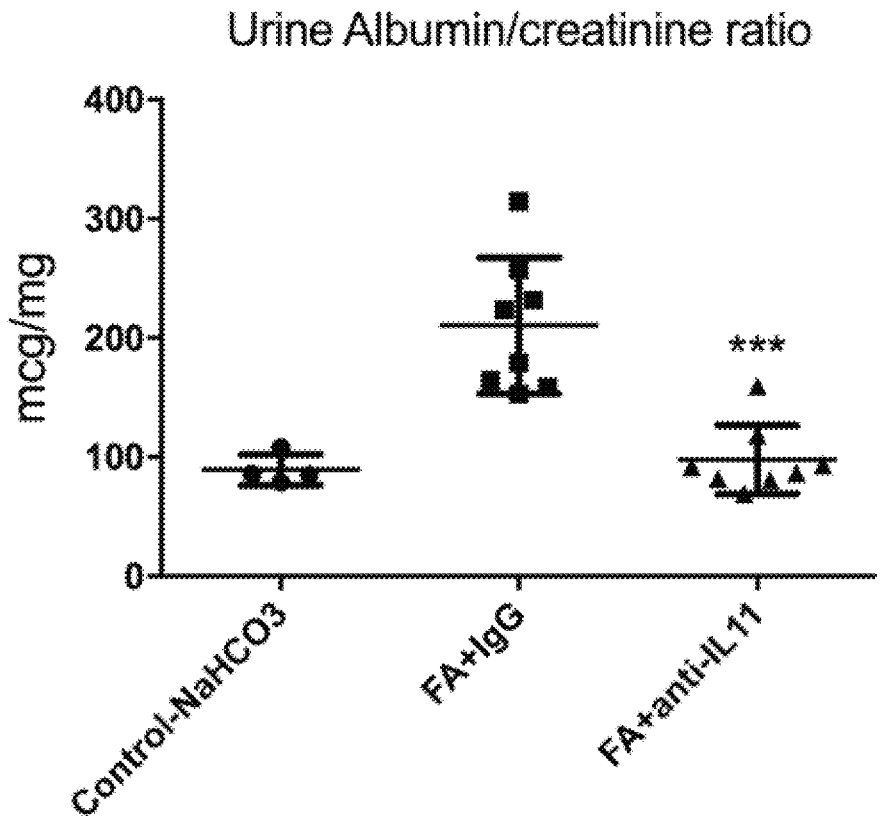
FIG. 59. Graph showing the urinary albumin/creatine ratio in mice subjected to different treatments in a mouse model of kidney fibrosis. Kidney fibrosis was induced by intraperitoneal (IP) injection of folic acid (FA, 180 mg/kg) in vehicle (0.3M NaHCO$_3$) mice; control mice were administered vehicle alone. FA treated mice were administered isotype control IgG2 (20 mg/kg, 3× per week, intraperitoneal) or anti-IL11 antibody (20 mg/kg, 3× per week, intraperitoneal) from day 1 post folic acid injury and for the duration of the experiment. Mice were placed in metabolic cages and urinary creatinine and albumin measured using commercial assays (Abcam) according to the manufacturer's instructions. ***, P<0.001 compared to FA+IgG, ANOVA.

FIG. 59 shows that the urinary albumin/creatine ratio was significantly reduced by treatment with anti-IL11 antibody, indicating a reduced level of kidney damage in mice treated with anti-IL-11 antibody.

Figure 60:
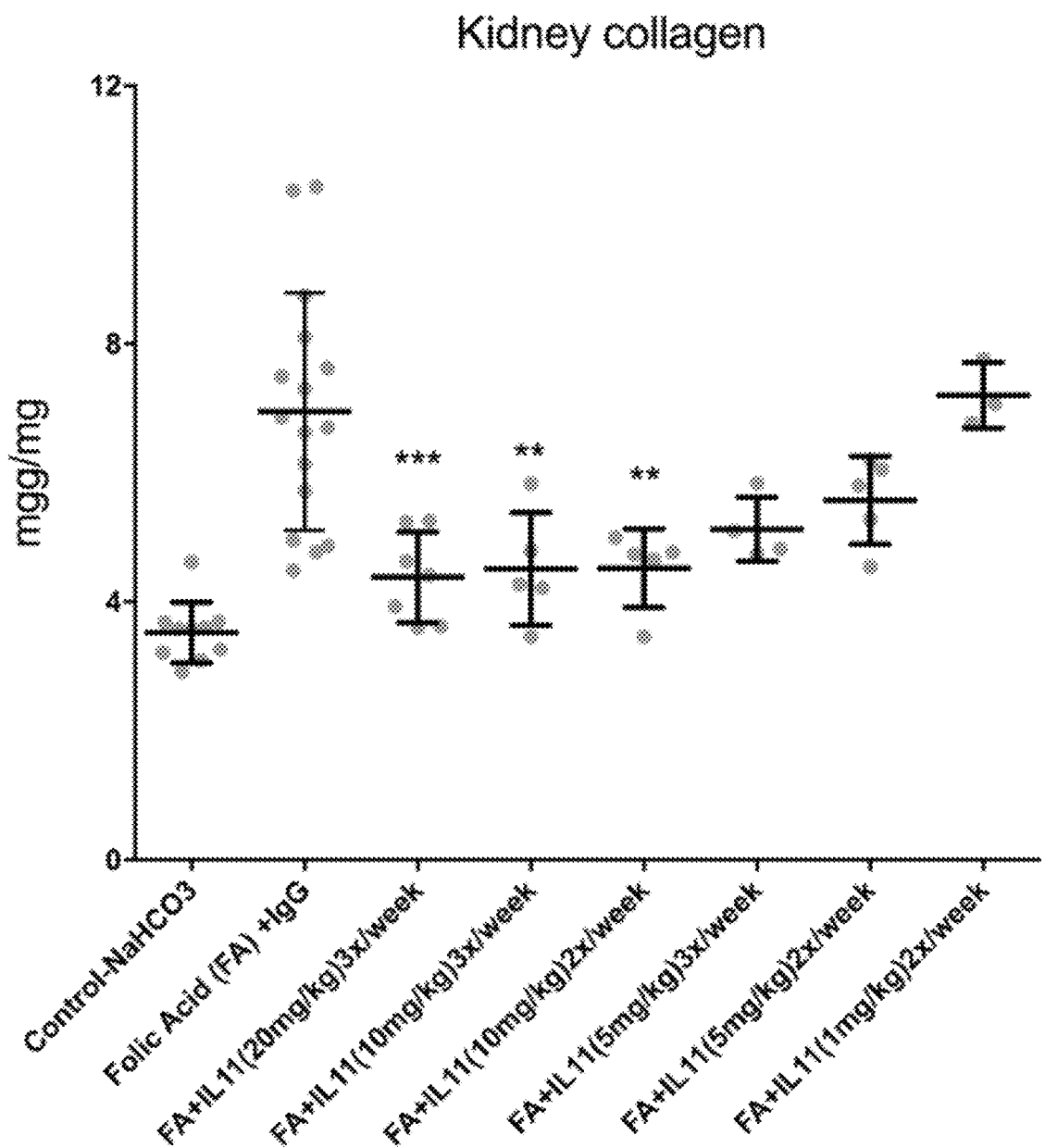
FIG. 60. Graph showing total collagen in kidney tissue in mice subjected to different treatments in a mouse model of kidney fibrosis. Kidney fibrosis was induced by intraperitoneal (IP) injection of folic acid (FA, 180 mg/kg) in vehicle (0.3M NaHCO$_3$) mice; control mice were administered vehicle alone. From day one of the experiment, mice in the treatment groups were given isotype control IgG2 (20 mg/kg, 3× per week) or neutralizing anti-IL11 antibody at varying doses: 20 mg/kg×3/week; 10 mg/kg×3/week; 10 mg/kg×2/week; 5 mg/kg×3/week; 5 mg/kg×2/week; 1 mg/kg×2/week), all intraperitoneal. Animals were sacrificed 28 days post-injection and kidney analysed for fibrosis (micrograms/g (μg/g)) by hydroxyproline assay using QUICKZYME™ Total Collagen assay kit (Quickzyme Biosciences) according to the manufacturer's protocol. , P<0.01; *, P<0.001 compared to FA+IgG, ANOVA.

FIG. 60 shows that treatment with the anti-IL-11 antibody inhibited folic acid-induced kidney fibrosis in a dose-dependent fashion.

In another experiment a mouse model of acute renal injury was induced by unilateral ureteric obstruction (UUO). Briefly, mice were treated by sham operation or ureteric obstruction of one ureter. Mice received IgG, anti-IL-11 antibody clone BSN-3C6 (20 mg/kg; on surgical days −1, 1, 3, 5) and injured kidneys ('UUO') or contralateral uninjured kidneys (Con) were harvested on day 7 post surgery.

Semi-quantitative assessment of tubular injury was performed by histological analysis of casts, tubular atrophy or tubular expansion blinded to experimental conditions (Tubular injury score: 0, none; 1, minimal; 2, mild; 3, moderate; 4, severe).

Figure 61A:
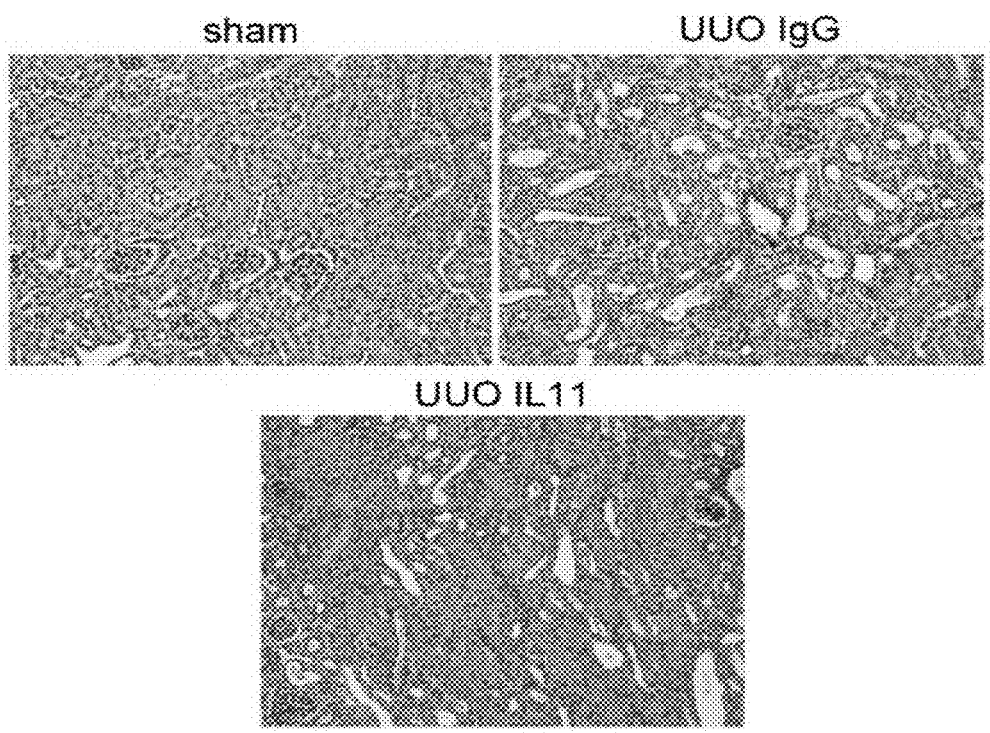
FIGS. 61A and 61B. Images and graph showing the results of histological analysis of kidney sections from mice subjected to different treatments in a mouse model of acute renal injury.
Figure 61B:
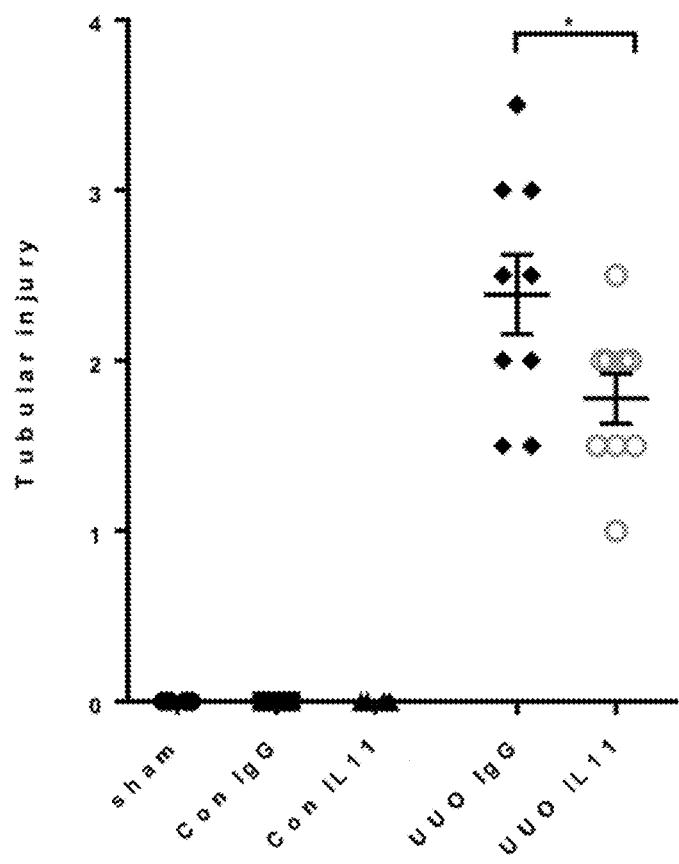

FIGS. 61A and 61B show that treatment with anti-IL-11 antibody reduced tubular damage in a mouse model of acute renal injury.

Example 18: IL-11 and Liver Fibrosis

Protein expression of IL-11 in healthy and diseased livers was confirmed by western blots in matched samples of human livers. Matched frozen liver samples were prepared for western blotting and levels of IL11 determined using Human IL-11 Antibody Monoclonal Mouse IgG2A Clone #22626, catalog number MAB218 from R&D Systems. Film images were generated.

Figure 62:
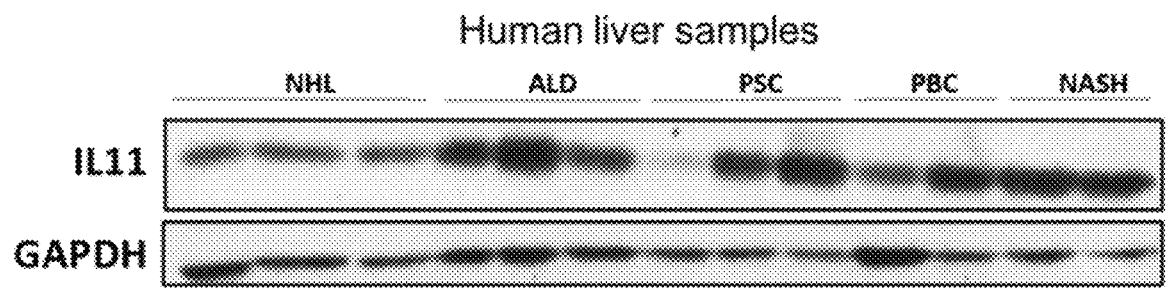
FIG. 62. Image showing the results of ELISA western blot for IL-11 of human liver samples. Liver samples obtained from patients undergoing liver surgery were used for western blot analysis. Blotting of GAPDH was used as a loading control. Samples from normal human liver (NHL) had low levels of IL-11 protein, whereas samples from patients with fibrotic liver diseases including alcoholic liver disease (ALD), primary sclerosing cholangitis (PSC), primary biliary cirrhosis (PBC) or non-alcoholic steatohepatitis (NASH) had higher levels of IL-11.

The results are shown in FIG. 62. Increased expression of IL-11 was detected in most diseased tissue as compared to normal healthy livers.

To determine whether IL-11 expression changed with disease, an ELISA was performed on media from Precision Cut Liver Slices (PCLS) was performed using Human IL-11 DuoSet 15 plate kit, catalog number DY218 from R&D Systems.

Human PCLS were cut and incubated with media treatments after a 24 h rest period for acclimatisation to media plates. Samples were treated with media only (control), media with LPS, a combination of profibrogenic stimuli inducing TGFβ1, or a combination of profibrogenic stimuli inducing TGFβ1 and the TGFβ1 inhibitor ALK5.

Figure 63:
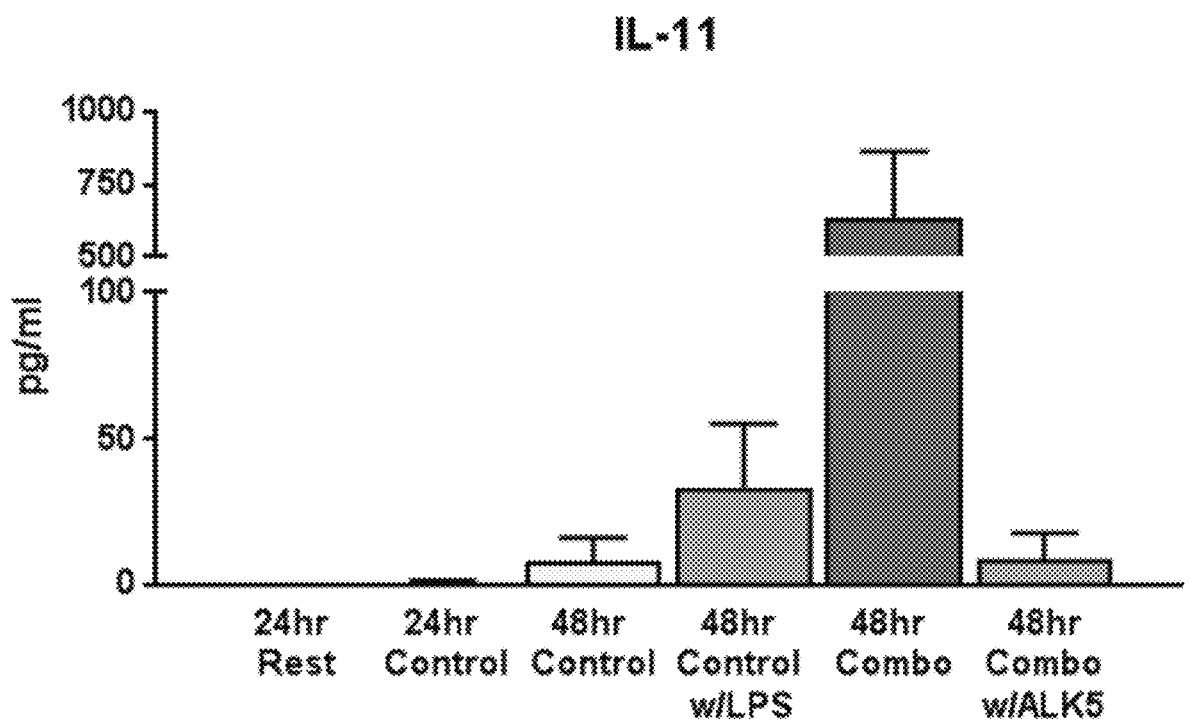
FIG. 63. Bar chart showing the results of ELISA analysis of secretion of IL-11 by human PCLS subjected to different treatments.

The results are shown in FIG. 63. The profibrogenic stimuli induced upregulation of IL-11 protein expression, and ALK5 inhibitor was found to inhibit TGFβ1 receptor signalling, which reduced the expression of IL-11 protein down to control levels.

Figure 64A:
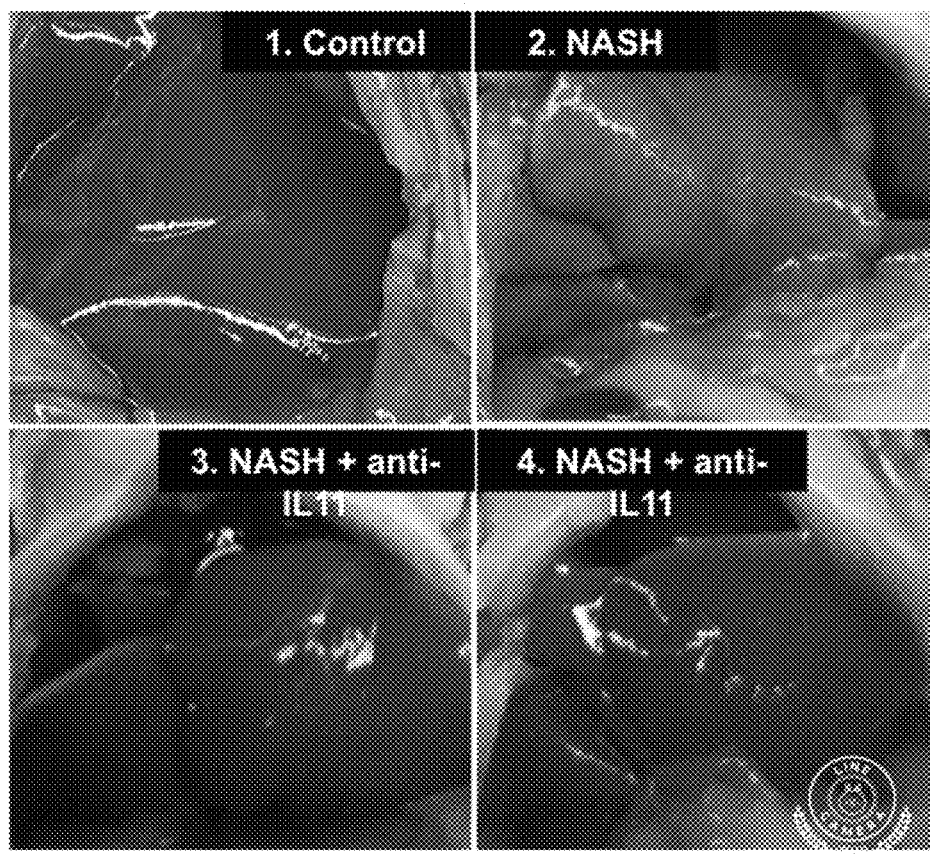
FIGS. 64A and 64B. Images and graph showing the results of analysis of liver tissue from mice subjected to different treatments in a mouse model of nonalcoholic steatohepatitis. Diabetic mice (db/db; deficient for the leptin receptor) were maintained for 8 weeks on a normal chow diet (left, round symbols) or on a NASH-inducing (methionine/choline deficient (MCD)) diet. In a subset of animals neutralizing anti-IL11 antibody was administered (20 mg/kg, 3×/week, intraperitoneal) for the final 3 weeks of the 8 week NASH diet. Liver samples were photographed (FIG. 64A) and assessed for collagen content per mg of liver tissue (FIG. 64B); each symbol represents an individual animal. P values shown on graph, ANOVA.

18.1 Inhibition of Liver Fibrosis Using Anti-IL-11 Antibodies in a Preclinical Model of NASH Diabetic mice (db/db; deficient for the leptin receptor) were maintained for 8 weeks on a normal chow diet or on a NASH-inducing (methionine/choline deficient (MCD)) diet. To test the efficacy of neutralizing anti-IL11 antibodies, we administered anti-IL-11 antibody clone BSN-3C6 (20 mg/kg, 3×/week, intraperitoneally) for the final 3 weeks of the 8 week NASH diet (FIG. 64A, bottom panels). Gross liver histology was assessed at time of euthanasia, and collagen content of the liver was analysed by hydroxyproline assay.

Figure 64B:
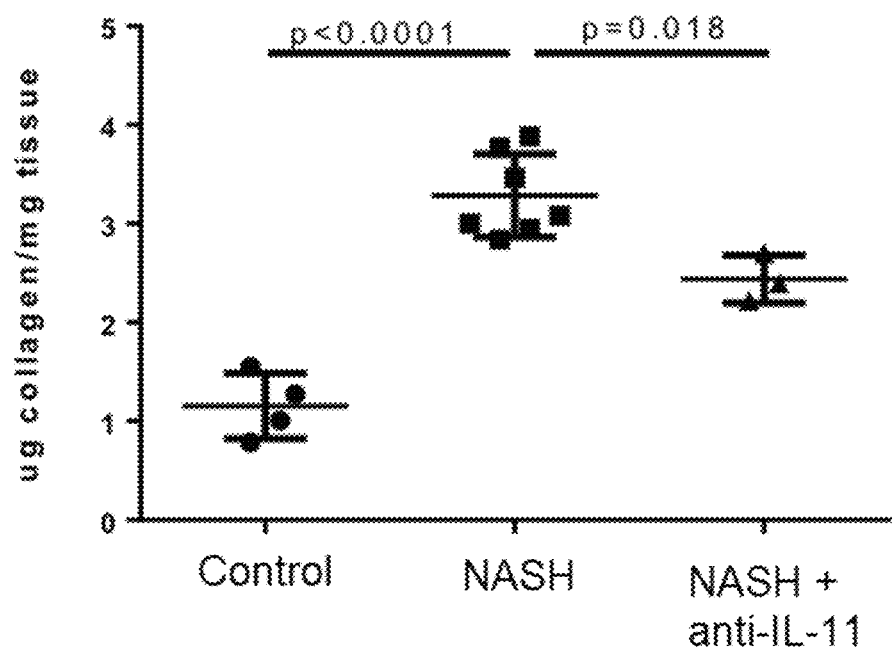

The results are shown in FIGS. 64A and 64B. Inhibition of IL-11 mediated signalling by anti-IL-11 antibody treatment improved liver histology in a mouse model of nonalcoholic steatohepatitis (FIG. 64A) as evidenced by partial restoration of liver morphology and texture in anti-IL-11 antibody-treated animals on NASH diet as compared to untreated animals on NASH diet. Livers from mice treated with anti-IL-11 antibody on NASH diet were also found to have reduced collagen content as compared to untreated animals on NASH diet (FIG. 64B).

Example 19: Inhibition of Eye Fibrosis Using Anti-IL-11 Antibodies

The anti-fibrotic effect of anti-IL-11 antibody treatment was assessed in a mouse model of retinal fibrosis in which Bruch's membrane is disrupted, as described in Caballero et al., Exp Eye Res. (2009) March; 88(3):367-77.

Briefly, mice were subjected to laser-induced retinal damage (4 burns per retina) and were then treated by intraocular administration of antibodies (0.5 μg of either IgG control or anti-IL11 antibody clone BSN-3C6) on days 1, 7, 14 and 21. Eyes were harvested for histological analyses on day 28. The area of fibrosis at burn sites was measured using Masson's Trichrome staining, blinded to treatment.

Figure 65A:
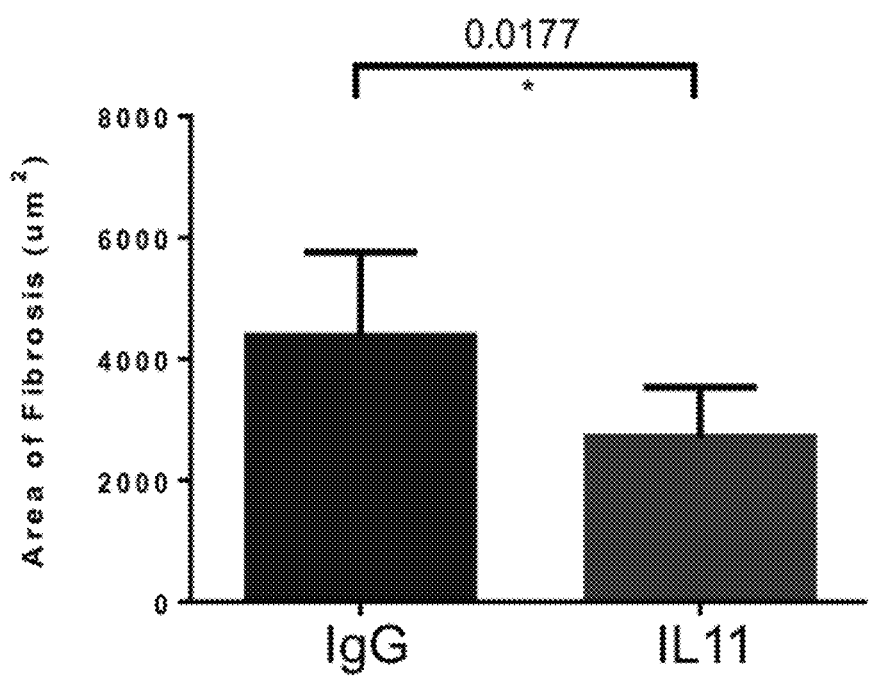
FIGS. 65A and 65B. Bar chart and images showing the results of analysis of eye fibrosis from mice subjected to different treatments in a mouse model of retinal fibrosis. Mice (10 per group) were subjected to laser-induced retinal damage (4 burns per retina) and administered intraocularly with 0.5 μg of anti-IL-11 antibody or IgG control antibody on days 1, 7, 14 and 21. Eyes were harvested for histological analyses on day 28. The area of fibrosis at burn sites were measured by Masson's Trichrome staining.
Figure 65B:
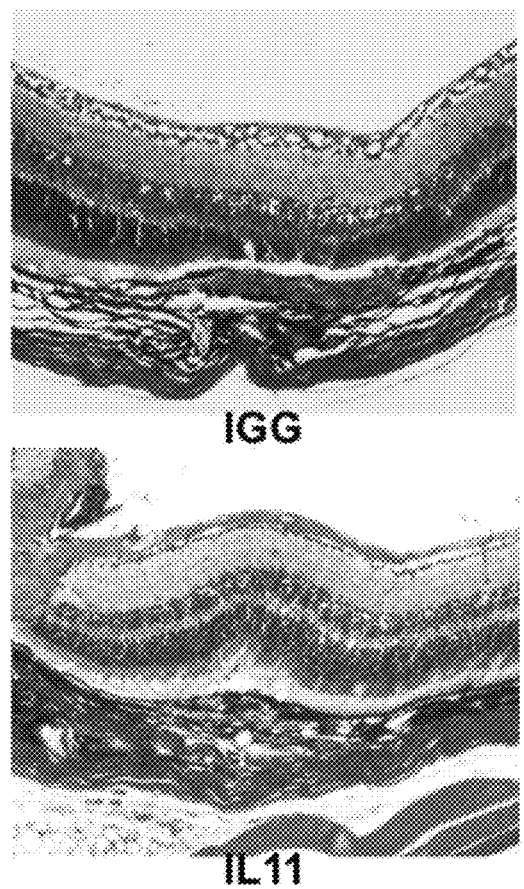

The results are shown in FIGS. 65A and 65B. The area of fibrosis was significantly greater in control IgG-treated mice as compared to anti-IL11 antibody treated mice.

Example 20: Inhibition of Skin Fibrosis Using Anti-IL-11 Antibodies

The anti-fibrotic effect of anti-IL-11 antibody treatment was analysed in a mouse model of skin fibrosis established by subcutaneous injection of bleomycin (BLM, Sigma B2434, 50 μg/day).

Briefly, the fur on the middle of the back of the mice (~9 cm$^2$) was trimmed using a scissors, and hair removal cream was applied to remove fur completely. Subcutaneous injections of 100 μL of bleomycin dissolved in PBS at a concentration of 0.5 mg/ml were performed on the top half of the injection site. Subcutaneous injections of 60 μL of anti-IL11 antibody clone BSN-3C6 or control IgG antibody were subsequently performed on the bottom half of the injection site (dosage=15 mg/kg/day). Injections were performed daily for 21 days and animals were sacrificed one day after the final injection and analysed histologically for dermal thickness and collagen content (by Masson's trichrome staining).

Figure 66A:
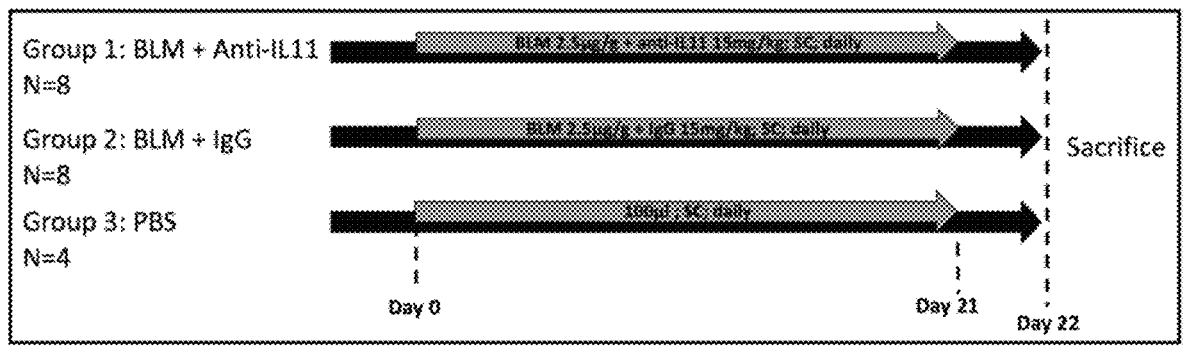
FIGS. 66A to 66C. Schematic, images and bar chart relating to analysis of skin fibrosis in mice subjected to different treatments in a mouse model of skin fibrosis.
Figure 66B:
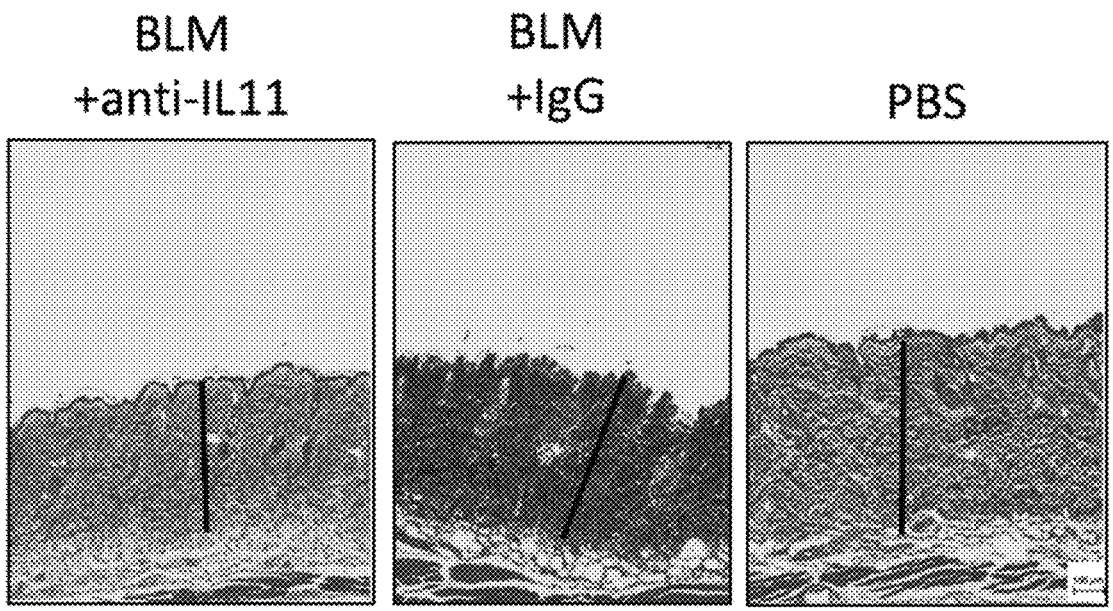
Figure 66C:
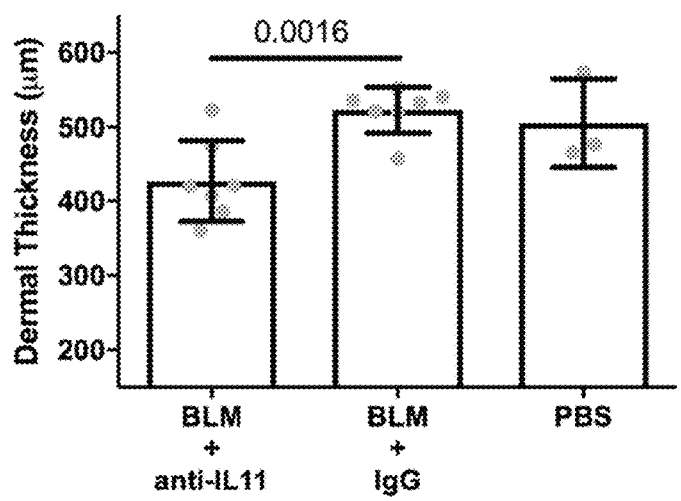

FIGS. 66B and 66C show that dermal thickness was significantly reduced in mice treated with neutralising anti-IL-11 antibody as compared to control IgG-treated mice. Increased collagen staining can also be seen for the control IgG-treated group (FIG. 66B, middle panel).

Example 21: Inhibition of Heart Fibrosis Using Anti-IL-11 Antibodies

The anti-fibrotic effect of anti-IL-11 antibody treatment was analysed in a mouse model of cardiac fibrosis.

Briefly, transverse aortic constriction (TAC) was performed in male mice as described previously (Tarnavski, O. et al. Mouse cardiac surgery: comprehensive techniques for the generation of mouse models of human diseases and their application for genomic studies. Physiol. Genomics 16, 349-360 (2004)). Age-matched mice underwent a sham operative procedure without TAC. Trans-thoracic two-dimensional Doppler echocardiography was used to confirm increased pressure gradients (>40 mm Hg), indicative of successful TAC.

Mice were euthanized at 2 weeks post-TAC for histological and molecular assessment. Anti-IL-11 antibody clone BSN-3C6 or control IgG antibody were administered intraperitoneally 3 times per week at a dose of 20 mg/kg. After two weeks hearts were harvested and assessed for fibrosis extent using Masson's Trichrome stain kit (HT15, Sigma-Aldrich), in accordance with the manufacturer's instructions.

Figure 67:
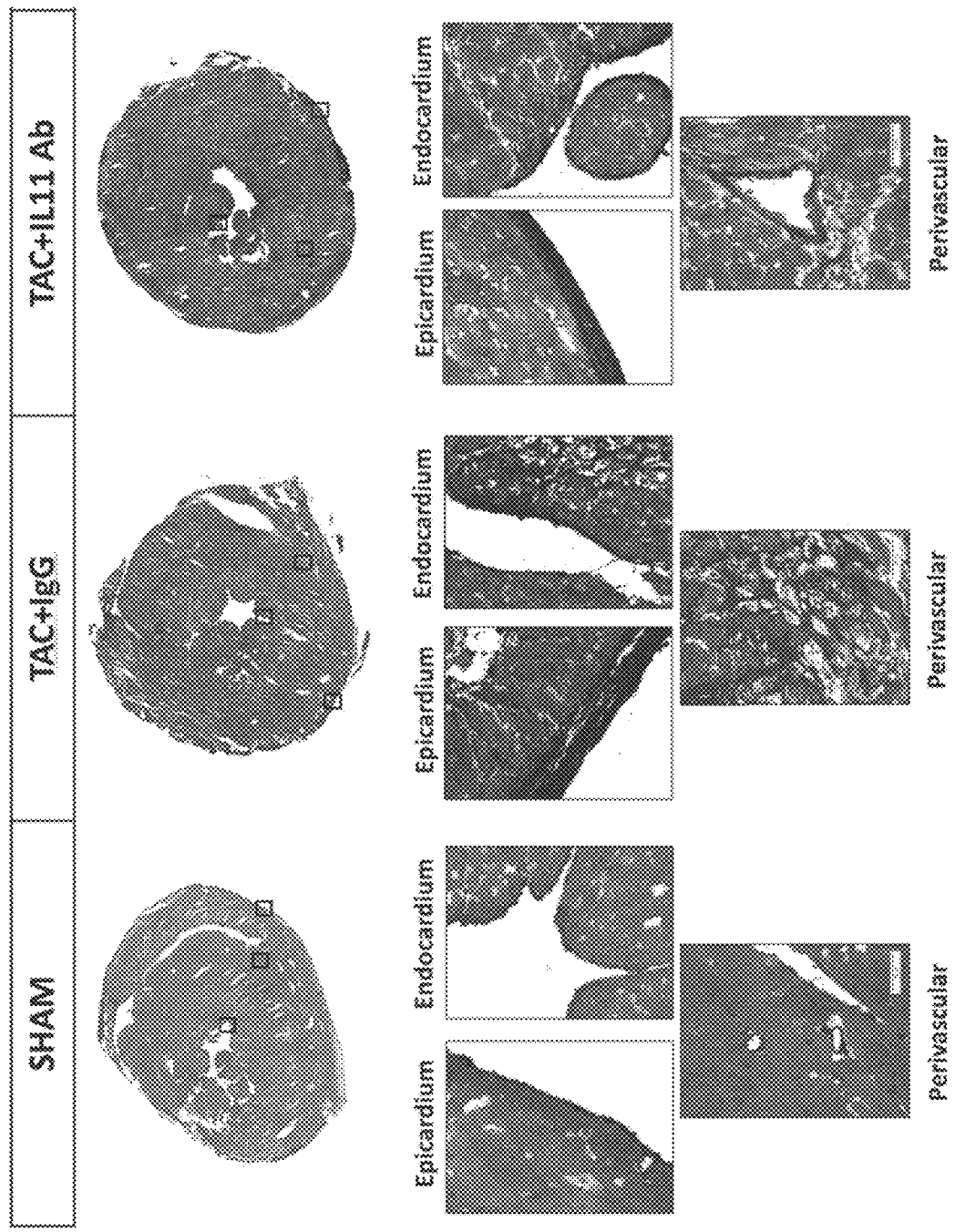
FIG. 67. Images showing the results of histological analysis of heart fibrosis in mice subjected to different treatments in a mouse model of cardiac fibrosis. Mice (C57616, male, 8-12 weeks old) were subjected to fibrosis-inducing transverse aortic constriction (TAC) or sham operations. TAC-treated animals received either control antibody (20 mg/kg, 3×/week, intraperitoneal) or neutralizing anti-IL-11 antibody (20 mg/kg, 3×/week, intraperitoneal). After two weeks hearts were harvested and assessed for fibrosis extent using Masson's Trichrome stain.

The results of the analysis is shown in FIG. 67. Mice treated with neutralising anti-IL-11 antibody were found to have reduced levels of fibrosis in the epicardium, endocardium and in perivascular regions as compared to mice treated with IgG control antibody.

---

The invention claimed is:

1. An antibody or antigen binding fragment, which is capable of binding to IL-11, comprising a light chain variable region sequence and a heavy chain variable region sequence, wherein:

the light chain variable region sequence comprises the following CDRs:

i) LC-CDR1:  (SEQ ID NO: 107)
   SSDVGGYNY;

ii) LC-CDR2:  (SEQ ID NO: 291)
   DVN;
   and iii) LC-CDR3:  (SEQ ID NO: 336)
   CSYAGRYTWM;

or a variant comprising 1 amino acid substitution in the sequence CSYAGRYTWM (SEQ ID NO: 336); and the heavy chain variable region sequence comprises the following CDRs:

i) HC-CDR1:  (SEQ ID NO: 186)
   GFTFSSYG ii) HC-CDR2:  (SEQ ID NO: 184)
   ISYDGSNK;
   and iii) HC-CDR3:  (SEQ ID NO: 187)
   AKIGATDPLDY.

2. The antibody or antigen binding fragment according to claim 1, wherein:
the light chain variable region sequence has at least 80% sequence identity to the light chain variable region sequence of SEQ ID NO: 335, and
the heavy chain variable region sequence has at least 80% sequence identity to the heavy chain variable region sequence of SEQ ID NO: 370.

3. The antibody or antigen binding fragment according to claim 1, wherein the light chain variable region sequence comprises the following CDRs:

i) LC-CDR1:  (SEQ ID NO: 107)
   SSDVGGYNY ii) LC-CDR2:  (SEQ ID NO: 291)
   DVN;
   and iii) LC-CDR3:  (SEQ ID NO: 336)
   CSYAGRYTWM, and wherein the heavy chain variable region sequence comprises the following CDRs:

iv) HC-CDR1:  (SEQ ID NO: 186)
   GFTFSSYG;

v) HC-CDR2:  (SEQ ID NO: 184)
   ISYDGSNK;
   and vi) HC-CDR3:  (SEQ ID NO: 187)
   AKIGATDPLDY.

4. The antibody or antigen binding fragment according to claim 1, which is capable of inhibiting IL-11 trans signalling.

5. The antibody or antigen binding fragment according claim 1, conjugated to a drug moiety or a detectable moiety.

6. A method for producing an antibody or antigen binding fragment according to claim 1, comprising culturing a cell comprising a nucleic acid or vector encoding the antibody or antigen binding fragment according to claim 1 under conditions suitable for the expression of the antibody or antigen binding fragment.

7. The method of claim 6, further comprising isolating the antibody or antigen binding fragment from the cell, thereby producing an isolated antibody or antigen binding fragment.

8. The method of claim 7, further comprising mixing the isolated antibody or antigen binding fragment with a pharmaceutically acceptable carrier, adjuvant, excipient or diluent.

9. A method of treating fibrosis or a disease/disorder characterised by fibrosis, comprising administering an antibody or antigen binding fragment to a subject suffering from fibrosis or a disease/disorder characterised by fibrosis, wherein the antibody or antigen binding fragment is capable of binding to IL-11, and comprises a light chain variable region sequence and a heavy chain variable region sequence, wherein:

the light chain variable region sequence comprises the following CDRs:

i) LC-CDR1:
   SSDVGGYNY; (SEQ ID NO: 107)

ii) LC-CDR2:
    DVN; (SEQ ID NO: 291)
    and iii) LC-CDR3:
     CSYAGRYTWM; (SEQ ID NO: 336)

or a variant comprising 1 amino acid substitution in the sequence CSYAGRYTWM (SEQ ID NO: 336); and the heavy chain variable region sequence comprises the following CDRs:

i) HC-CDR1:
   GFTFSSYG (SEQ ID NO: 186)

ii) HC-CDR2:
    ISYDGSNK; (SEQ ID NO: 184)
    and iii) HC-CDR3:
     AKIGATDPLDY. (SEQ ID NO: 187)

10. The method according to claim 9, wherein:

the light chain variable region sequence has at least 80% sequence identity to the light chain variable region sequence of SEQ ID NO: 335, and the heavy chain variable region sequence has at least 80% sequence identity to the heavy chain variable region sequence of SEQ ID NO: 370.

11. The method according to claim 9, wherein the light chain variable region sequence comprises the following CDRs:

i) LC-CDR1:
   SSDVGGYNY (SEQ ID NO: 107)

ii) LC-CDR2:
    DVN; (SEQ ID NO: 291)
    and iii) LC-CDR3:
     CSYAGRYTWM, (SEQ ID NO: 336)

and wherein the heavy chain variable region sequence comprises the following CDRs:

i) HC-CDR1:
   GFTFSSYG (SEQ ID NO: 186)

ii) HC-CDR2:
    ISYDGSNK; (SEQ ID NO: 184)
    and iii) HC-CDR3:
     AKIGATDPLDY. (SEQ ID NO: 187)

* * * * *